(12) United States Patent
Tanimoto et al.

(10) Patent No.: US 6,562,817 B1
(45) Date of Patent: May 13, 2003

(54) TRICYCLIC COMPOUND

(75) Inventors: Norihiko Tanimoto, Osaka (JP); Yasushi Hasegawa, Shiga-ken (JP); Nobuhiro Haga, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/600,790

(22) PCT Filed: Jan. 26, 1999

(86) PCT No.: PCT/JP99/00297

§ 371 (c)(1), (2), (4) Date: Jul. 21, 2000

(87) PCT Pub. No.: WO99/38829

PCT Pub. Date: Aug. 5, 1999

(30) Foreign Application Priority Data

Jan. 28, 1998 (JP) ............................................... 10-15554

(51) Int. Cl.$^7$ .................... C07D 213/02; C07D 239/26; A61K 31/4418; A61K 31/4427; A61K 31/505

(52) U.S. Cl. ................ 514/233.8; 546/300; 546/271.4; 546/272.1; 546/272.4; 546/272.7; 546/275.4; 546/276.1; 546/261; 546/257; 544/114; 544/124; 544/135; 544/140; 544/139; 544/357; 544/238; 544/405; 544/409; 544/410; 514/235.8; 514/236.5; 514/238.8; 514/252.06; 514/252.19; 514/253.01; 514/338; 514/255.05; 514/252.02

(58) Field of Search .............................. 546/300, 271.4, 546/272.1, 272.4, 272.7, 275.4, 276.1, 261, 257; 514/345, 332, 233.8, 235.8, 236.5, 238.8, 252.02, 252.06, 252.19, 253.01, 255.05, 338; 544/124, 114, 135, 140, 139, 357, 238, 405, 409, 410

(56) References Cited

U.S. PATENT DOCUMENTS

| | | | |
|---|---|---|---|
| 3,621,028 A | 11/1971 | Newberry | 260/306.7 |
| 4,791,200 A | 12/1988 | Press et al. | 544/369 |
| 4,808,333 A | 2/1989 | Huynh-ba et al. | 252/299.66 |
| 4,826,990 A | 5/1989 | Musser et al. | 548/203 |
| 4,895,953 A | * 1/1990 | Musser et al. | 548/204 |
| 5,047,170 A | * 9/1991 | Huynh-ba et al. | 252/299.6 |
| 5,179,111 A | 1/1993 | Biere et al. | 514/341 |
| 5,256,682 A | 10/1993 | Krueger et al. | 514/378 |
| 5,547,848 A | 8/1996 | Shinoki et al. | 435/7.9 |
| 5,643,932 A | 7/1997 | Chihiro et al. | 514/365 |
| 5,786,486 A | 7/1998 | Fukuda et al. | 548/421 |
| 5,801,170 A | 9/1998 | Gaster et al. | 514/236.2 |

FOREIGN PATENT DOCUMENTS

| | | | |
|---|---|---|---|
| EP | A2212848 | 3/1987 | |
| EP | A1310676 | 4/1989 | |
| ES | 2015648 | 9/1990 | |
| ES | 2 015 648 | * 9/1990 | |
| FR | 2301250 | 10/1976 | |
| JP | A5191259 | 8/1976 | |
| JP | A58121225 | 7/1983 | |
| JP | A63022044 | 1/1988 | |
| JP | A6345243 | 2/1988 | |
| JP | A63119425 | 5/1988 | |
| JP | A1143856 | 6/1989 | |
| JP | A1279872 | 11/1989 | |
| JP | A2500274 | 2/1990 | |
| JP | A348666 | 3/1991 | |
| JP | A4276551 | 10/1992 | |
| JP | A5507732 | 11/1993 | |
| JP | A8003163 | 1/1996 | |
| JP | A8208653 | 7/1996 | |
| JP | A9124571 | 5/1997 | |
| JP | A9506101 | 6/1997 | |
| JP | A1179993 | 3/1999 | |
| WO | A1-9727181 | 7/1997 | |
| WO | A1-9744333 | 11/1997 | |
| WO | A1-9856785 | 12/1998 | |

* cited by examiner

*Primary Examiner*—Richard L. Raymond
*Assistant Examiner*—Kahsay Habte
(74) *Attorney, Agent, or Firm*—Birch, Stewart, Kolasch & Birch, LLP

(57) ABSTRACT

The present invention provides a compound of the formula (I):

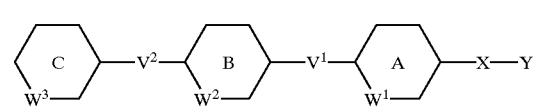

wherein A ring, B ring and C ring are each independently optionally substituted aromatic carbocycle or optionally substituted 5- or 6-membered heterocycle which may fuse with benzene ring, $W^1$, $W^2$ and/or $W^3$ represents a bond when A ring, B ring and/or C ring is optionally substituted 5-membered heterocycle, X is —O—, —$NR^1$— wherein $R^1$ is hydrogen, lower alkyl etc. or the like, Y is hydrogen, lower alkyl, lower alkenyl or the like, one of $V^1$ and $V^2$ is a bond, and the other is a bond, —O— or the like, and a pharmaceutical composition comprising the same.

75 Claims, No Drawings

TRICYCLIC COMPOUND

This application is the national phase under 35 U.S.C. §371 of PCT International Application No. PCT/JP99/00297 which has an International filing date of Jan. 26, 1999, which designated the United States of America.

TECHNICAL FIELD

The present invention relates to a novel tricyclic compound and a pharmaceutical composition for use as an immunosuppressant, an anti-allergic agent or a suppressant of the IgE production comprising the same.

BACKGROUND ART

A serious problem of a transplantation of a tissue or an organ which is frequently performed in recent years is a rejection symptom for excluding a transplanted part after an operation. Prevention of the rejection symptom is very important for a success of the transplantation.

Various immunosuppressants such as azathioprine, corticoid, Cyclosporin A, Tacrolimus and the like are developed and come into practical use for prevention and a treatment of a rejection symptom against a transplantation of an organ or a tissue or a graft-versus-host reaction which is caused by a bone marrow transplantation. But they are not so satisfactory in view of their effects and side effects.

Allergic diseases such as atopic dermatitis, allergic rhinitis, bronchial asthma, allergic conjunctivitis and the like tend to globally increase in recent years and become serious problems. The conventional antiinflammatory agents are suppressants of releasing chemical mediators from mast cells, receptor inhibitors of the released chemical mediators, suppressants of allergic inflammation response or the like. All of these are agents for symptomatic therapy and are not fundamental therapeutic agents for allergic diseases.

Therefore, the development of a more effective and safer medicinal agent has been expected.

The compounds having a similar structure to a compound of the present invention and exhibiting an immunosuppressive or anti-allergic effect are described in WO94/27980, WO95/13067, WO96/40659, WO96/40143, WO96/38412, WO97/24356, WO97/24324, WO97/46524, JP-A 8-3163, JP-A 9-12457, JP-A 9-71564, JP-A 9-124571 and the like. The liquid crystal compounds are described in JP-A 9-87253, JP-A 63-253065, JP-A 1-106864, JP-A 1-106871, JP-A 2-83346, JP-A 9-48760, JP-A 9-31063 and the like, the compounds exhibiting an insecticide or acaricide activity are described in JP-A 8-193067 and the compounds having a therapeutic activity for circulatory system or psychopathy diseases are described in EP0600717 A1, all of which have a similar structure to a compound of the present invention.

DISCLOSURE OF THE INVENTION

The present invention provides a compound of the formula (I):

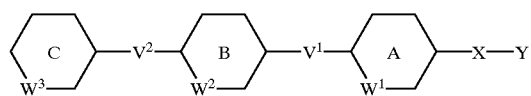

wherein A ring, B ring and C ring are each independently optionally substituted aromatic carbocycle or optionally substituted 5- or 6-membered heterocycle which may fuse with benzene ring, $W^1$, $W^2$ and/or $W^3$ represents a bond when A ring, B ring and/or C ring is optionally substituted 5-membered heterocycle, X is —O—, —CH$_2$—, —NR$^1$— wherein R$^1$ is hydrogen, optionally substituted lower alkyl, lower alkenyl, lower alkylcarbonyl or optionally substituted lower alkoxycarbonyl or —S(O)p— wherein p is an integer of 0 to 2, Y is hydrogen, optionally substituted lower alkyl, optionally substituted lower alkenyl, optionally substituted lower alkynyl, optionally substituted acyl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH$_2$—, Y may be optionally substituted lower alkoxycarbonyl; optionally substituted lower alkylsulfonyl or optionally substituted arylsulfonyl when X is —O— or —NR$^1$—, one of $V^1$ and $V^2$ is a bond and the other is a bond, —O—, —NH—, —OCH$_2$—, —CH$_2$O—, —CH=CH—, —C≡C—, —CH(OR$^2$)— wherein R$^2$ is hydrogen or lower alkyl, —CO— or —NHCHR$^3$— wherein R$^3$ is hydrogen or hydroxy, and at least one of A ring, B ring and C ring is optionally substituted aromatic carbocycle and at least another one is optionally substituted 5- or 6-membered heterocycle which may fuse with benzene ring when both of $V^1$ and $V^2$ are single bonds, pharmaceutically acceptable salt or hydrate thereof The present invention provides a pharmaceutical composition for use as an immunosuppressant, an anti-allergic agent or a suppressant of the IgE production comprising the compound (I), pharmaceutically acceptable salt or hydrate thereof.

In one of the other embodiments, the present invention provides a method for suppressing an immune response or a method for treating and/or preventing allergic diseases comprising administering the compound (I). In another embodiment, the present invention provides use of the compound (I) for manufacturing a medicament for suppressing an immune response or treating and/or preventing allergic diseases.

In the present specification, the term "halogen" includes fluorine, chlorine, bromine and iodine. Fluorine or chlorine is preferable.

The term "lower alkyl" includes straight or branched chain alkyl having 1 to 10 carbon atoms, preferably 1 to 8 carbon atoms, more preferably 1 to 6 carbon atoms, and most preferably 1 to 3 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

As substituents of "optionally substituted lower alkyl", exemplified are halogen; hydroxy; lower alkoxy optionally substituted with lower alkoxy; acyl; acyloxy; carboxy; lower alkoxycarbonyl; mercapt; lower alkylthio; amino optionally substituted with hydroxy, lower alkyl or optionally substituted acyl; imino optionally substituted with hydroxy, lower alkoxy, carboxy(lower)alkoxy, aryl(lower)alkoxy or 5- or 6-membered heterocycle; hydrazono optionally substituted with carbamoyl or lower alkoxycarbonyl; carbamoyl optionally substituted with lower alkyl or amino; thiocarbamoyl optionally substituted with lower alkyl; cycloalkyl optionally substituted with lower alkyl or lower alkoxy; cycloalkenyl optionally substituted with lower alkyl; cyano; phenyl optionally substituted with at least one substituent selected from the group of hydroxy, lower alkyl, carboxy, lower alkoxycarbonyl and lower alkoxy; 5- or 6-membered heterocycle which may be substituted with lower alkyl and may fuse with benzene ring; and the like. The lower alkyl may be substituted with one or more of these substituents at any possible positions. Halogen; hydroxy; acyloxy; phenyl optionally substituted with lower alkyl or lower alkoxy; pyridyl or the like is preferable.

The part of lower alkyl in "lower alkoxy" is the same as the above "lower alkyl".

As substituents for "optionally substituted lower alkoxy", exemplified are halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; heterocyclylcarbonyloxy and the like.

The parts of lower alkyl in "lower alkoxycarbonyl", "lower alkylsulfonyl", "lower alkylsulfonyloxy", "lower alkylthio", "lower alkylamino" and "lower alkylenedioxy" are the same as the above "lower alkyl". Substituents for "optionally substituted lower alkoxycarbonyl", "optionally substituted lower alkylsulfonyl" and "optionally substituted lower alkylthio" are the same as those for the above "optionally substituted lower alkoxy".

The term "lower alkenyl" includes straight or branched chain alkenyl of 2 to 10 carbon atoms, preferably 2 to 8 carbon atoms more preferably 3 to 6 carbon atoms having at least one double bond at any possible positions. For example, included are vinyl, propenyl such as 2-propenyl and the like, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like. Substituents for "optionally substituted lower alkenyl" are the same as those for the above "optionally substituted lower alkoxy" and alkenyl substituted with halogen or unsubstituted alkenyl is preferable.

The parts of lower alkenyl in "lower alkenyloxy", "lower alkenyloxycarbonyl" and "lower alkenylamino" are the same as the above "lower alkenyl". Substituents for "optionally substituted lower alkenyloxy", "optionally substituted lower alkenyloxycarbonyl" and "optionally substituted lower alkenylthio" are the same as those for the above "optionally substituted lower alkoxy".

The term "lower alkynyl" includes straight or branched chain alkynyl having 2 to 10 carbon atoms, preferably 2 to 8 carbon atoms, and more preferably 3 to 6 carbon atoms and is exemplified by ethynyl, propynyl such as 2-propynyl, butynyl such as 2-butynyl, pentynyl, hexynyl, heptynyl, octynyl, nonynyl, decynyl and the like. These have at least one triple bond and may have some double bonds at any possible positions. Substituents for "optionally substituted lower alkynyl" are the same as those for the above "optionally substituted lower alkoxy".

The term "acyl" includes straight or branched chain aliphatic acyl having 1 to 20 carbon atoms, preferably 1 to 15 carbon atoms, more preferably 1 to 8 carbon atoms, more preferably 1 to 6 carbon atoms, most preferably 1 to 4 carbon atoms, cyclic aliphatic acyl having 4 to 9 carbon atoms, preferably 4 to 7 carbon atoms and aroyl. For example, formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like are included. Substituents for "optionally substituted acyl" are the same as those for the above "optionally substituted lower alkoxy" and aroyl may further be substituted with lower alkyl. Among the substituents, halogen is preferable.

The part of acyl in "acyloxy" is the same as the above "acyl" and substituents for "optionally substituted acyloxy" are the same as those for the above "optionally substituted acyl".

The term "lower alkylcarbonyl" includes aliphatic acyl having 2 to 4 carbon atoms and included are acetyl, propyl, butyryl, isobutyryl and the like. Acetyl is preferable.

The term "cycloalkyl" includes carbocycle having 3 to 6 carbon atoms and cyclopropyl, cyclobutyl, cyclopentyl, cyclohexyl and the like. As substituents for "optionally substituted cycloalkyl" exemplified are lower alkyl, halogen, hydroxy, carboxy, lower alkoxycarbonyl, lower alkoxy, lower alkylenedioxy, imino optionally substituted with lower alkoxy, aryl, 5- or 6-membered heterocycle and the like and the cycloalkyl may be substituted at any possible positions.

The term "cycloalkenyl" includes the group having at least one double bond at any possible positions in the above cycloalkyl and is exemplified by cyclopropenyl, cyclobutenyl, cyclopentenyl, cyclohexenyl, cyclohexadienyl and the like. Substituents for "optionally substituted cycloalkenyl" are the same as those for the above "cycloalkyl".

As substituents for "optionally substituted amino", exemplified are optionally substituted lower alkyl {wherein the substituents are lower alkoxy, cycloalkyl, optionally substituted amino (wherein the substituents are aroyl optionally substituted with acyloxy(lower)alkoxy), optionally substituted aryl (wherein the substituents are lower alkyl, lower alkoxy, carboxy or lower alkoxycarbonyl) or heterocycle}; lower alkenyl; lower alkynyl; cycloalkyl; aryl optionally substituted with lower alkyl, carboxy, acyl, lower alkoxycarbonyl; sulfamoyl optionally substituted with lower alkyl; optionally substituted lower alkoxycarbonyl (the substituents are halogen, acyloxy, acyloxy substituted with hydroxy, acyloxy substituted with carboxy or heterocyclylcarbonyloxy or the like); lower alkylsulfonyl and the like.

The term "optionally substituted carbamoyl" includes carbamoyl optionally substituted with lower alkyl, lower alkenyl, lower alkynyl or the like.

The term "optionally substituted sulfamoyl" includes sulfamoyl optionally substituted with lower alkyl, lower alkenyl, lower alkynyl or the like.

The term "aromatic carbocycle" includes benzene ring, naphthalene ring, anthracene ring, phenanthrene ring, indene ring and the like and benzene ring is preferable.

The term "aryl" includes phenyl, naphthyl, anthryl, phenanthryl, indenyl and the like and phenyl is preferable.

As substituents for "optionally substituted aromatic carbocycle" and "optionally substituted aryl", exemplified are halogen; hydroxy; lower alkyl optionally substituted with halogen or carboxy; lower alkoxy optionally substituted with halogen, aryl, heteroaryl or lower alkoxy; lower alkenyl; lower alkynyl; cycloalkyl; lower alkenyloxy; lower alkynyloxy; cycloalkoxy; acyl; acyloxy; carboxy; lower alkoxycarbonyl; lower alkenyloxycarbonyl; lower alkylthio; lower alkynylthio; amino optionally substituted with lower alkyl, cycloalkyl(lower)alkyl, heteroaryl(lower)alkyl, lower alkenyl, cycloalkyl, acyl optionally substituted with halogen, lower alkoxycarbonyl, or lower alkylsulfonyl; guanidino; nitro; lower alkylsulfonyl; dihydroxyborane; lower alkylsulfonyloxy optionally substituted with halogen; arylsulfonyl; arylsulfonyloxy; aryl; 5- or 6-membered heterocycle and the like. The aromatic carbocycle and aryl may be substituted with these substituents at one or more of any possible positions. Preferable examples are halogen; hydroxy; lower alkyl optionally substituted with halogen; lower alkoxy optionally substituted with aryl or lower alkoxy; lower alkenyloxy; acyloxy; lower alkylthio; amino optionally substituted with lower alkyl, lower alkenyl, acyl optionally substituted with halogen, or lower alkylsulfonyl; nitro; lower alkylsulfonyl; lower alkylsulfonyloxy optionally substituted with halogen; or arylsulfonyloxy.

The parts of aryl in "arylsulfonyl" and "arylsulfonyloxy" are the same as the above "aryl" and phenyl is preferable. Substituents for "optionally substituted arylsulfonyl" are the same as those for the above "optionally substituted aryl" and unsubstituted arylsulfonyl is preferable.

The term "5- or 6-membered heterocycle" includes 5- or 6-membered heterocycle which contains at least one of hetero atoms arbitrarily selected from a group of O, S and N. Examples of heterocycle include aromatic heterocycle such as pyrrole ring, imidazole ring, pyrazole ring, pyridine ring such as 4-pyridyl, pyridazine ring, pyrimidine ring, pyrazine ring, triazole ring, triazine ring, isoxazole ring, oxazole ring, oxadiazole ring, isothiazole ring, thiazole ring, thiadiazole ring, furan ring such as 2-furyl or 3-furyl, thiophene ring such as 3-thienyl and the like, aliphatic heterocycle such as tetrahydropyrane ring, dihydropyridine ring such as 1,2-dihydropyridyl, dihydropyridazine such as 2,3-dihydropyridazinyl, dihydropyrazine ring such as 1,2-dihydropyrazinyl, dioxane ring, oxathiorane ring, thiane ring, pyrrolidine ring, pyrroline ring, imidazolidine ring, imidazoline ring, pyrazolidine ring, pyrazoline ring, piperidine ring, piperazine ring, morpholine ring and the like.

The term "5- or 6-membered heterocycle which contains one or two hetero atoms" includes aromatic heterocycle such as pyrrole ring, imidazole ring, pyrazole ring, pyridine ring, pyridazine ring, pyrimicline ring, pyrazine ring, isoxazole ring, oxazole ring, isothiazole ring, thiazole ring, furan ring, thiophene ring or the like and aliphatic heterocycle such as dioxane ring, oxathiorane ring, thiane ring, dihydropyridine ring, pyrrolidine ring, pyrroline ring, imidazolidine ring, imidazoline ring, pyrazolidine ring, pyrazoline ring, piperidine ring, piperazine ring, morpholine ring or the like among the above "5- or 6-membered heterocycle". Aromatic heterocycle is preferable.

As "5- or 6-membered ring which may fuse with benzene ring", exemplified are indole ring, isoindole ring, benzimidazole ring, indazole ring, cinnoline ring, phthalazine ring, quinazoline ring, benzisoxazole ring, benzoxazole ring, benzoxadiazole ring, benzothiazole ring, benzisothiazole ring, benzofuran ring, benzothiophen ring, benzotriazole ring, isobenzofuran ring, chromen ring, indoline ring, isoindoline ring and the like.

As substituents for "optionally substituted 5- or 6-membered heterocycle" and "optionally substituted 5- or 6-membered heterocycle which may fuse with benzene ring" exemplified are halogen; hydroxy; lower alkyl optionally substituted with hydroxy or acyloxy; lower alkoxy optionally substituted with halogen, aryl or 5- or 6-membered heterocycle; lower alkenyl; lower alkenyloxy; lower alkynyl; lower alkynyloxy; acyloxy; carboxy; lower alkoxycarbonyl; mercapt; lower alkylthio; lower alkenylthio; amino which may be mono- or di-substituted with halogen, optionally substituted lower alkyl wherein the substituents are cycloalkyl or 5- or 6-membered heterocycle, acyl optionally substituted with halogen, lower alkenyl, cycloalkyl, or lower alkylsulfonyl; imino optionally substituted with lower alkylsulfonyl; nitro; lower alkylsulfonyl; aryl; 5- or 6-membered heterocycle; oxo; oxide and the like. These substituents may substitute at one or more of any possible positions.

The substituents for "optionally substituted 5- or 6-membered heterocycle which contains one or two of hetero atoms" are the same as the above. 5- or 6-membered heterocycle substituted with lower alkyl or unsubstituted one is preferable.

The term "$W^1$, $W^2$ and/or $W^3$ represents a bond when A ring, B ring and/or C ring is optionally substituted 5-membered heterocycle" means as follows: $W^1$ represents a bond when A ring is optionally substituted 5-membered heterocycle, resulting in the binding positions of $V^1$ and X to A ring as shown below.

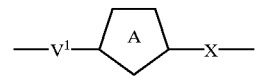

Each of $W^2$ and $W^3$ represents a bond when B ring or C ring is 5-membered heterocycle, resulting in the binding positions of $V^1$ and $V^2$ shown below.

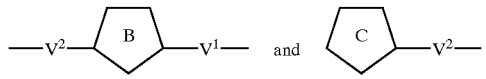

Each of X, $V^1$ and $V^2$ may directly bind to a hetero atom constituting A ring, B ring or C ring.

The term "compound (I)" includes formable and pharmaceutically acceptable salts of each compound. As "the pharmaceutically acceptable salt", exemplified are salts with mineral acids such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid and the like; salts with organic base such as ammonium, trimethylammonium, triethylammonium and the like; salts with alkaline metals such as sodium, potassium and the like and salts with alkaline earth metals such as calcium, magnesium and the like.

The compound of the present invention includes hydrates and all of stereoisomers, for example, atropisomers etc. thereof.

BEST MODE FOR CARRYING OUT THE INVENTION

All of the compounds (I) have an immunosuppressive effect, an anti-allergic effect and/or a suppressive effect on the IgE production and the following compounds are specifically preferable.

In the formula (I),
1) a compound wherein A ring is optionally substituted benzene ring,
   preferably A ring is optionally substituted benzene ring {wherein the substituents are halogen, hydroxy, lower alkyl, lower alkoxy, acyloxy, lower alkylsulfonyl, optionally substituted lower alkylsulfonyloxy (wherein the substituents are halogen) or arylsulfonyloxy},
   more preferably A ring is optionally substituted benzene ring (wherein the substituents are halogen, hydroxy, lower alkyl, lower alkoxy or lower alkylsulfonyloxy), 2) a compound wherein B ring is optionally substituted benzene ring, optionally substituted pyridine ring, optionally substituted pyrimidine ring, optionally substituted pyridazine ring, optionally substituted pyrazine ring, optionally substituted thiophene ring, optionally substituted furan ring, optionally substituted pyrazole ring or optionally substituted oxazole ring, preferably B ring is optionally substituted benzene ring (wherein the substituents are halogen, hydroxy, lower alkyl, lower alkoxy, lower alkenyloxy, lower alkylthio, cycloalkoxy, lower alkoxycarbonyl or lower alkylsulfonyloxy), optionally substituted pyridine ring (wherein the substituents are halogen, hydroxy, lower alkyl, lower alkoxy, lower alkylthio, lower alkenyl, amino, carboxy or lower alkoxycarbonyl), optionally substituted pyrimidine ring {wherein the substituents are halogen, optionally substituted lower alkyl (wherein the substituents are hydroxy or acyloxy), lower alkoxy, lower alkylthio, optionally substituted amino (wherein the substituents are lower alkyl), carboxy or lower alkoxycarbonyl}, optionally substituted pyridazine ring (wherein the substituents are halogen, hydroxy, lower alkyl, lower alkoxy, lower alkylthio, lower alkenyl, amino, carboxy, lower alkoxycarbonyl or oxide), optionally substituted thiophene ring (wherein the substituents are lower alkyl), optionally substituted pyrazole ring {wherein the substituents are optionally substituted lower alkyl (wherein the substituents are hydroxy), lower alkoxy, carboxy or lower alkoxycarbonyl}, or optionally substituted oxazole ring (wherein the substituents are lower alkyl), more preferably B ring is optionally substituted benzene ring (wherein the substituents are hydroxy, lower alkyl, lower alkoxy or lower alkylsulfonyloxy), optionally substituted pyridine ring wherein the substituents are halogen or lower alkyl), optionally substituted pyrimidine ring {wherein the substituents are optionally substituted lower alkyl (wherein the substituents are hydroxy or acyloxy), lower alkoxy, lower alkylthio, optionally substituted amino (wherein the substituents are lower alkyl), carboxy or lower alkoxycarbonyl}, optionally substituted pyrazole ring {wherein the substituents are optionally substituted lower alkyl(wherein the substituents are hydroxy), lower alkoxy, carboxy or lower alkoxycarbonyl}, 3) a compound wherein C ring is optionally substituted benzene ring, optionally substituted pyridine ring, optionally substituted pyrimidine ring, optionally substituted pyridazine ring, optionally substituted pyrazine ring, optionally substituted isoxazole ring, optionally substituted pyrazole ring, optionally substituted benzothiazole ring, optionally substituted morpholine ring, optionally substituted piperazine ring, optionally substituted imidazole ring, optionally substituted triazole ring, optionally substituted dihydropyridine ring, optionally substituted dihydropyridazine ring or optionally substituted dihydropyrazine ring, preferably C ring is optionally substituted benzene ring {wherein the substituents are halogen, hydroxy, optionally substituted lower alkyl (wherein the substituents are halogen), optionally substituted lower alkoxy (wherein the substituents are aryl or lower alkoxy), lower alkenyloxy, lower alkylthio, optionally substituted amino {wherein the substituents are lower alkyl, lower alkenyl, optionally substituted acyl (wherein the substituents are halogen) or lower alkylsulfonyl], nitro, lower alkylsulfonyl or lower alkylsulfonyloxy}, optionally substituted pyridine ring, optionally substituted pyrimidine ring, optionally substituted pyridazine ring, optionally substituted pyrazine ring, optionally substituted isoxazole ring, optionally substituted pyrazole ring (wherein the substituents are halogen, hydroxy, optionally substituted lower alkyl (wherein the substituents are hydroxy or acyloxy), optionally substituted lower alkoxy (wherein the substituents are halogen, aryl or 5- or 6-membered heterocycle), lower alkenyl, lower alkenyloxy, lower alkynyl, lower alkynyloxy, acyloxy, carboxy, lower alkoxycarbonyl, mercapt, lower alkylthio, lower alkenylthio, optionally mono- or di-substituted amino {wherein the substituents are halogen, optionally substituted lower alkyl (wherein the substituents are cycloalkyl or 5- or 6-membered heterocycle), optionally substituted acyl (wherein the substituents are halogen), lower alkenyl, cycloalkyl or lower alkylsulfonyl}, optionally substituted imino (wherein the substituents are lower alkylsulfonyl), nitro, lower alkylsulfonyl, aryl, 5- or 6-membered heterocycle, oxo or oxide}, benzothiazole ring, optionally substituted dihydropyridine (wherein the substituents are oxo), optionally substituted dihydropyridazine ring (wherein the substituents are oxo), optionally substituted dihydropyrazine ring (wherein the substituents are oxo), more preferably C ring is optionally substituted benzene ring {wherein the substituents are halogen, hydroxy, optionally substituted lower alkyl (wherein the substituents are halogen), optionally substituted lower alkoxy (wherein the substituents are aryl), lower alkenyloxy, lower alkylthio, optionally mono- or di-substituted amino {wherein the substituents are lower alkyl, lower alkenyl, optionally substituted acyl (wherein the substituents are halogen) or lower alkylsulfonyl], nitro, lower alkylsulfonyl or lower alkylsulfonyloxy}, optionally substituted pyridine ring {wherein the substituents are halogen, hydroxy, lower alkyl, lower alkenyl, lower alkynyl, optionally substituted lower alkoxy (wherein the substituents are halogen, aryl or 5- or 6-membered heterocycle), lower alkenyloxy, lower alkynyloxy, lower alkylthio, lower alkenylthio, optionally substituted amino (wherein the substituents are lower alkyl, heterocyclyl(lower)alkyl, cycloalkylalkyl, lower alkenyl or cycloalkyl), lower alkylsulfonyl, 5- or 6-membered heterocycle, nitro or oxo}, optionally substituted pyrimidine ring {wherein the substituents are halogen, hydroxy, optionally substituted lower alkoxy (wherein the substituents are aryl), lower alkenyloxy, or optionally substituted amino (wherein the substituents are lower alkyl or lower alkenyl)}, optionally substituted pyridazine ring {wherein the substituents are halogen, optionally substituted lower alkoxy (wherein the substituents are aryl), lower alkenyloxy, or optionally substituted amino (wherein the substituents are lower alkyl, lower alkoxy or lower alkenyl)}, optionally substituted pyrazine ring {wherein the substituents are halogen, optionally substituted lower alkoxy (wherein the substituents are aryl), lower alkenyloxy or optionally substituted amino (wherein the substituents are lower alkenyl)}, 4) a compound wherein X is —O— or —NR$^1$— (wherein R$^1$ is hydrogen, methyl or prenyl), preferably X is —O—, —NH— or —NMe—,
   more preferably X is —O— or —NH—,
5) a compound wherein Y is hydrogen, optionally substituted lower alkyl, optionally substituted lower alkenyl, lower alkylsulfonyl or optionally substituted acyl, preferably Y is optionally substituted lower alkyl, optionally substituted lower alkenyl, lower alkylsulfonyl or optionally substituted acyl,
   more preferably Y is optionally substituted lower alkyl {wherein the substituents are 5- or 6-membered heterocycle, or optionally substituted phenyl (wherein the substituents are lower alkyl or lower alkoxy)} or optionally substituted lower alkenyl (wherein the substituents are halogen),
   most preferably Y is methyl, optionally substituted prenyl (wherein the substituents are halogen) or optionally substituted benzyl (wherein the substituents are lower alkyl or lower alkoxy),
6) a compound wherein X is —O— or —NH— and Y is optionally substituted prenyl (wherein the substituents are halogen), or optionally substituted benzyl(wherein the substituents are lower alkyl or lower alkoxy), or X is —NR$^1$ and Y is methyl, preferably —X—Y is —OCH$_2$CH=CMe$_2$, —OBn, —OCH$_2$C$_6$H$_4$-2-Me, —OCH$_2$C$_6$H$_4$-3-Me, —OCH$_2$C$_6$H$_4$-4-Me, —OCH$_2$C$_6$H$_4$-4-OMe, —NMe$_2$ or —NHCH$_2$CH=CMe$_2$, more preferably —X—Y is —OCH$_2$CH=CMe$_2$, —OBn or —NMe$_2$,
7) a compound wherein one of V$^1$ and V$^2$ is a single bond and the other is a single bond, —O— or —NH—,
   preferably V$^1$ is a single bond and V$^2$ is a single bond, —O— or —NH—, more preferably both of V$^1$ and V$^2$ are single bonds,
8) a compound wherein A ring is optionally substituted benzene ring,
   B ring is optionally substituted benzene ring, optionally substituted pyridine ring, optionally substituted pyrimidine ring, optionally substituted pyridazine ring, optionally substituted pyrazine ring, optionally substituted thiophene ring, optionally substituted furan ring, optionally substituted pyrazole ring or optionally substituted oxazole ring,
   C ring is optionally substituted benzene ring, optionally substituted pyridine ring, optionally substituted pyrimidine ring, optionally substituted pyridazine ring, optionally substituted pyrazine ring, optionally substituted isoxazole ring, optionally substituted pyrazole ring, optionally substituted benzothiazole ring, optionally substituted morpholine ring, optionally substituted piperazine ring, optionally substituted imidazole ring or optionally substituted triazole ring,
   X is —O— or —NR$^1$— wherein R$^1$ is hydrogen, methyl or prenyl,
   Y is optionally substituted lower alkyl or optionally substituted lower alkenyl, and one of V$^1$ and V$^2$ is a single bond and the other is a single bond, —O— or —NH—, preferably A ring is optionally substituted benzene ring {wherein the substituents are halogen, hydroxy, lower alkoxy, acyloxy, lower alkylsulfonyl, optionally substituted lower alkylsulfonyloxy (wherein the substituents are halogen) or arylsulfonyloxy},
   B ring is optionally substituted benzene ring (wherein the substituents are halogen, hydroxy, lower alkyl, lower alkoxy, lower alkoxycarbonyl, lower alkenyloxy or lower alkylsulfonyloxy),
   optionally substituted pyridine ring (wherein the substituents are halogen or lower alkyl),
   optionally substituted pyrimidine ring {wherein the substituents are optionally substituted lower alkyl (wherein the substituents are hydroxy or acyloxy), lower alkoxy, lower alkylthio, optionally substituted amino (wherein the substituents are lower alkyl), carboxy or lower alkoxycarbonyl)},
   optionally substituted pyridazine ring (wherein the substituents are lower alkyl or oxide),
   optionally substituted thiophene ring (wherein the substituents are lower alkyl), optionally substituted pyrazole ring {wherein the substituents are optionally substituted lower alkyl (wherein the substituents are hydroxy), lower alkoxy, carboxy, or lower alkoxycarbonyl},
   or optionally substituted oxazole ring (wherein the substituents are lower alkyl),
   C ring is optionally substituted benzene ring {wherein the substituents are halogen, hydroxy, optionally substituted lower alkyl (wherein the substituents are halogen), optionally substituted lower alkoxy (wherein the substituents are aryl or lower alkoxy), lower alkenyloxy, lower alkylthio, optionally substituted amino {wherein the substituents are lower alkyl, lower alkenyl, optionally substituted acyl (wherein the substituents are halogen) or lower alkylsulfonyl}, nitro, lower alkylsulfonyl or lower alkylsulfonyloxy},
   optionally substituted pyridine ring {wherein the substituents are halogen, hydroxy, lower alkyl, lower alkenyl, lower alkynyl, optionally substituted lower alkoxy (wherein the substituents are halogen, aryl or 5- or 6-membered heterocycle), lower alkenyloxy, lower alkynyloxy, lower alkylthio, lower alkenylthio, optionally substituted amino (wherein the substituents are lower alkyl, heterocyclyl(lower)alkyl, cycloalkylalkyl, lower alkenyl or cycloalkyl), lower alkylsulfonyl, 5- or 6-membered heterocycle, nitro or oxo},
   optionally substituted pyrimidine ring {wherein the substituents are halogen, hydroxy, optionally substituted lower alkoxy (wherein the substituents are aryl), lower alkenyloxy or optionally substituted amino (wherein the substituents are lower alkyl or lower alkenyl)},
   optionally substituted pyridazine ring {wherein the substituents are halogen, optionally substituted lower alkoxy (wherein the substituents are aryl), lower alkenyloxy or optionally substituted amino (wherein the substituents are lower alkyl, lower alkoxy or lower alkenyl)},
   optionally substituted pyrazine ring {the substituents are halogen, optionally substituted lower alkoxy (wherein the substituents are aryl), lower alkenyloxy, optionally substituted amino (wherein the substituents are lower alkenyl)},
   optionally substituted isoxazole ring {wherein the substituents are optionally substituted lower alkoxy (wherein the substituents are aryl), lower alkenyloxy, or optionally substituted amino (wherein the substituents are lower alkenyl or lower alkylsulfonyl)},
   optionally substituted pyrazole ring {wherein the substituents are lower alkyl, optionally substituted lower alkoxy (wherein the substituents are aryl), lower alkenyloxy, or optionally substituted amino (wherein the substituents are lower alkenyl or lower alkylsulfonyl)}, or benzothiazole ring, X is —O—, —NH— or —NMe—, Y is optionally substituted lower alkyl {wherein the substituents are 5- or 6-membered heterocycle or optionally substituted phenyl (wherein the substituents are lower alkyl or lower alkoxy)} or lower alkenyl (wherein the substituents are halogen), and one of $V^1$ and $V^2$ is a single bond and the other is a single bond, —O— or —NH—, more preferably A ring is optionally substituted benzene ring (wherein the substituents are halogen, hydroxy, lower alkoxy or lower alkylsulfonyloxy), B ring is benzene ring (wherein the substituents are halogen, hydroxy, lower alkyl, lower alkoxy or lower alkoxycarbonyl), optionally substituted pyridine ring (wherein the substituents are halogen or lower alkyl), optionally substituted pyrimidine ring {wherein the substituents are optionally substituted lower alkyl (wherein the substituents are hydroxy or acyloxy), lower alkoxy, lower alkylthio, optionally substituted amino (wherein the substituents are lower alkyl), carboxy or lower alkoxycarbonyl}, optionally substituted pyrazole ring {wherein the substituents are optionally substituted lower alkyl (wherein the substituents are hydroxy), lower alkoxy, carboxy, or lower alkoxycarbonyl}, C ring is optionally substituted benzene ring {wherein the substituents are halogen, hydroxy, optionally substituted lower alkyl (wherein the substituents are halogen), optionally substituted lower alkoxy (wherein the substituents are aryl), lower alkenyloxy, lower alkylthio, optionally substituted amino {wherein the substituents are lower alkyl, lower alkenyl, optionally substituted acyl (wherein the substituents are halogen), or lower alkylsulfonyl}, nitro, lower alkylsulfonyl or lower alkylsulfonyloxy}, optionally substituted pyridine ring {wherein the substituents are halogen, hydroxy, lower alkyl, lower alkenyl, lower alkynyl, optionally substituted lower alkoxy (wherein the substituents are halogen, aryl or 5- or 6-membered heterocycle), lower alkenyloxy, lower alkynyloxy, lower alkylthio, lower alkenylthio, optionally substituted amino (wherein the substituents are lower alkyl, heterocyclyl(lower)alkyl, cycloalkylalkyl, lower alkenyl or cycloalkyl), lower alkylsulfonyl, 5- or 6-membered heterocycle, nitro or oxo}, optionally substituted pyrimidine ring {wherein the substituents are halogen, hydroxy, optionally substituted lower alkoxy (wherein the substituents are aryl), lower alkenyloxy or optionally substituted amino (wherein the substituents are lower alkyl or lower alkenyl)}, optionally substituted pyridazine ring {wherein the substituents are halogen, optionally substituted lower alkoxy (wherein the substituents are aryl), lower alkenyloxy or optionally substituted amino (wherein the substituents are lower alkyl, lower alkoxy or lower alkenyl)}, or optionally substituted pyrazine ring {wherein the substituents are halogen, optionally substituted lower alkoxy (wherein the substituents are aryl), lower alkenyloxy or optionally substituted amino (wherein the substituents are lower alkenyl)}, X is —O— and Y is prenyl or optionally substituted benzyl (wherein the substituents are lower alkyl or lower alkoxy) or X is —$NR^1$— and Y is methyl.

$V^1$ is a single bond and $V^2$ is a single bond, —O— or —NH—, more preferably A ring is optionally substituted benzene ring (wherein the substituents are halogen, hydroxy, lower alkoxy or lower alkylsulfonyloxy), B ring is optionally substituted benzene ring (wherein the substituents are halogen, hydroxy, lower alkyl, lower alkoxy or lower alkoxycarbonyl), optionally substituted pyridine ring (wherein the substituents are lower alkyl), optionally substituted pyrimidine ring (wherein the substituents are lower alkyl, lower alkoxy, carboxy or lower alkoxycarbonyl), optionally substituted pyrazole ring (wherein the substituents are lower alkyl, lower alkoxy, carboxy or lower alkoxycarbonyl), C ring is optionally substituted benzene ring {wherein the substituents are halogen, hydroxy, lower alkoxy, lower alkenyloxy, optionally substituted amino (wherein the substituents are lower alkyl) or lower alkylsulfonyloxy}, optionally substituted pyridine ring {wherein the substituents are optionally substituted amino {wherein the substituents are halogen, lower alkyl, optionally substituted lower alkoxy (wherein the substituents are aryl or 5- or 6-membered heterocycle), lower alkenyloxy or optionally substituted amino (wherein the substituents are lower alkyl, heterocyclyl(lower)alkyl or lower alkenyl)}, optionally substituted pyrimidine ring (wherein the substituents are halogen, hydroxy, lower alkoxy, lower alkenyloxy, amino or lower alkenylamino), optionally substituted pyridazine ring (wherein the substituents are halogen, lower alkoxy, lower alkenyloxy, amino, lower alkylamino or lower alkenylamino), or optionally substituted pyrazine ring (wherein the substituents are lower alkenyloxy, amino or lower alkenylamino), X is —O— and Y is prenyl or optionally substituted benzyl (wherein the substituents are lower alkyl or lower alkoxy) or X is $NR^1$ and Y is methyl or prenyl, $V^1$ is a single bond and $V^2$ is a single bond, —O— or —NH, 9) a compound wherein two of A ring, B ring and C ring are optionally substituted benzene ring and the other one is optionally substituted 5- or 6-membered heterocycle which may fuse with benzene ring, preferably A ring is optionally substituted benzene ring, one of B ring and C ring is optionally substituted benzene ring and the other is optionally substituted 5- or 6-membered heterocycle which may fuse with benzene ring, more preferably A ring is optionally substituted benzene ring, one of B ring and C ring is optionally substituted benzene ring and the other is optionally substituted 5- or 6-membered heterocycle which may fuse with benzene ring and both of $V^1$ and $V^2$ are single bonds, 10) a compound wherein all of A ring, B ring and C ring are optionally substituted benzene ring, $V^1$ is a single bond and $V^2$ is —O— or —NH—, 11) a compound wherein both of A ring and B ring are optionally substituted benzene ring and —X—Y is —$NMe_2$, prenyloxy or prenylamino, preferably both of A ring and B ring are optionally substituted benzene ring and C ring is optionally substituted pyridine ring, optionally substituted pyrimidine ring, optionally substituted pyridazine ring, optionally substituted isoxazole ring or optionally substituted pyrazole ring, —X—Y is —NMe₂, prenyloxy or prenylamino and both of V¹ and V² are single bonds, 12) a compound of any of following formulas

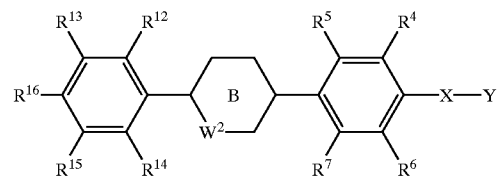
Ia

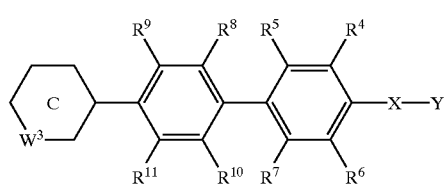
Ib

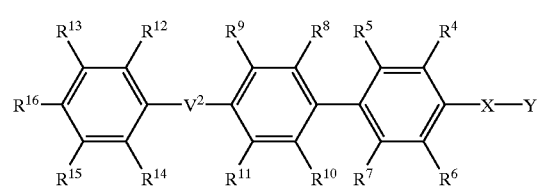
Ic

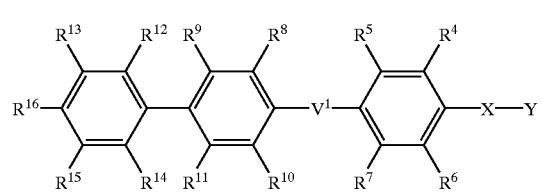
Id

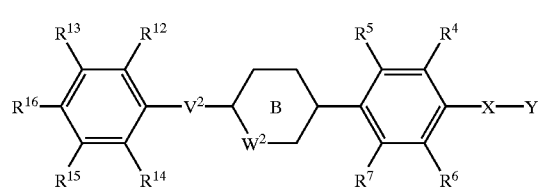
Ie

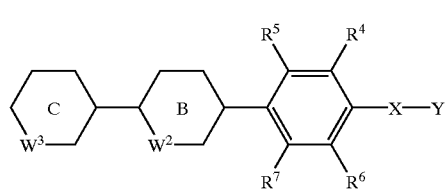
If wherein $R^4$, $R^5$, $R^6$ and $R^7$ are each independently hydrogen, halogen, hydroxy, lower alkoxy, acyloxy, optionally substituted lower alkylsulfonyloxy (wherein the substituents are halogen) or arylsulfonyloxy, $R^8$, $R^9$, $R^{10}$ and $R^{11}$ are each independently hydrogen, hydroxy, lower alkyl, lower alkoxy or lower alkylsulfonyloxy, $R^{12}$, $R^{13}$, $R^{14}$, $R^{15}$ and $R^{16}$ are each independently hydrogen, halogen, hydroxy, optionally substituted lower alkyl(wherein the substituents are halogen), optionally substituted lower alkoxy (wherein the substituents are aryl), lower alkenyloxy, lower alkylthio, lower alkylsulfonyl, lower alkylsulfonyloxy, nitro or optionally substituted amino {wherein the substituents are lower alkyl, lower alkenyl, optionally substituted acyl (wherein the substituents are halogen) or lower alkylsulfonyl}, B ring is optionally substituted pyridine ring (wherein the substituents are halogen or lower alkyl), optionally substituted pyrimidine ring {wherein the substituents are optionally substituted lower alkyl (wherein the substituents are hydroxy or acyloxy), lower alkoxy, lower alkylthio, optionally substituted amino (wherein the substituents are lower alkyl), carboxy or lower alkoxycarbonyl}, optionally substituted pyridazine (wherein the substituents are lower alkyl or oxide), optionally substituted thiophene ring (wherein the substituents are lower alkyl), optionally substituted pyrazole ring (wherein the substituents are optionally substituted lower alkyl (wherein the substituents are hydroxy), lower alkoxy, carboxy or lower alkoxycarbonyl}, or optionally substituted oxazole ring (wherein the substituents are lower alkyl), C ring is optionally substituted pyridine ring {wherein the substituents are hydroxy, halogen, lower alkyl, optionally substituted lower alkoxy (wherein the substituents are aryl), lower alkenyloxy, optionally substituted amino (wherein the substituents are lower alkyl, optionally substituted acyl (wherein the substituents are halogen), lower alkenyl, or lower alkylsulfonyl}, nitro, lower alkylthio, lower alkylsulfonyl or optionally substituted imino (wherein the substituents are lower alkylsulfonyl)}, optionally substituted pyrimidine ring {wherein the substituents are halogen, hydroxy, optionally substituted lower alkoxy (wherein the substituents are aryl), lower alkenyloxy or optionally substituted amino (wherein the substituents are lower alkyl or lower alkenyl)}, optionally substituted pyridazine ring {wherein the substituents are halogen, optionally substituted lower alkoxy (wherein the substituents are aryl), lower alkenyloxy or optionally substituted amino (wherein the substituents are lower alkyl, lower alkoxy, lower alkenyl or lower alkenyloxy)}, optionally substituted pyrazine ring {wherein the substituents are halogen, optionally substituted lower alkoxy (wherein the substituents are aryl), lower alkenyloxy or optionally substituted amino (wherein the substituents are lower alkyl or lower alkenyl)}, optionally substituted isoxazole ring {wherein the substituents are optionally substituted lower alkoxy (wherein the substituents are aryl), lower alkenyloxy or optionally substituted amino (wherein the substituents are lower alkenyl or lower alkylsulfonyl)}, optionally substituted pyrazole ring {wherein the substituents are lower alkyl, optionally substituted lower alkoxy (wherein the substituents are aryl), lower alkenyloxy or optionally substituted amino (wherein the substituents are lower alkenyl or lower alkylsulfonyl)}, benzothiazole ring, morpholine ring, piperazine ring (wherein the substituents are lower alkyl or phenyl), imidazole ring or triazole ring, V¹ is a single bond or —O—, V² is a single bond, —O—, —NH—, —OCH₂—, —CH₂O—, —CH=CH—, —C≡C—, —CH(OEt)—, —CH(OH)—, —CO—, —NHCH₂— or —NHCH(OH)—, X is —O— or —NR¹— (wherein R¹ is hydrogen, optionally substituted lower alkyl, lower alkenyl, lower alkylcarbonyl or optionally substituted lower alkoxycarbonyl), and Y is methyl, optionally substituted prenyl (wherein the substituents are halogen) or optionally substituted benzyl (wherein the substituents are lower alkyl or lower alkoxy)

13) a compound wherein both of A ring and B ring are optionally substituted benzene ring and C ring is

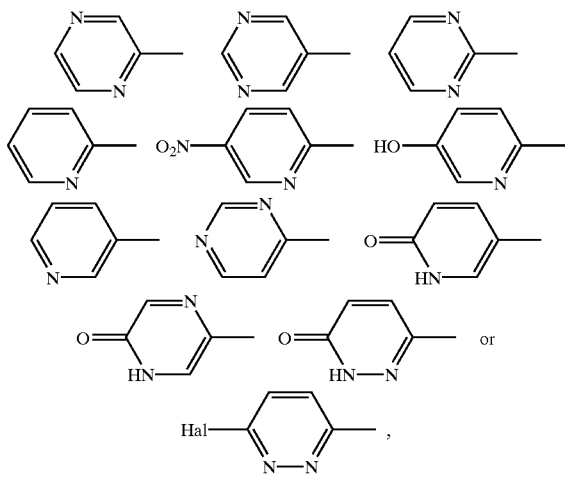

Y is CH₂CH=CMe₂ and both of V¹ and V² are single bonds, 14) a compound wherein both of A ring and B ring are benzene ring, C ring is

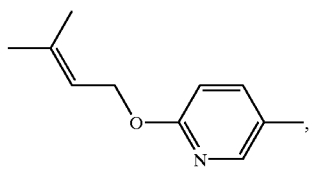

X is —O—, Y is hydrogen, and both of V¹ and V² are single bonds, 15) a compound wherein both of A ring and B ring is optionally substituted benzene ring, C ring is

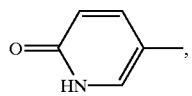

X is —NH— and both of V¹ and V² are single bonds.

Another preferable embodiment is,

[1] a compound of the following formula (Ib'):

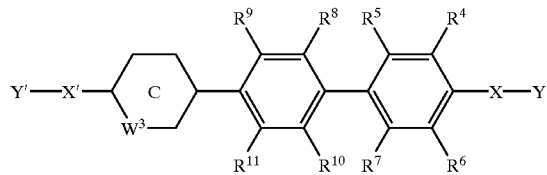

wherein C ring is optionally substituted 5- or 6-membered heterocycle which contains one or two hetero atoms and W³ represents a bond when C ring is 5-membered heterocycle, X and X' are each independently —O—, —CH₂—, —NR¹— wherein R¹ is hydrogen, optionally substituted lower alkyl, lower alkenyl, lower alkylcarbonyl or optionally substituted lower alkoxycarbonyl, or —S(O)p— wherein p is an integer of 0–2, Y and Y' are each independently optionally substituted lower alkyl, optionally substituted lower alkenyl, optionally substituted lower alkynyl, optionally substituted acyl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R¹, taken together with Y or Y', may form —(CH₂)m—, —(CH₂)₂—Q—(CH₂)₂— wherein Q is CH₂, O, S or NR', —CR'=CH—CH=CR'—, —CH=N—CH=CH—, —N=CH—N=CH—, —C(=O)—O(CH₂)n—, —C(=O)—NR'—(CH₂)n— or —C(=O)—NR'—N=CH— wherein m is 4 or 5, n is 2 or 3, R' is hydrogen, lower alkyl or lower alkenyl, Y may be optionally substituted lower alkoxy when X is —CH₂—, Y' may be optionally substituted lower alkoxy when X' is —CH₂—, Y may be optionally substituted lower alkoxycarbonyl, optionally substituted lower alkylsulfonyl or optionally substituted arylsulfonyl when X is —O— or NR¹, Y' may be optionally substituted lower alkoxycarbonyl, optionally substituted lower alkylsulfonyl or optionally substituted arylsulfonyl when X' is —O— or —NR¹—, Y may be hydrogen or halogen when X is —CH₂— or NR¹—, Y' may be hydrogen or halogen when X' is —CH₂— or —NR¹—.

R⁴, R⁵, R⁶, R⁷, R⁸, R⁹, R¹⁰ and R¹¹ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding compounds wherein all of R⁸, R⁹, R¹⁰ and R¹¹ are selected from hydrogen and halogen.

In the following compound of the formula (Ib'), preferable is:

a compound wherein $R^4$ and $R^5$ are each independently hydrogen, hydroxy, halogen, optionally substituted lower alkyl, optionally substituted lower alkoxy, optionally substituted acyloxy, optionally substituted lower alkylsulfonyloxy or optionally substituted arylsulfonyloxy (hereinafter referred to as "$R^4$ and $R^5$ are R45-1"), a compound wherein $R^4$ and $R^5$ are each independently hydrogen, hydroxy, halogen, lower alkyl, lower alkoxy, acyloxy, optionally substituted lower alkylsulfonyloxy or arylsulfonyloxy (hereinafter referred to as "$R^4$ and $R^5$ are R45-2"), a compound wherein $R^4$ and $R^5$ are each independently hydrogen, halogen or lower alkoxy (hereinafter referred to as "$R^4$ and $R^5$ are R45-3"), a compound wherein one of $R^4$ and $R^5$ is hydrogen and the other is halogen (hereinafter referred to as "$R^4$ and $R^5$ are R45-4"), a compound wherein one of $R^4$ and $R^5$ is hydrogen and the other is chloro or fluoro (hereinafter referred to as "$R^4$ and $R^5$ are R45-5"), a compound wherein $R^4$ is hydrogen and $R^5$ is halogen (hereinafter referred to as "$R^4$ and $R^5$ are R45-6"), a compound wherein $R^4$ is hydrogen and $R^5$ is chloro or fluoro (hereinafter referred to as "$R^4$ and $R^5$ are R45-7"), a compound wherein $R^6$ and $R^7$ are each independently hydrogen, halogen or lower alkyl (hereinafter referred to as "$R^6$ and $R^7$ are R67-1"), a compound wherein both of $R^6$ and $R^7$ are hydrogen (hereinafter referred to as "$R^6$ and $R^7$ are R67-2"), a compound wherein $R^8$ and $R^{11}$ are each independently hydrogen, halogen, hydroxy, optionally substituted lower alkyl, optionally substituted lower alkoxy, optionally substituted cycloalkoxy, optionally substituted lower alkylthio, optionally substituted lower alkoxycarbonyl or optionally substituted lower alkylsulfonyloxy (hereinafter referred to as "$R^8$ and $R^{11}$ are R811-1"), compound wherein $R^8$ and $R^{11}$ are each independently hydrogen, halogen, hydroxy, optionally substituted lower alkyl, optionally substituted lower alkoxy, optionally substituted cycloalkoxy, optionally substituted lower alkylthio, optionally substituted lower alkoxycarbonyl or optionally substituted lower alkylsulfonyloxy (hereinafter referred to as "$R^8$ and $R^{11}$ are R811-2"), a compound wherein $R^8$ and $R^{11}$ are each independently hydrogen, halogen hydroxy, optionally substituted lower alkyl, optionally substituted lower alkoxy or optionally substituted lower alkoxycarbonyl (hereinafter referred to as "$R^8$ and $R^{11}$ are R811-3"), a compound wherein $R^8$ and $R^{11}$ are each independently hydrogen, halogen, optionally substituted lower alkyl, optionally substituted lower alkoxy or lower alkoxycarbonyl (hereinafter referred to as "$R^8$ and $R^{11}$ are R811-4"), a compound wherein $R^8$ and $R^{11}$ are each independently hydrogen, optionally substituted lower alkyl, optionally substituted lower alkoxy or lower alkoxycarbonyl (hereinafter referred to as "$R^8$ and $R^{11}$ are R811-5"), a compound wherein $R^8$ and $R^{11}$ are each independently hydrogen, optionally substituted lower alkyl or optionally substituted lower alkoxy (hereinafter referred to as "$R^8$ and $R^{11}$ are R811-6"), a compound wherein $R^8$ and $R^{11}$ are each independently optionally substituted lower alkyl or optionally substituted lower alkoxy (hereinafter referred to as "$R^8$ and $R^{11}$ are R811-7"), a compound wherein $R^8$ and $R^{11}$ are each independently lower alkyl or lower alkoxy (hereinafter referred to as "$R^8$ and $R^{11}$ are R811-8"), a compound wherein both of $R^8$ and $R^{11}$ are optionally substituted lower alkyl or optionally substituted lower alkoxy (hereinafter referred to as "$R^8$ and $R^{11}$ are R811-9"), a compound wherein both of $R^8$ and $R^{11}$ are lower alkyl, or one of $R^8$ and $R^{11}$ is lower alkyl and the other is lower alkoxy (hereinafter referred to as "$R^8$ and $R^{11}$ are R811-10"), a compound wherein both of $R^8$ and $R^{11}$ are lower alkyl (hereinafter referred to as "$R^8$ and $R^{11}$ are R811-11"), a compound wherein $R^8$ and $R^{11}$ are each independently methyl or methoxy (hereinafter referred to as "$R^8$ and $R^{11}$ are R811-12"), a compound wherein $R^9$ and $R^{10}$ are each independently hydrogen, halogen, hydroxy, optionally substituted lower alkyl, optionally substituted lower alkoxy, optionally substituted cycloalkoxy, optionally substituted lower alkylthio, optionally substituted lower alkoxycarbonyl or optionally substituted lower alkylsulfonyloxy (hereinafter referred to as "$R^9$ and $R^{10}$ are R910-1"), a compound wherein $R^9$ and $R^{10}$ are each independently hydrogen, halogen, hydroxy, optionally substituted lower alkyl, optionally substituted lower alkoxy, cycloalkoxy, lower alkylthio, lower alkoxycarbonyl or optionally substituted lower alkylsulfonyloxy (hereinafter referred to as "$R^9$ and $R^{10}$ are R910-2"), a compound wherein $R^9$ and $R^{10}$ are each independently hydrogen, halogen, hydroxy, optionally substituted lower alkyl, optionally substituted lower alkoxy or optionally substituted lower alkylsulfonyloxy (hereinafter referred to as "$R^9$ and $R^{10}$ are R910-3"), a compound wherein $R^9$ and $R^{10}$ are each independently hydrogen, halogen, hydroxy, optionally substituted lower alkyl or optionally substituted lower alkoxy (hereinafter referred to as "$R^9$ and $R^{10}$ are R910-4"), a compound wherein $R^9$ and $R^{10}$ are each independently hydrogen, optionally substituted lower alkyl or optionally substituted lower alkoxy (hereinafter referred to as "$R^9$ and $R^{10}$ are R910-5"), a compound wherein $R^9$ and $R^{10}$ are each independently hydrogen or optionally substituted lower alkyl (hereinafter referred to as "$R^9$ and $R^{10}$ are R910-6"), a compound wherein both of $R^9$ and $R^{10}$ are hydrogen or optionally substituted lower alkyl (hereinafter referred to as "$R^9$ and $R^{10}$ are R910-7"), a compound wherein both of $R^9$ and $R^{10}$ are hydrogen or lower alkyl (hereinafter referred to as "$R^9$ and $R^{10}$ are R910-8"), a compound wherein both of $R^9$ and $R^{10}$ are hydrogen (hereinafter referred to as "$R^9$ and $R^{10}$ are R910-9"), a compound wherein both of $R^9$ and $R^{10}$ are lower alkyl (hereinafter referred to as "$R^9$ and $R^{10}$ are R910-10"), a compound wherein $R^9$ and $R^{10}$ are each independently hydrogen or lower alkyl (hereinafter referred to as "$R^9$ and $R^{10}$ are R910-11"), a compound wherein C ring is 5- or 6-membered heterocycle which contains at least one N atom (hereinafter referred to as "C ring is C-1"), a compound wherein C ring is a 6-membered heterocycle which contains at least one N atom (hereinafter referred to as "C ring is C-2"), a compound wherein C ring is optionally substituted pyridine, optionally substituted pyrimidine, optionally substituted pyridazine or optionally substituted pyrazine (hereinafter referred to as "C ring is C-3"), a compound wherein C ring is optionally substituted pyridine or optionally substituted pyrimidine (hereinafter referred to as "C ring is C-4"), a compound wherein C ring is

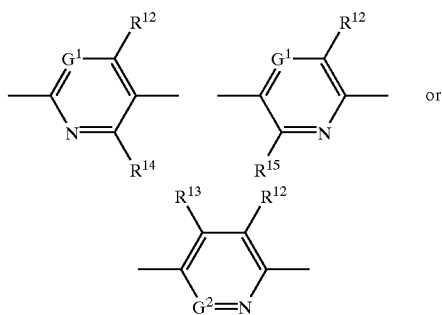

wherein $G^1$ is $CR^{13}$ or N, $G^2$ is $CR^{15}$ or N and $R^{12}$, $R^{13}$, $R^{14}$ and $R^{15}$ are each independently hydrogen, halogen, hydroxy, optionally substituted lower alkyl, optionally substituted lower alkoxy optionally substituted lower alkenyl, optionally substituted lower alkenyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, guanidino, nitro, optionally substituted lower alkylsulfonyl, optionally substituted lower alkylsulfonyloxy, optionally substituted arylsulfonyl or optionally substituted arylsulfonyloxy (hereinafter referred to as "C ring is C-5"), a compound wherein C ring is

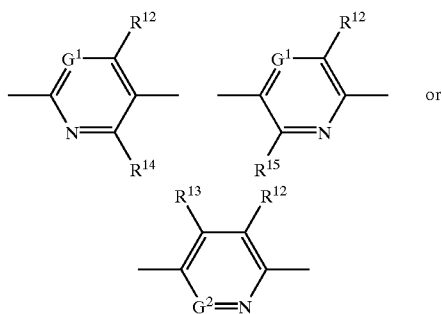

wherein $G^1$ is $CR^{13}$ or N, $G^2$ is $CR^{15}$ or N and $R^{12}$, $R^{13}$, $R^{14}$ and $R^{15}$ are each independently hydrogen, halogen, hydroxy, lower alkyl, optionally substituted lower alkenyl, optionally substituted lower alkoxy, optionally substituted amino or nitro (hereinafter referred to as "C ring is C-6"), a compound wherein C ring is C-5 and $G^1$ and $G^2$ are each independently CH or N (hereinafter referred to as "C ring is C-7"), a compound wherein C ring is C-6 and $G^1$ and $G^2$ are each independently CH or N (hereinafter referred to as "C ring is C-8"), a compound wherein C ring is

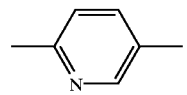

(hereinafter referred to as "C ring is C-9")

a compound wherein X and X' are —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O)p— wherein p is an integer of 0–2, Y and Y' are each independently optionally substituted lower alkyl, optionally substituted lower alkenyl, optionally substituted lower alkynyl, optionally substituted cycloalkyl, optionally substituted cycloalkenyl, optionally substituted amino, optionally substituted sulfamoyl, optionally substituted aryl or optionally substituted 5- or 6-membered heterocycle, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or NR$^1$ and Y' may be hydrogen or halogen when X' is —CH$_2$— or —NR$^1$— provided that Y and Y' are not simultaneously hydrogen (hereinafter referred to as "X, X', Y and Y' are XY-1"), a compound wherein X and X' are each independently —O—, —CH$_2$—, —NR$^1$— wherein R$^1$ is hydrogen, optionally substituted lower alkyl, lower alkenyl, lower alkylcarbonyl or optionally substituted lower alkoxycarbonyl or —S(O)p— wherein p is an integer of 0–2, Y and Y' are each independently optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle hereinafter referred to as "X, X', Y and Y' are XY-2"), a compound wherein one of X and X' is —O— and the other is —NR$^1$— wherein R$^1$ is hydrogen, optionally substituted lower alkyl, lower alkenyl, lower alkylcarbonyl or optionally substituted lower alkoxycarbonyl (hereinafter referred to as "X, X', Y and Y' are XY-3"), a compound wherein one of X and X' is —O— and the other is —NH— (hereinafter referred to as "X, X', Y and Y' are XY-4"), a compound wherein at least one of Y and Y' is prenyl (hereinafter referred to as "X, X', Y and Y' are XY-5"), a compound wherein X and X' are each independently —O— or —NR$^1$— wherein R$^1$ is hydrogen, lower alkyl, lower alkenyl or optionally substituted lower alkoxycarbonyl, Y and Y' are each independently optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle (hereinafter referred to as "X, X', Y and Y' are XY-6"), a compound wherein one of X and X' is —O— and the other is —NR$^1$— wherein R$^1$ is hydrogen, lower alkyl, lower alkenyl or optionally substituted lower alkoxycarbonyl, Y and Y' are each independently optionally substituted lower alkyl, optionally substituted lower alkenyl or optionally substituted lower alkynyl (hereinafter referred to as "X, X', Y and Y' are XY-7"), a compound wherein one of X and X' is —O— and the other is —NH, Y and Y' are each independently optionally substituted lower alkyl, optionally substituted lower alkenyl, optionally substituted alkynyl, optionally substituted cycloalkyl, optionally substituted sulfamoyl, optionally substituted aryl or optionally substituted 5- or 6-membered heterocycle (hereinafter referred to as "X, X', Y and Y' are XY-8"), a compound wherein one of X and X' is —O— and the other is —NR$^1$— wherein R$^1$ is hydrogen, lower alkyl or lower alkenyl, Y and Y' are each independently optionally substituted lower alkyl, or optionally substituted lower alkenyl (hereinafter referred to as "X, X', Y and Y' are XY-9"), a compound wherein one of X and X' is —O— and the other is —NH—, Y and Y' are each independently optionally substituted lower alkyl or optionally substituted lower alkenyl (hereinafter referred to as "X, X', Y and Y' are XY-10"), a compound wherein one of X and X' is —O— and the other is —NR$^1$— wherein R$^1$ is hydrogen, lower alkyl, lower alkenyl or optionally substituted lower alkoxycarbonyl, one of Y and Y' is lower alkyl or lower alkenyl and the other is optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle (hereinafter referred to as "X, X', Y and Y' are XY-11"), a compound wherein one of X and X' is —O— and the other is —NH—, one of Y and Y' is lower alkyl or lower alkenyl and the other is optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle (hereinafter referred to as "X, X', Y and Y' are XY-12"), a compound wherein one of X and X' is —O— and the other is —NR$^1$— wherein R$^1$ is hydrogen, lower alkyl, lower alkenyl or optionally substituted lower alkoxycarbonyl, one of Y and Y' is lower alkyl or lower alkenyl and the other is hydrogen or optionally substituted lower alkyl, optionally substituted lower alkenyl or optionally substituted lower alkynyl (hereinafter referred to as "X, X', Y and Y' are XY-13"), a compound wherein one of X and X' is —O— and the other is —NH—, one of Y and Y' is lower alkyl or lower alkenyl and the other is hydrogen, optionally substituted lower alkyl, optionally substituted lower alkenyl or optionally substituted lower alkynyl (hereinafter referred to as "X, X', Y and Y' are XY-14"), a compound wherein one of X and X' is —O— and the other is —NR$^1$— wherein R$^1$ is hydrogen, lower alkyl, lower alkenyl or optionally substituted lower alkoxycarbonyl, one of Y and Y' is prenyl and the other is optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle (hereinafter referred to as "X, X', Y and Y' are XY-15"), a compound wherein one of X and X' is —O— and the other is —NH—, one of Y and Y' is prenyl and the other is optionally substituted lower alkyl, optionally substituted lower alkenyl, optionally substituted lower alkynyl, optionally substituted cycloalkyl, optionally substituted sulfamoyl, optionally substituted aryl or optionally substituted 5- or 6-membered heterocycle (hereinafter referred to as "X, X', Y and Y' are XY-16"), a compound wherein one of X and X' is —O— and the other is —NR$^1$— wherein R$^1$ is hydrogen, lower alkyl, lower alkenyl or optionally substituted lower alkoxycarbonyl, one of Y and Y' is prenyl and the other is hydrogen, optionally substituted lower alkyl, optionally substituted lower alkenyl or optionally substituted lower alkynyl (hereinafter referred to as "X, X', Y and Y' are XY-17"), a compound wherein one of X and X' is —O— and the other is —NH—, one of Y and Y' is prenyl and the other is hydrogen, optionally substituted lower alkyl, optionally substituted lower alkenyl or optionally substituted lower alkynyl (hereinafter referred to as "X, X', Y and Y' are XY-18"), a compound wherein one of —X—Y and —X'—Y' is optionally substituted lower alkylamino or optionally substituted lower alkenylamino and the other is optionally substituted lower alkoxy or optionally substituted lower alkenyloxy (hereinafter referred to as "X, X', Y and Y' are XY-19"), a compound wherein one of —X—Y and —X'—Y' is optionally substituted lower alkylamino or optionally substituted lower alkenylamino and the other is prenyloxy (hereinafter referred to as "X, X', Y and Y' are XY-20"), a compound wherein R$^4$ and R$^5$ are R45-1 and R$^6$ and R$^7$ are R67-1, a compound wherein R$^4$ and R$^5$ are R45-1 and R$^6$ and R$^7$ are R67-2, a compound wherein R$^4$ and R$^5$ are R45-2 and R$^6$ and R$^7$ are R67-1, a compound wherein R$^4$ and R$^5$ are R45-2 and R$^6$ and R$^7$ are R67-2, a compound wherein R$^4$ and R$^5$ are R45-3 and R$^6$ and R$^7$ are R67-1, a compound wherein R$^4$ and R$^5$ are R45-3 and R$^6$ and R$^7$ are R67-2, a compound wherein R$^4$ and R$^5$ are R45-4 and R$^6$ and R$^7$ are R67-1, a compound wherein R$^4$ and R$^5$ are R45-4 and R$^6$ and R$^7$ are R67-2, a compound wherein R$^4$ and R$^5$ are R45-5 and R$^6$ and R$^7$ are R67-1, a compound wherein R$^4$ and R$^5$ are R45-5 and R$^6$ and R$^7$ are R67-2, a compound wherein R$^4$ and R$^5$ are R45-6 and R$^6$ and R$^7$ are R67-1, a compound wherein R$^4$ and R$^5$ are R45-6 and R$^6$ and R$^7$ are R67-2, a compound wherein $R^4$ and $R^5$ are R45-7 and $R^6$ and $R^7$ are R67-1, a compound wherein $R^4$ and $R^5$ are R45-7 and $R^6$ and $R^7$ are R67-2, a compound wherein $R^8$ and $R^{11}$ are R811-2 and $R^9$ and $R^{10}$ are R910-3, a compound wherein $R^8$ and $R^{11}$ are R811-2 and $R^9$ and $R^{10}$ are R910-4, a compound wherein $R^8$ and $R^{11}$ are R811-2 and $R^9$ and $R^{10}$ are R910-5, a compound wherein $R^8$ and $R^{11}$ are R811-2 and $R^9$ and $R^{10}$ are R910-6, a compound wherein $R^8$ and $R^{11}$ are R811-2 and $R^9$ and $R^{10}$ are R910-7, a compound wherein $R^8$ and $R^{11}$ are R811-2 and $R^9$ and $R^{10}$ are R910-8, a compound wherein $R^8$ and $R^{11}$ are R811-2 and $R^9$ and $R^{10}$ are R910-9, a compound wherein $R^8$ and $R^{11}$ are R811-2 and $R^9$ and $R^{10}$ are R910-10, a compound wherein $R^8$ and $R^{11}$ are R811-2 and $R^9$ and $R^{10}$ are R910-11, a compound wherein $R^8$ and $R^{11}$ are R811-3 and $R^9$ and $R^{10}$ are R910-3, a compound wherein $R^8$ and $R^{11}$ are R811-3 and $R^9$ and $R^{10}$ are R910-4, a compound wherein $R^8$ and $R^{11}$ are R811-3 and $R^9$ and $R^{10}$ are R910-5, a compound wherein $R^8$ and $R^{11}$ are R811-3 and $R^9$ and $R^{10}$ are R910-6, a compound wherein $R^8$ and $R^{11}$ are R811-3 and $R^9$ and $R^{10}$ are R910-7, a compound wherein $R^8$ and $R^{11}$ are R811-3 and $R^9$ and $R^{10}$ are R910-8, a compound wherein $R^8$ and $R^{11}$ are R811-3 and $R^9$ and $R^{10}$ are R910-9, a compound wherein $R^8$ and $R^{11}$ are R811-3 and $R^9$ and $R^{10}$ are R910-10, a compound wherein $R^8$ and $R^{11}$ are R811-3 and $R^9$ and $R^{10}$ are R910-11, a compound wherein $R^8$ and $R^{11}$ are R811-4 and $R^9$ and $R^{10}$ are R910-3, a compound wherein $R^8$ and $R^{11}$ are R811-4 and $R^9$ and $R^{10}$ are R910-4, a compound wherein $R^8$ and $R^{11}$ are R811-4 and $R^9$ and $R^{10}$ are R910-5, a compound wherein $R^8$ and $R^{11}$ are R811-4 and $R^9$ and $R^{10}$ are R910-6, a compound wherein $R^8$ and $R^{11}$ are R811-4 and $R^9$ and $R^{10}$ are R910-7, a compound wherein $R^8$ and $R^{11}$ are R811-4 and $R^9$ and $R^{10}$ are R910-8, a compound wherein $R^8$ and $R^{11}$ are R811-4 and $R^9$ and $R^{10}$ are R910-9, a compound wherein $R^8$ and $R^{11}$ are R811-4 and $R^9$ and $R^{10}$ are R910-10, a compound wherein $R^8$ and $R^{11}$ are R811-4 and $R^9$ and $R^{10}$ are R910-11, a compound wherein $R^8$ and $R^{11}$ are R811-5 and $R^9$ and $R^{10}$ are R910-1, a compound wherein $R^8$ and $R^{11}$ are R811-5 and $R^9$ and $R^{10}$ are R910-2, a compound wherein $R^8$ and $R^{11}$ are R811-5 and $R^9$ and $R^{10}$ are R910-3, a compound wherein $R^8$ and $R^{11}$ are R811-5 and $R^9$ and $R^{10}$ are R910-4, a compound wherein $R^8$ and $R^{11}$ are R811-5 and $R^9$ and $R^{10}$ are R910-5, a compound wherein $R^8$ and $R^{11}$ are R811-5 and $R^9$ and $R^{10}$ are R910-6, a compound wherein $R^8$ and $R^{11}$ are R811-5 and $R^9$ and $R^{10}$ are R910-7, a compound wherein $R^8$ and $R^{11}$ are R811-5 and $R^9$ and $R^{10}$ are R910-8, a compound wherein $R^8$ and $R^{11}$ are R811-5 and $R^9$ and $R^{10}$ are R910-9, a compound wherein $R^8$ and $R^{11}$ are R811-5 and $R^9$ and $R^{10}$ are R910-10, a compound wherein $R^8$ and $R^{11}$ are R811-5 and $R^9$ and $R^{10}$ are R910-11, a compound wherein $R^8$ and $R^{11}$ are R811-6 and $R^9$ and $R^{10}$ are R910-1, a compound wherein $R^8$ and $R^{11}$ are R811-6 and $R^9$ and R10 are R910-2, a compound wherein $R^8$ and $R^{11}$ are R811-6 and $R^9$ and $R^{10}$ are R910-3, a compound wherein $R^8$ and $R^{11}$ are R811-6 and $R^9$ and $R^{10}$ are R910-4, a compound wherein $R^8$ and $R^{11}$ are R811-6 and $R^9$ and $R^{10}$ are R910-5, a compound wherein $R^8$ and $R^{11}$ are R811-6 and $R^9$ and $R^{10}$ are R910-6, a compound wherein $R^8$ and $R^{11}$ are R811-6 and $R^9$ and $R^{10}$ are R910-7, a compound wherein $R^8$ and $R^{11}$ are R811-6 and $R^9$ and $R^{10}$ are R910-8, a compound wherein $R^8$ and $R^{11}$ are R811-6 and $R^9$ and $R^{10}$ are R910-9, a compound wherein $R^8$ and $R^{11}$ are R811-6 and $R^9$ and $R^{10}$ are R910-10, a compound wherein $R^8$ and $R^{11}$ are R811-6 and $R^9$ and $R^{10}$ are R910-11, a compound wherein $R^8$ and $R^{11}$ are R811-7 and $R^9$ and $R^{10}$ are R910-1, a compound wherein $R^8$ and $R^{11}$ are R811-7 and $R^9$ and $R^{10}$ are R910-2, a compound wherein $R^8$ and $R^{11}$ are R811-7 and $R^9$ and $R^{10}$ are R910-3, a compound wherein $R^8$ and $R^{11}$ are R811-7 and $R^9$ and $R^{10}$ are R910-4, a compound wherein $R^8$ and $R^{11}$ are R811-7 and $R^9$ and $R^{10}$ are R910-5, a compound wherein $R^8$ and $R^{11}$ are R811-7 and $R^9$ and $R^{10}$ are R910-6, a compound wherein $R^8$ and $R^{11}$ are R811-7 and $R^9$ and $R^{10}$ are R910-7, a compound wherein $R^8$ and $R^{11}$ are R811-7 and $R^9$ and $R^{10}$ are R910-8, a compound wherein $R^8$ and $R^{11}$ are R811-7 and $R^9$ and $R^{10}$ are R910-9, a compound wherein $R^8$ and $R^{11}$ are R811-7 and $R^9$ and $R^{10}$ are R910-10, a compound wherein $R^8$ and $R^{11}$ are R811-7 and $R^9$ and $R^{10}$ are R910-11, a compound wherein $R^8$ and $R^{11}$ are R811-8 and $R^9$ and $R^{10}$ are R910-1,
a compound wherein $R^8$ and $R^{11}$ are R811-8 and $R^9$ and $R^{10}$ are R910-2,
a compound wherein $R^8$ and $R^{11}$ are R811-8 and $R^9$ and $R^{10}$ are R910-3,
a compound wherein $R^8$ and $R^{11}$ are R811-8 and $R^9$ and $R^{10}$ are R910-4,
a compound wherein $R^8$ and $R^{11}$ are R811-8 and $R^9$ and $R^{10}$ are R910-5,
a compound wherein $R^8$ and $R^{11}$ are R811-8 and $R^9$ and $R^{10}$ are R910-6,
a compound wherein $R^8$ and $R^{11}$ are R811-8 and $R^9$ and $R^{10}$ are R910-7,
a compound wherein $R^8$ and $R^{11}$ are R811-8 and $R^9$ and $R^{10}$ are R910-8,
a compound wherein $R^8$ and $R^{11}$ are R811-8 and $R^9$ and $R^{10}$ are R910-9,
a compound wherein $R^8$ and $R^{11}$ are R811-8 and $R^9$ and $R^{10}$ are R910-10,
a compound wherein $R^8$ and $R^{11}$ are R811-8 and $R^9$ and $R^{10}$ are R910-11,
a compound wherein $R^8$ and $R^{11}$ are R811-9 and $R^9$ and $R^{10}$ are R910-1,
a compound wherein $R^8$ and $R^{11}$ are R811-9 and $R^9$ and $R^{10}$ are R910-2,
a compound wherein $R^8$ and $R^{11}$ are R811-9 and $R^9$ and $R^{10}$ are R910-3,
a compound wherein $R^8$ and $R^{11}$ are R811-9 and $R^9$ and $R^{10}$ are R910-4,
a compound wherein $R^8$ and $R^{11}$ are R811-9 and $R^9$ and $R^{10}$ are R910-5,
a compound wherein $R^8$ and $R^{11}$ are R811-9 and $R^9$ and $R^{10}$ are R910-6,
a compound wherein $R^8$ and $R^{11}$ are R811-9 and $R^9$ and $R^{10}$ are R910-7,
a compound wherein $R^8$ and $R^{11}$ are R811-9 and $R^9$ and $R^{10}$ are R910-8,
a compound wherein $R^8$ and $R^{11}$ are R811-9 and $R^9$ and $R^{10}$ are R910-9,
a compound wherein $R^8$ and $R^{11}$ are R811-9 and $R^9$ and $R^{10}$ are R910-10,
a compound wherein $R^8$ and $R^{11}$ are R811-9 and $R^9$ and $R^{10}$ are R910-11,
a compound wherein $R^8$ and $R^{11}$ are R811-10 and $R^9$ and $R^{10}$ are R910-1,
a compound wherein $R^8$ and $R^{11}$ are R811-10 and $R^9$ and $R^{10}$ are R910-2,
a compound wherein $R^8$ and $R^{11}$ are R811-10 and $R^9$ and $R^{10}$ are R910-3,
a compound wherein $R^8$ and $R^{11}$ are R811-10 and $R^9$ and $R^{10}$ are R910-4,
a compound wherein $R^8$ and $R^{11}$ are R811-10 and $R^9$ and $R^{10}$ are R910-5,
a compound wherein $R^8$ and $R^{11}$ are R811-10 and $R^9$ and $R^{10}$ are R910-6,
a compound wherein $R^8$ and $R^{11}$ are R811-10 and $R^9$ and $R^{10}$ are R910-7,
a compound wherein $R^8$ and $R^{11}$ are R811-10 and $R^9$ and $R^{10}$ are R910-8,
a compound wherein $R^8$ and $R^{11}$ are R811-10 and $R^9$ and $R^{10}$ are R910-9,
a compound wherein $R^8$ and $R^{11}$ are R811-10 and $R^9$ and $R^{10}$ are R910-10,
a compound wherein $R^8$ and $R^{11}$ are R811-10 and $R^9$ and $R^{10}$ are R910-11,
a compound wherein $R^8$ and $R^{11}$ are R811-11 and $R^9$ and $R^{10}$ are R910-1,
a compound wherein $R^8$ and $R^{11}$ are R811-11 and $R^9$ and $R^{10}$ are R910-2,
a compound wherein $R^8$ and $R^{11}$ are R811-11 and $R^9$ and $R^{10}$ are R910-3,
a compound wherein $R^8$ and $R^{11}$ are R811-11 and $R^9$ and $R^{10}$ are R910-4,
a compound wherein $R^8$ and $R^{11}$ are R811-11 and $R^9$ and $R^{10}$ are R910-5,
a compound wherein $R^8$ and $R^{11}$ are R811-11 and $R^9$ and $R^{10}$ are R910-6,
a compound wherein $R^8$ and $R^{11}$ are R811-11 and $R^9$ and $R^{10}$ are R910-7,
a compound wherein $R^8$ and $R^{11}$ are R811-11 and $R^9$ and $R^{10}$ are R910-8,
a compound wherein $R^8$ and $R^{11}$ are R811-11 and $R^9$ and $R^{10}$ are R910-9,
a compound wherein $R^8$ and $R^{11}$ are R811-11 and $R^9$ and $R^{10}$ are R910-10,
a compound wherein $R^8$ and $R^{11}$ are R811-11 and $R^9$ and $R^{10}$ are R910-11,
a compound wherein $R^8$ and $R^{11}$ are R811-12 and $R^9$ and $R^{10}$ are R910-1,
a compound wherein $R^8$ and $R^{11}$ are R811-12 and $R^9$ and $R^{10}$ are R910-2,
a compound wherein $R^8$ and $R^{11}$ are R811-12 and $R^9$ and $R^{10}$ are R910-3,
a compound wherein $R^8$ and $R^{11}$ are R811-12 and $R^9$ and $R^{10}$ are R910-4,
a compound wherein $R^8$ and $R^{11}$ are R811-12 and $R^9$ and $R^{10}$ are R910-5,
a compound wherein $R^8$ and $R^{11}$ are R811-12 and $R^9$ and $R^{10}$ are R910-6,
a compound wherein $R^8$ and $R^{11}$ are R811-12 and $R^9$ and $R^{10}$ are R910-7,
a compound wherein $R^8$ and $R^{11}$ are R811-12 and $R^9$ and $R^{10}$ are R910-8,
a compound wherein $R^8$ and $R^{11}$ are R811-12 and $R^9$ and $R^{10}$ are R910-9,
a compound wherein $R^8$ and $R^{11}$ are R811-12 and $R^9$ and $R^{10}$ are R910-10,
a compound wherein $R^8$ and $R^{11}$ are R811-12 and $R^9$ and $R^{10}$ are R910-11,
a compound wherein $R^4$ and $R^5$ are R45-1 and $R^8$ and $R^{11}$ are R811-3,
a compound wherein $R^4$ and $R^5$ are R45-1 and $R^8$ and $R^{11}$ are R811-4,
a compound wherein $R^4$ and $R^5$ are R45-1 and $R^8$ and $R^{11}$ are R811-5,
a compound wherein $R^4$ and $R^5$ are R45-1 and $R^8$ and $R^{11}$ are R811-6,
a compound wherein $R^4$ and $R^5$ are R45-1 and $R^8$ and $R^{11}$ are R811-7,
a compound wherein $R^4$ and $R^5$ are R45-1 and $R^8$ and $R^{11}$ are R811-8,
a compound wherein $R^4$ and $R^5$ are R45-1 and $R^8$ and $R^{11}$ are R811-9, a compound wherein $R^4$ and $R^5$ are R45-1 and $R^8$ and $R^{11}$ are R811-10,
a compound wherein $R^4$ and $R^5$ are R45-1 and $R^8$ and $R^{11}$ are R811-11,
a compound wherein $R^4$ and $R^5$ are R45-1 and $R^8$ and $R^{11}$ are R811-12,
a compound wherein $R^4$ and $R^5$ are R45-2 and $R^8$ and $R^{11}$ are R811-3,
a compound wherein $R^4$ and $R^5$ are R45-2 and $R^8$ and $R^{11}$ are R811-4,
a compound wherein $R^4$ and $R^5$ are R45-2 and $R^8$ and $R^{11}$ are R811-5,
a compound wherein $R^4$ and $R^5$ are R45-2 and $R^8$ and $R^{11}$ are R811-6,
a compound wherein $R^4$ and $R^5$ are R45-2 and $R^8$ and $R^{11}$ are R811-7,
a compound wherein $R^4$ and $R^5$ are R45-2 and $R^8$ and $R^{11}$ are R811-8,
a compound wherein $R^4$ and $R^5$ are R45-2 and $R^8$ and $R^{11}$ are R811-9,
a compound wherein $R^4$ and $R^5$ are R45-2 and $R^8$ and $R^{11}$ are R811-10,
a compound wherein $R^4$ and $R^5$ are R45-2 and $R^8$ and $R^{11}$ are R811-11,
a compound wherein $R^4$ and $R^5$ are R45-2 and $R^8$ and $R^{11}$ are R811-12,
a compound wherein $R^4$ and $R^5$ are R45-3 and $R^8$ and $R^{11}$ are R811-1,
a compound wherein $R^4$ and $R^5$ are R45-3 and $R^8$ and $R^{11}$ are R811-2,
a compound wherein $R^4$ and $R^5$ are R45-3 and $R^8$ and $R^{11}$ are R811-3,
a compound wherein $R^4$ and $R^5$ are R45-3 and $R^8$ and $R^{11}$ are R811-4,
a compound wherein $R^4$ and $R^5$ are R45-3 and $R^8$ and $R^{11}$ are R811-5,
a compound wherein $R^4$ and $R^5$ are R45-3 and $R^8$ and $R^{11}$ are R811-6,
a compound wherein $R^4$ and $R^5$ are R45-3 and $R^8$ and $R^{11}$ are R811-7,
a compound wherein $R^4$ and $R^5$ are R45-3 and $R^8$ and $R^{11}$ are R811-8,
a compound wherein $R^4$ and $R^5$ are R45-3 and $R^8$ and $R^{11}$ are R811-9,
a compound wherein $R^4$ and $R^5$ are R45-3 and $R^8$ and $R^{11}$ are R811-10,
a compound wherein $R^4$ and $R^5$ are R45-3 and $R^8$ and $R^{11}$ are R811-11,
a compound wherein $R^4$ and $R^5$ are R45-3 and $R^8$ and $R^{11}$ are R811-12,
a compound wherein $R^4$ and $R^5$ are R45-4 and $R^8$ and $R^{11}$ are R811-1,
a compound wherein $R^4$ and $R^5$ are R45-4 and $R^8$ and $R^{11}$ are R811-2,
a compound wherein $R^4$ and $R^5$ are R45-4 and $R^8$ and $R^{11}$ are R811-3,
a compound wherein $R^4$ and $R^5$ are R45-4 and $R^8$ and $R^{11}$ are R811-4,
a compound wherein $R^4$ and $R^5$ are R45-4 and $R^8$ and $R^{11}$ are R811-5,
a compound wherein $R^4$ and $R^5$ are R45-4 and $R^8$ and $R^{11}$ are R811-6,
a compound wherein $R^4$ and $R^5$ are R45-4 and $R^8$ and $R^{11}$ are R811-7,
a compound wherein $R^4$ and $R^5$ are R45-4 and $R^8$ and $R^{11}$ are R811-8,
a compound wherein $R^4$ and $R^5$ are R45-4 and $R^8$ and $R^{11}$ are R811-9,
a compound wherein $R^4$ and $R^5$ are R45-4 and $R^8$ and $R^{11}$ are R811-10,
a compound wherein $R^4$ and $R^5$ are R45-4 and $R^8$ and $R^{11}$ are R811-11,
a compound wherein $R^4$ and $R^5$ are R45-4 and $R^8$ and $R^{11}$ are R811-12,
a compound wherein $R^4$ and $R^5$ are R45-5 and $R^8$ and $R^{11}$ are R811-1,
a compound wherein $R^4$ and $R^5$ are R45-5 and $R^8$ and $R^{11}$ are R811-2,
a compound wherein $R^4$ and $R^5$ are R45-5 and $R^8$ and $R^{11}$ are R811-3,
a compound wherein $R^4$ and $R^5$ are R45-5 and $R^8$ and $R^{11}$ are R811-4,
a compound wherein $R^4$ and $R^5$ are R45-5 and $R^8$ and $R^{11}$ are R811-5,
a compound wherein $R^4$ and $R^5$ are R45-5 and $R^8$ and $R^{11}$ are R811-6,
a compound wherein $R^4$ and $R^5$ are R45-5 and $R^8$ and $R^{11}$ are R811-7,
a compound wherein $R^4$ and $R^5$ are R45-5 and $R^8$ and $R^{11}$ are R811-8,
a compound wherein $R^4$ and $R^5$ are R45-5 and $R^8$ and $R^{11}$ are R811-9,
a compound wherein $R^4$ and $R^5$ are R45-5 and $R^8$ and $R^{11}$ are R811-10,
a compound wherein $R^4$ and $R^5$ are R45-5 and $R^8$ and $R^{11}$ are R811-11,
a compound wherein $R^4$ and $R^5$ are R45-5 and $R^8$ and $R^{11}$ are R811-12,
a compound wherein $R^4$ and $R^5$ are R45-6 and $R^8$ and $R^{11}$ are R811-1,
a compound wherein $R^4$ and $R^5$ are R45-6 and $R^8$ and $R^{11}$ are R811-2,
a compound wherein $R^4$ and $R^5$ are R45-6 and $R^8$ and $R^{11}$ are R811-3,
a compound wherein $R^4$ and $R^5$ are R45-6 and $R^8$ and $R^{11}$ are R811-4,
a compound wherein $R^4$ and $R^5$ are R45-6 and $R^8$ and $R^{11}$ are R811-5,
a compound wherein $R^4$ and $R^5$ are R45-6 and $R^8$ and $R^{11}$ are R811-6,
a compound wherein $R^4$ and $R^5$ are R45-6 and $R^8$ and $R^{11}$ are R811-7,
a compound wherein $R^4$ and $R^5$ are R45-6 and $R^8$ and $R^{11}$ are R811-8,
a compound wherein $R^4$ and $R^5$ are R45-6 and $R^8$ and $R^{11}$ are R811-9,
a compound wherein $R^4$ and $R^5$ are R45-6 and $R^8$ and $R^{11}$ are R811-10,
a compound wherein $R^4$ and $R^5$ are R45-6 and $R^8$ and $R^{11}$ are R811-11,
a compound wherein $R^4$ and $R^5$ are R45-6 and $R^8$ and $R^{11}$ are R811-12,
a compound wherein $R^4$ and $R^5$ are R45-7 and $R^8$ and $R^{11}$ are R811-1, a compound wherein $R^4$ and $R^5$ are R45-7 and $R^8$ and $R^{11}$ are R811-2, a compound wherein $R^4$ and $R^5$ are R45-7 and $R^8$ and $R^{11}$ are R811-3, a compound wherein $R^4$ and $R^5$ are R45-7 and $R^8$ and $R^{11}$ are R811-4, a compound wherein $R^4$ and $R^5$ are R45-7 and $R^8$ and $R^{11}$ are R811-5, a compound wherein $R^4$ and $R^5$ are R45-7 and $R^8$ and $R^{11}$ are R811-6, a compound wherein $R^4$ and $R^5$ are R45-7 and $R^8$ and $R^{11}$ are R811-7, a compound wherein $R^4$ and $R^5$ are R45-7 and $R^8$ and $R^{11}$ are R811-8, a compound wherein $R^4$ and $R^5$ are R45-7 and $R^8$ and $R^{11}$ are R811-9, a compound wherein $R^4$ and $R^5$ are R45-7 and $R^8$ and $R^{11}$ are R811-10, a compound wherein $R^4$ and $R^5$ are R45-7 and $R^8$ and $R^{11}$ are R811-11, a compound wherein $R^4$ and $R^5$ are R45-7 and $R^8$ and $R^{11}$ are R811-12, a compound wherein $R^4$ and $R^5$ are R45-1, $R^6$ and $R^7$ are R67-1, $R^8$ and $R^{11}$ are R811-4 and $R^9$ and $R^{10}$ are R910-3, a compound wherein $R^4$ and $R^5$ are R45-1, $R^6$ and $R^7$ are R67-1, $R^8$ and $R^{11}$ are R811-4 and $R^9$ and $R^{10}$ are R910-4, a compound wherein $R^4$ and $R^5$ are R45-1, $R^6$ and $R^7$ are R67-1, $R^8$ and $R^{11}$ are R811-4 and $R^9$ and $R^{10}$ are R910-5, a compound wherein $R^4$ and $R^5$ are R45-1, $R^6$ and $R^7$ are R67-1, $R^8$ and $R^{11}$ are R811-4 and $R^9$ and $R^{10}$ are R910-8, a compound wherein $R^4$ and $R^5$ are R45-1, $R^6$ and $R^7$ are R67-1, $R^8$ and $R^{11}$ are R811-7 and $R^9$ and $R^{10}$ are R910-3, a compound wherein $R^4$ and $R^5$ are R45-1, $R^6$ and $R^7$ are R67-1, $R^8$ and $R^{11}$ are R811-7 and $R^9$ and $R^{10}$ are R910-4, a compound wherein $R^4$ and $R^5$ are R45-1, $R^6$ and $R^7$ are R67-1, $R^8$ and $R^{11}$ are R811-7 and $R^9$ and $R^{10}$ are R910-5, a compound wherein $R^4$ and $R^5$ are R45-1, $R^6$ and $R^7$ are R67-1, $R^8$ and $R^{11}$ are R811-7 and $R^9$ and $R^{10}$ are R910-8, a compound wherein $R^4$ and $R^5$ are R45-1, $R^6$ and $R^7$ are R67-1, $R^8$ and $R^{11}$ are R811-10 and $R^9$ and $R^{10}$ are R910-3, a compound wherein $R^4$ and $R^5$ are R45-1, $R^6$ and $R^7$ are R67-1, $R^8$ and $R^{11}$ are R811-10 and $R^9$ and $R^{10}$ are R910-4, a compound wherein $R^4$ and $R^5$ are R45-1, $R^6$ and $R^7$ are R67-1, $R^8$ and $R^{11}$ are R811-10 and $R^9$ and $R^{10}$ are R910-5, a compound wherein $R^4$ and $R^5$ are R45-1, $R^6$ and $R^7$ are R67-1, $R^8$ and $R^{11}$ are R811-10 and $R^9$ and $R^{10}$ are R910-8, a compound wherein $R^4$ and $R^5$ are R45-1, $R^6$ and $R^7$ are R67-1, $R^8$ and $R^{11}$ are R811-12 and $R^9$ and $R^{10}$ are R910-3, a compound wherein $R^4$ and $R^5$ are R45-1, $R^6$ and $R^7$ are R67-1, $R^8$ and $R^{11}$ are R811-12 and $R^9$ and $R^{10}$ are R910-4, a compound wherein $R^4$ and $R^5$ are R45-1, $R^6$ and $R^7$ are R67-1, $R^8$ and $R^{11}$ are R811-12 and $R^9$ and $R^{10}$ are R910-5, a compound wherein $R^4$ and $R^5$ are R45-1, $R^6$ and $R^7$ are R67-1, $R^8$ and $R^{11}$ are R811-12 and $R^9$ and $R^{10}$ are R910-8, a compound wherein $R^4$ and $R^5$ are R45-2, $R^6$ and $R^7$ are R67-1, $R^8$ and $R^{11}$ are R811-4 and $R^9$ and $R^{10}$ are R910-3, a compound wherein $R^4$ and $R^5$ are R45-2, $R^6$ and $R^7$ are R67-1, $R^8$ and $R^{11}$ are R811-4 and $R^9$ and $R^{10}$ are R910-4, a compound wherein $R^4$ and $R^5$ are R45-2, $R^6$ and $R^7$ are R67-1, $R^8$ and $R^{11}$ are R811-4 and $R^9$ and $R^{10}$ are R910-5, a compound wherein $R^4$ and $R^5$ are R45-2, $R^6$ and $R^7$ are R67-1, $R^8$ and $R^{11}$ are R811-4 and $R^9$ and $R^{10}$ are R910-8, a compound wherein $R^4$ and $R^5$ are R45-2, $R^6$ and $R^7$ are R67-1, $R^8$ and $R^{11}$ are R811-7 and $R^9$ and $R^{10}$ are R910-3, a compound wherein $R^4$ and $R^5$ are R45-2, $R^6$ and $R^7$ are R67-1, $R^8$ and $R^{11}$ are R811-7 and $R^9$ and $R^{10}$ are R910-4, a compound wherein $R^4$ and $R^5$ are R45-2, $R^6$ and $R^7$ are R67-1, $R^8$ and $R^{11}$ are R811-7 and $R^9$ and $R^{10}$ are R910-5, a compound wherein $R^4$ and $R^5$ are R45-2, $R^6$ and $R^7$ are R67-1, $R^8$ and $R^{11}$ are R811-7 and $R^9$ and $R^{10}$ are R910-8, a compound wherein $R^4$ and $R^5$ are R45-2, $R^6$ and $R^7$ are R67-1, $R^8$ and $R^{11}$ are R811-10 and $R^9$ and $R^{10}$ are R910-3, a compound wherein $R^4$ and $R^5$ are R45-2, $R^6$ and $R^7$ are R67-1, $R^8$ and $R^{11}$ are R811-10 and $R^9$ and $R^{10}$ are R910-4, a compound wherein $R^4$ and $R^5$ are R45-2, $R^6$ and $R^7$ are R67-1, $R^8$ and $R^{11}$ are R811-10 and $R^9$ and $R^{10}$ are R910-5, a compound wherein $R^4$ and $R^5$ are R45-2, $R^6$ and $R^7$ are R67-1, $R^8$ and $R^{11}$ are R811-10 and $R^9$ and $R^{10}$ are R910-8, a compound wherein $R^4$ and $R^5$ are R45-2, $R^6$ and $R^7$ are R67-1, $R^8$ and $R^{11}$ are R811-12 and $R^9$ and $R^{10}$ are R910-3, a compound wherein $R^4$ and $R^5$ are R45-2, $R^6$ and $R^7$ are R67-1, $R^8$ and $R^{11}$ are R811-12 and $R^9$ and $R^{10}$ are R910-4, a compound wherein $R^4$ and $R^5$ are R45-2, $R^6$ and $R^7$ are R67-1, $R^8$ and $R^{11}$ are R811-12 and $R^9$ and $R^{10}$ are R910-5, a compound wherein $R^4$ and $R^5$ are R45-2, $R^6$ and $R^7$ are R67-1, $R^8$ and $R^{11}$ are R811-12 and $R^9$ and $R^{10}$ are R910-8, a compound wherein $R^4$ and $R^5$ are R45-3, $R^6$ and $R^7$ are R67-1, $R^8$ and $R^{11}$ are R811-4 and $R^9$ and $R^{10}$ are R910-3, a compound wherein $R^4$ and $R^5$ are R45-3, $R^6$ and $R^7$ are R67-1, $R^8$ and $R^{11}$ are R811-4 and $R^9$ and $R^{10}$ are R910-4, a compound wherein $R^4$ and $R^5$ are R45-3, $R^6$ and $R^7$ are R67-1, $R^8$ and $R^{11}$ are R811-4 and $R^9$ and $R^{10}$ are R910-5, a compound wherein $R^4$ and $R^5$ are R45-3, $R^6$ and $R^7$ are R67-1, $R^8$ and $R^{11}$ are R811-4 and $R^9$ and $R^{10}$ are R910-8, a compound wherein $R^4$ and $R^5$ are R45-3, $R^6$ and $R^7$ are R67-1, $R^8$ and $R^{11}$ are R811-7 and $R^9$ and $R^{10}$ are R910-3, a compound wherein $R^4$ and $R^5$ are R45-3, $R^6$ and $R^7$ are R67-1, $R^8$ and $R^{11}$ are R811-7 and $R^9$ and $R^{10}$ are R910-4, a compound wherein $R^4$ and $R^5$ are R45-3, $R^6$ and $R^7$ are R67-1, $R^8$ and $R^{11}$ are R811-7 and $R^9$ and $R^{10}$ are R910-5, a compound wherein $R^4$ and $R^5$ are R45-3, $R^6$ and $R^7$ are R67-1, $R^8$ and $R^{11}$ are R811-7 and $R^9$ and $R^{10}$ are R910-8, a compound wherein $R^4$ and $R^5$ are R45-3, $R^6$ and $R^7$ are R67-1, $R^8$ and $R^{11}$ are R811-10 and $R^9$ and $R^{10}$ are R910-3, a compound wherein $R^4$ and $R^5$ are R45-3, $R^6$ and $R^7$ are R67-1, $R^8$ and $R^{11}$ are R811-10 and $R^9$ and $R^{10}$ are R910-4, a compound wherein $R^4$ and $R^5$ are R45-3, $R^6$ and $R^7$ are R67-1, $R^8$ and $R^{11}$ are R811-10 and $R^9$ and $R^{10}$ are R910-5, a compound wherein $R^4$ and $R^5$ are R45-3, $R^6$ and $R^7$ are R67-1, $R^8$ and $R^{11}$ are R811-10 and $R^9$ and $R^{10}$ are R910-8, a compound wherein $R^4$ and $R^5$ are R45-3, $R^6$ and $R^7$ are R67-1, $R^8$ and $R^{11}$ are R811-12 and $R^9$ and $R^{10}$ are R910-3, a compound wherein $R^4$ and $R^5$ are R45-3, $R^6$ and $R^7$ are R67-1, $R^8$ and $R^{11}$ are R811-12 and $R^9$ and $R^{10}$ are R910-4, a compound wherein $R^4$ and $R^5$ are R45-3, $R^6$ and $R^7$ are R67-1, $R^8$ and $R^{11}$ are R811-12 and $R^9$ and $R^{10}$ are R910-5, a compound wherein $R^4$ and $R^5$ are R45-3, $R^6$ and $R^7$ are R67-1, $R^8$ and $R^{11}$ are R811-12 and $R^9$ and $R^{10}$ are R910-8, a compound wherein $R^4$ and $R^5$ are R45-4, $R^6$ and $R^7$ are R67-1, $R^8$ and $R^{11}$ are R811-4 and $R^9$ and $R^{10}$ are R910-3, a compound wherein $R^4$ and $R^5$ are R45-4, $R^6$ and $R^7$ are R67-1, $R^8$ and $R^{11}$ are R811-4 and $R^9$ and $R^{10}$ are R910-4, a compound wherein $R^4$ and $R^5$ are R45-4, $R^6$ and $R^7$ are R67-1, $R^8$ and $R^{11}$ are R811-4 and $R^9$ and $R^{10}$ are R910-5, a compound wherein $R^4$ and $R^5$ are R45-4, $R^6$ and $R^7$ are R67-1, $R^8$ and $R^{11}$ are R811-4 and $R^9$ and $R^{10}$ are R910-8, a compound wherein $R^4$ and $R^5$ are R45-4, $R^6$ and $R^7$ are R67-1, $R^8$ and $R^{11}$ are R811-7 and $R^9$ and $R^{10}$ are R910-3, a compound wherein $R^4$ and $R^5$ are R45-4, $R^6$ and $R^7$ are R67-1, $R^8$ and $R^{11}$ are R811-7 and $R^9$ and $R^{10}$ are R910-4, a compound wherein $R^4$ and $R^5$ are R45-4, $R^6$ and $R^7$ are R67-1, $R^8$ and $R^{11}$ are R811-7 and $R^9$ and $R^{10}$ are R910-5, a compound wherein $R^4$ and $R^5$ are R45-4, $R^6$ and $R^7$ are R67-1, $R^8$ and $R^{11}$ are R811-7 and $R^9$ and $R^{10}$ are R910-8, a compound wherein $R^4$ and $R^5$ are R45-4, $R^6$ and $R^7$ are R67-1, $R^8$ and $R^{11}$ are R811-10 and $R^9$ and $R^{10}$ are R910-3, a compound wherein $R^4$ and $R^5$ are R45-4, $R^6$ and $R^7$ are R67-1, $R^8$ and $R^{11}$ are R811-10 and $R^9$ and $R^{10}$ are R910-4, a compound wherein $R^4$ and $R^5$ are R45-4, $R^6$ and $R^7$ are R67-1, $R^8$ and $R^{11}$ are R811-10 and $R^9$ and $R^{10}$ are R910-5, a compound wherein $R^4$ and $R^5$ are R45-4, $R^6$ and $R^7$ are R67-1, $R^8$ and $R^{11}$ are R811-10 and $R^9$ and $R^{10}$ are R910-8, a compound wherein $R^4$ and $R^5$ are R45-4, $R^6$ and $R^7$ are R67-1, $R^8$ and $R^{11}$ are R811-12 and $R^9$ and $R^{10}$ are R910-3, a compound wherein $R^4$ and $R^5$ are R45-4, $R^6$ and $R^7$ are R67-1, $R^8$ and $R^{11}$ are R811-12 and $R^9$ and $R^{10}$ are R910-4, a compound wherein $R^4$ and $R^5$ are R45-4, $R^6$ and $R^7$ are R67-1, $R^8$ and $R^{11}$ are R811-12 and $R^9$ and $R^{10}$ are R910-5, a compound wherein $R^4$ and $R^5$ are R45-4, $R^6$ and $R^7$ are R67-1, $R^8$ and $R^{11}$ are R811-12 and $R^9$ and $R^{10}$ are R910-8, a compound described in [1] wherein X' is —O—, —$NR^1$—, or —S(O)p— and C ring is an optionally substituted 5-membered heterocycle which contains one or two hetero atoms, a compound wherein $R^4$ and $R^5$ are R45-4 and C ring is C-1, a compound wherein $R^8$ and $R^{11}$ are R811-9, $R^9$ and $R^{10}$ are R910-7 and C ring is C-1, a compound wherein $R^4$ and $R^5$ are R45-4 and C ring is C-2, a compound wherein $R^8$ and $R^{11}$ are R811-9, $R^9$ and $R^{10}$ are R910-7 and C ring is C-2, a compound wherein $R^4$ and $R^5$ are R45-4 and C ring is C-4, a compound wherein $R^8$ and $R^{11}$ are R811-9, $R^9$ and $R^{10}$ are R910-7 and C ring is C-4, a compound wherein X, Y, X' and Y' are XY-3 and C ring is C-2, a compound wherein X, Y, X' and Y' are XY-3 and C ring is C-3, a compound wherein X, Y, X' and Y' are XY-3 and C ring is C-4, a compound wherein X, Y, X' and Y' are XY-3 and C ring is C-6, a compound wherein X, Y, X' and Y' are XY-3 and C ring is C-8, a compound wherein X, Y, X' and Y' are XY-3 and C ring is C-9, a compound wherein X, Y, X' and Y' are XY-4 and C ring is C-2, a compound wherein X, Y, X' and Y' are XY-4 and C ring is C-3, a compound wherein X, Y, X' and Y' are XY-4 and C ring is C-4, a compound wherein X, Y, X' and Y' are XY-4 and C ring is C-6, a compound wherein X, Y, X' and Y' are XY-4 and C ring is C-8, a compound wherein X, Y, X' and Y' are XY-4 and C ring is C-9, a compound wherein X, Y, X' and Y' are XY-5 and C ring is C-2, a compound wherein X, Y, X' and Y' are XY-5 and C ring is C-3, a compound wherein X, Y, X' and Y' are XY-5 and C ring is C-4, a compound wherein X, Y, X' and Y' are XY-5 and C ring is C-6, a compound wherein X, Y, X' and Y' are XY-5 and C ring is C-8, a compound wherein X, Y, X' and Y' are XY-5 and C ring is C-9, a compound wherein X, Y, X' and Y' are XY-6 and C ring is C-2, a compound wherein X, Y, X' and Y' are XY-6 and C ring is C-3, a compound wherein X, Y, X' and Y' are XY-6 and C ring is C-4, a compound wherein X, Y, X' and Y' are XY-6 and C ring is C-6, a compound wherein X, Y, X' and Y' are XY-6 and C ring is C-8, a compound wherein X, Y, X' and Y' are XY-6 and C ring is C-9, a compound wherein X, Y, X' and Y' are XY-7 and C ring is C-2, a compound wherein X, Y, X' and Y' are XY-7 and C ring is C-3, a compound wherein X, Y, X' and Y' are XY-7 and C ring is C-4, a compound wherein X, Y, X' and Y' are XY-7 and C ring is C-6, a compound wherein X, Y, X' and Y' are XY-7 and C ring is C-8, a compound wherein X, Y, X' and Y' are XY-7 and C ring is C-9, a compound wherein X, Y, X' and Y' are XY-8 and C ring is C-2, a compound wherein X, Y, X' and Y' are XY-8 and C ring is C-3, a compound wherein X, Y, X' and Y' are XY-8 and C ring is C-4, a compound wherein X, Y, X' and Y' are XY-8 and C ring is C-6, a compound wherein X, Y, X' and Y' are XY-8 and C ring is C-8, a compound wherein X, Y, X' and Y' are XY-8 and C ring is C-9, a compound wherein X, Y, X' and Y' are XY-9 and C ring is C-2, a compound wherein X, Y, X' and Y' are XY-9 and C ring is C-3, a compound wherein X, Y, X' and Y' are XY-9 and C ring is C-4, a compound wherein X, Y, X' and Y' are XY-9 and C ring is C-6, a compound wherein X, Y, X' and Y' are XY-9 and C ring is C-8, a compound wherein X, Y, X' and Y' are XY-9 and C ring is C-9, a compound wherein X, Y, X' and Y' are XY-10 and C ring is C-2, a compound wherein X, Y, X' and Y' are XY-10 and C ring is C-3, a compound wherein X, Y, X' and Y' are XY-10 and C ring is C-4, a compound wherein X, Y, X' and Y' are XY-10 and C ring is C-6, a compound wherein X, Y, X' and Y' are XY-10 and C ring is C-8, a compound wherein X, Y, X' and Y' are XY-10 and C ring is C-9, a compound wherein X, Y, X' and Y' are XY-11 and C ring is C-2, a compound wherein X, Y, X' and Y' are XY-11 and C ring is C-3, a compound wherein X, Y, X' and Y' are XY-11 and C ring is C-4, a compound wherein X, Y, X' and Y' are XY-11 and C ring is C-6, a compound wherein X, Y, X' and Y' are XY-11 and C ring is C-8, a compound wherein X, Y, X' and Y' are XY-11 and C ring is C-9, a compound wherein X, Y, X' and Y' are XY-12 and C ring is C-2, a compound wherein X, Y, X' and Y' are XY-12 and C ring is C-3, a compound wherein X, Y, X' and Y' are XY-12 and C ring is C-4, a compound wherein X, Y, X' and Y' are XY-12 and C ring is C-6, a compound wherein X, Y, X' and Y' are XY-12 and C ring is C-8, a compound wherein X, Y, X' and Y' are XY-12 and C ring is C-9, a compound wherein X, Y, X' and Y' are XY-13 and C ring is C-2, a compound wherein X, Y, X' and Y' are XY-13 and C ring is C-3, a compound wherein X, Y, X' and Y' are XY-13 and C ring is C-4, a compound wherein X, Y, X' and Y' are XY-13 and C ring is C-6, a compound wherein X, Y, X' and Y' are XY-13 and C ring is C-8, a compound wherein X, Y, X' and Y' are XY-13 and C ring is C-9, a compound wherein X, Y, X' and Y' are XY-14 and C ring is C-2, a compound wherein X, Y, X' and Y' are XY-14 and C ring is C-3, a compound wherein X, Y, X' and Y' are XY-14 and C ring is C-4, a compound wherein X, Y, X' and Y' are XY-14 and C ring is C-6, a compound wherein X, Y, X' and Y' are XY-14 and C ring is C-8, a compound wherein X, Y, X' and Y' are XY-14 and C ring is C-9, a compound wherein X, Y, X' and Y' are XY-15 and C ring is C-2, a compound wherein X, Y, X' and Y' are XY-15 and C ring is C-3,
a compound wherein X, Y, X' and Y' are XY-15 and C ring is C-4,
a compound wherein X, Y, X' and Y' are XY-15 and C ring is C-6,
a compound wherein X, Y, X' and Y' are XY-15 and C ring is C-8,
a compound wherein X, Y, X' and Y' are XY-15 and C ring is C-9,
a compound wherein X, Y, X' and Y' are XY-16 and C ring is C-2,
a compound wherein X, Y, X' and Y' are XY-16 and C ring is C-3,
a compound wherein X, Y, X' and Y' are XY-16 and C ring is C-4,
a compound wherein X, Y, X' and Y' are XY-16 and C ring is C-6,
a compound wherein X, Y, X' and Y' are XY-16 and C ring is C-8,
a compound wherein X, Y, X' and Y' are XY-16 and C ring is C-9,
a compound wherein X, Y, X' and Y' are XY-17 and C ring is C-2,
a compound wherein X, Y, X' and Y' are XY-17 and C ring is C-3,
a compound wherein X, Y, X' and Y' are XY-17 and C ring is C-4,
a compound wherein X, Y, X' and Y' are XY-17 and C ring is C-6,
a compound wherein X, Y, X' and Y' are XY-17 and C ring is C-8,
a compound wherein X, Y, X' and Y' are XY-17 and C ring is C-9,
a compound wherein X, Y, X' and Y' are XY-18 and C ring is C-2,
a compound wherein X, Y, X' and Y' are XY-18 and C ring is C-3,
a compound wherein X, Y, X' and Y' are XY-18 and C ring is C-4,
a compound wherein X, Y, X' and Y' are XY-18 and C ring is C-6,
a compound wherein X, Y, X' and Y' are XY-18 and C ring is C-8,
a compound wherein X, Y, X' and Y' are XY-18 and C ring is C-9,
a compound wherein X, Y, X' and Y' are XY-19 and C ring is C-2,
a compound wherein X, Y, X' and Y' are XY-19 and C ring is C-3,
a compound wherein X, Y, X' and Y' are XY-19 and C ring is C-4,
a compound wherein X, Y, X' and Y' are XY-19 and C ring is C-6,
a compound wherein X, Y, X' and Y' are XY-19 and C ring is C-8,
a compound wherein X, Y, X' and Y' are XY-19 and C ring is C-9,
a compound wherein X, Y, X' and Y' are XY-20 and C ring is C-2,
a compound wherein X, Y, X' and Y' are XY-20 and C ring is C-3,
a compound wherein X, Y, X' and Y' are XY-20 and C ring is C-4,
a compound wherein X, Y, X' and Y' are XY-20 and C ring is C-6,
a compound wherein X, Y, X' and Y' are XY-20 and C ring is C-8,
a compound wherein X, Y, X' and Y' are XY-20 and C ring is C-9,
a compound wherein $R^4$ and $R^5$ are R45-1, $R^6$ and $R^7$ are R67-1, $R^8$ and $R^{11}$ are R811-4 $R^9$ and $R^{10}$ are R910-4, X, Y, X' and Y' are XY-5 and C ring is C-3,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-5 and C ring is C-4,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-5 and C ring is C-6,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-5 and C ring is C-9,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-6 and C ring is C-3,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-6 and C ring is C-4,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-6 and C ring is C-6,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-6 and C ring is C-9,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-9 and C ring is C-3,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-9 and C ring is C-4,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-9 and C ring is C-6,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-9 and C ring is C-9,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-17 and C ring is C-3,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-17 and C ring is C-4,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-17 and C ring is C-6,
a compound wherein $R^4$ and $R^5$ are R45-1, $R^6$ and $R^7$ are R67-1, $R^8$ and $R^{11}$ are R811-4, $R^9$ and $R^{10}$ are R910-4, X, Y, X' and Y' are XY-17 and C ring is C-9,
a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-5 and C ring is C-3,
a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-5 and C ring is C-4,
a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-4, $R^9$ and $R^{11}$ are R910-5, X, Y, X' and Y' are XY-6 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-6 and C ring is C-6.

a compound wherein $R^4$ and $R^5$ are R45 1, $R^6$ and $R^7$ are R67-1, $R^8$ and $R^{11}$ are R811-4, $R^9$ and $R^{10}$ are R910-5, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-9 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-17 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-5, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-5 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-6 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-9 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-17 and C ring is C-3, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-4, $R^9$ and $R^{10}$ are R910-7, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-5 and C ring is C-3, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-6 and C ring is C-3, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-4, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-5, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-8, $R^9$ and $R^{10}$ are R910-7, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-4, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-5, X, Y, X' and Y' are XY-17 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-5 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-5 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-5 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-6 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-6 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-6 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-9 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-9 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-9 and C ring is C-9, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-17 and C ring is C-4, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-17 and C ring is C-6, a compound wherein $R^4$ and $R^5$ are R45-1, $R^6$ and $R^7$ are R67-1, $R^8$ and $R^{11}$ are R811-10, $R^9$ and $R^{10}$ are R910-7, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-4, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-5, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-4, $R^9$ and $R^{10}$ are R910-7, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-5, $R^9$ and $R^{10}$ are R910-5, X, Y, X' and Y' are XY-7 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-4, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-5, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-8, $R^9$ and $R^{10}$ are R910-7, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-4, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-20 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-20 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-5, X, Y, X' and Y' are XY-20 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-5 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-5 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-5 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-6 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-6 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-6 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-9 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-9 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-9 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-17 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-17 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-17 and C ring is C-9, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-20 and C ring is C-4, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-20 and C ring is C-6, a compound wherein $R^4$ and $R^5$ are R45-3, $R^6$ and $R^7$ are R67-1, $R^8$ and $R^{11}$ are R811-10, $R^9$ and $R^{10}$ are R910-7, X, Y, X' and Y' are XY-20 and C ring is C-9, a compound wherein X' is —O—, —NR$^1$— or —S(O)p— and C ring is an optionally substituted 5-membered heterocycle which contains one or two hetero atoms, a compound wherein C ring is pyridine ring, one of —X—Y and —X'—Y' is 1-pyrolidinyl, 1-piperidinyl, 4-morphorinyl, 4-thiomorpholinyl, optionally substituted 1-piperadinyl (wherein the substituents are lower alkyl or lower alkenyl) or optionally substituted 1-pyrolyl (wherein the substituents are lower alkyl), and the other is —NHCH$_2$CH=CMe$_2$, —OCH$_2$CH=CMe$_2$ or —SCH$_2$CH=CMe$_2$, a compound wherein C ring is pyridine ring, one of —X—Y and —X'—Y' is 1-pyrolidinyl, optionally substituted 1-pyrolyl (wherein the substituents are lower alkyl), and the other is —NHCH$_2$CH=CMe$_2$, —OCH$_2$CH=CMe$_2$ or —SCH$_2$CH=CMe$_2$, salt or hydrate thereof.

Another embodiment of the present invention is

[2] a compound of the formula:

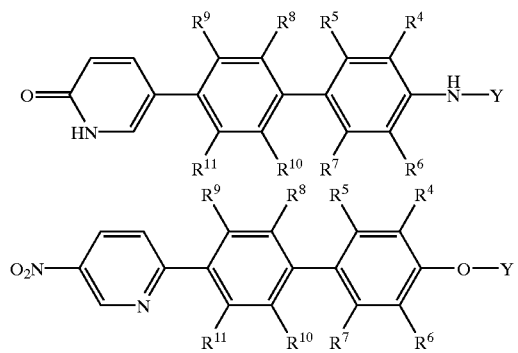

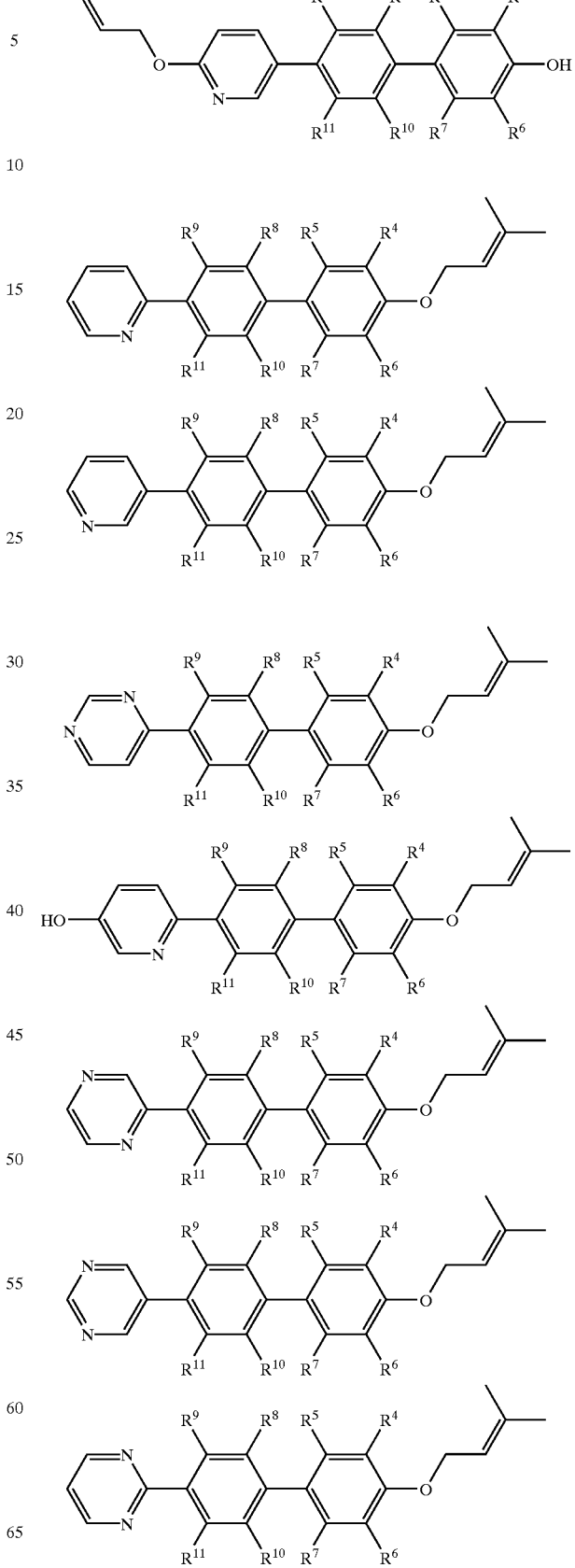

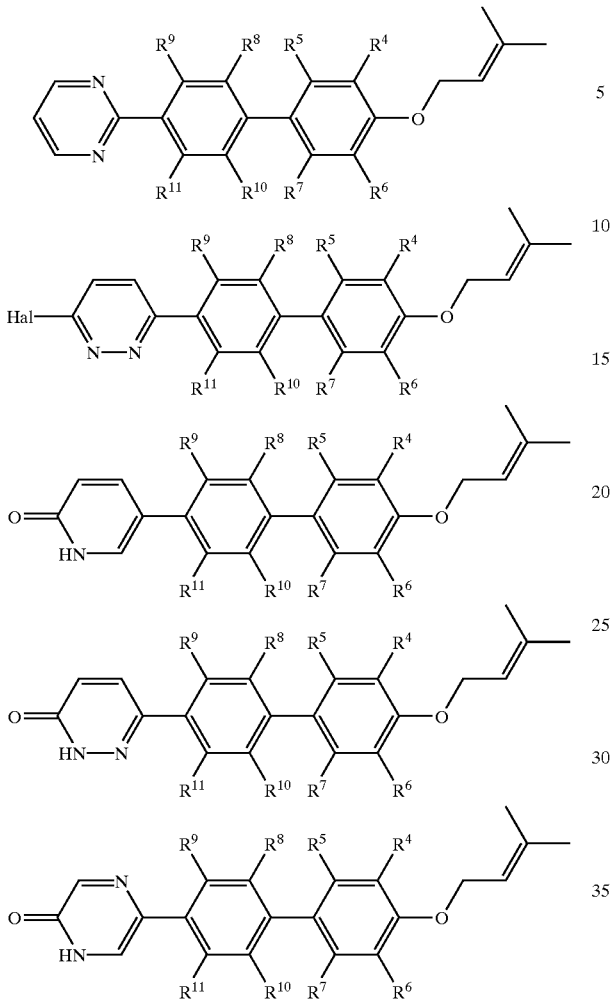

wherein each symbol is the same as defined in the above [1],
[3] a compound of the formula (Ia'):

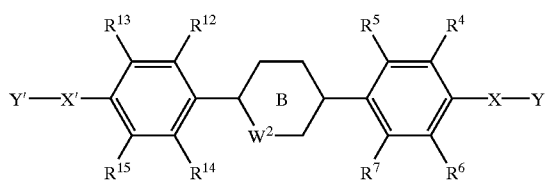

wherein B ring is optionally substituted 5- or 6-membered heterocycle which contains one or two hetero atoms (wherein the substituent is halogen, hydroxy, optionally substituted lower alkyl, optionally substituted lower alkoxy, optionally substituted lower alkenyl, optionally substituted lower alkenyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, guanidino, nitro, optionally substituted lower alkylsulfonyl, optionally substituted lower alkylsulfonyloxy, optionally substituted arylsulfonyl or optionally substituted arylsulfonyloxy, excluding a compound wherein B ring is substituted with only halogen(s)) and $W^2$ represents a bond when B ring is 5-membered heterocycle, X, X', Y and Y' are the same defined in [1], $R^1$, taken together with Y or Y', may form —(CH$_2$)m—, —(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O(CH$_2$)n-, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or —NR$^1$—, Y' may be hydrogen or halogen when X' is —CH$_2$— or —NR$^1$—, $R^4$, $R^5$, $R^6$, $R^7$, $R^{12}$, $R^{13}$, $R^{14}$ and $R^{15}$ are each independently hydrogen, halogen, hydroxy, optionally substituted lower alkyl, optionally substituted lower alkoxy, optionally substituted lower alkenyl, optionally substituted alkenyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding (i) a compound wherein Y and Y' are simultaneously hydrogen, (ii) a compound wherein at least one of Y and Y' is optionally substituted acyl, (iii) a compound wherein at least one of —X—Y and —X'—Y' is unsubstituted lower alkoxy, and (iv) a compound wherein —X—Y and —X'—Y' are simultaneously optionally substituted lower alkoxy or amino substituted with phenyl, salt or hydrate thereof.

The following compounds of (Ia'), salt or hydrate thereof are more preferable.

a compound wherein $R^4$ and $R^5$ are R45-1,
a compound wherein $R^4$ and $R^5$ are R45-2,
a compound wherein $R^4$ and $R^5$ are R45-3,
a compound wherein $R^4$ and $R^5$ are R45-4,
a compound wherein $R^4$ and $R^5$ are R45-5,
a compound wherein $R^4$ and $R^5$ are R45-6,
a compound wherein $R^4$ and $R^5$ are R45-7,
a compound wherein $R^6$ and $R^7$ are R67-1,
a compound wherein $R^6$ and $R^7$ are R67-2,
a compound wherein B ring is 5-or 6-membered heterocycle which contains at least one N atom (hereinafter referred to as "B ring is B-1"),
a compound wherein B ring is a 6-membered heterocycle which contains at least one N atom (hereinafter referred to as "B ring is B-2"), a compound wherein B ring is optionally substituted pyridine, optionally substituted pyrimidine, optionally substituted pyridazine or optionally substituted pyrazine (hereinafter referred to as "B ring is B-3"), a compound wherein B ring is optionally substituted pyridine or optionally substituted pyrimidine (hereinafter referred to as "B ring is B-4"), a compound wherein B ring is optionally substituted pyridine or optionally substituted pyrimidine (wherein the substituents are optionally substituted lower alkyl or optionally substituted lower alkoxy) (hereinafter referred to as "B ring is B-5"), a compound wherein B ring is optionally substituted pyridine wherein "B ring is B-6"), a compound wherein B ring is

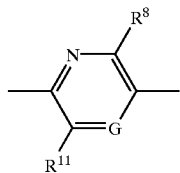

wherein G is CH or N, $R^8$ and $R^{11}$ are each independently halogen, hydroxy, optionally substituted lower alkyl, optionally substituted lower alkoxy, optionally substituted lower alkenyl, optionally substituted lower alkenyloxy, optionally substituted acyloxy, carboxy or optionally substituted lower alkoxycarbonyl (hereinafter referred to as "B ring is B-7"), a compound wherein $R^{12}$, $R^{13}$, $R^{14}$ and $R^{15}$ are each independently hydrogen, hydroxy, halogen, optionally substituted lower alkoxy, optionally substituted acyloxy, optionally substituted lower alkylsulfonyloxy or optionally substituted arylsulfonyloxy (hereinafter referred to as "$R^{12}$, $R^{13}$, $R^{14}$, $R^{15}$ and $R^{16}$ are R12-15-1"), a compound wherein $R^{12}$, $R^{13}$, $R^{14}$ and $R^{15}$ are each independently hydrogen, hydroxy, halogen, lower alkoxy, acyloxy, optionally substituted lower alkylsulfonyloxy or arylsulfonyloxy (hereinafter referred to as "$R^{12}$, $R^{13}$, $R^{14}$ and $R^{15}$ are R12-15-2"), a compound wherein $R^{12}$, $R^{13}$, $R^{14}$ and $R^{15}$ are each independently hydrogen, halogen or lower alkyl (hereinafter referred to as "$R^{12}$, $R^{13}$, $R^{14}$ and $R^{15}$ are 12-15-3"), a compound wherein $R^{12}$, $R^{13}$, $R^{14}$ and $R^{15}$ are each independently hydrogen, chloro or fluoro (hereinafter referred to as "$R^{12}$, $R^{13}$, $R^{14}$ and $R^{15}$ are R12-15-4"), a compound wherein X, Y, X' and Y' are XY-1,
a compound wherein X, Y, X' and Y' are XY-2,
a compound wherein X, Y, X' and Y' are XY-3,
a compound wherein X, Y, X' and Y' are XY-4,
a compound wherein X, Y, X' and Y' are XY-5,
a compound wherein X, Y, X' and Y' are XY-6,
a compound wherein X, Y, X' and Y' are XY-7,
a compound wherein X, Y, X' and Y' are XY-8,
a compound wherein X, Y, X' and Y' are XY-9,
a compound wherein X, Y, X' and Y' are XY-10,
a compound wherein X, Y, X' and Y' are XY-11,
a compound wherein X, Y, X' and Y' are XY-12,
a compound wherein X, Y, X' and Y' are XY-13,
a compound wherein X, Y, X' and Y' are XY-14,
a compound wherein X, Y, X' and Y' are XY-15,
a compound wherein X, Y, X' and Y' are XY-16,
a compound wherein X, Y, X' and Y' are XY-17,
a compound wherein X, Y, X' and Y' are XY-18,
a compound wherein X, Y, X' and Y' are XY-19,
a compound wherein X, Y, X' and Y' are XY-20, a compound wherein $R^4$ and $R^5$ are R45-3 and $R^6$ and $R^7$ are R67-2, a compound wherein $R^4$ and $R^5$ are R45-4 and $R^6$ and $R^7$ are R67-2, a compound wherein $R^4$ and $R^5$ are R45-4 and B ring is B-1, a compound wherein $R^4$ and $R^5$ are R45-4 and B ring is B-2, a compound wherein $R^4$ and $R^5$ are R45-4 and B ring is B-4, a compound wherein $R^4$ and $R^5$ are R45-4 and $R^{12}$, $R^{13}$, $R^{14}$ and $R^{15}$ are R12-15-3, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-3 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-3 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-5 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-5 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-7 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-2, B ring is B-7 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-3 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-3 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-5 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-5 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-7 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-3, B ring is B-7 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-3 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-3 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-5 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-5 and X, X', Y and Y' are XY-17, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-7 and X, X', Y and Y' are XY-6, a compound wherein $R^4$ and $R^5$ are R45-1, $R^6$ and $R^7$ are R67-1, $R^{12}$, $R^{13}$, $R^{14}$ and $R^{15}$ are R12-15-4, B ring is B-7 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-3 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-3 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-4 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-5 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-5 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-7 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-2, B ring is B-7 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-3 and X, X', Y and Y' are XY-6, a compound wherein $R^4$ and $R^5$ are R45-3, $R^6$ and $R^7$ are R67-1, $R^{12}$, R13, $R^{14}$ and $R^{15}$ are R12-15-3, B ring is B-3 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-5 and X, X', Y and Y' are XY-5, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-5 and X, X', Y and Y' are XY-6, a compound wherein $R^4$ and $R^5$ are R45-3, $R^6$ and $R^7$ are R67-1, $R^{12}$, R13, $R^{14}$ and $R^{15}$ are R12-15-3, B ring is B-5 and X, X', Y and Y' are XY-7, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-5 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-7 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-3, B ring is B-7 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-3 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-3 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-5 and X, X', Y and X' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-5 and X, X', Y and Y' are XY-17, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-7 and X, X', Y and Y' are XY-6, a compound wherein $R^4$ and $R^5$ are R45-3, $R^6$ and $R^7$ are R67-1, $R^{12}$, $R^{13}$, $R^{14}$ and $R^{15}$ are R12-15-4, B ring is B-7 and X, X', Y and Y' are XY-17, a compound wherein B ring is B-7, X and X' are each independently —O—, $NR^1$— (wherein $R^1$ is hydrogen, lower alkyl, lower alkenyl or lower alkylcarbonyl) or —S(O)p- wherein p is an integer of 0–2, Another embodiment of the present invention is

[4] a compounds of the formula (If'):

wherein one of B ring and C ring is optionally substituted 5- or 6-membered heterocycle which contains one or two hetero atoms and the other is 6-membered heterocycle which contains at least one N atom, excluding a compound wherein every substituent of B ring is selected from cyano and halogen, X, X', Y, X' and $W^3$ are the same as defined in [1] and $W^2$ is the same as defined in [3], $R^1$, taken together with Y or Y', may form —(CH$_2$)m-, —(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O (CH$_2$)n-, —C(=O)—NR'—(CH$_2$)n- or —C(=O)—NR'—N=CH— wherein m is 4 or 5, n is 2 or 3 and R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —$NR^1$, Y' may be optionally substituted lower alkoxycarbonyl, optionally substituted lower alkylsulfonyl or optionally substituted arylsulfonyl when X is —O— or $NR^1$—, Y may be hydrogen or halogen when X is —CH$_2$— or $NR^1$—, Y' may be hydrogen or halogen when X is —CH$_2$— or —$NR^1$—, $R^4$, $R^5$, $R^6$ and $R^7$ are the same as defined in [1], salt or hydrate thereof. The following compounds among the compound (If') are preferable.

a compound wherein B ring is B-2, a compound wherein B ring is B-3, a compound wherein B ring is B-4, a compound wherein B ring is B-5, a compound wherein B ring is B-6, a compound wherein B ring is pyridine which may be substituted with lower alkyl or lower alkoxy, a compound wherein C ring is C-1, a compound wherein C ring is C-2, a compound wherein C ring is optionally substituted morpholine ring, optionally substituted piperazine ring, optionally substituted imidazole ring, optionally substituted triazole ring or optionally substituted pyridine ring, a compound wherein C ring is optionally substituted morpholine ring, optionally substituted piperazine ring, optionally substituted imidazole ring, optionally substituted triazole ring or optionally substituted pyridine ring (wherein the substituent is lower alkyl, aryl or lower alkenyloxy), a compound wherein $R^4$, $R^5$, $R^6$ and $R^7$ are each independently hydrogen, hydroxy or lower alkylsulfonyloxy, a compound wherein B ring is pyridine ring which may be substituted with lower alkyl or lower alkoxy, C ring is optionally substituted morpholine ring, optionally substituted piperazine ring, optionally substituted imidazole ring, optionally substituted triazole ring or optionally substituted pyridine ring (wherein the substituents are lower alkyl, aryl or lower alkenyloxy) and $R^4$, $R^5$, $R^6$ and $R^7$ are each independently hydrogen, hydroxy or lower alkylsulfonyloxy.

Another embodiment of the present invention is

[5] a compound of the formula (Ig'):

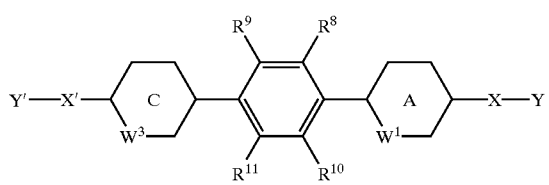

Ig' wherein A ring and C ring are each independently optionally substituted 5- or 6-membered ring which contains one or two hetero atoms and $W^1$ is a bond when A ring is 5-membered heterocycle, X, X' Y and Y' are the same as defined in [1], $R^1$, taken together with Y or Y', may form —(CH$_2$)m—, —(CH$_2$)$_2$—Q—(CH$_2$)$_2$— (wherein Q is CH$_2$, O, S or NR'), —CR'═CH—CH═CR'—, —CH═N—CH═CH—, —N═CH—N═CH—, —C(═O)—O (CH$_2$)n—, —C(═O)—NR'—(CH$_2$)n— or C(═O)—NR'—N═CH— wherein m is 4 or 5, n is 2 or 3 and R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or NR$^1$, Y' may be optionally substituted lower alkoxycarbonyl, optionally substituted lower alkylsulfonyl or optionally substituted arylsulfonyl when X' is —O— or NR$^1$—, Y may be hydrogen or halogen when X is —CH$_2$— or NR$^1$, Y' may be hydrogen or halogen when X' is —CH$_2$— or NR$^1$—, $R^8$, $R^9$, $R^{10}$ and $R^{11}$ are the same as defined in [1] excluding a compound wherein all of $R^8$, $R^9$, $R^{10}$ and $R^{11}$ are selected from hydrogen and halogen, salt or hydrate thereof. The following compounds among the compound (Ig') are preferable.

a compound wherein at least one of A ring and C ring is a 6-membered ring, a compound wherein at least one of A ring and C ring is a 6-membered ring which contains N atom, a compound wherein A ring is optionally substituted pyridine ring, a compound wherein A ring is unsubstituted pyridine ring, a compound wherein $R^8$, $R^9$, $R^{10}$ and $R^{11}$ are each independently hydrogen, lower alkyl or lower alkoxy, a compound wherein C ring is optionally substituted pyridine ring, optionally substituted pyrimidine ring or optionally substituted pyrazine ring, a compound wherein C ring is unsubstituted pyridine ring, unsubstituted pyrimidine ring or unsubstituted pyrazine ring, a compound wherein —X—Y is lower alkenyloxy or lower alkenylamino, a compound wherein —X'—Y' is amino which may be substituted with lower alkenyl, a compound wherein A ring is unsubstituted pyridine ring, $R^8$, $R^9$, $R^{10}$ and $R^{11}$ are each independently hydrogen, lower alkyl or lower alkoxy, C ring is unsubstituted pyridine ring, unsubstituted pyrimidine ring or unsubstituted pyrazine ring, —X—Y is lower alkenyloxy or lower alkenylamino and —X'—Y' is amino which may be substituted with lower alkenyl, or salt or hydrate thereof.

Other preferable embodiments of the present invention are as follows.

[6] A pharmaceutical composition for use as an immunosuppressant comprising the compound of the formula (Ib'):

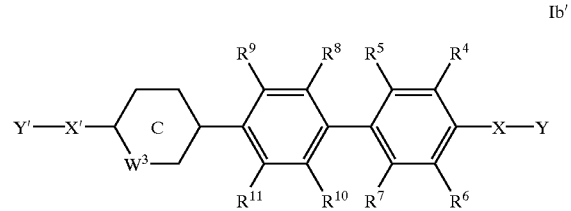

Ib' wherein C ring and $W^3$ are the same as defined in [1],

X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl), —S(O)p— (wherein p is an integer of 0–2) or a bond, Y and Y' are the same as defined in [1], $R^1$, taken together with Y or Y', may form —(CH$_2$)m—, —(CH$_2$)$_2$—Q—(CH$_2$)$_2$— (wherein Q is CH$_2$, O, S or NR'), —CR'═CH—CH═CR'—, —CH═N—CH═CH—, —N═CH—N═CH—, —C(═O)—O (CH$_2$)n—, —C(═O)—NR'—(CH$_2$)n— or —C(=O)—NR'—N=CH— wherein m is 4 or 5, n is 2 or 3 and R' is hydrogen, lower alkyl or lower alkenyl, Y may be lower alkoxy when X is —CH$_2$—, Y' may be lower alkoxy when X' is —CH$_2$—, Y may be optionally substituted lower alkoxycarbonyl, optionally substituted lower alkylsulfonyl or optionally substituted arylsulfonyl when X is —O— or NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or —NR$^1$—, Y' may be hydrogen or halogen when X' is —CH$_2$— or NR$^1$, Y' may be hydrogen, hydroxy, halogen, nitro or oxo when X' is a bond, R$^4$, R$^5$, R$^6$, R$^7$, R$^8$, R$^9$, R$^{10}$ and R$^{11}$ are the same as defined in [1], excluding a compound wherein all of R$^8$, R$^9$, R$^{10}$ and R$^{11}$ are selected from hydrogen and halogen, salt or hydrate thereof,

[7] a pharmaceutical composition for use as an immunosuppressant comprising the compound of the formula (Ia'):

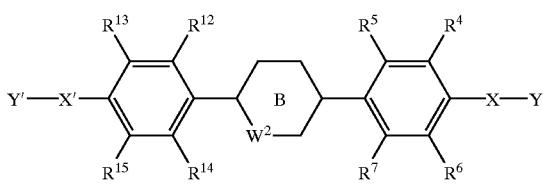

wherein B ring is optionally substituted 5- or 6-membered heterocycle which contains one or two hetero atoms excluding a compound wherein every substituent of B ring is selected from cyano and halogen, W$^2$ is a bond when B ring is 5-membered heterocycle, X, X', Y and Y' are the same as defined in [3], R$^1$, taken together with Y or Y', may form —(CH$_2$)m—, —(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O (CH$_2$)n—, —C(=O)—NR'—(CH$_2$)n— or —C(=O)—NR'—N=CH— wherein m is 4 or 5, n is 2 or 3 and R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or NR$^1$—, Y' may be optionally substituted lower alkoxycarbonyl, optionally substituted lower alkylsulfonyl or optionally substituted arylsulfonyl when X' is —O— or NR$^1$—, Y may be hydrogen or halogen when X is —CH$_2$— or —NR$^1$—, Y' may be hydrogen or halogen when.X' is —CH$_2$— or NR$^1$, R$^4$, R$^5$, R$^6$, R$^7$, R$^{12}$, R$^{13}$, R$^{14}$ and R$^{15}$ are the same as defined in [3], excluding (i) a compound wherein —X—Y and —X'—Y' are simultaneously unsubstituted lower alkyl, optionally substituted lower alkoxy or unsubstituted acyloxy, (ii) a compound wherein one of —X—Y and —X'—Y' is methyl and the other is methoxy, and (iii) a compound wherein —X'—Y' is hydrogen or halogen and —X—Y is unsubstituted lower alkyl, unsubstituted lower alkoxy or di(lower)alkylamino, salt or hydrate thereof,

[8] a pharmaceutical composition for use as an immunosuppressant comprising the compound of the formula (If'), salt or hydrate thereof described in [4],

[9] a pharmaceutical composition for use as an immunosuppressant comprising the compound (Ig'), salt or hydrate thereof described in [5],

[10] a pharmaceutical composition for use as an antiallergic agent comprising the compound of the formula (If') described in [4], the compound of the formula (Ig') described in [5], the compound of the formula (Ib') described in [6], the compound of the formula (Ia') described in [7], salt, hydrate thereof,

[11] a pharmaceutical composition for use as a suppressant of the IgE production comprising the compound of the formula (If') described in [4]the compound of the formula (Ig') described in [5], the compound of the formula (Ib') described in [6], the compound of the formula (Ia') described in [7], salt, or hydrate thereof,

[12] Use of the compound of the formula (If') described in [4], the compound of the formula (Ig') described in [5], the compound of the formula (Ib') described in [6], the compound of the formula (Ia') described in [7], salt, or hydrate thereof for manufacturing a medicament for suppressing an immune response, treating and/or preventing allergic diseases,

[13] a method for suppressing an immune response or treating and/or preventing allergic diseases comprising administering the compound of the formula (If') described in [4], the compound of the formula (Ig') described in [5]), the compound of the formula (Ib') described in [6], the compound of the formula (Ia') described in [7], salt, or hydrate thereof and

[14] a method for treating and/or preventing allergic diseases comprising administering the compound of the formula (If') described in [4], the compound of the formula (Ig') described in [5], the compound of the formula (Ib') described in [6], the compound of the formula (Ia') described in [7], salt, or hydrate thereof.

The preferable compounds of the present invention are the ones of following structures. The symbols A2, A5, . . . B1, B4, . . . T1, T2 . . . in the tables means as follows.

TABLE 1

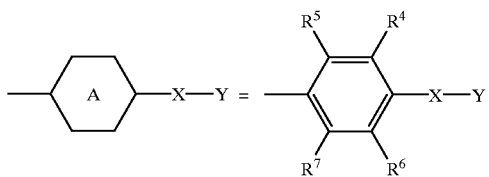

| | R$^4$ | R$^5$ | R$^6$ | R$^7$ | X | Y |
|---|---|---|---|---|---|---|
| A2 | H | H | H | H | O | CH$_2$-2-furyl |
| A5 | H | H | H | H | O | CH$_2$CH=CMe$_2$ |
| A35 | OMe | H | H | H | O | CH$_2$CH=CMe$_2$ |
| A37 | F | H | H | H | O | CH$_2$CH=CMe$_2$ |
| A45 | H | H | H | H | NH | CH$_2$CH=CH2 |

TABLE 1-continued

![Structure with cyclohexane ring A connected via X-Y to a benzene ring with R4, R5, R6, R7 substituents and X-Y]

| | R⁴ | R⁵ | R⁶ | R⁷ | X | Y |
|---|---|---|---|---|---|---|
| A46 | H | H | H | H | NH | CH₂CH=CMe₂ |
| A49 | H | H | H | H | NH | CH₂-c-Hex |
| A54 | H | H | H | H | NH | CH₂-2-furyl |
| A66 | H | F | H | H | NH | iBu |
| A67 | H | F | H | H | NH | CH₂CH=CMe₂ |
| A68 | H | F | H | H | NH | cPent |
| A69 | H | F | H | H | NH | cHex |
| A70 | H | F | H | H | NH | CH₂cHex |
| A76 | H | F | H | H | N-iPr | SO₂NHMe |
| A77 | H | F | H | H | NCH₂CH=CMe₂ | SO₂NHMe |
| A78 | F | H | H | H | NH | CH₂CH=CMe₂ |
| A106 | H | F | H | H | NH | CH₂C₆H₅ |
| A110 | F | H | H | H | O | CH₂C₆H₅ |

TABLE 2

![Structure with cyclohexane ring B and benzene ring with R8, R9, R10, R11 substituents]

| | R⁸ | R⁹ | R¹⁰ | R¹¹ |
|---|---|---|---|---|
| B1 | OMe | H | H | OMe |
| B4 | Me | H | H | Me |
| B7 | Me | Me | Me | Me |
| B8 | Me | Me | OMe | Me |
| B9 | Me | Me | OH | Me |
| B10 | Me | Me | Me | OMe |
| B12 | OMe | Me | Me | OMe |
| B14 | Me | Me | H | Me |
| B16 | Me | F | H | Me |
| B17 | OMe | H | H | Me |
| B24 | Me | Me | Me | COOMe |
| B28 | Me | Me | Me | Cl |
| B29 | Me | OMe | H | Me |
| B30 | COOMe | Me | Me | Me |
| B31 | Cl | Me | Me | Me |
| B32 | H | Me | Me | Cl |
| B33 | Me | H | Cl | Me |
| B34 | H | Me | Cl | H |
| B35 | Me | H | H | Cl |
| B36 | Me | Me | H | H |
| B37 | H | Me | H | Me |
| B38 | Me | H | Me | H |
| B39 | OMe | OMe | H | H |
| B40 | H | OMe | H | OMe |
| B41 | OMe | H | OMe | H |
| B42 | H | Me | H | OMe |
| B43 | OMe | H | Me | H |

TABLE 3

![Structures T1, T2, T5, T7 - cyclohexane with W³ connected via Y'-X' to pyridine/pyrimidine/pyridazine rings with R12, R13, R14, R15 substituents]

| | R¹² | R¹³ | R¹⁴ | R¹⁵ | | R¹² | R¹³ | R¹⁴ | R¹⁵ |
|---|---|---|---|---|---|---|---|---|---|
| T1-1 | H | H | — | H | T2-4 | H | H | Me | — |
| T2-1 | H | H | H | — | T2-5 | H | NO₂ | H | — |
| T2-2 | Me | H | H | — | T5-1 | H | — | H | — |
| T2-3 | H | Me | H | — | T7-1 | H | H | — | — |

TABLE 4

![Structures with three linked rings C-B-A with W³, W², W¹]

| C | B | A | C | B | A |
|---|---|---|---|---|---|
| T1-1 | B1 | A2 | T2-1 | B1 | A2 |
| T1-1 | B1 | A5 | T2-1 | B1 | A5 |
| T1-1 | B1 | A35 | T2-1 | B1 | A35 |
| T1-1 | B1 | A37 | T2-1 | B1 | A37 |
| T1-1 | B1 | A45 | T2-1 | B1 | A45 |

TABLE 4-continued

| C W³ | B W² | A W¹ | C W³ | B W² | A W¹ |
|---|---|---|---|---|---|
| T1-1 | B1 | A46 | T2-1 | B1 | A46 |
| T1-1 | B1 | A49 | T2-1 | B1 | A49 |
| T1-1 | B1 | A54 | T2-1 | B1 | A54 |
| T1-1 | B1 | A66 | T2-1 | B1 | A66 |
| T1-1 | B1 | A67 | T2-1 | B1 | A67 |
| T1-1 | B1 | A68 | T2-1 | B1 | A68 |
| T1-1 | B1 | A69 | T2-1 | B1 | A69 |
| T1-1 | B1 | A70 | T2-1 | B1 | A70 |
| T1-1 | B1 | A76 | T2-1 | B1 | A76 |
| T1-1 | B1 | A77 | T2-1 | B1 | A77 |
| T1-1 | B1 | A78 | T2-1 | B1 | A78 |
| T1-1 | B1 | A106 | T2-1 | B1 | A106 |
| T1-1 | B1 | A110 | T2-1 | B1 | A110 |
| T2-2 | B1 | A2 | T2-3 | B1 | A2 |
| T2-2 | B1 | A5 | T2-3 | B1 | A5 |
| T2-2 | B1 | A35 | T2-3 | B1 | A35 |
| T2-2 | B1 | A37 | T2-3 | B1 | A37 |
| T2-2 | B1 | A45 | T2-3 | B1 | A45 |
| T2-2 | B1 | A46 | T2-3 | B1 | A46 |
| T2-2 | B1 | A49 | T2-3 | B1 | A49 |
| T2-2 | B1 | A54 | T2-3 | B1 | A54 |
| T2-2 | B1 | A66 | T2-3 | B1 | A66 |
| T2-2 | B1 | A67 | T2-3 | B1 | A67 |

TABLE 5

| T2-2 | B1 | A68 | T2-3 | B1 | A68 |
|---|---|---|---|---|---|
| T2-2 | B1 | A69 | T2-3 | B1 | A69 |
| T2-2 | B1 | A70 | T2-3 | B1 | A70 |
| T2-2 | B1 | A76 | T2-3 | B1 | A76 |
| T2-2 | B1 | A77 | T2-3 | B1 | A77 |
| T2-2 | B1 | A78 | T2-3 | B1 | A78 |
| T2-2 | B1 | A106 | T2-3 | B1 | A106 |
| T2-2 | B1 | A110 | T2-3 | B1 | A110 |
| T2-4 | B1 | A2 | T2-5 | B1 | A2 |
| T2-4 | B1 | A5 | T2-5 | B1 | A5 |
| T2-4 | B1 | A35 | T2-5 | B1 | A35 |
| T2-4 | B1 | A37 | T2-5 | B1 | A37 |
| T2-4 | B1 | A45 | T2-5 | B1 | A45 |
| T2-4 | B1 | A46 | T2-5 | B1 | A46 |
| T2-4 | B1 | A49 | T2-5 | B1 | A49 |
| T2-4 | B1 | A54 | T2-5 | B1 | A54 |
| T2-4 | B1 | A66 | T2-5 | B1 | A66 |
| T2-4 | B1 | A67 | T2-5 | B1 | A67 |
| T2-4 | B1 | A68 | T2-5 | B1 | A68 |
| T2-4 | B1 | A69 | T2-5 | B1 | A69 |
| T2-4 | B1 | A70 | T2-5 | B1 | A70 |
| T2-4 | B1 | A76 | T2-5 | B1 | A76 |
| T2-4 | B1 | A77 | T2-5 | B1 | A77 |
| T2-4 | B1 | A78 | T2-5 | B1 | A78 |
| T2-4 | B1 | A106 | T2-5 | B1 | A106 |
| T2-4 | B1 | A110 | T2-5 | B1 | A110 |
| T5-1 | B1 | A2 | T7-1 | B1 | A2 |
| T5-1 | B1 | A5 | T7-1 | B1 | A5 |
| T5-1 | B1 | A35 | T7-1 | B1 | A35 |
| T5-1 | B1 | A37 | T7-1 | B1 | A37 |
| T5-1 | B1 | A45 | T7-1 | B1 | A45 |
| T5-1 | B1 | A46 | T7-1 | B1 | A46 |
| T5-1 | B1 | A49 | T7-1 | B1 | A49 |
| T5-1 | B1 | A54 | T7-1 | B1 | A54 |
| T5-1 | B1 | A66 | T7-1 | B1 | A66 |
| T5-1 | B1 | A67 | T7-1 | B1 | A67 |
| T5-1 | B1 | A68 | T7-1 | B1 | A68 |
| T5-1 | B1 | A69 | T7-1 | B1 | A69 |
| T5-1 | B1 | A70 | T7-1 | B1 | A70 |
| T5-1 | B1 | A76 | T7-1 | B1 | A76 |
| T5-1 | B1 | A77 | T7-1 | B1 | A77 |
| T5-1 | B1 | A78 | T7-1 | B1 | A78 |

TABLE 5-continued

| T5-1 | B1 | A106 | T7-1 | B1 | A106 |
|---|---|---|---|---|---|
| T5-1 | B1 | A110 | T7-1 | B1 | A110 |

TABLE 6

| T1-1 | B4 | A2 | T2-1 | B4 | A2 |
|---|---|---|---|---|---|
| T1-1 | B4 | A5 | T2-1 | B4 | A5 |
| T1-1 | B4 | A35 | T2-1 | B4 | A35 |
| T1-1 | B4 | A37 | T2-1 | B4 | A37 |
| T1-1 | B4 | A45 | T2-1 | B4 | A45 |
| T1-1 | B4 | A46 | T2-1 | B4 | A46 |
| T1-1 | B4 | A49 | T2-1 | B4 | A49 |
| T1-1 | B4 | A54 | T2-1 | B4 | A54 |
| T1-1 | B4 | A66 | T2-1 | B4 | A66 |
| TI-1 | B4 | A67 | T2-1 | B4 | A67 |
| T1-1 | B4 | A68 | T2-1 | B4 | A68 |
| T1-1 | B4 | A69 | T2-1 | B4 | A69 |
| T1-1 | B4 | A70 | T2-1 | B4 | A70 |
| T1-1 | B4 | A76 | T2-1 | B4 | A76 |
| T1-1 | B4 | A77 | T2-1 | B4 | A77 |
| T1-1 | B4 | A78 | T2-1 | B4 | A78 |
| T1-1 | B4 | A106 | T2-1 | B4 | A106 |
| T1-1 | B4 | A110 | T2-1 | B4 | A110 |
| T2-2 | B4 | A2 | T2-3 | B4 | A2 |
| T2-2 | B4 | A5 | T2-3 | B4 | A5 |
| T2-2 | B4 | A35 | T2-3 | B4 | A35 |
| T2-2 | B4 | A37 | T2-3 | B4 | A37 |
| T2-2 | B4 | A45 | T2-3 | B4 | A45 |
| T2-2 | B4 | A46 | T2-3 | B4 | A46 |
| T2-2 | B4 | A49 | T2-3 | B4 | A49 |
| T2-2 | B4 | A54 | T2-3 | B4 | A54 |
| T2-2 | B4 | A66 | T2-3 | B4 | A66 |
| T2-2 | B4 | A67 | T2-3 | B4 | A67 |
| T2-2 | B4 | A68 | T2-3 | B4 | A68 |
| T2-2 | B4 | A69 | T2-3 | B4 | A69 |
| T2-2 | B4 | A70 | T2-3 | B4 | A70 |
| T2-2 | B4 | A76 | T2-3 | B4 | A76 |
| T2-2 | B4 | A77 | T2-3 | B4 | A77 |
| T2-2 | B4 | A78 | T2-3 | B4 | A78 |
| T2-2 | B4 | A106 | T2-3 | B4 | A106 |

TABLE 6-continued

| | | | | | |
|---|---|---|---|---|---|
| T2-2 | B4 | A110 | T2-3 | B4 | A110 |
| T2-4 | B4 | A2 | T2-5 | B4 | A2 |
| T2-4 | B4 | A5 | T2-5 | B4 | A5 |
| T2-4 | B4 | A35 | T2-5 | B4 | A35 |
| T2-4 | B4 | A37 | T2-5 | B4 | A37 |
| T2-4 | B4 | A45 | T2-5 | B4 | A45 |
| T2-4 | B4 | A46 | T2-5 | B4 | A46 |
| T2-4 | B4 | A49 | T2-5 | B4 | A49 |
| T2-4 | B4 | A54 | T2-5 | B4 | A54 |

TABLE 7

| | | | | | |
|---|---|---|---|---|---|
| T2-4 | B4 | A66 | T2-5 | B4 | A66 |
| T2-4 | B4 | A67 | T2-5 | B4 | A67 |
| T2-4 | B4 | A68 | T2-5 | B4 | A68 |
| T2-4 | B4 | A69 | T2-5 | B4 | A69 |
| T2-4 | B4 | A70 | T2-5 | B4 | A70 |
| T2-4 | B4 | A76 | T2-5 | B4 | A76 |
| T2-4 | B4 | A77 | T2-5 | B4 | A77 |
| T2-4 | B4 | A78 | T2-5 | B4 | A78 |
| T2-4 | B4 | A106 | T2-5 | B4 | A106 |
| T2-4 | B4 | A110 | T2-5 | B4 | A110 |
| T5-1 | B4 | A2 | T7-1 | B4 | A2 |
| T5-1 | B4 | A5 | T7-1 | B4 | A5 |
| T5-1 | B4 | A35 | T7-1 | B4 | A35 |
| T5-1 | B4 | A37 | T7-1 | B4 | A37 |
| T5-1 | B4 | A45 | T7-1 | B4 | A45 |
| T5-1 | B4 | A46 | T7-1 | B4 | A46 |
| T5-1 | B4 | A49 | T7-1 | B4 | A49 |
| T5-1 | B4 | A54 | T7-1 | B4 | A54 |
| T5-1 | B4 | A66 | T7-1 | B4 | A66 |
| T5-1 | B4 | A67 | T7-1 | B4 | A67 |
| T5-1 | B4 | A68 | T7-1 | B4 | A68 |
| T5-1 | B4 | A69 | T7-1 | B4 | A69 |
| T5-1 | B4 | A70 | T7-1 | B4 | A70 |
| T5-1 | B4 | A76 | T7-1 | B4 | A76 |
| T5-1 | B4 | A77 | T7-1 | B4 | A77 |
| T5-1 | B4 | A78 | T7-1 | B4 | A78 |
| T5-1 | B4 | A106 | T7-1 | B4 | A106 |
| T5-1 | B4 | A110 | T7-1 | B4 | A110 |
| T1-1 | B7 | A2 | T2-1 | B7 | A2 |
| T1-1 | B7 | A5 | T2-1 | B7 | A5 |
| T1-1 | B7 | A35 | T2-1 | B7 | A35 |
| T1-1 | B7 | A37 | T2-1 | B7 | A37 |
| T1-1 | B7 | A45 | T2-1 | B7 | A45 |
| T1-1 | B7 | A46 | T2-1 | B7 | A46 |
| T1-1 | B7 | A49 | T2-1 | B7 | A49 |
| T1-1 | B7 | A54 | T2-1 | B7 | A54 |
| T1-1 | B7 | A66 | T2-1 | B7 | A66 |
| T1-1 | B7 | A67 | T2-1 | B7 | A67 |
| T1-1 | B7 | A68 | T2-1 | B7 | A68 |
| T1-1 | B7 | A69 | T2-1 | B7 | A69 |
| T1-1 | B7 | A70 | T2-1 | B7 | A70 |
| T1-1 | B7 | A76 | T2-1 | B7 | A76 |
| T1-1 | B7 | A77 | T2-1 | B7 | A77 |
| T1-1 | B7 | A78 | T2-1 | B7 | A78 |

TABLE 8

| | | | | | |
|---|---|---|---|---|---|
| T1-1 | B7 | A106 | T2-1 | B7 | A106 |
| T1-1 | B7 | A110 | T2-1 | B7 | A110 |
| T2-2 | B7 | A2 | T2-3 | B7 | A2 |
| T2-2 | B7 | A5 | T2-3 | B7 | A5 |
| T2-2 | B7 | A35 | T2-3 | B7 | A35 |
| T2-2 | B7 | A37 | T2-3 | B7 | A37 |
| T2-2 | B7 | A45 | T2-3 | B7 | A45 |
| T2-2 | B7 | A46 | T2-3 | B7 | A46 |
| T2-2 | B7 | A49 | T2-3 | B7 | A49 |
| T2-2 | B7 | A54 | T2-3 | B7 | A54 |
| T2-2 | B7 | A66 | T2-3 | B7 | A66 |
| T2-2 | B7 | A67 | T2-3 | B7 | A67 |
| T2-2 | B7 | A68 | T2-3 | B7 | A68 |

TABLE 8-continued

| | | | | | |
|---|---|---|---|---|---|
| T2-2 | B7 | A69 | T2-3 | B7 | A69 |
| T2-2 | B7 | A76 | T2-3 | B7 | A70 |
| T2-2 | B7 | A76 | T2-3 | B7 | A76 |
| T2-2 | B7 | A77 | T2-3 | B7 | A77 |
| T2-2 | B7 | A78 | T2-3 | B7 | A78 |
| T2-2 | B7 | A106 | T2-3 | B7 | A106 |
| T2-2 | B7 | A110 | T2-3 | B7 | A110 |
| T2-4 | B7 | A2 | T2-5 | B7 | A2 |
| T2-4 | B7 | A5 | T2-5 | B7 | A5 |
| T2-4 | B7 | A35 | T2-5 | B7 | A35 |
| T2-4 | B7 | A37 | T2-5 | B7 | A37 |
| T2-4 | B7 | A45 | T2-5 | B7 | A45 |
| T2-4 | B7 | A46 | T2-5 | B7 | A46 |
| T2-4 | B7 | A49 | T2-5 | B7 | A49 |
| T2-4 | B7 | A54 | T2-5 | B7 | A54 |
| T2-4 | B7 | A66 | T2-5 | B7 | A66 |
| T2-4 | B7 | A67 | T2-5 | B7 | A67 |
| T2-4 | B7 | A68 | T2-5 | B7 | A68 |
| T2-4 | B7 | A69 | T2-5 | B7 | A69 |
| T2-4 | B7 | A70 | T2-5 | B7 | A70 |
| T2-4 | B7 | A76 | T2-5 | B7 | A76 |
| T2-4 | B7 | A77 | T2-5 | B7 | A77 |
| T2-4 | B7 | A78 | T2-5 | B7 | A78 |
| T2-4 | B7 | A106 | T2-5 | B7 | A106 |
| T2-4 | B7 | A110 | T2-5 | B7 | A110 |
| T5-1 | B7 | A2 | T7-1 | B7 | A2 |
| T5-1 | B7 | A5 | T7-1 | B7 | A5 |
| T5-1 | B7 | A35 | T7-1 | B7 | A35 |
| T5-1 | B7 | A37 | T7-1 | B7 | A37 |
| T5-1 | B7 | A45 | T7-1 | B7 | A45 |

TABLE 9

| | | | | | |
|---|---|---|---|---|---|
| T5-1 | B7 | A46 | T7-1 | B7 | A46 |
| T5-1 | B7 | A49 | T7-1 | B7 | A49 |
| T5-1 | B7 | A54 | T7-1 | B7 | A54 |
| T5-1 | B7 | A66 | T7-1 | B7 | A66 |
| T5-1 | B7 | A67 | T7-1 | B7 | A67 |
| T5-1 | B7 | A68 | T7-1 | B7 | A68 |
| T5-1 | B7 | A69 | T7-1 | B7 | A69 |
| T5-1 | B7 | A70 | T7-1 | B7 | A70 |
| T5-1 | B7 | A76 | T7-1 | B7 | A76 |
| T5-1 | B7 | A77 | T7-1 | B7 | A77 |
| T5-1 | B7 | A78 | T7-1 | B7 | A78 |
| T5-1 | B7 | A106 | T7-1 | B7 | A106 |
| T5-1 | B7 | A110 | T7-1 | B7 | A110 |
| T1-1 | B8 | A2 | T2-1 | B8 | A2 |
| T1-1 | B8 | A5 | T2-1 | B8 | A5 |
| T1-1 | B8 | A35 | T2-1 | B8 | A35 |
| T1-1 | B8 | A37 | T2-1 | B8 | A37 |
| T1-1 | B8 | A45 | T2-1 | B8 | A45 |
| T1-1 | B8 | A46 | T2-1 | B8 | A46 |
| T1-1 | B8 | A49 | T2-1 | B8 | A49 |
| T1-1 | B8 | A54 | T2-1 | B8 | A54 |
| T1-1 | B8 | A66 | T2-1 | B8 | A66 |
| T1-1 | B8 | A67 | T2-1 | B8 | A67 |
| T1-1 | B8 | A68 | T2-1 | B8 | A68 |
| T1-1 | B8 | A69 | T2-1 | B8 | A69 |
| T1-1 | B8 | A70 | T2-1 | B8 | A70 |
| T1-1 | B8 | A76 | T2-1 | B8 | A76 |
| T1-1 | B8 | A77 | T2-1 | B8 | A77 |
| T1-1 | B8 | A78 | T2-1 | B8 | A78 |
| T1-1 | B8 | A106 | T2-1 | B8 | A106 |
| T1-1 | B8 | A110 | T2-1 | B8 | A110 |
| T2-2 | B8 | A2 | T2-3 | B8 | A2 |
| T2-2 | B8 | A5 | T2-3 | B8 | A5 |
| T2-2 | B8 | A35 | T2-3 | B8 | A35 |
| T2-2 | B8 | A37 | T2-3 | B8 | A37 |
| T2-2 | B8 | A45 | T2-3 | B8 | A45 |
| T2-2 | B8 | A46 | T2-3 | B8 | A46 |
| T2-2 | B8 | A49 | T2-3 | B8 | A49 |
| T2-2 | B8 | A54 | T2-3 | B8 | A54 |
| T2-2 | B8 | A66 | T2-3 | B8 | A66 |
| T2-2 | B8 | A67 | T2-3 | B8 | A67 |

TABLE 9-continued

| | | | | | |
|---|---|---|---|---|---|
| T2-2 | B8 | A68 | T2-3 | B8 | A68 |
| T2-2 | B8 | A69 | T2-3 | B8 | A69 |

TABLE 10

| | | | | | |
|---|---|---|---|---|---|
| T2-2 | B8 | A70 | T2-3 | B8 | A70 |
| T2-2 | B8 | A76 | T2-3 | B8 | A76 |
| T2-2 | B8 | A77 | T2-3 | B8 | A77 |
| T2-2 | B8 | A78 | T2-3 | B8 | A78 |
| T2-2 | B8 | A106 | T2-3 | B8 | A106 |
| T2-2 | B8 | A110 | T2-3 | B8 | A110 |
| T2-4 | B8 | A2 | T2-5 | B8 | A2 |
| T2-4 | B8 | A5 | T2-5 | B8 | A5 |
| T2-4 | B8 | A35 | T2-5 | B8 | A35 |
| T2-4 | B8 | A37 | T2-5 | B8 | A37 |
| T2-4 | B8 | A45 | T2-5 | B8 | A45 |
| T2-4 | B8 | A46 | T2-5 | B8 | A46 |
| T2-4 | B8 | A49 | T2-5 | B8 | A49 |
| T2-4 | B8 | A54 | T2-5 | B8 | A54 |
| T2-4 | B8 | A66 | T2-5 | B8 | A66 |
| T2-4 | B8 | A67 | T2-5 | B8 | A67 |
| T2-4 | B8 | A68 | T2-5 | B8 | A68 |
| T2-4 | B8 | A69 | T2-5 | B8 | A69 |
| T2-4 | B8 | A70 | T2-5 | B8 | A70 |
| T2-4 | B8 | A76 | T2-5 | B8 | A76 |
| T2-4 | B8 | A77 | T2-5 | B8 | A77 |
| T2-4 | B8 | A78 | T2-5 | B8 | A78 |
| T2-4 | B8 | A106 | T2-5 | B8 | A106 |
| T2-4 | B8 | A110 | T2-5 | B8 | A110 |
| T5-1 | B8 | A2 | T7-1 | B8 | A2 |
| T5-1 | B8 | A5 | T7-1 | B8 | A5 |
| T5-1 | B8 | A35 | T7-1 | B8 | A35 |
| T5-1 | B8 | A37 | T7-1 | B8 | A37 |
| T5-1 | B8 | A45 | T7-1 | B8 | A45 |
| T5-1 | B8 | A46 | T7-1 | B8 | A46 |
| T5-1 | B8 | A49 | T7-1 | B8 | A49 |
| T5-1 | B8 | A54 | T7-1 | B8 | A54 |
| T5-1 | B8 | A66 | T7-1 | B8 | A66 |
| T5-1 | B8 | A67 | T7-1 | B8 | A67 |
| T5-1 | B8 | A68 | T7-1 | B8 | A68 |
| T5-1 | B8 | A69 | T7-1 | B8 | A69 |
| T5-1 | B8 | A76 | T7-1 | B8 | A70 |
| T5-1 | B8 | A76 | T7-1 | B8 | A76 |
| T5-1 | B8 | A77 | T7-1 | B8 | A77 |
| T5-1 | B8 | A78 | T7-1 | B8 | A78 |
| T5-1 | B8 | A106 | T7-1 | B8 | A106 |
| T5-1 | B8 | A110 | T7-1 | B8 | A110 |
| T1-1 | B9 | A2 | T2-1 | B9 | A2 |

TABLE 11

| | | | | | |
|---|---|---|---|---|---|
| T1-1 | B9 | A5 | T2-1 | B9 | A5 |
| T1-1 | B9 | A35 | T2-1 | B9 | A35 |
| T1-1 | B9 | A37 | T2-1 | B9 | A37 |
| T1-1 | B9 | A45 | T2-1 | B9 | A45 |
| T1-1 | B9 | A46 | T2-1 | B9 | A46 |
| T1-1 | B9 | A49 | T2-1 | B9 | A49 |
| T1-1 | B9 | A54 | T2-1 | B9 | A54 |
| T1-1 | B9 | A66 | T2-1 | B9 | A66 |
| T1-1 | B9 | A67 | T2-1 | B9 | A67 |
| T1-1 | B9 | A68 | T2-1 | B9 | A68 |
| T1-1 | B9 | A69 | T2-1 | B9 | A69 |
| T1-1 | B9 | A70 | T2-1 | B9 | A70 |
| T1-1 | B9 | A76 | T2-1 | B9 | A76 |
| T1-1 | B9 | A77 | T2-1 | B9 | A77 |
| T1-1 | B9 | A78 | T2-1 | B9 | A78 |
| T1-1 | B9 | A106 | T2-1 | B9 | A106 |
| T1-1 | B9 | A110 | T2-1 | B9 | A110 |
| T2-2 | B9 | A2 | T2-3 | B9 | A2 |
| T2-2 | B9 | A5 | T2-3 | B9 | A5 |
| T2-2 | B9 | A35 | T2-3 | B9 | A35 |
| T2-2 | B9 | A37 | T2-3 | B9 | A37 |

TABLE 11-continued

| | | | | | |
|---|---|---|---|---|---|
| T2-2 | B9 | A45 | T2-3 | B9 | A45 |
| T2-2 | B9 | A46 | T2-3 | B9 | A46 |
| T2-2 | B9 | A49 | T2-3 | B9 | A49 |
| T2-2 | B9 | A54 | T2-3 | B9 | A54 |
| T2-2 | B9 | A66 | T2-3 | B9 | A66 |
| T2-2 | B9 | A67 | T2-3 | B9 | A67 |
| T2-2 | B9 | A68 | T2-3 | B9 | A68 |
| T2-2 | B9 | A69 | T2-3 | B9 | A69 |
| T2-2 | B9 | A70 | T2-3 | B9 | A70 |
| T2-2 | B9 | A76 | T2-3 | B9 | A76 |
| T2-2 | B9 | A77 | T2-3 | B9 | A77 |
| T2-2 | B9 | A78 | T2-3 | B9 | A78 |
| T2-2 | B9 | A106 | T2-3 | B9 | A106 |
| T2-2 | B9 | A110 | T2-3 | B9 | A110 |
| T2-4 | B9 | A2 | T2-5 | B9 | A2 |
| T2-4 | B9 | A5 | T2-5 | B9 | A5 |
| T2-4 | B9 | A35 | T2-5 | B9 | A35 |
| T2-4 | B9 | A37 | T2-5 | B9 | A37 |
| T2-4 | B9 | A45 | T2-5 | B9 | A45 |
| T2-4 | B9 | A46 | T2-5 | B9 | A46 |
| T2-4 | B9 | A49 | T2-5 | B9 | A49 |
| T2-4 | B9 | A54 | T2-5 | B9 | A54 |

TABLE 12

| | | | | | |
|---|---|---|---|---|---|
| T2-4 | B9 | A66 | T2-5 | B9 | A66 |
| T2-4 | B9 | A67 | T2-5 | B9 | A67 |
| T2-4 | B9 | A68 | T2-5 | B9 | A68 |
| T2-4 | B9 | A69 | T2-5 | B9 | A69 |
| T2-4 | B9 | A70 | T2-5 | B9 | A70 |
| T2-4 | B9 | A76 | T2-5 | B9 | A76 |
| T2-4 | B9 | A77 | T2-5 | B9 | A77 |
| T2-4 | B9 | A78 | T2-5 | B9 | A78 |
| T2-4 | B9 | A106 | T2-5 | B9 | A106 |
| T2-4 | B9 | A110 | T2-5 | B9 | A110 |
| T5-1 | B9 | A2 | T7-1 | B9 | A2 |
| T5-1 | B9 | A5 | T7-1 | B9 | A5 |
| T5-1 | B9 | A35 | T7-1 | B9 | A35 |
| T5-1 | B9 | A37 | T7-1 | B9 | A37 |
| T5-1 | B9 | A45 | T7-1 | B9 | A45 |
| T5-1 | B9 | A46 | T7-1 | B9 | A46 |
| T5-1 | B9 | A49 | T7-1 | B9 | A49 |
| T5-1 | B9 | A54 | T7-1 | B9 | A54 |
| T5-1 | B9 | A66 | T7-1 | B9 | A66 |
| T5-1 | B9 | A67 | T7-1 | B9 | A67 |
| T5-1 | B9 | A68 | T7-1 | B9 | A68 |
| T5-1 | B9 | A69 | T7-1 | B9 | A69 |
| T5-1 | B9 | A70 | T7-1 | B9 | A70 |
| T5-1 | B9 | A76 | T7-1 | B9 | A76 |
| T5-1 | B9 | A77 | T7-1 | B9 | A77 |
| T5-1 | B9 | A78 | T7-1 | B9 | A78 |
| T5-1 | B9 | A106 | T7-1 | B9 | A106 |
| T5-1 | B9 | A110 | T7-1 | B9 | A110 |
| T1-1 | B10 | A2 | T2-1 | B10 | A2 |
| T1-1 | B10 | A5 | T2-1 | B10 | A5 |
| T1-1 | B10 | A35 | T2-1 | B10 | A35 |
| T1-1 | B10 | A37 | T2-1 | B10 | A37 |
| T1-1 | B10 | A45 | T2-1 | B10 | A45 |
| T1-1 | B10 | A46 | T2-1 | B10 | A46 |
| T1-1 | B10 | A49 | T2-1 | B10 | A49 |
| T1-1 | B10 | A54 | T2-1 | B10 | A54 |
| T1-1 | B10 | A66 | T2-1 | B10 | A66 |
| T1-1 | B10 | A67 | T2-1 | B10 | A67 |
| T1-1 | B10 | A68 | T2-1 | B10 | A68 |
| T1-1 | B10 | A69 | T2-1 | B10 | A69 |
| T1-1 | B10 | A70 | T2-1 | B10 | A70 |
| T1-1 | B10 | A76 | T2-1 | B10 | A76 |
| T1-1 | B10 | A77 | T2-1 | B10 | A77 |
| T1-1 | B10 | A78 | T2-1 | B10 | A78 |

TABLE 13

| | | | | | |
|---|---|---|---|---|---|
| T1-1 | B10 | A106 | T2-1 | B10 | A106 |
| T1-1 | B10 | A110 | T2-1 | B10 | A110 |
| T2-2 | B10 | A2 | T2-3 | B10 | A2 |
| T2-2 | B10 | A5 | T2-3 | B10 | A5 |
| T2-2 | B10 | A35 | T2-3 | B10 | A35 |
| T2-2 | B10 | A37 | T2-3 | B10 | A37 |
| T2-2 | B10 | A45 | T2-3 | B10 | A45 |
| T2-2 | B10 | A46 | T2-3 | B10 | A46 |
| T2-2 | B10 | A49 | T2-3 | B10 | A49 |
| T2-2 | B10 | A54 | T2-3 | B10 | A54 |
| T2-2 | B10 | A66 | T2-3 | B10 | A66 |
| T2-2 | B10 | A67 | T2-3 | B10 | A67 |
| T2-2 | B10 | A68 | T2-3 | B10 | A68 |
| T2-2 | B10 | A69 | T2-3 | B10 | A69 |
| T2-2 | B10 | A70 | T2-3 | B10 | A70 |
| T2-2 | B10 | A76 | T2-3 | B10 | A76 |
| T2-2 | B10 | A77 | T2-3 | B10 | A77 |
| T2-2 | B10 | A78 | T2-3 | B10 | A78 |
| T2-2 | B10 | A106 | T2-3 | B10 | A106 |
| T2-2 | B10 | A110 | T2-3 | B10 | A110 |
| T2-4 | B10 | A2 | T2-5 | B10 | A2 |
| T2-4 | B10 | A5 | T2-5 | B10 | A5 |
| T2-4 | B10 | A35 | T2-5 | B10 | A35 |
| T2-4 | B10 | A37 | T2-5 | B10 | A37 |
| T2-4 | B10 | A45 | T2-5 | B10 | A45 |
| T2-4 | B10 | A46 | T2-5 | B10 | A46 |
| T2-4 | B10 | A49 | T2-5 | B10 | A49 |
| T2-4 | B10 | A54 | T2-5 | B10 | A54 |
| T2-4 | B10 | A66 | T2-5 | B10 | A66 |
| T2-4 | B10 | A67 | T2-5 | B10 | A67 |
| T2-4 | B10 | A68 | T2-5 | B10 | A68 |
| T2-4 | B10 | A69 | T2-5 | B10 | A69 |
| T2-4 | B10 | A70 | T2-5 | B10 | A70 |
| T2-4 | B10 | A76 | T2-5 | B10 | A76 |
| T2-4 | B10 | A77 | T2-5 | B10 | A77 |
| T2-4 | B10 | A78 | T2-5 | B10 | A78 |
| T2-4 | B10 | A106 | T2-5 | B10 | A106 |
| T2-4 | B10 | A110 | T2-5 | B10 | A110 |
| T5-1 | B10 | A2 | T7-1 | B10 | A2 |
| T5-1 | B10 | A5 | T7-1 | B10 | A5 |
| T5-1 | B10 | A35 | T7-1 | B10 | A35 |
| T5-1 | B10 | A37 | T7-1 | B10 | A37 |
| T5-1 | B10 | A45 | T7-1 | B10 | A45 |

TABLE 14

| | | | | | |
|---|---|---|---|---|---|
| T5-1 | B10 | A46 | T7-1 | B10 | A46 |
| T5-1 | B10 | A49 | T7-1 | B10 | A49 |
| T5-1 | B10 | A54 | T7-1 | B10 | A54 |
| T5-1 | B10 | A66 | T7-1 | B10 | A66 |
| T5-1 | B10 | A67 | T7-1 | B10 | A67 |
| T5-1 | B10 | A68 | T7-1 | B10 | A68 |
| T5-1 | B10 | A69 | T7-1 | B10 | A69 |
| T5-1 | B10 | A70 | T7-1 | B10 | A70 |
| T5-1 | B10 | A76 | T7-1 | B10 | A76 |
| T5-1 | B10 | A77 | T7-1 | B10 | A77 |
| T5-1 | B10 | A78 | T7-1 | B10 | A78 |
| T5-1 | B10 | A106 | T7-1 | B10 | A106 |
| T5-1 | B10 | A110 | T7-1 | B10 | A110 |
| T1-1 | B12 | A2 | T2-1 | B12 | A2 |
| T1-1 | B12 | A5 | T2-1 | B12 | A5 |
| T1-1 | B12 | A35 | T2-1 | B12 | A35 |
| T1-1 | B12 | A37 | T2-1 | B12 | A37 |
| T1-1 | B12 | A45 | T2-1 | B12 | A45 |
| T1-1 | B12 | A46 | T2-1 | B12 | A46 |
| T1-1 | B12 | A49 | T2-1 | B12 | A49 |
| T1-1 | B12 | A54 | T2-1 | B12 | A54 |
| T1-1 | B12 | A66 | T2-1 | B12 | A66 |
| T1-1 | B12 | A67 | T2-1 | B12 | A67 |
| T1-1 | B12 | A68 | T2-1 | B12 | A68 |
| T1-1 | B12 | A69 | T2-1 | B12 | A69 |
| T1-1 | B12 | A70 | T2-1 | B12 | A70 |
| T1-1 | B12 | A76 | T2-1 | B12 | A76 |
| T1-1 | B12 | A77 | T2-1 | B12 | A77 |
| T1-1 | B12 | A78 | T2-1 | B12 | A78 |

TABLE 14-continued

| | | | | | |
|---|---|---|---|---|---|
| T1-1 | B12 | A106 | T2-1 | B12 | A106 |
| T1-1 | B12 | A110 | T2-1 | B12 | A110 |
| T2-2 | B12 | A2 | T2-3 | B12 | A2 |
| T2-2 | B12 | A5 | T2-3 | B12 | A5 |
| T2-2 | B12 | A35 | T2-3 | B12 | A35 |
| T2-2 | B12 | A37 | T2-3 | B12 | A37 |
| T2-2 | B12 | A45 | T2-3 | B12 | A45 |
| T2-2 | B12 | A46 | T2-3 | B12 | A46 |
| T2-2 | B12 | A49 | T2-3 | B12 | A49 |
| T2-2 | B12 | A54 | T2-3 | B12 | A54 |
| T2-2 | B12 | A66 | T2-3 | B12 | A66 |
| T2-2 | B12 | A67 | T2-3 | B12 | A67 |
| T2-2 | B12 | A68 | T2-3 | B12 | A68 |
| T2-2 | B12 | A69 | T2-3 | B12 | A69 |

TABLE 15

| | | | | | |
|---|---|---|---|---|---|
| T2-2 | B12 | A70 | T2-3 | B12 | A70 |
| T2-2 | B12 | A76 | T2-3 | B12 | A76 |
| T2-2 | B12 | A77 | T2-3 | B12 | A77 |
| T2-2 | B12 | A78 | T2-3 | B12 | A78 |
| T2-2 | B12 | A106 | T2-3 | B12 | A106 |
| T2-2 | B12 | A110 | T2-3 | B12 | A110 |
| T2-4 | B12 | A2 | T2-5 | B12 | A2 |
| T2-4 | B12 | A5 | T2-5 | B12 | A5 |
| T2-4 | B12 | A35 | T2-5 | B12 | A35 |
| T2-4 | B12 | A37 | T2-5 | B12 | A37 |
| T2-4 | B12 | A45 | T2-5 | B12 | A45 |
| T2-4 | B12 | A46 | T2-5 | B12 | A46 |
| T2-4 | B12 | A49 | T2-5 | B12 | A49 |
| T2-4 | B12 | A54 | T2-5 | B12 | A54 |
| T2-4 | B12 | A66 | T2-5 | B12 | A66 |
| T2-4 | B12 | A67 | T2-5 | B12 | A67 |
| T2-4 | B12 | A68 | T2-5 | B12 | A68 |
| T2-4 | B12 | A69 | T2-5 | B12 | A69 |
| T2-4 | B12 | A70 | T2-5 | B12 | A70 |
| T2-4 | B12 | A76 | T2-5 | B12 | A76 |
| T2-4 | B12 | A77 | T2-5 | B12 | A77 |
| T2-4 | B12 | A78 | T2-5 | B12 | A78 |
| T2-4 | B12 | A106 | T2-5 | B12 | A106 |
| T2-4 | B12 | A110 | T2-5 | B12 | A110 |
| T5-1 | B12 | A2 | T7-1 | B12 | A2 |
| T5-1 | B12 | A5 | T7-1 | B12 | A5 |
| T5-1 | B12 | A35 | T7-1 | B12 | A35 |
| T5-1 | B12 | A37 | T7-1 | B12 | A37 |
| T5-1 | B12 | A45 | T7-1 | B12 | A45 |
| T5-1 | B12 | A46 | T7-1 | B12 | A46 |
| T5-1 | B12 | A49 | T7-1 | B12 | A49 |
| T5-1 | B12 | A54 | T7-1 | B12 | A54 |
| T5-1 | B12 | A66 | T7-1 | B12 | A66 |
| T5-1 | B12 | A67 | T7-1 | B12 | A67 |
| T5-1 | B12 | A68 | T7-1 | B12 | A68 |
| T5-1 | B12 | A69 | T7-1 | B12 | A69 |
| T5-1 | B12 | A70 | T7-1 | B12 | A70 |
| T5-1 | B12 | A76 | T7-1 | B12 | A76 |
| T5-1 | B12 | A77 | T7-1 | B12 | A77 |
| T5-1 | B12 | A78 | T7-1 | B12 | A78 |
| T5-1 | B12 | A106 | T7-1 | B12 | A106 |
| T5-1 | B12 | A110 | T7-1 | B12 | A110 |
| T1-1 | B14 | A2 | T2-1 | B14 | A2 |

TABLE 16

| | | | | | |
|---|---|---|---|---|---|
| T1-1 | B14 | A5 | T2-1 | B14 | A5 |
| T1-1 | B14 | A35 | T2-1 | B14 | A35 |
| T1-1 | B14 | A37 | T2-1 | B14 | A37 |
| T1-1 | B14 | A45 | T2-1 | B14 | A45 |
| T1-1 | B14 | A46 | T2-1 | B14 | A46 |
| T1-1 | B14 | A49 | T2-1 | B14 | A49 |
| T1-1 | B14 | A54 | T2-1 | B14 | A54 |
| T1-1 | B14 | A66 | T2-1 | B14 | A66 |
| T1-1 | B14 | A67 | T2-1 | B14 | A67 |

TABLE 16-continued

| | | | | | |
|---|---|---|---|---|---|
| T1-1 | B14 | A68 | T2-1 | B14 | A68 |
| T1-1 | B14 | A69 | T2-1 | B14 | A69 |
| T1-1 | B14 | A70 | T2-1 | B14 | A70 |
| T1-1 | B14 | A76 | T2-1 | B14 | A76 |
| T1-1 | B14 | A77 | T2-1 | B14 | A77 |
| T1-1 | B14 | A78 | T2-1 | B14 | A78 |
| T1-1 | B14 | A106 | T2-1 | B14 | A106 |
| T1-1 | B14 | A110 | T2-1 | B14 | A110 |
| T2-2 | B14 | A2 | T2-3 | B14 | A2 |
| T2-2 | B14 | A5 | T2-3 | B14 | A5 |
| T2-2 | B14 | A35 | T2-3 | B14 | A35 |
| T2-2 | B14 | A37 | T2-3 | B14 | A37 |
| T2-2 | B14 | A45 | T2-3 | B14 | A45 |
| T2-2 | B14 | A46 | T2-3 | B14 | A46 |
| T2-2 | B14 | A49 | T2-3 | B14 | A49 |
| T2-2 | B14 | A54 | T2-3 | B14 | A54 |
| T2-2 | B14 | A66 | T2-3 | B14 | A66 |
| T2-2 | B14 | A67 | T2-3 | B14 | A67 |
| T2-2 | B14 | A68 | T2-3 | B14 | A68 |
| T2-2 | B14 | A69 | T2-3 | B14 | A69 |
| T2-2 | B14 | A70 | T2-3 | B14 | A70 |
| T2-2 | B14 | A76 | T2-3 | B14 | A76 |
| T2-2 | B14 | A77 | T2-3 | B14 | A77 |
| T2-2 | B14 | A78 | T2-3 | B14 | A78 |
| T2-2 | B14 | A106 | T2-3 | B14 | A106 |
| T2-2 | B14 | A110 | T2-3 | B14 | A110 |
| T2-4 | B14 | A2 | T2-5 | B14 | A2 |
| T2-4 | B14 | A5 | T2-5 | B14 | A5 |
| T2-4 | B14 | A35 | T2-5 | B14 | A35 |
| T2-4 | B14 | A37 | T2-5 | B14 | A37 |
| T2-4 | B14 | A45 | T2-5 | B14 | A45 |
| T2-4 | B14 | A46 | T2-5 | B14 | A46 |
| T2-4 | B14 | A49 | T2-5 | B14 | A49 |
| T2-4 | B14 | A54 | T2-5 | B14 | A54 |

TABLE 17

| | | | | | |
|---|---|---|---|---|---|
| T2-4 | B14 | A66 | T2-5 | B14 | A66 |
| T2-4 | B14 | A67 | T2-5 | B14 | A67 |
| T2-4 | B14 | A68 | T2-5 | B14 | A68 |
| T2-4 | B14 | A69 | T2-5 | B14 | A69 |
| T2-4 | B14 | A70 | T2-5 | B14 | A70 |
| T2-4 | B14 | A76 | T2-5 | B14 | A76 |
| T2-4 | B14 | A77 | T2-5 | B14 | A77 |
| T2-4 | B14 | A78 | T2-5 | B14 | A78 |
| T2-4 | B14 | A106 | T2-5 | B14 | A106 |
| T2-4 | B14 | A110 | T2-5 | B14 | A110 |
| T5-1 | B14 | A2 | T7-1 | B14 | A2 |
| T5-1 | B14 | A5 | T7-1 | B14 | A5 |
| T5-1 | B14 | A35 | T7-1 | B14 | A35 |
| T5-1 | B14 | A37 | T7-1 | B14 | A37 |
| T5-1 | B14 | A45 | T7-1 | B14 | A45 |
| T5-1 | B14 | A46 | T7-1 | B14 | A46 |
| T5-1 | B14 | A49 | T7-1 | B14 | A49 |
| T5-1 | B14 | A54 | T7-1 | B14 | A54 |
| T5-1 | B14 | A66 | T7-1 | B14 | A66 |
| T5-1 | B14 | A67 | T7-1 | B14 | A67 |
| T5-1 | B14 | A68 | T7-1 | B14 | A68 |
| T5-1 | B14 | A69 | T7-1 | B14 | A69 |
| T5-1 | B14 | A70 | T7-1 | B14 | A70 |
| T5-1 | B14 | A76 | T7-1 | B14 | A76 |
| T5-1 | B14 | A77 | T7-1 | B14 | A77 |
| T5-1 | B14 | A78 | T7-1 | B14 | A78 |
| T5-1 | B14 | A106 | T7-1 | B14 | A106 |
| T5-1 | B14 | A110 | T7-1 | B14 | A110 |
| T1-1 | B16 | A2 | T2-1 | B16 | A2 |
| T1-1 | B16 | A5 | T2-1 | B16 | A5 |
| T1-1 | B16 | A35 | T2-1 | B16 | A35 |
| T1-1 | B16 | A37 | T2-1 | B16 | A37 |
| T1-1 | B16 | A45 | T2-1 | B16 | A45 |
| T1-1 | B16 | A46 | T2-1 | B16 | A46 |
| T1-1 | B16 | A49 | T2-1 | B16 | A49 |
| T1-1 | B16 | A54 | T2-1 | B16 | A54 |
| T1-1 | B16 | A66 | T2-1 | B16 | A66 |
| T1-1 | B16 | A67 | T2-1 | B16 | A67 |

TABLE 17-continued

| | | | | | |
|---|---|---|---|---|---|
| T1-1 | B16 | A68 | T2-1 | B16 | A68 |
| T1-1 | B16 | A69 | T2-1 | B16 | A69 |
| T1-1 | B16 | A70 | T2-1 | B16 | A70 |
| T1-1 | B16 | A76 | T2-1 | B16 | A76 |
| T1-1 | B16 | A77 | T2-1 | B16 | A77 |

TABLE 18

| | | | | | |
|---|---|---|---|---|---|
| T1-1 | B16 | A78 | T2-1 | B16 | A78 |
| T1-1 | B16 | A106 | T2-1 | B16 | A106 |
| T1-1 | B16 | A110 | T2-1 | B16 | A110 |
| T2-2 | B16 | A2 | T2-3 | B16 | A2 |
| T2-2 | B16 | A5 | T2-3 | B16 | A5 |
| T2-2 | B16 | A35 | T2-3 | B16 | A35 |
| T2-2 | B16 | A37 | T2-3 | B16 | A37 |
| T2-2 | B16 | A45 | T2-3 | B16 | A45 |
| T2-2 | B16 | A46 | T2-3 | B16 | A46 |
| T2-2 | B16 | A49 | T2-3 | B16 | A49 |
| T2-2 | B16 | A54 | T2-3 | B16 | A54 |
| T2-2 | B16 | A66 | T2-3 | B16 | A66 |
| T2-2 | B16 | A67 | T2-3 | B16 | A67 |
| T2-2 | B16 | A68 | T2-3 | B16 | A68 |
| T2-2 | B16 | A69 | T2-3 | B16 | A69 |
| T2-2 | B16 | A70 | T2-3 | B16 | A70 |
| T2-2 | B16 | A76 | T2-3 | B16 | A76 |
| T2-2 | B16 | A77 | T2-3 | B16 | A77 |
| T2-2 | B16 | A78 | T2-3 | B16 | A78 |
| T2-2 | B16 | A106 | T2-3 | B16 | A106 |
| T2-2 | B16 | A110 | T2-3 | B16 | A110 |
| T2-4 | B16 | A2 | T2-5 | B16 | A2 |
| T2-4 | B16 | A5 | T2-5 | B16 | A5 |
| T2-4 | B16 | A35 | T2-5 | B16 | A35 |
| T2-4 | B16 | A37 | T2-5 | B16 | A37 |
| T2-4 | B16 | A45 | T2-5 | B16 | A45 |
| T2-4 | B16 | A46 | T2-5 | B16 | A46 |
| T2-4 | B16 | A49 | T2-5 | B16 | A49 |
| T2-4 | B16 | A54 | T2-5 | B16 | A54 |
| T2-4 | B16 | A66 | T2-5 | B16 | A66 |
| T2-4 | B16 | A67 | T2-5 | B16 | A67 |
| T2-4 | B16 | A68 | T2-5 | B16 | A68 |
| T2-4 | B16 | A69 | T2-5 | B16 | A69 |
| T2-4 | B16 | A70 | T2-5 | B16 | A70 |
| T2-4 | B16 | A76 | T2-5 | B16 | A76 |
| T2-4 | B16 | A77 | T2-5 | B16 | A77 |
| T2-4 | B16 | A78 | T2-5 | B16 | A78 |
| T2-4 | B16 | A106 | T2-5 | B16 | A106 |
| T2-4 | B16 | A110 | T2-5 | B16 | A110 |
| T5-1 | B16 | A2 | T7-1 | B16 | A2 |
| T5-1 | B16 | A5 | T7-1 | B16 | A5 |
| T5-1 | B16 | A35 | T7-1 | B16 | A35 |
| T5-1 | B16 | A37 | T7-1 | B16 | A37 |

TABLE 19

| | | | | | |
|---|---|---|---|---|---|
| T5-1 | B16 | A45 | T7-1 | B16 | A45 |
| T5-1 | B16 | A46 | T7-1 | B16 | A46 |
| T5-1 | B16 | A49 | T7-1 | B16 | A49 |
| T5-1 | B16 | A54 | T7-1 | B16 | A54 |
| T5-1 | B16 | A66 | T7-1 | B16 | A66 |
| T5-1 | B16 | A67 | T7-1 | B16 | A67 |
| T5-1 | B16 | A68 | T7-1 | B16 | A68 |
| T5-1 | B16 | A69 | T7-1 | B16 | A69 |
| T5-1 | B16 | A70 | T7-1 | B16 | A70 |
| T5-1 | B16 | A76 | T7-1 | B16 | A76 |
| T5-1 | B16 | A77 | T7-1 | B16 | A77 |
| T5-1 | B16 | A78 | T7-1 | B16 | A78 |
| T5-1 | B16 | A106 | T7-1 | B16 | A106 |
| T5-1 | B16 | A110 | T7-1 | B16 | A110 |
| T1-1 | B17 | A2 | T2-1 | B17 | A2 |
| T1-1 | B17 | A5 | T2-1 | B17 | A5 |
| T1-1 | B17 | A35 | T2-1 | B17 | A35 |
| T1-1 | B17 | A37 | T2-1 | B17 | A37 |

TABLE 19-continued

| | | | | | |
|---|---|---|---|---|---|
| T1-1 | B17 | A45 | T2-1 | B17 | A45 |
| T1-1 | B17 | A46 | T2-1 | B17 | A46 |
| T1-1 | B17 | A49 | T2-1 | B17 | A49 |
| T1-1 | B17 | A54 | T2-1 | B17 | A54 |
| T1-1 | B17 | A66 | T2-1 | B17 | A66 |
| T1-1 | B17 | A67 | T2-1 | B17 | A67 |
| T1-1 | B17 | A68 | T2-1 | B17 | A68 |
| T1-1 | B17 | A69 | T2-1 | B17 | A69 |
| T1-1 | B17 | A70 | T2-1 | B17 | A70 |
| T1-1 | B17 | A76 | T2-1 | B17 | A76 |
| T1-1 | B17 | A77 | T2-1 | B17 | A77 |
| T1-1 | B17 | A78 | T2-1 | B17 | A78 |
| T1-1 | B17 | A106 | T2-1 | B17 | A106 |
| T1-1 | B17 | A110 | T2-1 | B17 | A110 |
| T2-2 | B17 | A2 | T2-3 | B17 | A2 |
| T2-2 | B17 | A5 | T2-3 | B17 | A5 |
| T2-2 | B17 | A35 | T2-3 | B17 | A35 |
| T2-2 | B17 | A37 | T2-3 | B17 | A37 |
| T2-2 | B17 | A45 | T2-3 | B17 | A45 |
| T2-2 | B17 | A46 | T2-3 | B17 | A46 |
| T2-2 | B17 | A49 | T2-3 | B17 | A49 |
| T2-2 | B17 | A54 | T2-3 | B17 | A54 |
| T2-2 | B17 | A66 | T2-3 | B17 | A66 |
| T2-2 | B17 | A67 | T2-3 | B17 | A67 |
| T2-2 | B17 | A68 | T2-3 | B17 | A68 |

TABLE 20

| | | | | | |
|---|---|---|---|---|---|
| T2-2 | B17 | A69 | T2-3 | B17 | A69 |
| T2-2 | B17 | A70 | T2-3 | B17 | A70 |
| T2-2 | B17 | A76 | T2-3 | B17 | A76 |
| T2-2 | B17 | A77 | T2-3 | B17 | A77 |
| T2-2 | B17 | A78 | T2-3 | B17 | A78 |
| T2-2 | B17 | A106 | T2-3 | B17 | A106 |
| T2-2 | B17 | A110 | T2-3 | B17 | A110 |
| T2-4 | B17 | A2 | T2-5 | B17 | A2 |
| T2-4 | B17 | A5 | T2-5 | B17 | A5 |
| T2-4 | B17 | A35 | T2-5 | B17 | A35 |
| T2-4 | B17 | A37 | T2-5 | B17 | A37 |
| T2-4 | B17 | A45 | T2-5 | B17 | A45 |
| T2-4 | B17 | A46 | T2-5 | B17 | A46 |
| T2-4 | B17 | A49 | T2-5 | B17 | A49 |
| T2-4 | B17 | A54 | T2-5 | B17 | A54 |
| T2-4 | B17 | A66 | T2-5 | B17 | A66 |
| T2-4 | B17 | A67 | T2-5 | B17 | A67 |
| T2-4 | B17 | A68 | T2-5 | B17 | A68 |
| T2-4 | B17 | A69 | T2-5 | B17 | A69 |
| T2-4 | B17 | A70 | T2-5 | B17 | A70 |
| T2-4 | B17 | A76 | T2-5 | B17 | A76 |
| T2-4 | B17 | A77 | T2-5 | B17 | A77 |
| T2-4 | B17 | A78 | T2-5 | B17 | A78 |
| T2-4 | B17 | A106 | T2-5 | B17 | A106 |
| T2-4 | B17 | A110 | T2-5 | B17 | A110 |
| T5-1 | B17 | A2 | T7-1 | B17 | A2 |
| T5-1 | B17 | A5 | T7-1 | B17 | A5 |
| T5-1 | B17 | A35 | T7-1 | B17 | A35 |
| T5-1 | B17 | A37 | T7-1 | B17 | A37 |
| T5-1 | B17 | A45 | T7-1 | B17 | A45 |
| T5-1 | B17 | A46 | T7-1 | B17 | A46 |
| T5-1 | B17 | A49 | T7-1 | B17 | A49 |
| T5-1 | B17 | A54 | T7-1 | B17 | A54 |
| T5-1 | B17 | A66 | T7-1 | B17 | A66 |
| T5-1 | B17 | A67 | T7-1 | B17 | A67 |
| T5-1 | B17 | A68 | T7-1 | B17 | A68 |
| T5-1 | B17 | A69 | T7-1 | B17 | A69 |
| T5-1 | B17 | A70 | T7-1 | B17 | A70 |
| T5-1 | B17 | A76 | T7-1 | B17 | A76 |
| T5-1 | B17 | A77 | T7-1 | B17 | A77 |
| T5-1 | B17 | A78 | T7-1 | B17 | A78 |
| T5-1 | B17 | A106 | T7-1 | B17 | A106 |
| T5-1 | B17 | A110 | T7-1 | B17 | A110 |

TABLE 21

| | | | | | |
|---|---|---|---|---|---|
| T1-1 | B24 | A2 | T2-1 | B24 | A2 |
| T1-1 | B24 | A5 | T2-1 | B24 | A5 |
| T1-1 | B24 | A35 | T2-1 | B24 | A35 |
| T1-1 | B24 | A37 | T2-1 | B24 | A37 |
| T1-1 | B24 | A45 | T2-1 | B24 | A45 |
| T1-1 | B24 | A46 | T2-1 | B24 | A46 |
| T1-1 | B24 | A49 | T2-1 | B24 | A49 |
| T1-1 | B24 | A54 | T2-1 | B24 | A54 |
| T1-1 | B24 | A66 | T2-1 | B24 | A66 |
| T1-1 | B24 | A67 | T2-1 | B24 | A67 |
| T1-1 | B24 | A68 | T2-1 | B24 | A68 |
| T1-1 | B24 | A69 | T2-1 | B24 | A69 |
| T1-1 | B24 | A70 | T2-1 | B24 | A70 |
| T1-1 | B24 | A76 | T2-1 | B24 | A76 |
| T1-1 | B24 | A77 | T2-1 | B24 | A77 |
| T1-1 | B24 | A78 | T2-1 | B24 | A78 |
| T1-1 | B24 | A106 | T2-1 | B24 | A106 |
| T1-1 | B24 | A110 | T2-1 | B24 | A110 |
| T2-2 | B24 | A2 | T2-3 | B24 | A2 |
| T2-2 | B24 | A5 | T2-3 | B24 | A5 |
| T2-2 | B24 | A35 | T2-3 | B24 | A35 |
| T2-2 | B24 | A37 | T2-3 | B24 | A37 |
| T2-2 | B24 | A45 | T2-3 | B24 | A45 |
| T2-2 | B24 | A46 | T2-3 | B24 | A46 |
| T2-2 | B24 | A49 | T2-3 | B24 | A49 |
| T2-2 | B24 | A54 | T2-3 | B24 | A54 |
| T2-2 | B24 | A66 | T2-3 | B24 | A66 |
| T2-2 | B24 | A67 | T2-3 | B24 | A67 |
| T2-2 | B24 | A68 | T2-3 | B24 | A68 |
| T2-2 | B24 | A69 | T2-3 | B24 | A69 |
| T2-2 | B24 | A70 | T2-3 | B24 | A70 |
| T2-2 | B24 | A76 | T2-3 | B24 | A76 |
| T2-2 | B24 | A77 | T2-3 | B24 | A77 |
| T2-2 | B24 | A78 | T2-3 | B24 | A78 |
| T2-2 | B24 | A106 | T2-3 | B24 | A106 |
| T2-2 | B24 | A110 | T2-3 | B24 | A110 |
| T2-4 | B24 | A2 | T2-5 | B24 | A2 |
| T2-4 | B24 | A5 | T2-5 | B24 | A5 |
| T2-4 | B24 | A35 | T2-5 | B24 | A35 |
| T2-4 | B24 | A37 | T2-5 | B24 | A37 |
| T2-4 | B24 | A45 | T2-5 | B24 | A45 |
| T2-4 | B24 | A46 | T2-5 | B24 | A46 |
| T2-4 | B24 | A49 | T2-5 | B24 | A49 |

TABLE 22

| | | | | | |
|---|---|---|---|---|---|
| T2-4 | B24 | A54 | T2-5 | B24 | A54 |
| T2-4 | B24 | A66 | T2-5 | B24 | A66 |
| T2-4 | B24 | A67 | T2-5 | B24 | A67 |
| T2-4 | B24 | A68 | T2-5 | B24 | A68 |
| T2-4 | B24 | A69 | T2-5 | B24 | A69 |
| T2-4 | B24 | A70 | T2-5 | B24 | A70 |
| T2-4 | B24 | A76 | T2-5 | B24 | A76 |
| T2-4 | B24 | A77 | T2-5 | B24 | A77 |
| T2-4 | B24 | A78 | T2-5 | B24 | A78 |
| T2-4 | B24 | A106 | T2-5 | B24 | A106 |
| T2-4 | B24 | A110 | T2-5 | B24 | A110 |
| T5-1 | B24 | A2 | T7-1 | B24 | A2 |
| T5-1 | B24 | A5 | T7-1 | B24 | A5 |
| T5-1 | B24 | A35 | T7-1 | B24 | A35 |
| T5-1 | B24 | A37 | T7-1 | B24 | A37 |
| T5-1 | B24 | A45 | T7-1 | B24 | A45 |
| T5-1 | B24 | A46 | T7-1 | B24 | A46 |
| T5-1 | B24 | A49 | T7-1 | B24 | A49 |
| T5-1 | B24 | A54 | T7-1 | B24 | A54 |
| T5-1 | B24 | A66 | T7-1 | B24 | A66 |
| T5-1 | B24 | A67 | T7-1 | B24 | A67 |
| T5-1 | B24 | A68 | T7-1 | B24 | A68 |
| T5-1 | B24 | A69 | T7-1 | B24 | A69 |
| T5-1 | B24 | A70 | T7-1 | B24 | A70 |
| T5-1 | B24 | A76 | T7-1 | B24 | A76 |
| T5-1 | B24 | A77 | T7-1 | B24 | A77 |
| T5-1 | B24 | A78 | T7-1 | B24 | A78 |
| T5-1 | B24 | A106 | T7-1 | B24 | A106 |
| T5-1 | B24 | A110 | T7-1 | B24 | A110 |

TABLE 22-continued

| | | | | | |
|---|---|---|---|---|---|
| T1-1 | B28 | A2 | T2-1 | B28 | A2 |
| T1-1 | B28 | A5 | T2-1 | B28 | A5 |
| T1-1 | B28 | A35 | T2-1 | B28 | A35 |
| T1-1 | B28 | A37 | T2-1 | B28 | A37 |
| T1-1 | B28 | A45 | T2-1 | B28 | A45 |
| T1-1 | B28 | A46 | T2-1 | B28 | A46 |
| T1-1 | B28 | A49 | T2-1 | B28 | A49 |
| T1-1 | B28 | A54 | T2-1 | B28 | A54 |
| T1-1 | B28 | A66 | T2-1 | B28 | A66 |
| T1-1 | B28 | A67 | T2-1 | B28 | A67 |
| T1-1 | B28 | A68 | T2-1 | B28 | A68 |
| T1-1 | B28 | A69 | T2-1 | B28 | A69 |
| T1-1 | B28 | A70 | T2-1 | B28 | A70 |
| T1-1 | B28 | A76 | T2-1 | B28 | A76 |

TABLE 23

| | | | | | |
|---|---|---|---|---|---|
| T1-1 | B28 | A77 | T2-1 | B28 | A77 |
| T1-1 | B28 | A78 | T2-1 | B28 | A78 |
| T1-1 | B28 | A106 | T2-1 | B28 | A106 |
| T1-1 | B28 | A110 | T2-1 | B28 | A110 |
| T2-2 | B28 | A2 | T2-3 | B28 | A2 |
| T2-2 | B28 | A5 | T2-3 | B28 | A5 |
| T2-2 | B28 | A35 | T2-3 | B28 | A35 |
| T2-2 | B28 | A37 | T2-3 | B28 | A37 |
| T2-2 | B28 | A45 | T2-3 | B28 | A45 |
| T2-2 | B28 | A46 | T2-3 | B28 | A46 |
| T2-2 | B28 | A49 | T2-3 | B28 | A49 |
| T2-2 | B28 | A54 | T2-3 | B28 | A54 |
| T2-2 | B28 | A66 | T2-3 | B28 | A66 |
| T2-2 | B28 | A67 | T2-3 | B28 | A67 |
| T2-2 | B28 | A68 | T2-3 | B28 | A68 |
| T2-2 | B28 | A69 | T2-3 | B28 | A69 |
| T2-2 | B28 | A70 | T2-3 | B28 | A70 |
| T2-2 | B28 | A76 | T2-3 | B28 | A76 |
| T2-2 | B28 | A77 | T2-3 | B28 | A77 |
| T2-2 | B28 | A78 | T2-3 | B28 | A78 |
| T2-2 | B28 | A106 | T2-3 | B28 | A106 |
| T2-2 | B28 | A110 | T2-3 | B28 | A110 |
| T2-4 | B28 | A2 | T2-5 | B28 | A2 |
| T2-4 | B28 | A5 | T2-5 | B28 | A5 |
| T2-4 | B28 | A35 | T2-5 | B28 | A35 |
| T2-4 | B28 | A37 | T2-5 | B28 | A37 |
| T2-4 | B28 | A45 | T2-5 | B28 | A45 |
| T2-4 | B28 | A46 | T2-5 | B28 | A46 |
| T2-4 | B28 | A49 | T2-5 | B28 | A49 |
| T2-4 | B28 | A54 | T2-5 | B28 | A54 |
| T2-4 | B28 | A66 | T2-5 | B28 | A66 |
| T2-4 | B28 | A67 | T2-5 | B28 | A67 |
| T2-4 | B28 | A68 | T2-5 | B28 | A68 |
| T2-4 | B28 | A69 | T2-5 | B28 | A69 |
| T2-4 | B28 | A70 | T2-5 | B28 | A70 |
| T2-4 | B28 | A76 | T2-5 | B28 | A76 |
| T2-4 | B28 | A77 | T2-5 | B28 | A77 |
| T2-4 | B28 | A78 | T2-5 | B28 | A78 |
| T2-4 | B28 | A106 | T2-5 | B28 | A106 |
| T2-4 | B28 | A110 | T2-5 | B28 | A110 |
| T5-1 | B28 | A2 | T7-1 | B28 | A2 |
| T5-1 | B28 | A5 | T7-1 | B28 | A5 |
| T5-1 | B28 | A35 | T7-1 | B28 | A35 |

TABLE 24

| | | | | | |
|---|---|---|---|---|---|
| T5-1 | B28 | A37 | T7-1 | B28 | A37 |
| T5-1 | B28 | A45 | T7-1 | B28 | A45 |
| T5-1 | B28 | A46 | T7-1 | B28 | A46 |
| T5-1 | B28 | A49 | T7-1 | B28 | A49 |
| T5-1 | B28 | A54 | T7-1 | B28 | A54 |
| T5-1 | B28 | A66 | T7-1 | B28 | A66 |
| T5-1 | B28 | A67 | T7-1 | B28 | A67 |
| T5-1 | B28 | A68 | T7-1 | B28 | A68 |
| T5-1 | B28 | A69 | T7-1 | B28 | A69 |

TABLE 24-continued

| | | | | | |
|---|---|---|---|---|---|
| T5-1 | B28 | A70 | T7-1 | B28 | A70 |
| T5-1 | B28 | A76 | T7-1 | B28 | A76 |
| T5-1 | B28 | A77 | T7-1 | B28 | A77 |
| T5-1 | B28 | A78 | T7-1 | B28 | A78 |
| T5-1 | B28 | A106 | T7-1 | B28 | A106 |
| T5-1 | B28 | A110 | T7-1 | B28 | A110 |
| T1-1 | B29 | A2 | T2-1 | B29 | A2 |
| T1-1 | B29 | A5 | T2-1 | B29 | A5 |
| T1-1 | B29 | A35 | T2-1 | B29 | A35 |
| T1-1 | B29 | A37 | T2-1 | B29 | A37 |
| T1-1 | B29 | A45 | T2-1 | B29 | A45 |
| T1-1 | B29 | A46 | T2-1 | B29 | A46 |
| T1-1 | B29 | A49 | T2-1 | B29 | A49 |
| T1-1 | B29 | A54 | T2-1 | B29 | A54 |
| T1-1 | B29 | A66 | T2-1 | B29 | A66 |
| T1-1 | B29 | A67 | T2-1 | B29 | A67 |
| T1-1 | B29 | A68 | T2-1 | B29 | A68 |
| T1-1 | B29 | A69 | T2-1 | B29 | A69 |
| T1-1 | B29 | A70 | T2-1 | B29 | A70 |
| T1-1 | B29 | A76 | T2-1 | B29 | A76 |
| T1-1 | B29 | A77 | T2-1 | B29 | A77 |
| T1-1 | B29 | A78 | T2-1 | B29 | A78 |
| T1-1 | B29 | A106 | T2-1 | B29 | A106 |
| T1-1 | B29 | A110 | T2-1 | B29 | A110 |
| T2-2 | B29 | A2 | T2-3 | B29 | A2 |
| T2-2 | B29 | A5 | T2-3 | B29 | A5 |
| T2-2 | B29 | A35 | T2-3 | B29 | A35 |
| T2-2 | B29 | A37 | T2-3 | B29 | A37 |
| T2-2 | B29 | A45 | T2-3 | B29 | A45 |
| T2-2 | B29 | A46 | T2-3 | B29 | A46 |
| T2-2 | B29 | A49 | T2-3 | B29 | A49 |
| T2-2 | B29 | A54 | T2-3 | B29 | A54 |
| T2-2 | B29 | A66 | T2-3 | B29 | A66 |
| T2-2 | B29 | A67 | T2-3 | B29 | A67 |

TABLE 25

| | | | | | |
|---|---|---|---|---|---|
| T2-2 | B29 | A68 | T2-3 | B29 | A68 |
| T2-2 | B29 | A69 | T2-3 | B29 | A69 |
| T2-2 | B29 | A70 | T2-3 | B29 | A70 |
| T2-2 | B29 | A76 | T2-3 | B29 | A76 |
| T2-2 | B29 | A77 | T2-3 | B29 | A77 |
| T2-2 | B29 | A78 | T2-3 | B29 | A78 |
| T2-2 | B29 | A106 | T2-3 | B29 | A106 |
| T2-2 | B29 | A110 | T2-3 | B29 | A110 |
| T2-4 | B29 | A2 | T2-5 | B29 | A2 |
| T2-4 | B29 | A5 | T2-5 | B29 | A5 |
| T2-4 | B29 | A35 | T2-5 | B29 | A35 |
| T2-4 | B29 | A37 | T2-5 | B29 | A37 |
| T2-4 | B29 | A45 | T2-5 | B29 | A45 |
| T2-4 | B29 | A46 | T2-5 | B29 | A46 |
| T2-4 | B29 | A49 | T2-5 | B29 | A49 |
| T2-4 | B29 | A54 | T2-5 | B29 | A54 |
| T2-4 | B29 | A66 | T2-5 | B29 | A66 |
| T2-4 | B29 | A67 | T2-5 | B29 | A67 |
| T2-4 | B29 | A68 | T2-5 | B29 | A68 |
| T2-4 | B29 | A69 | T2-5 | B29 | A69 |
| T2-4 | B29 | A76 | T2-5 | B29 | A70 |
| T2-4 | B29 | A76 | T2-5 | B29 | A76 |
| T2-4 | B29 | A77 | T2-5 | B29 | A77 |
| T2-4 | B29 | A78 | T2-5 | B29 | A78 |
| T2-4 | B29 | A106 | T2-5 | B29 | A106 |
| T2-4 | B29 | A110 | T2-5 | B29 | A110 |
| T5-1 | B29 | A2 | T7-1 | B29 | A2 |
| T5-1 | B29 | A5 | T7-1 | B29 | A5 |
| T5-1 | B29 | A35 | T7-1 | B29 | A35 |
| T5-1 | B29 | A37 | T7-1 | B29 | A37 |
| T5-1 | B29 | A45 | T7-1 | B29 | A45 |
| T5-1 | B29 | A46 | T7-1 | B29 | A46 |
| T5-1 | B29 | A49 | T7-1 | B29 | A49 |
| T5-1 | B29 | A54 | T7-1 | B29 | A54 |
| T5-1 | B29 | A66 | T7-1 | B29 | A66 |
| T5-1 | B29 | A67 | T7-1 | B29 | A67 |
| T5-1 | B29 | A68 | T7-1 | B29 | A68 |
| T5-1 | B29 | A69 | T7-1 | B29 | A69 |

TABLE 25-continued

| T5-1 | B29 | A70 | T7-1 | B29 | A70 |
| T5-1 | B29 | A76 | T7-1 | B29 | A76 |
| T5-1 | B29 | A77 | T7-1 | B29 | A77 |
| T5-1 | B29 | A78 | T7-1 | B29 | A78 |
| T5-1 | B29 | A106 | T7-1 | B29 | A106 |

TABLE 26

| T5-1 | B29 | A110 | T7-1 | B29 | A110 |
| T1-1 | B30 | A2 | T2-1 | B30 | A2 |
| T1-1 | B30 | A5 | T2-1 | B30 | A5 |
| T1-1 | B30 | A35 | T2-1 | B30 | A35 |
| T1-1 | B30 | A37 | T2-1 | B30 | A37 |
| T1-1 | B30 | A45 | T2-1 | B30 | A45 |
| T1-1 | B30 | A46 | T2-1 | B30 | A46 |
| T1-1 | B30 | A49 | T2-1 | B30 | A49 |
| T1-1 | B30 | A54 | T2-1 | B30 | A54 |
| T1-1 | B30 | A66 | T2-1 | B30 | A66 |
| T1-1 | B30 | A67 | T2-1 | B30 | A67 |
| T1-1 | B30 | A68 | T2-1 | B30 | A68 |
| T1-1 | B30 | A69 | T2-1 | B30 | A69 |
| T1-1 | B30 | A70 | T2-1 | B30 | A70 |
| T1-1 | B30 | A76 | T2-1 | B30 | A76 |
| T1-1 | B30 | A77 | T2-1 | B30 | A77 |
| T1-1 | B30 | A78 | T2-1 | B30 | A78 |
| T1-1 | B30 | A106 | T2-1 | B30 | A106 |
| T1-1 | B30 | A110 | T2-1 | B30 | A110 |
| T2-2 | B30 | A2 | T2-3 | B30 | A2 |
| T2-2 | B30 | A5 | T2-3 | B30 | A5 |
| T2-2 | B30 | A35 | T2-3 | B30 | A35 |
| T2-2 | B30 | A37 | T2-3 | B30 | A37 |
| T2-2 | B30 | A45 | T2-3 | B30 | A45 |
| T2-2 | B30 | A46 | T2-3 | B30 | A46 |
| T2-2 | B30 | A49 | T2-3 | B30 | A49 |
| T2-2 | B30 | A54 | T2-3 | B30 | A54 |
| T2-2 | B30 | A66 | T2-3 | B30 | A66 |
| T2-2 | B30 | A67 | T2-3 | B30 | A67 |
| T2-2 | B30 | A68 | T2-3 | B30 | A68 |
| T2-2 | B30 | A69 | T2-3 | B30 | A69 |
| T2-2 | B30 | A70 | T2-3 | B30 | A70 |
| T2-2 | B30 | A76 | T2-3 | B30 | A76 |
| T2-2 | B30 | A77 | T2-3 | B30 | A77 |
| T2-2 | B30 | A78 | T2-3 | B30 | A78 |
| T2-2 | B30 | A106 | T2-3 | B30 | A106 |
| T2-2 | B30 | A110 | T2-3 | B30 | A110 |
| T2-4 | B30 | A2 | T2-5 | B30 | A2 |
| T2-4 | B30 | A5 | T2-5 | B30 | A5 |
| T2-4 | B30 | A35 | T2-5 | B30 | A35 |
| T2-4 | B30 | A37 | T2-5 | B30 | A37 |
| T2-4 | B30 | A45 | T2-5 | B30 | A45 |
| T2-4 | B30 | A46 | T2-5 | B30 | A46 |

TABLE 27

| T2-4 | B30 | A49 | T2-5 | B30 | A49 |
| T2-4 | B30 | A54 | T2-5 | B30 | A54 |
| T2-4 | B30 | A66 | T2-5 | B30 | A66 |
| T2-4 | B30 | A67 | T2-5 | B30 | A67 |
| T2-4 | B30 | A68 | T2-5 | B30 | A68 |
| T2-4 | B30 | A69 | T2-5 | B30 | A69 |
| T2-4 | B30 | A70 | T2-5 | B30 | A70 |
| T2-4 | B30 | A76 | T2-5 | B30 | A76 |
| T2-4 | B30 | A77 | T2-5 | B30 | A77 |
| T2-4 | B30 | A78 | T2-5 | B30 | A78 |
| T2-4 | B30 | A106 | T2-5 | B30 | A106 |
| T2-4 | B30 | A110 | T2-5 | B30 | A110 |
| T5-1 | B30 | A2 | T7-1 | B30 | A2 |
| T5-1 | B30 | A5 | T7-1 | B30 | A5 |
| T5-1 | B30 | A35 | T7-1 | B30 | A35 |
| T5-1 | B30 | A37 | T7-1 | B30 | A37 |
| T5-1 | B30 | A45 | T7-1 | B30 | A45 |
| T5-1 | B30 | A46 | T7-1 | B30 | A46 |

TABLE 27-continued

| T5-1 | B36 | A49 | T7-1 | B30 | A49 |
| T5-1 | B30 | A54 | T7-1 | B30 | A54 |
| T5-1 | B30 | A66 | T7-1 | B30 | A66 |
| T5-1 | B30 | A67 | T7-1 | B30 | A67 |
| T5-1 | B36 | A68 | T7-1 | B30 | A68 |
| T5-1 | B30 | A69 | T7-1 | B30 | A69 |
| T5-1 | B30 | A70 | T7-1 | B30 | A70 |
| T5-1 | B30 | A76 | T7-1 | B30 | A76 |
| T5-1 | B30 | A77 | T7-1 | B30 | A77 |
| T5-1 | B30 | A78 | T7-1 | B30 | A78 |
| T5-1 | B30 | A106 | T7-1 | B30 | A106 |
| T5-1 | B30 | A110 | T7-1 | B30 | A110 |
| T1-1 | B31 | A2 | T2-1 | B31 | A2 |
| T1-1 | B31 | A5 | T2-1 | B31 | A5 |
| T1-1 | B31 | A35 | T2-1 | B31 | A35 |
| T1-1 | B31 | A37 | T2-1 | B31 | A37 |
| T1-1 | B31 | A45 | T2-1 | B31 | A45 |
| T1-1 | B31 | A46 | T2-1 | B31 | A46 |
| T1-1 | B31 | A49 | T2-1 | B31 | A49 |
| T1-1 | B31 | A54 | T2-1 | B31 | A54 |
| T1-1 | B31 | A66 | T2-1 | B31 | A66 |
| T1-1 | B31 | A67 | T2-1 | B31 | A67 |
| T1-1 | B31 | A68 | T2-1 | B31 | A68 |
| T1-1 | B31 | A69 | T2-1 | B31 | A69 |
| T1-1 | B31 | A70 | T2-1 | B31 | A70 |

TABLE 28

| T1-1 | B31 | A76 | T2-1 | B31 | A76 |
| T1-1 | B31 | A77 | T2-1 | B31 | A77 |
| T1-1 | B31 | A78 | T2-1 | B31 | A78 |
| T1-1 | B31 | A106 | T2-1 | B31 | A106 |
| T1-1 | B31 | A110 | T2-1 | B31 | A110 |
| T2-2 | B31 | A2 | T2-3 | B31 | A2 |
| T2-2 | B31 | A5 | T2-3 | B31 | A5 |
| T2-2 | B31 | A35 | T2-3 | B31 | A35 |
| T2-2 | B31 | A37 | T2-3 | B31 | A37 |
| T2-2 | B31 | A45 | T2-3 | B31 | A45 |
| T2-2 | B31 | A46 | T2-3 | B31 | A46 |
| T2-2 | B31 | A49 | T2-3 | B31 | A49 |
| T2-2 | B31 | A54 | T2-3 | B31 | A54 |
| T2-2 | B31 | A66 | T2-3 | B31 | A66 |
| T2-2 | B31 | A67 | T2-3 | B31 | A67 |
| T2-2 | B31 | A68 | T2-3 | B31 | A68 |
| T2-2 | B31 | A69 | T2-3 | B31 | A69 |
| T2-2 | B31 | A70 | T2-3 | B31 | A70 |
| T2-2 | B31 | A76 | T2-3 | B31 | A76 |
| T2-2 | B31 | A77 | T2-3 | B31 | A77 |
| T2-2 | B31 | A78 | T2-3 | B31 | A78 |
| T2-2 | B31 | A106 | T2-3 | B31 | A106 |
| T2-2 | B31 | A110 | T2-3 | B31 | A110 |
| T2-4 | B31 | A2 | T2-5 | B31 | A2 |
| T2-4 | B31 | A5 | T2-5 | B31 | A5 |
| T2-4 | B31 | A35 | T2-5 | B31 | A35 |
| T2-4 | B31 | A37 | T2-5 | B31 | A37 |
| T2-4 | B31 | A45 | T2-5 | B31 | A45 |
| T2-4 | B31 | A46 | T2-5 | B31 | A46 |
| T2-4 | B31 | A49 | T2-5 | B31 | A49 |
| T2-4 | B31 | A54 | T2-5 | B31 | A54 |
| T2-4 | B31 | A66 | T2-5 | B31 | A66 |
| T2-4 | B31 | A67 | T2-5 | B31 | A67 |
| T2-4 | B31 | A68 | T2-5 | B31 | A68 |
| T2-4 | B31 | A69 | T2-5 | B31 | A69 |
| T2-4 | B31 | A70 | T2-5 | B31 | A70 |
| T2-4 | B31 | A76 | T2-5 | B31 | A76 |
| T2-4 | B31 | A77 | T2-5 | B31 | A77 |
| T2-4 | B31 | A78 | T2-5 | B31 | A78 |
| T2-4 | B31 | A106 | T2-5 | B31 | A106 |
| T2-4 | B31 | A110 | T2-5 | B31 | A110 |
| T5-1 | B31 | A2 | T7-1 | B31 | A2 |
| T5-1 | B31 | A5 | T7-1 | B31 | A5 |

TABLE 29

| | | | | | |
|---|---|---|---|---|---|
| T5-1 | B31 | A35 | T7-1 | B31 | A35 |
| T5-1 | B31 | A37 | T7-1 | B31 | A37 |
| T5-1 | B31 | A45 | T7-1 | B31 | A45 |
| T5-1 | B31 | A46 | T7-1 | B31 | A46 |
| T5-1 | B31 | A49 | T7-1 | B31 | A49 |
| T5-1 | B31 | A54 | T7-1 | B31 | A54 |
| T5-1 | B31 | A66 | T7-1 | B31 | A66 |
| T5-1 | B31 | A67 | T7-1 | B31 | A67 |
| T5-1 | B31 | A68 | T7-1 | B31 | A68 |
| T5-1 | B31 | A69 | T7-1 | B31 | A69 |
| T5-1 | B31 | A70 | T7-1 | B31 | A70 |
| T5-1 | B31 | A76 | T7-1 | B31 | A76 |
| T5-1 | B31 | A77 | T7-1 | B31 | A77 |
| T5-1 | B31 | A78 | T7-1 | B31 | A78 |
| T5-1 | B31 | A106 | T7-1 | B31 | A106 |
| T5-1 | B31 | A110 | T7-1 | B31 | A110 |
| T1-1 | B32 | A2 | T2-1 | B32 | A2 |
| T1-1 | B32 | A5 | T2-1 | B32 | A5 |
| T1-1 | B32 | A35 | T2-1 | B32 | A35 |
| T1-1 | B32 | A37 | T2-1 | B32 | A37 |
| T1-1 | B32 | A45 | T2-1 | B32 | A45 |
| T1-1 | B32 | A46 | T2-1 | B32 | A46 |
| T1-1 | B32 | A49 | T1-1 | B32 | A49 |
| T1-1 | B32 | A54 | T2-1 | B32 | A54 |
| T1-1 | B32 | A66 | T2-1 | B32 | A66 |
| T1-1 | B32 | A67 | T2-1 | B32 | A67 |
| T1-1 | B32 | A68 | T2-1 | B32 | A68 |
| T1-1 | B32 | A69 | T2-1 | B32 | A69 |
| T1-1 | B32 | A70 | T2-1 | B32 | A76 |
| T1-1 | B32 | A76 | T2-1 | B32 | A76 |
| T1-1 | B32 | A77 | T2-1 | B32 | A77 |
| T1-1 | B32 | A78 | T2-1 | B32 | A78 |
| T1-1 | B32 | A106 | T2-1 | B32 | A106 |
| T1-1 | B32 | A110 | T2-1 | B32 | A110 |
| T2-2 | B32 | A2 | T2-3 | B32 | A2 |
| T2-2 | B32 | A5 | T2-3 | B32 | A5 |
| T2-2 | B32 | A5 | T2-3 | B32 | A35 |
| T2-2 | B32 | A37 | T2-3 | B32 | A37 |
| T2-2 | B32 | A45 | T2-3 | B32 | A45 |
| T2-2 | B32 | A46 | T2-3 | B32 | A46 |
| T2-2 | B32 | A49 | T2-3 | B32 | A49 |
| T2-2 | B32 | A54 | T2-3 | B32 | A54 |
| T2-2 | B32 | A66 | T2-3 | B32 | A66 |

TABLE 30

| | | | | | |
|---|---|---|---|---|---|
| T2-2 | B32 | A67 | T2-3 | B32 | A67 |
| T2-2 | B32 | A68 | T2-3 | B32 | A68 |
| T2-2 | B32 | A69 | T2-3 | B32 | A69 |
| T2-2 | B32 | A70 | T2-3 | B32 | A70 |
| T2-2 | B32 | A76 | T2-3 | B32 | A76 |
| T2-2 | B32 | A77 | T2-3 | B32 | A77 |
| T2-2 | B32 | A78 | T2-3 | B32 | A78 |
| T2-2 | B32 | A106 | T2-3 | B32 | A106 |
| T2-2 | B32 | A110 | T2-3 | B32 | A110 |
| T2-4 | B32 | A2 | T2-5 | B32 | A2 |
| T2-4 | B32 | A5 | T2-5 | B32 | A5 |
| T2-4 | B32 | A35 | T2-5 | B32 | A35 |
| T2-4 | B32 | A37 | T2-5 | B32 | A37 |
| T2-4 | B32 | A45 | T2-5 | B32 | A45 |
| T2-4 | B32 | A46 | T2-5 | B32 | A46 |
| T2-4 | B32 | A49 | T2-5 | B32 | A49 |
| T2-4 | B32 | A54 | T2-5 | B32 | A54 |
| T2-4 | B32 | A66 | T2-5 | B32 | A66 |
| T2-4 | B32 | A67 | T2-5 | B32 | A67 |
| T2-4 | B32 | A68 | T2-5 | B32 | A68 |
| T2-4 | B32 | A69 | T2-5 | B32 | A69 |
| T2-4 | B32 | A70 | T2-5 | B32 | A70 |
| T2-4 | B32 | A76 | T2-5 | B32 | A76 |
| T2-4 | B32 | A77 | T2-5 | B32 | A77 |
| T2-4 | B32 | A78 | T2-5 | B32 | A78 |
| T2-4 | B32 | A106 | T2-5 | B32 | A106 |
| T2-4 | B32 | A110 | T2-5 | B32 | A110 |
| T5-1 | B32 | A2 | T7-1 | B32 | A2 |
| T5-1 | B32 | A5 | T7-1 | B32 | A5 |

TABLE 30-continued

| | | | | | |
|---|---|---|---|---|---|
| T5-1 | B32 | A35 | T7-1 | B32 | A35 |
| T5-1 | B32 | A37 | T7-1 | B32 | A37 |
| T5-1 | B32 | A45 | T7-1 | B32 | A45 |
| T5-1 | B32 | A46 | T7-1 | B32 | A46 |
| T5-1 | B32 | A49 | T7-1 | B32 | A49 |
| T5-1 | B32 | A54 | T7-1 | B32 | A54 |
| T5-1 | B32 | A66 | T7-1 | B32 | A66 |
| T5-1 | B32 | A67 | T7-1 | B32 | A67 |
| T5-1 | B32 | A68 | T7-1 | B32 | A68 |
| T5-1 | B32 | A69 | T7-1 | B32 | A69 |
| T5-1 | B32 | A70 | T7-1 | B32 | A70 |
| T5-1 | B32 | A76 | T7-1 | B32 | A76 |
| T5-1 | B32 | A77 | T7-1 | B32 | A77 |
| T5-1 | B32 | A78 | T7-1 | B32 | A78 |

TABLE 31

| | | | | | |
|---|---|---|---|---|---|
| T5-1 | B32 | A106 | T7-1 | B32 | A106 |
| T5-1 | B32 | A110 | T7-1 | B32 | A110 |
| T1-1 | B33 | A2 | T2-1 | B33 | A2 |
| T1-1 | B33 | A5 | T2-1 | B33 | A5 |
| T1-1 | B33 | A35 | T2-1 | B33 | A35 |
| T1-1 | B33 | A37 | T2-1 | B33 | A37 |
| T1-1 | B33 | A45 | T2-1 | B33 | A45 |
| T1-1 | B33 | A46 | T2-1 | B33 | A46 |
| T1-1 | B33 | A49 | T2-1 | B33 | A49 |
| T1-1 | B33 | A54 | T2-1 | B33 | A54 |
| T1-1 | B33 | A66 | T2-1 | B33 | A66 |
| T1-1 | B33 | A67 | T2-1 | B33 | A67 |
| T1-1 | B33 | A68 | T2-1 | B33 | A68 |
| T1-1 | B33 | A69 | T2-1 | B33 | A69 |
| T1-1 | B33 | A70 | T2-1 | B33 | A70 |
| T1-1 | B33 | A76 | T2-1 | B33 | A76 |
| T1-1 | B33 | A77 | T2-1 | B33 | A77 |
| T1-1 | B33 | A78 | T2-1 | B33 | A78 |
| T1-1 | B33 | A106 | T2-1 | B33 | A106 |
| T1-1 | B33 | A110 | T2-1 | B33 | A110 |
| T2-2 | B33 | A2 | T2-3 | B33 | A2 |
| T2-2 | B33 | A5 | T2-3 | B33 | A5 |
| T2-2 | B33 | A35 | T2-3 | B33 | A35 |
| T2-2 | B33 | A37 | T2-3 | B33 | A37 |
| T2-2 | B33 | A45 | T2-3 | B33 | A45 |
| T2-2 | B33 | A46 | T2-3 | B33 | A46 |
| T2-2 | B33 | A49 | T2-3 | B33 | A49 |
| T2-2 | B33 | A54 | T2-3 | B33 | A54 |
| T2-2 | B33 | A66 | T2-3 | B33 | A66 |
| T2-2 | B33 | A67 | T2-3 | B33 | A67 |
| T2-2 | B33 | A68 | T2-3 | B33 | A68 |
| T2-2 | B33 | A69 | T2-3 | B33 | A69 |
| T2-2 | B33 | A70 | T2-3 | B33 | A70 |
| T2-2 | B33 | A76 | T2-3 | B33 | A76 |
| T2-2 | B33 | A77 | T2-3 | B33 | A77 |
| T2-2 | B33 | A78 | T2-3 | B33 | A78 |
| T2-2 | B33 | A106 | T2-3 | B33 | A106 |
| T2-2 | B33 | A110 | T2-3 | B33 | A110 |
| T2-4 | B33 | A2 | T2-5 | B33 | A2 |
| T2-4 | B33 | A5 | T2-5 | B33 | A5 |
| T2-4 | B33 | A35 | T2-5 | B33 | A35 |
| T2-4 | B33 | A37 | T2-5 | B33 | A37 |
| T2-4 | B33 | A45 | T2-5 | B33 | A45 |

TABLE 32

| | | | | | |
|---|---|---|---|---|---|
| T2-4 | B33 | A46 | T2-5 | B33 | A46 |
| T2-4 | B33 | A49 | T2-5 | B33 | A49 |
| T2-4 | B33 | A54 | T2-5 | B33 | A54 |
| T2-4 | B33 | A66 | T2-5 | B33 | A66 |
| T2-4 | B33 | A67 | T2-5 | B33 | A67 |
| T2-4 | B33 | A68 | T2-5 | B33 | A68 |
| T2-4 | B33 | A69 | T2-5 | B33 | A69 |
| T2-4 | B33 | A70 | T2-5 | B33 | A70 |
| T2-4 | B33 | A76 | T2-5 | B33 | A76 |

TABLE 32-continued

| | | | | | |
|---|---|---|---|---|---|
| T2-4 | B33 | A77 | T2-5 | B33 | A77 |
| T2-4 | B33 | A78 | T2-5 | B33 | A78 |
| T2-4 | B33 | A106 | T2-5 | B33 | A106 |
| T2-4 | B33 | A110 | T2-5 | B33 | A110 |
| T5-1 | B33 | A2 | T7-1 | B33 | A2 |
| T5-1 | B33 | A5 | T7-1 | B33 | A5 |
| T5-1 | B33 | A35 | T7-1 | B33 | A35 |
| T5-1 | B33 | A37 | T7-1 | B33 | A37 |
| T5-1 | B33 | A45 | T7-1 | B33 | A45 |
| T5-1 | B33 | A46 | T7-1 | B33 | A46 |
| T5-1 | B33 | A49 | T7-1 | B33 | A49 |
| T5-1 | B33 | A54 | T7-1 | B33 | A54 |
| T5-1 | B33 | A66 | T7-1 | B33 | A66 |
| T5-1 | B33 | A67 | T7-1 | B33 | A67 |
| T5-1 | B33 | A68 | T7-1 | B33 | A68 |
| T5-1 | B33 | A69 | T7-1 | B33 | A69 |
| T5-1 | B33 | A70 | T7-1 | B33 | A70 |
| T5-1 | B33 | A76 | T7-1 | B33 | A76 |
| T5-1 | B33 | A77 | T7-1 | B33 | A77 |
| T5-1 | B33 | A78 | T7-1 | B33 | A78 |
| T5-1 | B33 | A106 | T7-1 | B33 | A106 |
| T5-1 | B33 | A110 | T7-1 | B33 | A110 |
| T1-1 | B34 | A2 | T2-1 | B34 | A2 |
| T1-1 | B34 | A5 | T2-1 | B34 | A5 |
| T1-1 | B34 | A35 | T2-1 | B34 | A35 |
| T1-1 | B34 | A37 | T2-1 | B34 | A37 |
| T1-1 | B34 | A45 | T2-1 | B34 | A45 |
| T1-1 | B34 | A46 | T2-1 | B34 | A46 |
| T1-1 | B34 | A49 | T2-1 | B34 | A49 |
| T1-1 | B34 | A54 | T2-1 | B34 | A54 |
| T1-1 | B34 | A66 | T2-1 | B34 | A66 |
| T1-1 | B34 | A67 | T2-1 | B34 | A67 |
| T1-1 | B34 | A68 | T2-1 | B34 | A68 |
| T1-1 | B34 | A69 | T2-1 | B34 | A69 |

TABLE 33

| | | | | | |
|---|---|---|---|---|---|
| T1-1 | B34 | A70 | T2-1 | B34 | A70 |
| T1-1 | B34 | A76 | T2-1 | B34 | A76 |
| T1-1 | B34 | A77 | T2-1 | B34 | A77 |
| T1-1 | B34 | A78 | T2-1 | B34 | A78 |
| T1-1 | B34 | A106 | T2-1 | B34 | A106 |
| T1-1 | B34 | A110 | T2-1 | B34 | A110 |
| T2-2 | B34 | A2 | T2-3 | B34 | A2 |
| T2-2 | B34 | A5 | T2-3 | B34 | A5 |
| T2-2 | B34 | A35 | T2-3 | B34 | A35 |
| T2-2 | B34 | A37 | T2-3 | B34 | A37 |
| T2-2 | B34 | A45 | T2-3 | B34 | A45 |
| T2-2 | B34 | A46 | T2-3 | B34 | A46 |
| T2-2 | B34 | A49 | T2-3 | B34 | A49 |
| T2-2 | B34 | A54 | T2-3 | B34 | A54 |
| T2-2 | B34 | A66 | T2-3 | B34 | A66 |
| T2-2 | B34 | A67 | T2-3 | B34 | A67 |
| T2-2 | B34 | A68 | T2-3 | B34 | A68 |
| T2-2 | B34 | A69 | T2-3 | B34 | A69 |
| T2-2 | B34 | A70 | T2-3 | B34 | A70 |
| T2-2 | B34 | A76 | T2-3 | B34 | A76 |
| T2-2 | B34 | A77 | T2-3 | B34 | A77 |
| T2-2 | B34 | A78 | T2-3 | B34 | A78 |
| T2-2 | B34 | A106 | T2-3 | B34 | A106 |
| T2-2 | B34 | A110 | T2-3 | B34 | A110 |
| T2-4 | B34 | A2 | T2-5 | B34 | A2 |
| T2-4 | B34 | A5 | T2-5 | B34 | A5 |
| T2-4 | B34 | A35 | T2-5 | B34 | A35 |
| T2-4 | B34 | A37 | T2-5 | B34 | A37 |
| T2-4 | B34 | A45 | T2-5 | B34 | A45 |
| T2-4 | B34 | A46 | T2-5 | B34 | A46 |
| T2-4 | B34 | A49 | T2-5 | B34 | A49 |
| T2-4 | B34 | A54 | T2-5 | B34 | A54 |
| T2-4 | B34 | A66 | T2-5 | B34 | A66 |
| T2-4 | B34 | A67 | T2-5 | B34 | A67 |
| T2-4 | B34 | A68 | T2-5 | B34 | A68 |
| T2-4 | B34 | A69 | T2-5 | B34 | A69 |
| T2-4 | B34 | A70 | T2-5 | B34 | A70 |
| T2-4 | B34 | A76 | T2-5 | B34 | A76 |

TABLE 33-continued

| | | | | | |
|---|---|---|---|---|---|
| T2-4 | B34 | A77 | T2-5 | B34 | A77 |
| T2-4 | B34 | A78 | T2-5 | B34 | A78 |
| T2-4 | B34 | A106 | T2-5 | B34 | A106 |
| T2-4 | B34 | A110 | T2-5 | B34 | A110 |

TABLE 34

| | | | | | |
|---|---|---|---|---|---|
| T5-1 | B34 | A2 | T7-1 | B34 | A2 |
| T5-1 | B34 | A5 | T7-1 | B34 | A5 |
| T5-1 | B34 | A35 | T7-1 | B34 | A35 |
| T5-1 | B34 | A37 | T7-1 | B34 | A37 |
| T5-1 | B34 | A45 | T7-1 | B34 | A45 |
| T5-1 | B34 | A46 | T7-1 | B34 | A46 |
| T5-1 | B34 | A49 | T7-1 | B34 | A49 |
| T5-1 | B34 | A54 | T7-1 | B34 | A54 |
| T5-1 | B34 | A66 | T7-1 | B34 | A66 |
| T5-1 | B34 | A67 | T7-1 | B34 | A67 |
| T5-1 | B34 | A68 | 77-1 | B34 | A68 |
| T5-1 | B34 | A69 | T7-1 | B34 | A69 |
| T5-1 | B34 | A70 | T7-1 | B34 | A70 |
| T5-1 | B34 | A76 | T7-1 | B34 | A76 |
| T5-1 | B34 | A77 | T7-1 | B34 | A77 |
| T5-1 | B34 | A78 | T7-1 | B34 | A78 |
| T5-1 | B34 | A106 | T7-1 | B34 | A106 |
| T5-1 | B34 | A110 | T7-1 | B34 | A110 |
| T1-1 | B35 | A2 | T2-1 | B35 | A2 |
| T1-1 | B35 | A5 | T2-1 | B35 | A5 |
| T1-1 | B35 | A35 | T2-1 | E35 | A35 |
| T1-1 | B35 | A37 | T2-1 | B35 | A37 |
| T1-1 | B35 | A45 | T2-1 | B35 | A45 |
| T1-1 | B35 | A46 | T2-1 | B35 | A46 |
| T1-1 | B35 | A49 | T2-1 | B35 | A49 |
| T1-1 | B35 | A54 | T2-1 | B35 | A54 |
| T1-1 | B35 | A66 | T2-1 | B35 | A66 |
| T1-1 | B35 | A67 | T2-1 | B35 | A67 |
| T1-1 | B35 | A68 | T2-1 | B35 | A68 |
| T1-1 | P35 | A69 | T2-1 | B35 | A69 |
| T1-1 | B35 | A70 | T2-1 | B35 | A70 |
| T1-1 | B35 | A76 | T2-1 | B35 | A76 |
| T1-1 | B35 | A77 | T2-1 | B35 | A77 |
| T1-1 | B35 | A78 | T2-1 | B35 | A78 |
| T1-1 | B35 | A106 | T2-1 | B35 | A106 |
| T1-1 | B35 | A110 | T2-1 | B35 | A110 |
| T2-2 | B35 | A2 | T2-3 | B35 | A2 |
| T2-2 | B35 | A5 | T2-3 | B35 | A5 |
| T2-2 | B35 | A35 | T2-3 | B35 | A35 |
| T2-2 | B35 | A37 | T2-3 | B35 | A37 |
| T2-2 | B35 | A45 | T2-3 | B35 | A45 |
| T2-2 | B35 | A46 | T2-3 | B35 | A46 |
| T2-2 | B35 | A49 | T2-3 | B35 | A49 |

TABLE 35

| | | | | | |
|---|---|---|---|---|---|
| T2-2 | B35 | A54 | T2-3 | B35 | A54 |
| T2-2 | B35 | A66 | T2-3 | B35 | A66 |
| T2-2 | B35 | A67 | T2-3 | B35 | A67 |
| T2-2 | B35 | A68 | T2-3 | B35 | A68 |
| T2-2 | B35 | A69 | T2-3 | B35 | A69 |
| T2-2 | B35 | A70 | T2-3 | B35 | A70 |
| T2-2 | B35 | A76 | T2-3 | B35 | A76 |
| T2-2 | B35 | A77 | T2-3 | B35 | A77 |
| T2-2 | B35 | A78 | T2-3 | B35 | A78 |
| T2-2 | B35 | A106 | T2-3 | B35 | A106 |
| T2-2 | B35 | A110 | T2-3 | B35 | A110 |
| T2-4 | B35 | A2 | T2-5 | B35 | A2 |
| T2-4 | B35 | A5 | T2-5 | B35 | A5 |
| T2-4 | B35 | A35 | T2-5 | B35 | A35 |
| T2-4 | B35 | A37 | T2-5 | B35 | A37 |
| T2-4 | B35 | A45 | T2-5 | B35 | A45 |
| T2-4 | B35 | A46 | T2-5 | B35 | A46 |
| T2-4 | B35 | A49 | T2-5 | B35 | A49 |
| T2-4 | B35 | A54 | T2-5 | B35 | A54 |

TABLE 35-continued

| | | | | | |
|---|---|---|---|---|---|
| T2-4 | B35 | A66 | T2-5 | B35 | A66 |
| T2-4 | B35 | A67 | T2-5 | B35 | A67 |
| T2-4 | B35 | A68 | T2-5 | B35 | A68 |
| T2-4 | B35 | A69 | T2-5 | B35 | A69 |
| T2-4 | B35 | A70 | T2-5 | B35 | A70 |
| T2-4 | B35 | A76 | T2-5 | B35 | A76 |
| T2-4 | B35 | A77 | T2-5 | B35 | A77 |
| T2-4 | B35 | A78 | T2-5 | B35 | A78 |
| T2-4 | B35 | A106 | T2-5 | B35 | A106 |
| T2-4 | B35 | A110 | T2-5 | B35 | A110 |
| T5-1 | B35 | A2 | T7-1 | B35 | A2 |
| T5-1 | B35 | A5 | T7-1 | B35 | A5 |
| T5-1 | B35 | A35 | T7-1 | B35 | A35 |
| T5-1 | B35 | A37 | T7-1 | B35 | A37 |
| T5-1 | B35 | A45 | T7-1 | B35 | A45 |
| T5-1 | B35 | A46 | T7-1 | B35 | A46 |
| T5-1 | B35 | A49 | T7-1 | B35 | A49 |
| T5-1 | B35 | A54 | T7-1 | B35 | A54 |
| T5-1 | B35 | A66 | T7-1 | B35 | A66 |
| T5-1 | B35 | A67 | T7-1 | B35 | A67 |
| T5-1 | B35 | A68 | T7-1 | B35 | A68 |
| T5-1 | B35 | A69 | T7-1 | B35 | A69 |
| T5-1 | B35 | A70 | T7-1 | B35 | A70 |
| T5-1 | B35 | A76 | T7-1 | B35 | A76 |

TABLE 36

| | | | | | |
|---|---|---|---|---|---|
| T5-1 | B35 | A77 | T7-1 | B35 | A77 |
| T5-1 | B35 | A78 | T7-1 | B35 | A78 |
| T5-1 | B35 | A106 | T7-1 | B35 | A106 |
| T5-1 | B35 | A110 | T7-1 | B35 | A110 |
| T1-1 | B36 | A2 | T2-1 | B36 | A2 |
| T1-1 | B36 | A5 | T2-1 | B36 | A5 |
| T1-1 | B36 | A35 | T2-1 | B36 | A35 |
| T1-1 | B36 | A37 | T2-1 | B36 | A37 |
| T1-1 | B36 | A45 | T2-1 | B36 | A45 |
| T1-1 | B36 | A46 | T2-1 | B36 | A46 |
| T1-1 | B36 | A49 | T2-1 | B36 | A49 |
| T1-1 | B36 | A54 | T2-1 | B36 | A54 |
| T1-1 | B36 | A66 | T2-1 | B36 | A66 |
| T1-1 | B36 | A67 | T2-1 | B36 | A67 |
| T1-1 | B36 | A68 | T2-1 | B36 | A68 |
| T1-1 | B36 | A69 | T2-1 | B36 | A69 |
| T1-1 | B36 | A70 | T2-1 | B36 | A70 |
| T1-1 | B36 | A76 | T2-1 | B36 | A76 |
| T1-1 | B36 | A77 | T2-1 | B36 | A77 |
| T1-1 | B36 | A78 | T2-1 | B36 | A78 |
| T1-1 | B36 | A106 | T2-1 | B36 | A106 |
| T1-1 | B36 | A110 | T2-1 | B36 | A110 |
| T2-2 | B36 | A2 | T2-3 | B36 | A2 |
| T2-2 | B36 | A5 | T2-3 | B36 | A5 |
| T2-2 | B36 | A35 | T2-3 | B36 | A35 |
| T2-2 | B36 | A37 | T2-3 | B36 | A37 |
| T2-2 | B36 | A45 | T2-3 | B36 | A45 |
| T2-2 | B36 | A46 | T2-3 | B36 | A46 |
| T2-2 | B36 | A49 | T2-3 | B36 | A49 |
| T2-2 | B36 | A54 | T2-3 | B36 | A54 |
| T2-2 | B36 | A66 | T2-3 | B36 | A66 |
| T2-2 | B36 | A67 | T2-3 | B36 | A67 |
| T2-2 | B36 | A68 | T2-3 | B36 | A68 |
| T2-2 | B36 | A69 | T2-3 | B36 | A69 |
| T2-2 | B36 | A70 | T2-3 | B36 | A70 |
| T2-2 | B36 | A76 | T2-3 | B36 | A76 |
| T2-2 | B36 | A77 | T2-3 | B36 | A77 |
| T2-2 | B36 | A78 | T2-3 | B36 | A78 |
| T2-2 | B36 | A106 | T2-3 | B36 | A106 |
| T2-2 | B36 | A110 | T2-3 | B36 | A110 |
| T2-4 | B36 | A2 | T2-5 | B36 | A2 |
| T2-4 | B36 | A5 | T2-5 | B36 | A5 |
| T2-4 | B36 | A35 | T2-5 | B36 | A35 |

TABLE 37

| | | | | | |
|---|---|---|---|---|---|
| T2-4 | B36 | A37 | T2-5 | B36 | A37 |
| T2-4 | B36 | A45 | T2-5 | B36 | A45 |
| T2-4 | B36 | A46 | T2-5 | B36 | A46 |
| T2-4 | B36 | A49 | T2-5 | B36 | A49 |
| T2-4 | B36 | A54 | T2-5 | B36 | A54 |
| T2-4 | B36 | A66 | T2-5 | B36 | A66 |
| T2-4 | B36 | A67 | T2-5 | B36 | A67 |
| T2-4 | B36 | A65 | T2-5 | B36 | A68 |
| T2-4 | B36 | A69 | T2-5 | B36 | A69 |
| T2-4 | B36 | A70 | T2-5 | B36 | A70 |
| T2-4 | B36 | A76 | T2-5 | B36 | A76 |
| T2-4 | B36 | A77 | T2-5 | B36 | A77 |
| T2-4 | B36 | A78 | T2-5 | B36 | A78 |
| T2-4 | B36 | A106 | T2-5 | B36 | A106 |
| T2-4 | B36 | A110 | T2-5 | B36 | A110 |
| T5-1 | B36 | A2 | T7-1 | B36 | A2 |
| T5-1 | B36 | A5 | T7-1 | B36 | A5 |
| T5-1 | B36 | A35 | T7-1 | B36 | A35 |
| T5-1 | B36 | A37 | T7-1 | B36 | A37 |
| T5-1 | B36 | A45 | T7-1 | B36 | A45 |
| T5-1 | B36 | A46 | T7-1 | B36 | A46 |
| T5-1 | B36 | A49 | T7-1 | B36 | A49 |
| T5-1 | B36 | A54 | T7-1 | B36 | A54 |
| T5-1 | B36 | A66 | T7-1 | B36 | A66 |
| T5-1 | B36 | A67 | T7-1 | B36 | A67 |
| T5-1 | B36 | A68 | T7-1 | B36 | A68 |
| T5-1 | B36 | A69 | T7-1 | B36 | A69 |
| T5-1 | B36 | A70 | T7-1 | B36 | A70 |
| T5-1 | B36 | A76 | T7-1 | B36 | A76 |
| T5-1 | B36 | A77 | T7-1 | B36 | A77 |
| T5-1 | B36 | A78 | T7-1 | B36 | A78 |
| T5-1 | B36 | A106 | T7-1 | B36 | A106 |
| T5-1 | B36 | A110 | T7-1 | B36 | A110 |
| T1-1 | B37 | A2 | T2-1 | B37 | A2 |
| T1-1 | B37 | A5 | T2-1 | B37 | A5 |
| T1-1 | B37 | A35 | T2-1 | B37 | A35 |
| T1-1 | B37 | A37 | T2-1 | B37 | A37 |
| T1-1 | B37 | A45 | T2-1 | B37 | A45 |
| T1-1 | B37 | A46 | T2-1 | B37 | A46 |
| T1-1 | B37 | A49 | T2-1 | B37 | A49 |
| T1-1 | B37 | A54 | T2-1 | B37 | A54 |
| T1-1 | B37 | A66 | T2-1 | B37 | A66 |
| T1-1 | B37 | A67 | T2-1 | B37 | A67 |

TABLE 38

| | | | | | |
|---|---|---|---|---|---|
| T1-1 | B37 | A68 | T2-1 | B37 | A68 |
| T1-1 | B37 | A69 | T2-1 | B37 | A69 |
| T1-1 | B37 | A70 | T2-1 | B37 | A70 |
| T1-1 | B37 | A76 | T2-1 | B37 | A76 |
| T1-1 | B37 | A77 | T2-1 | B37 | A77 |
| T1-1 | B37 | A78 | T2-1 | B37 | A78 |
| T1-1 | B37 | A106 | T2-1 | B37 | A106 |
| T1-1 | B37 | A110 | T2-1 | B37 | A110 |
| T2-2 | B37 | A2 | T2-3 | B37 | A2 |
| T2-2 | B37 | A5 | T2-3 | B37 | A5 |
| T2-2 | B37 | A35 | T2-3 | B37 | A35 |
| T2-2 | B37 | A37 | T2-3 | B37 | A37 |
| T2-2 | B37 | A45 | T2-3 | B37 | A45 |
| T2-2 | B37 | A46 | T2-3 | B37 | A46 |
| T2-2 | B37 | A49 | T2-3 | B37 | A49 |
| T2-2 | B37 | A54 | T2-3 | B37 | A54 |
| T2-2 | B37 | A66 | T2-3 | B37 | A66 |
| T2-2 | B37 | A67 | T2-3 | B37 | A67 |
| T2-2 | B37 | A68 | T2-3 | B37 | A68 |
| T2-2 | B37 | A69 | T2-3 | B37 | A69 |
| T2-2 | B37 | A70 | T2-3 | B37 | A70 |
| T2-2 | B37 | A76 | T2-3 | B37 | A76 |
| T2-2 | B37 | A77 | T2-3 | B37 | A77 |
| T2-2 | B37 | A78 | T2-3 | B37 | A78 |
| T2-2 | B37 | A106 | T2-3 | B37 | A106 |
| T2-2 | B37 | A110 | T2-3 | B37 | A110 |
| T2-4 | B37 | A2 | T2-5 | B37 | A2 |
| T2-4 | B37 | A5 | T2-5 | B37 | A5 |
| T2-4 | B37 | A35 | T2-5 | B37 | A35 |

TABLE 38-continued

| | | | | | |
|---|---|---|---|---|---|
| T2-4 | B37 | A37 | T2-5 | B37 | A37 |
| T2-4 | B37 | A45 | T2-5 | B37 | A45 |
| T2-4 | B37 | A46 | T2-5 | B37 | A46 |
| T2-4 | B37 | A49 | T2-5 | B37 | A49 |
| T2-4 | B37 | A54 | T2-5 | B37 | A54 |
| T2-4 | B37 | A66 | T2-5 | B37 | A66 |
| T2-4 | B37 | A67 | T2-5 | B37 | A67 |
| T2-4 | B37 | A68 | T2-5 | B37 | A68 |
| T2-4 | B37 | A69 | T2-5 | B37 | A69 |
| T2-4 | B37 | A70 | T2-5 | B37 | A70 |
| T2-4 | B37 | A76 | T2-5 | B37 | A76 |
| T2-4 | B37 | A77 | T2-5 | B37 | A77 |
| T2-4 | B37 | A78 | T2-5 | B37 | A78 |
| T2-4 | B37 | A106 | T2-5 | B37 | A106 |

TABLE 39

| | | | | | |
|---|---|---|---|---|---|
| T2-4 | B37 | A110 | T2-5 | B37 | A110 |
| T5-1 | B37 | A2 | T7-1 | B37 | A2 |
| T5-1 | B37 | A5 | T7-1 | B37 | A5 |
| T5-1 | B37 | A35 | T7-1 | B37 | A35 |
| T5-1 | B37 | A37 | T7-1 | B37 | A37 |
| T5-1 | B37 | A45 | T7-1 | B37 | A45 |
| T5-1 | B37 | A46 | T7-1 | B37 | A46 |
| T5-1 | B37 | A49 | T7-1 | B37 | A49 |
| T5-1 | B37 | A54 | T7-1 | B37 | A54 |
| T5-1 | B37 | A66 | T7-1 | B37 | A66 |
| T5-1 | B37 | A67 | T7-1 | B37 | A67 |
| T5-1 | B37 | A68 | T7-1 | B37 | A68 |
| T5-1 | B37 | A69 | T7-1 | B37 | A69 |
| T5-1 | B37 | A70 | T7-1 | B37 | A70 |
| T5-1 | B37 | A76 | T7-1 | B37 | A76 |
| T5-1 | B37 | A77 | T7-1 | B37 | A77 |
| T5-1 | B37 | A78 | T7-1 | B37 | A78 |
| T5-1 | B37 | A106 | T7-1 | B37 | A106 |
| T5-1 | B37 | A110 | T7-1 | B37 | A110 |
| T1-1 | B38 | A2 | T2-1 | B38 | A2 |
| T1-1 | B38 | A5 | T2-1 | B38 | A5 |
| T1-1 | B38 | A35 | T2-1 | B38 | A35 |
| T1-1 | B38 | A37 | T2-1 | B38 | A37 |
| T1-1 | B38 | A45 | T2-1 | B38 | A45 |
| T1-1 | B38 | A46 | T2-1 | B38 | A46 |
| T1-1 | B38 | A49 | T2-1 | B38 | A49 |
| T1-1 | B38 | A54 | T2-1 | B38 | A54 |
| T1-1 | B38 | A66 | T2-1 | B38 | A66 |
| T1-1 | B38 | A67 | T2-1 | B38 | A67 |
| T1-1 | B38 | A68 | T2-1 | B38 | A68 |
| T1-1 | B38 | A69 | T2-1 | B38 | A69 |
| T1-1 | B38 | A70 | T2-1 | B38 | A70 |
| T1-1 | B38 | A76 | T2-1 | B38 | A76 |
| T1-1 | B38 | A77 | T2-1 | B38 | A77 |
| T1-1 | B38 | A78 | T2-1 | B38 | A78 |
| T1-1 | B38 | A106 | T2-1 | B38 | A106 |
| T1-1 | B38 | A110 | T2-1 | B38 | A110 |
| T2-2 | B38 | A2 | T2-3 | B38 | A2 |
| T2-2 | B38 | A5 | T2-3 | B38 | A5 |
| T2-2 | B38 | A35 | T2-3 | B38 | A35 |
| T2-2 | B38 | A37 | T2-3 | B38 | A37 |
| T2-2 | B38 | A45 | T2-3 | B38 | A45 |
| T2-2 | B38 | A46 | T2-3 | B38 | A46 |

TABLE 40

| | | | | | |
|---|---|---|---|---|---|
| T2-2 | B38 | A49 | T2-3 | B38 | A49 |
| T2-2 | B38 | A54 | T2-3 | B38 | A54 |
| T2-2 | B38 | A66 | T2-3 | B38 | A66 |
| T2-2 | B38 | A67 | T2-3 | B38 | A67 |
| T2-2 | B38 | A68 | T2-3 | B38 | A68 |
| T2-2 | B38 | A69 | T2-3 | B38 | A69 |
| T2-2 | B38 | A70 | T2-3 | B38 | A70 |
| T2-2 | B38 | A76 | T2-3 | B38 | A76 |
| T2-2 | B38 | A77 | T2-3 | B38 | A77 |

TABLE 40-continued

| | | | | | |
|---|---|---|---|---|---|
| T2-2 | B38 | A78 | T2-3 | B38 | A78 |
| T2-2 | B38 | A106 | T2-3 | B38 | A106 |
| T2-2 | B38 | A110 | T2-3 | B38 | A110 |
| T2-4 | B38 | A2 | T2-5 | B38 | A2 |
| T2-4 | B38 | A5 | T2-5 | B38 | A5 |
| T2-4 | B38 | A35 | T2-5 | B38 | A35 |
| T2-4 | B38 | A37 | T2-5 | B38 | A37 |
| T2-4 | B38 | A45 | T2-5 | B38 | A45 |
| T2-4 | B38 | A46 | T2-5 | B38 | A46 |
| T2-4 | B38 | A49 | T2-5 | B38 | A49 |
| T2-4 | B38 | A54 | T2-5 | B38 | A54 |
| T2-4 | B38 | A66 | T2-5 | B38 | A66 |
| T2-4 | B38 | A67 | T2-5 | B38 | A67 |
| T2-4 | B38 | A68 | T2-5 | B38 | A68 |
| T2-4 | B38 | A69 | T2-5 | B38 | A69 |
| T2-4 | B38 | A70 | T2-5 | B38 | A70 |
| T2-4 | B38 | A76 | T2-5 | B38 | A76 |
| T2-4 | B38 | A77 | T2-5 | B38 | A77 |
| T2-4 | B38 | A78 | T2-5 | B38 | A78 |
| T2-4 | B38 | A106 | T2-5 | B38 | A106 |
| T2-4 | B38 | A110 | T2-5 | B38 | A110 |
| T5-1 | B38 | A2 | T7-1 | B38 | A2 |
| T5-1 | B38 | A5 | T7-1 | B38 | A5 |
| T5-1 | B38 | A35 | T7-1 | B38 | A35 |
| T5-1 | B38 | A37 | T7-1 | B38 | A37 |
| T5-1 | B38 | A45 | T7-1 | B38 | A45 |
| T5-1 | B38 | A46 | T7-1 | B38 | A46 |
| T5-1 | B38 | A49 | T7-1 | B38 | A49 |
| T5-1 | B38 | A54 | T7-1 | B38 | A54 |
| T5-1 | B38 | A66 | T7-1 | B38 | A66 |
| T5-1 | B38 | A67 | T7-1 | B38 | A67 |
| T5-1 | B38 | A68 | T7-1 | B38 | A68 |
| T5-1 | B38 | A69 | T7-1 | B38 | A69 |
| T5-1 | B38 | A70 | T7-1 | B38 | A70 |

TABLE 41

| | | | | | |
|---|---|---|---|---|---|
| T5-1 | B38 | A76 | T7-1 | B38 | A76 |
| T5-1 | B38 | A77 | T7-1 | B38 | A77 |
| T5-1 | B38 | A78 | T7-1 | B38 | A78 |
| T5-1 | B38 | A106 | T7-1 | B38 | A106 |
| T5-1 | B38 | A110 | T7-1 | B38 | A110 |
| T1-1 | B39 | A2 | T2-1 | B39 | A2 |
| T1-1 | B39 | A5 | T2-1 | B39 | A5 |
| T1-1 | B39 | A35 | T2-1 | B39 | A35 |
| T1-1 | B39 | A37 | T2-1 | B39 | A37 |
| T1-1 | B39 | A45 | T2-1 | B39 | A45 |
| T1-1 | B39 | A46 | T2-1 | B39 | A46 |
| T1-1 | B39 | A49 | T2-1 | B39 | A49 |
| T1-1 | B39 | A54 | T2-1 | B39 | A54 |
| T1-1 | B39 | A66 | T2-1 | B39 | A66 |
| T1-1 | B39 | A67 | T2-1 | B39 | A67 |
| T1-1 | B39 | A68 | T2-1 | B39 | A68 |
| T1-1 | B39 | A69 | T2-1 | B39 | A69 |
| T1-1 | B39 | A70 | T2-1 | B39 | A70 |
| T1-1 | B39 | A76 | T2-1 | B39 | A76 |
| T1-1 | B39 | A77 | T2-1 | B39 | A77 |
| T1-1 | B39 | A78 | T2-1 | B39 | A78 |
| T1-1 | B39 | A106 | T2-1 | B39 | A106 |
| T1-1 | B39 | A110 | T2-1 | B39 | A110 |
| T2-2 | B39 | A2 | T2-3 | B39 | A2 |
| T2-2 | B39 | A5 | T2-3 | B39 | A5 |
| T2-2 | B39 | A35 | T2-3 | B39 | A35 |
| T2-2 | B39 | A37 | T2-3 | B39 | A37 |
| T2-2 | B39 | A45 | T2-3 | B39 | A45 |
| T2-2 | B39 | A46 | T2-3 | B39 | A46 |
| T2-2 | B39 | A49 | T2-3 | B39 | A49 |
| T2-2 | B39 | A54 | T2-3 | B39 | A54 |
| T2-2 | B39 | A66 | T2-3 | B39 | A66 |
| T2-2 | B39 | A67 | T2-3 | B39 | A67 |
| T2-2 | B39 | A68 | T2-3 | B39 | A68 |
| T2-2 | B39 | A69 | T2-3 | B39 | A69 |
| T2-2 | B39 | A70 | T2-3 | B39 | A70 |
| T2-2 | B39 | A76 | T2-3 | B39 | A76 |
| T2-2 | B39 | A77 | T2-3 | B39 | A77 |

TABLE 41-continued

| | | | | | |
|---|---|---|---|---|---|
| T2-2 | B39 | A78 | T2-3 | B39 | A78 |
| T2-2 | B39 | A106 | T2-3 | B39 | A106 |
| T2-2 | B39 | A110 | T2-3 | B39 | A110 |
| T2-4 | B39 | A2 | T2-5 | B39 | A2 |

TABLE 42

| | | | | | |
|---|---|---|---|---|---|
| T2-4 | B39 | A5 | T2-5 | B39 | A5 |
| T2-4 | B39 | A35 | T2-5 | B39 | A35 |
| T2-4 | B39 | A37 | T2-5 | B39 | A37 |
| T2-4 | B39 | A45 | T2-5 | B39 | A45 |
| T2-4 | B39 | A46 | T2-5 | B39 | A46 |
| T2-4 | B39 | A49 | T2-5 | B39 | A49 |
| T2-4 | B39 | A54 | T2-5 | B39 | A54 |
| T2-4 | B39 | A66 | T2-5 | B39 | A66 |
| T2-4 | B39 | A67 | T2-5 | B39 | A67 |
| T2-4 | B39 | A68 | T2-5 | B39 | A68 |
| T2-4 | B39 | A69 | T2-5 | B39 | A69 |
| T2-4 | B39 | A70 | T2-5 | B39 | A70 |
| T2-4 | B39 | A76 | T2-5 | B39 | A76 |
| T2-4 | B39 | A77 | T2-5 | B39 | A77 |
| T2-4 | B39 | A78 | T2-5 | B39 | A78 |
| T2-4 | B39 | A106 | T2-5 | B39 | A106 |
| T2-4 | B39 | A110 | T2-5 | B39 | A110 |
| T5-1 | B39 | A2 | T7-1 | B39 | A2 |
| T5-1 | B39 | A5 | T7-1 | B39 | A5 |
| T5-1 | B39 | A35 | T7-1 | B39 | A35 |
| T5-1 | B39 | A37 | T7-1 | B39 | A37 |
| T5-1 | B39 | A45 | T7-1 | B39 | A45 |
| T5-1 | B39 | A46 | T7-1 | B39 | A46 |
| T5-1 | B39 | A49 | T7-1 | B39 | A49 |
| T5-1 | B39 | A54 | T7-1 | B39 | A54 |
| T5-1 | B39 | A66 | T7-1 | B39 | A66 |
| T5-1 | B39 | A67 | T7-1 | B39 | A67 |
| T5-1 | B39 | A68 | T7-1 | B39 | A68 |
| T5-1 | B39 | A69 | T7-1 | B39 | A69 |
| T5-1 | B39 | A70 | T7-1 | B39 | A70 |
| T5-1 | B39 | A76 | T7-1 | B39 | A76 |
| T5-1 | B39 | A77 | T7-1 | B39 | A77 |
| T5-1 | B39 | A78 | T7-1 | B39 | A78 |
| T5-1 | B39 | A106 | T7-1 | B39 | A106 |
| T5-1 | B39 | A110 | T7-1 | B39 | A110 |
| T1-1 | B40 | A2 | T2-1 | B40 | A2 |
| T1-1 | B40 | A5 | T2-1 | B40 | A5 |
| T1-1 | B40 | A35 | T2-1 | B40 | A35 |
| T1-1 | B40 | A37 | T2-1 | B40 | A37 |
| T1-1 | B40 | A45 | T2-1 | B40 | A45 |
| T1-1 | B40 | A46 | T2-1 | B40 | A46 |
| T1-1 | B40 | A49 | T2-1 | B40 | A49 |

TABLE 43

| | | | | | |
|---|---|---|---|---|---|
| T1-1 | B40 | A54 | T2-1 | B40 | A54 |
| T1-1 | B40 | A66 | T2-1 | B40 | A66 |
| T1-1 | B40 | A67 | T2-1 | B40 | A67 |
| T1-1 | B40 | A68 | T2-1 | B40 | A68 |
| T1-1 | B40 | A69 | T2-1 | B40 | A69 |
| T1-1 | B40 | A70 | T2-1 | B40 | A70 |
| T1-1 | B40 | A76 | T2-1 | B40 | A76 |
| T1-1 | B40 | A77 | T2-1 | B40 | A77 |
| T1-1 | B40 | A78 | T2-1 | B40 | A78 |
| T1-1 | B40 | A106 | T2-1 | B40 | A106 |
| T1-1 | B40 | A110 | T2-1 | B40 | A110 |
| T2-2 | B40 | A2 | T2-3 | B40 | A2 |
| T2-2 | B40 | A5 | T2-3 | B40 | A5 |
| T2-2 | B40 | A35 | T2-3 | B40 | A35 |
| T2-2 | B40 | A37 | T2-3 | B40 | A37 |
| T2-2 | B40 | A45 | T2-3 | B40 | A45 |
| T2-2 | B40 | A46 | T2-3 | B40 | A46 |
| T2-2 | B40 | A49 | T2-3 | B40 | A49 |
| T2-2 | B40 | A54 | T2-3 | B40 | A54 |
| T2-2 | B40 | A66 | T2-3 | B40 | A66 |

TABLE 43-continued

| | | | | | |
|---|---|---|---|---|---|
| T2-2 | B40 | A67 | T2-3 | B40 | A67 |
| T2-2 | B40 | A68 | T2-3 | B40 | A68 |
| T2-2 | B40 | A69 | T2-3 | B40 | A69 |
| T2-2 | B40 | A70 | T2-3 | B40 | A70 |
| T2-2 | B40 | A76 | T2-3 | B40 | A76 |
| T2-2 | B40 | A77 | T2-3 | B40 | A77 |
| T2-2 | B40 | A78 | T2-3 | B40 | A78 |
| T2-2 | B40 | A106 | T2-3 | B40 | A106 |
| T2-2 | B40 | A110 | T2-3 | B40 | A110 |
| T2-4 | B40 | A2 | T2-5 | B40 | A2 |
| T2-4 | B40 | A5 | T2-5 | B40 | A5 |
| T2-4 | B40 | A35 | T2-5 | B40 | A35 |
| T2-4 | B40 | A37 | T2-5 | B40 | A37 |
| T2-4 | B40 | A45 | T2-5 | B40 | A45 |
| T2-4 | B40 | A46 | T2-5 | B40 | A46 |
| T2-4 | B40 | A49 | T2-5 | B40 | A49 |
| T2-4 | B40 | A54 | T2-5 | B40 | A54 |
| T2-4 | B40 | A66 | T2-5 | B40 | A66 |
| T2-4 | B40 | A67 | T2-5 | B40 | A67 |
| T2-4 | B40 | A68 | T2-5 | B40 | A68 |
| T2-4 | B40 | A69 | T2-5 | B40 | A69 |
| T2-4 | B40 | A70 | T2-5 | B40 | A70 |

TABLE 44

| | | | | | |
|---|---|---|---|---|---|
| T2-4 | B40 | A76 | T2-5 | B40 | A76 |
| T2-4 | B40 | A77 | T2-5 | B40 | A77 |
| T2-4 | B40 | A78 | T2-5 | B40 | A78 |
| T2-4 | B40 | A106 | T2-5 | B40 | A106 |
| T2-4 | B40 | A110 | T2-5 | B40 | A110 |
| T5-1 | B40 | A2 | T7-1 | B40 | A2 |
| T5-1 | B40 | A5 | T7-1 | B40 | A5 |
| T5-1 | B40 | A35 | T7-1 | B40 | A35 |
| T5-1 | B40 | A37 | T7-1 | B40 | A37 |
| T5-1 | B40 | A45 | T7-1 | B40 | A45 |
| T5-1 | B40 | A46 | T7-1 | B40 | A46 |
| T5-1 | B40 | A49 | T7-1 | B40 | A49 |
| T5-1 | B40 | A54 | T7-1 | B40 | A54 |
| T5-1 | B40 | A66 | T7-1 | B40 | A66 |
| T5-1 | B40 | A67 | T7-1 | B40 | A67 |
| T5-1 | B40 | A68 | T7-1 | B40 | A68 |
| T5-1 | B40 | A69 | T7-1 | B40 | A69 |
| T5-1 | B40 | A70 | T7-1 | B40 | A70 |
| T5-1 | B40 | A76 | T7-1 | B40 | A76 |
| T5-1 | B40 | A77 | T7-1 | B40 | A77 |
| T5-1 | B40 | A78 | T7-1 | B40 | A78 |
| T5-1 | B40 | A106 | T7-1 | B40 | A106 |
| T5-1 | B40 | A110 | T7-1 | B40 | A110 |
| T1-1 | B41 | A2 | T2-1 | B41 | A2 |
| T1-1 | B41 | A5 | T2-1 | B41 | A5 |
| T1-1 | B41 | A35 | T2-1 | B41 | A35 |
| T1-1 | B41 | A37 | T2-1 | B41 | A37 |
| T1-1 | B41 | A45 | T2-1 | B41 | A45 |
| T1-1 | B41 | A46 | T2-1 | B41 | A46 |
| T1-1 | B41 | A49 | T2-1 | B41 | A49 |
| T1-1 | B41 | A54 | T2-1 | B41 | A54 |
| T1-1 | B41 | A66 | T2-1 | B41 | A66 |
| T1-1 | B41 | A67 | T2-1 | B41 | A67 |
| T1-1 | B41 | A68 | T2-1 | B41 | A68 |
| T1-1 | B41 | A69 | T2-1 | B41 | A69 |
| T1-1 | B41 | A70 | T2-1 | B41 | A70 |
| T1-1 | B41 | A76 | T2-1 | B41 | A76 |
| T1-1 | B41 | A77 | T2-1 | B41 | A77 |
| T1-1 | B41 | A78 | T2-1 | B41 | A78 |
| T1-1 | B41 | A106 | T2-1 | B41 | A106 |
| T1-1 | B41 | A110 | T2-1 | B41 | A110 |

TABLE 45

| | | | | | |
|---|---|---|---|---|---|
| T2-4 | B40 | A76 | T2-5 | B40 | A76 |
| T2-2 | B41 | A2 | T2-3 | B41 | A2 |
| T2-2 | B41 | A5 | T2-3 | B41 | A5 |

TABLE 45-continued

| | | | | | |
|---|---|---|---|---|---|
| T2-2 | B41 | A35 | T2-3 | B41 | A35 |
| T2-2 | B41 | A37 | T2-3 | B41 | A37 |
| T2-2 | B41 | A45 | T2-3 | B41 | A45 |
| T2-2 | B41 | A46 | T2-3 | B41 | A46 |
| T2-2 | B41 | A49 | T2-3 | B41 | A49 |
| T2-2 | B41 | A54 | T2-3 | B41 | A54 |
| T2-2 | B41 | A66 | T2-3 | B41 | A66 |
| T2-2 | B41 | A67 | T2-3 | B41 | A67 |
| T2-2 | B41 | A68 | T2-3 | B41 | A68 |
| T2-2 | B41 | A69 | T2-3 | B41 | A69 |
| T2-2 | B41 | A70 | T2-3 | B41 | A70 |
| T2-2 | B41 | A76 | T2-3 | B41 | A76 |
| T2-2 | B41 | A77 | T2-3 | B41 | A77 |
| T2-2 | B41 | A78 | T2-3 | B41 | A78 |
| T2-2 | B41 | A106 | T2-3 | B41 | A106 |
| T2-2 | B41 | A110 | T2-3 | B41 | A110 |
| T2-4 | B41 | A2 | T2-5 | B41 | A2 |
| T2-4 | B41 | A5 | T2-5 | B41 | A5 |
| T2-4 | B41 | A35 | T2-5 | B41 | A35 |
| T2-4 | B41 | A37 | T2-5 | B41 | A37 |
| T2-4 | B41 | A45 | T2-5 | B41 | A45 |
| T2-4 | B41 | A46 | T2-5 | B41 | A46 |
| T2-4 | B41 | A49 | T2-5 | B41 | A49 |
| T2-4 | B41 | A54 | T2-5 | B41 | A54 |
| T2-4 | B41 | A66 | T2-5 | B41 | A66 |
| T2-4 | B41 | A67 | T2-5 | B41 | A67 |
| T2-4 | B41 | A68 | T2-5 | B41 | A68 |
| T2-4 | B41 | A69 | T2-5 | B41 | A69 |
| T2-4 | B41 | A70 | T2-5 | B41 | A70 |
| T2-4 | B41 | A76 | T2-5 | B41 | A76 |
| T2-4 | B41 | A77 | T2-5 | B41 | A77 |
| T2-4 | B41 | A78 | T2-5 | B41 | A78 |
| T2-4 | B41 | A106 | T2-5 | B41 | A106 |
| T2-4 | B41 | A110 | T2-5 | B41 | A110 |
| T5-1 | B41 | A2 | T7-1 | B41 | A2 |
| T5-1 | B41 | A5 | T7-1 | B41 | A5 |
| T5-1 | B41 | A35 | T7-1 | B41 | A35 |
| T5-1 | B41 | A37 | T7-1 | B41 | A37 |
| T5-1 | B41 | A45 | T7-1 | B41 | A45 |
| T5-1 | B41 | A46 | T7-1 | B41 | A46 |

TABLE 46

| | | | | | |
|---|---|---|---|---|---|
| T5-1 | B41 | A49 | T7-1 | B41 | A49 |
| T5-1 | B41 | A54 | T7-1 | B41 | A54 |
| T5-1 | B41 | A66 | T7-1 | B41 | A66 |
| T5-1 | B41 | A67 | T7-1 | B41 | A67 |
| T5-1 | B41 | A68 | T7-1 | B41 | A68 |
| T5-1 | B41 | A69 | T7-1 | B41 | A69 |
| T5-1 | B41 | A70 | T7-1 | B41 | A70 |
| T5-1 | B41 | A76 | T7-1 | B41 | A76 |
| T5-1 | B41 | A77 | T7-1 | B41 | A77 |
| T5-1 | B41 | A78 | T7-1 | B41 | A78 |
| T5-1 | B41 | A106 | T7-1 | B41 | A106 |
| T5-1 | B41 | A110 | T7-1 | B41 | A110 |
| T1-1 | B42 | A2 | T2-1 | B42 | A2 |
| T1-1 | B42 | A5 | T2-1 | B42 | A5 |
| T1-1 | B42 | A35 | T2-1 | B42 | A35 |
| T1-1 | B42 | A37 | T2-1 | B42 | A37 |
| T1-1 | B42 | A45 | T2-1 | B42 | A45 |
| T1-1 | B42 | A46 | T2-1 | B42 | A46 |
| T1-1 | B42 | A49 | T2-1 | B42 | A49 |
| T1-1 | B42 | A54 | T2-1 | B42 | A54 |
| T1-1 | B42 | A66 | T2-1 | B42 | A66 |
| T1-1 | B42 | A67 | T2-1 | B42 | A67 |
| T1-1 | B42 | A68 | T2-1 | B42 | A68 |
| T1-1 | B42 | A69 | T2-1 | B42 | A69 |
| T1-1 | B42 | A70 | T2-1 | B42 | A70 |
| T1-1 | B42 | A76 | T2-1 | B42 | A76 |
| T1-1 | B42 | A77 | T2-1 | B42 | A77 |
| T1-1 | B42 | A78 | T2-1 | B42 | A78 |
| T1-1 | B42 | A106 | T2-1 | B42 | A106 |
| T1-1 | B42 | A110 | T2-1 | B42 | A110 |
| T2-2 | B42 | A2 | T2-3 | B42 | A2 |
| T2-2 | B42 | A5 | T2-3 | B42 | A5 |

TABLE 46-continued

| | | | | | |
|---|---|---|---|---|---|
| T2-2 | B42 | A35 | T2-3 | B42 | A35 |
| T2-2 | B42 | A37 | T2-3 | B42 | A37 |
| T2-2 | B42 | A45 | T2-3 | B42 | A45 |
| T2-2 | B42 | A46 | T2-3 | B42 | A46 |
| T2-2 | B42 | A49 | T2-3 | B42 | A49 |
| T2-2 | B42 | A54 | T2-3 | B42 | A54 |
| T2-2 | B42 | A66 | T2-3 | B42 | A66 |
| T2-2 | B42 | A67 | T2-3 | B42 | A67 |
| T2-2 | B42 | A68 | T2-3 | B42 | A68 |
| T2-2 | B42 | A69 | T2-3 | B42 | A69 |

TABLE 47

| | | | | | |
|---|---|---|---|---|---|
| T2-2 | B42 | A70 | T2-3 | B42 | A70 |
| T2-2 | B42 | A76 | T2-3 | B42 | A76 |
| T2-2 | B42 | A77 | T2-3 | B42 | A77 |
| T2-2 | B42 | A78 | T2-3 | B42 | A78 |
| T2-2 | B42 | A106 | T2-3 | B42 | A106 |
| T2-2 | B42 | A110 | T2-3 | B42 | A110 |
| T2-4 | B42 | A2 | T2-5 | B42 | A2 |
| T2-4 | B42 | A5 | T2-5 | B42 | A5 |
| T2-4 | B42 | A35 | T2-5 | B42 | A35 |
| T2-4 | B42 | A37 | T2-5 | B42 | A37 |
| T2-4 | B42 | A45 | T2-5 | B42 | A45 |
| T2-4 | B42 | A46 | T2-5 | B42 | A46 |
| T2-4 | B42 | A49 | T2-5 | B42 | A49 |
| T2-4 | B42 | A54 | T2-5 | B42 | A54 |
| T2-4 | B42 | A66 | T2-5 | B42 | A66 |
| T2-4 | B42 | A67 | T2-5 | B42 | A67 |
| T2-4 | B42 | A68 | T2-5 | B42 | A68 |
| T2-4 | B42 | A69 | T2-5 | B42 | A69 |
| T2-4 | B42 | A70 | T2-5 | B42 | A70 |
| T2-4 | B42 | A76 | T2-5 | B42 | A76 |
| T2-4 | B42 | A77 | T2-5 | B42 | A77 |
| T2-4 | B42 | A78 | T2-5 | B42 | A78 |
| T2-4 | B42 | A106 | T2-5 | B42 | A106 |
| T2-4 | B42 | A110 | T2-5 | B42 | A110 |
| T5-1 | B42 | A2 | T7-1 | B42 | A2 |
| T5-1 | B42 | A5 | T7-1 | B42 | A5 |
| T5-1 | B42 | A35 | T7-1 | B42 | A35 |
| T5-1 | B42 | A37 | T7-1 | B42 | A37 |
| T5-1 | B42 | A45 | T7-1 | B42 | A45 |
| T5-1 | B42 | A46 | T7-1 | B42 | A46 |
| T5-1 | B42 | A49 | T7-1 | B42 | A49 |
| T5-1 | B42 | A54 | T7-1 | B42 | A54 |
| T5-1 | B42 | A66 | T7-1 | B42 | A66 |
| T5-1 | B42 | A67 | T7-1 | B42 | A67 |
| T5-1 | B42 | A68 | T7-1 | B42 | A68 |
| T5-1 | B42 | A69 | T7-1 | B42 | A69 |
| T5-1 | B42 | A70 | T7-1 | B42 | A70 |
| T5-1 | B42 | A76 | T7-1 | B42 | A76 |
| T5-1 | B42 | A77 | T7-1 | B42 | A77 |
| T5-1 | B42 | A78 | T7-1 | B42 | A78 |
| T5-1 | B42 | A106 | T7-1 | B42 | A106 |
| T5-1 | B42 | A110 | T7-1 | B42 | A110 |

TABLE 48

| | | | | | |
|---|---|---|---|---|---|
| T1-1 | B43 | A2 | T2-1 | B43 | A2 |
| T1-1 | B43 | A5 | T2-1 | B43 | A5 |
| T1-1 | B43 | A35 | T2-1 | B43 | A35 |
| T1-1 | B43 | A37 | T2-1 | B43 | A37 |
| T1-1 | B43 | A45 | T2-1 | B43 | A45 |
| T1-1 | B43 | A46 | T2-1 | B43 | A46 |
| T1-1 | B43 | A49 | T2-1 | B43 | A49 |
| T1-1 | B43 | A54 | T2-1 | B43 | A54 |
| T1-1 | B43 | A66 | T2-1 | B43 | A66 |
| T1-1 | B43 | A67 | T2-1 | B43 | A67 |
| T1-1 | B43 | A68 | T2-1 | B43 | A68 |
| T1-1 | B43 | A69 | T2-1 | B43 | A69 |
| T1-1 | B43 | A70 | T2-1 | B43 | A70 |
| T1-1 | B43 | A76 | T2-1 | B43 | A76 |

TABLE 48-continued

| | | | | | |
|---|---|---|---|---|---|
| T1-1 | B43 | A77 | T2-1 | B43 | A77 |
| T1-1 | B43 | A78 | T2-1 | B43 | A78 |
| T1-1 | B43 | A106 | T2-1 | B43 | A106 |
| T1-1 | B43 | A110 | T2-1 | B43 | A110 |
| T2-2 | B43 | A2 | T2-3 | B43 | A2 |
| T2-2 | B43 | A5 | T2-3 | B43 | A5 |
| T2-2 | B43 | A35 | T2-3 | B43 | A35 |
| T2-2 | B43 | A37 | T2-3 | B43 | A37 |
| T2-2 | B43 | B45 | T2-3 | B43 | A45 |
| T2-2 | B43 | A46 | T2-3 | B43 | A46 |
| T2-2 | B43 | A49 | T2-3 | B43 | A49 |
| T2-2 | B43 | A54 | T2-3 | B43 | A54 |
| T2-2 | B43 | A66 | T2-3 | B43 | A66 |
| T2-2 | B43 | A67 | T2-3 | B43 | A67 |
| T2-2 | B43 | A68 | T2-3 | B43 | A68 |
| T2-2 | B43 | A69 | T2-3 | B43 | A69 |
| T2-2 | B43 | A70 | T2-3 | B43 | A70 |
| T2-2 | B43 | A76 | T2-3 | B43 | A76 |
| T2-2 | B43 | A77 | T2-3 | B43 | A77 |
| T2-2 | B43 | A78 | T2-3 | B43 | A78 |
| T2-2 | B43 | A106 | T2-3 | B43 | A106 |
| T2-2 | B43 | A110 | T2-3 | B43 | A110 |
| T2-4 | B43 | A2 | T2-5 | B43 | A2 |
| T2-4 | B43 | A5 | T2-5 | B43 | A5 |
| T2-4 | B43 | A35 | T2-5 | B43 | A35 |
| T2-4 | B43 | A37 | T2-5 | B43 | A37 |
| T2-4 | B43 | A45 | T2-5 | B43 | A45 |
| T2-4 | B43 | A46 | T2-5 | B43 | A46 |

TABLE 49

| | | | | | |
|---|---|---|---|---|---|
| T2-4 | B43 | A49 | T2-5 | B43 | A49 |
| T2-4 | B43 | A54 | T2-5 | B43 | A54 |
| T2-4 | B43 | A66 | T2-5 | B43 | A66 |
| T2-4 | B43 | A67 | T2-5 | B43 | A67 |
| T2-4 | B43 | A68 | T2-5 | B43 | A68 |
| T2-4 | B43 | A69 | T2-5 | B43 | A69 |
| T2-4 | B43 | A70 | T2-5 | B43 | A70 |
| T2-4 | B43 | A76 | T2-5 | B43 | A76 |
| T2-4 | B43 | A77 | T2-5 | B43 | A77 |
| T2-4 | B43 | A78 | T2-5 | B43 | A78 |
| T2-4 | B43 | A106 | T2-5 | B43 | A106 |
| T2-4 | B43 | A110 | T2-5 | B43 | A110 |
| T5-1 | B43 | A2 | T7-1 | B43 | A2 |
| T5-1 | B43 | A5 | T7-1 | B43 | A5 |
| T5-1 | B43 | A35 | T7-1 | B43 | A35 |
| T5-1 | B43 | A37 | T7-1 | B43 | A37 |
| T5-1 | B43 | A45 | T7-1 | B43 | A45 |
| T5-1 | B43 | A46 | T7-1 | B43 | A46 |
| T5-1 | B43 | A49 | T7-1 | B43 | A49 |
| T5-1 | B43 | A54 | T7-1 | B43 | A54 |
| T5-1 | B43 | A66 | T7-1 | B43 | A66 |
| T5-1 | B43 | A67 | T7-1 | B43 | A67 |
| T5-1 | B43 | A68 | T7-1 | B43 | A68 |
| T5-1 | B43 | A69 | T7-1 | B43 | A69 |

TABLE 49-continued

| | | | | | |
|---|---|---|---|---|---|
| T5-1 | B43 | A70 | T7-1 | B43 | A70 |
| T5-1 | B43 | A76 | T7-1 | B43 | A76 |
| T5-1 | B43 | A77 | T7-1 | B43 | A77 |
| T5-1 | B43 | A78 | T7-1 | B43 | A78 |
| T5-1 | B43 | A106 | T7-1 | B43 | A106 |
| T5-1 | B43 | A110 | T7-1 | B43 | A110 |

Furthermore, the compounds having the above-mentioned structure wherein —X'—Y' is one selected from a group of $OCH_2CH=CMe_2$, $OCH_2$-2-furyl, $OCH_2$-3-furyl, $OCH_2C\equiv CMe$, $NHCH_2CH=CMe_2$, $N(iPr)SO_2NHMe$, $NHCH(Me)CH_2OMe$, NHiPr, NH-iBu, NHc-Pent, $NHCH_2$c-Hex, NHc-Hex, NHc-Hex-4-(=NOMe), NHcHex-4, 4-$(OMe)_2$, $NHCH_2C_6H_4$-4-$B(OH)_2$, $NHCH_2C_6H_4$-2-OH, $NHCH_2C_6H_3$-3,4-$(OH)_2$, $NHCH_2C_6H_2$-3, 4, 5-$(OMe)_3$, $NHCH_2C_6H_4$-4-COOH, $NHCH_2C_6H_4$-4-OH, $NHCH_2C_6H_4$-3-OH, $NHCH_2$-2-furyl, $NHCH_2$-3-furyl, NH-4-tetrahydropyran, $NHCH_2$-benzopyrrolyl, $NHCH_2$-2-thiazolyl, $NHCH_2$-quinolyl, NHcHex-4, 4-ethylenedioxy, 1-pyrolidinyl, 4-morpholinyl, 1-piperadinyl, 4-thiomorpholinyl, 1-piperidyl,

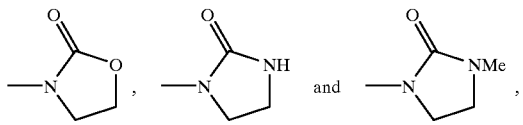

are preferable. The compounds wherein —X'—Y' is —$OCH_2$-2-furyl, —$NHCH_2CH=CMe_2$ or —$OCH_2CH=CMe_2$ are more preferable.

A process for producing the compound (I) is as follows.

A Process for Producing the Compound (I')

A compound of the following formula (I') (hereinafter referred to as "a compound (I')") can be produced by reacting a compound of the formula (IIa) (hereinafter referred to as "a compound (IIa)") with a bicyclic compound of the formula (IIIa) (hereinafter referred to as "a compound (IIIa)") or by reacting a compound of the formula (IIb) (hereinafter referred to as "a compound (IIb)") with a bicyclic compound of the formula (IIIb) (hereinafter referred to as "a compound (IIIb)").

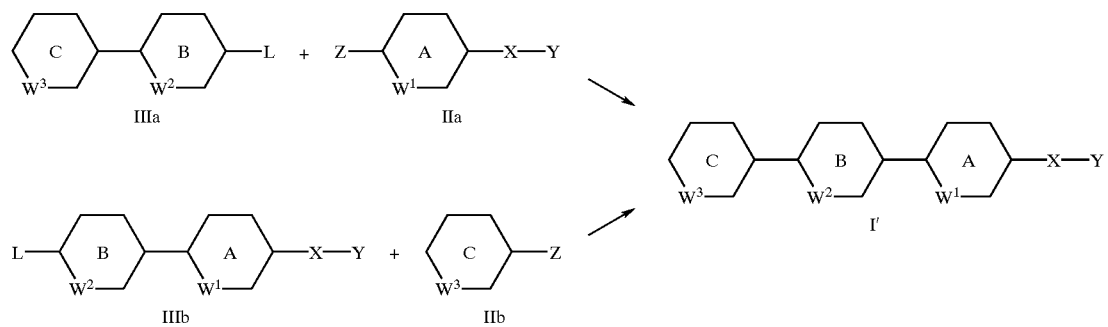

wherein either of L and Z is dihydroxyborane, di(lower) alkyl borane or di(lower) alkoxyborane and the other is halogen or —OSO$_2$(C$_q$F$_{2q+1}$) (q is an integer of 0 to 4) and other symbols are the same as defined above.

The compound (I') can be produced by reacting the compound (Ia) with the compound (IIIa) or by reacting the compound (IIb) with the compound (IIIb) in a mixture of an appropriate solvent such as benzene, toluene, N, N-dimethylformamide, dimethoxyethane, tetrahydrofuran, dioxane, ethanol, methanol or the like and water or in an anhydrous solution in the presence of a palladium catalyst such as Pd(PPh$_3$)$_4$, PdCl$_2$(PPh$_3$)$_2$, PdCl$_2$(OAc)$_2$, PdCl$_2$(CH$_3$CN)$_2$ or the like, preferably Pd(PPh$_3$)$_4$, under a basic condition (for example, by K$_3$PO$_4$, NaHCO$_3$, NaOEt, Na$_2$CO$_3$, Et$_4$NCl, Ba(OH)$_2$, Cs$_2$CO$_3$, CsF, NaOH, Ag$_2$CO$_3$ or the like) at room temperature or with heating for several tens minutes to several tens hours.

One of substituents L and Z of the compounds to be reacted may be any of the borane groups which are applicable in the Suzuki Reaction (Chemical Communication 1979, 866, Journal of Synthetic Organic Chemistry, Japan, 1993, Vol.51, No.11, 91-100) and dihydroxyborane is preferable. The other may be any of the leaving groups which are applicable in the Suzuki Reaction, for example, halogen, —OSO$_2$(C$_q$F$_{2q+1}$) wherein q is an integer of 0 to 4, or the like. Specifically, halogen, trifluoromethanesulfonyloxy (hereinafter referred to as OTf) or the like is preferable and bromine, iodine or OTf is more preferable.

The other substituents of A ring, B ring and C ring and —X—Y of the compounds (IIa), (IIIa), (IIb) and (IIIb) may be any of the groups which do not affect the Suzuki Reaction, for example, any groups other than halogen and —OSO$_2$(C$_q$F$_{2q+1}$) wherein q is an integer of 0 to 4.

For example, Y may be optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted 5- or 6-membered heterocycle which may be fused with benzene ring, Y may be optionally substituted lower alkoxy when X is —CH$_2$— and Y may be optionally substituted lower alkoxycarbonyl, optionally substituted lower alkylsulfonyl or optionally substituted arylsulfonyl when X is —O— or —NR$^1$—.

Even if any substituent of A ring, B ring or C ring is halogen, these reactions can be carried out without difficulty when the reactivity of the substituent L with the substituent Z is higher than that of halogen with either of substituents L and Z.

Even if either of substituents of A ring, B ring and C ring or —X—Y is hydroxy, the above reactions can be preferably carried out. Preferably the above reactions may be carried out after the protection of hydroxy group with a usual hydroxy-protecting group such as methoxymethyl, benzyl, tert-butyldimethylsilyl, methanesulfonyl, p-toluenesulfonyl or the like, followed by deprotection by the usual methods.

As processes for producing the compound (I'), the above mentioned Suzuki Reaction is most preferable in view of the efficiency and easiness but silicon, zinc, tin or the like can be used in place of the borane group in the above scheme.

For example, in the case that one of A and Z is —SiR$^{17}$$_{3-r}$(Hal)$_r$ wherein R$^{17}$ are independently lower alkyl, Hal is halogen and r is an integer of 1 to 3 and the other is halogen or —OSO$_2$(C$_q$F$_{2q+1}$) wherein q is an integer of 0 to 4, the coupling reaction may be carried out using a usual palladium catalyst (Synlett (1991) 845–853, J. Org. Chem. 1996, 61, 7232–7233). Examples of preferable palladium catalysts are (i-Pr$_3$P)$_2$PdCl$_2$, [(dcpe)PdCl$_2$](dcpe=Cy$_2$PCH$_2$CH$_2$PCy$_2$), ($\eta^3$-C$_3$H$_5$PdCl)$_2$ and the like.

Even in the case that one of L and Z is —SnR$^{18}$$_3$ wherein R$^{18}$ are each independently lower alkyl and the other is halogen, acetyloxy or —OSO$_2$(C$_q$F$_{2q+1}$) wherein q is an integer of 0 to 4, an objective compound can be obtained using a usual palladium catalyst (preferably Pd(PPh$_3$)$_4$ or the like) (Angew. Chem. Int. Ed. Engl. 25 (1986) 508–524).

In the case that one of L and Z is —Zn(Hal) wherein Hal is halogen and the other is halogen, an objective compound can be obtained (Acc, Chem. Res. 1982, 15, 340–348). Any usual palladium catalyst is applicable and Pd(PPh$_3$)$_4$, PdCl$_2$(dppf), PdCl$_2$(PPh$_3$)$_2$, PdCl$_2$(P(o-Tolyl)$_3$)$_2$, Pd(OAc)$_2$ and the like are exemplified as preferable examples.

All of these reactions may be carried out in a suitable solvent such as N,N-dimethylformamide, tetrahydrofuran or the like at room temperature or with heating for several tens minutes to several tens hours.

As compound (IIIa) and (IIIb) in the above reactions, may be used known compounds or compounds which are derived from a compound of the following formula (Va) (hereinafter referred to as "a compound (Va)") or the following formula (Vb) (hereinafter referred to as "a compound (Vb)") which can be produced by the known method or the following method.

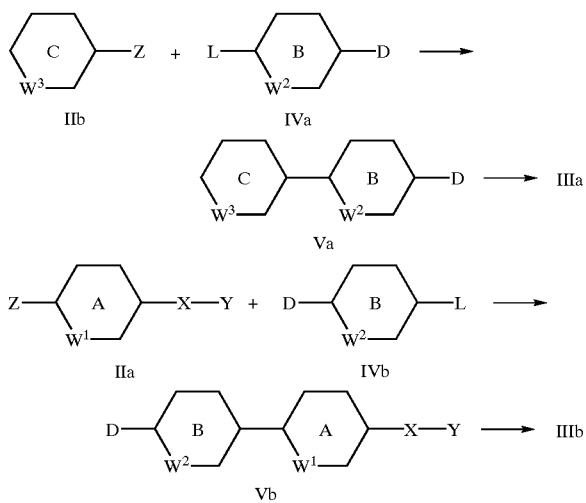

wherein D is any of the groups which do not affect the Suzuki Reaction of L with Z, and may be the same group as L when a compound of the formula (IVb) is a bisymmetric compound. The other symbols are the same as above.

The compound (IIb) is reacted with the compound (IVa) or the compound (IIa) is reacted with (IVb) to give the compound (Va) or (Vb). When the compound (IVa) or (IVb) is not a bisymmetric compound, D is preferably a group which does not affect the Suzuki Reaction of L with Z and can be easily converted to L. For example, hydroxy, hydrogen, formyl, nitro or the like is preferable. In the reaction of L with Z, silicon, zinc, tin or the like can be used in place of the borane group as mentioned above.

D is converted into a group L which is applicable to the Suzuki Reaction.

A compound wherein D is hydroxy may be reacted with a trifluoromethanesulfonating agent such as trifluoromethanesulfonic anhydride, trifluoromethansulfonyl chloride, N-phenyltrifluorometbanesulfone imide or the like in a suitable solvent such as dichloromethane, chloroform, tetrahydrofuran or benzene in the presence of a base such as sodium hydride, pyridine, triethylamine, potassium carbonate or the like at −20° C. or with heating for several minutes to several tens hours to give an objective compound wherein L is OTf.

For example, a compound wherein D is hydrogen may be reacted with a halogenating agent such as bromine, chlorine, iodine, N-bromosuccinimide or the like in a suitable solvent such as acetic acid, dichloromethane, chloroform, carbon tetrachloride, benzene, water or the like at −20° C. or with heating for several minutes to several tens hours to give an objective compound wherein L is halogen.

A compound wherein D is formyl may be oxidated by the Baeyer-Villiger reaction to give a compound wherein D is formyloxy, followed by hydrolysis to give a compound wherein D is hydroxy. The compound wherein L is OTf can be obtained by the similar process as mentioned above.

A compound wherein D is nitro may be reduced to give a compound wherein D is amino, followed by the Sandmeyer Reaction to give a compound L is halogen.

A Process for Producing the Compound (I")

A compound of the following formula (I") (hereinafter referred to as "a compound (I")") can be produced by the Suzuki Reaction of a compound of the formula (VI) (hereinafter referred to as "a compound (VI)") with a compound of the formula (IIa) (hereinafter referred to as "a compound (IIa)") or by condensation of a compound of the formula (VII) (hereinafter referred to as "a compound (VII)") with a compound of the formula (VIII) (hereinafter referred to as "a compound (VIII)")

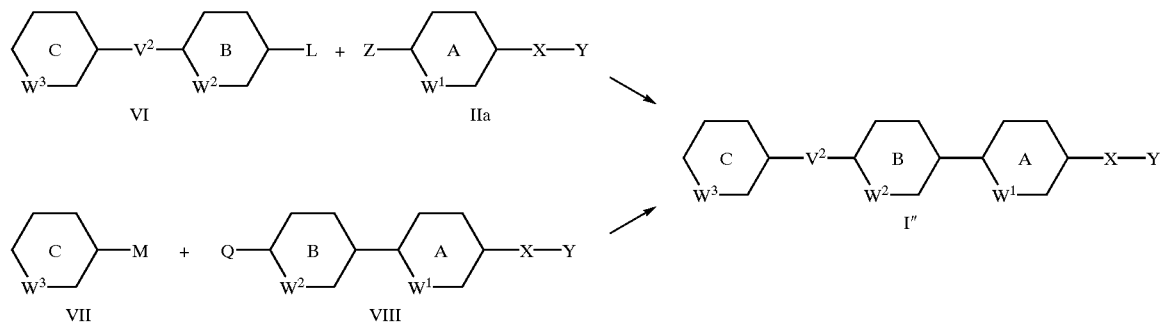

wherein either of M and Q is hydroxy or amino and the other is halogen, lower alkylsulfonyloxy, arylsulfonyloxy, lower alkylsulfonyl, arylsulfonyl or methyl having them as substituents, either of M and Q is lithium or Mg(Hal) wherein Hal is halogen and the other is carboxy, lower alkoxycarbonyl, carbamoyl or formyl, either of M and Q is formyl and the other is halogenomethyl, or either of M and Q is ethynyl and the other is halogen; and the other symbols are the same as defined above.

Various conditions for a reaction of the compound (VI) with the compound (IIa) are the same as those for the process for producing the compound (I').

In a reaction of the compound (VII) with a compound (VIII), when $V^2$ of an objective compound is —O—, —NH—, —OCH$_2$—, —CH$_2$O— or —NHCH$_2$—, either of M and Q is hydroxy or amino and the other is a leaving group such as halogen, lower alkylsulfonyloxy, arylsulfonyloxy, lower alkylsulfonyl, arylsulfonyl or the like or methyl having the leaving group as substituents. These two compounds are reacted in a suitable solvent such as benzene, toluene, acetone, acetonitrile, N,N-dimethylformamide, dimethylsulfoxide, pyridine, methanol, ethanol or the like in the presence of a base such as sodium hydride, pyridine, triethylamine, potassium carbonate, sodium hydroxide, potassium hydroxide or the like, if necessary by adding a copper catalyst such as copper powder, CuCl, CuO or the like at 0° C. or with heating for several minutes to several tens hours to give the objective compound.

In a reaction of the compound (VII) with the compound (VIII), when $V^2$ of an objective compound is —CO— or —CH(OH)—, either of M and Q is an organic metal such as lithium or Mg(Hal) wherein Hal is halogen and the other is carboxy, lower alkoxycarbonyl, carbamoyl or formyl. These two compounds are reacted in a suitable solvent such as diethylether, tetrahydrofuran, dimethoxyethan, dioxane or the like at −78° C. to with heating for several minutes to several hours to give an objective compound.

When $V^2$ of an objective compound is —CH(OR)— wherein R is lower alkyl, after a compound wherein $V^2$ is —CH(OH)— is obtained, the obtained compound may be subjected to alkylation.

A compound wherein $V^2$ is —CO— may be obtained by reacting a compound wherein $V^2$ is —CH(OH)— with an oxidizing agent such as chromic anhydride, Jone's reagent or the like in a solvent such as t-butylalcohol, acetone or the like depending on the oxidizing agent at 0° C. or with heating for several hours. A compound wherein $V^2$ is —CH(OH)— can be obtained also by reacting a compound wherein $V^2$ is —CO— with an reducing agent such as sodium borohydride, aluminium lithium hydride or the like in a suitable solvent such as diethyl ether, tetrahydrofuran, dimethoxyethane, dioxane, methanol, ethanol or the like.

When a compound wherein $V^2$ of an objective compound is —CH=CH—, either of M and Q is formyl and the other is halogenomethyl (for example, halogen is chloro, bromo or iodo). An objective compound can be obtained by the Wittig Reaction (Organic Reaction, vol.14, p. 270, 1965).

When $V^2$ of an objective compound is —CH≡CH—, either of M and Q is ethynyl and the other is halogen (preferably bromo or iodo). The objective compound can be synthesized by a coupling reaction with a generally used palladium catalyst (for example, Synthesis. (1980) 627, Tetrahedron, 1982, 38, 631).

Other substituents of A ring, B ring, C ring and —X—Y of the compound (VI), (IIa), (VII) and (VIII) may be any substituent which does not affect the Suzuki Reaction of L with Z or a condensing reaction of M with Q. Even if in a reaction of the compound (VI) with the compound (IIa) wherein either of substituents is halogen, this reaction may be carried out without difficulty if the reactivity of a substituent L with a substituent Z is higher than the reactivity with halogen. Even if either of substituents is hydroxy, the above reaction can be carried out. Preferably hydroxy is previously protected, followed a deprotection after the above reaction.

As the compound (VI) in the above scheme, it may be used a known compound or a compound of the formula (X) which is synthesized in the following method.

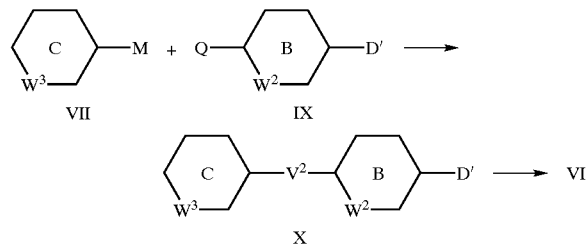

wherein D' is a group which does not affect a condensing reaction of M with Q and when a compound of the formula (IX) is a symmetric compound, D' may be the same group as Q, and the other symbols are the same as defined above.

When the compound (IX) is not a symmetric compound, D' is preferably a group which does not affect the condensing reaction of M with Q and which can easily be converted to L. For example, hydrogen, formyl, protected hydroxy, nitro or the like is preferable. As a hydroxy-protecting group, exemplified are benzyl, t-butyldimethylsilyl, methoxymethyl and the like. A method for converting D' to L is similar to the above method for converting D to L. Other various conditions are similar to that for reacting the compound (VII) with the compound (VIII).

A known compound may be used as a compound (VIII) in the above reaction scheme and a compound synthesized by the usual method or derived from the above compound (Vb) by the usual method also may be used.

In the case that a compound has a substituent interfering of the above reaction, the substituent may be protected with a suitable protecting group in advance and the protecting group may be removed in a suitable step by the usual method. For example, if hydroxy interferes the reaction, it may be protected with methoxymethyl, methanesulfonyl, benzyl, trifluoromethanesulfonyl, tert-butyldimethylsilyl or the like, followed by deprotection in a suitable step.

For example, for a protection of hydroxy with methanesulfonyl, a compound which has hydroxy may be reacted with methanesulfonyl chloride in a solvent such as dichloromethane, chloroform, carbon tetrachloride or the like in the presence of a base such as triethylamine, pyridine or the like under ice-cooling or at room temperature for several hours. The protected compound may be deprotected with 1–4 N sodium hydroxide, potassium hydroxide, aqueous solution thereof, sodium methoxide, ethyl magnesium bromide or the like in a solvent such as dimethylsulfoxide, dimethylformamide, tetrahydrofuran, dioxane, dimethoxyethane or the like at room temperature or with heating for several tens minutes to several hours.

When methoxymethyl is used as a hydroxy-protecting group, a compound which has hydroxy may be reacted with chloromethylmethylether in a solvent such as tetrahydrofuran, dioxane, dimethoxyethane or the like in the presence of sodium hydride, diisopropylethylamine or the like to give a compound which has a protected hydroxy group. The compound may be subjected to a usual deprotection reaction with hydrochloric acid, sulfuric acid or the like in a solvent such as methanol, tetrahydrofuran, acetic acid or the like for a deprotection.

When tert-butyldimethylsilyl is used as a protecting group, a compound which has hydroxy may be reacted with tert-butyldimethylsilyl chloride, tert-butyldimethylsilyl triflate or the like in a solvent such as dimethylformamide, acetonitrile, tetrahydrofuran, dimethylformamide, dichloromethane or the like in the presence of imidazole, triethylamine, 2,6-lutidine or the like. For a deprotection reaction the protected compound may be reacted with tetrabutylammonium fluoride or the like in a solvent such as tetrahydrofuran or the like.

A compound of the present invention thus obtained can be converted into a prodrug thereof. The term "prodrug" includes compounds which can easily be converted to the compound having the activity of the present invention in a living body. Any usual method for conversion into a prodrug may be used.

For example, hydroxy or amino which is attached to any possible position of a compound of the present invention may be substituted with a usual group for manufacturing a prodrug. For example, substituted acyl (wherein the substituent is carboxy, sulfo, amino, lower alkylamino or the like), phosphonoxy or the like may be introduced into the hydroxy, and substituted alkoxycarbonyl (wherein the substituent is halogen, acyloxy, hydroxyacyloxy, carboxyacyloxy, heterocyclylcarbonyloxy or the like) or substituted alkyl (wherein the substituent is aroylamino which may be substituted with acyloxy(lower)alkoxy or the like) may be introduced into the amino.

More definitely, when A ring or C ring has hydroxy as a substituent, a substituent such as —COCH$_2$CH$_2$COOH, —COCH=CHCOOH, —COCH$_2$SO$_3$H, —PO$_3$H$_2$, —COCH$_2$NMe$_2$, —CO-Py wherein Py is pyridine or the like may be introduced. When A ring or C ring has amino as a substituent(e.g., X, X' or the like), —COOCH$_2$O(C=O)CH$_2$OH, —COOCH$_2$O(C=O)CH$_2$CH$_2$COOH, —COOCH$_2$OAc, —COOCH(Me)OAc, —COOCH(Me)OCOCMe$_3$, —COOCH$_2$OCO(CH$_2$)$_{14}$Me, —COOCH$_2$OCO-Pyr, —CH$_2$NHCO-C$_6$H$_4$-o-OCH$_2$OAc or the like may be introduced.

The immunosuppressant or anti-allergic agent of the present invention is useful for prevention or treatment of allergic diseases such as rejection symptom against transplantation of an organ or a tissue, graft-versus-host reaction caused by bone marrow transplantation, atopic allergic diseases (for example, bronchial asthma, allergic rhinitis, allergic dermatitis and the like), hypereosinophils syndrome, allergic conjunctivitis, systemic lupus erythematosus, polymyositis, dermatomyositis, scleriasis, MCTD, chronic rheumatoid arthritis, inflammatory bowel disease, injury caused by ischemia-reperfusion, pollenosis, allergic rhinitis, urticaria, psoriasis and the like.

A compound of the present invention can be administered orally or parenterally as a immunosuppressant, anti-allergic agent and/or suppressant on the IgE production. In the case of oral administration, it may be in any usual form such as tablets, granules, powders, capsules, pills, solutions, syrups, buccal tablets, sublingual tablets and the like. When the compound is parenterally administered, any usual form is preferable, for example, injections (e.g., intravenous, intramuscular), suppositories, endermic agents, vapors and the like. Oral administration is particularly preferable.

A pharmaceutical composition may be manufactured by mixing an effective amount of a compound of the present invention with various pharmaceutical ingredients suitable for the administration form, such as excipients, binders, moistening agents, disintegrators, lubricants, diluents and the like. When the composition is of an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxymethylcellulose, hydroxypropylcellulose, gelatin, polyvinylpyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methyl cellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added. For oral administration, sweetening agents, flavors and the like may be added.

Although the dosage of a compound of the present invention as an immunosuppressant, anti-allergic agent and/or suppressant on the IgE production should be determined in consideration of the patient's age and body weight, the type and degree of diseases, the administration route or the like, a usual oral dosage for human adults is 0.05–100 mg/kg/day and preferable is 0.1–10 mg/kg/day. For parenteral administration, although the dosage highly varies with administration routes, a usual dosage is 0.005–10 mg/kg/day, preferably, 0.01–1 mg/kg/day. The dosage may be administered in one or several divisions per day.

The present invention is further explained by the following Examples and Experiments, which are not intended to limit the scope of the present invention.

EXAMPLE

The abbreviations used in EXAMPLE mean the following.

| | |
|---|---|
| Ac | acetyl |
| Bn | benzyl |
| Et | ethyl |
| $^{i}$Pr | isopropyl |
| Me | methyl |
| Ms | methanesulfonyl |
| Ph | phenyl |
| Py | pyridyl |
| TBS | tert-butyldimethylsilyl |
| TFAA | trifluoroacetic anhydride |
| THF | tetrahydrofuran |

Example 1
Synthesis of Compounds (Ia-71), (Ia-73, (Ia-75) and (Ia-76)

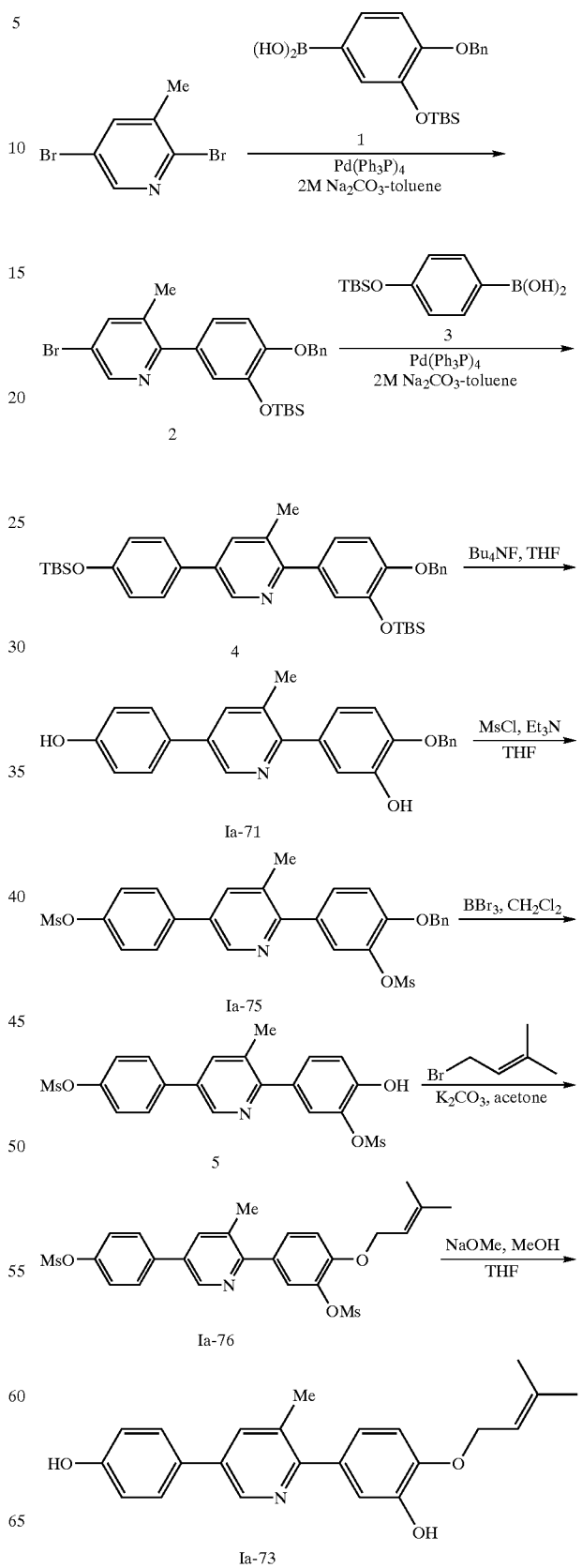

(Step 1) Synthesis of Compound (2)

To a solution of 831 mg (2.32 mmol) of compound (1) (WO98/04508, Reference Example 1) in 12 ml of toluene were added 701 mg (2.79 mmol) of 2, 5-dibromo-3-methylpyridine, 80 mg (0.07 mmol) of tetrakis (triphenylphosphin)palladium (0), and 6 ml of an aqueous solution of 2 M sodium carbonate at room temperature. The mixture was heated refluxed under a nitrogen atmosphere for 4 hours. After cooling, the mixture was diluted with water and extracted with ethyl acetate. The extract was washed with saturated brine, dried and concentrated. The residue was purified by silica gel chromatography (hexane-ethyl 97:3) to give compound (2) (808 mg; 60% yield).

(Step 2) Synthesis of Compound (4)

According to the method of Step 1, 404 mg (0.83 mmol) of compound (2) was reacted with 231 mg (0.92 mmol) of boronic acid (3) (GB 2276162 A) to give compound (4) (411 mg; 81% yield).

(Step 3) Synthesis of Compound (Ia-71)

To a solution of 411 mg (0.67 mmol) of compound (4) in 3.4 ml of tetrahydrofuran was added a solution of 1 M tetrabutyl ammonium fluoride in 1.4 ml (1.40 mmol) of tetrahydrofuran and the mixture was stirred for 3 hours. The solution was poured into an aqueous solution of 5% potassium hydrogen sulfate and extracted with ethyl acetate. The extract was washed with saturated brine, dried and concentrated. The residue was crystallized from ethyl acetate to give compound (Ia-71) (247 mg; 96% yield).

(Step 4) Synthesis of Compound (Ia-75)

To a solution of 227 mg (0.59 mmol) of compound (Ia-71) in 3 ml of tetrahydrofuran were added 0.17 ml (1.18 mmol) of triethylamine and 0.07 ml (0.89 mmol) of methanesulfonyl chloride successively and the mixture was stirred for 20 hours at room temperature. The solution was diluted with ethyl acetate, washed with water, 5% aqueous solution of sodium hydrogencarbonate and saturated saline successively, dried and concentrated. The residue was crystallized from hexane-ethyl acetate to give compound (Ia-75) (303 mg; 95% yield).

(Step 5) Synthesis of Compound (5)

To a solution of 283 mg (0.52 mmol) of compound (Ia-75) in 2.6 ml of dichloromethane was added a solution of 1 M boron tribromide in 0.63 ml (0.63 mmol) of dichloromethane at −78° C. and the mixture was stirred for an hour at the same temperature. After the excessive reagent was decomposed by addition of methanol, the solution was poured into 5% aqueous solution of sodium hydrogencarbonate and extracted with ethyl acetate. The extract was washed with saturated brine, dried and concentrated. The residue was crystallized from hexane-ethyl acetate to give compound (5) (204 mg; 87% yield).

(Step 6) Synthesis of Compound (Ia-76)

To a solution of 184 mg (0.41 mmol) of compound (5) in 2 ml of acetone were added 169 mg (1.23 mmol) of potassium carbonate and 0.12 ml (1.02 mmol) of prenyl bromide successively and the mixture was stirred for 14 hours at room temperature. The solution was diluted ethyl acetate, washed with water and saturated brine successively, dried and concentrated. The residue was purified by silica gel chromatography (hexane-ethyl acetate 1:1) and crystallized from hexane-ethyl acetate to give compound (Ia-76) (170 mg; 80% yield).

(Step 7) Synthesis of Compound (Ia-73)

To a solution of 149 mg (0.29 mmol) of compound (Ia-76) in 1.4 ml of tetrahydrofuran was added a solution of 28% sodium methoxide in 0.6 ml (2.89 mmol) of methanol under ice-cooling and the mixture was stirred at room temperature for 17 hours. The solution was poured into 5% aqueous solution of ammonium chloride and extracted with ethyl acetate. The extract was washed with saturated brine, dried and concentrated. After the residue was purified by silica gel chromatography (hexane-ethyl 7:3), the obtained product was crystallized from diethylether-hexane to give compound (Ia-73) (88mg; 84 % yield).

Example 2

Synthesis of Compounds (Ib-15), (Ib-37) and (Ib-49)

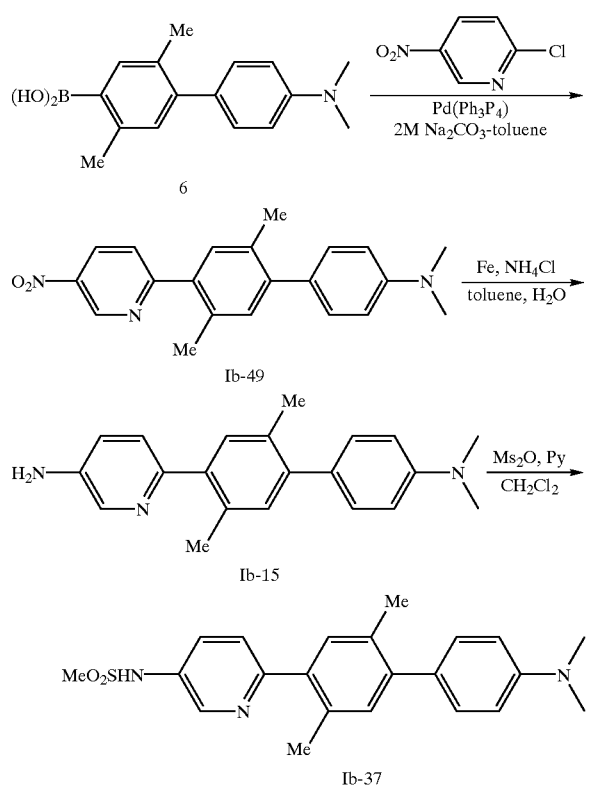

(Step 1) Synthesis of Compound (Ib-49)

According to the method of Example 1 Step 1, 200 mg (0.74 mmol) of boronic acid (6) was reacted with 236 mg (1.49 mmol) of 2-chloro-5-nitropyridine to give compound (Ib-49) (232 mg; 90% yield).

(Step 2) Synthesis of Compound (Ib-15)

To a solution of 257 mg (0.74 mmol) of compound (Ib-49) in 5 ml of toluene were added 5 ml of water, 207 mg (3.70 mmol) of iron powder and 213 mg (3.70 mmol) of ammonium chloride and the mixture was refluxed for 15 hours. After cooling, insoluble material was filtered off with celite. The filtrate was extracted with ethyl acetate and the extract was washed with saturated brine, dried and concentrated. After the residue was purified by silica gel chromatography (hexane-ethyl acetate 1:3), the obtained product was crystallized from ethyl acetate to give compound (Ib-15) (161 mg; 69% yield).

(Step 3) Synthesis of Compound (Ib-37)

To a solution of 130 mg (0.41 mmol) of compound (Ib-15) in 4 ml of dichloromethane were added 0.05 ml (0.61 mmol) of pyridine and 86 mg (0.49 mmol) of methanesulfonic anhydride under ice-cooling and the mixture was stirred for an hour. The solution was diluted with ethyl acetate, washed with water, 5% aqueous solution of sodium hydrogencarbonate and saturated brine successively, dried and concentrated. The residue was crystallized from ethyl acetate to give compound (Ib-37) (124 mg; 77% yield).

Example 3
Synthesis of Compounds of (Ib-11), (Ib-12), (Ib-16), (Ib-21), (Ib-46) and (Ib-47)
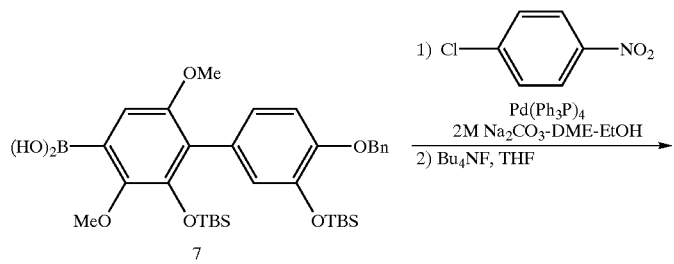
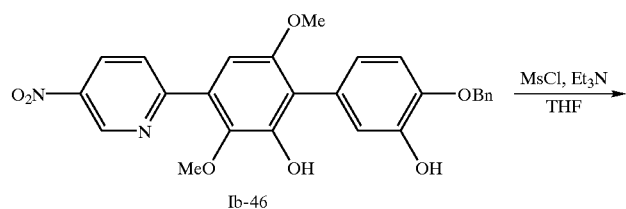
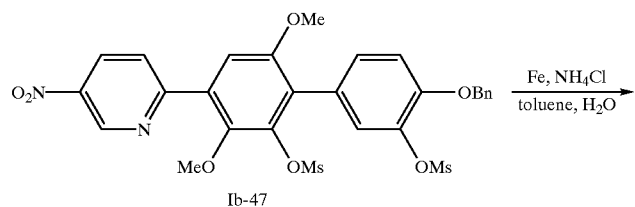
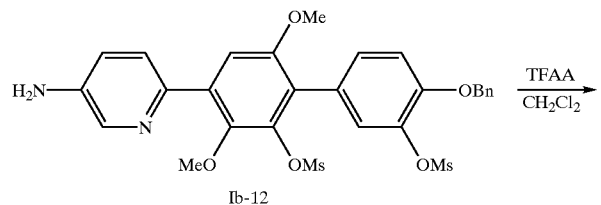
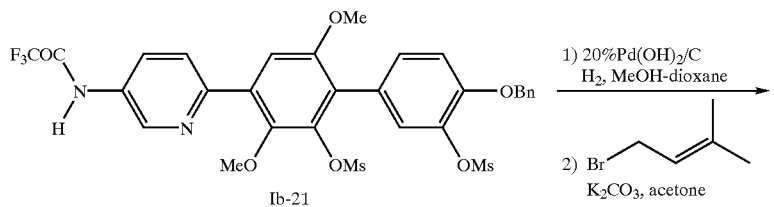
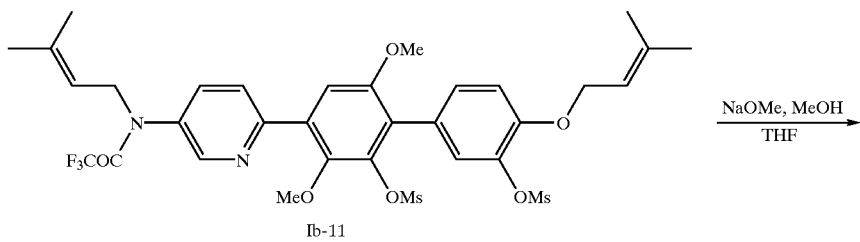

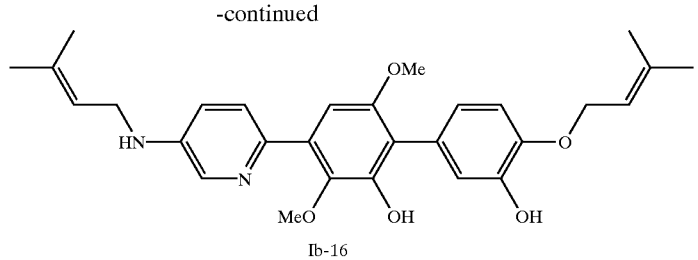

Ib-16

(Step 1) Synthesis of Compound (Ib-46)

To a mixture of a solution of 867 mg (1.36 mmol) of compound (7) (WO98/04508, Reference Examples 4 and 6) in 16 ml of 1, 2-dimethoxyethane and 5 ml of ethanol were added 200 mg (1.26 mmol) of 2-chloro-5-nitropyridine, 44 mg(0.04 mmol) of tetrakis(triphenylphosphine)palladium (0) and 5 ml of aqueous solution of 2 M sodium carbonate at room temperature and the solution was refluxed under a nitrogen atmosphere for 3 hours. After cooling, the mixture was diluted with water and extracted with ethyl acetate. The extract was washed with saturated brine, dried, concentrated and the obtained residue was dissolved in 6 ml of tetrahydrofuran. To the solution was added a solution of 1 M tetrabutylammonium fluoride in 2 ml (2.02 mmol) of tetrahydrofuran under ice-cooling and the mixture was stirred for 1.5 hours. After the solution was poured into water and extracted with ethyl acetate, the extract was washed with saturated brine, dried and concentrated. The residue was purified by silica gel chromatography (hexane-ethyl acetate 7:3) and crystallized from hexane-ethyl acetate to give compound (Ib-46) (472 mg; 79% yield).

(Step 2) Synthesis of Compound (Ib-47)

According to the method of Example 1 Step 4, a solution of 458 mg (0.97 mmol) of compound (Ib-46) in 4.8 ml of tetrahydrofuran was treated with 0.40 ml (2.89 mmol) of triethylamine and 0.19 ml (2.41 mmol) of methanesulfonyl chloride to give compound (ab-47) (572 mg; 94% yield).

(Step 3) Synthesis of Compound (Ib-12)

According to the method of Example 2 Step 2, 547 mg (0.87 mmol) of compound (Ib-47) was treated with 242 mg (4.34 mmol) of iron powder and 232 mg (4.34 mmol) of ammonium chloride to give compound (Ib-12) (461 mg;89 % yield).

(Step 4) Synthesis of Compound (Ib-21)

To a solution of 110 mg (0.18 mmol) of compound (Ib-12) in 1.8 ml of dichloromethane was added 0.03 ml (0.22 mmol) of trifluoroacetic anhydride under ice-cooling and the mixture was stirred for 2 hours at room temperature. The solution was diluted with ethyl acetate, washed with water, 5% aqueous solution of sodium hydrogencarbonate and saturated brine successively, dried and concentrated. The residue was crystallized from diethylether-hexane to give compound (Ib-21) (122 mg; 96% yield).

(Step 5) Synthesis of Compound (Ib-11)

A mixture of 122 mg (0.18 mmol) of compound (Ib-21), 24 mg of 20% palladium hydroxide-carbon in 1.8 ml of methanol and 1.8 ml of 1,4-dioxane was stirred for 15 hours under a nitrogen atmosphere at room temperature. After an insoluble material was filtered off with celite, the filtrate was concentrated to give 110 mg of the residue.

To a solution of the residue in 3.5 ml of N,N-dimethylformamide were added 73 mg (0.53 mmol) of potassium carbonate and 0.05 ml (0.39 mmol) of prenyl bromide successively and the mixture was stirred for 4 hours. The solution was diluted with ethyl acetate, washed with water and saturated brine successively, dried and concentrated. The residue was purified by silica gel chromatography (hexane-ethyl acetate 7:3) and crystallized from diethyl ether-hexane to give compound (Ib-11) (121 mg, 93% yield).

(Step 6) Synthesis of Compound (Ib-16)

According to the method of Example 1 Step 7, compound (Ib-16) was obtained (73 mg; 99% yield) from 111 mg (0.15 mmol) of compound (Ib-11).

Example 4

Synthesis of Compounds (Ic-23) and (Ic-24)

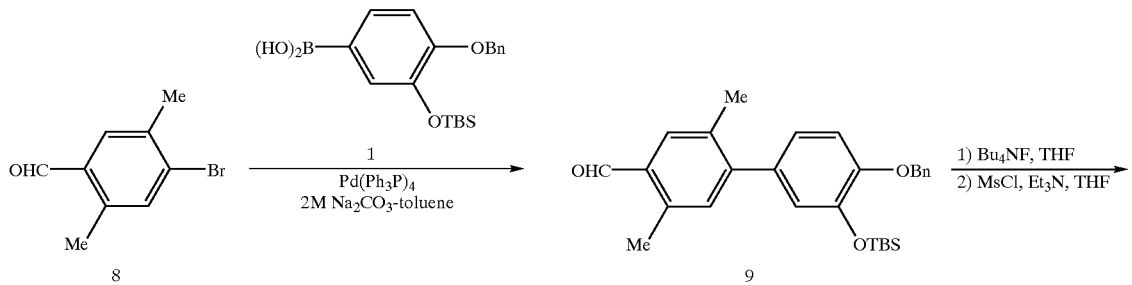

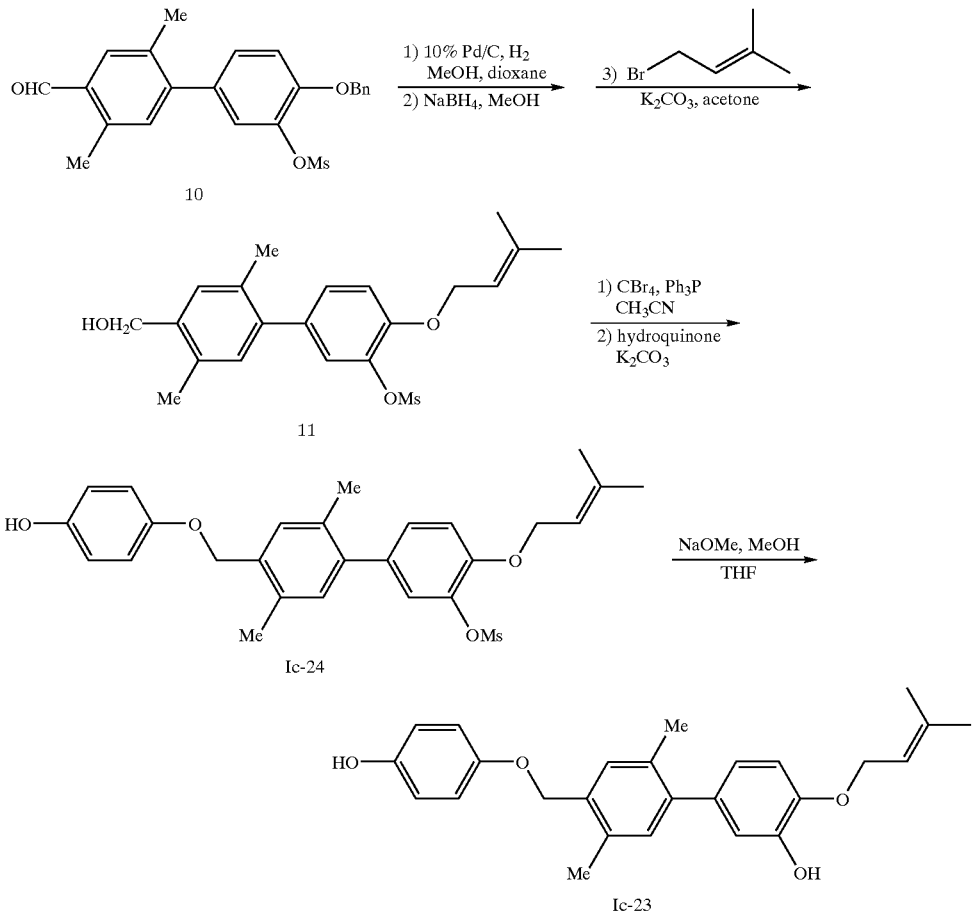

(Step 1) Synthesis of Compound (9)
According to the method of Example 1 Step 1, 500 mg (2.35 mmol) of compound (8) was reacted with 883 mg (2.46 mmol) of boronic acid (1) to give compound (9) (983 mg; 94% yield).

(Step 2) Synthesis of Compound (10)
To a solution of 983 mg (2.20 mmol) of compound (9) in 10 ml of tetrahydrofuran was added 1 M tetrabutylammonium fluoride in 2.2 ml (2.20 mmol) of tetrahydrofuran under ice-cooling and the mixture was stirred for an hour at room temperature. The solution was poured into water, extracted with ethyl acetate. washed with saturated brine dried and concentrated. The residue was dissolved in 10 ml of tetrahydrofuran, then 0.46 ml (3.29 mmol) of triethylamine and 0.20 ml (2.64 mmol) of methanesulfonyl chloride was successively added to the solution under ice-cooling and the mixture was stirred for 30 minutes at the same temperature. The solution was diluted with ethyl acetate, washed with water, 5% aqueous solution of sodium hydrogencarbonate, saturated brine successively, dried and concentrated. The residue was purified by silica gel chromatography (hexane-ethyl acetate 7:3) to give compound (10) (881 mg; 98% yield).

(Step 3) Synthesis of Compound (11)
A solution of 120 mg (0.29 mmol) of compound (10) and 11 mg of 10% palladium-carbon in 2 ml of methanol and 2 ml of 1,4-dioxane was stirred under a nitrogen atmosphere at room temperature for 2 hours. An insoluble material was filtered off with celite and the filtrate was concentrated. To a solution of the residue in 3 ml of methanol was added 11 mg (0.29 mmol) of sodium borohydride under ice-cooling and the mixture was stirred for 30 minutes. The solution was poured into water and extracted with ethyl acetate. The extract was washed with saturated brine, dried and concentrated. To a solution of the obtained crude product in 3 ml of acetone were added 122 mg (0.88 mmol) of potassium carbonate and 0.10 ml (0.88 mmol) of prenyl bromide successively and the mixture was stirred for 2 hours at room temperature. The mixture was diluted with ethyl acetate and washed with water and saturated brine successively, dried and concentrated. The residue was purified by silica gel chromatography (hexane-ethyl acetate 7:3) to give compound (11) (108 mg; 95% yield).

(Step 4) Synthesis of Compound (Ic-24)
To a solution of 108 mg (0.28 mmol) of compound (11) in 2 ml of acetonitrile were added 87 mg (0.33 mmol) of triphenylphosphine and 110 mg (0.33 mmol) of carbon tetrabromide under ice-cooling and the mixture was stirred for 1 hour at room temperature. To the mixture were added 152 mg (1.38 mmol) of hydroquinone and 114 mg (0.83 mmol) of potassium carbonate and the mixture was stirred for 20 hours at room temperature. The mixture was poured into diluted hydrochloric acid and extracted with ethyl acetate. The extract was washed with an aqueous solution of 5% sodium hydrogencarbonate and saturated brine, dried and concentrated. The residue was purified by silica gel chromatography (hexane-ethyl acetate 7:3) to give compound (Ic-24) (61 mg; 46% yield).

(Step 5) Synthesis of Compound (Ic-23)

According to the method of Example 1 Step 7, compound (Ic-23) was obtained (34 mg; 69% yield) from 59 mg (0.12 mmol) of compound (Ic-24).

Example 5

Synthesis of Compounds (Ib-539) and (Ib-540)

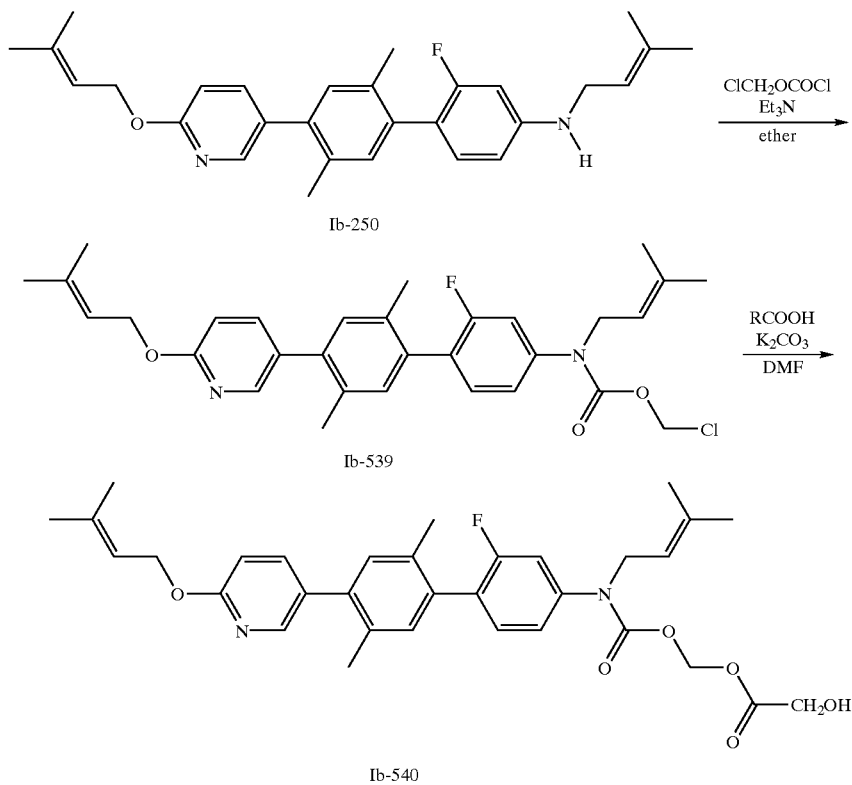

(Step 1) Synthesis of Compound (Ib-539)

The compound (Ib-250) (444 mg, 1 mmol) was dissolved in anhydrous ether (40 mL) under ice-cooling. Chloromethyl chloroformate (194 mg, 1 mmol) and triethylamine (210 ml, 1 mmol) were added successively to the solution under a nitrogen atmosphere with stirred, and the mixture was stirred for 4 hours without ice-cooling. Precipitate in the reaction mixture was filtered off and the filtrate was washed with water, dried over sodium sulfuric anhydride and concentrated under reduced pressure to give 540 mg of compound (Ib-539) as oil.

Elementary Analysis for $C_{31}H_{34}N_2O_3FCl$; Calculated: C, 69.33; H, 6.38; N, 5.22; F, 3.54; Cl, 6.60. Analyzed : C, 68.85; H, 6.42; N, 5.21; F, 3.58; Cl, 7.06.

(Step 2) Synthesis of Compound (Ib-540)

A mixture of glycol acid (38 mg, 0.5 mmol), potassium carbonate (35 mg, 0.25 mmol) and N,N-dimethylformamide (1 mL) was stirred under reduced pressure at room temperature for 10 minutes. A solution of compound 1 (54 mg, 0.1 mmol) in N,N-dimethylformamide (0.5 ml) and potassium bromide (12 mg, 0.1 mmol) were added and the mixture was vigorously stirred for 20 hours under an argon atmosphere. The mixture was diluted with ether (5 ml) and an insoluble material was filtered off. The filtrate was washed with water, dried over sodium sulfate anhydride and concentrated under reduced pressure. The residual crude product was purified by silica gel chromatography (elution solvent: hexane-ethyl acetate (2:1)) to give 27 mg of compound (Ib-540) as an oil.

Elementary Analysis for $C_{33}H_{37}N_2O_6F$; Calculated: C, 68.73; H, 6.47; N, 4.86; F, 3.29. Analyzed: C, 68.59; H, 6.68; N, 4.98; F, 3.25.

Example 6

Synthesis of Compound (Ib-541)

A mixture of succinic acid (590 mg, 5 mmol), potassium carbonate (345 mg, 2.5 mmol) and N,N-dimethylformamide (6 ml) was stirred for 10 minutes under reduced pressure at room temperature. The solution of compound (Ib-539) (537 mg, 1 mmol) in N,N-dimethylformamide (5 ml) obtained by the method in Example 5 Step 1 and sodium iodide (70 mg, 0.5 mmol) were successively added and vigorously stirred for 5 days under an argon atmosphere. The mixture was poured into an aqueous solution of 5% acetic acid and extracted with ether-hexane (4:1). After the obtained mixture was dried over anhydrous sodium sulfate, the solvent was removed off. The residual crude product was purified by silica gel chromatography (elution solvent: chloroform-methanol (20:1)) to give 60 mg of compound (Ib-541) as an oil.

Elementary Analysis for $C_{35}H_{39}N_2O_7F$; Calculated: C, 67.95; H, 6.35; N, 4.53; F, 3.07. Analyzed: C, 68.25; H, 5.96; N, 4.64; F, 3.13. LSIMS: m/Z=618 [M+H]$^+$.

Example 7

Synthesis of Other Compounds (I)

Using analogous procedure, the following compounds (I) were synthesized. The structures and physical constants are shown below. Tables 50 to 55 represents partial structures used in Table 56 or later as abbreviations, A1, A2, B1, B2, . . . C1, C2 . . .

TABLE 50

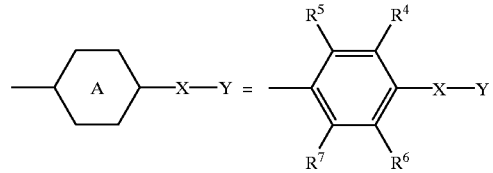

| | $R^4$ | $R^5$ | $R^6$ | $R^7$ | X | Y |
|---|---|---|---|---|---|---|
| A1 | H | H | H | H | O | H |
| A2 | H | H | H | H | O | $CH_2$-2-furyl |
| A3 | H | H | H | H | O | $CH_2C_6H_5$ |
| A4 | H | H | H | H | O | $CH_2C_6H_4$-4-Me |
| A5 | H | H | H | H | O | $CH_2CH=CMe_2$ |
| A6 | OH | H | H | H | O | $CH_2C_6H_5$ |
| A7 | OAc | H | H | H | O | $CH_2C_6H_5$ |
| A8 | OMs | H | H | H | O | $CH_2C_6H_5$ |
| A9 | $OSO_2CF_3$ | H | H | H | O | $CH_2C_6H_5$ |
| A10 | $OSO_2Ph$ | H | H | H | O | $CH_2C_6H_5$ |
| A11 | OMe | H | H | H | O | $CH_2C_6H_5$ |
| A12 | OH | H | H | H | O | $CH_2C_6H_4$-2-Me |
| A13 | OH | H | H | H | O | $CH_2C_6H_4$-3-Me |
| A14 | OH | H | H | H | O | $CH_2C_6H_4$-4-Me |
| A15 | OMs | H | H | H | O | $CH_2C_6H_4$-2-Me |
| A16 | OMs | H | H | H | O | $CH_2C_6H_4$-3-Me |
| A17 | OMs | H | H | H | O | $CH_2C_6H_4$-4-Me |
| A18 | OH | H | H | H | O | $CH_2C_6H_4$-2-OMe |
| A19 | OH | H | H | H | O | $CH_2C_6H_4$-3-OMe |
| A20 | OH | H | H | H | O | $CH_2C_6H_4$-4-OMe |
| A21 | OMs | H | H | H | O | $CH_2C_6H_4$-2-OMe |
| A22 | OMs | H | H | H | O | $CH_2C_6H_4$-3-OMe |
| A23 | OMs | H | H | H | O | $CH_2C_6H_4$-4-OMe |
| A24 | OH | H | H | H | O | $CH_2$-2-Py |
| A25 | OH | H | H | H | O | $CH_2$-3-Py |
| A26 | OH | H | H | H | O | $CH_2$-4-Py |
| A27 | OMs | H | H | H | O | $CH_2$-2-Py |
| A28 | OMs | H | H | H | O | $CH_2$-3-Py |
| A29 | OMs | H | H | H | O | $CH_2$-4-Py |
| A30 | OH | H | H | H | O | $CH_2CH_2C_6H_5$ |
| A31 | OMs | H | H | H | O | $CH_2CH_2C_6H_5$ |
| A32 | OH | H | H | H | O | $CH_2CH=CMe_2$ |
| A33 | OMs | H | H | H | O | $CH_2CH=CMe_2$ |
| A34 | OH | H | H | H | O | $CH_2CH=CCl_2$ |
| A35 | OMe | H | H | H | O | $CH_2CH=CMe_2$ |

TABLE 51

| | $R^4$ | $R^5$ | $R^6$ | $R^7$ | X | Y |
|---|---|---|---|---|---|---|
| A36 | OMe | H | H | H | O | $CH_2CH=CCl_2$ |
| A37 | F | H | H | H | O | $CH_2CH=CMe_2$ |
| A38 | F | H | H | H | O | $CH_2CH=CCl_2$ |
| A39 | OH | H | H | H | O | $CH_2CH_2CH=CMe_2$ |
| A40 | OMs | H | H | H | O | $CH_2CH_2CH=CMe_2$ |
| A41 | H | H | H | H | NMe | Me |
| A42 | H | H | H | H | NH | H |
| A43 | H | H | H | H | NH | Me |
| A44 | H | H | H | H | NH | iPr |
| A45 | H | H | H | H | NH | $CH_2CH=CH_2$ |
| A46 | H | H | H | H | NH | $CH_2CH=CMe_2$ |
| A47 | H | H | H | H | NH | $CH_2C≡CH$ |
| A48 | H | H | H | H | NH | c-Hex |
| A49 | H | H | H | H | NH | $CH_2$-c-Hex |
| A50 | H | H | H | H | NH | $CH_2C_6H_5$ |
| A51 | H | H | H | H | NH | $CH_2C_6H_4$-4-COOMe |
| A52 | H | H | H | H | NH | $CH_2C_6H_4$-4-COOH |
| A53 | H | H | H | H | NH | $CH_2$-4-Pyr |
| A54 | H | H | H | H | NH | $CH_2$-2-furyl |
| A55 | H | H | H | H | NH | $CH_2$-3-furyl |

TABLE 51-continued

| | $R^4$ | $R^5$ | $R^6$ | $R^7$ | X | Y |
|---|---|---|---|---|---|---|
| A56 | H | H | H | H | NH | $CH_2$-2-thienyl |
| A57 | H | H | H | H | NH | $CH_2$-3-thienyl |
| A58 | H | H | H | H | $NCH_2CH=CMe_2$ | $SO_2NHMe$ |
| A59 | H | H | H | H | NMe | $SO_2NH_2$ |
| A60 | OMe | H | H | H | NH | $CH_2CH=CMe_2$ |
| A61 | OMe | H | H | H | NH | $CH_2C_6H_5$ |
| A62 | Me | H | H | H | NH | $CH_2CH=CMe_2$ |
| A63 | Me | H | H | H | NH | $CH_2C_6H_5$ |
| A64 | H | F | H | H | NH | H |
| A65 | H | F | H | H | NH | iPr |
| A66 | H | F | H | H | NH | iBu |
| A67 | H | F | H | H | NH | $CH_2CH=CMe_2$ |
| A68 | H | F | H | H | NH | cPent |
| A69 | H | F | H | H | NH | cHex |
| A70 | H | F | H | H | NH | $CH_2cHex$ |
| A71 | H | F | H | H | NH | $CH_2C_6H_4$-4-Et |
| A72 | H | F | H | H | NH | $CH_2C_6H_4$-4-iPr |
| A73 | H | F | H | H | NH | $CH_2C_6H_4$-4-COOH |
| A74 | H | F | H | H | NH | $CH_2C_6H_4$-4-COOMe |
| A75 | H | F | H | H | N-iPr | $SO_2NH_2$ |
| A76 | H | F | H | H | N-iPr | $SO_2NHMe$ |
| A77 | H | F | H | H | $NCH_2CH=CMe_2$ | $SO_2NHMe$ |

TABLE 52

| | $R^4$ | $R^5$ | $R^6$ | $R^7$ | X | Y |
|---|---|---|---|---|---|---|
| A78 | F | H | H | H | NH | $CH_2CH=CMe_2$ |
| A79 | F | H | H | H | NH | $CH_2C_6H_5$ |
| A80 | H | Cl | H | H | NH | H |
| A81 | H | Cl | H | H | NH | $CH_2CH=CMe_2$ |
| A82 | H | Cl | H | H | NH | cHex |
| A83 | H | Cl | H | H | NH | $CH_2cHex$ |
| A84 | Cl | H | H | H | NH | $CH_2CH=CMe_2$ |
| A85 | Cl | H | H | H | NH | $CH_2C_6H_5$ |
| A86 | H | H | H | H | NH | 4-tetrahydropyran |
| A87 | H | H | H | H | NH | $C_6H_4$-4-$B(OH)_2$ |
| A88 | H | H | H | H | NH | $CH_2C_6H_4$-2-OMe |
| A89 | H | H | H | H | NH | $CH_2C_6H_2$-3,4,5-$(OMe)_3$ |
| A90 | H | H | H | H | NH | $CH(Me)CH_2OMe$ |
| A91 | H | H | H | H | NH | $CH_2cHex$-4,4-$(OMe)_2$ |
| A92 | H | H | H | H | NH | $CH_2C_6H_3$-3,4-$(OH)_2$ |
| A93 | H | H | H | H | NH | $CH_2C_6H_4$-4-OH |
| A94 | H | H | H | H | NH |  |
| A95 | H | H | H | H | NH | $CH_2C_6H_4$-3-OH |
| A96 | H | H | H | H | | N-pyrroryl |
| A97 | H | H | H | H | NH | $CH_2$-2-thienyl |
| A98 | H | H | H | H | NH | cHex-4-(=NOMe) |
| A99 | H | H | H | H | NH | $CH_2$-2-Thiazol |
| A100 | H | H | H | H | NH | 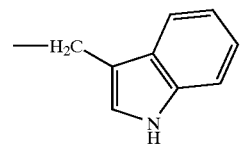 |
| A101 | H | H | H | H | NH | $CH_2C_6H_4$-4-OMe |
| A102 | H | H | H | H | NH | 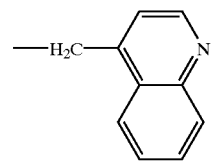 |

TABLE 52-continued

| | R⁴ | R⁵ | R⁶ | R⁷ | X | Y |
|---|---|---|---|---|---|---|
| A103 | H | H | H | H | O | CH₂C≡CMe |
| A104 | H | Me | H | H | NH | CH₂CH=CMe₂ |
| A105 | H | Me | H | H | NH | CH₂C₆H₅ |
| A106 | H | F | H | H | NH | CH₂C₆H₅ |
| A107 | F | H | H | H | O | H |
| A108 | F | H | H | H | O | Me |
| A109 | F | H | H | H | O | CH₂-2-furyl |
| A110 | F | H | H | H | O | CH₂C₆H₅ |

TABLE 52-continued

| | R⁴ | R⁵ | R⁶ | R⁷ | X | Y |
|---|---|---|---|---|---|---|
| A111 | H | H | H | H | | 1-(2,5-dimethylpyrrolyl) |
| A112 | H | H | H | H | S | CH₂CH=CMe₂ |
| A113 | H | H | H | H | SO₂ | NH₂ |
| A114 | H | F | H | H | SO₂ | NH₂ |

TABLE 53

| | R⁴ | R⁵ | R⁶ | R⁷ | X | Y |
|---|---|---|---|---|---|---|
| A115 | H | H | H | H | NH | —H₂C-(5-methyl-2-furyl) |
| A116 | H | H | H | H | NH | CH₂C(Me)=CHMe |
| A117 | H | H | H | H | NH | CH₂C≡CMe |
| A118 | H | H | H | H | NCH₂CH=CMe₂ | CH₂CH=CMe₂ |
| A119 | H | F | H | H | NCOOCH₂Cl | CH₂CH=CMe₂ |
| A120 | H | F | H | H | NCOOCH₂OCOCH₂OH | CH₂CH=CMe₂ |
| A121 | H | F | H | H | NCOOCH₂OCOCH₂CH₂COOH | CH₂CH=CMe₂ |
| A122 | H | F | H | H | NCOOCH₂OCOMe | CH₂CH=CMe₂ |
| A123 | H | F | H | H | NCOOCH(Me)OCOMe | CH₂CH=CMe₂ |
| A124 | H | F | H | H | NCOOCH(Me)OCOCMe₃ | CH₂CH=CMe₂ |
| A125 | H | F | H | H | NCOOCH2OCO(CH₂)₁₄Me | CH₂CH=CMe₂ |
| A126 | H | F | H | H | NCOOCH₂OCO-3-Pyr | CH₂CH=CMe₂ |
| A127 | H | F | H | H | NCH₂NHCO—C₆H₄-o-OCH₂OCOMe | CH₂CH=CMe₂ |
| A128 | H | H | H | H | NCOOCH₂OCOCH₂OH | CH₂CH=CMe₂ |
| A129 | H | H | H | H | NCOOCH₂OCOMe | CH₂CH=CMe₂ |
| A130 | H | H | H | H | NCOOCH(Me)OCOCMe₃ | CH₂CH=CMe₂ |
| A131 | H | H | H | H | NCOOCH₂OCO-3-Pyr | CH₂CH=CMe₂ |
| A132 | F | H | H | H | NCOOCH₂OCOCH₂CH₂COOH | CH₂CH=CMe₂ |
| A133 | F | H | H | H | NCOOCH(Me)OCOMe | CH₂CH=CMe₂ |
| A134 | F | H | H | H | NCOOCH₂OCO(CH₂)₁₄Me | CH₂CH=CMe₂ |
| A135 | F | H | H | H | NCH₂NHCO—C₆H₄-o-OCH₂OCOMe | CH₂CH=CMe₂ |
| A136 | H | F | H | H | NCOOCH₂OCOCH₂OH | cPent |
| A137 | H | F | H | H | NCOOCH₂OCOMe | cPent |
| A138 | H | F | H | H | NCOOCH(Me)OCOCMe₃ | cPent |
| A139 | H | F | H | H | NCOOCH₂OCO-3-Pyr | cPent |
| A140 | H | Cl | H | H | NCOOCH₂OCOCH₂CH₂COOH | CH₂CH=CMe₂ |
| A141 | H | Cl | H | H | NCOOCH(Me)OCOMe | CH₂CH=CMe₂ |
| A142 | H | Cl | H | H | NCOOCH2OCO(CH₂)₁₄Me | CH₂CH=CMe₂ |
| A143 | H | Cl | H | H | NCH₂NHCO—C₆H₄-o-OCH₂OCOMe | CH₂CH=CMe₂ |

TABLE 54

![structure with cyclohexane-B connected to benzene ring with R8, R9, R10, R11 substituents]

| | R8 | R9 | R10 | R11 |
|---|---|---|---|---|
| B1 | OMe | H | H | OMe |
| B2 | OMe | H | OH | OMe |
| B3 | OMe | H | OMs | OMe |
| B4 | Me | H | H | Me |
| B5 | Me | H | OH | Me |
| B6 | Me | H | OMs | Me |
| B7 | Me | Me | Me | Me |
| B8 | Me | Me | OMe | Me |
| B9 | Me | Me | OH | Me |
| B10 | Me | Me | Me | OMe |
| B11 | Me | Me | Me | OH |
| B12 | OMe | Me | Me | OMe |
| B13 | Me | H | Me | Me |
| B14 | Me | Me | H | Me |
| B15 | Me | H | F | Me |
| B16 | Me | F | H | Me |
| B17 | OMe | H | H | Me |
| B18 | Me | H | H | OMe |
| B19 | Cl | H | H | Cl |
| B20 | OEt | H | H | OEt |
| B21 | OiPr | H | H | OiPr |
| B22 | OcPr | H | H | OcPr |
| B23 | OMe | Me | Me | COOMe |
| B24 | Me | Me | Me | COOMe |
| B25 | SMe | H | H | SMe |

TABLE 54-continued

| | R8 | R9 | R10 | R11 |
|---|---|---|---|---|
| B26 | SEt | H | H | SEt |
| B27 | COOMe | Me | Me | OMe |
| B28 | Me | Me | Me | Cl |
| B29 | Me | OMe | H | Me |
| B30 | COOMe | Me | Me | Me |
| B31 | Cl | Me | Me | Me |
| B32 | H | Me | Me | Cl |
| B33 | Me | H | Cl | Me |
| B34 | H | Me | Cl | H |
| B35 | Me | H | H | Cl |
| B36 | Me | Me | H | H |
| B37 | H | Me | H | Me |
| B38 | Me | H | Me | H |
| B39 | OMe | OMe | H | H |
| B40 | H | OMe | H | OMe |
| B41 | OMe | H | OMe | H |
| B42 | H | Me | H | OMe |
| B43 | OMe | H | Me | H |

TABLE 55

![structure with cyclohexane-C connected via Y'-X' to benzene ring with R12, R13, R14, R15 substituents]

| | R12 | R13 | R14 | R15 | —X'—Y' |
|---|---|---|---|---|---|
| C1 | H | H | H | H | H |
| C2 | H | H | H | H | OH |
| C3 | H | H | H | H | OMs |
| C4 | H | H | H | H | OMe |
| C5 | H | H | H | H | NH2 |
| C6 | H | H | H | H | NMe2 |
| C7 | H | H | H | H | SMe |
| C8 | H | H | H | H | Ms |
| C9 | H | H | H | H | F |
| C10 | H | CF3 | H | H | H |
| C11 | H | NO2 | H | H | H |
| C12 | H | NH2 | H | H | H |
| C13 | H | NHAc | H | H | H |
| C14 | H | NHMs | H | H | H |
| C15 | H | N(Ms)CH2CH=CMe2 | H | H | H |
| C16 | H | OH | H | H | OCH2C6H5 |
| C17 | H | OMs | H | H | OCH2C6H5 |
| C18 | H | OH | H | H | OCH2CH=CMe2 |
| C19 | H | OMe | H | H | OCH2CH=CMe2 |
| C20 | H | OMs | H | H | OCH2CH=CMe2 |
| C21 | NO2 | H | H | H | H |
| C22 | NH2 | H | H | H | H |
| C23 | NHAc | H | H | H | H |
| C24 | NHMs | H | H | H | H |
| C25 | Cl | H | H | H | NO2 |
| C26 | Cl | H | H | H | NH2 |
| C27 | Cl | H | H | H | NHMs |

TABLE 55-continued
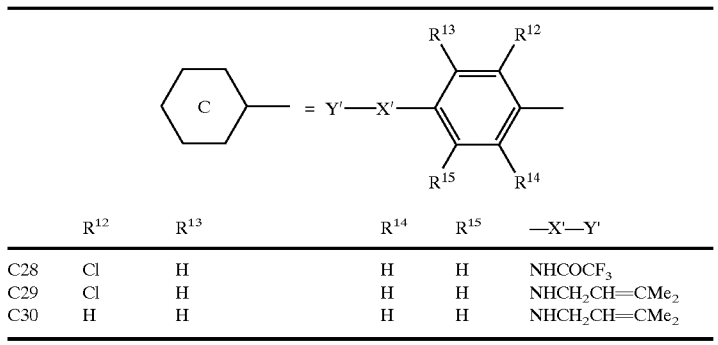
|  | R[12] | R[13] | R[14] | R[15] | —X'—Y' |
|---|---|---|---|---|---|
| C28 | Cl | H | H | H | NHCOCF$_3$ |
| C29 | Cl | H | H | H | NHCH$_2$CH=CMe$_2$ |
| C30 | H | H | H | H | NHCH$_2$CH=CMe$_2$ |
TABLE 56
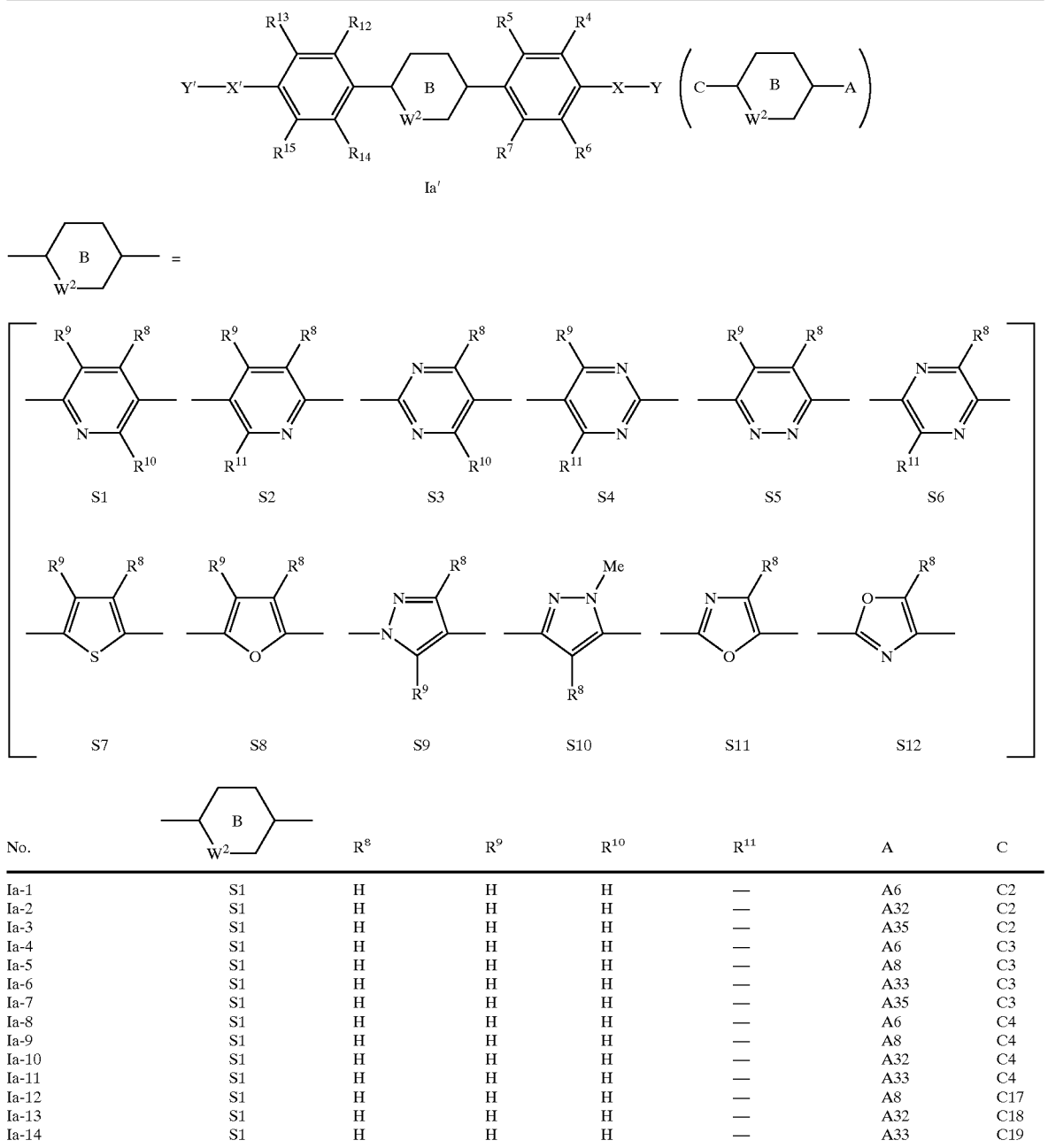
| No. | -B(W²)- | R[8] | R[9] | R[10] | R[11] | A | C |
|---|---|---|---|---|---|---|---|
| Ia-1 | S1 | H | H | H | — | A6 | C2 |
| Ia-2 | S1 | H | H | H | — | A32 | C2 |
| Ia-3 | S1 | H | H | H | — | A35 | C2 |
| Ia-4 | S1 | H | H | H | — | A6 | C3 |
| Ia-5 | S1 | H | H | H | — | A8 | C3 |
| Ia-6 | S1 | H | H | H | — | A33 | C3 |
| Ia-7 | S1 | H | H | H | — | A35 | C3 |
| Ia-8 | S1 | H | H | H | — | A6 | C4 |
| Ia-9 | S1 | H | H | H | — | A8 | C4 |
| Ia-10 | S1 | H | H | H | — | A32 | C4 |
| Ia-11 | S1 | H | H | H | — | A33 | C4 |
| Ia-12 | S1 | H | H | H | — | A8 | C17 |
| Ia-13 | S1 | H | H | H | — | A32 | C18 |
| Ia-14 | S1 | H | H | H | — | A33 | C19 |

TABLE 56-continued

| | | | | | | | |
|---|---|---|---|---|---|---|---|
| Ia-15 | S1 | H | H | Cl | — | A6 | C2 |
| Ia-16 | S1 | H | H | Cl | — | A32 | C2 |
| Ia-17 | S1 | H | H | Cl | — | A8 | C3 |
| Ia-18 | S1 | H | H | Cl | — | A33 | C3 |
| Ia-19 | S1 | H | H | Cl | — | A35 | C6 |
| Ia-20 | S1 | Me | H | H | — | A6 | C2 |
| Ia-21 | S1 | Me | H | H | — | A32 | C2 |
| Ia-22 | S1 | Me | H | H | — | A35 | C2 |
| Ia-23 | S1 | Me | H | H | — | A6 | C3 |
| Ia-24 | S1 | Me | H | H | — | A8 | C3 |
| Ia-25 | S1 | Me | H | H | — | A33 | C3 |
| Ia-26 | S1 | Me | H | H | — | A35 | C3 |
| Ia-27 | S1 | H | Me | H | — | A6 | C2 |

TABLE 57

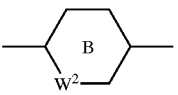

| No. | W² | R⁸ | R⁹ | R¹⁰ | R¹¹ | A | C |
|---|---|---|---|---|---|---|---|
| Ia-28 | S1 | H | Me | H | — | A32 | C2 |
| Ia-29 | S1 | H | Me | H | — | A35 | C2 |
| Ia-30 | S1 | H | Me | H | — | A6 | C3 |
| Ia-31 | S1 | H | Me | H | — | A8 | C3 |
| Ia-32 | S1 | H | Me | H | — | A33 | C3 |
| Ia-33 | S1 | H | Me | H | — | A35 | C3 |
| Ia-34 | S1 | H | H | Me | — | A6 | C2 |
| Ia-35 | S1 | H | H | Me | — | A32 | C2 |
| Ia-36 | S1 | H | H | Me | — | A35 | C2 |
| Ia-37 | S1 | H | H | Me | — | A6 | C3 |
| Ia-38 | S1 | H | H | Me | — | A8 | C3 |
| Ia-39 | S1 | H | H | Me | — | A33 | C3 |
| Ia-40 | S1 | H | H | Me | — | A35 | C3 |
| Ia-41 | S1 | H | Me | Me | — | A6 | C2 |
| Ia-42 | S1 | H | Me | Me | — | A32 | C2 |
| Ia-43 | S1 | H | Me | Me | — | A35 | C2 |
| Ia-44 | S1 | H | Me | Me | — | A37 | C2 |
| Ia-45 | S1 | H | Me | Me | — | A6 | C3 |
| Ia-46 | S1 | H | Me | Me | — | A8 | C3 |
| Ia-47 | S1 | H | Me | Me | — | A33 | C3 |
| Ia-48 | S1 | H | Me | Me | — | A35 | C3 |
| Ia-49 | S1 | H | Me | Me | — | A6 | C6 |
| Ia-50 | S1 | H | Me | Me | — | A32 | C6 |
| Ia-51 | S1 | H | Me | Me | — | A34 | C6 |
| Ia-52 | S1 | H | Me | Me | — | A35 | C6 |
| Ia-53 | S1 | H | Me | Me | — | A36 | C6 |
| Ia-54 | S1 | H | Me | Me | — | A37 | C6 |
| Ia-55 | S1 | H | Me | Me | — | A38 | C6 |
| Ia-56 | S1 | Me | Me | Me | — | A6 | C2 |
| Ia-57 | S1 | Me | Me | Me | — | A32 | C2 |
| Ia-58 | S1 | Me | Me | Me | — | A35 | C2 |
| Ia-59 | S1 | Me | Me | Me | — | A37 | C2 |
| Ia-60 | S1 | Me | Me | Me | — | A6 | C3 |
| Ia-61 | S1 | Me | Me | Me | — | A8 | C3 |
| Ia-62 | S1 | Me | Me | Me | — | A33 | C3 |
| Ia-63 | S1 | Me | Me | Me | — | A35 | C3 |
| Ia-64 | S2 | H | H | — | H | A6 | C2 |

TABLE 58

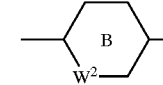

| No. | W² | R⁸ | R⁹ | R¹⁰ | R¹¹ | A | C |
|---|---|---|---|---|---|---|---|
| Ia-65 | S2 | H | H | — | H | A8 | C2 |
| Ia-66 | S2 | H | H | — | H | A32 | C2 |
| Ia-67 | S2 | H | H | — | H | A35 | C2 |
| Ia-68 | S2 | H | H | — | H | A8 | C3 |

TABLE 58-continued

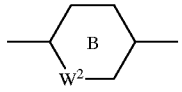

| No. | W² | R⁸ | R⁹ | R¹⁰ | R¹¹ | A | C |
|---|---|---|---|---|---|---|---|
| Ia-69 | S2 | H | H | — | H | A33 | C3 |
| Ia-70 | S2 | H | H | — | H | A35 | C3 |
| Ia-71 | S2 | Me | H | — | H | A6 | C2 |
| Ia-72 | S2 | Me | H | — | H | A8 | C2 |
| Ia-73 | S2 | Me | H | — | H | A32 | C2 |
| Ia-74 | S2 | Me | H | — | H | A35 | C2 |
| Ia-75 | S2 | Me | H | — | H | A8 | C3 |
| Ia-76 | S2 | Me | H | — | H | A33 | C3 |
| Ia-77 | S2 | Me | H | — | H | A35 | C3 |
| Ia-78 | S2 | H | Me | — | H | A6 | C2 |
| Ia-79 | S2 | H | Me | — | H | A8 | C2 |
| Ia-80 | S2 | H | Me | — | H | A32 | C2 |
| Ia-81 | S2 | H | Me | — | H | A35 | C2 |
| Ia-82 | S2 | H | Me | — | H | A8 | C3 |
| Ia-83 | S2 | H | Me | — | H | A33 | C3 |
| Ia-84 | S2 | H | Me | — | H | A35 | C3 |
| Ia-85 | S2 | H | H | — | Me | A6 | C2 |
| Ia-86 | S2 | H | H | — | Me | A8 | C2 |
| Ia-87 | S2 | H | H | — | Me | A32 | C2 |
| Ia-88 | S2 | H | H | — | Me | A35 | C2 |
| Ia-89 | S2 | H | H | — | Me | A8 | C3 |
| Ia-90 | S2 | H | H | — | Me | A33 | C3 |
| Ia-91 | S2 | H | H | — | Me | A35 | C3 |
| Ia-92 | S2 | Me | H | — | Me | A6 | C2 |
| Ia-93 | S2 | Me | H | — | Me | A8 | C2 |
| Ia-94 | S2 | Me | H | — | Me | A32 | C2 |
| Ia-95 | S2 | Me | H | — | Me | A35 | C2 |
| Ia-96 | S2 | Me | H | — | Me | A8 | C3 |
| Ia-97 | S2 | Me | H | — | Me | A33 | C3 |
| Ia-98 | S2 | Me | H | — | Me | A35 | C3 |
| Ia-99 | S2 | Me | H | — | Me | A6 | C6 |
| Ia-100 | S2 | Me | H | — | Me | A32 | C6 |
| Ia-101 | S2 | Me | H | — | Me | A34 | C6 |

TABLE 59

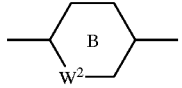

| No. | W² | R⁸ | R⁹ | R¹⁰ | R¹¹ | A | C |
|---|---|---|---|---|---|---|---|
| Ia-102 | S2 | Me | H | — | Me | A35 | C6 |
| Ia-103 | S2 | Me | H | — | Me | A36 | C6 |
| Ia-104 | S2 | Me | H | — | Me | A37 | C6 |
| Ia-105 | S2 | Me | H | — | Me | A38 | C6 |
| Ia-106 | S2 | Me | Me | — | Me | A6 | C2 |
| Ia-107 | S2 | Me | Me | — | Me | A8 | C2 |
| Ia-108 | S2 | Me | Me | — | Me | A32 | C2 |
| Ia-109 | S2 | Me | Me | — | Me | A35 | C2 |
| Ia-110 | S2 | Me | Me | — | Me | A8 | C3 |

TABLE 59-continued

| No. | W² | R⁸ | R⁹ | R¹⁰ | R¹¹ | A | C |
|---|---|---|---|---|---|---|---|
| Ia-111 | S2 | Me | Me | — | Me | A33 | C3 |
| Ia-112 | S2 | Me | Me | — | Me | A35 | C3 |
| Ia-113 | S2 | Me | Me | — | Me | A6 | C6 |
| Ia-114 | S2 | Me | Me | — | Me | A32 | C6 |
| Ia-115 | S2 | Me | Me | — | Me | A34 | C6 |
| Ia-116 | S2 | Me | Me | — | Me | A35 | C6 |
| Ia-117 | S2 | Me | Me | — | Me | A37 | C6 |
| Ia-118 | S3 | Me | — | H | — | A6 | C2 |
| Ia-119 | S3 | Me | — | H | — | A32 | C2 |
| Ia-120 | S3 | Me | — | H | — | A35 | C2 |
| Ia-120 | S3 | OMe | — | H | — | A6 | C2 |
| Ia-121 | S3 | OMe | — | H | — | A32 | C2 |
| Ia-122 | S3 | OMe | — | H | — | A35 | C2 |
| Ia-123 | S3 | Me | — | Me | — | A6 | C2 |
| Ia-124 | S3 | Me | — | Me | — | A32 | C2 |
| Ia-125 | S3 | Me | — | OMe | — | A11 | C1 |
| Ia-126 | S3 | Me | — | Me | — | A35 | C2 |
| Ia-127 | S3 | Me | — | OMe | — | A3 | C1 |
| Ia-128 | S3 | Me | — | OMe | — | A4 | C1 |
| Ia-129 | S3 | Me | — | OMe | — | A5 | C1 |
| Ia-131 | S3 | Me | — | OMe | — | A6 | C1 |
| Ia-132 | S3 | Me | — | OMe | — | A7 | C1 |
| Ia-133 | S3 | Me | — | OMe | — | A8 | C1 |
| Ia-134 | S3 | Me | — | OMe | — | A9 | C1 |
| Ia-135 | S3 | Me | — | OMe | — | A10 | C1 |
| Ia-136 | S3 | Me | — | OMe | — | A12 | C1 |
| Ia-137 | S3 | Me | — | OMe | — | A13 | C1 |
| Ia-138 | S3 | Me | — | OMe | — | A14 | C1 |
| Ia-139 | S3 | Me | — | OMe | — | A15 | C1 |

TABLE 60

| No. | W² | R⁸ | R⁹ | R¹⁰ | R¹¹ | A | C |
|---|---|---|---|---|---|---|---|
| Ia-140 | S3 | Me | — | OMe | — | A16 | C1 |
| Ia-141 | S3 | Me | — | OMe | — | A17 | C1 |
| Ia-142 | S3 | Me | — | OMe | — | A18 | C1 |
| Ia-143 | S3 | Me | — | OMe | — | A19 | C1 |
| Ia-144 | S3 | Me | — | OMe | — | A20 | C1 |
| Ia-145 | S3 | Me | — | OMe | — | A21 | C1 |
| Ia-146 | S3 | Me | — | OMe | — | A22 | C1 |
| Ia-147 | S3 | Me | — | OMe | — | A23 | C1 |
| Ia-148 | S3 | Me | — | OMe | — | A24 | C1 |
| Ia-149 | S3 | Me | — | OMe | — | A25 | C1 |
| Ia-150 | S3 | Me | — | OMe | — | A26 | C1 |
| Ia-151 | S3 | Me | — | OMe | — | A27 | C1 |
| Ia-152 | S3 | Me | — | OMe | — | A28 | C1 |
| Ia-153 | S3 | Me | — | OMe | — | A29 | C1 |
| Ia-154 | S3 | Me | — | OMe | — | A30 | C1 |
| Ia-155 | S3 | Me | — | OMe | — | A31 | C1 |
| Ia-156 | S3 | Me | — | OMe | — | A32 | C1 |
| Ia-157 | S3 | Me | — | OMe | — | A33 | C1 |
| Ia-158 | S3 | Me | — | OMe | — | A35 | C1 |
| Ia-159 | S3 | Me | — | OMe | — | A39 | C1 |
| Ia-160 | S3 | Me | — | OMe | — | A40 | C1 |
| Ia-161 | S3 | Me | — | OMe | — | A6 | C2 |
| Ia-162 | S3 | Me | — | OMe | — | A8 | C2 |
| Ia-163 | S3 | Me | — | OMe | — | A32 | C2 |
| Ia-164 | S3 | Me | — | OMe | — | A33 | C2 |
| Ia-165 | S3 | Me | — | OMe | — | A35 | C2 |
| Ia-166 | S3 | Me | — | OMe | — | A37 | C2 |
| Ia-167 | S3 | Me | — | OMe | — | A8 | C3 |
| Ia-168 | S3 | Me | — | OMe | — | A33 | C3 |
| Ia-169 | S3 | Me | — | OMe | — | A32 | C4 |
| Ia-170 | S3 | Me | — | OMe | — | A35 | C4 |
| Ia-171 | S3 | Me | — | OMe | — | A32 | C6 |

TABLE 60-continued

| No. | W² | R⁸ | R⁹ | R¹⁰ | R¹¹ | A | C |
|---|---|---|---|---|---|---|---|
| Ia-172 | S3 | Me | — | OMe | — | A35 | C6 |
| Ia-173 | S3 | Me | — | OMe | — | A8 | C7 |
| Ia-174 | S3 | Me | — | OMe | — | A32 | C7 |
| Ia-175 | S3 | Me | — | OMe | — | A8 | C8 |
| Ia-176 | S3 | Me | — | OMe | — | A8 | C9 |
| Ia-177 | S3 | Me | — | OMe | — | A32 | C9 |
| Ia-178 | S3 | Me | — | OMe | — | A33 | C9 |

TABLE 61

| No. | W² | R⁸ | R⁹ | R¹⁰ | R¹¹ | A | C |
|---|---|---|---|---|---|---|---|
| Ia-179 | S3 | Me | — | OMe | — | A8 | C10 |
| Ia-180 | S3 | Me | — | OMe | — | A32 | C10 |
| Ia-181 | S3 | Me | — | OMe | — | A33 | C10 |
| Ia-182 | S3 | Me | — | OMe | — | A6 | C11 |
| Ia-183 | S3 | Me | — | OMe | — | A8 | C11 |
| Ia-184 | S3 | Me | — | OMe | — | A8 | C12 |
| Ia-185 | S3 | Me | — | OMe | — | A8 | C13 |
| Ia-186 | S3 | Me | — | OMe | — | A8 | C14 |
| Ia-187 | S3 | Me | — | OMe | — | A32 | C14 |
| Ia-188 | S3 | Me | — | OMe | — | A8 | C15 |
| Ia-189 | S3 | Me | — | OMe | — | A32 | C15 |
| Ia-190 | S3 | Me | — | OMe | — | A33 | C15 |
| Ia-191 | S3 | Me | — | OMe | — | A6 | C21 |
| Ia-192 | S3 | Me | — | OMe | — | A8 | C21 |
| Ia-193 | S3 | Me | — | OMe | — | A6 | C22 |
| Ia-194 | S3 | Me | — | OMe | — | A8 | C23 |
| Ia-195 | S3 | Me | — | OMe | — | A32 | C23 |
| Ia-196 | S3 | Me | — | OMe | — | A33 | C23 |
| Ia-197 | S3 | Me | — | OMe | — | A8 | C24 |
| Ia-198 | S3 | Me | — | OEt | — | A6 | C1 |
| Ia-199 | S3 | Me | — | OEt | — | A8 | C1 |
| Ia-200 | S3 | Me | — | OEt | — | A14 | C1 |
| Ia-201 | S3 | Me | — | OEt | — | A17 | C1 |
| Ia-202 | S3 | Me | — | OEt | — | A32 | C1 |
| Ia-203 | S3 | Me | — | OEt | — | A33 | C1 |
| Ia-204 | S3 | Me | — | OEt | — | A6 | C2 |
| Ia-205 | S3 | Me | — | OEt | — | A32 | C2 |
| Ia-206 | S3 | Me | — | OⁱPr | — | A6 | C1 |
| Ia-207 | S3 | Me | — | OⁱPr | — | A8 | C1 |
| Ia-208 | S3 | Me | — | OⁱPr | — | A14 | C1 |
| Ia-209 | S3 | Me | — | OⁱPr | — | A17 | C1 |
| Ia-210 | S3 | Me | — | OⁱPr | — | A32 | C1 |
| Ia-211 | S3 | Me | — | OⁱPr | — | A33 | C1 |
| Ia-212 | S3 | Me | — | OⁱPr | — | A6 | C2 |
| Ia-213 | S3 | Me | — | OⁱPr | — | A32 | C2 |
| Ia-214 | S3 | Et | — | OMe | — | A6 | C1 |
| Ia-215 | S3 | Et | — | OMe | — | A8 | C1 |
| Ia-216 | S3 | Et | — | OMe | — | A14 | C1 |
| Ia-217 | S3 | Et | — | OMe | — | A17 | C1 |

TABLE 62

| No. | W² | R⁸ | R⁹ | R¹⁰ | R¹¹ | A | C |
|---|---|---|---|---|---|---|---|
| Ia-218 | S3 | Et | — | OMe | — | A32 | C1 |
| Ia-219 | S3 | Et | — | OMe | — | A33 | C1 |
| Ia-220 | S3 | Et | — | OMe | — | A6 | C2 |
| Ia-221 | S3 | Et | — | OMe | — | A32 | C2 |

TABLE 62-continued

| No. | W² B | R⁸ | R⁹ | R¹⁰ | R¹¹ | A | C |
|---|---|---|---|---|---|---|---|
| Ia-222 | S3 | H | — | CO₂H | — | A6 | C1 |
| Ia-223 | S3 | H | — | CO₂H | — | A8 | C1 |
| Ia-224 | S3 | H | — | CO₂H | — | A32 | C1 |
| Ia-225 | S3 | H | — | CO₂H | — | A33 | C1 |
| Ia-226 | S3 | H | — | CO₂Me | — | A6 | C1 |
| Ia-227 | S3 | H | — | CO₂Me | — | A8 | C1 |
| Ia-228 | S3 | H | — | CO₂Me | — | A11 | C1 |
| Ia-229 | S3 | H | — | CO₂Me | — | A32 | C1 |
| Ia-230 | S3 | H | — | CO₂Me | — | A33 | C1 |
| Ia-231 | S3 | H | — | CH₂OH | — | A32 | C1 |
| Ia-232 | S3 | H | — | CH₂OAc | — | A8 | C1 |
| Ia-233 | S3 | Me | — | SMe | — | A8 | C1 |
| Ia-234 | S3 | Me | — | SMe | — | A32 | C1 |
| Ia-235 | S3 | Me | — | NHMe | — | A6 | C1 |
| Ia-236 | S3 | Me | — | NHMe | — | A8 | C1 |
| Ia-237 | S3 | Me | — | NHMe | — | A32 | C1 |
| Ia-238 | S4 | — | Me | — | OMe | A32 | C2 |
| Ia-239 | S4 | — | Me | — | OMe | A6 | C3 |
| Ia-240 | S4 | — | Me | — | OMe | A8 | C3 |
| Ia-241 | S4 | — | Me | — | OMe | A33 | C3 |
| Ia-242 | S4 | — | Me | — | OMe | A35 | C6 |
| Ia-243 | S4 | — | Me | — | Me | A32 | C2 |
| Ia-244 | S4 | — | Me | — | Me | A6 | C3 |
| Ia-245 | S4 | — | Me | — | Me | A8 | C3 |
| Ia-246 | S4 | — | Me | — | Me | A33 | C3 |
| Ia-247 | S4 | — | Me | — | Me | A35 | C6 |
| Ia-248 | S5 | H | H | — | — | A6 | C1 |
| Ia-249 | S5 | H | H | — | — | A8 | C1 |
| Ia-250 | S5 | H | H | — | — | A32 | C1 |
| Ia-251 | S5 | H | H | — | — | A33 | C1 |
| Ia-252 | S5 | H | H | — | — | A32 | C2 |
| Ia-253 | S5 | H | H | — | — | A8 | C3 |
| Ia-254 | S5 | H | H | — | — | A33 | C3 |
| Ia-255 | S5 | H | H | — | — | A6 | C4 |
| Ia-256 | S5 | H | H | — | — | A8 | C4 |
| Ia-257 | S5 | H | H | — | — | A32 | C4 |

TABLE 63

| No. | W² B | R⁸ | R⁹ | R¹⁰ | R¹¹ | A | C |
|---|---|---|---|---|---|---|---|
| Ia-258 | S5 | H | H | — | — | A33 | C4 |
| Ia-259 | S5 | H | H | — | — | A35 | C6 |
| Ia-260 | S5 | Me | Me | — | — | A32 | C2 |
| Ia-261 | S5 | Me | Me | — | — | A35 | C2 |
| Ia-262 | S5 | Me | Me | — | — | A35 | C6 |
| Ia-263 | S6 | H | — | — | H | A32 | C2 |
| Ia-264 | S6 | H | — | — | H | A35 | C2 |
| Ia-265 | S6 | H | — | — | H | A35 | C6 |
| Ia-266 | S6 | Me | — | — | Me | A32 | C2 |
| Ia-267 | S6 | Me | — | — | Me | A35 | C2 |
| Ia-268 | S6 | Me | — | — | Me | A35 | C6 |
| Ia-269 | S7 | H | H | — | — | A6 | C2 |
| Ia-270 | S7 | H | H | — | — | A8 | C2 |
| Ia-271 | S7 | H | H | — | — | A32 | C2 |
| Ia-272 | S7 | H | H | — | — | A8 | C3 |
| Ia-273 | S7 | H | H | — | — | A33 | C3 |
| Ia-274 | S7 | H | H | — | — | A35 | C6 |
| Ia-275 | S7 | H | H | — | — | A6 | C16 |
| Ia-276 | S7 | Me | H | — | — | A8 | C2 |
| Ia-277 | S7 | Me | H | — | — | A32 | C2 |
| Ia-278 | S7 | Me | H | — | — | A8 | C3 |
| Ia-279 | S7 | Me | H | — | — | A33 | C3 |
| Ia-280 | S7 | H | Me | — | — | A8 | C2 |
| Ia-281 | S7 | H | Me | — | — | A32 | C2 |
| Ia-282 | S7 | H | Me | — | — | A8 | C3 |

TABLE 63-continued

| No. | W² B | R⁸ | R⁹ | R¹⁰ | R¹¹ | A | C |
|---|---|---|---|---|---|---|---|
| Ia-283 | S7 | H | Me | — | — | A33 | C3 |
| Ia-284 | S7 | Me | Me | — | — | A8 | C2 |
| Ia-285 | S7 | Me | Me | — | — | A32 | C2 |
| Ia-286 | S7 | Me | Me | — | — | A8 | C3 |
| Ia-287 | S7 | Me | Me | — | — | A33 | C3 |
| Ia-288 | S7 | Me | Me | — | — | A35 | C6 |
| Ia-289 | S8 | H | H | — | — | A32 | C2 |
| Ia-290 | S8 | H | H | — | — | A35 | C2 |
| Ia-291 | S8 | H | H | — | — | A35 | C6 |
| Ia-292 | S8 | Me | H | — | — | A32 | C2 |
| Ia-293 | S8 | Me | H | — | — | A35 | C2 |
| Ia-294 | S8 | Me | H | — | — | A35 | C6 |
| Ia-295 | S8 | H | Me | — | — | A32 | C2 |
| Ia-296 | S8 | H | Me | — | — | A35 | C2 |
| Ia-297 | S8 | H | Me | — | — | A35 | C6 |

TABLE 64

| No. | W² B | R⁸ | R⁹ | R¹⁰ | R¹¹ | A | C |
|---|---|---|---|---|---|---|---|
| Ia-298 | S8 | Me | Me | — | — | A32 | C2 |
| Ia-299 | S8 | Me | Me | — | — | A35 | C2 |
| Ia-300 | S8 | Me | Me | — | — | A35 | C6 |
| Ia-301 | S9 | Me | Me | — | — | A6 | C1 |
| Ia-302 | S9 | Me | Me | — | — | A8 | C1 |
| Ia-303 | S9 | Me | Me | — | — | A32 | C1 |
| Ia-304 | S9 | Me | Me | — | — | A33 | C1 |
| Ia-305 | S9 | Me | Me | — | — | A6 | C4 |
| Ia-306 | S9 | Me | Me | — | — | A8 | C4 |
| Ia-307 | S9 | Me | Me | — | — | A32 | C4 |
| Ia-308 | S9 | Me | Me | — | — | A33 | C4 |
| Ia-309 | S9 | Me | OMe | — | — | A6 | C1 |
| Ia-310 | S9 | Me | OMe | — | — | A8 | C1 |
| Ia-311 | S9 | Me | OMe | — | — | A14 | C1 |
| Ia-312 | S9 | Me | OMe | — | — | A17 | C1 |
| Ia-313 | S9 | Me | OMe | — | — | A32 | C1 |
| Ia-314 | S9 | Me | OMe | — | — | A33 | C1 |
| Ia-315 | S9 | Me | OMe | — | — | A6 | C4 |
| Ia-316 | S9 | Me | OMe | — | — | A8 | C4 |
| Ia-317 | S9 | Me | OMe | — | — | A14 | C4 |
| Ia-318 | S9 | Me | OMe | — | — | A17 | C4 |
| Ia-319 | S9 | Me | OMe | — | — | A32 | C4 |
| Ia-320 | S9 | Me | OMe | — | — | A33 | C4 |
| Ia-321 | S9 | Me | OMe | — | — | A35 | C4 |
| Ia-322 | S9 | Me | CO₂H | — | — | A33 | C4 |
| Ia-323 | S9 | Me | CO₂Et | — | — | A6 | C4 |
| Ia-324 | S9 | Me | CO₂Et | — | — | A8 | C4 |
| Ia-325 | S9 | Me | CO₂Et | — | — | A32 | C4 |
| Ia-326 | S9 | Me | CO₂Et | — | — | A33 | C4 |
| Ia-327 | S9 | Me | CO₂Et | — | — | A35 | C4 |
| Ia-328 | S9 | Me | CH₂OH | — | — | A32 | C4 |
| Ia-329 | S9 | Me | CH₂OH | — | — | A35 | C4 |
| Ia-330 | S10 | H | — | — | — | A6 | C1 |
| Ia-331 | S10 | H | — | — | — | A8 | C1 |
| Ia-332 | S10 | H | — | — | — | A32 | C1 |
| Ia-333 | S10 | H | — | — | — | A33 | C1 |
| Ia-334 | S10 | Me | — | — | — | A6 | C1 |
| Ia-335 | S10 | Me | — | — | — | A8 | C1 |
| Ia-336 | S10 | Me | — | — | — | A32 | C1 |

TABLE 65
| No. | W² | R⁸ | R⁹ | R¹⁰ | R¹¹ | A | C |
|---|---|---|---|---|---|---|---|
| Ia-337 | S10 | Me | — | — | — | A33 | C1 |
| Ia-338 | S11 | H | — | — | — | A6 | C1 |
| Ia-339 | S11 | H | — | — | — | A8 | C1 |
| Ia-340 | S11 | H | — | — | — | A14 | C1 |
| Ia-341 | S11 | H | — | — | — | A17 | C1 |
| Ia-342 | S11 | H | — | — | — | A32 | C1 |
| Ia-343 | S11 | H | — | — | — | A33 | C1 |
| Ia-344 | S11 | Me | — | — | — | A6 | C1 |
| Ia-345 | S11 | Me | — | — | — | A8 | C1 |
| Ia-346 | S11 | Me | — | — | — | A32 | C1 |
TABLE 65-continued
| No. | W² | R⁸ | R⁹ | R¹⁰ | R¹¹ | A | C |
|---|---|---|---|---|---|---|---|
| Ia-347 | S11 | Me | — | — | — | A33 | C1 |
| Ia-348 | S12 | H | — | — | — | A6 | C1 |
| Ia-349 | S12 | H | — | — | — | A8 | C1 |
| Ia-350 | S12 | H | — | — | — | A32 | C1 |
| Ia-351 | S12 | H | — | — | — | A33 | C1 |
| Ia-352 | S12 | Me | — | — | — | A6 | C1 |
| Ia-353 | S12 | Me | — | — | — | A8 | C1 |
| Ia-354 | S12 | Me | — | — | — | A32 | C1 |
| Ia-355 | S12 | Me | — | — | — | A33 | C1 |
| Ia-356 | S2 | Me | H | — | Me | A37 | C30 |
| Ia-357 | S1 | H | Me | Me | — | A37 | C30 |
TABLE 66
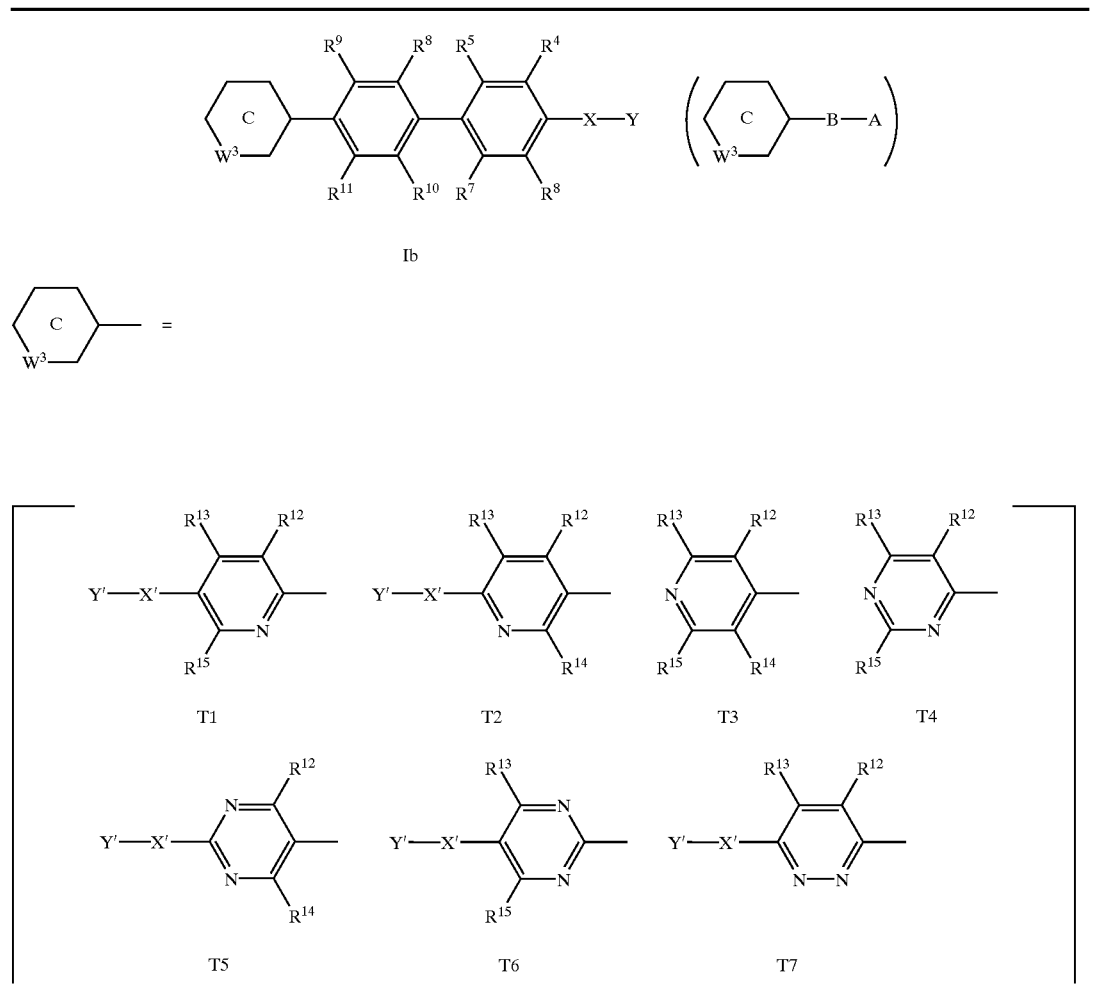

TABLE 66-continued

Structures shown: T8, T9, T10, T11, T12, T13, T14

| No. | W³ | R¹² | R¹³ | R¹⁴ | R¹⁵ | X'—Y' | B | A |
|---|---|---|---|---|---|---|---|---|
| Ib-1 | T1 | H | H | — | H | H | B2 | A6 |
| Ib-2 | T1 | H | H | — | H | H | B3 | A8 |
| Ib-3 | T1 | H | H | — | H | H | B2 | A32 |
| Ib-4 | T1 | H | H | — | H | H | B3 | A33 |
| Ib-5 | T1 | H | H | — | H | H | B2 | A35 |
| Ib-6 | T1 | H | H | — | H | H | B4 | A11 |
| Ib-7 | T1 | H | H | — | H | H | B4 | A32 |
| Ib-8 | T1 | H | H | — | H | H | B4 | A35 |
| Ib-9 | T1 | H | H | — | H | H | B4 | A1 |
| Ib-10 | T1 | H | H | — | H | H | B4 | A41 |
| Ib-11 | T1 | H | H | — | H | N(COCF₃)CH₂CH=CMe₂ | B3 | A33 |
| Ib-12 | T1 | H | H | — | H | NH₂ | B3 | A8 |
| Ib-13 | T1 | H | H | — | H | NH₂ | B4 | A35 |
| Ib-14 | T1 | H | H | — | H | NH₂ | B4 | A1 |
| Ib-15 | T1 | H | H | — | H | NH₂ | B4 | A41 |
| Ib-16 | T1 | H | H | — | H | NHCH₂CH=CMe₂ | B2 | A32 |
| Ib-17 | T1 | H | H | — | H | NHCH₂CH=CMe₂ | B4 | A35 |
| Ib-18 | T1 | H | H | — | H | NHCH₂CH=CMe₂ | B1 | A41 |
| Ib-19 | T1 | H | H | — | H | NHCH₂CH=CMe₂ | B4 | A1 |
| Ib-20 | T1 | H | H | — | H | NHCH₂CH=CMe₂ | B4 | A41 |

TABLE 67

| No. | W³ | R¹² | R¹³ | R¹⁴ | R¹⁵ | X'—Y' | B | A |
|---|---|---|---|---|---|---|---|---|
| Ib-21 | T1 | H | H | — | H | NHCOCF₃ | B3 | A8 |
| Ib-22 | T1 | H | H | — | H | NHCOCF₃ | B3 | A33 |
| Ib-23 | T1 | H | H | — | H | NHCOCF₃ | B4 | A35 |
| Ib-24 | T1 | H | H | — | H | NHCOCF₃ | B4 | A1 |
| Ib-25 | T1 | H | H | — | H | NHCOCF₃ | B4 | A41 |
| Ib-26 | T1 | H | H | — | H | NHCOMe | B2 | A32 |
| Ib-27 | T1 | H | H | — | H | NHCOMe | B3 | A33 |
| Ib-28 | T1 | H | H | — | H | NHCOMe | B4 | A35 |
| Ib-29 | T1 | H | H | — | H | NHCOMe | B4 | A1 |
| Ib-30 | T1 | H | H | — | H | NHCOMe | B4 | A41 |
| Ib-31 | T1 | H | H | — | H | NHSO₂Et | B1 | A41 |
| Ib-32 | T1 | H | H | — | H | NHSO₂Et | B4 | A1 |
| Ib-33 | T1 | H | H | — | H | NHSO₂Et | B4 | A41 |
| Ib-34 | T1 | H | H | — | H | NHMs | B2 | A32 |
| Ib-35 | T1 | H | H | — | H | NHMs | B1 | A41 |
| Ib-36 | T1 | H | H | — | H | NHMs | B4 | A1 |
| Ib-37 | T1 | H | H | — | H | NHMs | B4 | A41 |

TABLE 67-continued

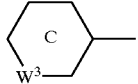

| No. | W³ | R¹² | R¹³ | R¹⁴ | R¹⁵ | X'—Y' | B | A |
|---|---|---|---|---|---|---|---|---|
| Ib-38 | T1 | H | H | — | H | NMe₂ | B2 | A6 |
| Ib-39 | T1 | H | H | — | H | NMe₂ | B3 | A8 |
| Ib-40 | T1 | H | H | — | H | NMe₂ | B2 | A32 |
| Ib-41 | T1 | H | H | — | H | NMe₂ | B3 | A33 |
| Ib-42 | T1 | H | H | — | H | NMe₂ | B2 | A35 |
| Ib-43 | T1 | H | H | — | H | NMe₂ | B4 | A32 |
| Ib-44 | T1 | H | H | — | H | NMe₂ | B4 | A35 |
| Ib-45 | T1 | H | H | — | H | NMe₂ | B5 | A32 |
| Ib-46 | T1 | H | H | — | H | NO₂ | B2 | A6 |
| Ib-47 | T1 | H | H | — | H | NO₂ | B3 | A8 |
| Ib-48 | T1 | H | H | — | H | NO₂ | B4 | A1 |
| Ib-49 | T1 | H | H | — | H | NO₂ | B4 | A41 |
| Ib-50 | T2 | H | H | H | — | Cl | B4 | A1 |
| Ib-51 | T2 | H | H | H | — | Cl | B4 | A41 |
| Ib-52 | T2 | H | H | H | — | H | B2 | A6 |
| Ib-53 | T2 | H | H | H | — | H | B3 | A8 |
| Ib-54 | T2 | H | H | H | — | H | B2 | A32 |
| Ib-55 | T2 | H | H | H | — | H | B3 | A33 |
| Ib-56 | T2 | H | H | H | — | H | B2 | A35 |
| Ib-57 | T2 | H | H | H | — | H | B4 | A32 |
| Ib-58 | T2 | H | H | H | — | H | B4 | A35 |
| Ib-59 | T2 | H | H | H | — | H | B4 | A1 |
| Ib-60 | T2 | H | H | H | — | H | B4 | A41 |

TABLE 68

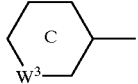

| No. | W³ | R¹² | R¹³ | R¹⁴ | R¹⁵ | X'—Y' | B | A |
|---|---|---|---|---|---|---|---|---|
| Ib-61 | T2 | H | H | H | — | NH₂ | B2 | A6 |
| Ib-62 | T2 | H | H | H | — | NH₂ | B3 | A8 |
| Ib-63 | T2 | H | H | H | — | NH₂ | B1 | A41 |
| Ib-64 | T2 | H | H | H | — | NH₂ | B4 | A1 |
| Ib-65 | T2 | H | H | H | — | NH₂ | B4 | A41 |
| Ib-66 | T2 | H | H | Me | — | NH₂ | B4 | A1 |
| Ib-67 | T2 | H | H | Me | — | NH₂ | B4 | A41 |
| Ib-68 | T2 | H | H | H | — | NHCH₂CH=CMe₂ | B4 | A1 |
| Ib-69 | T2 | H | H | H | — | NHCH₂CH=CMe₂ | B4 | A41 |
| Ib-70 | T2 | H | H | Me | — | NHCH₂CH=CMe₂ | B4 | A1 |
| Ib-71 | T2 | H | H | Me | — | NHCH₂CH=CMe₂ | B4 | A41 |
| Ib-72 | T2 | H | H | H | — | NHCOMe | B4 | A1 |
| Ib-73 | T2 | H | H | H | — | NHCOMe | B4 | A41 |
| Ib-74 | T2 | H | H | Me | — | NHCOMe | B4 | A1 |
| Ib-75 | T2 | H | H | Me | — | NHCOMe | B4 | A41 |
| Ib-76 | T2 | H | H | H | — | NHMs | B4 | A1 |
| Ib-77 | T2 | H | H | H | — | NHMs | B4 | A41 |
| Ib-78 | T2 | H | H | Me | — | NHMs | B4 | A1 |
| Ib-79 | T2 | H | H | Me | — | NHMs | B4 | A41 |
| Ib-80 | T2 | H | H | H | — | NMe₂ | B2 | A6 |
| Ib-81 | T2 | H | H | H | — | NMe₂ | B3 | A8 |
| Ib-82 | T2 | H | H | H | — | NMe₂ | B2 | A32 |
| Ib-83 | T2 | H | H | H | — | NMe₂ | B3 | A33 |
| Ib-84 | T2 | H | H | H | — | NMe₂ | B4 | A32 |
| Ib-85 | T2 | H | H | H | — | NMe₂ | B4 | A35 |
| Ib-86 | T2 | H | H | H | — | OCH₂C₆H₅ | B4 | A1 |
| Ib-87 | T2 | H | H | H | — | OCH₂C₆H₅ | B4 | A41 |
| Ib-88 | T2 | H | H | H | — | OCH₂CH=CMe₂ | B1 | A41 |
| Ib-89 | T2 | H | H | H | — | OCH₂CH=CMe₂ | B4 | A1 |
| Ib-90 | T2 | H | H | H | — | OCH₂CH=CMe₂ | B4 | A41 |
| Ib-91 | T2 | H | H | H | — | OMe | B2 | A6 |
| Ib-92 | T2 | H | H | H | — | OMe | B3 | A8 |
| Ib-93 | T2 | H | H | H | — | OMe | B2 | A32 |
| Ib-94 | T2 | H | H | H | — | OMe | B3 | A33 |
| Ib-95 | T2 | H | H | H | — | OMe | B2 | A35 |
| Ib-96 | T2 | H | H | H | — | OMe | B4 | A32 |
| Ib-97 | T2 | H | H | H | — | OMe | B4 | A35 |
| Ib-98 | T2 | H | H | H | — | Ms | B4 | A1 |
| Ib-99 | T2 | H | H | H | — | Ms | B4 | A41 |

TABLE 68-continued

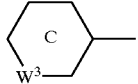

| No. | W³ | R¹² | R¹³ | R¹⁴ | R¹⁵ | X'—Y' | B | A |
|---|---|---|---|---|---|---|---|---|
| Ib-100 | T3 | H | H | H | H | — | B2 | A6 |

TABLE 69

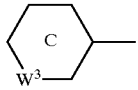

| No. | W³ | R¹² | R¹³ | R¹⁴ | R¹⁵ | X'—Y' | B | A |
|---|---|---|---|---|---|---|---|---|
| Ib-101 | T3 | H | H | H | H | — | B2 | A32 |
| Ib-102 | T3 | H | H | H | H | — | B2 | A35 |
| Ib-103 | T3 | H | H | H | H | — | B3 | A8 |
| Ib-104 | T3 | H | H | H | H | — | B3 | A33 |
| Ib-105 | T3 | H | H | H | H | — | B4 | A11 |
| Ib-106 | T3 | H | H | H | H | — | B4 | A32 |
| Ib-107 | T3 | H | H | H | H | — | B4 | A35 |
| Ib-108 | T3 | H | H | H | H | — | B4 | A37 |
| Ib-109 | T3 | H | H | H | H | — | B4 | A38 |
| Ib-110 | T3 | H | H | H | H | — | B4 | A1 |
| Ib-111 | T3 | H | H | H | H | — | B4 | A41 |
| Ib-112 | T4 | H | H | — | H | — | B3 | A8 |
| Ib-113 | T4 | H | H | — | H | — | B2 | A32 |
| Ib-114 | T4 | H | H | — | H | — | B3 | A33 |
| Ib-115 | T4 | H | H | — | OMe | — | B4 | A1 |
| Ib-116 | T4 | H | H | — | OMe | — | B4 | A41 |
| Ib-117 | T4 | H | Cl | — | H | — | B2 | A6 |
| Ib-118 | T4 | H | Cl | — | H | — | B3 | A8 |
| Ib-119 | T4 | H | Cl | — | H | — | B3 | A33 |
| Ib-120 | T4 | H | Cl | — | H | — | B4 | A1 |
| Ib-121 | T4 | H | Cl | — | H | — | B4 | A41 |
| Ib-122 | T4 | H | OH | — | H | — | B4 | A1 |
| Ib-123 | T4 | H | OH | — | H | — | B4 | A41 |
| Ib-124 | T4 | H | OMe | — | H | — | B2 | A32 |
| Ib-125 | T4 | H | OMe | — | H | — | B4 | A35 |
| Ib-126 | T4 | H | OMe | — | H | — | B4 | A1 |
| Ib-127 | T4 | H | OMe | — | H | — | B4 | A41 |
| Ib-128 | T5 | H | — | H | — | H | B2 | A32 |
| Ib-129 | T5 | H | — | H | — | H | B3 | A33 |
| Ib-130 | T5 | H | — | H | — | H | B4 | A35 |
| Ib-131 | T5 | H | — | H | — | OH | B4 | A35 |
| Ib-132 | T5 | H | — | H | — | OCH₂C₆H₅ | B4 | A1 |
| Ib-133 | T5 | H | — | H | — | OCH₂C₆H₅ | B4 | A41 |
| Ib-134 | T5 | H | — | H | — | OCH₂CH=CMe₂ | B4 | A1 |
| Ib-135 | T5 | H | — | H | — | OCH₂CH=CMe₂ | B4 | A41 |
| Ib-136 | T5 | H | — | H | — | NMe₂ | B2 | A32 |
| Ib-137 | T5 | H | — | H | — | NMe₂ | B4 | A35 |
| Ib-138 | T5 | H | — | H | — | NHCH₂CH=CMe₂ | B4 | A1 |
| Ib-139 | T5 | H | — | H | — | NHCH₂CH=CMe₂ | B4 | A41 |
| Ib-140 | T6 | — | H | — | H | H | B2 | A32 |

TABLE 70

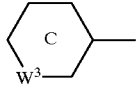

| No. | W³ | R¹² | R¹³ | R¹⁴ | R¹⁵ | X'—Y' | B | A |
|---|---|---|---|---|---|---|---|---|
| Ib-141 | T6 | — | H | — | H | H | B4 | A35 |
| Ib-142 | T7 | H | H | — | — | H | B2 | A32 |
| Ib-143 | T7 | H | H | — | — | H | B3 | A33 |
| Ib-144 | T7 | H | H | — | — | Cl | B2 | A6 |
| Ib-145 | T7 | H | H | — | — | Cl | B3 | A8 |

TABLE 70-continued

| No. | W³ | R¹² | R¹³ | R¹⁴ | R¹⁵ | X'—Y' | B | A |
|---|---|---|---|---|---|---|---|---|
| Ib-146 | T7 | H | H | — | — | Cl | B2 | A32 |
| Ib-147 | T7 | H | H | — | — | Cl | B3 | A33 |
| Ib-148 | T7 | H | H | — | — | Cl | B4 | A35 |
| Ib-149 | T7 | H | H | — | — | Cl | B4 | A1 |
| Ib-150 | T7 | H | H | — | — | Cl | B4 | A41 |
| Ib-151 | T7 | H | H | — | — | NHCH$_2$CH=CMe$_2$ | B4 | A1 |
| Ib-152 | T7 | H | H | — | — | NHCH$_2$CH=CMe$_2$ | B4 | A41 |
| Ib-153 | T7 | H | H | — | — | NMe$_2$ | B2 | A6 |
| Ib-154 | T7 | H | H | — | — | NMe$_2$ | B3 | A8 |
| Ib-155 | T7 | H | H | — | — | NMe$_2$ | B2 | A32 |
| Ib-156 | T7 | H | H | — | — | NMe$_2$ | B3 | A33 |
| Ib-157 | T7 | H | H | — | — | NMe$_2$ | B4 | A35 |
| Ib-158 | T7 | H | H | — | — | OCH$_2$C$_6$H$_5$ | B4 | A1 |
| Ib-159 | T7 | H | H | — | — | OCH$_2$C$_6$H$_5$ | B4 | A41 |
| Ib-160 | T7 | H | H | — | — | OCH$_2$CH=CMe$_2$ | B4 | A1 |
| Ib-161 | T7 | H | H | — | — | OCH$_2$CH=CMe$_2$ | B4 | A41 |
| Ib-162 | T7 | H | H | — | — | OMe | B2 | A32 |
| Ib-163 | T7 | H | H | — | — | OMe | B4 | A35 |
| Ib-164 | T7 | H | H | — | — | OMe | B4 | A1 |
| Ib-165 | T7 | H | H | — | — | OMe | B4 | A41 |
| Ib-166 | T8 | H | — | — | H | H | B2 | A6 |
| Ib-167 | T8 | H | — | — | H | H | B3 | A8 |
| Ib-168 | T8 | H | — | — | H | H | B2 | A32 |
| Ib-169 | T8 | H | — | — | H | H | B3 | A33 |
| Ib-170 | T8 | H | — | — | H | H | B4 | A35 |
| Ib-171 | T8 | H | — | — | H | OMe | B2 | A32 |
| Ib-172 | T8 | H | — | — | H | OMe | B4 | A35 |
| Ib-173 | T8 | H | — | — | H | NMe$_2$ | B2 | A32 |
| Ib-174 | T8 | H | — | — | H | NMe$_2$ | B4 | A35 |
| Ib-175 | T8 | H | — | — | H | Cl | B4 | A1 |
| Ib-176 | T8 | H | — | — | H | Cl | B4 | A41 |
| Ib-177 | T8 | H | — | — | H | OCH$_2$C$_6$H$_5$ | B4 | A1 |
| Ib-178 | T8 | H | — | — | H | OCH$_2$C$_6$H$_5$ | B4 | A41 |
| Ib-179 | T8 | H | — | — | H | OCH$_2$CH=CMe$_2$ | B4 | A1 |
| Ib-180 | T8 | H | — | — | H | OCH$_2$CH=CMe$_2$ | B4 | A41 |

TABLE 71

| No. | W³ | R¹² | R¹³ | R¹⁴ | R¹⁵ | X'—Y' | B | A |
|---|---|---|---|---|---|---|---|---|
| Ib-181 | T8 | H | — | — | H | NHCH$_2$CH=CMe$_2$ | B4 | A1 |
| Ib-182 | T8 | H | — | — | H | NHCH$_2$CH=CMe$_2$ | B4 | A41 |
| Ib-183 | T9 | H | OCH$_2$C$_6$H$_5$ | — | — | — | B4 | A1 |
| Ib-184 | T9 | H | OCH$_2$C$_6$H$_5$ | — | — | — | B4 | A41 |
| Ib-185 | T9 | H | OCH$_2$CH=CMe$_2$ | — | — | — | B4 | A1 |
| Ib-186 | T9 | H | OCH$_2$CH=CMe$_2$ | — | — | — | B4 | A41 |
| Ib-187 | T9 | H | NH$_2$ | — | — | — | B4 | A1 |
| Ib-188 | T9 | H | NH$_2$ | — | — | — | B4 | A41 |
| Ib-189 | T9 | H | NHCH$_2$CH=CMe$_2$ | — | — | — | B4 | A1 |
| Ib-190 | T9 | H | NHCH$_2$CH=CMe$_2$ | — | — | — | B4 | A41 |
| Ib-191 | T9 | H | NHMs | — | — | — | B4 | A1 |
| Ib-192 | T9 | H | NHMs | — | — | — | B4 | A41 |
| Ib-193 | T10 | H | OCH$_2$C$_6$H$_5$ | — | — | — | B4 | A1 |
| Ib-194 | T10 | H | OCH$_2$C$_6$H$_5$ | — | — | — | B4 | A41 |
| Ib-195 | T10 | H | OCH$_2$CH=CMe$_2$ | — | — | — | B4 | A1 |
| Ib-196 | T10 | H | OCH$_2$CH=CMe$_2$ | — | — | — | B4 | A41 |
| Ib-197 | T10 | H | NH$_2$ | — | — | — | B4 | A1 |
| Ib-198 | T10 | H | NH$_2$ | — | — | — | B4 | A41 |
| Ib-199 | T10 | H | NHCH$_2$CH=CMe$_2$ | — | — | — | B4 | A1 |
| Ib-200 | T10 | H | NHCH$_2$CH=CMe$_2$ | — | — | — | B4 | A41 |
| Ib-201 | T10 | H | NHMs | — | — | — | B4 | A1 |
| Ib-202 | T10 | H | NHMs | — | — | — | B4 | A41 |
| Ib-203 | T11 | H | H | H | H | — | B2 | A6 |
| Ib-204 | T11 | H | H | H | H | — | B3 | A8 |
| Ib-205 | T11 | H | H | H | H | — | B2 | A32 |

TABLE 71-continued

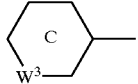

| No. | W³ | R¹² | R¹³ | R¹⁴ | R¹⁵ | X'—Y' | B | A |
|---|---|---|---|---|---|---|---|---|
| Ib-206 | T11 | H | H | H | H | — | B3 | A33 |
| Ib-207 | T1 | H | H | — | H | NHCH₂CH=CMe₂ | B4 | A37 |
| Ib-208 | T1 | H | H | — | H | NH₂ | B4 | A37 |
| Ib-209 | T1 | H | H | — | H | NO₂ | B4 | A37 |
| Ib-210 | T1 | H | H | — | H | H | B4 | A5 |
| Ib-211 | T1 | H | H | — | H | H | B4 | A37 |
| Ib-212 | T1 | H | H | — | H | NH-cHex | B4 | A37 |
| Ib-213 | T1 | H | H | — | H | OMe | B4 | A37 |
| Ib-214 | T1 | H | H | — | H | OCH₂CH=CMe₂ | B4 | A37 |
| Ib-215 | T1 | H | H | — | H | NH₂ | B7 | A37 |
| Ib-216 | T1 | H | H | — | H | NHCH₂CH=CMe₂ | B7 | A37 |
| Ib-217 | T1 | H | H | — | H | OH | B7 | A37 |

TABLE 72

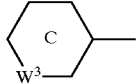

| No. | W³ | R¹² | R¹³ | R¹⁴ | R¹⁵ | X'—Y' | B | A |
|---|---|---|---|---|---|---|---|---|
| Ib-218 | T2 | H | H | H | — | OCH₂CH=CMe₂ | B1 | A64 |
| Ib-219 | T2 | H | H | H | — | OCH₂CH=CMe₂ | B1 | A65 |
| Ib-220 | T2 | H | H | H | — | OCH₂CH=CMe₂ | B1 | A75 |
| Ib-221 | T2 | H | H | H | — | OCH₂CH=CMe₂ | B1 | A76 |
| Ib-222 | T2 | H | H | H | — | OCH₂CH=CMe₂ | B1 | A67 |
| Ib-223 | T2 | H | H | H | — | OCH₂CH=CMe₂ | B1 | A77 |
| Ib-224 | T2 | H | H | H | — | OCH₂CH=CMe₂ | B4 | A64 |
| Ib-225 | T2 | H | H | H | — | OCH₂CH=CMe₂ | B4 | A65 |
| Ib-226 | T2 | H | H | H | — | OCH₂CH=CMe₂ | B4 | A69 |
| Ib-227 | T2 | H | H | H | — | OCH₂CH=CMe₂ | B4 | A76 |
| Ib-228 | T2 | H | H | H | — | OCH₂CH=CMe₂ | B4 | A83 |
| Ib-229 | T2 | H | H | H | — | OCH₂CH=CMe₂ | B4 | A82 |
| Ib-230 | T2 | H | H | H | — | OCH₂CH=CMe₂ | B4 | A81 |
| Ib-231 | T2 | H | H | H | — | OCH₂CH=CMe₂ | B4 | A69 |
| Ib-232 | T2 | H | H | H | — | OCH₂CH=CMe₂ | B4 | A68 |
| Ib-233 | T2 | H | H | H | — | OCH₂CH=CMe₂ | B4 | A66 |
| Ib-234 | T2 | H | H | H | — | OCH₂CH=CMe₂ | B4 | A71 |
| Ib-235 | T2 | H | H | H | — | OCH₂CH=CMe₂ | B4 | A72 |
| Ib-236 | T2 | H | H | H | — | OCH₂CH=CMe₂ | B4 | A73 |
| Ib-237 | T2 | H | H | H | — | OCH₂CH=CMe₂ | B4 | A74 |
| Ib-238 | T2 | H | H | H | — | OCH₂CH=CMe₂ | B4 | A104 |
| Ib-239 | T2 | H | H | H | — | OCH₂CH=CMe₂ | B4 | A45 |
| Ib-240 | T2 | H | H | H | — | OCH₂CH=CMe₂ | B4 | A47 |
| Ib-241 | T2 | H | H | H | — | OCH₂CH=CMe₂ | B4 | A49 |
| Ib-242 | T2 | H | H | H | — | OCH₂CH=CMe₂ | B4 | A48 |
| Ib-243 | T2 | H | H | H | — | OCH₂CH=CMe₂ | B4 | A53 |
| Ib-244 | T2 | H | H | H | — | OCH₂CH=CMe₂ | B4 | A50 |
| Ib-245 | T2 | H | H | H | — | OCH₂CH=CMe₂ | B4 | A59 |
| Ib-246 | T2 | H | H | H | — | OCH₂CH=CMe₂ | B4 | A57 |
| Ib-247 | T2 | H | H | H | — | OCH₂CH=CMe₂ | B4 | A55 |
| Ib-248 | T2 | H | H | H | — | OCH₂CH=CMe₂ | B4 | A42 |
| Ib-249 | T2 | H | H | H | — | OCH₂CH=CMe₂ | B4 | A43 |
| Ib-250 | T2 | H | H | H | — | OCH₂CH=CMe₂ | B4 | A67 |
| Ib-251 | T2 | H | H | H | — | OCH₂CH=CMe₂ | B4 | A62 |
| Ib-252 | T2 | H | H | H | — | OCH₂CH=CMe₂ | B4 | A63 |

TABLE 73

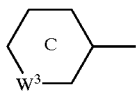

| No. | W³ | R¹² | R¹³ | R¹⁴ | R¹⁵ | X'—Y' | B | A |
|---|---|---|---|---|---|---|---|---|
| Ib-253 | T2 | H | H | H | — | OCH₂CH=CMe₂ | B4 | A78 |
| Ib-254 | T2 | H | H | H | — | OCH₂CH=CMe₂ | B4 | A79 |

TABLE 73-continued

| No. | W³ | R¹² | R¹³ | R¹⁴ | R¹⁵ | X'—Y' | B | A |
|---|---|---|---|---|---|---|---|---|
| Ib-255 | T2 | H | H | H | — | OCH₂CH=CMe₂ | B4 | A84 |
| Ib-256 | T2 | H | H | H | — | OCH₂CH=CMe₂ | B4 | A85 |
| Ib-257 | T2 | H | H | H | — | OCH₂CH=CMe₂ | B4 | A60 |
| Ib-258 | T2 | H | H | H | — | OCH₂CH=CMe₂ | B4 | A61 |
| Ib-259 | T2 | H | H | H | — | OCH₂CH=CMe₂ | B4 | A46 |
| Ib-260 | T2 | H | NO₂ | H | — | OCH₂CH=CMe₂ | B4 | A46 |
| Ib-261 | T2 | H | H | H | — | OCH₂CH=CMe₂ | B4 | A107 |
| Ib-262 | T2 | H | H | H | — | OCH₂CH=CMe₂ | B4 | A37 |
| Ib-263 | T2 | H | H | H | — | OCH₂CH=CMe₂ | B4 | A108 |
| Ib-264 | T2 | H | H | H | — | OCH₂CH=CMe₂ | B4 | A109 |
| Ib-265 | T2 | H | H | H | — | OCH₂CH=CMe₂ | B4 | A110 |
| Ib-266 | T2 | H | H | H | — | OCH₂CH=CMe₂ | B4 | A113 |
| Ib-267 | T2 | H | H | H | — | OCH₂CH=CMe₂ | B4 | A114 |
| Ib-268 | T2 | H | H | Me | — | OCH₂CH=CMe₂ | B4 | A67 |
| Ib-269 | T2 | H | Me | H | — | OCH₂CH=CMe₂ | B4 | A67 |
| Ib-270 | T2 | Me | H | H | — | OCH₂CH=CMe₂ | B4 | A67 |
| Ib-271 | T2 | H | Me | H | — | OCH₂CH=CMe₂ | B4 | A64 |
| Ib-272 | T2 | Me | H | H | — | OCH₂CH=CMe₂ | B4 | A64 |
| Ib-273 | T2 | H | H | Me | — | OCH₂CH=CMe₂ | B4 | A46 |
| Ib-274 | T2 | H | Me | H | — | OCH₂CH=CMe₂ | B4 | A46 |
| Ib-275 | T2 | Me | H | H | — | OCH₂CH=CMe₂ | B4 | A46 |
| Ib-276 | T2 | H | H | Me | — | OCH₂CH=CMe₂ | B4 | A42 |
| Ib-277 | T2 | H | Me | H | — | OCH₂CH=CMe₂ | B4 | A42 |
| Ib-278 | T2 | Me | H | H | — | OCH₂CH=CMe₂ | B4 | A42 |
| Ib-279 | T2 | H | H | H | — | OCH₂CH₂F | B4 | A46 |
| Ib-280 | T2 | H | H | H | — | OCH₂C≡CH | B4 | A47 |
| Ib-281 | T2 | H | H | H | — | OCH₂CH=CH₂ | B4 | A45 |
| Ib-282 | T2 | H | H | H | — | CH₂CH₂CH=CMe₂ | B4 | A67 |
| Ib-283 | T2 | H | H | H | — | NHCH₂CH=CMe₂ | B4 | A37 |
| Ib-284 | T2 | H | H | H | — | NHCH₂CH=CMe₂ | B4 | A5 |
| Ib-285 | T2 | H | H | H | — | NH₂ | B4 | A37 |
| Ib-286 | T2 | H | H | H | — | NH₂ | B4 | A5 |
| Ib-287 | T2 | H | H | H | — | NH-cHex | B4 | A5 |
| Ib-288 | T2 | H | H | H | — | OCH₂-2-furyl | B4 | A67 |

TABLE 74

| No. | W³ | R¹² | R¹³ | R¹⁴ | R¹⁵ | X'—Y' | B | A |
|---|---|---|---|---|---|---|---|---|
| Ib-289 | T2 | H | H | H | — | CH2C≡CMe | B4 | A67 |
| Ib-290 | T2 | H | H | H | — | 1-pyrrolyl | B4 | A67 |
| Ib-291 | T2 | H | H | H | — | 1-pyrrolidinyl | B4 | A67 |
| Ib-292 | T2 | H | H | H | — | H | B4 | A5 |
| Ib-293 | T2 | H | H | H | — | OMe | B4 | A46 |
| Ib-294 | T2 | H | NO₂ | H | — | OMe | B4 | A46 |
| Ib-295 | T2 | H | H | H | — | OBn | B4 | A37 |
| Ib-296 | T2 | H | H | H | — | OMe | B4 | A37 |
| Ib-297 | T2 | H | H | H | — | OCH₂CH=CMe₂ | B7 | A42 |
| Ib-298 | T2 | H | H | H | — | OCH₂CH=CMe₂ | B7 | A46 |
| Ib-299 | T2 | H | H | H | — | OCH₂CH=CMe₂ | B7 | A44 |
| Ib-300 | T2 | H | H | H | — | OMe | B7 | A37 |
| Ib-301 | T2 | H | H | H | — | NHCH₂CH=CMe₂ | B7 | A37 |
| Ib-302 | T2 | H | H | H | — | NH-i-Pr | B7 | A37 |
| Ib-303 | T2 | H | H | H | — | NHCH₂-cHex | B7 | A37 |
| Ib-304 | T2 | H | H | H | — | NHCH₂-3-Pyr | B7 | A37 |
| Ib-305 | T2 | H | H | H | — | NH-i-Pent | B7 | A37 |
| Ib-306 | T2 | H | H | H | — | NH-i-Bu | B7 | A37 |
| Ib-307 | T2 | H | H | H | — | NHCH₂-2-thienyl | B7 | A37 |
| Ib-308 | T2 | H | H | H | — | NHCH₂-3-thienyl | B7 | A37 |
| Ib-309 | T2 | H | H | H | — | NHCH₂-2-furyl | B7 | A37 |
| Ib-310 | T2 | H | H | H | — | NHCH₂-3-furyl | B7 | A37 |
| Ib-311 | T2 | H | H | H | — | NHCH₂-2-Py | B7 | A37 |
| Ib-312 | T2 | H | H | H | — | NH₂ | B7 | A37 |
| Ib-313 | T2 | H | H | H | — | NHCH₂CH=CMe₂ | B7 | A42 |
| Ib-314 | T2 | H | H | H | — | NHCH₂CH=CMe₂ | B7 | A46 |

TABLE 74-continued

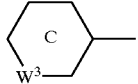

| No. | W³ | R¹² | R¹³ | R¹⁴ | R¹⁵ | X'—Y' | B | A |
|---|---|---|---|---|---|---|---|---|
| Ib-315 | T2 | H | H | H | — | SCH$_2$CH=CMe$_2$ | B7 | A42 |
| Ib-316 | T2 | H | H | H | — | SCH$_2$CH=CMe$_2$ | B7 | A46 |
| Ib-317 | T2 | H | H | H | — | SCH$_2$CH=CMe$_2$ | B7 | A111 |
| Ib-318 | T2 | H | H | Me | — | NHCH$_2$CH=CMe$_2$ | B7 | A46 |
| Ib-319 | T2 | H | Me | H | — | NHCH$_2$CH=CMe$_2$ | B7 | A46 |
| Ib-320 | T2 | Me | H | H | — | NHCH$_2$CH=CMe$_2$ | B7 | A46 |
| Ib-321 | T2 | H | H | H | — | NHCH$_2$CH=CMe$_2$ | B7 | A112 |
| Ib-322 | T2 | H | H | H | — | NHCH$_2$CH=CMe$_2$ | B8 | A37 |

TABLE 75

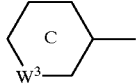

| No. | W³ | R¹² | R¹³ | R¹⁴ | R¹⁵ | X'—Y' | B | A |
|---|---|---|---|---|---|---|---|---|
| Ib-323 | T2 | H | H | H | — | OCH$_2$CH=CMe$_2$ | B8 | A42 |
| Ib-324 | T2 | H | H | H | — | OCH$_2$CH=CMe$_2$ | B8 | A46 |
| Ib-325 | T2 | H | H | H | — | OCH$_2$CH=CMe$_2$ | B8 | A51 |
| Ib-326 | T2 | H | H | H | — | OCH$_2$CH=CMe$_2$ | B8 | A52 |
| Ib-327 | T2 | H | H | H | — | OCH$_2$CH=CMe$_2$ | B8 | A89 |
| Ib-328 | T2 | H | H | H | — | OCH$_2$CH=CMe$_2$ | B8 | A54 |
| Ib-329 | T2 | H | H | H | — | OCH$_2$CH=CMe$_2$ | B10 | A42 |
| Ib-330 | T2 | H | H | H | — | OCH$_2$CH=CMe$_2$ | B10 | A46 |
| Ib-331 | T2 | H | H | H | — | OCH$_2$CH=CMe$_2$ | B10 | A44 |
| Ib-332 | T2 | H | H | H | — | OCH$_2$CH=CMe$_2$ | B10 | A48 |
| Ib-333 | T2 | H | H | H | — | OCH$_2$CH=CMe$_2$ | B10 | A54 |
| Ib-334 | T2 | H | H | H | — | OCH$_2$CH=CMe$_2$ | B10 | A117 |
| Ib-335 | T2 | H | H | H | — | OCH$_2$CH=CMe$_2$ | B10 | A50 |
| Ib-336 | T2 | H | H | H | — | OCH$_2$CH=CMe$_2$ | B10 | A115 |
| Ib-337 | T2 | H | H | H | — | OCH$_2$CH=CMe$_2$ | B10 | A116 |
| Ib-338 | T2 | H | H | H | — | OCH$_2$CH=CMe$_2$ | B10 | A89 |
| Ib-339 | T2 | H | H | H | — | OCH$_2$CH=CHMe | B10 | A46 |
| Ib-340 | T2 | H | H | H | — | OCH$_2$CH$_2$CH=CH$_2$ | B10 | A46 |
| Ib-341 | T2 | H | H | H | — | OCH$_2$CH=CHEt | B10 | A46 |
| Ib-342 | T2 | H | H | H | — | OCH$_2$C≡CMe | B10 | A46 |
| Ib-343 | T2 | H | H | H | — | OCH$_2$-2-furyl | B10 | A46 |
| Ib-344 | T2 | H | H | H | — | OCH$_2$-2-furyl | B10 | A42 |
| Ib-345 | T2 | H | H | H | — | OCH$_2$CH$_2$F | B10 | A46 |
| Ib-346 | T2 | H | H | H | — | OCH$_2$CF$_3$ | B10 | A46 |
| Ib-347 | T2 | H | H | H | — | OCH$_2$-2-furyl | B10 | A117 |
| Ib-348 | T2 | H | H | H | — | OCH$_2$C≡CMe | B10 | A117 |
| Ib-349 | T2 | H | H | H | — | SMe | B10 | A46 |
| Ib-350 | T2 | H | H | H | — | SO$_2$Me | B10 | A46 |
| Ib-351 | T2 | H | H | H | — | OCH$_2$CH=CMe$_2$ | B12 | A42 |
| Ib-352 | T2 | H | H | H | — | OCH$_2$CH=CMe$_2$ | B12 | A46 |
| Ib-353 | T2 | H | H | H | — | OCH$_2$CH=CMe$_2$ | B12 | A58 |
| Ib-354 | T2 | H | H | H | — | OCH$_2$CH=CMe$_2$ | B12 | A48 |
| Ib-355 | T2 | H | H | Me | — | OCH$_2$CH=CMe$_2$ | B12 | A46 |
| Ib-356 | T2 | H | Me | H | — | OCH$_2$CH=CMe$_2$ | B12 | A46 |
| Ib-357 | T2 | Me | H | H | — | OCH$_2$CH=CMe$_2$ | B12 | A46 |

TABLE 76

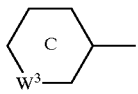

| No. | W³ | R¹² | R¹³ | R¹⁴ | R¹⁵ | X'—Y' | B | A |
|---|---|---|---|---|---|---|---|---|
| Ib-358 | T2 | H | H | H | — | SMe | B12 | A46 |
| Ib-359 | T2 | H | H | H | — | NHCH$_2$CH=CMe$_2$ | B12 | A46 |
| Ib-360 | T2 | H | H | H | — | NH2 | B12 | A78 |

TABLE 76-continued

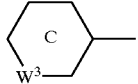

| No. | W³ | R¹² | R¹³ | R¹⁴ | R¹⁵ | X'—Y' | B | A |
|---|---|---|---|---|---|---|---|---|
| Ib-361 | T2 | H | H | H | — | NHCH$_2$CH=CMe$_2$ | B12 | A78 |
| Ib-362 | T2 | H | H | H | — | NH-cHex | B12 | A37 |
| Ib-363 | T2 | H | H | H | — | OCH$_2$CH=CMe$_2$ | B13 | A46 |
| Ib-364 | T2 | H | H | H | — | OCH$_2$CH=CMe$_2$ | B13 | A50 |
| Ib-365 | T2 | H | H | H | — | OCH$_2$CH=CMe$_2$ | B17 | A46 |
| Ib-366 | T2 | H | H | H | — | OCH$_2$CH=CMe$_2$ | B17 | A44 |
| Ib-367 | T2 | H | H | H | — | OCH$_2$CH=CMe$_2$ | B17 | A50 |
| Ib-368 | T2 | H | H | H | — | OCH$_2$CH=CMe$_2$ | B17 | A94 |
| Ib-369 | T2 | H | H | H | — | OCH$_2$CH=CMe$_2$ | B17 | A86 |
| Ib-370 | T2 | H | H | H | — | OCH$_2$-2-furyl | B17 | A46 |
| Ib-371 | T2 | H | H | H | — | OCH$_2$-2-furyl | B17 | A44 |
| Ib-372 | T2 | H | H | H | — | OCH$_2$-2-furyl | B17 | A94 |
| Ib-373 | T2 | H | H | H | — | OCH$_2$CH=CMe$_2$ | B23 | A46 |
| Ib-374 | T2 | H | H | H | — | OCH$_2$-2-furyl | B23 | A46 |
| Ib-375 | T2 | H | H | H | — | OCH$_2$CH=CMe$_2$ | B28 | A46 |
| Ib-376 | T2 | H | H | H | — | OCH$_2$CH=CMe$_2$ | B28 | A50 |
| Ib-377 | T2 | H | H | H | — | OCH$_2$CH=CMe$_2$ | B29 | A104 |
| Ib-378 | T2 | H | H | H | — | OCH$_2$CH=CMe$_2$ | B29 | A105 |
| Ib-379 | T2 | H | H | H | — | OCH$_2$CH=CMe$_2$ | B29 | A67 |
| Ib-380 | T2 | H | H | H | — | OCH$_2$CH=CMe$_2$ | B29 | A106 |
| Ib-381 | T2 | H | H | H | — | OCH$_2$CH=CMe$_2$ | B30 | A46 |
| Ib-382 | T2 | H | H | H | — | OCH$_2$-2-furyl | B30 | A46 |
| Ib-383 | T2 | H | H | H | — | OCH$_2$C≡CMe | B30 | A46 |
| Ib-384 | T4 | H | Cl | — | H | — | B4 | A37 |
| Ib-385 | T4 | H | OMe | — | H | — | B4 | A37 |
| Ib-386 | T4 | H | NMe$_2$ | — | H | — | B4 | A37 |
| Ib-387 | T5 | H | — | H | — | H | B4 | A5 |
| Ib-388 | T5 | H | — | H | — | H | B4 | A37 |
| Ib-389 | T5 | H | — | H | — | NH$_2$ | B4 | A5 |
| Ib-390 | T5 | H | — | H | — | NH$_2$ | B4 | A37 |
| Ib-391 | T5 | H | — | H | — | NHCH$_2$CH=CMe$_2$ | B4 | A5 |
| Ib-392 | T5 | H | — | H | — | NHCH$_2$CH=CMe$_2$ | B4 | A37 |
| Ib-393 | T5 | H | — | H | — | NHCH$_2$CH=CMe$_2$ | B4 | A42 |
| Ib-394 | T5 | H | — | H | — | NHCH$_2$CH=CMe$_2$ | B4 | A46 |

TABLE 77

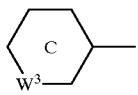

| No. | W³ | R¹² | R¹³ | R¹⁴ | R¹⁵ | X'—Y' | B | A |
|---|---|---|---|---|---|---|---|---|
| Ib-395 | T5 | H | — | H | — | NHCH$_2$CH=CMe$_2$ | B4 | A118 |
| Ib-396 | T5 | H | — | H | — | OCH$_2$CH=CMe$_2$ | B4 | A67 |
| Ib-397 | T5 | H | — | H | — | OCH$_2$CH=CMe$_2$ | B7 | A46 |
| Ib-398 | T5 | H | — | H | — | NHCH$_2$CH=CMe$_2$ | B7 | A37 |
| Ib-399 | T5 | H | — | H | — | NH$_2$ | B7 | A37 |
| Ib-400 | T5 | H | — | H | — | NHCH$_2$CH=CMe$_2$ | B12 | A37 |
| Ib-401 | T6 | — | H | — | H | H | B4 | A5 |
| Ib-402 | T6 | — | H | — | H | H | B4 | A37 |
| Ib-403 | T7 | H | H | — | — | OCH$_2$CH=CMe$_2$ | B4 | A46 |
| Ib-404 | T7 | H | H | — | — | Cl | B4 | A5 |
| Ib-405 | T7 | H | H | — | — | OMe | B4 | A5 |
| Ib-406 | T7 | H | H | — | — | NMe$_2$ | B4 | A5 |
| Ib-407 | T7 | H | H | — | — | Cl | B4 | A37 |
| Ib-408 | T7 | H | H | — | — | OMe | B4 | A37 |
| Ib-409 | T7 | H | H | — | — | NMe$_2$ | B4 | A37 |
| Ib-410 | T7 | H | H | — | — | NH$_2$ | B4 | A5 |
| Ib-411 | T7 | H | H | — | — | NH$_2$ | B4 | A37 |
| Ib-412 | T7 | H | H | — | — | NHCH$_2$CH=CMe$_2$ | B4 | A5 |
| Ib-413 | T7 | H | H | — | — | NHCH$_2$CH=CMe$_2$ | B4 | A37 |
| Ib-414 | T7 | H | H | — | — | NHCH$_2$CH=CMe$_2$ | B4 | A42 |
| Ib-415 | T7 | H | H | — | — | NHCH$_2$CH=CMe$_2$ | B4 | A46 |
| Ib-416 | T7 | H | H | — | — | NHCH$_2$CH=CMe$_2$ | B4 | A118 |
| Ib-417 | T7 | H | H | — | — | NH$_2$ | B7 | A37 |
| Ib-418 | T7 | H | H | — | — | NHCH$_2$CH=CMe$_2$ | B7 | A37 |
| Ib-419 | T7 | H | H | — | — | OCH$_2$CH=CMe$_2$ | B7 | A46 |
| Ib-420 | T7 | H | H | — | — | NHCH$_2$CH=CMe$_2$ | B12 | A37 |

TABLE 77-continued

| No. | W³ | R¹² | R¹³ | R¹⁴ | R¹⁵ | X'—Y' | B | A |
|---|---|---|---|---|---|---|---|---|
| Ib-421 | T8 | H | — | — | H | H | B4 | A5 |
| Ib-422 | T8 | H | — | — | H | H | B4 | A37 |
| Ib-423 | T8 | H | — | — | H | NH₂ | B4 | A5 |
| Ib-424 | T8 | H | — | — | H | NH₂ | B4 | A37 |
| Ib-425 | T8 | H | — | — | H | NH-cHex | B4 | A5 |
| Ib-426 | T8 | H | — | — | H | NH-cHex | B4 | A37 |
| Ib-427 | T8 | H | — | — | H | NHCH₂CH=CMe₂ | B4 | A5 |
| Ib-428 | T8 | H | — | — | H | NHCH₂CH=CMe₂ | B4 | A37 |
| Ib-429 | T8 | H | — | — | H | NHCH₂CH=CMe₂ | B4 | A46 |
| Ib-430 | T8 | H | — | — | H | NHCH₂CH=CMe₂ | B4 | A118 |
| Ib-431 | T8 | H | — | — | H | OCH₂CH=CMe₂ | B7 | A46 |
| Ib-432 | T8 | H | — | — | H | NH₂ | B7 | A37 |

TABLE 78

| No. | W³ | R¹² | R¹³ | R¹⁴ | R¹⁵ | X'—Y' | B | A |
|---|---|---|---|---|---|---|---|---|
| Ib-433 | T8 | H | — | — | H | NHCH₂CH=CMe₂ | B7 | A37 |
| Ib-434 | T8 | H | — | — | H | NHCH₂CH=CMe₂ | B7 | A42 |
| Ib-435 | T8 | H | — | — | H | NHCH₂CH=CMe₂ | B7 | A46 |
| Ib-436 | T8 | H | — | — | H | NHCH₂CH=CMe₂ | B12 | A37 |
| Ib-437 | T12 | H | H | H | — | — | B4 | A64 |
| Ib-438 | T12 | H | H | H | — | — | B4 | A80 |
| Ib-439 | T12 | H | H | H | — | — | B4 | A81 |
| Ib-440 | T12 | H | H | H | — | — | B4 | A67 |
| Ib-441 | T12 | H | H | H | — | — | B7 | A37 |
| Ib-442 | T13 | H | H | — | — | — | B7 | A37 |
| Ib-443 | T14 | — | H | H | — | — | B7 | A37 |
| Ib-444 | T2 | H | H | H | — | OCH₂CH=CMe₂ | B6 | A46 |
| Ib-445 | T2 | H | H | H | — | OCH₂CH=CMe₂ | B11 | A46 |
| Ib-446 | T2 | H | H | H | — | OCH₂CH=CMe₂ | B14 | A46 |
| Ib-447 | T2 | H | H | H | — | OCH₂CH=CMe₂ | B15 | A46 |
| Ib-448 | T2 | H | H | H | — | OCH₂CH=CMe₂ | B16 | A46 |
| Ib-449 | T2 | H | H | H | — | OCH₂CH=CMe₂ | B18 | A46 |
| Ib-450 | T2 | H | H | H | — | OCH₂CH=CMe₂ | B19 | A46 |
| Ib-451 | T2 | H | H | H | — | OCH₂CH=CMe₂ | B20 | A46 |
| Ib-452 | T2 | H | H | H | — | OCH₂CH=CMe₂ | B21 | A46 |
| Ib-453 | T2 | H | H | H | — | OCH₂CH=CMe₂ | B22 | A46 |
| Ib-454 | T2 | H | H | H | — | OCH₂CH=CMe₂ | B23 | A46 |
| Ib-455 | T2 | H | H | H | — | OCH₂CH=CMe₂ | B24 | A46 |
| Ib-456 | T2 | H | H | H | — | OCH₂CH=CMe₂ | B25 | A46 |
| Ib-457 | T2 | H | H | H | — | OCH₂CH=CMe₂ | B26 | A46 |
| Ib-458 | T2 | H | H | H | — | OCH₂CH=CMe₂ | B27 | A46 |
| Ib-459 | T2 | H | H | H | — | OCH₂CH=CMe₂ | B28 | A46 |
| Ib-460 | T2 | H | H | H | — | OCH₂CH=CMe₂ | B29 | A46 |
| Ib-461 | T2 | H | H | H | — | OCH₂CH=CMe₂ | B30 | A46 |
| Ib-462 | T2 | H | H | H | — | OCH₂CH=CMe₂ | B31 | A46 |
| Ib-463 | T2 | H | H | H | — | OCH₂CH=CMe₂ | B32 | A46 |
| Ib-464 | T2 | H | H | H | — | OCH₂CH=CMe₂ | B33 | A46 |
| Ib-465 | T2 | H | H | H | — | OCH₂CH=CMe₂ | B34 | A46 |
| Ib-466 | T2 | H | H | H | — | OCH₂CH=CMe₂ | B35 | A46 |
| Ib-467 | T2 | H | H | H | — | OCH₂CH=CMe₂ | B36 | A46 |
| Ib-468 | T2 | H | H | H | — | OCH₂CH=CMe₂ | B37 | A46 |
| Ib-469 | T2 | H | H | H | — | OCH₂CH=CMe₂ | B38 | A46 |

TABLE 79

| No. | W³ | R¹² | R¹³ | R¹⁴ | R¹⁵ | X'—Y' | B | A |
|---|---|---|---|---|---|---|---|---|
| Ib-470 | T2 | H | H | H | — | OCH₂CH=CMe₂ | B39 | A46 |
| Ib-471 | T2 | H | H | H | — | OCH₂CH=CMe₂ | B40 | A46 |
| Ib-472 | T2 | H | H | H | — | OCH₂CH=CMe₂ | B41 | A46 |

TABLE 79-continued

| No. | W³ | R¹² | R¹³ | R¹⁴ | R¹⁵ | X'—Y' | B | A |
|---|---|---|---|---|---|---|---|---|
| Ib-473 | T2 | H | H | H | — | OCH$_2$CH=CMe$_2$ | B42 | A46 |
| Ib-474 | T2 | H | H | H | — | OCH$_2$CH=CMe$_2$ | B43 | A46 |
| Ib-475 | T2 | H | H | H | — | NHCH$_2$CH=CMe$_2$ | B4 | A2 |
| Ib-476 | T2 | H | H | H | — | NHCH$_2$CH=CMe$_2$ | B4 | A3 |
| Ib-477 | T2 | H | H | H | — | NHCH$_2$CH=CMe$_2$ | B4 | A4 |
| Ib-478 | T2 | H | H | H | — | NHCH$_2$CH=CMe$_2$ | B4 | A7 |
| Ib-479 | T2 | H | H | H | — | NHCH$_2$CH=CMe$_2$ | B4 | A9 |
| Ib-480 | T2 | H | H | H | — | NHCH$_2$CH=CMe$_2$ | B4 | A10 |
| Ib-481 | T2 | H | H | H | — | NHCH$_2$CH=CMe$_2$ | B4 | A12 |
| Ib-482 | T2 | H | H | H | — | NHCH$_2$CH=CMe$_2$ | B4 | A13 |
| Ib-483 | T2 | H | H | H | — | NHCH$_2$CH=CMe$_2$ | B4 | A14 |
| Ib-484 | T2 | H | H | H | — | NHCH$_2$CH=CMe$_2$ | B4 | A15 |
| Ib-485 | T2 | H | H | H | — | NHCH$_2$CH=CMe$_2$ | B4 | A16 |
| Ib-486 | T2 | H | H | H | — | NHCH$_2$CH=CMe$_2$ | B4 | A17 |
| Ib-487 | T2 | H | H | H | — | NHCH$_2$CH=CMe$_2$ | B4 | A18 |
| Ib-488 | T2 | H | H | H | — | NHCH$_2$CH=CMe$_2$ | B4 | A19 |
| Ib-489 | T2 | H | H | H | — | NHCH$_2$CH=CMe$_2$ | B4 | A20 |
| Ib-490 | T2 | H | H | H | — | NHCH$_2$CH=CMe$_2$ | B4 | A21 |
| Ib-491 | T2 | H | H | H | — | NHCH$_2$CH=CMe$_2$ | B4 | A22 |
| Ib-492 | T2 | H | H | H | — | NHCH$_2$CH=CMe$_2$ | B4 | A23 |
| Ib-493 | T2 | H | H | H | — | NHCH$_2$CH=CMe$_2$ | B4 | A24 |
| Ib-494 | T2 | H | H | H | — | NHCH$_2$CH=CMe$_2$ | B4 | A25 |
| Ib-495 | T2 | H | H | H | — | NHCH$_2$CH=CMe$_2$ | B4 | A26 |
| Ib-496 | T2 | H | H | H | — | NHCH$_2$CH=CMe$_2$ | B4 | A27 |
| Ib-497 | T2 | H | H | H | — | NHCH$_2$CH=CMe$_2$ | B4 | A28 |
| Ib-498 | T2 | H | H | H | — | NHCH$_2$CH=CMe$_2$ | B4 | A29 |
| Ib-499 | T2 | H | H | H | — | NHCH$_2$CH=CMe$_2$ | B4 | A30 |
| Ib-500 | T2 | H | H | H | — | NHCH$_2$CH=CMe$_2$ | B4 | A31 |
| Ib-501 | T2 | H | H | H | — | NHCH$_2$CH=CMe$_2$ | B4 | A34 |
| Ib-502 | T2 | H | H | H | — | NHCH$_2$CH=CMe$_2$ | B4 | A36 |
| Ib-503 | T2 | H | H | H | — | NHCH$_2$CH=CMe$_2$ | B4 | A39 |
| Ib-504 | T2 | H | H | H | — | NHCH$_2$CH=CMe$_2$ | B4 | A40 |
| Ib-505 | T2 | H | H | H | — | OCH$_2$CH=CMe$_2$ | B4 | A56 |
| Ib-506 | T2 | H | H | H | — | OCH$_2$CH=CMe$_2$ | B4 | A70 |
| Ib-507 | T2 | H | H | H | — | OCH$_2$CH=CMe$_2$ | B4 | A87 |
| Ib-508 | T2 | H | H | H | — | OCH$_2$CH=CMe$_2$ | B4 | A88 |
| Ib-509 | T2 | H | H | H | — | OCH$_2$CH=CMe$_2$ | B4 | A89 |

TABLE 80

| No. | W³ | R¹² | R¹³ | R¹⁴ | R¹⁵ | X'—Y' | B | A |
|---|---|---|---|---|---|---|---|---|
| Ib-510 | T2 | H | H | H | — | OCH$_2$CH=CMe$_2$ | B4 | A90 |
| Ib-511 | T2 | H | H | H | — | OCH$_2$CH=CMe$_2$ | B4 | A91 |
| Ib-512 | T2 | H | H | H | — | OCH$_2$CH=CMe$_2$ | B4 | A92 |
| Ib-513 | T2 | H | H | H | — | OCH$_2$CH=CMe$_2$ | B4 | A93 |
| Ib-514 | T2 | H | H | H | — | OCH$_2$CH=CMe$_2$ | B4 | A94 |
| Ib-515 | T2 | H | H | H | — | OCH$_2$CH=CMe$_2$ | B4 | A95 |
| Ib-516 | T2 | H | H | H | — | OCH$_2$CH=CMe$_2$ | B4 | A96 |
| Ib-517 | T2 | H | H | H | — | OCH$_2$CH=CMe$_2$ | B4 | A97 |
| Ib-518 | T2 | H | H | H | — | OCH$_2$CH=CMe$_2$ | B4 | A98 |
| Ib-519 | T2 | H | H | H | — | OCH$_2$CH=CMe$_2$ | B4 | A99 |
| Ib-520 | T2 | H | H | H | — | OCH$_2$CH=CMe$_2$ | B4 | A100 |
| Ib-521 | T2 | H | H | H | — | OCH$_2$CH=CMe$_2$ | B4 | A101 |
| Ib-522 | T2 | H | H | H | — | OCH$_2$CH=CMe$_2$ | B4 | A102 |
| Ib-523 | T2 | H | H | H | — | NHCH$_2$CH=CMe$_2$ | B4 | A103 |
| Ib-524 | T2 | H | H | H | — | OCH$_2$CH=CMe$_2$ | B4 | A104 |
| Ib-525 | T2 | H | H | H | — | OCH$_2$CH=CMe$_2$ | B4 | A105 |
| Ib-526 | T2 | H | H | H | — | OCH$_2$CH=CMe$_2$ | B4 | A106 |
| Ib-527 | T2 | H | H | H | — | NHCH$_2$CH=CMe$_2$ | B4 | A107 |
| Ib-528 | T2 | H | H | H | — | NHCH$_2$CH=CMe$_2$ | B4 | A108 |
| Ib-529 | T2 | H | H | H | — | NHCH$_2$CH=CMe$_2$ | B4 | A109 |
| Ib-530 | T2 | H | H | H | — | NHCH$_2$CH=CMe$_2$ | B4 | A110 |
| Ib-531 | T2 | H | H | H | — | OCH$_2$CH=CMe$_2$ | B4 | A111 |
| Ib-532 | T2 | H | H | H | — | OCH$_2$CH=CMe$_2$ | B4 | A112 |

TABLE 80-continued

| No. | W³ | R¹² | R¹³ | R¹⁴ | R¹⁵ | X'—Y' | B | A |
|---|---|---|---|---|---|---|---|---|
| Ib-533 | T2 | H | H | H | — | OCH$_2$CH=CMe$_2$ | B4 | A113 |
| Ib-534 | T2 | H | H | H | — | OCH$_2$CH=CMe$_2$ | B4 | A114 |
| Ib-535 | T2 | H | H | H | — | OCH$_2$CH=CMe$_2$ | B4 | A115 |
| Ib-536 | T2 | H | H | H | — | OCH$_2$CH=CMe$_2$ | B4 | A116 |
| Ib-537 | T2 | H | H | H | — | OCH$_2$CH=CMe$_2$ | B4 | A117 |
| Ib-538 | T2 | H | H | H | — | OCH$_2$CH=CMe$_2$ | B4 | A118 |
| Ib-539 | T2 | H | H | H | — | OCH$_2$CH=CMe$_2$ | B4 | A119 |
| Ib-540 | T2 | H | H | H | — | OCH$_2$CH=CMe$_2$ | B4 | A120 |
| Ib-541 | T2 | H | H | H | — | OCH$_2$CH=CMe$_2$ | B4 | A121 |
| Ib-542 | T2 | H | H | H | — | OCH$_2$CH=CMe$_2$ | B4 | A122 |
| Ib-543 | T2 | H | H | H | — | OCH$_2$CH=CMe$_2$ | B4 | A123 |
| Ib-544 | T2 | H | H | H | — | OCH$_2$CH=CMe$_2$ | B4 | A124 |
| Ib-545 | T2 | H | H | H | — | OCH$_2$CH=CMe$_2$ | B4 | A125 |
| Ib-546 | T2 | H | H | H | — | OCH$_2$CH=CMe$_2$ | B4 | A126 |

TABLE 81

| No. | W³ | R¹² | R¹³ | R¹⁴ | R¹⁵ | X'—Y' | B | A |
|---|---|---|---|---|---|---|---|---|
| Ib-547 | T2 | H | H | H | — | OCH$_2$CH=CMe$_2$ | B4 | A127 |
| Ib-548 | T2 | H | H | H | — | OCH$_2$CH=CMe$_2$ | B1 | A120 |
| Ib-549 | T2 | H | H | H | — | OCH$_2$CH=CMe$_2$ | B1 | A122 |
| Ib-550 | T2 | H | H | H | — | OCH$_2$CH=CMe$_2$ | B1 | A124 |
| Ib-551 | T2 | H | H | H | — | OCH$_2$CH=CMe$_2$ | B1 | A126 |
| Ib-552 | T2 | H | H | H | — | OCH$_2$-2-furyl | B10 | A128 |
| Ib-553 | T2 | H | H | H | — | OCH$_2$-2-furyl | B10 | A129 |
| Ib-554 | T2 | H | H | H | — | OCH$_2$-2-furyl | B10 | A130 |
| Ib-555 | T2 | H | H | H | — | OCH$_2$-2-furyl | B10 | A131 |
| Ib-556 | T2 | H | H | H | — | —N(CH$_2$CH=CMe$_2$)(COOCH$_2$OCO(CH$_2$)$_2$COOH) | B12 | A132 |
| Ib-557 | T2 | H | H | H | — | —N(CH$_2$CH=CMe$_2$)(COOCH(Me)OCOMe) | B12 | A133 |
| Ib-558 | T2 | H | H | H | — | —N(CH$_2$CH=CMe$_2$)(COOCH$_2$OCO(CH$_2$)$_{14}$Me) | B12 | A134 |
| Ib-559 | T2 | H | H | H | — | —N(CH$_2$CH=CMe$_2$)(CH$_2$NHCO—C$_6$H$_4$-o-OCH$_2$OCOMe) | B12 | A135 |
| Ib-560 | T5 | H | — | H | — | OCH$_2$CH=CMe$_2$ | B4 | A121 |
| Ib-561 | T5 | H | — | H | — | OCH$_2$CH=CMe$_2$ | B4 | A123 |
| Ib-562 | T5 | H | — | H | — | OCH$_2$CH=CMe$_2$ | B4 | A125 |
| Ib-563 | T5 | H | — | H | — | OCH$_2$CH=CMe$_2$ | B4 | A127 |
| Ib-564 | T2 | H | H | H | — | OCH$_2$CH=CMe$_2$ | B4 | A136 |
| Ib-565 | T2 | H | H | H | — | OCH$_2$CH=CMe$_2$ | B4 | A137 |
| Ib-566 | T2 | H | H | H | — | OCH$_2$CH=CMe$_2$ | B4 | A138 |
| Ib-567 | T2 | H | H | H | — | OCH$_2$CH=CMe$_2$ | B4 | A139 |

TABLE 81-continued

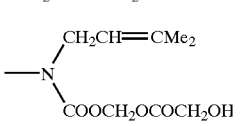

| No. | W³ | R¹² | R¹³ | R¹⁴ | R¹⁵ | X'—Y' | | B | A |
|---|---|---|---|---|---|---|---|---|---|
| Ib-568 | T2 | H | H | H | — | OCH₂CH=CMe₂ | | B4 | A140 |
| Ib-569 | T2 | H | H | H | — | OCH₂CH=CMe₂ | | B4 | A141 |
| Ib-570 | T2 | H | H | H | — | OCH₂CH=CMe₂ | | B4 | A142 |
| Ib-571 | T2 | H | H | H | — | OCH₂CH=CMe₂ | | B4 | A143 |
| Ib-572 | T2 | H | H | H | — | —N(CH₂CH=CMe₂)(COOCH₂OCOCH₂OH) | | B12 | A78 |
| Ib-573 | T2 | H | H | H | — | —N(CH₂CH=CMe₂)(COOCH₂OCO(CH₂)₂COOH) | | B12 | A78 |
| Ib-574 | T2 | H | H | H | — | —N(CH₂CH=CMe₂)(COOCH₂OCOMe) | | B12 | A78 |
| Ib-575 | T2 | H | H | H | — | —N(CH₂CH=CMe₂)(COOCH(Me)OCOCMe₃) | | B12 | A78 |

TABLE 82

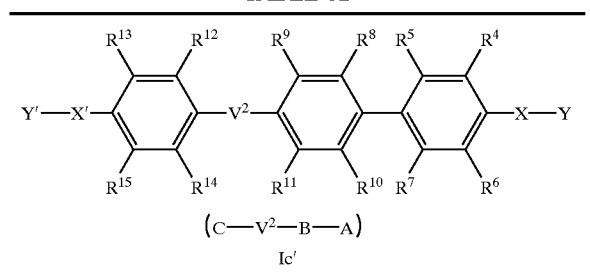

Ic'

| No. | V² | C | B | A |
|---|---|---|---|---|
| Ic-1 | O | C2 | B4 | A32 |
| Ic-2 | O | C2 | B4 | A35 |
| Ic-3 | O | C3 | B4 | A6 |
| Ic-4 | O | C3 | B4 | A8 |
| Ic-5 | O | C3 | B4 | A11 |
| Ic-6 | O | C3 | B4 | A33 |
| Ic-7 | O | C3 | B4 | A35 |
| Ic-8 | O | C5 | B4 | A11 |
| Ic-9 | O | C5 | B4 | A35 |
| Ic-10 | O | C6 | B1 | A35 |
| Ic-11 | O | C6 | B1 | A37 |
| Ic-12 | O | C6 | B4 | A11 |
| Ic-13 | O | C6 | B4 | A32 |
| Ic-14 | O | C6 | B4 | A35 |
| Ic-15 | O | C19 | B4 | A35 |
| Ic-16 | O | C25 | B4 | A41 |
| Ic-17 | O | C26 | B4 | A41 |
| Ic-18 | O | C27 | B4 | A41 |
| Ic-19 | O | C28 | B4 | A41 |
| Ic-20 | O | C29 | B4 | A41 |
| Ic-21 | NH | C2 | B4 | A32 |
| Ic-22 | NH | C2 | B4 | A35 |
| Ic-23 | OCH₂ | C2 | B4 | A32 |

TABLE 82-continued

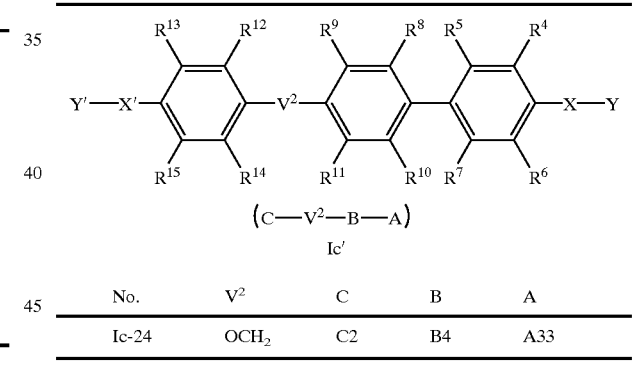

Ic'

| No. | V² | C | B | A |
|---|---|---|---|---|
| Ic-24 | OCH₂ | C2 | B4 | A33 |

TABLE 83

| No. | V² | C | B | A |
|---|---|---|---|---|
| Ic-25 | OCH₂ | C2 | B4 | A35 |
| Ic-26 | OCH₂ | C6 | B4 | A35 |
| Ic-27 | OCH₂ | C19 | B4 | A35 |
| Ic-28 | CH₂O | C2 | B1 | A32 |
| Ic-29 | CH₂O | C2 | B1 | A35 |
| Ic-30 | CH₂O | C2 | B4 | A35 |
| Ic-31 | CH₂O | C3 | B1 | A33 |
| Ic-32 | CH₂O | C3 | B4 | A33 |
| Ic-33 | NHCH₂ | C2 | B4 | A35 |
| Ic-34 | NHCH₂ | C6 | B4 | A35 |
| Ic-35 | CH=CH | C2 | B4 | A32 |
| Ic-36 | CH=CH | C2 | B4 | A33 |
| Ic-37 | CH=CH | C2 | B4 | A35 |
| Ic-38 | CH=CH | C3 | B4 | A33 |
| Ic-39 | CH=CH | C6 | B4 | A32 |
| Ic-40 | CH=CH | C6 | B4 | A35 |

TABLE 83-continued

| No. | V² | C | B | A |
|---|---|---|---|---|
| Ic-41 | CH=CH | C19 | B4 | A35 |
| Ic-42 | C≡C | C2 | B4 | A32 |
| Ic-43 | C≡C | C2 | B4 | A35 |
| Ic-44 | C≡C | C3 | B4 | A35 |
| Ic-45 | C≡C | C19 | B4 | A35 |
| Ic-46 | CO | C2 | B4 | A32 |
| Ic-47 | CO | C2 | B4 | A35 |
| Ic-48 | CH(OH) | C2 | B4 | A32 |
| Ic-49 | CH(OH) | C2 | B4 | A35 |

TABLE 84

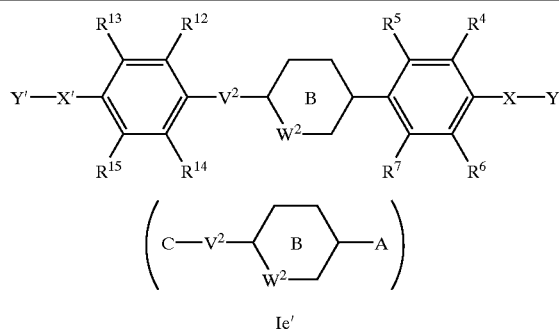

Ie'

| No. | V² | C | | R⁸ | R⁹ | R¹⁰ | A |
|---|---|---|---|---|---|---|---|
| Ie-1 | O | C6 | S1 | H | H | H | A6 |
| Ie-2 | O | C6 | S1 | H | H | H | A8 |
| Ie-3 | O | C6 | S1 | H | H | H | A32 |
| Ie-4 | O | C9 | S1 | H | H | H | A6 |
| Ie-5 | O | C9 | S1 | H | H | H | A8 |
| Ie-6 | O | C9 | S1 | H | H | H | A14 |
| Ie-7 | O | C9 | S1 | H | H | H | A17 |
| Ie-8 | O | C9 | S1 | H | H | H | A32 |
| Ie-9 | O | C9 | S1 | H | H | H | A33 |
| Ie-10 | O | C6 | S1 | H | Me | Me | A32 |

TABLE 85

| No. | V² | C | | R⁸ | R⁹ | R¹⁰ | A |
|---|---|---|---|---|---|---|---|
| Ie-11 | O | C6 | S1 | H | Me | Me | A35 |
| Ie-12 | O | C1 | S3 | Me | — | OMe | A6 |
| Ie-13 | O | C1 | S3 | Me | — | OMe | A8 |
| Ie-14 | O | C1 | S3 | Me | — | OMe | A14 |
| Ie-15 | O | C1 | S3 | Me | — | OMe | A17 |
| Ie-16 | O | C1 | S3 | Me | — | OMe | A32 |
| Ie-17 | O | C4 | S3 | Me | — | OMe | A8 |
| Ie-18 | O | C4 | S3 | Me | — | OMe | A14 |
| Ie-19 | O | C4 | S3 | Me | — | OMe | A17 |
| Ie-20 | O | C4 | S3 | Me | — | OMe | A32 |
| Ie-21 | O | C4 | S3 | Me | — | OMe | A33 |
| Ie-22 | O | C9 | S3 | Me | — | OMe | A6 |
| Ie-23 | O | C9 | S3 | Me | — | OMe | A8 |
| Ie-24 | O | C9 | S3 | Me | — | OMe | A32 |
| Ie-25 | O | C9 | S3 | Me | — | OMe | A33 |
| Ie-26 | NH | C1 | S3 | Me | — | OMe | A6 |
| Ie-27 | NH | C1 | S3 | Me | — | OMe | A8 |

TABLE 85-continued

| No. | V² | C | | R⁸ | R⁹ | R¹⁰ | A |
|---|---|---|---|---|---|---|---|
| Ie-28 | NH | C1 | S3 | Me | — | OMe | A14 |
| Ie-29 | NH | C1 | S3 | Me | — | OMe | A17 |
| Ie-30 | NH | C1 | S3 | Me | — | OMe | A32 |
| Ie-31 | NH | C4 | S3 | Me | — | OMe | A8 |
| Ie-32 | NH | C4 | S3 | Me | — | OMe | A14 |
| Ie-33 | NH | C4 | S3 | Me | — | OMe | A17 |
| Ie-34 | NH | C4 | S3 | Me | — | OMe | A32 |
| Ie-35 | NH | C4 | S3 | Me | — | OMe | A33 |
| Ie-36 | NH | C9 | S3 | Me | — | OMe | A6 |
| Ie-37 | NH | C9 | S3 | Me | — | OMe | A8 |
| Ie-38 | NH | C9 | S3 | Me | — | OMe | A14 |
| Ie-39 | NH | C9 | S3 | Me | — | OMe | A17 |
| Ie-40 | NH | C9 | S3 | Me | — | OMe | A32 |
| Ie-41 | NH | C9 | S3 | Me | — | OMe | A33 |

TABLE 86

If

| No. | | | R⁸ | R⁹ | R¹⁰ | A |
|---|---|---|---|---|---|---|
| If-1 | morpholino | S1 | H | H | H | A6 |
| If-2 | morpholino | S1 | H | H | H | A8 |
| If-3 | morpholino | S1 | H | H | H | A32 |
| If-4 | morpholino | S1 | H | H | H | A33 |
| If-5 | morpholino | S1 | H | Me | Me | A6 |
| If-6 | morpholino | S1 | H | Me | Me | A8 |
| If-7 | morpholino | S1 | H | Me | Me | A32 |
| If-8 | morpholino | S1 | H | Me | Me | A33 |
| If-9 | morpholino | S3 | Me | — | OMe | A6 |
| If-10 | morpholino | S3 | Me | — | OMe | A8 |
| If-11 | morpholino | S3 | Me | — | OMe | A32 |
| If-12 | morpholino | S3 | Me | — | OMe | A33 |
| If-13 | 4-Me-piperazinyl | S3 | Me | — | OMe | A6 |
| If-14 | 4-Me-piperazinyl | S3 | Me | — | OMe | A8 |
| If-15 | 4-Me-piperazinyl | S3 | Me | — | OMe | A32 |
| If-16 | 4-Me-piperazinyl | S3 | Me | — | OMe | A33 |
| If-17 | 4-Ph-piperazinyl | S3 | Me | — | OMe | A6 |
| If-18 | 4-Ph-piperazinyl | S3 | Me | — | OMe | A8 |
| If-19 | 4-Ph-piperazinyl | S3 | Me | — | OMe | A32 |
| If-20 | 4-Ph-piperazinyl | S3 | Me | — | OMe | A33 |
| If-21 | 1-imidazolyl | S3 | Me | — | OMe | A6 |
| If-22 | 1-imidazolyl | S3 | Me | — | OMe | A8 |
| If-23 | 1-imidazolyl | S3 | Me | — | OMe | A32 |
| If-24 | 1-imidazolyl | S3 | Me | — | OMe | A33 |
| If-25 | 1-triazolyl | S3 | Me | — | OMe | A6 |

TABLE 86-continued

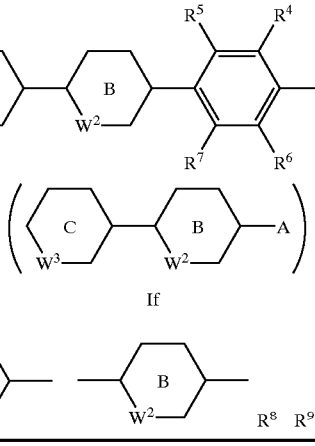

| No. | C W³ | B W² | R⁸ | R⁹ | R¹⁰ | A |
|---|---|---|---|---|---|---|
| If-26 | 1-triazolyl | S3 | Me | — | OMe | A8 |
| If-27 | 1-triazolyl | S3 | Me | — | OMe | A32 |
| If-28 | 1-triazolyl | S3 | Me | — | OMe | A33 |
| If-29 | 2-prenyloxypyridin-5-yl | S1 | H | Me | Me | A46 |
| If-30 | 2-prenyloxypyridin-5-yl | S1 | H | Me | Me | A42 |

TABLE 87

Ig'

| No. | A W¹ | R⁴ | R⁵ | R⁶ | R⁷ | B | C W³ | R¹² | R¹³ | R¹⁴ | R¹⁵ | X—Y | X'—Y' |
|---|---|---|---|---|---|---|---|---|---|---|---|---|---|
| Ig-1 | U1 | H | H | — | H | B7 | T2 | H | H | H | — | OCH₂CH=CMe₂ | NH₂ |
| Ig-2 | U1 | H | H | — | H | B7 | T2 | H | H | H | — | OCH₂CH=CMe₂ | NHCH₂CH=CMe₂ |
| Ig-3 | U1 | H | H | — | H | B12 | T2 | H | H | H | — | OCH₂CH=CMe₂ | NH₂ |
| Ig-4 | U1 | H | H | — | H | B12 | T2 | H | H | H | — | OCH₂CH=CMe₂ | NHCH₂CH=CMe₂ |
| Ig-5 | U1 | H | H | — | H | B7 | T2 | H | H | H | — | NHCH₂CH=CMe₂ | NHCH₂CH=CMe₂ |
| Ig-6 | U1 | H | H | — | H | B12 | T2 | H | H | H | — | NHCH₂CH=CMe₂ | NHCH₂CH=CMe₂ |
| Ig-7 | U1 | H | H | — | H | B12 | T5 | H | — | H | — | OCH₂CH=CMe₂ | NH₂ |
| Ig-8 | U1 | H | H | — | H | B12 | T5 | H | — | H | — | OCH₂CH=CMe₂ | NHCH₂CH=CMe₂ |
| Ig-9 | U1 | H | H | — | H | B12 | T8 | H | — | — | H | OCH₂CH=CMe₂ | NH₂ |
| Ig-10 | U1 | H | H | — | H | B12 | T8 | H | — | — | H | OCH₂CH=CMe₂ | NHCH₂CH=CMe₂ |
| Ig-11 | U2 | H | H | H | — | B7 | T2 | H | H | H | — | OCH₂CH=CMe₂ | NH₂ |
| Ig-12 | U2 | H | H | H | — | B7 | T2 | H | H | H | — | OCH₂CH=CMe₂ | NHCH₂CH=CMe₂ |
| Ig-13 | U2 | H | H | H | — | B12 | T2 | H | H | H | — | OCH₂CH=CMe₂ | NH₂ |
| Ig-14 | U2 | H | H | H | — | B12 | T2 | H | H | H | — | OCH₂CH=CMe₂ | NHCH₂CH=CMe₂ |
| Ig-15 | U2 | H | H | H | — | B7 | T2 | H | H | H | — | NHCH₂CH=CMe₂ | NHCH₂CH=CMe₂ |
| Ig-16 | U2 | H | H | H | — | B12 | T2 | H | H | H | — | NHCH₂CH=CMe₂ | NHCH₂CH=CMe₂ |
| Ig-17 | U2 | H | H | H | — | B12 | T5 | H | — | H | — | OCH₂CH=CMe₂ | NH₂ |
| Ig-18 | U2 | H | H | H | — | B12 | T5 | H | — | H | — | OCH₂CH=CMe₂ | NHCH₂CH=CMe₂ |
| Ig-19 | U2 | H | H | H | — | B12 | T8 | H | — | — | H | OCH₂CH=CMe₂ | NH₂ |
| Ig-20 | U2 | H | H | H | — | B12 | T8 | H | — | — | H | OCH₂CH=CMe₂ | NHCH₂CH=CMe₂ |

TABLE 88

| No. | mp, ¹H-NMR |
|---|---|
| Ia-2 | 195–197° C., ¹H-NMR(CDCl₃-DMSO-d₆)δ1.77(3H, s), 1.82(3H, s), 4.63(2H, J=6.8), 5.52(1H, br t, J=6.8), 6.25(1H, s), 6.93–6.98(3H, m), 7.10(1H, dd, J=2.2, 8.3), 7.20(1H, d, J=2.2), 7.69(1H, d, J=8.1), 7.85(1H, dd, J=2.0, 8.1), 7.89(2H, d, J=8.8), 8.53(1H, br s), 8.82(1H, d, J=2.0) |
| Ia-4 | 181–182° C., ¹H-NMR(CDCl₃)δ3.18(3H, s), 5.19(2H, s), 5.78(1H, s), 7.04(1H, d, J=8.3), 7.12(1H, dd, J=2.2, 8.3), 7.25(1H, d, J=2.2), 7.38–7.45(7H, m), 7.76(1H, br d, J=8.3), 7.92(1H, dd, J=2.4, 8.3), 8.88(1H, br d, J=2.4) |
| Ia-5 | 171–172° C., ¹H-NMR(CDCl₃)δ3.40(3H, s), 3.43(3H, s), 5.29(2H, s), 7.36–7.53(8H, m), 7.78–7.81(2H, m), 8.09(1H, d, J=8.3), 8.21(1H, dd, J=2.2, 8.3), 8.25(2H, d, J=8.8), 9.02(1H, br s) |
| Ia-6 | 165–166° C., ¹H-NMR(CDCl₃)δ1.77(3H, s), 1.82(3H, s), 3.18(3H, s), 3.25(3H, s), 4.65(2H, d, J=6.8), 5.50(1H, br t, J=6.8), 7.13(1H, d, J=8.5), 7.42(2H, d, J=8.8), 7.53(1H, dd, J=2.2, 8.5), 7.58(1H, d, J=2.2), 7.77(1H, dd, J=0.7, 8.3), 7.92(1H, dd, J=2.2, 8.3), 8.10(2H, d, J=8.8), 8.88(1H, dd, J=0.7, 2.2) |
| Ia-8 | 176–177° C., ¹H-NMR(CDCl₃)δ3.87(3H, s), 5.18(2H, s), 5.77(1H, s), 7.01(2H, d, J=9.0), 7.02(1H, d, J=8.6), 7.11(1H, dd, J=2.2, 8.6), 7.24(1H, d, J=2.2), 7.40–7.45(5H, m), 7.71(1H, d, J=1.0, 8.3), 7.86(1H, dd, J=2.4, 8.3), 7.99(2H, d, J=9.0), 8.84(1H, dd, J=1.0, 2.4) |
| Ia-9 | 187–188° C., ¹H-NMR(CDCl₃)δ3.13(3H, s), 3.88(3H, s), 5.19(2H, s), 7.02(2H, d, J=8.8), 7.17(1H, d, J=8.6), 7.37–7.49(5H, m), 7.51(1H, dd, J=2.2, 8.6), 7.59(1H, d, J=2.2), 7.73(1H, br d, J=8.3), 7.86(1H, dd, J=2.4, 8.3), 8.00(2H, d, J=8.8), 8.83(1H, br d, J=2.4) |
| Ia-10 | 141–142° C., ¹H-NMR(CDCl₃)δ 1.77(3H, s), 1.82(3H, s), 3.88(3H, s), 4.63(2H, d, J=6.8), 5.52(1H, br t, J=6.8), 5.79(1H, s), 6.97(1H, d, J=8.3), 7.02(2H, d, J=9.0), 7.11(1H, dd, J=2.2, 8.3), 7.21(1H, d, J=2.2), 7.71(1H, dd, J=0.7, 8.3), 7.86(1H, dd, J=2.4, 8.3), 7.99(2H, d, J=9.0), 8.85(1H, dd, J=0.7, 2.4) |
| Ia-11 | 161–162° C., ¹H-NMR(CDCl₃)δ1.77(3H, s), 1.82(3H, s), 3.24(3H, s), 3.88(3H, s), 4.65(2H, d, J=6.8), 5.50(1H, br t, J=6.8), 7.02(2H, d, J=9.0), 7.11(1H, d, J=8.5), 7.52(1H, dd, J=2.4, 8.5), 7.57(1H, d, J=2.4), 7.73(1H, d, J=0.7, 8.3), 7.86(1H, dd, J=2.4, 8.3), 8.00(2H, d, J=9.0), 8.83(1H, dd, J=0.7, 2.4) |
| Ia-12 | 233–236° C., ¹H-NMR(CDCl₃)δ 3.13(3H, s), 3.14(3H, s), 5.20(2H, s), 5.21(2H, s), 7.17(2H, dd, J=1.7, 8.3), 7.36–7.54(11H, m), 7.59(1H, d, J=2.4), 7.73(1H, d, J=8.3), 7.78(1H, dd, J=2.4, 8.3), 7.98–8.02(2H, m), 8.84(1H, d, J=2.5) |
| Ia-13 | 150–151° C., ¹H-NMR(CDCl₃)δ1.77(3H, s), 1.82(6H, s), 4.63(4H, d, J=6.8), 5.52(2H, br t, J=6.8), 5.73(1H, s), 5.78(1H, s), 6.97(2H, d, J=8.3), 7.10(1H, dd, J=2.2, 8.3), 7.21(1H, d, J=2.2), 7.57(1H, d, J=2.2, 8.3), 7.60(1H, d, J=2.2), 7.69(1H, br d, J=8.3), 7.85(1H, dd, J=2.4, 8.3), 8.84(1H, br d, J=2.4) |
| Ia-15 | 172–173° C., ¹H-NMR(CDCl₃)δ5.11(1H, s), 5.17(2H, s), 5.75(1H, s), 6.93(2H, d, J=8.5), 6.95–7.03(2H, m), 7.11(1H, d, J=2.0), 7.38–7.45(5H, m), 7.62(1H, d, J=8.1), 7.67(1H, d, J=8.1), 7.96(2H, d, J=8.5) |

TABLE 89

| Ia-16 | 159–161° C., ¹H-NMR(CDCl₃)δ1.77(3H, s), 1.83(3H, s), 4.63(2H, d, J=6.8), 5.02(1H, s), 5.52(1h, br t, J=6.8), 5.75(1H, s), 6.92(1H, d, J=8.5), 6.94(1H, d, J=8.3), 6.97(1H, dd, J=2.2, 8.3), 7.08(1H, d, J=2.2), 7.62(1H, d, J=8.1), 7.66(1H, d, J=8.1), 7.95(2H, d, J=8.5) |
|---|---|
| Ia-17 | 134–134.5° C., ¹H-NMR(CDCl₃)δ3.13(3H, s), 3.18(3H, s), 5.20(2H, s), 7.16(1H, d, J=8.5), 7.37–7.50(9H, m), 7.71 and 7.74(each 1H, ABq, J=8.1), 8.10(2H, d, J=8.8) |
| Ia-18 | 99–100° C., ¹H-NMR(CDCl₃)δ1.77(3H, s), 1.82(3H, s), 3.19(3H, s), 3.24(3H, s), 4.66(2H, d, J=6.8), 5.51(1h, br t, J=6.8), 7.10(1H, d, J=8.5), 7.38–7.48(4H, m), 7.71 and 7.74(each 1H, ABq, J=8.1), 8.10(2H, d, J=8.8) |
| Ia-21 | 215–216° C., ¹H-NMR(CDCl₃-DMSO-d₆)δ1.77(3H, s), 1.82(3H, s), 2.35(3H, s), 4.63(2H, d, J=6.8), 5.54(1H, br t, J=6.8), 6.51(1H, s), 6.79(1H, dd, J=2.2, 8.1), 6.93–6.96(4H, m), 7.52(1H, s), 7.87(2H, d, J=8.8), 8.43(1H, s), 8.79(1H, s) |

TABLE 89-continued

| Ia-22 | 203–204° C., ¹H-NMR(CDCl₃)δ1.76(3H, s), 1.80(3H, s), 2.37(3H, s), 3.89(3H, s), 4.64(2H, d, J=6.8), 5.56(1H, br t, J=6.8), 6.20(1H, br s), 6.86–6.89(2H, m), 6.89(2H, d, J=8.8), 6.97(1H, d, J=8.5), 7.55(1H, s), 7.88(2H, d, J=8.8), 8.48(1H, s) |
|---|---|
| Ia-23 | 140–141° C., ¹H-NMR(CDCl₃)δ2.39(3H, s), 3.17(3H, s), 5.18(2H, s), 5.78(1H, s), 6.83(1H, dd, J=2.2, 8.3), 6.98(1H, d, J=2.2), 7.03(1H, d, J=8.3), 7.40(2H, d, J=8.8), 7.41–7.47(5H, m), 7.59(1H, s), 8.07(2H, d, J=8.8), 8.50(1H, s) |
| Ia-24 | 156–157° C., ¹H-NMR(CDCl₃)δ2.39(3H, s), 3.13(3H, s), 3.18(3H, s), 5.20(2H, s), 7.18(1H, d, J=8.5), 7.26(1H, dd, J=2.0, 8.5), 7.36–7.49(8H,,m), 7.61(1H, s), 8.07(2H, d, J=90.), 8.50(1H, s) |
| Ia-25 | 111–112° C., ¹H-NMR(CDCl₃)δ1.78(3H, s), 1.83(3H, s), 2.39(3H, s), 3.18(3H, s), 3.24(3H, s), 4.65(2H, d, J=6.8), 5.51(1H, br t, J=6.8), 7.11(1H, d, J=8.5), 7.26(1H, dd, J=2.2, 8.5), 7.34(1H, d, J=2.2), 7.40(2H, d, J=8.8), 7.60(1H, s), 8.07(2H, d, J=8.8), 8.50(1H, s) |
| Ia-26 | 124–127° C., ¹H-NMR(CDCl₃)δ1.77(3H, s), 1.80(3H, s), 2.39(3H, s), 3.18(3H, s), 3.90(3H, s), 4.65(2H, d, J=6.8), 5.57(1H, br t, J=6.8), 6.87–6.91(2H, m), 6.98(1H, d, J=8.3), 7.40(2H, d, J=8.8), 7.60(1H, s), 8.08(2H, d, J=8.8), 8.53(1H, s) |
| Ia-27 | 213–214° C., ¹H-NMR(CDCl₃)δ2.58(3H, s), 5.21(2H, s), 5.87(1H, s), 7.06–7.18(5H, m), 7.42–7.49(7H, m), 8.29(1H, brs), 8.86(1H, brs), 9.01(1H, brs) |
| Ia-28 | 198–199° C., ¹H-NMR(CDCl₃)δ1.77(3H, s), 1.82(3H, s), 2.42(3H, s), 4.63(2H, d, J=6.7), 5.51(1H, t, J=6.7), 5.68(1H, s), 5.77(1H, s), 6.87(2H, d, J=7.8), 6.96(1H, d, J=8.5), 7.10(1H, dd, J=8.5, 2.4), 7.21(1H, d, J=2.4), 7.44(2H, d, J=7.8), 7.71(1H, d, J=2.4), 8.68(1H, d, J=2.4), |
| Ia-31 | 198–199° C., ¹H-NMR(CDCl₃)δ2.53(3H, s), 3.14(3H, s), 3.21(3H, s), 5.21(2H, s), 7.22(1H, d, J=8.5), 7.39–7.49(7H, m), 7.55–7.62(2H, m), 7.73(2H, d, J=9.2), 8.05(1H, brs), 8.84(1H, brs) |
| Ia-32 | 142–144° C., ¹H-NMR(CDCl₃)δ1.78(3H, s), 1.82(3H, s), 2.43(3H, s), 3.17(3H, s), 3.24(3H, s), 4.65(2H, d, J=6.7), 5.50(1H, br t, J=6.7), 7.12(1H, d, J=8.5), 7.40(2H, dd, J=6.7, 1.8), 7.52(1H, dd, J=8.6, 2.4), 7.57(1H, s) 7.64(2H, d, J=8.5), 7.74(1H, s) 8.70(1H, d, J=2.5) |

TABLE 90

| Ia-35 | 152–154° C., ¹H-NMR(CDl₃)δ1.77(3H, s), 1.83(3H, s), 2.59(3H, s), 4.12(2H, d, J=7.3), 5.53(1H, t, J=7.3), 5.77(1H, brs), 6.79–6.95(5H, m), 7.49(1H, d, J=8.0), 7.55(1H, d, J=8.0), 7.88(2H, d, J=8.5) |
|---|---|
| Ia-38 | 109–112° C., ¹H-NMR(CDCl₃)δ2.60(3H, s), 3.12(3H, s), 3.16(3H, s), 5.19(2H, s), 7.15(1H, d, J=8.5), 7.27(1H, dd, J=7.8, 1.8), 7.35–7.50(8H, m), 7.59(2H, s), 8.09(2H, d, J=9.2) |
| Ia-39 | oil, 1.78(3H, s), 2.60(3H, s), 3.17(3H, s), 3.24(3H, s), 4.65(2H, d, J=6.7), 5.51(1H, br t, J=6.7), 7.09(1H, d, J=8.6), 7.24–7.27(1H, m), 7.34–7.35(2H, m), 7.40(1H, d, J=8.6) 7.59(2H, s), 8.09(2H, d, J=9.2) |
| Ia-42 | 175–176° C., ¹H-NMR(CDCl₃)δ1.77(3H, s), 1.83(3H, s), 2.32(3H, s), 2.54(3H, s), 4.63(2H, d, J=6.8), 5.52(1H, brs), 5.53(1H, t, J=6.8), 5.75(1H, brs), 6.80–6.84(3H, m), 6.93(1H, d, J=7.8), 6.95(1H, d, J=1.8), 7.38–7.41(3H, m) |
| Ia-43 | 177–178° C., ¹H-NMR(CDCl₃)δ1.77(3H, s), 1.79(3H, s), 2.32(3H, s), 2.56(3H, s), 3.90(3H, s), 4.64(2H, d, J=6.8), 5.56(1H, t, J=6.8), 6.75(2H, d, J=8.5), 6.87–6.97(3H, m), 7.33(2H, d, J=8.5), 7.43(1H, s) |
| Ia-45 | 79–81° C., ¹H-NMR(CDCl₃)δ2.33(3H, s), 2.53(3H, s), 3.16(3H, s), 5.18(2H, s), 5.75(1H, s), 6.83(1H, dd, J=7.8, 1.8), 6.98(1H, d, J=1.8), 7.00(1H, d, J=8.5), 737–7.55(8H, m), 7.63(2H, d, J=8.5) |
| Ia-46 | 163–164° C., ¹H-NMR(CDCl₃)δ2.34(3H, s), 2.54(3H, s), 3.13(3H, s), 3.17(3H, s), 5.19(2H, s), 7.15(1H, d, J=8.5), 7.27(1H, dd, J=8.5, 2.5), 7.35–7.50(9H, m), 7.62(2H, d, J=8.5) |
| Ia-47 | oil, ¹H-NMR(CDCl₃)δ1.77(3H, s), 1.82(3H, s), 2.34(3H, s), 2.54(3H, s), 3.17(3H, s), 3.23(3H, s), 4.66(2H, d, J=7.3), 5.51(1H, br t, J=7.3), 7.08(1H, d, J=8.6), 7.26(1H, dd, J=8.6, 2.4), 7.35(1H, d, J=2.4), 7.39(2H, d, J=8.6), 7.43(1H, s), 7.64(2H, d, J=8.6) |
| Ia-48 | 149–150° C., ¹H-NMR(CDCl₃)δ1.77(3H, s), 1.80(3H, s), 2.35(3H, s), 2.54(3H, s), 3.17(3H, s), 3.90(3H, s), 4.64(2H, d, J=6.8), 5.57(1H, t, J=6.8), 6.87(1H, s), |

TABLE 90-continued

| | |
|---|---|
| | 6.88–6.98(2H, m), 7.39(2H, d, J=8.5), 7.44(1H, s), 7.63(2H, d, J=8.5) |
| Ia-65 | 237–239° C., $^1$H-NMR(CDCl$_3$-CD$_3$OD)δ3.16(3H, s), 5.21(2H, s), 6.96(2H, d, J=8.6), 7.20(1H, d, J=9.3), 7.38–7.51(5H, m), 7.72(1H, br d, J=8.3), 7.90–7.95(3H, m), 8.80(1H, br d, J=2.4) |
| Ia-66 | 152–153° C., $^1$H-NMR(CDCl$_3$)δ1.76(3H, s), 1.81(3H, s), 4.63(2H, d, J=6.8), 5.51(1H, br t, J=6.8), 5.59(1H, br s), 5.75(1H, s), 6.95(2H, d, J=8.6), 6.97(1H, d, J=8.3), 7.50(2H, d, J=8.6), 7.56(1H, dd, J=2.2, 8.3), 7.59(1H, d, J=2.2), 7.69(1H, dd, J=0.7, 8.3), 7.86(1H, 2.4, 8.3), 8.83(1H, dd, J=0.7, 2.4) |
| Ia-68 | 167–168° C., $^1$H-NMR(CDCl$_3$)δ3.13(3H, s), 3.20(3H, s), 5.21(2H, s), 7.18(1H, d, J=8.3), 7.38–7.48(7H, m), 7.67(2H, d, J=8.8), 7.76(1H, br d, J=8.3), 7.91(1H, dd, J=2.4, 8.3), 7.99–8.03(2H, m), 8.85(1H, br d, J=2.4) |
| Ia-69 | 151–152.5° C., $^1$H-NMR(CDCl$_3$)δ1.77(3H, s), 1.81(3H, s), 3.20(3H, s), 3.24(3H, s), 4.66(2H, d, J=6.8), 5.50(1H, br t, J=6.8), 7.12(1H, d, J=9.3), 7.42(2H, d, J=8.5), 7.67(2H, d, J=8.5), 7.76(1H, br d, J=8.3), 7.90(1H, dd, J=2.4, 8.3), 8.00–8.03(2H, m), 8.85(1H, br d, J=2.4) |
| Ia-71 | 220–221° C.$^1$H-NMR(CDCl$_3$)δ2.57(3H, s), 3.51(2H, brs), 5.18(2H, s), 7.14(1H, d, J=7.3), 7.15–7.62(11H, m), 8.11(1H, d, J=1.8), 8.78(1H, d, J=1.8) |

TABLE 91

| | |
|---|---|
| Ia-73 | 180–181° C., $^1$H-NMR(CDCl$_3$)δ1.74(3H, s), 1.79(3H, s), 2.42(3H, s), 4.61(2H, d, J=6.8), 5.50(1H, t, J=6.8), 6.84–6.96(5H, m), 7.05(1H, dd, J=7.8, 1.8), 7.14(1H, d, J=1.8), 7.44(1H, d, J=9.2), 7.71(1H, d, J=1.8) 8.65(1H, d, J=1.8), |
| Ia-75 | 164–165° C., $^1$H-NMR(CDCl$_3$)δ2.53(3H, s), 3.13(3H, s), 3.21(3H, s), 5.19(2H, s), 7.16(1H, d, J=7.3), 7.32–7.50(7H, m), 7.61(2H, dd, J=8.5, 2.4), 7.70(2H, d, J=7.3), 7.79(1H, d, J=1.8) 8.76(1H, d, J=1.8) |
| Ia-76 | 151–152° C.$^1$H-NMR(CDCl$_3$)δ1.77(3H, s), 1.81(3H, s), 2.48(3H, s), 3.20(3H, s), 3,21(3H, s), 4.65(2H, d, J=6.8), 5.50(1H, t, J=6.8), 7.11(1H, d, J=7.9), 7.41(2H, d, J=9.2), 7.55(1H, dd, J=7.8, 1.8), 7.58(1H, s), 7.66(2H, d, J=7.9), 7.74(1H, d, J=1.8) 8.71(1H, d, J=1.8), |
| Ia-79 | 189–191° C., $^1$H-NMR(CDCl$_3$)δ2.34(3H, s), 5.18(2H, s), 5.29(1H, br s), 5.71(1H, s), 6.83(1H, dd, J=2.2, 8.3), 6.92(2H, d, J=8.6), 7.03(1H, d, J=8.3), 7.23(2H, d, J=8.6), 7.37–7.47(5H, m), 7.54(1H, d), 7.55(1H, dd, J==2.2, 8.3), 7.60(2H, d, J=2.2), 8.45(1H, s) |
| Ia-80 | 165–166° C., $^1$H-NMR(CDCl$_3$)δ1.76(3H, s), 1.81(3H, s), 2.35(3H, s), 4.63(2H, d, J=6.8), 5.51(1H, br t, J=6.8), 5.75(1H, s), 6.19(1H, br s), 6.92(2H, d, J=8.8), 6.96(1H, d, J=8.8), 7.21(2H, d, J=8.8), 7.52–7.57(3H, m), 8.44(1H, s) |
| Ia-82 | 189–190° C., $^1$H-NMR(CDCl$_3$)δ2.35(3H, s), 3.13(3H, s), 3.22(3H, s), 5.20(2H, s), 7.18(1H, d, J=9.0), 7.36–7.49(9H, m), 7.58(1H, s), 7.99–8.02(2H, m), 8.46(1H, s) |
| Ia-83 | 169–170° C., $^1$H-NMR(CDCl$_3$)δ1.77(3H, s), 1.81(3H, s), 2.35(3H, s), 3.22(3H, s), 3.24(3H, s), 4.66(2H, d, J=6.8), 5.50(1H, br t, J=6.8), 7.11(1H, d, J=8.6), 7.40(4H, s), 7.58(1H, s), 7.96(1H, d, J=2.2), 8.00(1H, dd, J==2.2, 8.6), 8.45(1H, s) |
| Ia-85 | 143–146° C., $^1$H-NMR(CDCl$_3$)δ2.53(3H, s), 5.03(1H, brs), 5.18(2H, s), 5.72(1H, s), 6.92(2H, dd, J=7.8, 1.8), 7.02(1H, d, J=6.8), 7.23(2H, dd, J=7.3, 1.8), 7.33–7.48(5H, m), 7.49–7.60(3H, m), 7.67(1H, d, J=1.8) |
| Ia-87 | 168–169° C., $^1$H-NMR(CDCl$_3$)δ1.76(3H, s), 1.81(3H, s), 2.56(3H, s), 4.63(2H, d, J=6.8), 4.84(1H, s), 5.51(1H, t, J=6.8), 5.70(2H, s), 6.91(2H, d, J=8.5), 6.95(1H, d, J=8.5), 7.22(2H, s), 7.51(2H, s), 7.55(1H, dd, J==8.5, 2.4), 7.62(1H, d, J=2.4) |
| Ia-89 | 174–175° C., $^1$H-NMR(CDCl$_3$)δ2.56(3H, s), 3.13(3H, s), 3.21(3H, s), 5.20(2H, s), 7.15(1H, d, J=8.5), 7.29–7.48(9H, m), 7.56(2H, s), 7.99(1H, dd, J=8.5, 2.4), 8.03(1H, d, J=2.4) |
| Ia-90 | 141–142° C., $^1$H-NMR(CDCl$_3$)δ1.77(3H, s), 1.81(3H, s), 2.56(3H, s), 3.21(3H, s), 3.24(3H, s), 4.65(2H, d, J=6.8), 5.50(1H, t, J=6.8), 7.10(1H, d, J=8.6), 7.36–7.43(4H, m), 7.55(2H, d, J=1.2), 7.98(1H, dd, J=8.6, 2.4), 8.01(1H, d, J=1.2) |

TABLE 91-continued

| | |
|---|---|
| Ia-93 | 118–121° C., $^1$H-NMR(CDCl$_3$)δ2.36(3H, s), 2.51(3H, s), 3.10(3H, s), 5.10(1H, brs), 5.18(2H, s), 6.90(2H, d, J=8.6), 7.14(1H, d, J=8.6), 7.21–7.48(8H, m), 7.52(1H, dd, J=8.6, 1.8), 7.58(1H, d, J=1.8) |
| Ia-94 | 168–169° C., $^1$H-NMR(CDCl$_3$)δ1.76(3H, s), 1.81(3H, s), 2.33(3H, s), 2.51(3H, s), 4.61(2H, d, J=6.8), 5.32(1H, brs), 5.51(1H, t, J=6.8), 5.73(1H, s), 6.87–6.95(3H, m), 7.04(1H, dd, J=8.5, 1.8), 7.14(1H, d, J=1.8), 7.21–7.24(2H, m), 7.37(1H, s) |
| Ia-96 | 140–141° C., $^1$H-NMR(CDCl$_3$)δ2.38(3H, s), 2.50(3H, s), 3.11(3H, s), 3.21(3H, s), 5.19(2H, s), 7.16(1H, d, J=8.5), 7.33–7.51(10H, m), 7.55(1H, dd, J=7.8, 1.8), 7.62(1H, d, J=1.8) |

TABLE 92

| | |
|---|---|
| Ia-97 | 106–107° C., $^1$H-NMR(CDl$_3$)δ1.77(3H, s), 1.81(3H, s), 2.38(3H, s), 2.51(3H, s), 3.20(3H, s), 3.21(3H, s), 4.64(2H, d, J=6.8), 5.49(1H, t, J=6.8), 7.10(1H, d, J=8.0), 7.35–7.44(5H, m), 7.51–7.65(2H, m) |
| Ia-125 | 121–122° C., $^1$H-NMR(CDCl$_3$)δ2.38(3H, s), 3.90(3H, s), 4.03(3H, s), 5.21(2H, s), 6.77(1H, dd, J=2.0, 8.3), 6.82(1H, d, J=2.0), 6.97(1H, d, J=8.3), 7.32–7.49(8H, m), 8.46–8.49(2H, m) |
| Ia-127 | 110–111° C., $^1$H-NMR(CDCl$_3$)δ2.39(3H, s), 4.03(3H, s), 5.11(2H, s), 7.06(2H, d, J=8.5), 7.22(2H, d, J=8.5), 7.34–7.51(8H, m), 8.44–8.50(2H, m) |
| Ia-128 | 115–116° C., $^1$H-NMR(CDCl$_3$)δ2.38(3H, s), 4.03(3H, s), 5.07(2H, s), 7.06(2H, d, J=9.2), 7.21(4H, d, J=9.2), 7.36(2H, d, J=8.5), 7.45–7.51(3H, m), 8.46–8.50(2H, m) |
| Ia-129 | 129–130° C., $^1$H-NMR(CDCl$_3$)δ1.77(3H, s), 1.82(3H, s), 2.39(3H, s), 4.03(3H, s), 4.56(2H, d, J=6.7), 5.55(1H, br t, J=6.7), 7.00(2H, d, J=8.5), 7.21(2H, d, J=8.5), 7.46–7.51(3H, m), 8.46–8.50(2H, m) |
| Ia-131 | 121–122° C., $^1$H-NMR(CDCl$_3$)δ2.39(3H, s), 4.03(3H, s), 5.16(2H, s), 5.75(1h, s), 6.76(1H, dd, J=2.2, 8.3), 6.90(1H, d, J=2.2), 7.0l(1H, d, J=8.1), 7.38–7.5(8H, m), 8.46–8.50(2H, m) |
| Ia-132 | 142–143° C., $^1$H-NMR(CDCl$_3$)δ2.29(3H, s), 2.41(3H, s), 4.02(3H, s), 5.14(2H, s), 7.02(1H, d, J=1.2), 7.05–7.11(2H, m), 7.33–7.49(8H, m), 8.45–8.50(2H, m) |
| Ia-133 | 161.5–162.5° C., $^1$H-NMR(CDCl$_3$)δ2.42(3H, s), 3.11(3H, s), 4.03(3H, s), 5.18(2H, s), 7.14(1H, d, J=8.6), 7.21(1H, dd, J=2.0, 8.6), 7.31(1H, d, J=2.0), 7.37–7.50(8H, m), 8.46–8.49(2H, m) |
| Ia-134 | 142–143° C., $^1$H-NMR(CDCl$_3$)δ2.39(3H, s), 4.03(3H, s), 5.23(2H, s), 7.15(1H, d, J=8.5), 7.17–7.25(2H, m), 7.33–7.51(8H, m), 8.45–8.50(2H, m) |
| Ia-135 | 132–133° C., $^1$H-NMR(CDCl$_3$)δ2.37(3ll, s), 4.03(3H, s), 4.94(2H, s), 6.98(1H, d, J=8.6), 7.15(1H, dd, J=1.8, 8.6), 7.17(1H, d, J=1.8), 7.33–7.60(11H, m), 7.87(2H, d, J=7.3), 8.45–8.59(2H, m) |
| Ia-136 | 127–128° C., $^1$H-NMR(CDCl$_3$)δ2.40(3H, s), 2.42(3H, s), 4.04(3H, s), 5.14(2H, s), 5.70(1H, s), 6.79(1H, dd, J=1.8, 7.9), 6.90(1H, d, J=1.8), 7.05(1H, d, J=7.9), 7.22–7.36(3H, m), 7.40(1H, d, J=6.7), 7.43–7.55(3ll, m), 8.44–8.50(2H, m) |
| Ia-137 | 87–89° C., $^1$H-NMR(CDCl$_3$)δ2.39(3H, s), 2.41(3H, s), 4.03(3H, s), 5.12(2H, s), 5.73(1H, s), 6.76(1H, dd, J=1.8, 7.9), 6.90(1H, d, J=1.8), 7.01(1H, d, J=7.9), 7.18–7.36(4H, m), 7.43–7.53(3H, m), 8.46–8.52(2H, m) |
| Ia-138 | 114–115° C., $^1$H-NMR(CDCl$_3$)δ2.39(6H, s), 4.02(3H, s), 5.10(2H, s), 5.74(1H, s), 6.75(1H, dd, J=2.0, 8.3), 6.89(1H, d, J=2.0), 7.01(1H, d, J=8.3), 7.24(2H, d, J=8.6), 7.36(2H, d, J=8.6), 7.45–7.50(3H, m), 8.46–8.50(2H, m) |
| Ia-139 | 192–193° C., $^1$H-NMR(CDCl$_3$)δ2.42(3H, s), 2.43(3H, s), 3.06(3H, s), 4.04(3H, s), 5.16(2H, s), 7.15–7.33(6H, m), 7.41–7.50(4H, m), 8.46–8.51(2H, m) |
| Ia-140 | 151–152° C., $^1$H-NMR(CDCl$_3$)δ2.39(3H, s), 2.42(3H, s), 3.12(3H, s), 4.03(3H, s), 5.14(2H, s), 7.14(1H, d, J=8.5), 7.18–7.31(6H, m), 7.46–7.50(3H, m), 8.45–8.50(2H, m) |
| Ia-141 | 188–189° C., $^1$H-NMR(CDCl$_3$)δ2.39(3H, s), 2.41(3H, s), 3.11(3H, s), 4.03(3H, s), 5.13(2H, s), 7.14(1H, d, J=8.6), 7.20(1H, dd, J=2.2, 8.6), 7.22(2H, d, J=8.0), 7.30(1H, d, J=2.2), 7.36(2H, d, J=8.0), 7.47–7.50(3H, m), 8.46–8.49(2H, m) |

TABLE 93

Ia-142  166–167° C., $^1$H-NMR(CDCl$_3$)δ2.39(3H, s), 3.91(3H, s), 4.03(3H, s), 5.15(2H, s), 6.18(1H, s), 6.75(1H, dd, J=1.8, 7.9), 6.89(1H, d, J=2.4), 6.97(1H, d, J=7.9), 7.03(1H, d, J=7.9), 7.34–7.49(5H, m), 8.46–8.50(2H, m)

Ia-143  166–167° C., $^1$H-NMR(CDCl$_3$)δ2.39(3H, s), 3.84(3H, s), 4.03(3H, s), 5.13(2H, s), 5.74(1H, s), 6.75(1H, dd, J=1.8, 8.5), 6.89(1H, d, J=1.8), 6.90–7.05(4H, m), 7.34(1H, d, J=7.9), 7.44–7.50(3H, m), 8.45–8.50(2H, m)

Ia-144  125–126° C., $^1$H-NMR(CDCl$_3$)δ2.39(3H, s), 3.85(3H, s), 4.03(3H, s), 5.08(2H, s), 5.70(1H, s), 6.76(1H, dd, J=1.8, 7.9), 6.89(1H, d, J=8.5), 6.96(2H, d, J=8.5), 7.02(1H, d, J=7.9), 7.38(2H, d, J=8.5), 7.44–7.50(3H, m), 8.45–8.50(2H, m)

Ia-145  193–195° C., $^1$H-NMR(CDCl$_3$)δ2.42(3H, s), 3.13(3H, s), 3.87(3H, s), 4.03(3H, s), 5.21(2H, s), 6.94(1H, d, J=7.9), 6.98–7.04(1H, m), 7.19–7.21(2H, m), 7.30(1H, d, J=1.8), 7.36(1H, d, J=7.9) 7.45–7.50(4H, m), 8.45–8.50(2H, m)

Ia-146  166–167° C., $^1$H-NMR(CDCl$_3$)δ2.41(3H, s), 3.15(3H, s), 3.84(3H, s), 4.03(3H, s), 5.16(2H, s), 6.91(1H, d, J=8.5), 7.02–7.06(2H, m), 7.12(1H, d, J=8.5), 7.20(1H, dd, J=1.8, 8.5), 7.30(1H, d, J=1.8), 7.35(1H, d, J=7.9) 7.45–7.49(3H, m), 8.45–8.50(2H, m)

Ia-147  171–172° C.$^1$H-NMR(CDCl$_3$)δ2.41(3H, s), 3.09(3H, s), 3.84(3H, s), 4.03(3H, s), 5.10(2H, s), 6.94(1H, d, J=8.5), 6.97–7.23(2H, m), 7.29(1H, d, J=1.8), 7.39(2H, d, J=8.5), 7.45–7.49(3H, m), 8.45–8.49(2H, m)

Ia-148  177–179° C., $^1$H-NMR(CDCl$_3$)δ2.39(3H, s), 4.03(3H, s), 5.27(2H, s), 6.72(1H, dd, J=2.4, 8.5), 6.93(1H, d, J=1.8), 7.12(1H, d, J=7.9), 7.31–7.36(2H, m), 7.46–7.49(3H, m), 7.78(1H, dt, J=1.8, 7.3), 8.46–8.50(2H, m), 8.68(1H, d, J=4.9), 9.76(1H, s)

Ia-149  221–212° C., $^1$H-NMR(CDCl$_3$)δ2.39(3H, s), 4.03(3H, s), 5.19(2H, s), 5.69(1H, s), 6.78(1H, dd, J=1.8, 7.9), 6.92(1H, d, J=2.4), 7.01(1H, d, J=8.5), 7.35–7.40(1H, m), 7.45–7.51(3H, m), 7.80(1H, d, J=7.9), 8.46–8.50(2H, m), 8.65(1H, d, J=4.9), 8.72(1H, s)

Ia-150  222–224° C., $^1$H-NMR(CDCl$_3$)δ2.39(3H, s), 4.03(3H, s), 5.19(2H, s), 6.08(1H, s), 6.75(1H, dd, J=1.8, 7.9), 6.92(1H, d, J=6.7), 6.94(1H, s), 7.35(2H, d, J=6.1), 7.45–7.51(3H, m), 8.25–8.50(2H, m), 8.65(2H, d, J=5.5)

Ia-151  195–197° C., $^1$H-NMR(CDCl$_3$)δ2.41(3H, s), 3.23(3H, s), 4.03(3H, s), 5.32(2H, s), 7.13(1H, d, J=8.5), 7.20(1H, dd, J=2.4, 8.5), 7.26–7.33(2H, m), 7.46–7.50(3H, m), 7.62(1H, d, J=7.3), 7.78(1H, dt, J=1.8, 7.9), 8.45–8.50(2H, m), 8.62(1H, d, J=4.9)

Ia-152  173–174° C., $^1$H-NMR(CDCl$_3$)δ2.42(3H, s), 3.13(3H, s), 4.03(3H, s), 5.21(2H, s), 7.15(1H, d, J=7.9), 7.21(1H, d, J=1.8), 7.31(1H, d, J=1.8), 7.36–7.41(1H, m), 7.47–7.89(3H, m), 8.46–8.50(2H, m), 8.73(1H, s), 8.65(1H, d, J=4.9), 8.73(1H, s)

Ia-153  186–187° C., $^1$H-NMR(CDCl$_3$)δ2.41(3H, s), 3.20(3H, s), 4.03(3H, s), 5.22(2H, s), 7.06(1H, d, J=8.5), 7.21(1H, dd, J=1.8, 8.5), 7.32(1H, d, J=2.4), 7.42(1H, d, J=6.1), 7.47–7.50(3H, m), 8.45–8.50(2H, m), 8.68(2H, d, J=4.9)

Ia-154  112–113° C., $^1$H-N-(CDCl$_3$)δ2.37(3H, s), 3.16(2H, t, J=6.7), 4.02(3H, s), 4.32(2H, t, J=6.7), 5.55(1H, s), 6.74(1H, dd, J=1.8, 8.5), 6.85(1H, d, J=1.8), 6.93(1H, d, J=8.5), 7.25–7.39(5H, m), 7.45–7.49(3H, m), 8.45–8.49(2H, m)

TABLE 94

Ia-155  169–170° C., $^1$H-NMR(CDCl$_3$)δ2.39(3H, s), 2.88(3H, s), 3.18(2H, t, J=6.7), 4.02(3H, s), 4.35(2H, t, J=6.7), 7.07(1H, d, J=8.5), 7.19(1H, dd, J=1.8, 7.9), 7.25–7.38(6H, m), 7.46–7.49(3H, m), 8.44–8.49(2H, m)

Ia-156  117–119° C., $^1$H-NMR(CDCl$_3$)δ1.77(3H, s), 1.83(3H, s), 2.39(3H, s), 4.03(3H, s), 4.62(2H, d, J=6.8), 5.52(1H, br t, J=6.8), 5.75(1H, s), 6.75(1H, dd, J=2.2, 8.3), 6.87(1H, d, J=2.2), 6.94(1H, d, J=8.3), 7.45–7.50(3H, m), 8.46–8.49(2H, m)

Ia-157  121–124° C., $^1$H-NMR(CDCl$_3$)δ1.77(3H, s), 1.82(3H, s), 2.42(3H, s), 3.23(3H, s), 3.40(3H, s), 4.63(2H, d, J=6.8), 5.51(1H, br t, J=6.8), 7.07(1H, d, J=8.6),

TABLE 94-continued 7.19(1H, dd, J=2.0, 8.6), 7.28(1H, d, J=2.0), 7.45–7.50(3H, m), 8.45–8.49(2H, m)

Ia-159  79–80° C., $^1$H-NMR(CDCl$_3$)δ1.75(3H, s), 1.76(3H, s), 2.38(3H, s), 2.54(2H, q, J=6.7), 4.03(3H, s), 4.08(2H, t, J=6.7), 5.23(1H, t, J=7.3), 5.71(1H, s), 6.74(1H, dd, J=1.8, 7.9), 6.87(1H, d, J=1.8), 6.92(1H, d, J=7.9), 7.44–7.51(3H, m), 8.45–8.50(2H, m)

Ia-160  152–153° C., $^1$H-NMR(CDCl$_3$)δ1.69(3H, s), 1.74(3H, s), 2.41(3H, s), 2.56(2H, q, J=6.7), 3.21(3H, s), 4.03(3H, s), 4.08(2H, t, J=6.7), 5.22(1H, t, J=6.7), 7.06(1H, d, J=7.9), 7.20(1H, dd, J=1.8, 7.9), 7.28(1H, d, J=1.8), 7.46–7.50(3H, m), 8.45–8.50(2H, m)

Ia-162  200.5–201.5° C., $^1$H-NMR(CDCl$_3$)δ2.38(3H, s), 3.11(3H, s), 4.01(3H, s), 5.17(2H, s), 5.38(1H, s), 6.90(1H, d, J=8.8), 7.13(1H, d, J=8.5), 7.19(1H, dd, J=2.0, 8.5), 7.29(1H, d, J=2.0), 7.37–7.49(5H, m), 8.37(2H, d, J=8.8)

Ia-163  163–168° C., $^1$H-NMR(CDCl$_3$)δ1.77(3H, s), 1.83(3H, s), 2.36(3H, s), 4.01(3H, s), 4.62(2H, d, J=6.6), 5.53(1H, br t, J=6.6), 5.58(1H, br), 5.74(1H, br s), 6.73(1H, dd, J=2.0, 8.3), 6.86(1H, d, J=2.0), 6.89(2H, d, J=8.8), 6.93(1H, d, J=8.3), 8.37(2H, d, J=8.8)

Ia-167  185.5–186.5° C., $^1$H-NMR(CDCl$_3$)δ2.41(3H, s), 3.11(3H, s), 3.18(3H, s), 4.02(3H, s), 5.18(2H, s), 7.15(1H, d, J=8.3), 7.21(1H, dd, J=2.0, 8.3), 7.30(1H, d, J=2.0), 7.36–7.49(7H, m), 8.54(2H, d, J=8.8)

Ia-168  138–139° C., $^1$H-NMR(CDCl$_3$)δ1.77(3H, s), 1.82(3H, s), 2.41(3H, s), 3.18(3H, s), 3.22(3H, s), 4.02(3H, s), 4.64(2H, d, J=6.8), 5.51(1H, br t, J=6.8), 7.08(1H, d, J=8.5), 7.19(1H, dd, J=2.0, 8.5), 7.28(1H, d, J=2.0), 7.39(2H, d, J=9.0), 8.54(2H, J=9.0)

Ia-173  202–204° C., $^1$H-NMR(CDCl$_3$)δ2.40(3H, s), 2.55(3H, s), 3.11(3H, s), 4.02(3H, s), 5.17(2H, s), 7.14(1H, d, J=8.5), 7.20(1H, d, J=2.0, 8.5), 7.30(1H, d, J=2.0), 7.33(2H, br d, J=8.6), 7.37–7.50(5H, m), 8.40(2H, br d, J=8.6)

Ia-175  205–206° C., $^1$H-NMR(CDCl$_3$)δ2.44(3H, s), 3.10(3H, s), 3.12(3H, s), 4.05(3H, s), 5.18(2H, s), 7.16(1H, d, J=8.5), 7.21(1H, d, J=2.0, 8.5), 7.31(1H, d, J=2.0), 7.37–7.50(5H, m), 8.05(2H, br d, J=8.6), 8.68(2H, br d, J=8.6)

Ia-176  178–179° C., $^1$H-NMR(CDCl$_3$)δ2.40(3H, s), 3.11(3H, s), 4.01(3H, s), 5.17(2H, s), 7.12–7.22(4H, m), 7.29(1H, d, J=2.0), 7.37–7.50(5h, m), 8.48(2H, dd, J=5.6, 9.0)

Ia-177  127–128° C., $^1$H-NMR(CDCl$_3$)δ1.77(3H, s), 1.83(3H, s), 2.37(3H, s), 4.01(3H, s), 4.62(2H, d, J=6.8), 5.53(1H, br t, J=6.8), 5.74(1H, s), 6.74(1H, dd, J=2.0, 8.3), 6.86(1H, d, J=2.0), 6.94(1H, d, J=8.3), 7.14(2H, d, J=8.8), 8.48(2H, dd, J=5.6, 8.8)

TABLE 95

Ia-178  143–144° C., $^1$H-NMR(CDl$_3$)δ1.77(3H, s), 1.82(3H, s), 2.40(3H, s), 3.23(3H, s), 4.02(3H, s), 4.63(2H, d, J=6.8), 5.51(1H, br t, J=6.8), 7.05–7.20(4H, m), 7.27(1H, d, J=2.2), 8.48(2H, dd, J=5.6, 9.0)

Ia-179  118–120° C., $^1$H-NMR(CDCl$_3$)δ2.43(3H, s), 3.12(3H, s), 4.05(3H, s), 5.18(2H, s), 7.15(1H, d, J=8.6), 7.21(1H, dd, J=2.0, 8.6), 7.31(1H, d, J=2.0), 7.38–7.50(5H, m), 7.60(1H, br t, J=7.8), 7.73(1H, br d, J=7.8), 8.67(1H, br d, J=7.8), 8.75(1H, br s)

Ia-180  114–115 CC, $^1$H-NMR(CDCl$_3$)δ1.77(3H, s), 1.83(3H, s), 2.40(3H, s), 4.04(3H, s), 4.63(2H, d, J=6.8), 5.53(1H, br t, J=6.8), 5.74(1H, s), 6.75(1H, dd, J=2.0, 8.3), 6.87(1H, d, J=2.0), 6.95(1H, d, J=8.3), 7.60(1H, t, J=7.8), 7.72(1H, br d, J=7.8), 8.67(1H, br d, J=7.8), 8.75(1H, s)

Ia-181  102–103° C., $^1$H-NMR(CDCl$_3$)δ1.77(3H, s), 1.82(3H, s), 2.43(3H, s), 3.23(3H, s), 4.05(3H, s), 4.64(2H, d, J=6.8), 5.51(1H, br t, J=6.8), 7.08(1H, d, J=8.6), 7.20(1H, dd, J=2.2, 8.6), 7.28(1H, d, J=2.2), 7.60(1H, t, J=7.6), 7.73(1H, d, J=7.6), 8.67(1H, d, J=7.6), 8.75(1H, s)

Ia-182  155–156° C., $^1$H-NMR(CDCl$_3$)δ2.41(3H, s), 4.06(3H, s), 5.17(2H, s), 5.75(1H, s), 6.76(1H, dd, J=2.0, 8.3), 6.90(1H, d, J=2.0), 7.02(1H, d, J=8.3), 7.40–7.48(5H, m), 7.65(1H, t, J=8.1), 8.31(1H, ddd, J=1.2, 2.5, 8.1), 8.83(1H, ddd, J=1.2, 1.5, 8.1), 9.31(1H, dd, J=1.5, 2.5)

Ia-183  160–167° C., $^1$H-NMR(CDCl$_3$)δ2.44(3H, s), 3.12(3H, s), 4.06(3H, s), 5.19(2H, s), 7.16(1H, d, J=8.5),

TABLE 95-continued

| | |
|---|---|
| | 7.22(1H, dd, J=2.2, 8.5), 7.31(1H, d, J=2.2), 7.38–7.49(5H, m), 7.65(1H, t, J=8.1), 8.32(1H, ddd, J=1.2, 2.4, 8.3), 8.83(1H, ddd, J=1.2, 1.5, 8.3), 9.31(1H, dd, J=1.5, 2.4) |
| Ia-184 | 153–155° C., $^1$H-NMR(CDCl$_3$)δ2.40(3H, s), 3.11(3H, s), 4.02(3H, s), 5.17(2H, s), 6.81(1H, ddd, J=1.2, 2.5, 7.8), 7.14(1H, d, J=8.5), 7.20(1H, dd, J=2.2, 8.5), 7.27(1H, t, J=7.8), 7.30(1H, d, J=2.2), 7.37–7.48(5H, m), 7.81(1H, dd, J=1.5, 2.5), 7.88(1H, ddd, J=1.2, 1.5, 7.8) |
| Ia-185 | 143–144° C., $^1$H-NMR(CDCl$_3$)δ2.22(3H, s), 2.40(3H, s), 3.11(3H, s), 4.03(3H, s), 5.17(2H, s), 7.14(1H, d, J=8.6), 7.21(1H, dd, J=2.0, 8.6), 7.30(1H, d, J=2.0), 7.31(1H, s), 7.37–7.48(6H, m), 7.91(1H, br d, J=8.1), 8.23(1H, br d, J=8.1), 8.35(1H, br s) |
| Ia-186 | 171–172° C., $^1$H-NMR(CDCl$_3$)δ2.40(3H, s), 3.05(3H, s), 3.12(3H, s), 4.02(3H, s), 5.18(2H, s), 6.59(1H, br s), 7.14(1H, d, J=8.6), 7.20(1H, dd, J=2.0, 8.6), 7.30(1H, d, J=2.0), 7.37–7.52(7H, m), 8.24(1H, br s), 8.31(1H, br d, J=6.8) |
| Ia-187 | 165–167° C., $^1$H-NMR(CDCl$_3$)δ1.77(3H, s), 1.83(3H, s), 2.39(3H, s), 3.05(3H, s), 4.03(3H, s), 4.6(2H, d, J=6.8), 5.5(1H, br t, J=6.8), 5.74(1H, s), 6.45(1H, br s), 6.73(1H, dd, J=2.2, 8.3), 6.86(1H, d, J=2.2), 6.94(1H, d, J=8.3), 7.45–7.52(2H, m), 8.24(1H, m), 8.30–8.34(1H, m) |
| Ia-188 | 150–151° C., $^1$H-NMR(CDCl$_3$)δ1.58(3H, s), 1.67(3H, s), 2.41(3H, s), 2.96(3H, s), 3.12(3H, s), 4.03(3H, s), 4.36(2H, d, J=7.3), 5.18(2H, s), 5.29(1H, br t, J=7.3), 7.15(1H, d, J=8.6), 7.20(1H, dd, J=2.0, 8.6), 7.29(1H, d, J=2.0), 7.37–7.48(7H, m), 8.42–8.45(2H, m) |
| Ia-189 | 91–94° C., $^1$H-NMR(CDCl$_3$)δ1.58(3H, s), 1.67(3H, s), 1.77(3H, s), 1.83(3H, s), 2.38(3H, s), 2.96(3H, s), 4.02(3H, s), 4.36(2H, d, J=6.8), 4.62(2H, d, J=6.8), 5.29(1H, br t, J=6.8), 5.52(1H, br t, J=6.8), 5.76(1H, s), 6.73(1H, dd, J=2.2, 8.3), 6.86(1H, d, J=2.2), 6.94(1H, d, J=8.3), 7.45–7.51(2H, m), 8.42–8.46(2H, m) |

TABLE 96

| | |
|---|---|
| Ia-190 | 110–111° C., $^1$H-NMR(CDCl$_3$)δ 1.58(3H, s), 1.67(3H, s), 1.77(3H, s), 1.82(3H, s), 2.41(3H, s), 2.97(3H, s), 3.23(3H, s), 4.02(3H, s), 4.36(2H, d, J=7.1), 4.64(2H, d, J=7.1), 5.29(1H, br t, J=7.1), 5.51(1H, br t, J=7.1), 7.08(1H, d, J=8.5), 7.19(1H, dd, J=2.0, 8.5), 7.27(1H, d, J=2.0), 7.46–7.52(2H, m), 8.43(2H, m) |
| Ia-191 | 131–132° C. |
| Ia-192 | 171.5–172° C., $^1$H-NMR(CDCl$_3$)δ2.40(3H, s), 3.11(3H, s), 3.89(3H, s), 5.18(2H, s), 7.15(1H, d, J=8.6), 7.22(1H, dd, J=2.0, 8.6), 7.30(1H, d, J=2.0), 7.38–7.50(5H, m), 7.56(1H, ddd, J=1.5, 7.6, 7.6), 7.66(1H, ddd, J=1.5, 7.6, 7.6), 7.73(1H, dd, J=1.5, 7.6), 8.17(1H, dd, J=1.5, 7.6) |
| Ia-194 | 249–251° C., $^1$H-NMR(CDCl$_3$)δ2.27(3H, s), 2.45(3H, s), 3.12(3H, s), 4.05(3H, s), 5.30(2H, s), 7.13–7.24(3H, m), 7.31(1H, d, J=2.0), 7.38–7.50(6H, m), 8.62(1H, dd, J=1.7, 8.3), 8.73(1H, br d, J=8.1), 13.18(1H, br s) |
| Ia-195 | 180–181° C., $^1$H-NMR(CDCl$_3$)δ1.77(3H, s), 1.83(3H, s), 2.27(3H, s), 2.42(3H, s), 4.04(3H, s), 4.63(2H, d, J=6.8), 5.53(1H, br t, J=6.8), 5.77(1H, s), 6.76(1H, dd, J=2.0, 8.3), 6.88(1H, d, J=2.0), 6.96(1H, d, J=8.3), 7.16(1H, ddd, J=1.2, 7.0, 8.1), 7.46(1H, ddd, J=1.7, 7.0, 8.5), 8.63(1H, dd, J=1.7, 8.1), 8.73(1H, br d, J=8.5), 13.28(1H, br s) |
| Ia-196 | 169–170° C., $^1$H-NMR(CDCl$_3$)δ1.77(3H, s), 1.82(3H, s), 2.27(3H, s), 2.45(3H, s), 3.23(3H, s), 4.04(3H, s), 4.65(2H, d, J=6.8), 5.52(1H, br t, J=6.8), 7.16(1H, ddd, J=1.2, 7.3, 8.1), 7.22(1H, dd, J=2.2, 8.6), 7.29(1H, d, J=2.2), 7.47(1H, ddd, J=1.5, 7.3, 8.1), 8.62(1H, dd, J=1.5, 8.1), 8.73(1H, br d, J=8.1), 13.21(1H, br s) |
| Ia-197 | 176–178° C., $^1$H-NMR(CDCl$_3$)δ2.45(3H, s), 3.03(3H, s), 3.12(3H, s), 4.05(3H, s), 5.18(2H, s), 7.14–7.24(3H, m), 7.30(1H, d, J=2.0), 7.38–7.51(6H, m), 7.76(1H, dd, J=1.0, 8.3), 8.69(1H, dd, J=1.7, 8.1), 13.19(1H, br s) |
| Ia-199 | 157–158° C., $^1$H-NMR(CDCl$_3$)δ1.36(3H, t, J=6.7), 2.42(3H, s), 3.11(3H, s), 4.54(2H, q, J=6.7), 5.18(2H, s), 7.14(1H, d, J=7.9), 7.21(1H, dd, J=1.8, 8.5), 7.32(1H, d, J=2.4), 7.37–7.49(8H, m), 8.43–8.48(2H, m) |

TABLE 96-continued

| | |
|---|---|
| Ia-200 | 122–123° C., $^1$H-NMR(CDCl$_3$)δ1.36(3H, t, J=7.3), 2.39(3H, s), 2.40(3H, s), 4.54(2H, q, J=7.3), 5.11(2H, s), 5.69(1H, s), 6.76(1H, dd, J=1.8, 8.5), 6.89(1H, d, J=1.8), 7.00(1H, d, J=8.5), 7.22–7.50(3H, m), 8.42–8.48(2H, m) |
| Ia-201 | 147–148° C., $^1$H-NMR(CDCl$_3$)δ1.36(3H, t, J=6.7), 2.39(3H, s), 2.42(3H, s), 3.10(3H, s), 4.54(2H, q, J=6.7), 5.13(2H, s), 7.14(1H, d, J=8.5), 7.18–7.28(3H, m), 7.31(1H, d, J=1.8), 7.36(2H, d, J=8.5), 7.46–7.50(3H, m), 8.43–8.48(2H, m) |
| Ia-202 | 99–100° C., $^1$H-NMR(CDCl$_3$)δ1.36(3H, s), 1.77(3H, s), 1.83(3H, s), 2.39(3H, s), 4.54(2H, q, J=7.3), 4.62(2H, d, J=6.7), 5.53(1H, br t, J=6.7), 5.72(1H, s), 6.75(1H, dd, J=2.4, 8.5), 6.87(1H, d, J=2.4), 6.93(1H, d, J=8.5), 7.42–7.52(3H, m), 8.42–8.50(2H, m) |
| Ia-203 | 128–129° C., $^1$H-NMR(CDCl$_3$)δ1.37(3H, t, J=6.7), 1.77(3H, s), 1.82(3H, s), 2.42(3H, s), 3.22(3H, s), 5.34(2H, q, J=6.7), 4.63(2H, d, J=6.7), 5.51(1H, br t, J=6.7), 7.06(1H, d, J=8.5), 7.20(1H, dd, J=2.4, 8.5), 7.30(1H, d, J=1.8), 7.45–7.49(3H, m), 8.43–8.48(2H, m) |
| Ia-206 | oil, $^1$H-NMR(CDCl$_3$)δ1.33(6H, d, J=6.1), 2.38(3H, s), 5.16(2H, s), 5.55(1H, sept, J=6.1), 5.68(1H, s), 6.75(1H, dd, J=1.8, 8.5), 6.89(1H, d, J=1.8), 6.99(1H, d, J=8.5), 7.36–7.48(8H, m), 8.42–8.47(2H, m) |

TABLE 97

| | |
|---|---|
| Ia-207 | 123–124° C., $^1$H-NMR(CDCl$_3$)δ1.33(3H, s), 1.36(3H, s), 2.41(3H, s), 3.11(3H, s), 5.18(2H, s), 5.55(1H, sept, J=6.1), 7.13(1H, d, J=8.5), 7.20 (1H, dd, J=1.8, 8.5), 7.31(1H, d, J=1.8), 7.37–7.50(8H, m), 8.42–8.46(2H, m) |
| Ia-208 | 157–158° C., $^1$H-NMR(CDCl$_3$)δ1.32(3H, s), 1.34(3H, s), 2.38(3H, s), 2.40(3H, s), 5.11(2H, s), 5.55(1H, sept, J=6.1), 5.68(1H, s), 6.75(1H, dd, J=2.4, 8.5), 6.88(1H, d, J=2.4), 6.99(1H, d, J=8.5), 7.24(1H, d, J=7.9), 7.36(2H, d, J=7.9), 7.45–7.52(3H, m), 8.42–8.47(2H, m) |
| Ia-209 | 159–160° C., $^1$H-NMR(CDCl$_3$)δ1.33(3H, s), 1.35(3H, s), 2.39(3H, s), 2.41(3H, s), 3.10(3H, s), 5.13(2H, s), 5.55(1H, sept, J=6.1), 7.13(1H, d, J=7.9), 7.18(1H, d, J=1.8), 7.23(1H, d, J=7.3), 7.30(1H, d, J=1.8), 7.36(2H, d, J=7.9), 7.44–7.49(3H, m), 8.42–8.46(2H, m) |
| Ia-210 | 113–114° C., $^1$H-NMR(CDCl$_3$)δ1.32(3H, s), 1.34(3H, s), 1.77(3H, s), 1.83(3H, s), 2.38(3H, s), 4.62(2H, d, J=7.3), 5.49–5.59(2H, m), 5.70(1H, s), 6.73(1H, dd, J=2.4, 8.5), 6.86(1H, d, J=2.4), 6.92(1H, d, J=8.5), 7.45–7.50(3H, m), 8.42–8.46(2H, m) |
| Ia-211 | 128–129° C., $^1$H-NMR(CDCl$_3$)δ1.33(3H, s), 1.35(3H, s), 1.77(3H, s), 1.82(3H, s), 2.41(3H, s), 3.22(3H, s), 4.64(2H, d, J=6.7), 5.49–5.60(2H, m), 7.05(1H, d, J=8.5), 7.18(1H, dd, J=1.8, 8.5), 7.29(1H, d, J=2.4), 7.45–7.49(3H, m), 8.42–8.46(2H, m) |
| Ia-214 | 110–111° C., $^1$H-NMR(CDCl$_3$)δ1.24(3H, t, J=7.6), 2.65(2H, q, J=7.6), 4.02(3H, s), 5.16(2H, s), 5.71(1H, s), 6.74(1H, dd, J=2.0, 8.3), 6.88(1H, d, J=2.0), 7.01(1H, d, J=8.3), 7.41–7.49(8H, m), 8.48–8.53(2H, m) |
| Ia-215 | 161–162° C., $^1$H-NMR(CDCl$_3$)δ1.25(3H, t, J=7.6), 2.66(2H, q, J=7.6), 3.11(3H, s), 4.02(3H, s), 5.17(2H, s), 7.14(1H, d, J=8.5), 7.18(1H, dd, J=2.0, 8.5), 7.28(1H, d, J=2.0), 7.37–7.49(8H, m), 8.49–8.53(2H, m) |
| Ia-216 | 121–122° C., $^1$H-NMR(CDCl$_3$)δ1.24(3H, t, J=7.6), 2.40(3H, s), 2.65(2H, q, J=7.6), 4.02(3H, s), 5.11(2H, s), 5.70(1H, s), 6.74(1H, dd, J=2.0, 8.3), 6.87(1H, d, J=2.0), 7.01(1H, d, J=8.3), 7.24(2H, d, J=8.1), 7.34(2H, d, J=8.1), 7.46–7.50(3H, m), 8.49–8.53(2H, m) |
| Ia-217 | 184–185° C., $^1$H-NMR(CDCl$_3$)δ1.25(3H, t, J=7.6), 2.39(3H, s), 2.66(2H, q, J=7.6), 3.10(3H, s), 4.02(3H, s), 5.13(2H, s), 7.14(1H, d, J=8.6), 7.18(1H, dd, J=2.0, 8.6), 7.22(2H, d, J=7.8), 7.27(1H, d, J=2.0), 7.36(2H, d, J=7.8), 7.47–7.51(3H, m), 8.49–8.53(2H, m) |
| Ia-218 | 119–120° C., $^1$H-NMR(CDCl$_3$)δ1.24(3H, t, J=7.6), 1.77(3H, s), 1.83(3H, s), 2.65(2H, q, J=7.6), 4.02(3H, s), 4.62(2H, d, J=6.8), 5.51(1H, br t, J=6.8), 5.73(1H, s), 6.73(1H, dd, J=2.0, 8.3), 6.85(1H, d, J=2.0), 6.94(1H, d, J=8.3), 7.46–7.50(3H, m), 8.49–8.53(2H, m) |

TABLE 97-continued

Ia-219 141–142° C., ¹H-NMR(CDCl₃)δ1.25(3H, t, J=7.6),
1.77(3H, s), 1.82(3H, s), 2.66(2H, q, J=7.6), 3.22(3H, s),
4.02(3H, s), 4.63(2H, d, J=6.6), 5.51(1H, br t, J=6.6),
7.07(1H, d, J=8.5), 7.17(1H, dd, J=2.0, 8.5), 7.26(1H, d, J=2.0),
7.46–7.50(3H, m), 8.49–8.53(2H, m)

Ia-222 187–189° C., ¹H-NMR(CDCl₃)δ5.18(2H, s), 5.76(1H, s),
6.93(1H, dd, J=2.2, 8.3), 7.04(1H, d, J=8.6), 7.05(1H, d, J=2.2),
7.42–7.58(8H, m), 8.45–8.49(2H, m), 8.97(1H, s)

Ia-223 163–166° C., ¹H-NMR(CDCl₃)δ3.13(3H, s), 5.21(2H, s),
7.19(1H, d, J=8.5), 7.36(1H, dd, J=2.0, 8.5),
7.38–7.54(9H, m), 8.45–8.49(2H, m), 8.99(2H, s)

TABLE 98

Ia-224 165–166° C., ¹H-NMR(CDCl₃)δ1.78(3H, s), 1.83(3H, s),
4.65(2H, d, J=6.8), 5.53(1H, t, J=6.8), 5.77(1H, s),
6.92(1H, dd, J=2.0, 8.3), 6.97(1H, d, J=8.3), 7.02(1H, d, J=2.0),
7.54–7.58(3H, m), 8.45–8.48(2H, m), 8.97(1H, s)

Ia-226 118–119° C., ¹H-NMR(CDCl₃)δ3.87(3H, s), 5.17(2H, s),
5.79(1H, s), 6.88(1H, dd, J=2.2, 8.3), 7.01(1H, d, J=8.3),
7.03(1H, d, J=2.2), 7.39–7.52(8H, m),
8.48–8.51(2H, m), 8.90(1H, s)

Ia-227 117–118° C., ¹H-NMR(CDCl₃)δ3.13(3H, s), 3.90(3H, s),
5.19(2H, s), 5.79(1H, s), 7.18(1H, d, J=8.6),
7.33(1H, dd, J=2.2, 8.3), 7.40(1H, d, J=2.2),
7.41–7.53(8H, m), 8.48–8.52(2H, m), 8.90(1H, s)

Ia-229 92–94° C., ¹H-NMR(CDCl₃)δ1.77(3H, s), 1.83(3H, s),
3.87(3H, s), 4.63(2H, d, J=6.8), 5.51(1H, t, J=6.8), 5.78(1H, s),
6.88(1H, dd, J=2.0, 8.3), 6.95(1H, d, J=8.3),
7.00(1H, d, J=2.0), 7.49–7.51(3H, m), 8.47–8.51(2H, m),
8.90(1H, s)

Ia-230 134–135° C., ¹H-NMR(CDCl₃)δ1.77(3H, s), 1.82(3H, s),
3.23(3H, s), 3.91(3H, s), 4.65(2H, d, J=6.6), 5.49(1H, t, J=6.6),
7.11(1H, d, J=8.3), 7.32(1H, dd, J=2.0, 8.3),
7.37(1H, d, J=2.0), 7.49–7.54(3H, m),
8.48–8.52(2H, m), 8.90(1H, s)

Ia-232 151–152° C., ¹H-NMR(CDCl₃)δ2.14(3H, s), 3.13(3H, s),
5.21(2H, s), 7.19(1H, d, J=8.5), 7.28(1H, dd, J=2.2, 8.5),
7.38–7.52(9H, m), 8.46–8.49(2H, m), 8.70(2H, s)

Ia-233 197–198° C., ¹H-NMR(CDCl₃)δ2.32(3H, s), 2.60(3H, s),
3.11(3H, s), 5.19(2H, s), 7.18(1H, br s), 7.28(1H, m),
7.38–7.50(8H, s), 8.49–8.53(2H, m)

Ia-235 184–185° C., ¹H-NMR(CDCl₃)δ2.23(3H, s),
3.04(3H, d, J=4.6), 4.55(1H, br q, J=4.6), 5.17(2H, s),
5.82(1H, s), 6.71(1H, dd, J=2.0, 8.1), 6.85(1H, d, J=2.0),
7.04(1H, d, J=8.1), 7.39–7.48(8H, m), 8.44–8.48(2H, m)

Ia-236 204–205° C., ¹H-NMR(CDCl₃)δ2.23(3H, s),
3.05(3H, d, J=4.6), 3.13(3H, s), 4.51(1H, br q, J=4.6),
5.19(2H, s), 7.16(1H, dd, J=2.0, 8.6), 7.19(1H, d, J=8.6),
7.25(1H, d, J=2.0), 7.38–7.50(8H, m), 8.44–8.48(2H, m)

Ia-238 oil, ¹H-NMR(CDCl₃)δ1.77(3H, s),
1.82(3H, s), 2.35(3H, s), 3.99(3H, s), 4.66(2H, d, J=6.7),
4.78(1H, s), 5.51(1H, br t, J=6.7), 5.69(1H, s),
6.91(2H, d, J=8.6), 6.95(1H, d, J=8.6), 8.01(1H, dd, J=8.6, 1.8),
8.07(1H, d, J=1.8)

Ia-239 189–190° C. ¹H-NMR(CDCl₃)δ2.34(3H, s), 3.21(3H, s),
3.99(3H, s), 5.20(2H, s), 5.70(1H, s), 7.02(1H, d, J=8.6),
7.31–7.47(9H, m), 8.03(1H, dd, J=8.6, 1.8),
8.10(1H, d, J=1.8)

Ia-240 190–192° C., ¹H-NMR(CDCl₃)δ2.34(3H, s), 3.12(3H, s),
3.21(3H, s), 4.00(3H, s), 5.21(2H, s), 7.14(1H, d, J=8.6),
7.28–7.49(9H, m), 8.41(1H, dd, J=8.6, 2.5), 8.44(1H, d, J=2.5)

Ia-241 72–74° C., ¹H-NMR(CDCl₃)δ1.78(3H, s), 1.81(3H, s),
2.34(3H, s), 3.21(3H, s), 3.24(3H, s), 4.01(3H, s),
4.67(2H, d, J=6.7), 5.50(1H, br t, J=6.7), 7.08(1H, d, J=8.6),
7.28–7.39(4H, m), 8.39(1H, dd, J=8.5, 1.8), 8.42(1H, d, J=1.8)

Ia-248 228–230° C., ¹H-NMR(CDCl₃)δ5.21(2H, s),
7.08(1H, d, J=9.0), 7.38–7.56(8H, m), 7.72–7.76(2H, m),
7.85 and 7.88(each 1H, Abq, J=9.0), 8.13–8.16(2H, m)

Ia-249 220–221° C., ¹H-NMR(CDCl₃)δ3.15(3H, s), 5.23(2H, s),
7.24(1H, d, J=8.8), 7.37–7.58(8H, m),
7.89 and 7.93(each 1H, Abq, J=9.0), 8.07(1H, d, J=2.2),
8.14–8.17(2H, m), 8.21(1H, dd, J=2.2, 8.8)

TABLE 99

Ia-252 185–186° C., ¹H-NMR(CDCl₃)δ1.78(3H, s),
1.82(3H, s), 4.66(2H, d, J=6.8), 5.52(1H, br t, J=6.8),
5.66(1H, br s), 5.78(1H, s), 6.99–7.03(3H, m),
7.68(2H, d, J=9.0), 7.72(1H, dd, J=2.2, 8.6), 7.82(2H, s),
8.06(2H, d, J=8.8)

Ia-253 198–200° C., ¹H-NMR(CDCl₃)δ3.15(3H, s), 3.21(3H, s),
5.23(2H, s), 7.24(1H, d, J=8.8), 7.38–7.46(5H, m),
7.47(2H, d, J=9.0), 7.91(2H, s), 8.07(1H, d, J=2.2),
8.19(1H, dd, J=2.2, 8.8), 8.22(2H, d, J=9.0)

Ia-254 192–193° C., ¹H-NMR(CDCl₃)δ1.78(3H, s), 1.82(3H, s),
3.21(3H, s), 3.25(3H, s), 4.69(2H, d, J=6.8),
5.51(1H, br t, J=6.8), 7.18(1H, d, J=8.8), 7.48(2H, d, J=9.0),
7.90(2H, s), 8.03(1H, d, J=2.2), 8.22(1H, dd, J=2.2, 8.8),
8.23(2H, d, J=8.8)

Ia-255 233–235° C., ¹H-NMR(CDCl₃)δ3.89(3H, s), 5.21(2H, s),
5.75(1H, s), 7.05(2H, d, J=8.8), 7.08(1H, d, J=9.0),
7.37–7.47(5H, m), 7.73–7.75(2H, m),
7.81 and 7.83(each 1H, ABq, J=9.3), 8.12(2H, d, J=8.8)

Ia-256 212–215° C., ¹H-NMR(CDCl₃)δ3.15(3H, s), 3.89(3H, s),
5.23(2H, s), 7.07(2H, d, J=9.0), 7.23(1H, d, J=8.8),
7.37–7.50(5H, m), 7.84 and 7.86(each 1H, ABq, J=9.3),
8.05(1H, d, J=2.0), 8.12(2H, d, J=9.0), 8.18(1H, dd, J=2.0, 8.8)

Ia-257 171–174° C., ¹H-NMR(CDCl₃)δ 1.77(3H, s), 1.82(3H, s),
3.89(3H, s), 4.66(2H, d, J=6.8), 5.52(1H, br t, J=6.8),
5.78(1H, s), 7.01(1H, d, J=8.3), 7.05(2H, d, J=8.8),
7.69(1H, d, J=2.2), 7.73(1H, dd, J=2.2, 8.3),
7.81 and 7.82 each 1H, ABq, J=9.0), 8.11(2H, d, J=8.8)

Ia-258 197–199° C., ¹H-NMR(CDCl₃)δ1.78(3H, s), 1.82(3H, s),
3.25(3H, s), 3.90(3H, s), 4.68(2H, d, J=6.8),
5.51(1H, br t, J=6.8), 7.06(2H, d, J=9.0), 7.17(1H, d, J=8.8),
7.84 and 7.85(each 1H, ABq, J=9.3), 8.00(1H, d, J=2.2),
8.12(2H, d, J=9.0), 8.20(1H, dd, J=2.2, 8.8)

Ia-269 198–199° C., ¹H-NMR(CDCl₃)δ4.83(1H, br s),
5.14(2H, s), 5.69(1H, s), 6.85(2H, d, J=8.8), 6.92(1H, d, J=8.3),
7.09(1H, dd, J=2.2, 8.3), 7.13 and 7.14(each 1H, ABq, J=3.9),
7.23(1H, d, J=2.2), 7.38–7.45(5H, m), 7.49(2H, d, J=8.8)

Ia-271 167–168° C., ¹H-NMR(CDCl₃)δ1.76(3H, s), 1.81(3H, s),
4.60(2H, d, J=6.8), 4.79(1H, s), 5.50(1H, br t, J=6.8),
5.71(1H, s), 6.85(2H, d, J=8.8), 6.87(1H, d, J=8.3),
7.09(1H, dd, J=2.2, 8.3), 7.12 and 7.14(each 1H, ABq, J=3.7),
7.20(1H, d, J=2.2), 7.50(2H, d, J=8.8)

Ia-272 162–164° C., ¹H-NMR(CDCl₃)δ3.12(3H, s), 3.17(3H, s),
5.16(2H, s), 7.08(1H, d, J=8.6), 7.21(1H, d, J=3.7),
7.25(1H, d, J=3.7), 7.31(2H, d, J=8.8), 7.39–7.44(5H, m),
7.48(1H, dd, J=2.2, 8.6), 7.57(1H, d, J=2.2), 7.64(2H, d, J=8.8)

Ia-273 128–129° C., ¹H-NMR(CDCl₃)δ1.76(3H, s), 1.80(3H, s),
3.17(3H, s), 3.23(3H, s), 4.62(2H, d, J=6.8),
5.48(1H, br c, J=6.8), 7.02(1H, d, J=8.5), 7.20(1H, d, J=3.9),
7.25(1H, d, J=3.9), 7.31(2H, d, J=8.8), 7.48(1H, dd, J=2.2, 8.5),
7.56(1H, d, J=2.2), 7.64(2H, d, J=8.8)

Ia-275 165–166° C., ¹H-NMR(CDCl₃)δ5.14(4H, s), 5.69(2H, s),
6.92(2H, d, J=8.3), 7.09(2H, dd, J=2.2, 8.3), 7.14(2H, s),
7.22(2H, d, J=2.2), 7.37–7.44(10H, m)

Ia-280 178–179° C., ¹H-NMR(CDCl₃)δ2.31(3H, s), 3.11(3H, s),
4.82(1H, s), 5.16(2H, s), 6.84(2H, d, J=8.8), 7.01(1H, s),
7.10(1H, d, J=8.6), 7.34–7.48(9H, m)

TABLE 100

Ia-281 128–129° C., ¹H-NMR(CDCl₃)δ1.76(3H, s), 1.82(3H, s),
2.31(3H, s), 4.61(2H, d, J=6.8), 4.81(1H, s),
5.51(1H, br t, J=6.8), 5.72(1H, s), 6.83(2H, d, J=8.8),
6.90(1H, d, J=8.3), 6.96(1H, dd, J=2.2, 8.3), 7.00(1H, s),
7.08(1H, d, J=2.2), 7.47(2H, d, J=8.8)

Ia-282 133–134° C., ¹H-NMR(CDCl₃)δ2.33(3H, s), 3.12(3H, s),
3.17(3H, s), 5.17(2H, s), 7.11(1H, d, J=8.6), 7.12(1H, s),
7.30(2H, d, J=8.8), 7.35–7.48(7H, m), 7.61(2H, d, J=8.8)

Ia-283 86–87° C., ¹H-NMR(CDCl₃)δ1.76(3H, s), 1.81(3H, s),
2.33(3H, s), 3.17(3H, s), 3.22(3H, s), 4.63(2H, d, J=6.8),
5.49(1H, br t, J=6.8), 7.05(1H, d, J=8.6), 7.11(1H, s),
7.29(2H, d, J=8.6), 7.36(1H, dd, J=2.2, 8.6), 7.44(1H, d, J=2.2),
7.61(2H, d, J=8.8)

Ia-309 128–129° C., ¹H-NMR(CDCl₃)δ2.31(3H, s), 3.64(3H, s),
5.15(2H, s), 5.70(1H, s), 6.92(1H, dd, J=2.0, 8.3),

TABLE 100-continued

| | |
|---|---|
| | 6.98(1H, d, J=8.3), 7.07(1H, d, J=2.0), 7.28(1H, br t, J=7.6), 7.38–7.47(7H, m), 7.71(2H, br d, J=7.6) |
| Ia-310 | 132–133° C., $^1$H-NMR(CDCl$_3$)δ2.34(3H, s), 3.11(3H, s), 3.65(3H, s), 5.16(2H, s), 7.13(1H, d, J=8.5), 7.29–7.48(m 10H), 7.70(2H, br d, J=7.6) |
| Ia-311 | 148–149° C., $^1$H-NMR(CDCl$_3$)δ2.30(3H, s), 2.39(3H, s), 3.64(3H, s), 5.10(2H, s), 5.69(1H, s), 6.92(1H, dd, J=2.0, 8.3), 6.99(1H, d, J=8.3), 7.06(1H, d, J=2.0), 7.23(2H, d, J=8.1), 7.30(1H, m), 7.33(2H, d, J=8.1), 7.43(2H, br t, J=8.1), 7.68–7.72(2H, m) |
| Ia-312 | 146–147° C., $^1$H-NMR(CDCl$_3$)δ2.33(3H, s), 2.38(3H, s), 3.11(3H, s), 3.65(3H, s), 5.16(2H, s), 7.13(1H, d, J=8.6), 7.22(2H, d, J=8.1), 7.29–7.47(7H, m), 7.68–7.72(2H, m) |
| Ia-313 | 78–79° C., $^1$H-NMR(CDCl$_3$)δ1.77(3H, s), 1.82(3H, s), 2.33(3H, s), 3.22(3H, s), 3.65(3H, s), 4.62(2H, d, J=6.8), 5.50(1H, br t, J=6.8), 7.06(1H, d, J=8.6), 7.29–7.47(5H, m), 7.68–7.72(2H, m) |
| Ia-314 | 120–121° C., $^1$H-NMR(CDCl$_3$)δ1.77(3H, s), 1.82(3H, s), 2.30(3H, s), 3.64(3H, s), 4.61(2H, d, J=6.8), 5.52(1H, br t, J=6.8), 5.72(1H, s), 6.91(2H, br s), 7.04(1H, br s), 7.27(1H, br t, J=7.3), 7.43(2H, br t, J=8.3), 7.70–7.73(2H, m) |
| Ia-315 | 136–137° C., $^1$H-NMR(CDCl$_3$)δ2.31(3H, s), 3.62(3H, s), 3.84(3H, s), 5.16(2H, s), 5.71(1H, s), 6.91–7.01(4H, m), 7.07(1H, d, J=1.8), 7.37–7.48(5H, m), 7.61(2H, d, J=8.9) |
| Ia-316 | 120–121° C., $^1$H-NMR(CDCl$_3$)δ2.32(3H, s), 3.11(3H, s), 3.63(3H, s), 3.84(3H, s), 5.16(2H, s), 6.96(2H, d, J=8.9), 7.13(1H, d, J=6.8), 7.32–7.49(7H, m), 7.59(2H, d, J=8.9) |
| Ia-317 | 130–131° C., $^1$H-NMR(CDCl$_3$)δ2.30(3H, s), 2.39(3H, s), 3.62(3H, s), 3.84(3H, s), 5.10(2H, s), 5.70(1H, s), 6.89–7.00(2H, m), 6.96(2H, d, J=9.2), 7.06(1H, d, J=1.8), 7.23(2H, d, J=7.9), 7.34(2H, d, J=7.9), 7.57(2H, d, J=9.2) |
| Ia-318 | 145–146° C., $^1$H-NMR(CDCl$_3$)δ2.33(3H, s), 2.38(3H, s), 3.10(3H, s), 3.63(3H, s), 3.85(3H, s), 5.11(2H, s), 6.97(2H, d, J=8.5), 7.12(1H, d, J=8.5), 7.22(2H, d, J=7.9), 7.34(1H, d, J=8.5), 7.35(2H, d, J=7.9), 7.46(1H, d, J=1.8), 7.57(2H, d, J=8.5) |
| Ia-319 | 113–114° C., $^1$H-NMR(CDCl$_3$)δ1.76(3H, s), 1.82(3H, s), 2.30(3H, s), 3.62(3H, s), 3.84(3H, s), 4.60(2H, d, J=6.7), 5.52(1H, br t, J=6.7), 6.91(2H, d, J=1.2), 6.96(2H, d, J=9.2), 7.04(1H, s), 7.58(2H, d, J=9.2) |

TABLE 101

| | |
|---|---|
| Ia-320 | 66–67° C., $^1$H-NMR(CDCl$_3$)δ1.76(3H, s), 1.81(3H, s), 2.32(3H, s), 3.22(3H, s), 3.63(3H, s), 3.85(3H, s), 4.62(2H, d, J=6.1), 5.50(1H, br t, J=6.1), 6.97(2H, d, J=8.5), 7.05(1H, d, J=8.5), 7.34(1H, dd, J=1.8, 8.5), 7.44(1H, d, J=1.8), 7.57(2H, d, J=8.5) |
| Ia-322 | 152–153° C., $^1$H-NMR(CDCl$_3$)δ1.76(3H, s), 1.82(3H, s), 2.24(3H, s), 3.44(1H, br), 3.84(3H, s), 4.60(2H, d, J=6.7), 5.51(1H, br t, J=6.7), 6.78–6.94(5H, m), 7.33(2H, d, J=8.5) |
| Ia-323 | oil, $^1$H-NMR(CDCl$_3$)δ0.96(3H, t, J=7.3), 2.27(3H, s), 3.82(3H, s), 4.06(2H, q, J=7.3), 5.13(2H, s), 6.18(1H, dd, J=1.8, 7.9), 6.91–6.97(4H, m), 7.32–7.45(7H, m) |
| Ia-324 | 108–109° C., $^1$H-NMR(CDCl$_3$)δ0.97(3H, t, J=7.3), 2.28(3H, s), 3.12(3H, s), 3.85(3H, s), 4.07(2H, q, J=7.3), 5.12(2H, s), 6.96(1H, d, J=6.7), 7.11(1H, d, J=8.5), 7.24–7.49(9H, m) |
| Ia-325 | oil, $^1$H-NMR(CDCl$_3$)δ0.99(3H, t, J=7.3), 1.76(3H, s), 1.82(3H, s), 2.28.(3H, s), 3.84., (3H, s), 4.07(2H, q, J=7.3), 4.61(2H, br d, J=6.7), 5.51(1H, br t, J=6.7), 5.78(1H, d, J=6.7), 6.82(1H, dd, J=1.8, 8.5), 6.89–6.98(4H, m), 7.36(2H, d, J=8.5) |
| Ia-326 | 85–86° C., $^1$H-NMR(CDCl$_3$)δ0.99(3H, t, J=7.3), 1.76(3H, s), 1.81(3H, s), 2.28(3H, s), 3.22(3H, s), 3.85(3H, s), 4.07(2H, q, J=7.3), 4.63(2H, d, J=6.7), 5.50(1H, br t, J=6.7), 6.96(2H, d, J=8.6), 7.04(1H, d, J=8.6), 7.24–7.29(1H, m), 7.33–7.37(2H, m) |
| Ia-328 | 140–141° C., $^1$H-NMR(CDCl$_3$)δ1.77(314, s), 1.83(3H, s), 2.34(3H, s), 3.85(3H, s), 4.52(2H, d, J=3.1), 4.62(2H, d, J=6.7), 5.52(1H, br t, J=6.7), 5.78(1H, s), 6.84–7.02(5H, m), 7.58(2H, d, J=8.6) |
| Ia-334 | 136–137° C., $^1$H-NMR(CDCl$_3$)δ2.13(3H, s), 3.80(3H, s), 5.18(2H, s), 5.85(1h, s), 6.83(1H, dd, J=2.0, 8.3), 6.96(1H, d, J=2.0), 7.04(1H, d, J=8.3), 7.32–7.46(8H, m), 7.69–7.73(2H, m) |
| Ia-335 | 165–165.5° C., $^1$H-NMR(CDCl$_3$)δ2.15(3H, s), 3.13(3H, s), 3.82(3H, s), 5.20(2H, s), 7.19(1H, d, J=8.3), 7.27(1H, dd, J= 2.2, 8.3), 7.33(1H, m), 7.35(1H, d, J=2.2), 7.38–7.50(7H, m), 7.67–7.71(2H, m) |
| Ia-336 | 143–144° C., $^1$H-NMR(CDCl$_3$)δ1.78(3H, s), 1.83(3H, s), 2.14(3H, s), 3.80(3H, s), 4.64(2H, d, J=6.8), 5.53(1H, br t, J=6.8), 5.84(1H, s),, 6.82(1H, dd, J=2.2, 8.3), 6.93(1H, d, J=2.2), 6.97(1H, d, J=8.3), 7.32(1H, m), 7.43(2H, m), 7.69–7.73(2H, m) |
| Ia-337 | 126.5–127.5° C., $^1$H-NMR(CDCl$_3$)δ1.78(3H, s), 1.83(3H, s), 2.15(3H, s), 3.24(3H, s), 3.82(3H, s), 4.66(2H, d, J=6.8), 5.51(1H, br t, J=6.8), 7.12(1H, d, J=8.5), 7.26(1H, dd, J=2.2, 8.5), 7.32(1H, m), 7.33(1H, d, J=2.2), 7.43(2H, m), 7.67–7.71(2H, m) |
| Ia-338 | 167–168° C. $^1$H-NMR(CDCl$_3$)δ5.17(2H, s), 5.75(1H, s), 6.99(1H, d, J=8.6), 7.22(1H, dd, J=2.4, 8.6), 7.32(1H, s), 7.33–7.52(8H, m), 8.06–8.11(2H, m) |
| Ia-339 | 149–150° C. $^1$H-NMR(CDCl$_3$)δ3.13(3H, s), 5.18(2H, s), 7.14(1H, d, J=8.5), 7.37–7.50(8H, m), 7.60(1H, dd, J=1.8, 8.5), 7.68(1H, d, J=8.07–8.12(2H, m) |
| Ia-340 | 184–186° C., $^1$H-NMR(CDCl$_3$)δ2.38(3H, s), 5.12(2H, s), 5.77(1H, s), 6.99(1H, d, J=8.6), 7.19–7.34(7H, m), 7.40–7.52(3H, m), 8.05–8.13(2H, m) |
| Ia-341 | 175–176° C., $^1$H-NMR(CDCl$_3$)δ2.38(3H, s), 3.12(3H, s), 5.14(2H, s), 7.14(1H, d, J=8.5), 7.22(2H, d, J=7.9), 7.34(2H, d, J=7.9), 7.37(1H, s), 7.47(2H, d, J=1.8), 7.49(1H, d, J=2.4), 7.60(1H, dd, J=2.4, 8.5), 8.06–8.12(2H, m) |

TABLE 102

| | |
|---|---|
| Ia-342 | 131—132° C., $^1$H-NMR(CDCl$_3$)δ1.77(3H, s), 1.82(3H, s), 4.63(2H, d, J=6.7), 5.50(1H, br t, J=6.7), 5.78(1H, s), 6.92(1H, d, J=8.5), 7.22(1H, dd, J=2.4, 8.5), 7.30–7.32(2H, m), 7.43–7.51(3H, m), 8.07–8.11(2H, m) |
| Ia-343 | 126–127° C., $^1$H-NMR(CDCl$_3$)δ1.77(3H, s), 1.81(3H, s), 3.25(3H, s), 4.64(2H, d, J=6.7), 5.49(1H, br t, J=6.7), 7.07(1H, d, J=8.6), 7.37(1H, s), 7.45–7.53(3H, m), 7.60(1H, dd, J=1.8, 8.6), 7.66(1H, d, J=2.4), 8.08–8.12(2H, m) |
| Ia-348 | 150–151° C., $^1$H-NMR(CDCl$_3$)δ3.85(3H, s), 5.16(2H, s), 5.71(1H, s), 6.98(4H, d, J=8.9), 7.31–7.46(6H, m), 7.82(1H, s), 8.04(2H, d, J=8.9) |
| Ia-349 | 112–113° C., $^1$H-NMR(CDCl$_3$)δ3.12(3H, s), 3.88(3H, s), 5.16(2H, s), 6.99(2H, d, J=9.2), 7.12(1H, d J=8.8), 7.33–7.48(5H, m), 7.73(1H, dd J=8.3, 1.8), 7.74(1H, s), 7.87(1H, s), 8.04(2H, d, J=9.2) |
| Ia-350 | 137–138° C., $^1$H-NMR(CDCl$_3$)δ1.75(3H, s), 1.81(3H, s), 3.87(3H, s), 4.60(2H, d, J=6.8), 5.49(1H, t, J=6.8), 5.70(1H, s), 6.91(1H, d, J=9.2), 6.98(2H, d, J=9.1), 7.32–7.35(2H, m), 7.82(1H, s), 8.04(2H, d, J=9.1) |
| Ia-351 | 127–128° C., $^1$H-NMR(CDCl$_3$)δ1.75(3H, s), 1.81(3H, s), 3.23(3H, s), 3.87(3H, s), 4.63(2H, d, J=6.8), 5.48(1H, t, J=6.8), 6.98(2H, d, J=9.1), 7.05(2H, d, J=9.1), 7.71–7.75(2H, m), 7.85(1H, s), 8.04(2H, d, J=9.1) |
| Ia-352 | 99–100° C., $^1$H-NMR(CDCl$_3$)δ2.58(3H, s), 3.83(3H, s), 5.17(2H, s), 5.71(1H, s), 6.93–7.01(3H, m), 7.23(1H, d, J=1.9), 7.32(1H, d, J=1.9), 7.34–7.44(5H, m), 8.01(2H, d, J=9.1) |
| Ia-353 | 159–160° C., $^1$H-NMR(CDCl$_3$)δ2.57(3H, s), 3.11(3H, s), 3.86(3H, s), 5.17(2H, s), 6.97(2H, d, J=9.1), 7.13(1H, d, J=8.5), 7.35–7.47(5H, m), 7.65(2H, d, J=9.1)7.99(2H, d, J=9.1) |
| Ia-354 | oil, $^1$H-NMR(CDCl$_3$)δ1.76(3H, s), 1.81(3H, s), 2.16(3H, s), 2.57(3H, s), 3.86(3H, s), 4.61(2H, d, J=6.7), 5.50(1H, br t, J=6.7), 5.71(1H, s), 6.94(2H, d, J=7.3), 6.97(1H, d, J=8.6), 7.23(1H, dd, J=8, 1.8), 7.28(1H, br, J=1.8), 8.00(2H, d, J=7.3) |
| Ia-355 | 130–131° C., $^1$H-NMR(CDCl$_3$)δ1.76(3H, s), 1.81(3H, s), 2.57(3H, s), 3.21(3H, s), 3.87(3H, s), 4.63(2H, d, J=6.7), 5.49(1H, t, J=6.7), 6.97(2H, d, J=6.7), 7.07(1H, d, J=9.1)7.62–7.67(2H, m), 7.99(2H, d, J=9.1) |
| Ia-356 | mp 91.5–92.5° C.; $^1$H NMR(CDCl$_3$)δ1.74(s, 3H), 1.76(s, 3H), 1.77(s, 3H), 1.80(s, 3H), 2.34(s, 3H), 2.54(s, 3H), 3.74(d, J=6.6Hz, 2H), 4.63(d, J=6.6Hz, 2H), 5.37(br t, J=6.6Hz, 1H), 5.54(br t, J=6.6Hz, 1H), 6.68(d, J=8.5Hz, 2H), 7.04(t, J=8.5Hz, 1H), 7.19(d, J=8.5Hz, 2H), 7.27(br d, J=8.5Hz, 1H), 7.33(dd, J=2.0, 12.0Hz, 1H)7.39(s, 1H) |

TABLE 102-continued

| | |
|---|---|
| Ia-357 | mp 136–136.5° C.; $^1$H NMR(CDCl$_3$)δ1.73(s, 3H), 1.76(s, 3H), 1.77(s, 3H), 1.82(s, 3H), 2.37(s, 3H), 2.52(s, 3H), 3.74(d, J=6.6Hz, 2H), 4.64(d, J=6.8Hz, 2H), 5.35(br t, J=6.6Hz, 1H), 5.55 (br t, J=6.8Hz, 1H), 6.68(d, J=8.8Hz, 2H), 7.01–7.12(m, 3H), 7.35(s, 1H), 7.43(d, J=8.8Hz, 2H) |

TABLE 103

| | |
|---|---|
| Ib-3 | 157–158° C., (CDCl$_3$)δ1.78(3H, s), 1.82(3H, s), 3.56(3H, s), 3.80 (3H, s), 4.62(2H, d, J=6.8), 5.52(1H, t, J=6.8), 5.69(1H, s), 5.84 (1H, s), 6.95(4H, d, J=2.4), 7.05(1H, s), 7.76(1H, td, J=7.8, 1.8), 7.94(1H, d, J=7.8), 8.75(1H, dd, J=4.9, 2.4) |
| Ib-8 | oil, $^1$H-NMR(CDCl$_3$)δ1.76(3H, s), 1.79(3H, s), 2.29(3H, s), 2.37 (3H, s), 3.89(3H, s), 4.64(2H, d, J=6.7), 5.57(1H, br t, J=6.7), 6.85–6.96(3H, m), 7.16(1H, s), 7.22–7.27(1H, m), 7.33(1H, s), 7.46(1H, d, J=7.9), 7.75(1H, dt, J=1.8, 7.9), 8.71(1H, dd, J=4.9, 1.8). |
| Ib-11 | 112–113° C., $^1$H-NMR(CDCl$_3$)δ1.45(3H, s), 1.73(3H, s), 1.76 (3H, s), 1.81(3H, s), 2.67(3H, s), 3.25(3H, s), 3.68(3H, s), 3.85 (3H, s), 4.39(2H, d, J=7.3), 4.64(2H, d, J=6.8), 5.27(1H, t, J=7.3), 5.49(1H, t, J=6.8), 7.09(1H, d, J=8.5), 7.33–7.39(2H, m), 7.49(1H, s), 7.60(1H, dd, J=8.5, 2.5), 8.16(1H, d, J=8.5), 8.56(1H, d, J=1.8) |
| Ib-12 | 139–141° C., $^1$H-NMR(CDCl$_3$)δ2.66(3H, s), 3.12(3H, s), 3.64 (3H, s), 3.82(3H, s), 3.84(2H, brs), 5.18(2H, s), 7.05(1H, dd, J=8.5, 3.0), 7.14(1H, d, J=8.5), 7.32–7.48(8H, m), 7.86(1H, d, J=8.5), 8.21(1H, d, J=3.0) |
| Ib-13 | oil, $^1$H-NMR(CDCl$_3$)δ1.76(3H, s), 1.79(3H, s), 2.28(3H, s), 2.36 (3H, s), 3.73(2H, br s), 3.88(3H, s), 4.63(2H, d, J=6.8), 5.57(1H, br t, J=6.8), 6.84–6.95(3H, m), 7.06(1H, dd, J=2.9, 8.3), 7.14(1H, s), 7.25(1H, dd, J=0.5, 8.3), 8.20(1H, d, J=0.5, 2.9) |
| Ib-15 | 157–158° C., $^1$H-NMR(CDCl$_3$)δ2.30(3H, s), 2.35(3H, s), 2.99 (6H, s), 3.70(2H, brs), 6.79(2H, d, J=8.9), 7.05(1H, dd, J=8.5, 2.4), 7.13(1H, s), 7.24–7.29(4H, m), 8.20(1H, d, J=2.4) |
| Ib-16 | 164–165° C., $^1$H-NMR(CDCl$_3$)δ1.75(3H, s), 1.78(3H, s), 1.81 (3H, s), 3.56(3H, s), 3.77(3H, d, J=6.8), 3.79(3H, s), 4.61(2H, d, J=7.3), 5.34(1H, t, J=6.8), 5.53(1H, t, J=7.3), 5.68(1H, s), 5.85 (1H, s), 6.92–6.98(4H, m), 7.05(1H, s), 7.77(1H, d, J=9.2), 8.14 (1H, d, J=3.1) |
| Ib-17 | oil, $^1$H-NMR(CDCl$_3$)δ1.75(6H, s), 1.78(3H, s), 1.79(3H, s), 2.29 (3H, s), 2.37(3H, s), 3.76(2H, d, J=6.6), 3.88(3H, s), 4.63(2H, d, J=6.8), 5.35(1H, br t, J=6.6), 5.57(1H, br t, J=6.8), 6.84–6.98(4H, m), 7.13(1H, s), 7.27(1H, d, J=8.6), 7.31(1H, s), 8.13(1H, d, J=2.4) |
| Ib-20 | 116–117° C., $^1$H-NMR(CDCl$_3$)δ1.75(3H, s), 1.78(3H, s), 2.30 (3H, s), 2.36(3H, s), 2.99(6H, s), 3.75(2H, d, J=6.8), 5.35(2H, t, J=6.8), 6.90(2H, d, J=8.5), 6.94(1H, dd, J=8.5, 3.1), 7.13(1H, s), 7.22–7.29(4H, m), 8.13(1H, d, J=2.4) |
| Ib-21 | 233–234° C., $^1$H-NMR(CDCl$_3$)δ2.65(3H, s), 3.13(3H, s), 3.69 (3H, s), 3.84(2H, s), 5.19(2H, s), 7.15(1H, d, J=8.5), 7.33–7.48 (8H, m), 8.10(1H, brs), 8.16(2H, d, J=1.4), 8.88(1H, s) |
| Ib-23 | 152–153° C., $^1$H-NMR(CDCl$_3$)δ1.75(3H, s), 1.79(3H, s), 2.30 (3H, s), 2.37(3H, s), 3.88(3H, s), 4.63(2H, d, J=6.6), 5.56(1H, br t, J=6.6), 6.84–6.96(3H, m), 7.17(1H, s), 7.32(1H, s), 7.53(1H, d, J=8.5), 8.25(1H, dd, J=2.7, 8.5), 8.76(1H, d, J=2.7) |
| Ib-25 | 178–180° C., $^1$H-NMR(CDCl$_3$)δ2.32(3H, s), 2.37(3H, s), 3.00 (6H, s), 6.80(2H, d, J=9.1), 7.17(1H, s), 7.25(2H, d, J=8.5), 7.32 (1H, s), 7.53(1H, d, J=8.5), 8.05(1H, brs), 8.24(1H, dd, J=8.5, 2.5), 8.74(1H, d, J=2.5) |
| Ib-35 | 219–221° C., $^1$H-NMR(CDCl$_3$)δ3.00(6H, s), 3.09(3H, s), 3.84 (3H, s), 3.86(3H, s), 6.50(1H, br), 6.80(2H, d, J=9.0), 6.99(1H, s), 7.51(2H, d, J=9.0), 7.52(1H, s), 7.71(1H, dd, J=2.7, 8.7), 8.02(1H, d, J=8.7), 8.52(1H, d, J=2.7) |

TABLE 104

| | |
|---|---|
| Ib-37 | 187–190° C., $^1$H-NMR(CDCl$_3$)δ2.32(3H, s), 2.36(3H, s), 3.00 (6H, s), 3.10(3H, s), 6.66(1H, brs), 6.80(2H, d, J=9.2), 7.16(1H, s), 7.18–7.32(3H, m), 7.48(1H, d, J=8.5), 7.76(1H, dd, J=8.5, 3.1), 8.51(1H, d, J=3.1) |
| Ib-39 | 169–170° C., $^1$H-NMR(CDCl$_3$)δ2.67(3H, s), 3.06(6H, s), 3.13 (3H, s), 3.65(3H, s), 3.83(3H, s), 5.18(2H, s), 7.04(1H, dd, J=8.5, 3.0), 7.13(1H, d, J=8.5), 7.32–7.47(8H, m), 7.93(1H, d, J=8.5), 8.25(1H, d, J=3.0) |
| Ib-40 | 205–206° C., $^1$H-NMR(CDCl$_3$)δ1.73(3H, s), 1.81(3H, s), 3.06 (6H, s), 3.59(3H, s), 3.80(3H, s), 4.61(2H, d, J=6.8), 5.51(1H, t, J=6.8), 5.70(1H, brs), 5.87(1H, brs), 6.92(3H, s), 7.04–7.10(2H, m), 7.82(1H, d, J=8.5), 8.24(1H, d, J=1.8) |
| Ib-41 | 157–158° C., $^1$H-NMR(CDCl$_3$)δ1.74(3H, s), 1.81(3H, s), 2.70 (3H, s), 3.05(6H, s), 3.21(3H, s), 3.61(3H, s), 3.81(3H, s), 4.61 (2H, d, J=6.8), 5.51(1H, t, J=6.8), 7.03–7.11(2H, m), 7.33(1H, dd, J=8.5, 2.0), 7.38(1H, d, J=2.0), 7.41(1H, s), 7.92(1H, d, J=8.5), 8.24(1H, d, J=2.0) |
| Ib-44 | 117–118° C., $^1$H-NMR(CDCl$_3$)δ1.76(3H, s), 1.80(3H, s), 2.29 (3H, s), 2.36(3H, s), 3.04(6H, s), 3.89(3H, s), 4.63(2H, d, J=6.8), 5.57(1H, br t, J=6.8), 6.86–6.95(3H, m), 7.08(1H, dd, J=2.9, 8.6), 7.14(1H, s), 7.31(1H, s), 7.32(1H, d, J=8.6), 8.22(1H, d, J=2.9) |
| Ib-46 | 216–218° C., $^1$H-NMR(CDCl$_3$)δ3.64(3H, s), 3.82(3H, s), 5.16 (2H, s), 5.73(1H, s), 5.77(1H, s), 6.94(1H, dd, J=8.5, 2.4), 7.07 (1H, s), 7.09(2H, d, J=6.7), 7.36–7.47(5H, m), 8.25(1H, d, J=8.5), 8.54(1H, dd, J=8.5, 2.4), 9.54(1H, d, J=2.4) |
| Ib-47 | 159–160° C., $^1$H-NMR(CDCl$_3$)δ2.63(3H, s), 3.14(3H, s), 3.73 (3H, s), 3.86(3H, s), 5.19(2H, s), 7.16(2H, d, J=8.5), 7.29–7.48 (6H, m), 7.56(1H, s), 8.35(1H, d J=9.1), 8.54(1H, d, J=9.1, 2.5), 9.54(1H, d, J=2.5) |
| Ib-49 | 194–195° C., $^1$H-NMR(CDCl$_3$)δ2.35(3H, s), 2.41(3H, s), 3.01 (6H, s), 6.80(2H, d, J=9.1), 7.20(1H, s), 7.26(2H, d, J=9.1), 7.37 (1H, s), 7.67(1H, d, J=9.1), 8.53(1H, dd, J=9.1, 2.5), 9.53(1H, d, J=2.4) |
| Ib-51 | 126–127° C., $^1$H-NMR(CDCl$_3$)δ2.25(3H, s), 2.32(3H, s), 3.01 (6H, s), 6.80(2H, d, J=8.5), 7.09(1H, s), 7.18(1H, s), 7.22–7.29 (2H, m), 7.38(1H, d, J=8.5), 7.66(1H, dd, J=8.0, 2.4), 8.76(1H, d, J=2.4) |
| Ib-54 | 162–163° C., $^1$H-NMR(CDCl$_3$)δ1.76(3H, s), 1.82(3H, s), 3.48 (3H, s), 3.76(3H, s), 4.62(2H, d, J=6.8), 5.53(1H, t, J=6.8), 5.72 (1H, s), 5.81(1H, s), 6.47(1H, s), 6.94–6.99(2H, m), 7.04(1H, s), 7.37–7.68(4H, m), 7.99(1H, dd, J=6.1, 1.8)8.62(1H, d, J=4.9), 8.89(1H, d, J=1.8), |
| Ib-58 | oil, $^1$H-NMR(CDCl$_3$)δ1.76(3H, s), 1.80(3H, s), 2.28(3H, s), 2.30 (3H, s), 3.89(3H, s), 4.64(2H, d, J=6.7), 5.57(1H, br t, J=6.7), 6.86–6.96(3H, m), 7.13(1H, s), 7.19(1H, s), 7.36(1H, dd, J=8.2, 4.9), 7.70(1H, dt, J=1.8, 8.2), 8.60(1H, dd, J=4.9, 1.8), 8.65(1H, d, J=1.8) |
| Ib-65 | 180–181° C., $^1$H-NMR(CDCl$_3$)δ2.28(3H, s), 2.31(3H, s), 3.00 (6H, s), 4.45(2H, br s), 6.57(1H, d, J=9.1), 6.80(2H, d, J=9.1), 7.09(1H, s), 7.15(1H, s), 7.25(2H, dd, J=8.0, 2.4), 7.47(1H, d, J=8.5, 2.4), 8.10(1H, d, J=2.4) |
| Ib-67 | 185–188° C. $^1$H-NMR(CDCl$_3$)δ2.07(3H, s), 2.21(3H, s), 2.28 (3H, s), 3.00(6H, s), 4.41(2H, brs), 6.41(1H, d, J=7.8), 6.80(2H, d, J=9.2), 6.97(1H, s), 7.12(1H, s), 7.22–7.29(3H, m) |

TABLE 105

| | |
|---|---|
| Ib-69 | mp 184–185.5° C.; $^1$H NMR(CDCl$_3$)δ1.75(s, 3H), 1.77(s, 3H), 2.29(s, 3H), 2.30(s, 3H), 3.00(s, 6H), 3.90(br t, J=5.6Hz, 2H), 4.45(br s, 1H), 5.37(br t, J 5.6Hz, 1H), 6.45(dd, J=0.5, 8.5Hz, 1H), 6.80(d, J=8.8Hz, 2H), 7.10(s, 1H), 7.15(s, 1H), 7.27(d, J=8.8Hz, 2H), 7.47(dd, J=2.4, 8.5Hz, 1H), 8.13(dd, J=0.5, 2.4Hz, 1H) |
| Ib-71 | 118–119° C., $^1$H-NMR(CDCl$_3$)δ1.73(3H, s), 1.76(3H, s), 2.08 (3H, s), 2.20(3H, s), 2.28(3H, s), 3.00(6H, s), 3.83(2H, d, J=6.8), 4.81(1H, brs), 5.35(1H, t, J=6.7), 6.29(1H, d, J=8.5), 6.79(2H, d, J=8.5), 6.97(1H, s), 7.12(1H, s), 7.24–7.29(3H, m) |
| Ib-73 | 196–197° C., $^1$H-NMR(CDCl$_3$)δ2.25(3H, s), 2.27(3H, s), 2.32 (3H, s), 3.02(6H, s), 6.86(2H, d, J=8.5), 7.11(1H, s), 7.17(1H, s), 7.28(2H, d, J=8.5), 7.75(1H, dd, J=8.0, 2.4), 8.19(1H, brs), 8.25–8.28(2H, m) |
| Ib-75 | 169–171° C., $^1$H-NMR(CDCl$_3$)δ2.05(3H, s), 2.22(3H, s), 2.27 (3H, s), 2.29(3H, s), 3.01(6H, s), 6.80(2H, d, J=8.5), 6.97(1H, s), 7.14(1H, s), 7.28(1H, d, J=8.5), 7.49(1H, d, J=8.5), 7.92(1H, brs), 8.05(1H, d, J=8.5) |
| Ib-79 | 149–152° C., $^1$H-NMR(CDCl$_3$)δ2.07(3H, s), 2.28(3H, s), 2.29 (3H, s), 3.00(6H, s), 3.19(3H, s), 6.80(2H, d, J=9.1), 6.94(1H, s), 7.03(1H, s), 7.15(1H, s), 7.24–7.27(2H, m), 7.47(1H, d, J=8.5) |
| Ib-81 | 164–165° C., $^1$H-NMR(CDCl$_3$)δ2.69(3H, s), 3.12(3H, s), 3.16 (6H, s), 3.59(3H, s), 3.77(3H, s), 5.18(2H, s), 6.59(1H, d, J= |

TABLE 105-continued

| | |
|---|---|
| | 8.5), 6.84(1H, s), 7.14(1H, d, J=8.5), 7.32–7.48(7H, m), 7.84 (1H, dd, J=8.5, 2.4), 8.40(1H, d, J=2.4) |
| Ib-82 | 72–74° C., $^1$H-NMR(CDCl$_3$)δ1.75(3H, s), 1.82(3H, s), 3.16 (6H, s), 3.52(3H, s), 3.74(3H, s), 4.62(2H, d, J=6.8), 5.52(1H, t, J=6.8), 5.68(1H, s), 5.85(1H, s), 6.45(1H, s), 6.61(1H, d, J=9.1), 6.94(2H, d, J=1.8), 7.05(1H, d, J=1.2), 7.81(1H, dd, J=8.5, 2.4) 8.46(1H, d, J=2.4), |
| Ib-83 | 132–133° C., $^1$H-NMR(CDCl$_3$)δ1.75(3H, s), 1.81(3H, s), 2.71 (3H, s), 3.15(6H, s), 3.25(3H, s), 3.61(3H, s), 3.77(3H, s), 4.62 (2H, d, J=6.8), 5.52(1H, t, J=6.8), 6.59(1H, d, J=8.5), 6.83(1H, s), 7.07(1H, d, J=8.5), 7.38(1H, dd, J=8.5, 1.8), 7.38(1H, d, J=1.8), 7.83(1H, dd, J=6.1, 1.2), 8.39(1H, d, J=1.2) |
| Ib-90 | 91–91.5° C., $^1$H-NMR(CDCl$_3$)δ1.79(3H, s), 1.82(3H, s), 2.27 (3H, s), 2.31(3H, s), 3.00(6H, s), 4.87(2H, d, J=7.1), 5.57(1H, br t, J=7.1), 6.79–6.83(3H, m), 7.10(1H, s), 7.16(1H, s), 7.27 (2H, d, J=8.8), 7.59(1H, dd, J=2.4, 8.3), 8.17(1H, dd, J=0.7, 2.4) |
| Ib-99 | 239–241° C., $^1$H-NMR(CDCl$_3$)δ2.28(3H, s), 2.34(3H, s), 3.02 (6H, s), 3.30(3H, s), 6.81(2H, d, J=8.8), 7.26(2H, d, J=8.8), 7.95(1H, dd, J=2.2, 8.0), 8.15(1H, dd, J=0.7, 8.0), 8.75(1H, dd, J=0.7, 2.2) |
| Ib-101 | 159–160° C., $^1$H-NMR(CDCl$_3$)δ1.76(3H, s), 1.82(3H, s), 3.50 (3H, s), 3.76(3H, s), 4.62(2H, d, J=6.8), 5.53(1H, t, J=6.8), 5.73(1H, s), 5.84(1H, s), 6.48(1H, s), 6.91–6.99(2H, m), 7.04 (1H, d, J=1.8), 7.59(2H, d, J=5.5), 8.70(2H, d, J=5.5) |
| Ib-105 | 113–114° C., 2.28(3H, s), 2.29(3H, s), 3.91(3H, s), 5.21(2H, s), 6.83(1H, dd, J=2.0, 8.3), 6.90(1H, d, J=2.0), 6.95(1H, d, J=8.3), 7.12(1H, s), 7.17(1H, s), 7.30(2H, d, J=6.1), 7.31–7.50(5H, m), 8.65(2H, d, J=6.1) |
| Ib-124 | 157–158° C., $^1$H-NMR(CDCl$_3$)δ1.76(3H, s), 1.82(3H, s), 3.66 (3H, s), 3.80(3H, s), 4.05(3H, s), 4.62(2H, d, J=6.8), 5.52(1H, t, J=6.8), 5.72(1H, s), 5.78(1H, s), 6.89–6.98(2H, m), 7.03(1H, d, J=1.8)7.09(1H, s), 7.45(1H, d, J=1.2)8.89(1H, d, J=1.2) |

TABLE 106

| | |
|---|---|
| Ib-127 | 99–100° C., $^1$H-NMR(CDCl$_3$)δ2.32(3H, s), 2.40(3H, s), 3.03 (6H, s), 4.04(3H, s), 6.79(2H, d, J=8.7), 6.87(1H, s), 7.16(1H, s), 7.25(2H, d, J=7.3), 7.34(1H, s), 8.86(1H, d, J=2.2) |
| Ib-145 | 184–185° C., $^1$H-NMR(CDCl$_3$)δ2.60(3H, s), 3.14(3H, s), 3.71 (3H, s), 3.84(3H, s), 5.19(2H, s), 7.16(1H, d, J=7.9), 7.33(7H, m), 7.58(1H, d, J=8.6), 7.59(1H, s), 8.24(1H, d, J=9.2) |
| Ib-146 | 154–155° C., $^1$H-NMR(CDCl$_3$)δ1.76(3H, s), 1.82(3H, s), 3.62 (3H, s), 3.80(3H, s), 4.62(2H, d, J=6.8), 5.53(1H, t, J=6.8), 5.69(1H, s), 5.76(1H, s), 6.89–7.03(3H, m), 7.12(1H, s), 7.57 (1H, d, J=8.5)8.14(1H, d, J=9.2) |
| Ib-147 | 195–196° C., $^1$H-NMR(CDCl$_3$)δ1.77(3H, s), 1.81(3H, s), 2.64 (3H, s), 3.26(3H, s), 3.71(3H, s), 3.84(3H, s), 4.64(2H, d, J=6.8), 5.49(1H, t, J=6.8), 7.10(1H, d, J=8.6), 7.34(1H, dd, J=8.5, 1.8), 7.39(1H, d, J=1.8)7.59(1H, s), 7.58(1H, d, J=9.2), 8.23(1H, d, J=9.2) |
| Ib-150 | 197–198° C., $^1$H-NMR(CDCl$_3$)δ2.34(3H, s), 2.39(3H, s), 3.01 (6H, s), 6.81(2H, d, J=9.1), 7.21(1H, s), 7.26(2H, d, J=8.5), 7.34(1H, s), 7.58(2H, d, J=4.2) |
| Ib-154 | 185–186° C., $^1$H-NMR(CDCl$_3$)δ2.61(3H, s), 3.14(3H, s), 3.25 (6H, s), 3.67(3H, s), 3.81(3H, s), 5.19(2H, s), 6.85(1H, d, J=9.7), 7.14(1H, d, J=8.8), 7.33–7.48(7H, m), 7.65(1H, s), 8.02 (1H, d, J=9.7) |
| Ib-162 | 188–189° C., $^1$H-NMR(CDCl$_3$)δ1.76(3H, s), 1.82(3H, s), 3.60 (3H, s), 3.79(3H, s), 4.21(3H, s), 4.62(2H, d, J=6.8), 5.52(1H, t, J=6.8), 5.69(1H, s), 5.72(1H, s), 6.91–7.07(4H, m), 7.13(1H, s), 8.06(1H, d, J=9.8) |
| Ib-165 | 152–153° C., $^1$H-NMR(CDCl$_3$)δ2.33(3H, s), 2.39(3H, s), 3.01 (6H, s), 4.19(3H, s), 6.80(2H, d, J=9.1), 7.03(1H, d, J=9.1), 7.19(1H, s), 7.26(2H, d, J=7.8), 7.33(1H, s), 7.53(1H, d, J=9.1) |
| Ib-168 | oil, $^1$H-NMR(CDCl$_3$)δ1.77(3H, s), 1.82(3H, s), 3.65(3H, s), 3.81(3H, s), 4.63(2H, d, J=6.7), 5.53(1H, br t, J=6.7), 5.74(1H, s), 5.77(1H, s), 6.92–6.99(3H, m), 7.04(1H, d, J=1.8), 8.53(1H, d, J=1.8), 8.69(1H, s), 9.25(1H, s) |
| Ib-169 | 165–166° C., $^1$H-NMR(CDCl$_3$)δ1.77(3H, s), 1.81(3H, s), 2.72 (3H, s), 3.24(3H, s), 3.77(3H, s), 3.84(3H, s), 4.64(2H, d, J=6.8), 5.49(1H, t, J=6.8), 7.10(1H, d, J=8.5), 7.35(1H, dd, J=8.5, 2.4), 7.41(1H, d, J=2.4), 7.45(1H, s), 8.57(1H, s), 8.69(1H, s), 9.32(1H, s) |

TABLE 106-continued

| | |
|---|---|
| Ib-188 | 165–168° C., $^1$H-NMR(CDCl$_3$)δ2.29(3H, s), 2.42(3H, s), 3.00 (6H, s), 4.46(2H, br s), 5.31(1H, s), 6.78(2H, d, J=8.5), 7.11 (1H, s), 7.23(2H, d, J=7.38(1H, s), |
| Ib-198 | 103–104° C., $^1$H-NMR(CDCl$_3$)δ2.28(3H, s), 2.43(3H, s), 2.99 (6H, s), 3.50(2H, br s), 3.74(3H, s), 5.76(1H, s), 6.79(2H, d, J=8.5), 7.09(1H, s), 7.24(2H, d, J=8.5), 7.43(1H, s) |
| Ib-200 | oil, $^1$H-NMR(CDCl$_3$)δ1.73(3H, s), 1.76(3H, s), 2.29(3H, s), 2.46(3H, s), 2.99(6H, s), 3.16(1H, brs), 3.68(3H, s), 3.70(2H, d, J=5.5), 5.37(1H, br t, J=5.5), 5.67(1H, s), 6.79(2H, d, J=9.2), 7.10(1H, s), 7.24(2H, d, J=9.2), 7.44(1H, s) |
| Ib-202 | 174–177° C. $^1$H-NMR(CDCl$_3$)δ2.31(3H, s), 2.43(3H, s), 3.01 (6H, s), 3.12(3H, s), 3.93(3H, s), 6.25(1H, br s), 6.37(1H, s), 6.79(2H, d, J=8.5), 7.10(1H, s), 7.25(2H, d, J=8.5), 7.42(1H, s) |
| Ib-203 | 234–235° C., $^1$H-NMR(CDCl$_3$)δ3.89(3H, s), 3.95(3H, s), 5.17 (2H, s), 5.56(1H, brs), 5.74(1H, brs), 6.92(1H, dd, J=8.2, 2.0), 7.05–7.07(2H, m), 7.39–7.53(7H, m), 7.58(1H, s), 7.95(1H, d, J=8.0), 8.11(1H, d, J=8.3), |

TABLE 107

| | |
|---|---|
| Ib-204 | 197–198° C., $^1$H-NMR(CDCl$_3$)δ2.68(3H, s), 3.14(3H, s), 3.93 (3H, s), 4.05(3H, s), 5.20(2H, s), 7.16(1H, d, J=7.3), 7.37–7.53 (9H, m), 7.96(1H, d, J=7.3), 8.06(1H, s), 8.11(1H, d, J=8.0) |
| Ib-205 | 189–190° C., $^1$H-NMR(CDCl$_3$)δ1.77(3H, s), 1.83(3H, s), 3.89 (3H, s), 3.95(3H, s), 4.63(2H, d, J=6.8), 5.53(1H, t, J=6.8), 5.55 (1H, s), 5.76(1H, s), 6.89–7.03(3H, m), 7.41(1H, td, J=7.3, 1.2), 7.52(1H, td, J=7.3, 1.2), 7.58(1H, s), 7.95(1H, d, J=7.3), 8.11(1H, d, J=7.3) |
| Ib-206 | 166–167° C., $^1$H-NMR(CDCl$_3$)δ1.77(3H, s), 1.81(3H, s), 2.72 (3H, s), 3.25(3H, s), 3.93(3H, s), 4.05(3H, s), 4.65(2H, d, J=6.8), 5.49(1H, t, J=6.8), 7.10(1H, d, J=8.5), 7.36–7.53(4H, m), 7.96(1H, d, J=7.3), 8.05(1H, s), 8.11(1H, d, J=8.5) |
| Ib-207 | mp 75–78° C.; $^1$H NMR(CDCl$_3$)δ1.75(s, 3H), 1.76(s, 3H), 1.77 (s, 3H), 1.81(s, 3H), 2.27(s, 3H), 2.36(s, 3H), 3.75(d, J=6.6Hz, 2H), 4.63(d, J=6.6Hz, 2H), 5.33–5.36(m, 1H), 5.52–5.57(m, 1H), 6.93–7.11(m, 5H), 7.24–7.30(m, 2H), 8.12(d, J=2.4Hz, 1H)IR(KBr): 3405, 2970, 2924, 1596, 1570, 1521, 1493, 1466, 1386, 1363, 1299, 1282, 1235, 1196, 1126, 1079, 964 cm$^{-1}$ |
| Ib-208 | mp 100–102° C.; $^1$H NMR(CDCl$_3$)δ1.76(s, 3H), 1.81(s, 3H), 2.27(s, 3H), 2.34(s, 3H), 3.73(br s, 3H), 4.63(d, J=6.6Hz, 2H), 5.53–5.58(m, 1H), 7.00–7.11(m, 5H), 7.23–7.29(m, 2H), 8.20(d, J=2.4Hz, 1H)IR(KBr): 3422, 3326, 3202, 2973, 2923, 1618, 1563, 1517, 1484, 1383, 1309, 1298, 1267, 1256, 1230, 1125, 1000 cm$^{-1}$ |
| Ib-209 | mp 107–108° C.; $^1$H NMR(CDCl$_3$)δ1.77(s, 3H), 1.81(s, 3H), 2.31(s, 3H), 2.40(s, 3H), 4.64(d, J=6.6Hz, 2H), 5.52–5.58(m, 1H), 7.02–7.11(m, 3H), 7.18(s, 1H), 7.37(s, 1H), 7.66(d, J=8.7Hz, 1H), 8.54(dd, J=2.4, 8.4Hz, 1H), 9.53(d, J=2.1Hz, 1H) IR(KBr): 3440, 2969, 1592, 1572, 1517, 1497, 1460, 1346, 1314, 1294, 1264, 1233, 1195, 1128, 990 cm$^{-1}$ |
| Ib-210 | Oil; $^1$H NMR(CDCl$_3$)δ1.77(s, 3H), 1.82(s, 3H), 2.29(s, 3H), 2.36(s, 3H), 4.56(d, J=6.6Hz, 2H), 5.54(t, J=6.6Hz, 1H), 6.97(d, J=8.1Hz, 2H), 7.15(s, 1H), 7.25(m, 1H), 7.28(d, J=8.1Hz, 2H), 7.32(s, 1H), 7.45(d, J=7.5Hz, 1H), 7.75(td, J=7.5, 1.8Hz, 1H), 8.71(d, J=5.1Hz, 1H). |
| Ib-211 | mp 91–92° C.; $^1$H NMR(CDCl$_3$)δ1.77(s, 3H), 1.81(s, 3H), 2.29 (s, 3H), 2.36(s, 3H), 4.64(d, J=6.6Hz, 2H), 5.55(t, J=6.6Hz, 1H), 6.98–7.15(m, 4H), 7.25(m, 1H), 7.32(s, 1H), 7.45(m, 1H)7.,75(m, 1H), 8.71(m, 1H); IR(KBr)1584, 1566, 1520, 1498, 1469, 1460, 1433, 1422, 1385, 1302, 1278, 1267, 1234, 1129, 998 cm$^{-1}$. |
| Ib-212 | mp 120–122° C.; $^1$H NMR(CDCl$_3$)δ1.13–1.25(m, 4H), 1.62–1.90(m, 4H), 1.77(s, 3H), 1.81(s, 3H), 2.03–2.16(m, 2H), 2.27 (s, 3H), 2.36(s, 3H), 3.31(m, 3H), 4.63(d, J=6.6Hz, 2H), 5.55(t, J=6.6Hz, 1H), 6.90–7.13(m, 5H), 7.21–7.32(m, 2H), 8.10(m, 1H); IR(KBr)3392, 1591, 1516, 1482, 1298, 1274, 1262, 1231, 1136, 1124, 994, 835 cm$^{-1}$. |
| Ib-213 | $^1$H NMR(CDCl$_3$)δ1.77(s, 3H), 1.82(s, 3H), 2.16(s, 6H), 2.27(s, 3H), 3.85(s, 3H), 4.63(d, J=6.6Hz, 2H), 5.53–5.58(m, 1H), 6.98–7.13(m, 4H), 7.22–7.30(m, 3H), 8.31(t, J=3.0Hz, 1H),; IR(neat): 2960, 2918, 1579, 1496, 1294, 1117, 991, 753 cm$^{-1}$ |
| Ib-214 | $^1$H NMR(CDCl$_3$)δ1.69(s, 3H), 1.74(s, 3H), 1.77(s, 3H), 1.81(s, 3H), 2.17(s, 3H), 2.26(s, 3H), 4.56(d, J=6.6Hz, 2H), 4.63(d, |

TABLE 107-continued

J=6.9Hz, 2H), 5.34–5.39(m, 1H), 5.53–5.58(m, 1H), 7.97–7.13(m, 4H), 7.21–7.29(m, 3H), 8.30(dd, J=1.5, 4.5Hz, 1H),; IR(neat): 2968, 2914, 1577, 1516, 1495, 1267, 1229, 1117, 995, 841, 782 cm$^{-1}$

TABLE 108

Ib-215  mp 134–136° C.; $^1$H NMR(CDCl$_3$)δ1.77(s, 3H); 1.82(s, 3H); 1.93(s, 6H); 1.94(s, 6H); 3.78(br s, 2H); 4.64(d, J=6.6Hz, 2H); 5.57(m, 1H); 6.73–7.13(m, 5H); 8.24(m, 1H); IR(KBr): 3465, 3333, 3216, 2920, 1633, 1512, 1493, 1461, 1296, 1262, 1242, 1209, 1115 cm$^{-1}$.

Ib-216  mp 124–126° C.; $^1$H NMR(CDCl$_3$)δ1.76(s, 3H); 1.77(s, 3H); 1.79(s, 3H); 1.82(s, 3H); 1.93(s, 6H); 1.95(s, 6H); 3.74(br, 1H); 3.77(d, J=6.3Hz, 2H); 4.64(d, J=6.9Hz, 2H); 5.38(m, 1H); 5.57(m, 1H); 6.73–7.10(m, 5H); 8.14(d, J=2.7Hz, 1H); IR(KBr): 3272, 2913, 1596, 1509, 1466, 1302, 1261, 1240, 1209, 1115 cm$^{-1}$.

Ib-217  mp 103–110° C.; $^1$H NMR(CDCl$_3$)δ1.77(s, 3H); 1.82(s, 3H); 1.91(s, 6H); 1.93(s, 6H); 4.64(d, J=6.6Hz, 2H); 5.57(m, 1H); 6.74–7.23(m, 5H); 8.28(d, J=2.7Hz, 1H); IR(KBr): 3441, 2921, 1570, 1514, 1462, 1298, 1264, 1241, 1210, 1113, 1004 cm$^{-1}$.

Ib-218  mp 109–110° C.; $^1$H NMR(CDCl$_3$)δ1.78(s, 3H), 1.82(s, 3H), 3.77(s, 3H), 3.78(s, 3H), 4.87(d, J=7.2Hz, 2H), 5.57(m, 1H), 6.45–6.55(m, 2H), 6.81(d, J=8.7, Hz, 1H), 6.83(s, 1H), 6.91(s, 1H), 7.19(t, J=8.1Hz, 1H), 7.83(dd, J=8.7, 2.4Hz, 1H), 8.37(d, J=2.4Hz, 1H)IR(KBr): 3425, 3348, 3223, 1634, 1604, 1524, 1484, 1463, 1443, 1396, 1359, 1279, 1209, 1053, 1032, 1003, 867, 832, 782, 661 cm$^{-1}$

Ib-219  mp 99–100° C.; $^1$H NMR(CDCl$_3$)δ1.25(d, J=6.3Hz, 6H), 1.78(s, 3H), 1.81(s, 3H), 3.63(m, 1H), 3.77(s, 3H), 3.79(s, 3H), 4.87(d, J=6.9Hz, 2H), 5.57(m, 1H), 6.33–6.47(m, 2H), 6.81(d, J=8.7Hz, 1H), 6.92(s, 2H), 7.20(t, J=8.4Hz, 1H), 7.83(dd, J=8.7, 2.4Hz, 1H), 8.36(d, J=2.4Hz, 1H)IR(KBr): 3408, 1627, 1599, 1526, 1502, 1477, 1280, 1246, 1210, 1182, 1133, 1121, 1054, 1030, 968, 869, 837, 783, 668 cm$^{-1}$

Ib-220  mp 139–145° C.; $^1$H NMR(CDCl$_3$)δ1.25(d, J=6.6Hz, 6H), 1.79(s, 3H), 1.82(s, 3H), 3.79(s, 3H), 3.80(s, 3H), 4.53(m, 1H), 4.61(s, 3H), 4.88(d, J=6.9Hz, 2H), 5.57(m, 1H), 6.82(d, J=9.0, Hz, 1H), 6.93(s, 1H), 6.96(s, 1H), 7.14–7.24(m, 1H), 7.45(m, 1H), 7.84(dd, J=9.0, 2.1Hz, 1H), 8.37(d, J=2.1Hz, 1H). IR(KBr): 3377, 3273, 1656, 1605, 1564, 1520, 1484, 1465, 1394, 1339, 1282, 1207, 1055, 1033, 1008, 984, 871, 829, 779, 688, 653, 602, 541 cm$^{-1}$

Ib-221  mp 137–138° C.; $^1$H NMR(CDCl$_3$)δ1.24(d, J=6.9Hz, 6H), 1.79(s, 3H), 1.82(s, 3H), 2.78(d, J=5.4Hz, 3H), 3.79(s, 3H), 3.81(s, 3H), 4.17(q, J=5.4Hz, 2H), 4.44(m, 1H), 4.88(d, J=7.2Hz, 2H), 5.57(m, 1H), 6.82(d, J=8.7Hz, 1H), 6.93(s, 1H), 6.96(s, 1H), 7.12–7.22(m, 2H), 7.44(t, J=8.1Hz, 1H), 7.84(dd, J=8.7, 2.7Hz, 1H), 8.38(d, J=2.7Hz, 1H)IR(KBr): 3294, 1604, 1566, 1519, 1484, 1464, 1395, 1334, 1281, 1208, 1187, 1153, 1103, 1055, 1035, 1007, 981, 870, 829, 779, 688 cm$^{-1}$

Ib-222  mp 79–80° C.; $^1$H NMR(CDCl$_3$)δ1.73(s, 3H), 1.77(s, 3H), 1.78(s, 3H), 1.81(s, 3H), 3.71(d, J=6.6Hz, 2H), 3.77(s, 3H), 3.79(s, 3H), 4.87(d, J=8.4Hz, 2H), 5.35(m, 1H), 5.57(m, 1H), 6.36–6.48(m, 2H), 6.81(d, J=8.4, Hz, 1H), 6.92(s, 2H), 7.21(t, J=8.4Hz, 1H), 7.83(dd, J=8.4, 2.4Hz, 1H), 8.37(d, J=2.4Hz, 1H) IR(KBr): 3416, 1629, 1603, 1570, 1526, 1464, 1395, 1278, 1209, 1051, 1034, 1006, 869, 830, 777, 666 cm$^{-1}$

TABLE 109

Ib-223  mp 103–104° C.; $^1$H NMR(CDCl$_3$)δ1.56(s, 3H), 1.72(s, 3H), 1.78(s, 3H), 1.82(s, 3H), 2.79(d, J=5.1Hz, 3H), 3.78(s, 3H), 3.79(s, 3H), 4.22(q, J=5.1Hz, 1H), 4.28(d, J=6.9Hz, 2H), 4.88(d, J=6.6Hz, 2H), 5.30(m, 1H), 5.57(m, 1H), 6.82(d, J=8.1Hz, 1H), 6.91(s, 2H), 6.95(s, 1H), 7.17–7.26(m, 1H), 7.37–7.44(m, 1H), 7.83(dd, J=8.1, 2.4Hz, 1H), 8.37(d, J=2.4Hz, 1H) IR(KBr): 3404, 3313, 1604, 1566, 1520, 1484, 1465, 1395, 1335, 1282, 1209, 1153, 1127, 1055, 1034, 867, 828, 669 cm$^{-1}$

Ib-224  mp 95–96° C.; $^1$H NMR(CDCl$_3$)δ1.70(s, 3H), 1.82(s, 3H), 2.27(s, 3H), 3.82(br, 2H), 4.87(d, J=7.2Hz, 2H), 5.57(m, 1H), 6.64–6.55(m, 2H), 6.81(d, J=8.4, Hz, 1H), 7.50(t, J=8.1Hz, 1H), 7.11(s, 1H), 7.12(s, 1H), 7.59(dd, J=8.4, 2.4Hz, 1H), 8.17(d, J=2.4Hz, 1H)IR(KBr): 3436, 3328, 3218, 1634, 1622, 1606, 1566, 1522, 1480, 1460, 1444, 1396, 1362, 1304, 1285, 1245, 1168, 1129, 1008, 834 cm$^{-1}$

Ib-225  mp 90–91° C.; $^1$H NMR(CDCl$_3$)δ1.26(d, J=6.3Hz, 2H), 1.79(s, 3H), 1.82(s, 3H), 2.22(s, 3H), 2.26(s, 3H), 3.64(m, 1H), 4.87(d, J=7.5Hz, 2H), 5.57(m, 1H), 6.33–6.47(m, 2H), 6.81(d, J=8.4, Hz, 1H), 7.05(t, J=8.1Hz, 1H), 7.10(s, 1H), 7.13(s, 1H), 7.59(dd, J=8.4, 2.4Hz, 1H), 8.17(d, J=2.4Hz, 1H)IR(KBr): 3335, 1628, 1606, 1527, 1481, 1283, 1240, 1183, 1116, 989, 835, 812, 635 cm$^{-1}$

Ib-226  mp 87–88° C.; $^1$H NMR(CDCl$_3$)δ0.91–1.09(m, 2H), 1.13–1.36(m, 4H), 1.40–1.92(m, 5H), 1.79(s, 3H), 1.82(s, 3H), 2.22(s, 3H), 2.26(s, 3H), 2.98(d, J=6.6Hz, 2H), 4.87(d, J=7.2Hz, 2H), 5.57(m, 1H), 6.32–6.46(m, 2H), 6.80(d, J=8.4Hz, 1H), 7.04(t, J=8.4Hz, 1H), 7.10(s, 1H), 7.12(s, 1H), 7.59(dd, J=8.4, 2.4Hz, 1H), 8.17(d, J=2.4Hz, 1H)IR(KBr): 3444, 1628, 1603, 1573, 1524, 1481, 1459, 1358, 1278, 1242, 1168; 1117, 1006, 974, 825 cm$^{-1}$.

Ib-227  mp 76–77° C.; $^1$H NMR(CDCl$_3$)δ1.55(s, 3H), 1.71(s, 3H), 1.79(s, 3H), 1.82(s, 3H), 2.19(s, 3H), 2.28(s, 3H), 2.80(d, J=5.4Hz, 3H), 4.20(q, J=5.4Hz, 1H), 4.27(d, J=7.2Hz, 2H), 4.87(d, J=7.2Hz, 2H), 5.29(m, 1H), 5.57(m, 1H), 6.82(d, J=8.1Hz, 1H), 7.13(s, 2H), 7.16–7.31(m, 3H), 7.59(dd, J=8.1, 2.4Hz, 1H), 8.17(d, J=2.4Hz, 1H)IR(KBr): 3314, 1605, 1562, 1514, 1481, 1346, 1328, 1307, 1283, 1154, 1125, 1072, 1003, 854, 831, 703, 666, cm$^{-1}$.

Ib-228  foam; $^1$H NMR(CDCl$_3$)δ1.00–1.74(m, 11H), 1.79(s, 3H), 1.82(s, 3H), 2.13(s, 3H), 2.27(s, 3H), 2.98(d, J=6.6Hz, 2H), 4.87(d, J=6.9Hz, 2H), 5.54–5.60(m, 1H), 6.53(dd, J=2.4, 8.1Hz, 1H), 6.68(d, J=2.7Hz, 1H), 6.80(d, J=7.8Hz, 1H), 7.01(d, J=8.4Hz, 1H), 7.06(s, 1H), 7.10(s, 1H), 7.60(dd, J=2.4, 8.4Hz, 1H), 8.18(d, J=2.1Hz, 1H)IR(KBr): 3413, 2926, 2853, 1607, 1517, 1479, 1449, 1376, 1281, 1240, 1033, 977 cm$^{-1}$.

Ib-229  mp 110–112° C.; $^1$H NMR(CDCl$_3$)δ1.17–1.79(m, 8H), 1.79(s, 3H), 1.82(s, 3H), 2.07–2.14(m, 2H), 2.14(s, 3H), 2.26(s, 3H), 3.23–3.30(m, 1H), 3.73(br s, 1H), 4.87(d, J=6.9Hz, 2H), 5.54–5.60(m, 1H), 6.52(dd, J=2.1, 8.1Hz, 1H), 6.68(d, J=2.7Hz, 1H), 6.80(d, J=8.7Hz, 1H), 7.01(d, J=8.4Hz, 1H), 7.06(s, 1H), 7.09(s, 1H), 7.60(dd, J=2.7, 8.7Hz, 1H), 8.18(d, J=1.8Hz, 1H)IR(KBr): 3411, 3310, 2926, 2852, 1607, 1517, 1479, 1376, 1357, 1302, 1284, 1241, 1013, 980 cm$^{-1}$

TABLE 110

Ib-230  mp oil; $^1$H NMR(CDCl$_3$)δ1.74(s, 3H), 1.78(s, 3H), 1.79(s, 3H), 1.82(s, 3H), 2.14(s, 3H), 2.27(s, 3H), 3.71(d, J=6.6Hz, 2H), 4.87(d, J=6.9Hz, 2H), 5.33–5.37(m, 1H), 5.55–5.60(m, 1H), 6.55(dd, J=2.4, 8.4Hz, 1H), 6.71(d, J=2.4Hz, 1H), 6.81(d, J=8.7Hz, 1H), 7.03(d, J=8.1Hz, 1H), 7.06(s, 1H), 7.09(s, 1H), 7.61(dd, J=2.7, 8.7Hz, 1H), 8.18(d, J=2.4Hz, 1H)IR(CDCl$_3$): 3017, 2975, 1607, 1517, 1479, 1378, 1358, 1282, 1240, 1227, 1220, 977 cm$^{-1}$ Ib-231  mp 137–139° C.; $^1$H NMR(CDCl$_3$)δ1.05–1.80(m, 8H), 1.79(s, 3H), 1.82(s, 3H), 2.05–2.12(m, 2H), 2.22(s, 3H), 2.26(s, 3H), 3.22–3.30(m, 1H), 3.75(br s, 1H), 4.87(d, J=7.2Hz, 2H), 5.54–5.60(m, 1H), 6.34–6.44(m, 2H), 6.81(d, J=9.0Hz, 1H), 7.03(d, J=8.4Hz, 1H), 7.10(s, 1H), 7.12(s, 1H), 7.59(dd, J=2.4, 8.4Hz, 1H), 8.17(d, J=2.7Hz, 1H)IR(KBr): 3331, 2924, 2852, 1628, 1605, 1526, 1481, 1452, 1425, 1375, 1334, 1302, 1283, 1241, 1176, 1114, 1016, 986 cm$^{-1}$ Ib-232  mp 108–109° C.; $^1$H NMR(CDCl$_3$)δ1.48–1.78(m, 6H), 1.79(s, 3H), 1.82(s, 3H), 2.00–2.09(m, 2H), 2.22(s, 3H), 2.26(s, 3H), 3.75–3.83(m, 3H), 3.84–3.90(m, 1H), 4.87(d, J=7.2Hz, 2H), 5.54–5.60(m, 1H), 6.35–6.45(m, 2H), 6.80(d, J=8.4Hz, 1H), 7.04(t, J=8.4Hz, 1H), 7.10(s, 1H), 7.12(s, 1H), 7.59(dd, J=2.7, 8.4Hz, 1H), 8.17(dd, J=0.6, 2.4Hz, 1H)IR(KBr): 3328, 2955, 2866, 1627, 1605, 1526, 1481, 1423, 1394, 1356, 1337, 1283, 1240, 1176, 1116, 1016, 974 cm$^{-1}$ Ib-233  mp 77–79° C.; $^1$H NMR(CDCl$_3$)δ1.00(d, J=0.6Hz, 3H), 1.02(d, J=0.6Hz, 3H), 1.79(s, 3H), 1.82(s, 3H), 1.86–1.99(m, 1H), 2.22(s, 3H), 2.26(s, 3H), 2.24(d, J=13.2Hz, 2H), 3.90(br s, 1H), 4.87(d, J=6.6Hz, 2H), 5.54–5.60(m, 1H), 6.34–6.50(m, 2H), 6.81(d, J=8.7Hz, 1H), 7.05(t, J=8.4Hz, 1H), 7.10(s, 1H), 7.12(s,

TABLE 110-continued

Ib-234 1H), 7.59–7.61(m, 1H), 8.16–8.17(m, 1H)IR(KBr): 3340, 2958, 2928, 2866, 1627, 1606, 1530, 1481, 1395, 1358, 1337, 1284, 1241, 1178, 1115, 1046, 991 cm$^{-1}$
Ib-234 mp 109–111° C.; $^1$H NMR(CDCl$_3$)δ1.25(t, J=7.2Hz, 3H), 1.78 (s, 3H), 1.82(s, 3H), 2.22(s, 3H), 2.26(s, 3H), 2.62–2.70(m, 2H), 4.19(br s, 1H), 4.31(s, 1H), 4.84(d, J=6.6Hz, 2H), 5.54–5.60(m, 1H), 6.39–6.50(m, 2H), 6.81(d, J=9.0Hz, 1H), 7.06(t, J=8.4Hz, 1H), 7.10(s, 1H); 7.12(s, 1H), 7.21(d, J=8.1Hz, 2H), 7.32(d, J=8.1Hz, 2H), 7.59(dd, J=2.7, 8.4Hz, 1H), 8.17(d, J= 1.8Hz, 1H)IR(KBr): 3286, 2967, 2927, 2871, 1628, 1598, 1529, 1481, 1469, 1376, 1356, 1336, 1274, 1237, 1173, 1149, 1121, 1003, 975 cm$^{-1}$
Ib-235 mp oil; $^1$H NMR(CDCl$_3$)δ1.26(s, 3H), 1.27(s, 3H), 1.79(s, 3H), 1.82(s, 3H),; 2.22(s, 3H), 2.26(s, 3H), 2.87–2.99(m, 1H), 4.31(s, 2H), 4.87(d, J=7.5Hz, 2H), 5.55–5.60(m, 1H), 6.40–6.51(m, 2H), 6.81(d, J=8.7Hz, 1H), 7.07(t, J=8.4Hz, 1H), 7.10(s, 1H), 7.12(s, 1H), 7.17(d, J=8.1Hz, 2H), 7.33(d, J=8.1Hz, 2H), 7.57–7.61(m, 1H), 8.16–8.18(m, 1H)IR(CDCl$_3$): 3010, 2964, 1628, 1603, 1523, 1480, 1357, 1282, 1241, 977 cm$^{-1}$
Ib-236 mp 203–204° C.; $^1$H NMR(CDCl$_3$)δ1.73(s, 3H), 1.75(s, 3H), 2.19(s, 3H), 2.21(s, 3H), 4.39(d, J=4.5Hz, 2H), 4.81(d, J=6.9Hz, 2H), 5.47–5.52(m, 1H), 6.48–6.49(m, 1H), 6.62(d, J=8.4Hz, 2H), 6.85(d, J=8.4Hz, 1H), 7.05–7.09(m, 4H), 7.50(d, J=8.1Hz, 2H), 7.71(dd, J=2.4, 8.7Hz, 1H), 7.92(d, J=8.1Hz, 2H), 8.13(d, J=2.1Hz, 1H)IR(KBr): 3422, 3004, 1686, 1609, 1523, 1482, 1423, 1392, 1377, 1356, 1283, 1240, 1182, 1124, 977 cm$^{-1}$

TABLE 111

Ib-237 mp 144–147° C.; $^1$H NMR(CDCl$_3$)δ1.79(s, 3H), 1.82(s, 3H), 2.26(s, 3H), 2.29(s, 3H), 3.92(s, 3H), 4.46(s, 3H), 4.46(s, 2H), 4.87(d, J=7.2Hz, 2H), 5.54–5.60(m, 1H), 6.65–6.70(m, 2H), 6.76(d, J=8.4Hz, 2H), 7.17–7.21(m, 2H), 7.47–7.50(m, 2H), 7.59(dd, J=2.7, 8.4Hz, 2H), 8.01–8.05(m, 2H), 8.16(d, J=2.7Hz, 1H)IR(KBr): 3366, 2951, 1709, 1609, 1523, 1478, 1469, 1437, 1313, 1282, 1235, 1180, 1115, 1105, 1019, 987 cm$^{-1}$
Ib-238 mp 75–76° C.; $^1$H NMR(CDCl$_3$)δ1.74(s, 3H), 1.77(s, 3H), 1.79 (s, 3H), 1.82(s, 3H), 2.06(s, 3H), 2.08(s, 3H), 2.25(s, 3H), 3.72(d, J=6.9Hz, 2H), 4.87(d, J=6.9Hz, 2H), 5.35–5.60(m, 1H), 6.49–6.55(m, 2H), 6.79–7.08(m, 4H), 7.60(dd, J=2.7, 8.4Hz, 1H), 8.18(dd, J=0.9, 2.7Hz, 1H)IR(KBr): 3331, 2965, 2916, 1610, 1522, 1480, 1449, 1393, 1302, 1283, 1251, 1240, 977 cm$^{-1}$
Ib-239 mp 87–89° C.; $^1$H NMR(CDCl$_3$)δ1.79(s, 3H), 1.82(s, 3H), 2.27(m, 3H), 2.30(s, 3H), 3.82(d, J=5.4Hz, 2H), 4.87(d, J= 6.9Hz, 2H), 5.18–5.36(m, 2H), 5.54–5.60(m, 1H), 5.93–6.06(m, 1H), 6.66–6.71(m, 2H), 6.80(d, J=8.7Hz, 1H), 7.10(s, 1H), 7.15(s, 1H), 7.17–7.22(m, 2H), 7.58(dd, J=2.4, 8.4Hz, 1H), 8.16(dd, J=0.6, 2.4Hz, 1H)IR(KBr): 3330, 3007, 2973, 2855, 1610, 1526, 1481, 1470, 1392, 1376, 1354, 1299, 1283, 1266, 1240, 1129, 1019, 988 cm$^{-1}$
Ib-240 mp 113–114° C.; $^1$H NMR(CDCl$_3$)δ1.79(s, 3H), 1.82(s, 3H), 2.25–2.27(m, 4H), 2.29(s, 3H), 3.99(d, J=2.4Hz, 2H), 4.87(d, J=5.1Hz, 2H), 5.50–5.60(m, 1H), 6.73–6.78(m, 2H), 6.81(dd, J=0.6, 8.4Hz, 1H), 7.09(s, 1H), 7.15(s, 1H), 7.21–7.25(m, 2H), 7.59(dd, J=2.7, 8.4Hz, 1H), 8.17(dd, J=0.6, 2.4Hz, 1H)IR(KBr): 3311, 3271, 2974, 2924, 1609, 1525, 1481, 1392, 1377, 1352, 1320, 1300, 1283, 1265, 1239, 1182, 1121, 987 cm$^{-1}$
Ib-241 mp 125–126° C.; $^1$H NMR(CDCl$_3$)δ0.94–1.87(m, 11H), 1.78(s, 3H), 1.82(s, 3H), 2.26(s, 3H), 2.30(s, 3H), 3.00(d, J=6.9Hz, 2H), 4.87(d, J=6.9Hz, 2H), 5.54–5.60(m, 1H), 6.60–6.67(m, 2H), 6.81(d, J=8.4Hz, 1H), 7.09(s, 1H), 7.15(s, 1H), 7.16–7.21(m, 2H), 7.58(dd, J=2.4, 8.4Hz, 1H), 8.17(dd, J=0.6, 2.1Hz, 1H)IR(KBr): 3356, 2919, 2851, 1613, 1528, 1482, 1470, 1447, 1395, 1355, 1325, 1299, 1284, 1262, 1241, 1182, 1020, 985 cm$^{-1}$
Ib-242 mp 173–175° C.; $^1$H NMR(CDCl$_3$)δ1.14–1.787(m, 8H), 1.78(s, 3H), 1.81(s, 3H), 2.08–2.12(m, 2H), 2.27(s, 3H), 2.30(s, 3H), 3.26–3.34(m, 1H), 4.87(d, J=7.2Hz, 2H), 5.54–5.60(m, 1H), 6.62–6.67(m, 2H), 6.81(dd, J=0.6, 8.4Hz, 1H), 7.09(s, 1H), 7.15(s, 1H), 7.15–7.19(m, 2H), 7.58(dd, J=2.4, 8.7Hz, 1H), 8.16(dd, J=0.6, 2.4Hz, 1H)IR(KBr): 3326, 2922, 2852, 1611, 1523, 1482, 1452, 1393, 1354, 1319, 1300, 1282, 1239, 1182, 1125, 983 cm$^{-1}$

TABLE 111-continued

Ib-243 mp 141–142° C.; $^1$H NMR(CDCl$_3$)δ1.78, 3H), 1.82(s, 3H), 2.26(s, 3H), 2.28(s, 3H), 4.27(br s, 1H), 4.43(br s, 2H), 4.87(d, J=7.2Hz, 2H), 5.54–5.60(m, 1H), 6.63–6.66(m, 2H), 6.81(d, J=8.4Hz, 1H), 7.09(s, 1H), 7.13(s, 1H), 7.17–7.20(m, 2H), 7.33–7.35(m, 2H), 7.57(dd, J=2.1, 8.4Hz, 1H), 8.16(d, J= 2.4Hz, 1H), 8.57–8.59(m, 2H)IR(KBr): 3279, 2972, 2925, 1603, 1522, 1479, 1459, 1418, 1375, 1351, 1318, 1282, 1272, 1240, 1179, 1120, 1001. cm$^{-1}$

TABLE 112

Ib-244 mp 123–125° C.; $^1$H NMR(CDCl$_3$)δ1.78(s, 3H), 1.82(s, 3H), 2.26(s, 3H), 2.29(s, 3H), 4.38(s, 2H), 4.87(d, J=6.9Hz, 2H), 5.54–5.60(m, 1H), 6.69–6.73(m, 2H), 6.81(dd, J=0.6, 8.4Hz, 1H), 7.09(s, 1H), 7.14(s, 1H), 7.17–7.22(m, 2H), 7.26–7.44(m, 5H), 7.58(dd, J=2.4, 8.4Hz, 1H), 8.16(d, J=1.8Hz, 1H)IR(KBr): 3348, 2966, 2921, 1613, 1527, 1482, 1469, 1453, 1394, 1356, 1326, 1297, 1285, 1264, 1241, 1020, 987 cm$^{-1}$
Ib-245 mp 137–138° C.; $^1$H NMR(CDCl$_3$)δ1.79(s, 3H), 1.82(s, 3H), 2.28(s, 6H), 3.33(s, 3H), 4.55(br s, 2H), 4.87(d, J=7.2Hz, 2H), 5.54–5.60(m, 1H), 6.81(dd, J=0.6, 8.7Hz, 1H), 7.12–7.14(m, 2H), 7.35–7.39(m, 2H), 7.44–7.49(m, 2H), 7.59(dd, J=2.4, 8.4Hz, 1H), 8.17(dd, J=0.6, 2.4Hz, 1H), IR(KBr): 3376, 3284, 2972, 2922, 1604, 1480, 1462, 1342, 1281, 1180, 1140, 999 cm$^{-1}$
Ib-246 mp 118–120° C.; $^1$H NMR(CDCl$_3$)δ1.78(s, 3H), 1.87(s, 3H), 2.26(s, 3H), 2.30(s, 3H), 4.39(s, 2H), 4.87(d, J=7.2Hz, 2H), 5.54–5.60(m, 1H), 6.70–6.73(m, 2H), 6.80(d, J=8.4Hz, 1H), 7.10–7.14(m, 3H), 7.15–7.24(m, 3H), 7.34(dd, J=3.0, 5.1Hz, 1H), 7.59(dd, J=2.4, 8.4Hz, 1H), 8.17(d, J=1.8Hz, 1H)IR(KBr): 3397, 2973, 2920, 2851, 1610, 1522, 1480, 1470, 1376, 1350, 1298, 1280, 1260, 1235, 1182, 1122, 980 cm$^{-1}$
Ib-247 mp 112–115° C.; $^1$H NMR(CDCl$_3$)δ1.79(s, 3H), 1.82(s, 3H), 2.27(s, 3H), 2.30(s, 3H), 4.22(s, 2H), 4.87(d, J=6.9Hz, 2H), 5.55–5.60(m, 1H), 6.44–6.45(m, 1H), 6.70–6.74(m, 2H), 6.81(dd, J=0.9, 8.4Hz, 1H), 7.09(s, 1H), 7.15(s, 1H), 7.18–7.23(m, 1H), 7.41–7.45(m, 1H), 7.59(dd, J=2.4, 8.7Hz, 1H), 8.17(dd, J=0.6, 2.4Hz, 1H), IR(KBr): 3338, 2924, 1613, 1526, 1501, 1482, 1471, 1394, 1355, 1317, 1298, 1285, 1241, 1156, 1020, 977 cm$^{-1}$
Ib-248 mp 123–125° C.; $^1$H NMR(CDCl$_3$)δ1.78(s, 3H), 1.81(s, 3H), 2.27(s, 3H), 2.29(s, 3H), 2.60(br s, 3H), 4.87(d, J=7.2Hz, 2H), 5.54–5.60(m, 1H), 6.73–6.77(m, 2H), 6.81(d, J=8.4Hz, 1H), 7.09(s, 1H), 7.14(s, 1H), 7.14–7.18(m, 2H), 7.59(dd, J=2.4, 8.4Hz, 1H), 8.17(d, J=2.4Hz, 1H), IR(KBr): 3449, 3341, 2972, 2925, 1623, 1604, 1521, 1481, 1394, 1359, 1281, 1241, 1128, 984 cm$^{-1}$
Ib-249 mp 70–72° C.; $^1$H NMR(CDCl$_3$)δ1.79(s, 3H), 1.82(s, 3H), 2.27 (s, 3H), 2.30(s, 3H), 2.89(s, 3H), 4.87(d, J=7.2Hz, 2H), 5.55–5.60(m, 1H), 6.66–6.71(m, 2H), 6.81(dd, J=0.9, 8.4Hz, 1H), 7.09(s, 1H), 7.15(s, 1H), 7.19–7.23(m, 2H), 7.59(dd, J=2.7, 8.4Hz, 1H), 8.17(dd, J=0.6, 2.4Hz, 1H), IR(KBr): 3356, 2923, 2883, 1614, 1603, 1529, 1482, 1393, 1357, 1320, 1298, 1282, 1264, 1241, 1182, 981 cm$^{-1}$
Ib-250 mp 87–88° C.; $^1$H NMR(CDCl$_3$)δ1.74(s, 3H), 1.78(s, 3H), 1.79 (s, 3H), 1.80(s, 3H), 2.22(s, 3H), 2.26(s, 3H), 3.71(d, J=6.9Hz, 2H), 4.87(d, J=7.2Hz, 2H), 5.32–5.37(m, 1H), 5.55–5.60(m, 1H), 6.35–6.47(m, 2H), 6.81(dd, J=0.6, 8.4Hz, 1H), 7.02–7.13(m, 3H), 7.59(dd, J=2.4, 8.4Hz, 1H), 8.16(dd, J=0.9, 5.7Hz, 1H), IR(Nujol): 3330, 2923, 2853, 1627, 1606, 1564, 1527, 1481, 1471, 1395, 1376, 1357, 1337, 1284, 1240, 1178, 1116, 990 cm$^{-1}$

TABLE 113

Ib-251 mp 102–103° C.; $^1$H NMR(CDCl$_3$)δ1.75(s, 3H), 1.79(s, 6H), 1.82(s, 3H), 2.19(s, 3H), 2.27(s, 3H), 2.31(s, 3H), 3.49(br s, 1H), 3.78(d, J=6.9Hz, 2H), 4.87(d, J=6.9Hz, 2H), 5.42(t, J= 6.9Hz, 1H), 5.57(t, J=7.2Hz, 1H), 6.68(d, J=8.1Hz, 1H), 6.80(d, J=8.4Hz, 1H), 7.09(s, 1H), 7.13–7.17(m, 2H), 7.59(dd, J=2.7, 8.4Hz, 1H), 8.17(d, J=2.4Hz, 1H); IR(KBr): 3363, 2969, 2918, 2884, 2854, 1609, 1601, 1517, 1482, 1468, 1442, 1378, 1283, 1250, 981, 891 cm$^1$.

TABLE 113-continued

Ib-252  mp 109–110° C.; $^1$H NMR(CDCl$_3$)δ1.79(s, 3H), 1.82(s, 3H), 2.23(s, 3H), 2.27(s, 3H), 2.30(s, 3H), 3.85(br s, 1H), 4.42(s, 2H), 4.87(d, J=7.2Hz, 2H), 5.57(t, J=6.6Hz, 1H), 6.69(d, J=8.1Hz, 1H), 7.09-7.15(m, 4H), 7.31–7.44(m, 5H), 7.59(dd, J=2.4, 8.7Hz, 1H), 8.17(d, J=1.5Hz, 1H); IR(KBr): 3431, 3351, 2970, 2919, 2854, 1602, 1517, 1483, 1466, 1451, 1377, 1285, 1250, 1132, 975, 836 cm$^{-1}$.

Ib-253  mp 72–73° C.; $^1$H NMR(CDCl$_3$)δ1.75(s, 3H), 1.79(s, 6H), 1.82 (s, 3H), 2.27(s, 3H), 2.30(s, 3H), 3.77(d, J=6.9Hz, 2H), 3.92 (br s, 1H), 4.87(d, J=7.2Hz, 2H), 5.38(t, J=6.9Hz, 1H), 5.57(t, J=6.9Hz, 1H), 6.74(dd, J=8.1, 8.7Hz, 1H), 6.81(dd, J=0.9, 6.3Hz, 1H), 6.99–7.00(m, 1H), 7.00(s, 1H), 7.03(s, 1H), 7.14(s, 1H), 7.58(dd, J=2.7, 8.7Hz, 1H), 8.16(d, J=2.7Hz, 1H); IR(KBr): 3431, 2971, 2915, 1624, 1599, 1528, 1479, 1465, 1335, 1241, 1122, 987, 833 cm$^{-1}$.

Ib-254  mp 106–107° C.; $^1$H NMR(CDCl$_3$)δ1.79(s, 3H), 1.82(s, 3H), 2.26(s, 3H), 2.29(s, 3H), 4.42(s, 2H), 3.85(br s, 1H), 4.87(d, J=7.2Hz, 2H), 5.57(t, J=7.2Hz, 1H), 6.73(dd, J=8.7, 8.7Hz, 1H), 6.81(d, J=8.4Hz, 1H), 6.96–6.99(m, 1H), 7.03(d, J=12.9Hz, 1H), 7.10(d, J=9.9Hz, 2H), 7.26–7.43(m, 5H), 7.58(d, J=2.4, 8.4Hz, 1H), 8.16(d, J=1.8Hz, 1H); IR(KBr): 3428, 2922, 2857, 1623, 1601, 1566, 1500, 1427, 1391, 1376, 1308, 1298, 1149, 1134, 1074, 1038, 1018, 927, 895 cm$^{-1}$.

Ib-255  mp 83–84° C.; $^1$H NMR(CDCl$_3$)δ1.75(s, 3H), 1.79(s, 6H), 1.82 (s, 3H), 2.27(s, 3H), 2.30(s, 3H), 3.79(d, J=6.3Hz, 2H), 4.29 (br s, 1H), 4.87(d, J=7.2Hz, 2H), 5.39(t, J=6.6Hz, 1H), 5.57(t, J=7.2Hz, 1H), 6.71(d, J=8.7Hz, 1H), 6.81(d, J=8.1Hz, 1H), 7.10(s, 1H), 7.13(s, 1H), 7.16(dd, J=2.1, 8.4Hz, 1H), 7.27(dd, J=2.1, 7.5Hz, 1H), 7.58(d, J=2.7, 8.7Hz, 1H), 8.16(d, J=1.8Hz, 1H); IR(KBr): 3420, 3356, 2968, 2924, 1603, 1520, 1482, 1468, 1284, 1248, 1078, 981, 838 cm$^{-1}$.

Ib-256  mp 89–90° C.; $^1$H NMR(CDCl$_3$)δ1.79(s, 3H), 1.82(s, 3H), 2.26 (s, 3H), 2.29(s, 3H), 4.46(s, 2H), 4.79(br s, 1H), 4.87(d, J=6.9Hz, 2H), 5.57(t, J=7.2Hz, 1H), 6.69(d, J=8.1Hz, 1H), 6.81(d, J=8.7Hz, 1H), 7.09–7.13(m, 3H), 7.31–7.43(m, 6H), 7.58(dd, J=2.7, 8.7Hz, 1H), 8.16(d, J=2.4Hz, 1H); IR(KBr): 3422, 3340, 2975, 2923, 1604, 1520, 1482, 1455, 1286, 1248, 975, 887 cm$^{-1}$.

Ib-257  mp 62–63° C.; $^1$H NMR(CDCl$_3$)δ1.74(s, 3H), 1.78(s, 3H), 1.79 (s, 3H), 1.82(s, 3H), 2.28(s, 3H), 2.32(s, 3H), 3.76(d, J=6.6Hz, 2H), 3.86(s, 3H), 4.27(br s, 1H), 4.87(d, J=6.9Hz, 2H), 5.41(t, J=6.6Hz, 2H), 5.58(t, J=6.9Hz, 1H), 6.67(d, J=8.1Hz, 1H), 6.78–6.79(m, 2H), 6.88(dd, J=1.8, 8.1Hz, 1H), 7.11(s, 1H), 7.18(s, 1H), 7.59(d, J=2.4, 8.4Hz, 1H), 8.17(d, J=1.8Hz, 1H); IR(KBr): 3437, 2880, 2856, 1560, 1416, 1378, 1306, 1176, 1075, 1017, 948, 898, 883 cm$^{-1}$.

TABLE 114

Ib-258  mp 86–87° C.; $^1$H NMR(CDCl$_3$)δ1.79(s, 3H), 1.82(s, 3H), 2.27(s, 3H), 3.31(s, 3H), 3.87(s, 3H), 4.40(s, 2H), 4.67(br s, 1H), 4.87(d, J=6.9Hz, 2H), 5.57(t, J=7.2Hz, 1H), 6.65(d, J=7.8Hz, 1H), 6.79–6.86(m, 3H), 7.10(s, 1H), 7.17(s, 1H), 7.31–7.44(m, 5H), 7.59(dd, J=2.4, 8.7Hz, 1H), 8.17(d, J=2.4Hz, 1H); IR(KBr): 3426, 2948, 2914, 2857, 1600, 1561, 1525, 1415, 1304, 1177, 1018, 948, 900, 883 cm$^{-1}$.

Ib-259  mp 108–109° C.; $^1$H NMR(CDCl$_3$)δ1.74(s, 3H), 1.77(s, 3H), 1.79(s, 3H), 1.82(s, 3H), 2.27(s, 3H), 2.31(s, 3H), 3.66(br s, 1H), 3.74(d, J=6.8Hz, 2H), 4.87(d, J=7.1Hz, 2H), 5.38(br t, J=6.8Hz, 1H), 5.58(br t, J=7.1Hz, 1H), 6.67(d, J=8.5Hz, 2H), 6.81(dd, J=0.7, 8.6Hz, 1H), 7.10(s, 1H), 7.15(s, 1H), 7.20(d, J=8.5Hz, 2H), 7.59(dd, J=2.4, 8.6Hz, 1H)8.17(dd, J=0.7, 2.4Hz, 1H)

Ib-260  mp 74–75° C.; $^1$H NMR(CDCl$_3$)δ1.72(s, 3H), 1.77(s, 3H), 1.81 (s, 6H), 2.29(s, 3H), 2.31(s, 3H), 3.76(d, 2H, J=6.9Hz), 5.07(d, J=7.2Hz, 2H), 5.39(m, 1H), 5.58(m, 1H), 6.77(d, J=7.8Hz, 2H), 7.11–7.23(m, 5H), 8.26(d, J=2.1Hz, 1H), 8.40(d, J=2.1Hz, 2H); IR(CHCl$_3$): 3426, 2975, 2918, 2862, 1612, 1556, 1528, 1498, 1471, 1379, 1354, 1299, 1241, 12256, 1185, 1091, 970, 947 cm$^{-1}$

Ib-261  $^1$H NMR(DMSO)δ1.73(s, 3H), 1.76(s, 3H), 2.22(s, 3H), 2.23(s, 3H), 4.82(d, J=6.9Hz, 2H), 5.50(t, J=6.9Hz 1H), 6.86(d, J=8.4Hz, 1H), 6.96–7.05(m, 2H), 7.11–7.17(m, 3H), 7.72(dd, J=2.7, 8.7Hz, 1H), 8.15(d, J=2.7Hz, 1H), 9.94(brs, 1H); IR(neat): 3350, 2964, 1601, 1520, 1480, 1377, 1355, 1283, 1241, 1113, 979, 755 cm$^{-1}$ Ib-262  mp 96° C. $^1$H NMR(DMSO)δ1.74(s, 6H), 1.76(s, 3H), 1.77(s, 3H), 2.22(s, 3H), 2.34(s, 3H), 4.65(d, J=6.9Hz, 2H), 4.82(d, J=6.6Hz, 2H), 5.44–5.54(m, 2H), 7.10–7.18(m, 3H), 7.21–7.27(m, 2H), 7.73(dd, J=2.4, 8.4Hz, 1H), 8.15(d, J=2.4Hz, 1H),; IR(nujol): 1600, 1517, 1280, 1269, 1127, 995, 836 cm$^{-1}$ Ib-263  mp 78–79° C. $^1$H NMR(CD$_3$OD)δ1.79(s, 3H), 1.80(s, 3H), 2.42(s, 6H), 3.92(s, 3H), 4.83(d, J=7.0Hz, 2H), 5.50–5.56(m, 1H), 6.84(dd, J=0.6, 8.7Hz, 1H), 7.05–7.18(m, 5H), 7.67(dd, J=2.7, 8.7Hz, 1H), 8.07(dd, J=2.7, 0.6Hz, 1H),; IR(nujol): 1600, 1577, 1280, 1270, 1127, 983, 838 cm$^{-1}$ Ib-264  mp 80–81° C. $^1$H NMR(CDCl$_3$)δ1.79(s, 3H), 1.82(s, 3H), 2.72 (s, 6H), 4.88(d, J=7.2Hz, 2H), 5.13(s, 2H), 5.55–5.60(m, 1H), 6.40(dd, J=1.5, 3.6Hz, 1H), 6.48(d, J=3.6Hz, 1H), 6.82(d, J=8.4Hz, 1H), 7.02–7.06(m, 1H), 7.08–7.16(m, 4H), 7.47–7.48(m, 1H), 7.58(dd, J=2.7, 8.4Hz, 1H)8.16(d, J=2.7Hz, 1H); IR(nujol): 1601, 1518, 1281, 1125, 984, 834 cm$^{-1}$ Ib-265  mp 105° C. $^1$H NMR(CDCl$_3$)δ1.79(s, 3H), 1.82(s, 3H), 2.27(s, 6H), 4.88(d, J=7.2Hz, 2H), 5.20(s, 2H), 5.50–5.60(m, 1H), 6.81(d, J=8.4Hz, 1H), 7.00–7.15(m, 5H), 7.32–7.50(m, 5H), 7.58(dd, J=2.4, 8.4Hz, 1H)8.16(d, J=2.4Hz, 1H); IR(nujol): 1602, 1299, 1276, 1128, 974, 749 cm$^{-1}$ Ib-266  mp 188–190° C.; $^1$H NMR(CDCl$_3$)δ1.79(s, 3H), 1.82(s, 3H), 2.27(s, 3H), 2.29(s, 3H), 4.88(d, J=7.1Hz, 2H), 4.89(s, 2H), 5.58(t, J=7.1Hz, 2H), 6.83(dd, J=8.4, 0.6Hz, 1H), 7.13(s, 1H), 7.15(s, 1H), 7.50–7.55(m, 2H), 7.59(dd, J=8.4, 2.4Hz, 1H), 7.97–8.02(m, 2H), 8.16(dd, J=2.4, 0.6Hz, 1H); IR(KBr): 3367, 3321, 3271, 1602, 1479, 1333, 1281, 1163, 1153, 995, 980, 785, 607, 553 cm$^{-1}$

TABLE 115

Ib-267  mp 176–178° C.; $^1$H NMR(CDCl$_3$)δ1.79(s, 3H), 1.82(s, 3H), 2.19(s, 3H), 2.28(s, 3H), 488(d, J=6.9Hz, 2H), 4.96(s, 2H), 5.57(t, J=7.1Hz, 2H), 6.82(dd, J=8.4, 0.6Hz, 1H), 7.11(s, 1H), 7.15(s, 1H), 7.47(d, J=8.1Hz, 1H), 7.59(dd, J=8.4, 2.6Hz, 1H), 7.74(dd, J=9.0, 1.8Hz, 1H), 7.80(dd, J=8.1, 1.8Hz, 1H), 8.16(dd, J=2.6, 0.6Hz, 1H); IR(KBr): 3352, 3261, 1603, 1479, 1317, 1152, 993, 831, 777, 600 cm$^{-1}$

Ib-268  oil; $^1$H NMR(CDCl$_3$)δ1.74(s, 3H), 1.78(s, 3H), 1.80(s, 3H), 1.81(s, 3H), 2.05(s, 3H), 2.19(s, 3H), 2.26(s, 3H), 3.72(d, J=6.6Hz, 2H), 3.77(br s, 2H), 4.85(m, 2H), 5.35(m, 1H), 5.56(m, 1H), 6.34(dd, J=2.1, 9.3Hz, 1H), 6.45(d, J=2.1, 8.4Hz, 1H), 6.61(d, J=8.4Hz, 1H), 6.97(s, 1H), 7.07(t, J=8.4Hz, 1H), 7.34(d, J=8.4Hz, 1H)

Ib-269  oil; $^1$H NMR(CDCl$_3$)δ1.74(s, 3H), 1.78(s, 6H), 1.82(s, 3H), 2.21(s, 3H), 2.25(s, 3H), 2.27(s, 3H), 3.71(d, J=6.6Hz, 2H), 4.89(d, J=6.6Hz, 2H), 5.35(br t, J=6.6Hz, 1H), 5.57(br t, J=6.6Hz, 1H), 6.39(dd, J=2.1, 12.6Hz, 1H), 6.45(dd, J=2.1, 8.4Hz, 1H), 7.06(t, J=8.4Hz, 1H), 7.10(s, 1H), 7.12(s, 1H), 7.41(d, J=2.4Hz, 1H), 8.01(d, J=2.4Hz, 1H)

Ib-270  oil; $^1$H NMR(CDCl$_3$)δ1.74(s, 3H), 1.78(s, 6H), 1.82(s, 3H), 2.05(s, 3H), 2.07(s, 3H), 2.20(s, 3H), 3.72(d, J=6.6Hz, 2H), 3.85(br, 1H), 4.85(d, J=7.8Hz, 2H), 5.36(m, 1H), 5.56(m, 1H), 6.39(dd, J=2.4, 12.3Hz, 1H), 6.45(dd, J=2.4, 8.1Hz, 1H), 6.68(s, 1H), 6.97(s, 1H), 7.07(d, J=8.4Hz, 1H), 7.10(s, 1H), 7.93(s, 1H)

Ib-271  oil, $^1$H NMR(CDCl$_3$)δ1.78(s, 3H), 1.81(s, 3H), 2.20(s, 3H), 2.25(s, 3H), 2.27(s, 3H), 4.90(d, J=6.6Hz, 2H), 5.58(br t, J=6.9Hz, 1H), 6.47(dd, J=2.1, 11.4Hz, 1H), 6.53(dd, J=2.1, 8.1Hz, 1H), 7.05(t, J=8.1Hz, 1H), 7.10(s, 1H), 7.11(s, 1H), 7.41(d, J=2.1Hz, 1H), 8.01(d, J=2.1Hz, 1H)

Ib-272  oil; $^1$H NMR(CDCl$_3$)δ1.78(s, 3H), 1.82(s, 3H), 2.05(s, 3H), 2.07(s, 3H), 2.19(s, 3H), 3.85(br s, 2H), 4.85(d, J=6.9Hz, 2H), 5.56(m, 1H), 6.48(dd, J=2.1, 11.7Hz, 1H), 6.53(dd, J=2.1, 8.4Hz, 1H), 6.68(s, 1H), 6.98(s, 1H), 7.07(t, J=8.4Hz, 1H), 7.10(s, 1H), 7.92(s, 1H)

Ib-273  oil; $^1$H NMR(CDCl$_3$)δ1.74(s, 3H), 1.77(s, 3H), 1.805(s, 3H), 1.810(s, 3H), 2.06(s, 3H), 2.26(s, 3H), 2.28(s, 3H), 3.74(d, J=6.6Hz, 2H), 4.83–4.87(m, 2H), 5.38(m, 1H), 5.56(m, 1H), 6.61(d, J=8.4Hz, 1H), 6.68(d, J=9.0Hz, 2H), 6.96(s, 1H), 7.21(d, J=9.0Hz, 2H), 7.34(d, J=8.4Hz, 1H)

Ib-274  oil; $^1$H NMR(CDCl$_3$)δ1.74(s, 3H), 1.77(s, 3H), 1.78(s, 3H), 1.81(s, 3H), 2.25(s, 3H), 2.27(s, 3H), 2.30(s, 3H), 3.74(d, J=6.6Hz, 2H), 4.89(d, J=6.9Hz, 2H), 5.38(m, 1H), 5.58(m, 1H), 6.68(d, J=8.7Hz, 2H), 7.09(s, 1H), 7.15(s, 1H), 7.20(d, J=8.7Hz,

TABLE 115-continued

| | |
|---|---|
| | 2H), 7.41(m, 1H), 8.01(m, 1H) |
| Ib-275 | oil; $^1$H NMR(CDCl$_3$)δ1.74(s, 3H), 1.78(s, 6H), 1.81(s, 3H), 2.05(s, 3H), 2.07(s, 3H), 2.28(s, 3H), 3.74(d, J=6.9Hz, 2H), 4.85(d, J=7.5Hz, 2H), 5.38(m, 1H), 5.56(m, 1H), 6.67–6.71(m, 3H), 6.96(s, 1H), 7.12(s, 1H), 7.21(d, J=8.7Hz, 1H), 7.92(s, 1H) |

TABLE 115-continued

| | |
|---|---|
| Ib-276 | oil; $^1$H NMR(CDCl$_3$)δ1.75(s, 3H), 1.81(s, 3H), 2.05(s, 3H), 2.06(s, 3H), 2.26(s, 3H), 3.75(br, 2H), 4.84–4.87(m, 2H), 5.57(m, 1H), 6.62(d, J=8.1Hz, 1H), 6.74–6.77(m, 3H), 6.96(s, 1H), 7.11(s, 1H), 7.17–7.20(m, 2H), 7.34(d, J=8.1Hz, 1H) |

TABLE 116

| | |
|---|---|
| Ib-277 | oil; $^1$H NMR (CDCl$_3$) δ 1.78(s, 3H), 1.81(s, 3H), 2.25(s, 3H), 2.27(s, 3H), 2.28(s, 3H), 4.90(d, J=6.8Hz, 2H), 5.58(m, 1H), 6.73–6.78(m, 2H), 7.08–7.41(m, 5H), 8.00(d, J=2.2Hz, 1H) |
| Ib-278 | oil; $^1$H NMR (CDCl$_3$) δ 1.78(s, 3H), 1.82(s, 3H), 2.05(s, 3H), 2.08(s, 3H), 2.27(s, 3H), 4.85(d, J=8.1Hz, 2H), 5.57(m, 1H), 6.68(s, 1H), 6.75–6.78 (m, 2H), 6.97(s, 1H), 7.12(s, 1H), 7.17–7.21(m, 2H), 7.92(s, 1H) |
| Ib-279 | mp 102–103° C.; $^1$H NMR (CDCl$_3$) δ 1.74(s, 3H), 1.77(s, 3H), 2.26(s, 3H), 2.31(s, 3H), 3.74(d, J=6.9Hz, 2H), 4.56–4.60(m, 1H), 4.66–4.73(m, 2H), 4.86–4.89(m, 1H), 5.35–5.40(m, 1H), 6.65–6.70(m, 2H), 6.86(d, J=8.4Hz, 1H), 7.09(s, 1H), 7.16(s, 1H), 7.18–7.22(m, 2H), 7.62(dd, J=2.4, 8.7Hz, 1H), 8.13–8.14(m, 1H) IR (KBr): 3356, 2983, 2925, 1611, 1526, 1482, 1452, 1391, 1348, 1307, 1289, 1263, 1242, 1073, 1020 cm$^{-1}$ |
| Ib-280 | mp 81–82° C.; $^1$H NMR (CDCl$_3$) δ 2.27(s, 3H), 2.30(s, 3H), 3.82–3.84(m, 2H), 4.88–4.91(m, 2H), 5.18–5.47(m, 4H), 5.93–6.21(m, 2H), 6.67–6.71(m, 2H), 6.83(d, J=8.4Hz, 1H), 7.09(s, 1H), 7.15(s, 1H), 7.17–7.22(m, 2H), 7.61(dd, J=2.4, 7.2Hz, 1H), 8.16(dd, J=0.9, 2.4Hz, 1H) IR (KBr): 3342, 3007, 2921, 1609, 1524, 1482, 1391, 1314, 1279, 1182, 1020, 996 cm$^{-1}$ |
| Ib-281 | mp 142–144° C.; $^1$H NMR (CDCl$_3$) δ 2.20–2.27(m, 4H), 2.29(s, 3H), 2.50(s, 1H), 3.99(d, J=2.4Hz, 1H), 5.04(d, J=2.7Hz, 1H), 6.73–6.78(m, 2H), 6.87 (dd, J=2.4, 8.7Hz, 1H), 7.10(s, 1H), 7.16(s, 1H), 7.21–7.26(m, 2H), 7.63 (dd, J=2.4, 8.7Hz, 1H), 8.18(dd, J=0.9, 2.4Hz, 1H) IR (KBr): 3360, 3292, 3266, 3005, 1608, 1523, 1479, 1438, 1391, 1299, 1280, 1265, 1233, 1022, 1010 cm$^{-1}$ |
| Ib-282 | mp 65–68° C.; $^1$H NMR (CDCl$_3$) δ 1.58(s, 3H), 1.70(s, 3H), 1.73(s, 3H), 1.78 (s, 3H), 2.23(s, 3H), 2.26(s, 3H), 2.43–2.50(m, 2H), 2.87(t, J=7.5Hz, 2H), 3.71(d, J=6.9Hz, 2H), 3.79(br s, 1H), 5.20–5.36(m, 2H), 6.36–6.47(m, 2H), 7.06(t, J=8.4Hz, 1H), 7.12(s, 1H), 7.14(s, 1H), 7.19(d, J=7.8Hz, 1H), 7.60(dd, J=2.1, 7.8Hz, 1H), 8.55(d, J=1.8Hz, 1H) IR (KBr): 3427, 3274, 2965, 2913, 2854, 1629, 1536, 1480, 1443, 1421, 1375, 1343, 1305, 1276, 1245, 1173, 1115, 1023 cm$^{-1}$ |
| Ib-283 | mp 112–113° C.; $^1$H NMR (CDCl$_3$) δ 1.69(s, 3H), 1.70(s, 3H), 1.73(s, 3H), 1.77(s, 3H), 2.22(s, 3H), 2.23(s, 3H), 3.83–3.88(m, 2H), 4.64(d, J=7.2Hz, 2H), 5.28–5.33(m, 1H), 5.46–5.51(m, 1H), 6.50–6.61(m, 2H), 7.07–7.11(m, 3H), 7.19–7.26(m, 2H), 7.40(dd, J=2.7, 8.7Hz, 1H), 7.97(d, J=2.4Hz, 1H), IR (KBr): 3222, 2971, 2922, 2858, 1605, 1536, 1493, 1468, 1428, 1396, 1318, 1297, 1272, 1262, 1229, 1194, 1125, 1090, 996 cm$^{-1}$ |
| Ib-284 | mp 141–143° C.; $^1$H NMR (CDCl$_3$) δ 1.74(s, 3H), 1.77(s, 6H), 1.82(s, 3H), 2.28(s, 3H), 2.29(s, 3H), 3.85–3.95(m, 2H), 4.56(d, J=6.6Hz, 2H), 5.36(m, 1H), 5.54(tm, J=6.6Hz, 1H), 6.45(m, 1H), 6.97(d, J=8.7Hz, 2H), 7.11(s, 1H), 7.14(s, 1H), 7.28(d, J=8.7Hz, 2H), 7.47(m, 1H), 8.13(m, 1H); IR (KBr) 3433, 3220, 1610, 1536, 1492, 1233, 1176, 998, 844 cm$^{-1}$. |
| Ib-285 | mp 113–114° C.; $^1$H NMR (DMSO-d6) δ 1.73(s, 3H), 1.77(s, 3H), 2.22(s, 6H), 4.64(d, J=6.9Hz, 2H), 5.46–5.50(m, 1H), 5.98(s, 2H), 6.51(d, J=8.4Hz, 1H), 7.07–7.11(m, 3H), 7.19–7.26(m, 2H), 7.41(dd, J=2.7, 8.4Hz, 1H), 7.90(d, J=2.7Hz, 1H), IR (KBr): 3456, 3292, 3173, 2917, 1631, 1617, 1521, 1485, 1442, 1395, 1378, 1298, 1268, 1232, 1193, 1126, 1004 cm$^{-1}$ |

TABLE 117

| | |
|---|---|
| Ib-286 | mp 134–136° C.; $^1$H NMR (CDCl$_3$) δ 1.77(s, 3H), 1.82(s, 3H), 2.28(s, 6H), 4.56(d, J 6.6Hz, 2H), 5.54(tm, J=6.6Hz, 1H), 6.58(m, 1H), 6.98(d, J=9.0Hz, 2H), 7.10(s, 1H), 7.14(s, 1H), 7.28(d, J=9.0Hz, 2H), 7.48(m, 1H), 8.10(m, 1H); IR (KBr) 3458, 3300, 3176, 1630, 1614, 1519, 1485, 1238, 1003, 837 cm$^{-1}$. |
| Ib-287 | mp 187–189° C.; $^1$H NMR (CDCl$_3$) δ 1.15–1.54(m, 4H), 1.58–1.86(m, 4H), 1.77(s, 3H), 1.82(s, 3H), 2.02–2.15(m, 2H), 2.28(s, 3H), 2.29(s, 3H), 3.58 (m, 1H), 4.56(d, J=6.9Hz, 2H), 5.54(tm, J=6.9Hz, 1H), 5.54(m, 1H), 6.44 (m, 1H), 6.97(d, J=8.7Hz, 2H), 7.10(s, 1H), 7.13(s, 1H), 7.28(d, J= 8.7Hz, 2H), 7.45(m, 1H), 8.10(m, 1H); IR (KBr) 3334, 1612, 1519, 1488, 1231, 1006, 833 cm$^{-1}$. |
| Ib-288 | mp 89–90° C.; $^1$H NMR (CDCl$_3$) δ 1.74(s, 3H), 1.78(s, 3H), 2.22(s, 3H), 2.26 (s, 3H), 3.71(d, J=6.9Hz, 2H), 5.32–5.36(m, 1H), 5.38(s, 2H), 6.36–6.49 |

TABLE 117-continued

| | |
|---|---|
| | (m, 4H), 6.84(dd, J=0.6, 8.4Hz, 1H), 7.06(t, J=8.1Hz, 1H), 7.11(s, 1H), 7.13(s, 1H), 7.46–7.48(m, 1H), 7.61(dd, J=2.4, 8.4Hz, 1H), 8.18(dd, J= 0.9, 2.4Hz, 1H) IR (KBr): 3423, 2963, 2926, 2860, 1627, 1604, 1523, 1480, 1448, 1393, 1378, 1343, 1282, 1269, 1240, 1169, 1150, 1117, 1014, 1000 cm$^{-1}$ |
| Ib-289 | mp oil ° C.; $^1$H NMR (CDCl$_3$) δ 1.74(s, 3H), 1.77(s, 3H), 1.90(t, J=2.1Hz, 3H), 2.22(s, 3H), 2.26(s, 3H), 3.71(d, J=6.9Hz, 2H), 4.99–5.01(m, 2H), 5.33–5.37(m, 1H), 6.37–6.47(m, 2H), 6.86(d, J=8.4Hz, 1H), 7.03–7.13(m, 3H), 7.61(dd, J=2.4, 8.4Hz, 1H), 8.17(d, J=2.1Hz, 1H) |
| Ib-290 | mp 104–105° C.; $^1$H NMR (CDCl$_3$) δ 1.74(s, 3H), 1.78(s, 3H), 2.24(s, 3H), 2.29(s, 3H), 3.72(d, J=6.9Hz, 2H), 5.33–5.36(m, 1H), 6.37–6.78(m, 4H), 7.06(t, J=8.4Hz, 1H), 7.14(s, 1H), 7.16(s, 1H), 7.38(d, J=8.4Hz, 1H), 7.56(t, J=2.4Hz, 1H), 7.77(dd, J=2.1, 8.1Hz, 1H), 8.45(dd, J=0.6, 2.4Hz, 1H) IR (KBr): 3396, 2976, 2929, 2855, 1626, 1596, 1573, 1523, 1482, 1378, 1367, 1335, 1130, 1065 cm$^{-1}$ |
| Ib-291 | mp 119–120° C.; $^1$H NMR (CDCl$_3$) δ 1.73(s, 3H), 1.77(s, 3H), 2.01–2.06(m, 4H), 2.21(s, 3H), 2.29(s, 3H), 3.49–3.54(m, 4H), 3.71(d, J=6.6Hz, 2H), 5.33–5.36(m, 1H), 6.35–6.46(m, 3H), 7.06(t, J=8.4Hz, 1H), 7.10(s, 2H), 7.48(dd, J=2.7, 9.0Hz, 1H), 8.20(d, J=2.1Hz, 1H) IR (KBr): 3438, 2957, 2914, 2855, 1628, 1602, 1540, 1525, 1490, 1457, 1416, 1341, 1306, 1235, 1168, 1115 cm$^{-1}$. |
| Ib-292 | Oil; $^1$H NMR (CDCl$_3$) δ 1.78(s, 3H), 1.82(s, 3H), 2.27(s, 3H), 2.30(s, 3H), 4.56(d, J=6.9Hz, 2H), 5.55(tm, J=6.9Hz, 1H), 6.99(d, J=8.7Hz, 2H), 7.13(s, 1H), 7.17(s, 1H), 7.29(d, J=8.7Hz, 2H), 7.37(m, 1H), 7.45(m, H), 8.56–8.70(m, 2H); IR (CHCl$_3$) 1672, 1607, 1514, 1494, 1471, 1450, 1383, 1234, 1230, 1174, 998, 978 cm$^{-1}$. |
| Ib-293 | mp 114–115° C.; $^1$H NMR (CDCl$_3$) δ 1.73(s, 3H), 1.77(s, 3H), 2.26(s, 3H), 2.31(s, 3H), 3.74(d, J=6.9Hz, 2H), 3.99(s, 3H), 5.35–5.44(m, 1H), 6.65–6.70(m, 2H), 6.81(d, J=8.4Hz, 1H), 7.10(s, 1H), 7.16(s, 1H), 7.17–7.22(m, 2H), 7.60(dd, J=2.4, 8.4Hz, 1H), 8.18(d, J=2.1Hz, 1H) IR (KBr): 3333, 3006, 2968, 1612, 1524, 1483, 1387, 1367, 1319, 1300, 1288, 1240, 1024 cm$^{-1}$ |
| Ib-294 | mp 75–76° C.; $^1$H NMR (CDCl$_3$) δ 1.73(s, 3H), 1.77(s, 3H), 2.28(s, 3H), 2.31 (s, 3H), 3.76(d, J=6.9Hz, 2H), 4.17(s, 2H), 5.39(m, 1H), 6.75(d, J=8.4Hz, 2H), 7.10–7.22(m, 4H), 8.29(d, J=2.4Hz, 1H), 8.42(d, J=2.4Hz, 1H); IR (CHCl$_3$): 3426, 2923, 2868, 1613, 1557, 1530, 1499, 1478, 1427, 1381, 1353, 1301, 1245, 1093, 1007, 956, 929, 894 cm$^{-1}$ |

TABLE 118

| | |
|---|---|
| Ib-295 | mp 88–89° C. $^1$H NMR (CDCl$_3$) δ 1.77(s, 3H), 1.82(s, 3H), 2.28(s, 6H), 4.64(d, J=6.9Hz, 2H), 5.44(s, 2H), 5.53–5.58(m, 1H), 6.89(dd, J=0.6, 8.7Hz, 1H), 7.00–7.14(m, 5H), 7.32–7.44(m, 3H), 7.49–7.53(m, 2H), 7.62 (dd, J=2.7, 8.7Hz, 1H) 8.19(dd, J=0.6, 2.7Hz, 1H); IR (nujol): 1602, 1285, 1129, 988, 836 cm$^{-1}$. |
| Ib-296 | mp 110° C. $^1$H NMR (CDCl$_3$) δ 1.77(s, 3H), 1.81(s, 3H), 2.27(s, 6H), 2.28 (s, 3H), 4.01(s, 3H), 4.64(d, J=6.9Hz, 2H), 5.53–5.58(m, 1H), 6.82(d, J=8.4Hz, 1H), 7.00–7.26(m, 5H), 7.60(dd, J=2.4, 8.4Hz, 1H), 8.18(d, J=2.4 Hz, 1H),; IR (nujol): 1598, 1283, 1273, 1124, 992, 838 cm$^{-1}$ |
| Ib-297 | mp 201–204° C.; $^1$H NMR (CDCl$_3$) δ 1.80(s, 3H), 1.83(s, 3H), 1.97(s, 6H), 1.98(s, 6H), 4.88(d, J=6.9Hz, 2H), 5.56–5.61(m, 1H), 6.75–6.80(m, 2H), 6.83(d, J=8.1Hz, 1H), 6.92–6.98(m, 2H), 7.41(dd, J=2.4, 8.7Hz, 1H), 7.98 (d, J=2.4Hz, 1H) IR (KBr): 3452, 3368, 2927, 1619, 1599, 1517, 1487, 1465, 1378, 1350, 1275, 1240, 1125, 980 cm$^{-1}$ |
| Ib-298 | mp 158–160° C.; $^1$H NMR (CDCl$_3$) δ 1.74(s, 3H), 1.78(s, 3H), 1.79(s, 3H), 1.83(s, 3H), 1.97(s, 6H), 2.00(s, 6H), 3.74(d, J=6.9Hz, 2H), 4.88(d, J= 6.9Hz, 2H), 5.37–5.42(m, 1H), 5.56–5.62(m, 1H), 6.67–6.72(m, 2H), 6.84(d, J=8.4Hz, 1H), 6.94–7.00(m, 2H), 7.41(dd, J=2.4, 8.7Hz, 1H), 7.99(dd, J= 0.6, 2.4Hz, 1H) IR (KBr): 3388, 2928, 2854, 1613, 1600, 1518, 1486, 1465, 1376, 1349, 1312, 1291, 1275, 1240, 1125, 983 cm$^{-1}$ |
| Ib-299 | mp 124–125° C.; $^1$H NMR (CDCl$_3$) δ 1.25(s, 3H), 1.27(s, 3H), 1.80(s, 3H), 1.83(s, 3H), 1.97(s, 6H), 2.00(s, 6H), 3.62–3.75(m, 1H), 4.88(d, J=6.9Hz, 2H), 5.56–5.62(m, 1H), 6.64–6.68(m, 2H), 6.83(d, J=8.4Hz, 1H), 6.93–6.98(m, 2H), 7.41(dd, J=2.4, 8.4Hz, 2H), 7.99(d, J=1.8Hz, 1H) IR (KBr): 3391, 2965, 2930, 1613, 1600, 1519, 1412, 1376, 1362, 1349, 1316, 1277, 1242, 1181, 1125, 977 cm$^{-1}$ |
| Ib-300 | mp 116–119° C.; $^1$H NMR (CDCl$_3$) δ 1.78(s, 3H); 1.82(s, 3H); 1.97(s, 12H); 4.01(s, 3H); 4.64(d, J=6.6Hz, 2H); 5.58(m, 1H); 6.82–6.87(m, 2H); 6.91 (ddd, J=1.8, 4.8, 11.7Hz, 1H); 7.05(dt, J=1.5, 8.7Hz, 1H); 7.41(ddd, J= 1.5, 2.4, 8.7Hz, 1H); 7.99(d, J=2.4Hz, 1H); IR (KBr): 3432, 2944, 1603, 1514, 1496, 1462, 1297, 1281, 1263, 1245, 1210, 1113 cm$^{-1}$. |
| Ib-301 | mp 150–153° C.; $^1$H NMR (CDCl$_3$) δ 1.75(s, 3H); 1.780(s, 3H); 1.784(s, 3H); 1.82(s, 3H); 1.96(s, 6H); 2.01(s, 6H); 3.91(t, J=6.0Hz, 2H); 4.50(br t, J= |

TABLE 118-continued

| | |
|---|---|
| | 4.5Hz, 1H); 4.64(d, J=6.9Hz, 2H); 5.38(m, 1H); 5.57(m, 1H); 6.49(m, 1H); 6.84(m, 1H); 6.91(ddd, J=2.1, 3.3, 12Hz, 1H); 7.04(dt, J=2.1, 8.4Hz, 1H); 7.27(m, 1H); 7.91(m, 1H); IR (KBr): 3235, 2917, 1608, 1540, 1513, 1381, 1294, 1261 cm$^{-1}$. |
| Ib-302 | mp 155–157° C.; $^1$H NMR (CDCl$_3$) δ 1.30(d, J=6.3Hz, 6H); 1.78(s, 3H); 1.83 (s, 3H); 1.96(s, 6H); 2.01(s, 6H); 3.92(sept, J=6.3Hz, 1H); 4.54(br, 1H); 4.64(d, J=6.6Hz, 2H); 5.58(m, 1H); 6.48(d, J=7.5Hz, 1H); 6.83–7.07(m, 3H); 7.27(m, 1H); 7.89(m, 1H); IR (KBr): 3419, 3249, 2969, 1610, 1537, 1513, 1463, 1389, 1293, 1263, 1241, 1209, 1180, 1113 cm$^{-1}$. |
| Ib-303 | mp 134–137° C.; $^1$H NMR (CDCl$_3$) δ 0.99–1.92(m, 11H); 1.77(s, 3H); 1.82(s, 3H); 1.96(s, 6H); 2.01(s, 6H); 3.16(t, J=6.0Hz, 2H); 4.64(d, J=6.6Hz, 2H); 4.73(br s, 1H); 5.57(m, 1H); 6.49(m, 1H); 6.82–6.94(m, 2H); 7.04(dt, J=1.5, 7.8Hz, 1H); 7.27(m, 1H); 7.88(m, 1H); IR (KBr): 3425, 3250, 2925, 2852, 1607, 1533, 1512, 1448, 1294, 1261, 1240, 1211, 1115 cm$^{-1}$. |

TABLE 119

| | |
|---|---|
| Ib-304 | mp 154–156° C.; $^1$H NMR (CDCl$_3$) δ 1.77(s, 3H); 1.82(s, 3H); 1.98(s, 6H); 2.00(s, 6H); 4.63(d, J 5.7Hz, 2H); 5.00(br, 1H); 5.57(m, 1H); 6.52(dd, J= 2.4, 8.4Hz, 1H); 6.85–7.01(m, 2H); 7.04(dt, J=1.8, 8.4Hz, 1H); 7.26–7.33 (m, 2H); 7.77(m, 1H); 7.994(m, 1H); 8.56(m, 1H); 8.69(br s, 1H); IR (KBr): 3256, 2917, 1603, 1514, 1463, 1427, 1381, 1296, 1263, 1239, 1210, 1112, 1004 cm$^{-1}$. |
| Ib-305 | mp 127–129° C.; $^1$H NMR (CDCl$_3$) δ 0.99(d, J=6.6Hz, 6H); 1.50–1.80(m, 3H); 1.77(s, 3H); 1.82(s, 3H); 1.96(s, 6H); 2.01(s, 6H); 3.29–3.36(m, 2H); 4.53(br t, 1H); 4.64(d, J=6.6Hz, 2H); 5.57(m, 1H); 6.49(d, J=8.4Hz, 1H); 6.81–6.94(m, 2H); 7.04(dt, J=1.5, 8.4Hz, 1H); 7.28(m, 2H); 7.90(m, 1H); IR (KBr): 3442, 3259, 2956, 1609, 1542, 1512, 1457, 1383, 1293, 1260, 1238, 1205, 1114 cm$^{-1}$. |
| Ib-306 | mp 86–89° C.; $^1$H NMR (CDCl$_3$) δ 1.04(d, J=6.6Hz, 5H); 1.77(s, 3H); 1.82(s, 3H); 1.86–1.95(m, 1H); 1.96(s, 6H); 2.01(s, 6H); 3.14(t, J=6.3Hz, 2H); 4.64(d, J=6.9Hz, 2H); 4.67(br t, 1H); 5.57(m, 1H); 6.49(m, 1H); 6.82–7.07 (m, 3H); 7.28(dt, J=1.8, 8.4Hz, 1H); 7.89(m, 1H); IR (KBr): 3343, 2957, 1610, 1513, 1465, 1382, 1294, 1263, 1240, 1114 cm$^{-1}$. |
| Ib-307 | mp 157–159° C.; $^1$H NMR (CDCl$_3$) δ 1.77(s, 3H); 1.82(s, 3H); 1.96(s, 6H); 2.00(s, 6H); 4.64(d, J=6.6Hz, 2H); 4.77(d, J=5.4Hz, 2H); 4.94(br, 1H); 5.57(m, 1H); 6.56(m, 1H); 6.81–7.09(m, 5H); 7.24–7.30(m, 2H); 7.96(d, J= 2.4Hz, 1H); IR (KBr): 3393, 2925, 1610, 1512, 1295, 1263, 1240 cm$^{-1}$. |
| Ib-308 | mp 175–177° C.; $^1$H NMR (CDCl$_3$) δ 1.77(s, 3H); 1.82(s, 3H); 1.96(s, 6H); 2.00(s, 6H); 4.58(d, J=6.0Hz, 2H); 4.64(d, J=6.9Hz, 2H); 4.98(br s, 1H); 5.57(m, 1H); 6.54(m, 1H); 6.81–6.94(m, 2H); 7.04(dt, J=1.8, 8.4Hz, 1H); 7.14(dd, J=1.8, 5.1Hz, 1H); 7.27(m, 1H); 7.35(dd, J=3.0, 4.8Hz, 1H); 7.94(m, 1H); IR (KBr): 3233, 2912, 1546, 1512, 1453, 1420, 1384, 1317, 1294, 1259, 1238, 1204, 1116 cm$^{-1}$. |
| Ib-309 | mp 134–137° C.; $^1$H NMR (CDCl$_3$) δ 1.77(s, 3H); 1.82(s, 3H); 1.98(s, 6H); 2.00(s, 6H); 4.58(d, J=5.4Hz, 2H); 4.64(d, J=6.6Hz, 2H); 4.88(br t, 1H); 5.57(m, 1H); 6.30(dd, J=0.9, 3.0Hz, 1H); 6.36(dd, J=4.2, 6.3Hz, 1H); 6.57(m, 1H); 6.86(m, 1H); 6.91(ddd, J=2.1, 3.6, 11.7Hz, 1H); 7.03(dt, J= 1.8, 8.4Hz, 1H); 7.28(m, 1H); 7.40(m, 1H); 7.94(m, 1H); IR (KBr): 3379, 2928, 1513, 1294, 1263, 1240 cm$^{-1}$. |
| Ib-310 | mp 124–126° C.; $^1$H NMR (CDCl$_3$) δ 1.77(s, 3H); 1.82(s, 3H); 1.97(s, 6H); 2.00(s, 6H); 4.41(d, J=5.4Hz, 2H); 4.64(d, J=6.3Hz, 2H); 4.73(br t, 1H); 5.57(m, 1H); 6.47(m, 1H); 6.54(m, 1H); 6.82–7.08(m, 3H); 7.27(m, 1H); 7.43(t, J=1.8Hz, 1H); 7.46(m, 1H); 7.94(d, J=2.4Hz, 1H); IR (KBr): 3456, 3236, 2254, 1605, 1512, 1468, 1382, 1293, 1261, 1240, 1209, 1114 cm$^{-1}$. |
| Ib-311 | mp 143–145° C.; $^1$H NMR (CDCl$_3$) δ 1.78(s, 3H); 1.82(s, 3H); 1.97(s, 6H); 2.00(s, 6H); 4.64(d, J=7.0Hz, 2H); 4.74(d, J=5.2Hz, 2H); 5.58(m, 1H); 5.76(m, 1H), 6.61(d, J=8.4Hz, 1H); 682–7.29(m, 4H); 7.40(d,J=8.0Hz, 1H); 7.70(m, 1H); 7.95(d, J=2.0Hz, 1H); 8.61(d, J=4.8Hz, 1H); IR (KBr): 3251, 2929, 1608, 1514, 1440, 1380, 1295, 1264, 1252, 1240, 1207 cm$^{-1}$. |
| Ib-312 | mp 166–167° C.; $^1$H NMR (CDCl$_3$) δ 1.77(s, 3H); 1.82(s, 3H); 1.96(s, 6H); 1.99(s, 6H); 4.51(br s, 2H); 4.64(d, J=6.6Hz, 2H); 5.57(m, 1H); 6.62(m, 1H); 6.84(m, 1H); 6.90(m, 1H); 7.04(m, 1H); 7.27(m, 1H); 7.90(m, 1H); IR (KBr): 3467, 3304, 3168, 2917, 1638, 1619, 1516, 1388, 1297, 1265, 1240, 1209 cm$^{-1}$. |

TABLE 120

| | |
|---|---|
| Ib-313 | amorphous; $^1$H NMR (CDCl$_3$) δ 1.75(s, 3H), 1.78(s, 3H), 1.98(s, 6H), 2.01(s, 6H), 3.69(br s, 1H), 3.91(t, J=5.6Hz, 2H), 4.64(br s, 1H), 5.38(t, J=6.9Hz, 1H), 6.50(d, J=8.7Hz, 1H), 6.75–6.79(m, 2H), 6.92–6.97(m, 2H), 7.30(dd, J=8.7, 2.1Hz, 1H), 7.91(d, J=2.1Hz, 1H), 7.56(dd, J=9.3, 2.4Hz, 1H); IR (KBr): 3447, 3414, 3364, 1605, 1518, 1464, 1377, 1278, 819 |

TABLE 120-continued

| | |
|---|---|
| | cm$^{-1}$ |
| Ib-314 | mp 172–173° C.; $^1$H NMR (CDCl$_3$) δ 1.75(s, 6H), 1.78(s, 3H), 1.78(s, 3H), 2.00(s, 6H), 2.01(s, 6H), 3.4(br s, 1H), 3.74(d, J=6.6Hz, 2H), 3.91(t, J= 6.0Hz, 2H), 4.53(br s, 1H), 5.35–5.42(m, 2H), 6.49(dd, J=8.4, 0.9Hz, 1H), 6.67–6.71(m, 2H), 6.94–7.00(m, 2H), 7.29(dd, J=8.4, 2.4Hz, 1H), 7.93(dd, J=2.4, 0.9Hz, 1H); IR (KBr): 3415, 3229, 1606, 1521, 1465, 1379, 1315, 1141, 985, 815 cm$^{-1}$ |
| Ib-315 | mp 207–209° C.; $^1$H NMR (CDCl$_3$) δ 1.76(s, 3H), 1.76(s, 3H), 1.96(s, 6H), 1.98(s, 6H), 3.4(br s, 1H), 3.88(d, J=7.8Hz, 2H), 5.42(t, J=7.8Hz, 1H), 6.76–6.82(m, 2H), 6.92–6.98(m, 2H), 7.26(d, J=7.8Hz, 1H), 7.34(dd, J= 7.8, 2.1Hz, 1H), 8.29(d, J=2.1Hz, 1H); IR (KBr): 3452, 3367, 1619, 1517, 1457, 1353, 1280, 1176, 1107, 820, 540 cm$^{-1}$ |
| Ib-316 | mp 156–158° C.; $^1$H NMR (CDCl$_3$) δ 1.75(s, 3H), 1.76(s, 3H), 1.76(s, 3H), 1.78(s, 3H), 1.97(s, 6H), 2.00(s, 6H), 3.75(d, J=6.6Hz, 2H), 3.88(d, J= 7.7Hz, 2H), 5.40(t, J=6.6Hz, 2H), 5.42(t, J=7.7Hz, 1H), 6.68–6.73(m, 2H), 6.93–7.00(m, 2H), 7.26(dd, J=8.1, 1.1Hz, 1H), 7.34(dd, J=8.1, 2.1 Hz, 1H), 8.29(dd, J=2.1, 1.1Hz, 1H); IR (KBr): 3391, 1612, 1518, 1462, 1180, 1108, 820, 807, 546 cm$^{-1}$. |
| Ib-317 | mp 161–164° C.; $^1$H NMR (CDCl$_3$) δ 1.77(s, 3H), 1.77(s, 3H), 1.99(s, 6H), 1.99(s, 6H), 2.11(s, 6H), 3.89(d, J=7.8Hz, 2H), 5.43(t, J=7.8Hz, 1H), 5.94(s, 2H), 7.21–7.39(m, 6H), 8.31(dd, J=2.3, 0.8Hz, 1H); IR (KBr): 3439, 1586, 1520, 1449, 1406, 1110, 999, 824, 750, 565 cm$^{-1}$ |
| Ib-318 | mp 137–138° C., $^1$H NMR (CDCl$_3$) δ 1.75(s, 3H), 1.78(s, 6H), 1.81(s, 3H), 1.82(s, 3H), 1.89(s, 6H), 1.98(s, 6H), 2.15(s, 3H), 3.75(d, J=6.9Hz, 2H), 4.86(d, J=7.2Hz, 2H), 5.40(m, 1H), 5.59(m, 1H), 6.64–6.71(m, 3H), 6.94–6.99(m, 2H), 7.26(d, J=8.4Hz, 1H). IR (KBr): 3412, 2914, 1611, 1592, 1460, 1311, 1297, 1282, 1237 cm$^{-1}$ |
| Ib-319 | mp 129–130° C., $^1$H NMR (CDCl$_3$) δ 1.74(s, 3H), 1.79(s, 6H), 1.82(s, 3H), 1.98(s, 6H), 1.99(s, 6H), 2.25(s, 3H), 3.75(d, J=6.9Hz, 2H), 4.90(d, J= 6.6Hz, 2H), 5.40 (br t, J=6.9Hz, 1H), 5.59(br t, J=6.9Hz, 1H), 6.70(m, 2H), 6.97(m, 2H), 7.23 d,J=2.1Hz, 1H), 7.82 d,J=2.1Hz, 1H) |
| Ib-320 | mp 153–154° C., $^1$H NMR (CDCl$_3$) δ 1.75(s, 3H), 1.79(s, 6H), 1.83(s, 3H), 1.89(s, 6H), 1.96(s, 3H), 1.99(s, 6H), 2.15(s, 3H), 3.75(d, J=6.9Hz, 2H), 4.86(d, J=6.9Hz, 2H), 5.40(m, 1H), 5.58(m, 1H), 6.69–6.73(m, 3H), 6.94–7.01(m, 2H), 7.84(s, 1H). IR (KBr): 3386, 2928, 1608, 1518, 1464, 1377, 1315, 1180, 1122, 1028 cm$^{-1}$ |
| Ib-321 | mp 115–117° C.; $^1$H NMR (CDCl$_3$) δ 1.60(s, 3H), 1.73(s, 3H), 1.75(s, 3H), 1.78(s, 3H), 1.95(s, 6H), 2.01(s, 6H), 3.60(d, J=7.7Hz, 2H), 3.91(t, J= 6.0Hz, 2H), 4.52(m, 1H), 5.32–5.42(m, 2H), 6.49(d, J=8.4Hz, 1H), 7.05–7.11(m, 2H), 7.28(dd, J=8.4, 2.3Hz, 1H), 7.39–7.44(m, 2H), 7.91(d, J= 2.3Hz, 1H): IR (KBr): 3425, 1609, 1541, 1391, 1378, 814, 550 cm$^{-1}$ |

TABLE 121

| | |
|---|---|
| Ib-322 | mp 119–122° C.; $^1$H NMR (CDCl$_3$) δ 1.75(s, 3H), 1.77(s, 3H), 1.78(s, 3H), 1.82(s, 3H), 2.01(s, 6H), 2.03(s, 3H), 3.34(s, 3H), 3.91(dd, J=5.9, 5.9Hz, 2H), 4.51(t, J=5.2Hz, 1H), 4.64(d, J=6.7Hz, 2H), 5.38(m, 1H), 5.57(m, 1H), 6.47(d, J=8.5Hz, 1H), 6.97–7.08(m, 3H), 7.23–7.28(m, 1H), 7.72(d, J=1.8Hz, 1H); IR (nujor): 3325, 1926, 2853, 1608, 1538, 1514, 1457, 1389, 1296, 1262, 1214, 1110, 1006 cm$^{-1}$ |
| Ib-323 | $^1$H NMR (300 MHz, CDCl$_3$) δ 1.80(d, J=0.9Hz, 3H), 1.83(d, J=0.9Hz, 3H), 1.98(s, 6H), 2.06(s, 3H), 3.32(s, 3H), 4.88(d, J=6.9Hz, 2H), 5.55–5.62(m, 1H), 6.80(d, J=7.8Hz, 2H), 6.85(dd, J=8.6, 0.8Hz, 1H), 7.11(d, J=7.8Hz, 2H), 7.40(dd, J=8.6, 2.6Hz, 1H), 7.98(dd, J=2.6, 0.8Hz, 1H) |
| Ib-324 | $^1$H NMR (300 MHz, CDCl$_3$) δ 1.74(s, 3H), 1.78(s, 3H), 1.80(s, 3H), 1.83(s, 3H), 1.98(s, 3H), 2.07(s, 3H), 3.33(s, 3H), 3.75(d, J=6.6Hz, 2H), 4.88(d, J=6.9Hz, 2H), 5.36–5.43(m, 1H), 5.55–5.62(m, 1H), 6.71(d, J=8.0Hz, 2H), 6.84(dd, J=2.4, 0.8Hz, 1H), 7.30(d, J=8.0Hz, 2H), 7.40(dd, J=8.6, 2.4Hz, 1H), 7.98(dd, J=2.4, 0.8Hz, 1H) |
| Ib-325 | $^1$H NMR (300 MHz, CDCl$_3$) δ 1.80(s, 3H), 1.83(s, 3H), 1.97(s, 6H), 2.06(s, 3H), 3.32(s, 3H), 3.92(s, 3H), 4.46(s, 2H), 4.88(d, J=6.9Hz, 2H), 5.55–5.62(m, 1H), 6.71(d, J=8.0Hz, 2H), 6.84(d, J=8.4Hz, 1H), 7.12(d, J= 8.0Hz, 2H), 7.40 H, dd, J=8.4, 2.2Hz, 1H), 7.50(d, J=8.1Hz, 2H), 7.98 (d, J=2.2Hz, 1H), 8.04(d, J=8.1Hz, 2H) |
| Ib-326 | $^1$H NMR (300 MHz, CDCl$_3$) δ 1.80(s, 3H), 1.83(s 3H), 1.97(s, 6H), 2.06(s, 3H), 3.32(s, 3H), 3.48(s, 2H), 4.88(d, J=6.9Hz, 2H), 5.55–5.61(m, 1H), 6.70(d, J=7.8Hz, 2H), 6.85(d, J=8.4Hz, 1H), 7.12(d, J=7.8Hz, 2H), 7.40(dd, J=8.4, 0.7Hz, 1H), 7.53(d, J=8.1Hz, 2H), 7.99(d, J=0.7Hz, 1H), 8.11(d, J=8.1Hz, 2H) |
| Ib-327 | $^1$H NMR (300 MHz, CDCl$_3$) δ 1.80(s, 3H), 1.83(s, 3H), 1.98(s, 3H), 2.07(s, 3H), 3.32(s, 3H), 3.86(s, 3H), 3.87(s, 6H), 4.33(s, 2H), 4.88(s, J=6.6Hz, 2H), 5.55–5.60(m, 1H), 6.67(s, 2H), 6.76(d, J=7.1Hz, 2H), 6.85(dd, J= 8.4, 0.6Hz, 1H), 7.15(d, J=7.1Hz, 2H), 7.40(dd, J=8.4, 2.4Hz, 1H), 7.98 |

TABLE 121-continued

| | |
|---|---|
| | (dd, J=2.4, 0.6Hz, 1H) |
| Ib-328 | $^1$H NMR (300 MHz, CDCl$_3$) δ 1.80(s, 3H), 1.83(s, 3H), 1.97(s, 6H), 2.06(s, 3H), 3.31(s, 3H), 4.38(s, 2H), 4.88(d, J=7.2Hz, 2H), 5.55–5.62(m, 1H), 6.29(d, J=3.0Hz, 1H), 6.35(dd, J=3.0, 1.8Hz, 1H), 6.77(d, J=8.1Hz, 2H), 6.84(dd, J=8.2, 0.6Hz, 1H), 7.14(d, J=8.1Hz, 2H), 7.399(dd, J=1.8, 0.8Hz, 1H), 7.40(dd, J=8.2, 2.4Hz, 1H), 7.98(dd, J=2.4, 0.6Hz, 1H) |
| Ib-329 | mp 110–111° C.; $^1$H NMR (CDCl$_3$) δ 1.80(s, 3H), 1.83(s, 3H), 1.98(s, 6H), 2.06(s, 3H), 3.33(s, 3H), 4.88(d, J=6.9Hz, 2H), 5.59(m, 1H), 6.79(d, J=8.7Hz, 2H), 6.84(dd, J=8.4 and J=0.9Hz, 1H), 6.95(d, J=7.2Hz, 2H), 7.56(dd, J=8.4 and 2.7Hz, 1H), 8.11(dd, J=2.4 and 0.6Hz, 1H); IR (CHCl$_3$): 3462, 3016, 2934, 1620, 1604, 1279, 1241, 1087, 982, cm$^{-1}$. |
| Ib-330 | mp 115–116° C.; $^1$H NMR (CDCl$_3$) δ 1.74(s, 3H), 1.78(s, 3H), 1.80(s, 3H), 1.83(s, 3H), 2.00(s,6H), 2.06(s, 3H) 3.33(s, 3H), 3.75(d, J=6.6Hz, 2H), 4.88(d, J=6.9Hz, 2H), 5.39(m, 1H), 5.59(m, 1H), 6.71(d, J=7.8Hz, 2H), 6.84(dd, J=8.4 and 0.6Hz, 1H), 6.97(d, J=7.5Hz, 2H), 7.56(dd, J=8.4 and 2.4Hz, 1H), 8.11(dd, J=2.4 and 0.9Hz, 1H); IR (CHCl$_3$): 3424, 3004, 2975, 2934, 2860, 1612, 1491, 1402, 1377, 1280, 1241, cm$^{-1}$. |

TABLE 122

| | |
|---|---|
| Ib-331 | mp 111–112° C.; $^1$H NMR (CDCl$_3$) δ 1.26(s, 3H), 1.28(s, 3H), 1.79(s, 3H), 1.83(s, 3H), 2.00(s,6H), 2.06(s, 3H), 3.33(s, 3H), 3.68(m, 1H), 4.88(d, J=6.9Hz, 2H), 5.59(m, 1H), 6.67(d, J=8.4Hz, 2H), 6.84(dd, J=8.4 and 6.0 Hz, 1H), 6.95(d, J=7.2Hz, 2H), 7.56(dd, J=8.4 and 2.4Hz, 1H), 8.12(dd, J=2.4 and 0.6Hz, 1H); IR (CHCl$_3$): 3423, 3018, 2975, 2934, 2872, 1612, 1354, 1317, 1377, 1280, 1242, cm$^{-1}$. |
| Ib-332 | mp 139–140° C.; $^1$H NMR (CDCl$_3$) δ 1.14–1.46(m 5H), 1.65–1.80(m 3H), 1.82 (s, 3H), 1.83(s, 3H), 2.00(s, 6H), 2.06(s, 3H), 3.33(s, 3H), 2.10–2.15(m, 2H), 3.30(m, 1H), 4.88(d, J=7.2Hz, 2H), 5.59(m, 1H), 6.87(d, J=8.7Hz, 2H), 6.84(dd, J=8.7 and 0.9Hz, 1H), 6.94(d, J=7.2Hz, 2H), 7.56(dd, J=8.7 and 2.7Hz, 1H), 8.11(dd, J=2.7 and 0.9Hz, 1H); IR (CHCl$_3$): 3422, 3002, 2933, 2856, 1612, 1354, 1318, 1280, 1242, 1130, 1087, cm$^{-1}$. |
| Ib-333 | mp 155–156° C.; $^1$H NMR (CDCl$_3$) δ 1.80(s, 3H), 1.83(s, 3H), 1.99(s, 6H), 2.06(s, 3H), 3.33(s, 3H), 4.38(s, 2H), 4.89(d, J=6.9Hz, 2H), 5.59(m, 1H), 6.30(m, 1H), 6.35–6.37(m, 1H), 6.77(d, J=8.4Hz, 2H), 6.83(dd, J=8.4 and 0.9Hz, 1H), 6.98(d, J=7.5Hz, 2H), 7.40(dd, J=2.1 and 0.9Hz, 1H) 7.57(dd, J=8.7 and 2.7Hz, 1H) 8.12(dd, J =2.4 and 0.6Hz, 1H); IR (CHCl$_3$): 3424, 2934, 2861, 1613, 1280, 1241, 1217, cm$^{-1}$. |
| Ib-334 | mp 142–145° C.; $^1$H NMR (CDCl$_3$) δ 1.99(s, 3H), 2.06(s, 3H), 3.33(s, 3H), 3.79 (brs, 2H), 5.40(s, 2H), 6.40(dd, J=2.0, 3.2Hz, 1H), 6.49(d, J=3.3Hz, 1H), 6.78(d, J=8.4Hz, 2H), 6.87(dd, J=0.8, 8.3Hz, 1H), 6.95(brd, J=7.2Hz, 2H), 7.47(dd, J=0.9, 1.5Hz, 1H), 7.58(dd, J=2.6, 8.6Hz, 1H), 8.13(dd, J=0.8, 2.6Hz, 1H); IR (nujor): 3342, 2924, 2854, 1611, 1523, 1493, 1458, 1283, 1011, 824 cm$^{-1}$ |
| Ib-335 | mp 158–159° C.; $^1$H NMR (CDCl$_3$) δ 1.80(s, 3H), 1.83(s, 3H), 2.00(s, 6H), 2.06(s, 3H), 3.33(s, 3H), 4.38(s, 2H), 4.89(d, J=7.0Hz, 2H), 5.59(m, 1H), 6.74(d, J=8.6Hz, 2H), 6.84(dd, J=0.7, 8.4Hz, 1H), 6.98(brd, J=6.9Hz, 2H), 7.28–7.46(m, 5H), 7.56(dd, J=2.5, 8.5Hz, 1H), 8.12(dd, J=0.7, 2.3Hz, 1H), IR (nujor): 3357, 2926, 2854, 1613, 1526, 1491, 1452, 1279, 1090, 997, 823, 732 cm$^{-1}$ |
| Ib-336 | mp 116–117° C.; $^1$H NMR (CDCl$_3$) δ 1.80(s, 3H), 1.83(s, 3H), 2.00(s, 6H), 2.06(s, 3H), 2.30(s, 3H), 3.33(s, 3H), 4.31(s, 2H), 4.88(d, J=6.9Hz, 2H), 5.59(m, 1H), 5.93(m, 1H), 6.17(d, J=3.1Hz, 1H), 6.76(d, J=8.6Hz, 2H), 6.84(d, J=8.5Hz, 1H), 6.98(brd, J=6.7Hz, 2H), 7.56(dd, J=2.3, 8.5Hz, 1H), 8.12(d, J=2.3Hz, 1H), IR (nujor): 3349, 2925, 2854, 1611, 1525, 1490, 1455, 1280, 1240, 979, 822, 782 cm$^{-1}$ |
| Ib-337 | mp 94–97° C.; $^1$H NMR (CDCl$_3$) δ 1.66(brd, J=6.7Hz; 3H), 1.73(s, 3H), 1.80 (s, 3H), 1.83(s, 3H), 1.99(s, 6H), 2.06(s, 3H), 3.33(s, 3H), 3.69(brs, 2H), 4.88(d, J=6.9Hz, 2H), 5.52–5.62(m, 2H), 6.70(d, J=8.6Hz, 2H), 6.83(dd, J=0.7, 8.4Hz, 1H), 6.95(brd, J=7.4Hz, 2H), 7.56(dd, J=2.5, 8.5Hz, 1H), 8.11(dd, J=0.7, 2.3Hz, 1H), IR (KBr): 3409, 3325, 2927, 2857, 1612, 1523, 1457, 1279, 1085, 1002, 986, 820 cm$^{-1}$ |
| Ib-338 | mp 161–163° C.; $^1$H NMR (CDCl$_3$) δ 1.80(s, 3H), 1.83(s, 3H), 2.00(s, 6H), 2.06(s, 3H), 3.33(s, 3H), 3.86(s, 3H), 3.87(s, 6H), 4.42(s, 2H), 4.88(d, J=7.0Hz, 2H), 5.59(m, 1H), 6.66(s, 2H), 6.75(d, J=8.6Hz, 2H), 6.84(dd, J=0.6, 8.5Hz, 1H), 6.99(brd, J=6.7Hz, 2H), 7.56(dd, J=2.4, 8.4Hz, 1H), 8.12(dd, J=0.6, 2.3Hz, 1H), IR (KBr): 3373, 2934, 2831, 1604, 1592, 1522, 1457, 1280, 1240, 1124, 981, 822 cm$^{-1}$ |

TABLE 123

| | |
|---|---|
| Ib-339 | mp 113–115° C.; $^1$H NMR (CDCl$_3$) δ 1.74(s, 3H), 1.78(s, 3H), 1.80(d, J=0.9Hz, 3H), 2.00(s, 6H), 2.06(s, 3H), 3.33(s, 3H), 3.75(d, J=6.7Hz, 2H), 4.83(dd, J=5.3Hz, 2H), 5.39(m, 1H), 5.78–5.96(m, 2H), 6.70(d, J=8.6Hz, |

TABLE 123-continued

| | |
|---|---|
| | 2H), 6.84(dd, J=0.7, 8.5Hz, 1H), 6.97(brd, J=7.3Hz, 2H), 7.57(dd, J=2.4, 8.4Hz, 1H), 8.11(dd, J=0.7, 2.4Hz, 1H); IR (njor): 3367, 2924, 2853, 1611, 1520, 1457, 1278, 1241, 992, 820 cm$^{-1}$ |
| Ib-340 | mp 90–92° C.; $^1$NMR (CDCl$_3$) δ 1.75(s, 3H), 1.78(s, 3H), 2.00(s, 6H), 2.06 (s, 3H), 2.59(dt, J=6.7, 6.7Hz), 3.33(s, 3H), 3.75(d, J=6.9Hz, 2H), 4.42(t, J=6.8Hz, 2H), 5.12(brd, J=10.2Hz, 1H), 5,20(ddt, J=1.6, 1.6, 17.2Hz, 1H), 5.39(m, 1H), 5.96(ddt, J=6.7, 10.3, 17.1Hz, 1H), 6.70(d, J=8.6Hz, 2H), 6.83(dd, J=0.7, 8.4Hz, 1H), 6.96(brd, J=6.9Hz, 2H), 7.57(dd, J=2.3, 8.5Hz, 1H), 8.11(dd, J=07, 2.4Hz, 1H); IR (nujor): 3362, 2952, 2925, 2854, 1611, 1604, 1519, 1466, 1280, 819 cm$^{-1}$ |
| Ib-341 | mp 97–98° C.; $^1$H NMR (CDCl$_3$) δ 1.04(t, J=7.5Hz, 3H), 1.75(s, 3H), 1.78(s, 3H), 2.00(s, 6H), 2.06(s, 3H), 2.22(dq, J=7.0, 7.1Hz, 2H), 3.33(s, 3H), 3.75 (d, J=6.9Hz, 2H), 4.95(d, J=5.3Hz, 2H), 5.39(m, 1H), 5.71(dt, J=6.1, 11.0Hz, 1H), 5.75(dt, J=6.1, 10.8Hz, 1H), 6.70(d, J=8.8Hz, 2H), 6.84(dd, J=0.7, 8.5Hz, 1H), 6.97(brd, J=6.9Hz, 2H), 7.57(dd, J=2.4, 8.4Hz, 1H), 8.12(dd, J=0.7, 2.5Hz, 1H), IR (KBr): 3341, 2965, 2930, 1612, 1523, 1491, 1456, 1281.1243, 1089, 991, 822 cm$^{-1}$ |
| Ib-342 | mp 129–130° C.; $^1$H NMR (CDCl$_3$) δ 1.74(s, 3H), 1.78(s, 3H), 1.92(t, J=2.1 Hz 3H), 2.00(s, 6H), 2.05(s, 3H), 3.32(s, 3H), 3.75(d, J=6.6Hz, 2H), 5.02(m, 2H), 5.40(m, 1H), 6.72(d, J=8.4Hz, 2H), 6.89(dd, J=8.4 and 0.6 Hz, 1H), 6.97(d, J=7.2Hz, 2H), 7.59(dd, J=8.4 and 2.4Hz, 1H), 8.12(dd, J=2.4 and 0.6Hz, 1H); IR (CHCl3): 3424, 3004, 2933, 2858, 1612, 1346, 1279, 1241, cm$^{-1}$. |
| Ib-343 | mp 137–138° C.; $^1$H NMR (CDCl$_3$) δ 1.75(s, 3H), 1.78(s, 3H), 2.00(s, 6H), 2.06(s, 3H), 3.33(s, 3H), 3.75(d, J=6.9Hz, 2H), 5.40(m, 3H), 6.40(dd, J= 3.3 and 1.8Hz, 1H), 6.49(d, J=3.3Hz, 1H), 6.70(d, J=8.7Hz, 2H), 6.87 (dd, J=9.0 and 0.6Hz, 1H), 6.97(d, J=7.5Hz, 2H), 7.47(dd, J=1.8 and 0.9Hz, 1H), 7.59(dd, J=8.4 and 2.4Hz, 1H), 8.13(dd, J=2.4 and 0.6Hz, 1H); IR (CHCl$_3$): 3424, 3004, 2933, 2860, 1612, 1402, 1453, 1346, 1280, cm$^{-1}$. |
| Ib-344 | mp 144–146° C.; $^1$H NMR (CDCl$_3$) δ 1.80(s, 3H), 1.84(s, 3H), 1.85(t, J=2.4Hz, 3H), 2.00(s, 6H), 2.07(s, 3H), 3.34(s, 3H), 3.94(q, J=2.4Hz, 2H), 4.89(d, J=6.9Hz, 2H), 5.60(m, 1H), 6.76(d, J=8.4Hz, 2H), 6.85(d, J=8.4Hz, 1H), 7.00(brd, J=7.5Hz, 2H), 7.57(dd, J=2.4, 8.4Hz, 1H), 8.13(d, J=2.4Hz, 1H); IR (CHCl$_3$): 3451, 3395, 3024, 3015, 2934, 1621, 1604, 1518, 1491, 1280, 993, 825 cm$^{-1}$ |
| Ib-345 | mp 113–115° C.; $^1$H NMR (CDCl$_3$) δ 1.75(s, 3H), 1.77(s, 3H), 2.00(s, 6H), 2.05(s, 3H), 3.32(s, 3H), 3.75(d, J=6.7Hz, 2H), 4.64(dd, J=3.9, 29.2Hz, 1H), 4.66(dd, J=2.9, 29.2Hz 1H), 4.81(dd, J=3.0, 47.5Hz, 1H), 4.82(dd, J=3.9, 47.4Hz, 1H), 5.40(m 1H), 6.70(d, J=8.6Hz, 2H), 6.90(dd.J=0.7, 8.4Hz.1H), 6.96(brd, J=7.5Hz, 2H), 7.59(dd, J=2.4, 8.4Hz, 1H), 8.09(dd, J=0.7, 2.5Hz, 1H); IR (nujor): 3399, 2925, 2854, 1612, 1519, 1491, 1450, 1283, 1087, 929 cm$^{-1}$ |

TABLE 124

| | |
|---|---|
| Ib-346 | mp 111–112° C.; $^1$H NMR (CDCl$_3$) δ 1.75(s, 3H), 1.78(s, 3H), 2.00(s, 6H), 2.05(s, 3H), 3.32(s, 3H), 3.75(d, J=6.9Hz, 2H), 4.82(dq, J=1.4, 8.6Hz, 2H), 5.39(m, 1H), 6.70(d, J=8.7Hz, 2H), 6.93–6.97(m, 3H), 7.64(dd, J=2.4, 8.4Hz, 1H), 8.10(dd, J=0.3, 2.1Hz, 1H), IR (KBr): 3407, 2931, 2860, 1613, 1521, 1292, 1274, 1259, 1240, 1164, 1070, 823 cm$^{-1}$ |
| Ib-347 | mp 154–156° C.; $^1$H NMR (CDCl$_3$) δ 1.85(t, J=2.6Hz, 3H), 1.99(s, 6H), 2.06 (s, 3H), 3.33(s, 3H), 3.93(q, J=2.4Hz, 2H), 5.40(s, 2H), 6.40(dd, J=1.7, 3.2Hz, 1H), 6.49(dd, J=0.9, 3.0Hz, 1H), 6.76(d, J=8.7Hz, 2H), 6.87(dd, J=0.9, 8.7Hz, 1H), 6.99(brd, J=7.5Hz, 2H), 7.48(dd, J=0.9, 1.8Hz, 1H), 7.58(dd, J=2.6, 8.6Hz, 1H), 8.14(dd, J=0.6, 2.4Hz, 1H), IR (KBr): 3410, 2989, 2934, 2860, 1610, 1520, 1278, 1242, 992, 822, 742 cm$^{-1}$ |
| Ib-348 | mp 165–168° C.; $^1$H NMR (CDCl$_3$) δ 1.85(t, J=2.4Hz, 3H), 1.91(t, J=2.4Hz, 3H), 1.99(s, 6H), 2.05(s, 3H), 3.32(s, 3H), 3.93(q, J=2.4Hz, 2H), 5.01(q, J=2.4Hz, 2H), 6.76(d, J=8.7Hz, 2H), 6.89(dd, J=0.8, 8.6Hz, 1H), 6.99(brd, J=7.2Hz, 2H), 7.58(dd, J=2.4, 8.4Hz, 1H), 8.12(dd, J=0.6, 2.4Hz, 1H), IR (KBr): 3393, 3338, 2923, 2862, 2237, 1612, 1604, 1521, 1279, 1243, 996, 824 cm$^{-1}$ |
| Ib-349 | mp 172–173° C.; $^1$H NMR (CDCl$_3$) δ 1.74(s, 3H),, 1.78(s, 3H), 2.05(s, 3H), 2.30(s, 6H), 2.63(s, 3H), 3.32(s, 3H), 2.30(s, 6H), 3.74(d, J=6.6Hz, 2H), 5.39(m, 1H), 6.70(d, J=8.7Hz, 2H), 6.96(d, J=6.6Hz, 2H), 7.27(dd, J= 8.4 and 0.6Hz, 1H), 7.51(dd, J=8.1 and 2.1Hz, 1H), 7.42(dd, J=2.1 and 0.9Hz, 1H), IR (CHCl$_3$): 3423, 3003, 2931, 28598, 1613, 1589, 1315, 14021, 1289, cm$^{-1}$. |
| Ib-350 | mp 183–184° C.; $^1$H NMR (CDCl$_3$) δ 1.75(s, 3H), 1.79(s, 3H), 2.01(s, 6H), 2.03(s, 3H), 3.32(s, 3H), 3.33(s, 3H), 3.75(d, J=6.9Hz, 2H), 5.40(m, 1H), 6.72(d, J=8.7Hz, 2H), 6.75(d, J=8.1Hz, 2H), 7.98(dd, J=8.1 and 2.1Hz, 1H), 8.17(dd, J=8.1 and 0.9Hz, 1H), 8.70(dd, J=2.7 and 0.6Hz, 1H),; IR (CHCl$_3$): 3424, 3016, 2934, 2860, 1613, 1315, 1292, 1231, cm$^{-1}$. |
| Ib-351 | mp 148–149° C.; $^1$H NMR (CDCl$_3$) δ 1.79(s, 3H), 1.83(s, 3H), 2.05(s, 3H), 2.06(s, 3H), 3.33(s, 3H), 3.34(s, 3H), 4.88(d, J=6.9Hz, 2H), 5.58(m, 1H), |

TABLE 124-continued

| | |
|---|---|
| | 6.78(d, J=8.7Hz, 2H), 6.84(d, J=8.4Hz, 1H), 7.11(d, J=8.7Hz, 2H), 7.56 (dd, J=8.4, 2.4Hz, 1H), 8.12(d, J=2.4Hz, 1H) IR (KBr): 3393, 1603, 1520, 1492, 1459, 1399, 1373, 1357, 1282, 1247, 1128, 1038, 1020, 982, 824 cm$^{-1}$ |
| Ib-352 | mp 106–107° C.; $^1$H NMR (CDCl$_3$) δ 1.75(s, 3H), 1.78(s, 3H), 1.80(s, 3H), 1.83(s, 3H), 2.07(s, 3H), 2.08(s, 3H), 3.33(s, 3H), 3.34(s, 3H), 3.75(d, J=6.6Hz, 2H), 4.88(d, J=7.2Hz, 2H), 5.38(m, 1H), 5.58(m, 1H), 6.70(d, J=8.4Hz, 2H), 6.84(d, J=8.4Hz, 1H), 7.12(d, J=8.4Hz, 2H), 7.56(dd, J=8.4, 2.4Hz, 1H), 8.12(d, J=2.4Hz, 1H) IR (KBr): 3401, 1614, 1603, 1561, 1522, 1491, 1463, 1281, 1242, 1182, 1128, 1037, 985, 821 cm$^{-1}$ |
| Ib-353 | mp 126–127° C.; $^1$H NMR (CDCl$_3$) δ 1.49(s, 3H), 1.67(s, 3H), 1.80(s, 3H), 1.83(s, 3H), 2.02(s, 3H), 2.07(s, 3H), 2.81(d, J=5.4Hz, 3H), 3.30(s, 3H), 3.34(s, 3H), 4.17(q, J=5.4Hz, 2H), 4.27(d, J=7.2Hz, 2H), 4.89(d, J=7.2Hz, 2H), 5.29(m, 1H), 5.58(m, 1H), 6.85(d, J=8.4Hz, 1H), 7.32(d, J=4.2Hz, 2H), 7.44(d, J=4.2Hz, 2H), 7.59(dd, J=8.4, 2.4Hz, 1H), 8.11(d, J=2.4Hz, 1H) IR (KBr): 3304, 1603, 1564, 1512, 1491, 1455, 1355, 1329, 1279, 1149, 1131, 1043, 1019, 986, 879, 823, 583 cm$^{-1}$ |

TABLE 125

| | |
|---|---|
| Ib-354 | mp 117–118° C.; $^1$H NMR (300 MHz, CDCl$_3$) δ 1.12–1.30(m, 2H), 1.30–1.48 (m, 2H), 1.62–1.75(m, 2H), 1.80(s, 3H), 1.83(s, 3H), 1.75–1.84(m, 2H), 2.06 (s, 3H), 2.07(s, 3H), 2.06–2.18(m, 2H), 3.33(s, 3H), 3.34(s, 3H), 3.30–3.37 (m, 1H), 4.88(d, J=6.9Hz, 2H), 5.56–5.61(m, 1H), 6.65–6.72(m, 2H), 6.84 (dd, J=8.7, 0.9Hz, 1H), 706–7.13(m, 2H), 7.56(dd, J=8.7, 2.4Hz, 1H), 8.11(dd, J=2.4, 0.9Hz, 1H). |
| Ib-355 | mp 108–110° C., $^1$H NMR (CDCl$_3$) δ 1.74(s, 3H), 1.78(s, 3H), 1.81(s, 3H), 1.82(s, 3H), 1.94(s, 3H), 2.06(s, 3H), 2.26(s, 3H), 3.32(s, 3H), 3.33(s, 3H), 3.75(d, J=6.9Hz, 2H), 4.87(d, J=7.2Hz, 2H), 5.40(m, 1H), 5.57(m, 1H), 6.65(d, J=8.4Hz, 2H), 6.72(d, J=8.4Hz, 2H), 7.14(d, J=8.4Hz, 2H), 7.37(d, J=8.4Hz, 1H). IR (KBr): 3417, 2930, 1613, 1595, 1520, 1449, 1391, 1297, 1281, 1246, 1133, 1101, 1038 cm$^{-1}$ |
| Ib-356 | mp 119–121° C., $^1$H NMR (CDCl$_3$) δ 1.74(s, 3H), 1.78(s, 3H), 1.79(s, 3H), 1.82(s, 3H), 2.06(s, 3H), 2.07(s, 3H), 2.25(s, 3H), 3.33(s, 3H), 3.35(s, 3H), 3.75(d, J=6.6Hz, 2H), 4.91(d, J=6.6Hz, 2H), 5.39(br t, J=6.6Hz, 1H), 5.59(br t, J=6.6Hz, 1H), 6.71(d, J=8.4Hz, 2H), 7.13(d, J=8.4Hz, 2H), 7.37(d, J=2.1Hz, 1H), 7.94(d, J=2.1Hz, 1H) |
| Ib-357 | mp 130–132° C., $^1$H NMR (CDCl$_3$) δ 1.74(s, 3H), 1.79(s, 6H), 1.82(s, 3H), 1.94(s, 3H), 2.06(s, 6H), 3.33(s, 3H), 3.37(s, 3H), 3.76(d, J=6.9Hz, 2H), 4.86(d, J=6.9Hz, 2H), 5.40(m, 1H), 5.57(m, 1H), 6.71–6.74(m, 3H), 7.14 (d, J=8.7Hz, 2H), 7.94(s, 1H). IR (KBr): 3392, 2927, 1611, 1521, 1448, 1390, 1349, 1322, 1286, 1270, 1236, 1179, 1115, 1026 cm$^{-1}$ |
| Ib-358 | mp 120–121° C., $^1$H NMR (CDCl$_3$) δ 1.74(s, 3H), 1.78(s, 3H), 2.06(s, 3H), 2.07(s, 3H), 2.63(s, 3H), 3.33(s, 6H), 3.75(d, J=9.6Hz, 2H), 5.39(m, 1H), 6.70(d, J=8.4Hz, 2H), 7.12(d, J=8.4Hz, 2H), 7.27(d, J=8.1Hz, 1H), 7.51 (dd, J=8.1, 2.4Hz, 1H), 8.42(d, J=2.4Hz, 1H) IR (KBr): 3379, 1614, 1587, 1523, 1459, 1395, 1351, 1319, 1286, 1136, 1109, 1038, 1016, 985, 818 cm$^{-1}$ |
| Ib-359 | mp 163–164° C.; $^1$H NMR (300 MHz, CDCl$_3$) δ 1.75(s, 3H), 1.78(s, 3H), 2.07 (s, 3H), 2.09(s, 3H), 3.33(s, 3H), 3.36(s, 3H), 3.75(d, J=6.6Hz, 2H), 3.91 (t, J=5.9Hz, 2H), 4.58(br s, 1H), 5.35–5.42(m, 2H), 6.49(d, J=8.3Hz, 1H), 6.65–6.72(m, 2H), 7.08–7.15(m, 2H), 7.44(dd, J=8.3, 2.0Hz, 1H), 8.06(d, J=2.0Hz, 1H). |
| Ib-360 | mp 145–146° C.; $^1$H NMR (300 MHz, CDCl$_3$) δ 1.79(s, 3H), 2.06(s, 3H), 2.08 (s, 3H), 3.35(s, 3H), 3.78(t, J=5.6Hz, 2H), 3.88(br s, 1H), 4.53(br s), 5.36–5.44(m, 1H), 6.61(dd, J=8.4, 0.75Hz, 1H), 6.73–6.79(m, 1H), 6.92–6.98(m, 2H), 7.45(dd, J=8.4, 2.1Hz, 1H), 8.04(d, J=2.1Hz, 1H). |
| Ib-361 | mp 143–144° C.; $^1$H NMR (300 MHz, CDCl$_3$) δ 1.75(s, 3H), 1.79(s, 3H), 2.06 (s, 3H), 2.09(s, 3H), 3.35(s, 3H), 3.36(s, 3H), 3.78(t, J=6.0Hz, 2H), 3.83–3.94(m, 3H), 4.53(br s, 1H), 5.34–5.44(m, 2H), 6.48(dd, J=8.4, 0.9 Hz, 1H), 6.73–6.79(m, 1H), 6.92–6.98(m, 2H), 7.43(dd, J=8.4, 2.4Hz, 1H), 8.05(dd, J=2.4, 0.6Hz, 1H). |
| Ib-362 | $^1$H NMR (300 MHz, CDCl$_3$) δ 1.20–1.35(m, 3H), 1.35–1.48(m, 2H), 1.77(s, 3H), 1.82(s, 3H), 1.60–1.96(m, 3H), 2.04(s, 3H), 2.09(s, 3H), 2.04–2.15(m, 2H), 3.34(s, 3H), 3.36(s, 3H), 3.53–3.64(m, 1H), 4.64(d, J=6.9Hz, 2H), 4.60–4.65(m, 1H), 5.54–560(m, 1H), 6.47(d, J=8.4Hz, 1H), 6.96–7.09(m, 3H), 7.41(dd, J=8.4.2.2Hz, 1H), 8.02(d, J=2.2Hz, 1H). |

TABLE 126

| | |
|---|---|
| Ib-363 | mp 96–97° C.; $^1$H NMR (CDCl$_3$) δ 1.74(s, 3H), 1.79(s, 6H), 1.82(s, 3H), 2.05 (s, 6H), 2.18(s, 3H), 3.74(d, J=6.6Hz, 2H), 4.87(d, J=7.2Hz, 2H), 5.39(t, J=6.9Hz, 1H), 5.58(t, J=7.2Hz, 1H), 6.70(d, J=8.4Hz, 2H), 6.81(d, J=8.4Hz, 1H), 6.96–6.99(m, 3H), 7.57(dd, J=0.9, 8.7Hz, 1H), 8.16(d, J= |

TABLE 126-continued

| | |
|---|---|
| | 2.1Hz, 1H); IR (KBr): 3345, 2972, 2913, 1613, 1560, 1522, 1490, 1466, 1281, 1240, 982, 827 cm$^{-1}$ |
| Ib-364 | mp 133–134° C.; $^1$H NMR (CDCl$_3$) δ 1.79(s, 3H), 1.82(s, 3H), 2.05(s, 6H), 2.18(s, 3H), 4.17(br s, 1H), 4.38(s, 2H), 4.87(d, J=7.2Hz, 2H), 5.58(t, J= 7.2Hz, 1H), 6.74(d, J=8.4Hz, 2H), 6.81(dd, J=0.6, 8.4Hz, 1H), 6.97–6.99 (m, 3H), 7.31–7.46(m, 5H), 7.57(dd, J=2.7, 8.7Hz, 1H), 8.15(dd, J=0.6, 2.4Hz, 1H); IR (KBr): 3357, 2962, 2922, 1614, 1526, 1491, 1465, 1359, 1280, 1241, 999, 828 cm$^{-1}$ |
| Ib-365 | mp 89–91° C.; $^1$H NMR (CDCl$_3$) δ 1.71(s, 3H), 1.75(s, 3H), 1.79(s, 3H), 1.82 (s, 3H), 2.25(s, 3H), 3.75(d, J=6.9Hz, 2H), 3.88(s, 3H), 4.87(d, J=6.9Hz, 2H), 5.37(m, 1H), 5.58(m, 1H), 6.74–6.84(m, 4H), 7.21(s, 1H), 7.41– 7.45(m, 2H), 7.76(dd, J=2.4, 8.4Hz, 1H), 8.19(d, J=2.4Hz, 1H); IR (CHCl$_3$): 3426, 2935, 2859, 1611, 1524, 1504, 1482, 1379, 1357, 1316, 1281, 1241, 1187, 1165, 1128, 1039, 979, 895 cm$^{-1}$ |
| Ib-366 | mp 93–94° C.; $^1$H NMR (CDCl$_3$) δ 1.25(d, J=6.3Hz, 6H), 1.79(s, 3H), 1.82(s, 3H), 2.24(s, 3H), 3.67(m, 1H), 3.79(s, 3H), 4.87(d, J=7.2Hz, 2H), 5.57(m, 1H), 6.69(d, J=7.5Hz, 2H), 6.79(s, 1H), 6.82(d, J=8.4Hz, 1H), 7.21(s, 1H), 7.42(d, J=8.4Hz, 2H), 7.60(dd, J=2.4, 8.7Hz, 1H), 8.19(d, J=2.4Hz, 1H); IR (CHCl$_3$): 3424, 2974, 2934, 2871, 1673, 1611, 1566, 1524, 1504, 1482, 1385, 1357, 1318, 1281, 1242, 1129, 1039, 979 cm$^{-1}$ |
| Ib-367 | mp 105–108° C.; $^1$H NMR (CDCl$_3$) δ 1.79(s, 3H), 1.82(s, 3H), 2.24(s, 3H), 3.78(s, 3H), 4.38(s, 2H), 4.87(d, J=7.2Hz, 2H), 5.57(m, 1H), 6.73(d, J=8.4Hz, 2H), 6.79(s, 1H), 6.82(d, J=8.4Hz, 1H), 7.20(s, 1H), 7.28–7.43(m, 7H), 7.60(dd, J=2.4, 8.4Hz, 1H), 8.18(d, J=2.4Hz, 1H); IR (CHCl$_3$): 3448, 3421, 2936, 2859, 1612, 1566, 1524, 1482, 1391, 1358, 1316, 1281, 1242, 1187, 1165, 1128, 1039, 979 cm$^{-1}$ |
| Ib-368 | mp 112–113° C.; $^1$H NMR (CDCl$_3$) δ 1.55–1.72(m, 6H), 1.79(s, 3H), 1.82(s, 3H), 2.07–2.12(m, 2H), 2.24(s, 3H), 3.41(m, 1H), 3.79(s, 3H), 3.96(s, 4H), 4.87(d, J=6.6Hz, 2H), 5.57(m, 1H), 6.70–6.83(m, 4H), 7.20(s, 1H), 7.42(d, J=8.4Hz, 2H), 7.42(d, J=8.4Hz, 2H), 7.60(dd, J=1.8, 8.4Hz, 1H), 8.18(d, J=1.8Hz, 1H); IR (CHCl$_3$): 3425, 2952, 2887, 1611, 1524, 1504, 1482, 1445, 1376, 1357, 1310, 1281, 1188, 1152, 1105, 1036, 977, 925 cm$^{-1}$ |
| Ib-369 | mp 141–142° C.; $^1$H NMR (CDCl$_3$) δ 1.56(m, 2H), 1.79(s, 3H), 1.82(s, 3H), 2.05–2.10(m, 2H), 225(s, 3H), 3.48–3.59(m, 3H), 3.79(s, 3H), 4.00–4.05(m, 2H), 4.87(d, J=6.9Hz, 2H), 5.57(m, 1H), 6.73–6.84(m, 4H), 7.20(s, 1H), 7.42(d, J=8.4Hz, 2H), 7.60(dd, J=2.4, 8.4Hz, 1H), 8.18(d, J=2.4Hz, 1H); IR (CHCl$_3$): 3424, 2966, 2939, 2850, 1611, 1566, 1523, 1482, 1386, 1357, 1316, 1188, 1136, 1087, 1039, 982, 870 cm$^{-1}$ |
| Ib-370 | mp 83–86° C.; $^1$H NMR (CDCl$_3$) δ 1.71(s, 3H), 1.75(s, 3H), 2.24(s, 3H), 3.74–3.81(m, 5H), 5.35–5.40(m, 3H), 6.40(m, 1H), 6.48(m, 1H), 6.74(d, J=8.7Hz, 2H), 6.80(s, 1H), 6.85(d, J=8.7Hz, 1H), 7.21(s, 1H), 7.42–7.48(m, 3H), 7.62(dd, J=2.4, 8.4Hz, 1H), 8.20(d, J=2.4Hz, 1H); IR (CHCl$_3$): 3427, 2935, 2858, 1611, 1567, 1524, 1503, 1480, 1390, 1346, 1316, 1282, 1187, 1165, 1150, 1127, 1039, 1015, 992, 920 cm$^{-1}$ |

TABLE 127

| | |
|---|---|
| Ib-371 | mp 100–101° C.; $^1$H NMR (CDCl$_3$) δ 1.26(d, J=6.3Hz, 6H), 2.24(s, 3H), 3.67(m, 1H), 3.79(s, 3H), 5.39(s, 2H), 6.40(m, 1H), 6.49(m, 1H), 6.70–6.73 (m, 2H), 6.79(s, 1H), 6.84(d, J=8.4Hz, 1H), 7.21(s, 1H), 7.43(d, J=8.4Hz, 2H), 7.48(m, 1H), 7.62(dd, J=2.4, 8.4Hz, 1H), 8.20(d, J=2.4Hz, 1H); IR (CHCl$_3$): 3424, 2967, 2934, 1611, 1567, 1524, 1479, 1384, 1346, 1318, 1282, 1243, 1187, 1151, 1127, 1039, 1015, 992, 920 cm$^{-1}$ |
| Ib-372 | mp 138–139° C.; $^1$H NMR (CDCl$_3$) δ 1.56–1.84(m, 6H), 2.09–2.12(m, 2H), 2.24(s, 3H), 3.42(m, 1H), 3.79(s, 3H), 3.97(s, 4H), 5.39(s, 2H), 6.40(m, 1H), 6.49(d, J=3.3Hz, 1H), 6.72(m, 2H), 6.79(s, 1H), 6.85(d, J=8.7Hz, 1H), 7.20(s, 1H), 7.42(d, J=8.7Hz, 2H), 7.47(d, J=1.8Hz, 1H), 7.62(dd, J=2.7, 8.7Hz, 1H), 8.20(d, J=2.7Hz, 1H); IR (CHCl$_3$): 3425, 2952, 2886, 1611, 1568, 1524, 1504, 1480, 1446, 1375, 1346, 1311, 1282, 1188, 1151, 1105, 1037, 993, 924 cm$^{-1}$ |
| Ib-373 | mp 128–130° C.; $^1$H NMR (CDCl$_3$) δ 1.73(s, 3H), 1.78(s, 3H), 1.79(s, 3H), 1.82(s, 3H), 2.04(s, 3H), 2.08(s, 3H), 3.34(s, 3H), 3.54(s, 3H), 3.75(d, J= 6.3Hz, 2H), 4.86(d, J=6.9Hz, 2H), 5.39(m, 1H), 5.56(m, 1H), 6.72(d, J= 8.4Hz, 2H), 6.79(dd, J=8.7, 0.6Hz, 1H), 7.11(d, J=8.4Hz, 2H), 7.48(dd, J= 8.7, 2.4Hz, 1H), 8.04(dd, J=2.4, 0.6Hz, 1H); IR (KBr) 3420, 1730, 1612, 1603, 1561, 1521, 1490, 1461, 1277, 1223, 1120, 1002, 983, 823 cm$^{-1}$ |
| Ib-374 | mp 172–173° C.; $^1$H NMR (CDCl$_3$) δ 1.73(s, 3H), 1.77(s, 3H), 2.04(s, 3H), 2.08(s, 3H), 3.35(s, 3H), 3.53(s, 3H), 3.75(d, J=6.9Hz, 2H), 5.38(s, 2H), 5.39(m, 1H), 6.39(dd, J=3.3, 1.8Hz, 1H), 6.48(d, J=3.3Hz, 1H), 6.73(d, J= 8.4Hz, 2H), 6.82(dd, J=8.4, 0.9Hz, 1H), 7.11(d, J=8.4Hz, 2H), 7.47(dd, J=1.8, 0.9Hz, 1H) 7.50(dd, J=8.4, 2.4Hz, 1H), 8.06(dd, J=2.4, 0.9Hz, 1H); IR (KBr) 3415, 1730, 1610, 1562, 1520, 1490, 1452, 1346, 1278, 1224, 1121, 989, 825, 736 cm$^{-1}$ |

TABLE 127-continued

| | |
|---|---|
| Ib-375 | mp 146–147° C.; $^1$H NMR (CDCl$_3$) δ 1.75(s, 3H), 1.78(s, 3H), 1.79(s, 3H), 1.83(s, 3H), 1.99(s, 6H), 2.02(s, 3H), 2.12(s, 3H), 3.75(d, J=6.9Hz, 2H), 3.80(br s, 1H), 4.89(d, J=6.9Hz, 2H), 5.39(t, J=6.9Hz, 1H), 5.59(t, J=7.2Hz, 1H), 6.70(d, J=8.7Hz, 2H), 6.85(d, J=8.4Hz, 1H), 6.91–6.99(m, 2H), 7.45(dd, J=2.4, 8.4Hz, 1H), 8.01(dd, J=0.9, 2.1Hz, 1H); IR (KBr): 3395, 2970, 2911, 2855, 1613, 1603, 1519, 1376, 1277, 1185, 1126, 977, 804 cm$^{-1}$ |
| Ib-376 | mp 187–188° C.; $^1$H NMR (CDCl$_3$) δ 1.79(s, 3H), 1.83(s, 3H), 1.99(s, 3H), 2.02(s, 3H), 2.12(s, 3H), 4.13(br s, 1H), 4.38(s, 2H), 4.89(d, J=6.9Hz, 2H), 5.59(t, J=7.2Hz, 1H), 6.74(d, J=8.4Hz, 2H), 6.85(d, J=8.4Hz, 1H), 6.93–6.96(m, 2H), 7.31–7.46(m, 6H), 8.01(d, J=1.8Hz, 1H); IR (KBr): 3358, 2964, 2929, 1613, 1526, 1490, 1451, 1280, 1244, 1184, 1125, 997, 975, 804, 732 cm$^{-1}$ |
| Ib-377 | mp 75–76° C.; $^1$H NMR (CDCl$_3$) δ 1.73(s, 3H), 1.77(s, 3H), 1.80(s, 3H), 1.83 (s, 3H), 2.01(s, 3H), 2.07(s, 3H), 2.11(s, 3H), 3.37(s, 3H), 3.73(d, J=6.6Hz, 2H), 4.09(br s, 1H), 4.88(d, J=6.9Hz, 2H), 5.38(t, J=6.6Hz, 1H), 5.59(t, J=7.2Hz, 1H), 6.52–6.56(m, 2H), 6.84(d, J=7.5Hz, 1H), 6.85(s, 1H), 6.96(d, J=7.8Hz, 1H), 7.59(dd, J=2.4, 8.4Hz, 1H), 8.14(d, J=1.8Hz, 1H); IR (KBr): 3424, 3339, 2969, 2927, 1611, 1509, 1460, 1353, 1282, 1252, 1103, 984, 813 cm$^{-1}$ |

TABLE 128

| | |
|---|---|
| Ib-378 | mp 150–151° C.; $^1$H NMR (CDCl$_3$) δ 1.80(s, 3H), 1.83(s, 3H), 2.01(s, 3H), 2.06(s, 3H), 2.11(s, 3H), 3.37(s, 3H), 4.36(s, 2H), 4.88(d, J=6.9Hz, 2H), 5.59(t, J=7.2Hz, 1H), 6.54–6.60(m, 2H), 6.84(d, J=8.4Hz, 1H), 6.84(s, 1H), 6.96(d, J=8.1Hz, 1H), 7.30–7.44(m, 5H), 7.58(dd, J=2.4, 8.4Hz, 1H), 8.14(dd, J=0.9, 2.4Hz, 1H); IR (KBr): 3412, 3272, 3018, 2927, 2858, 1611, 1517, 1459, 1375, 1355, 1317, 1283, 1243, 1106, 1050, 985 cm$^{-1}$ |
| Ib-379 | mp 69–70° C.; $^1$H NMR (CDCl$_3$) δ 1.74(s, 3H), 1.78(s, 3H), 1.80(s, 3H), 1.83 (s, 3H), 2.13(s, 3H), 2.15(s, 3H), 3.38(s, 3H), 3.72(d, J=6.9Hz, 2H), 4.88 (d, J=6.9Hz, 2H), 5.36(t, J=6.9Hz, 1H), 5.58(t, J=7.2Hz, 1H), 6.38–6.49 (m, 2H), 6.84(d, J=8.4Hz, 1H), 6.95(s, 1H), 7.06(dd, J=8.1, 8.4Hz, 1H), 7.57(dd, J=2.4, 8.4Hz, 1H), 8.13(d, J=1.8Hz, 1H); IR (KBr): 3416, 2972, 2930, 1627, 1522, 1462, 1376, 1269, 1240, 1171, 1098, 963, 832 cm$^{-1}$ |
| Ib-380 | mp 156–157° C.; $^1$H NMR (CDCl$_3$) δ 1.80(s, 3H), 1.83(s, 3H), 2.13(s, 3H), 2.14(s, 3H), 3.38(s, 3H), 4.36(s, 2H), 4.89(d, J=7.2Hz, 2H), 5.58(t, J=7.2Hz, 1H), 6.40–6.51(m, 2H), 6.84(d, J=8.4Hz, 1H), 6.94(s, 1H), 7.09(dd, J=8.1, 8.4Hz, 1H), 7.32–7.40(m, 5H), 7.58(dd, J=2.4, 8.4Hz, 1H), 8.13 (dd, J=0.6, 1.8Hz, 1H); IR (KBr): 3262, 3019, 2930, 1626, 1528, 1464, 1353, 1317, 1284, 1244, 1170, 1105, 986, 821 cm$^{-1}$ |
| Ib-381 | mp 121–123° C.; $^1$H NMR (CDCl$_3$) δ 1.74(s, 3H), 1.77(s, 3H), 1.80(s, 6H), 1.83(s, 3H), 1.97(s, 3H), 2.00(s, 3H), 2.07(s, 3H), 3.51(s, 3H), 3.72(d, J=6.9Hz, 2H), 4.88(d, J=6.9Hz, 2H), 5.37(m, 1H), 5.58(m, 1H), 6.64(d, J=8.7Hz, 2H), 6.85(d, J=8.4Hz, 1H), 7.01–7.08(m, 2H), 7.38(dd, J=8.4, 2.4Hz, 1H), 7.96(d, J=2.4Hz, 1H); IR (KBr) 3391, 1713, 1613, 1602, 1524, 1487, 1437, 1298, 1276, 1243, 1222, 1122, 979 cm$^{-1}$ |
| Ib-382 | mp 126–128° C.; $^1$H NMR (CDCl$_3$) δ 1.74(s, 3H), 1.77(s, 3H), 1.97(s, 3H), 2.00(s, 3H), 2.07(s, 3H), 3.51(s, 3H), 3.72(d, J=6.6Hz, 2H), 5.37(m, 1H), 5.39(s, 2H), 6.41(dd, J=3.0, 1.8Hz, 1H), 6.50(brd, J=3.0Hz, 1H), 6.64(d, J=8.7Hz, 2H), 6.89(dd, J=8.4, 0.6Hz, 1H), 7.01–7.09(m, 2H), 7.40(dd, J=8.4, 2.4Hz, 1H), 7.48(dd, J=1.8, 0.6Hz, 1H), 7.98(dd, J=2.4, 0.6Hz, 1H); IR (KBr) 3384, 1714, 1612, 1523, 1490, 1343, 1322, 1301, 1281, 1246, 1224, 1124, 990 cm$^{-1}$ |
| Ib-383 | mp 161–163° C.; $^1$H NMR (CDCl$_3$) δ 1.73(s, 3H), 1.77(s, 3H), 1.91(t, J=2.4Hz, 3H), 1.96(s, 3H), 1.99(s, 3H), 2.07(s, 3H), 3.51(s, 3H), 3.72(d, J=6.6Hz, 2H), 5.01(q, J=2.4Hz, 2H), 5.37(m, 1H), 6.65(d, J=9.0Hz, 2H), 6.90(dd, J=8.7, 0.9Hz, 1H), 7.01–7.08(m, 2H), 7.40(dd, J=8.7, 2.4Hz, 1H), 7.97(dd, J=2.4, 0.9Hz, 1H); IR (KBr) 3385, 1725, 1613, 1603, 1525, 1488, 1344, 1329, 1303, 1281, 1246, 1221, 999 cm$^{-1}$ |
| Ib-384 | Oil $^1$H NMR (CDCl$_3$) δ 1.78(s, 3H), 1.82(s, 3H), 2.30(s, 3H), 2.44(s, 3H), 4.64(d, J=6.6Hz, 2H), 5.55(m, 1H), 6.99–7.12(m, 3H), 7.17(s, 1H), 7.37(s, 1H), 7.53(d, J=1.2Hz, 1H), 9.07(d, J=1.2Hz, 1H) |
| Ib-385 | mp 93–94° C.; $^1$H NMR (CDCl$_3$) δ 1.77(s, 3H), 1.81(s, 3H), 2.28(s, 3H), 2.40 (s, 3H), 4.05(s, 3H), 4.64(d, J=6.9Hz, 2H), 5.55(m, 1H), 6.86(d, J=1.2Hz, 1H), 6.98–7.12(m, 3H), 7.26(s, 1H), 7.34(s, 1H), 8.87(d, J=1.2Hz, 1H); IR (KBr) 1589, 1533, 1518, 1496, 1394, 1364, 1299, 1263, 1232, 1123, 1040, 997, 986, 872 cm$^{-1}$ |

TABLE 129

| | |
|---|---|
| Ib-386 | mp 95–96° C.; $^1$H NMR (CDCl$_3$) δ 1.77(s, 3H), 1.81(s, 3H), 2.28(s, 3H), 2.38 (s, 3H), 3.17(s, 6H), 4.64(d, J=6.9Hz, 2H), 5.55(m, 1H), 6.53(d, J=1.2Hz, 1H), 6.98–7.14(m, 4H), 7.29(s, 1H), 8.69(d, J=1.2Hz, 1H); IR |

TABLE 129-continued

| | |
|---|---|
| | (KBr) 1591, 1512, 1417, 1405, 1299, 1278, 1261, 1228, 1123, 1000, 836, 827 cm$^{-1}$ |
| Ib-387 | mp 88–90° C.; $^1$H NMR (CDCl$_3$) δ 1.78(s, 3H), 1.83(s, 3H), 2.29(s, 3H), 2.30 (s, 3H), 4.57(d, J=6.6Hz, 2H), 5.55(t, J=6.6Hz, 1H), 6.99(d, J=8.4Hz, 2H), 7.12(s, 1H), 7.20(s, 1H), 7.28(d, J=8.4Hz, 2H), 8.79(s, 2H), 9.22(s, 1H); IR (KBr) 1611, 1519, 1497, 1415, 1384, 1240, 1007, 820, 731 cm$^{-1}$. |
| Ib-388 | mp 97–98° C.; $^1$H NMR (CDCl$_3$) δ 1.78(s, 3H), 1.82(s, 3H), 2.29(s, 3H), 2.30 (s, 3H), 4.64(d, J=6.6Hz, 2H), 5.55(t, J=6.6Hz, 1H), 7.00–7.14(m, 4H), 7.18(s, 1H), 8.78(s, 2H), 9.22(s 1H); IR (KBr) 1523, 1502, 1415, 1386, 1313, 1285, 1274, 1263, 1233, 1200, 1131, 995, 858 cm$^{-1}$. |
| Ib-389 | mp 163–166° C.; $^1$H NMR (CDCl$_3$) δ 1.77(s, 3H), 1.82(s, 3H), 2.29(s, 3H), 4.56(d, J=6.6Hz, 2H), 5.11(tm, J=6.6Hz, 1H), 6.98(d, J=8.7Hz, 2H), 7.08(s, 1H), 7.16(s, 1H), 7.27(d, J=8.7Hz, 2H), 8.35(s, 2H); IR (KBr) 3393, 3315, 3196, 1639, 1605, 1595, 1518, 1480, 1236, 1002, 838, 802 cm$^{-1}$. |
| Ib-390 | mp 158–160° C.; $^1$H NMR (CDCl$_3$) δ 1.77(s, 3H), 1.82(s, 3H), 2.28(s, 3H), 2.29(s, 3H), 4.64(d, J=6.6Hz, 2H), 5.17(s, 2H), 5.56(t, J=6.6Hz, 1H), 6.98–7.16(m, 5H), 8.35(s, 2H); IR (KBr) 3334, 3187, 1655, 1598, 1522, 1486, 1296, 1269, 1230, 1125, 998 cm$^{-1}$. |
| Ib-391 | mp 156–158° C.; $^1$H NMR (CDCl$_3$) δ 1.75(s, 3H), 1.77(s, 6H), 1.82(s, 3H), 2.28(s, 3H), 2.30(s, 3H), 4.05(t, J=6.0Hz, 2H), 4.56(d, J=6.6Hz, 2H), 5.11(t, J=5.4Hz, 1H), 5.36(tm, J=6.6Hz, 1H), 5.54(t, J=6.6Hz, 1H), 6.97(d, J=9.0Hz, 2H), 7.08(s, 1H), 7.15(s, 1H), 7.27(d, J=9.0Hz, 2H), 8.34(s, 2H); IR (KBr) 3236, 1608, 1598, 1522, 1495, 1436, 1264, 1244, 1181, 998, 833, 803 cm$^{-1}$. |
| Ib-392 | mp 105–106° C.; $^1$H NMR (CDCl$_3$) δ 1.75(s, 3H), 1.77(s, 6H), 1.82(s, 3H), 2.28(s, 3H), 2.30(s, 3H), 4.00–4.09(m, 2H), 4.63(d, J=6.6Hz, 2H), 5.14(m, 1H), 5.37(m, 1H), 5.55(t, J=6.6Hz, 1H), 6.98–7.17(m 5H), 8.34(s, 2H); IR (KBr) 3254, 1607, 1524, 1495, 1440, 1300, 1271, 1235, 1129, 995 cm$^{-1}$. |
| Ib-393 | mp 182–184° C.; $^1$H NMR (CDCl$_3$) δ 1.74(s, 3H), 1.77(s, 3H), 2.29(s, 6H), 4.05(dd, J=6.6, 5.7Hz, 2H), 5.17(brs, 1H), 5.37(tm, J=6.6Hz, 1H), 6.75 (d, J=8.7Hz, 2H), 7.07(s, 1H), 7.14(s, 1H), 7.15(d, J=8.7Hz, 2H), 8.34(s, 2H); IR (KBr) 3443, 3327, 3245, 3110, 1631, 1602, 1525, 1493, 1440, 1301, 828, 802 cm$^{-1}$ |
| Ib-394 | mp 160–162° C.; $^1$H NMR (CDCl$_3$) δ 1.74(s, 6H), 1.77(s, 6H), 2.29(s, 3H), 2.30(s, 3H), 3.74(d, J=6.9Hz, 2H), 4.05(dd, J=6.6, 6.0Hz, 2H), 5.15(brs, 1H), 5.37(m, 2H), 6.67(d, J=8.4Hz, 2H), 7.07(s, 1H), 7.16(s, 1H), 7.18(d, J=8.4Hz, 2H), 8.34(s, 2H); IR (KBr) 3423, 3240, 3104, 1612, 1598, 1525, 1496, 1436, 1321, 1262, 1187, 1087, 824, 802 cm$^{-1}$ |
| Ib-395 | mp 106–108° C.; $^1$H NMR (CDCl$_3$) δ 1.72(s, 6H), 1.74(s, 9H), 1.77(s, 3H), 2.29(s, 3H), 2.32(s, 3H), 3.91(d, J=5.7Hz, 4H), 4.04(dd, J=6.3, 5.7Hz, 2H), 5.08(m, 1H), 5.27(m, 2H), 5.37(m, 1H), 6.72(brd, J=8.7Hz, 2H), 7.07(s, 1H), 7.17(s, 1H), 7.21(d, J=8.7Hz, 2H), 8.34(s, 2H); IR (KBr) 3433, 3254, 3110, 1599, 1523, 1494, 1434, 1378, 1232, 1196, 1092, 817, 801 cm$^{-1}$ |

TABLE 130

| | |
|---|---|
| Ib-396 | mp 84–86° C.; $^1$H NMR (CDCl$_3$) δ 1.74(s, 3H), 1.77(s, 3H), 1.79(s, 3H), 2.23 (s, 3H), 2.28(s, 3H), 3.71(d, J=6.9Hz, 2H), 4.93(d, J 6.9Hz, 2H), 5.32– 5.61(m, 2H), 6.36–6.48(m, 2H), 7.05(t, J=8.4Hz, 1H), 7.09(s, 1H), 7.15(s, 1H), 8.53(s, 2H) IR (KBr): 3224, 3315, 2970, 2923, 1628, 1592, 1534, 1474, 1438, 1377, 1341, 1317, 1249, 1173, 1110, 993 cm$^{-1}$ |
| Ib-397 | mp 150–152° C.; $^1$H NMR (CDCl$_3$) δ 1.74(s, 3H), 1.78(s, 3H), 1.80(s, 3H), 1.81(s, 3H), 1.99(s, 6H), 2.00(s, 6H), 3.74(d, J=6.9Hz, 2H), 4.95(d, J= 7.2Hz, 2H), 5.37–5.42(m, 1H), 5.58–5.64(m, 1H), 6.68–6.71(m, 2H), 6.93– 6.97(m, 2H), 8.36(s, 2H) IR (KBr): 3360, 2973, 2928, 2857, 1610, 1587, 1519, 1436, 1406, 1379, 1310, 1245, 1181, 983 cm$^{-1}$ |
| Ib-398 | mp 156–158° C.; $^1$H NMR (CDCl$_3$) δ 1.60(s, 3H), 1.75(s, 3H), 1.77(s, 3H), 1.82(s, 3H), 1.97(s, 6H), 2.03(s, 6H), 4.04–4.08(m, 2H), 4.64(d, J=6.6Hz, 2H), 5.05–5.08(m, 1H), 5.30–5.41(m, 1H), 5.54–5.60(m, 1H), 6.81–6.84(m, 1H), 6.89(dd, J=1.8, 12.0Hz, 1H), 7.05(t, J=8.7Hz, 1H), 8.15(s, 1H), IR (KBr): 3320, 2971, 2931, 2850, 1627, 1604, 1525, 1483, 1395, 1373, 1338, 1309, 1288, 1263, 1240, 1175, 1115, 1038 cm$^{-1}$. |
| Ib-399 | mp 161–163° C.; $^1$H NMR (CDCl$_3$) δ 1.77(s, 3H), 1.82(s, 3H), 1.97(s, 6H), 2.02(s, 6H), 4.64(d, J=6.6Hz, 2H), 5.13(br s, 2H), 5.54–5.60(m, 1H), 6.80–6.84(m, 1H), 6.88(dd, J=1.8, 11.7Hz, 1H), 7.05(t, J=8.7Hz, 1H), 8.16(s, 1H) IR (KBr): 3344, 3210, 2987, 2917, 2859, 1654, 1618, 1597, 1541, 1513, 1479, 1427, 1382, 1295, 1263, 1240, 1212, 1114, 993 cm$^{-1}$. |
| Ib-400 | $^1$H NMR (300 MHz, CDCl$_3$) δ 1.75(s, 3H), 1.77(s, 6H), 1.82(s, 3H), 2.05(s, 3H), 2.12(s, 3H), 3.34(s, 3H), 3.39(s, 3H), 4.06(t, J=6.0Hz, 2H), 4.65(d, J=6.9Hz, 2H), 5.18(t, J=5.3Hz, 1H), 5.35–5.42(m, 1H), 5.53–5.60(m, 1H), 7.08–6.95(m, 3H), 8.30(s, 2H). |
| Ib-401 | Oil; $^1$H NMR (CDCl$_3$) δ 1.77(s, 3H), 1.82(s, 3H), 2.31(s, 3H), 2.54(s, 3H), 4.56(d, J=6.6Hz, 2H), 5.54(t, J=6.6Hz, 1H), 6.98(d, J=8.4Hz, 2H), 7.16 (s, 1H), 7.21(t, J=5.1Hz, 1H), 7.28(d, J=8.4Hz, 2H), 7.73(s, 1H), 8.85(d, J=5.1Hz, 2H). |

TABLE 130-continued

Ib-402 mp 93–94° C.; ¹H NMR (CDCl₃) δ 1.77(s, 3H), 1.82(s, 3H), 2.31(s, 3H), 2.54 (s, 3H), 4.64(d, J=6.6Hz, 2H), 5.55(t, J=6.6Hz, 1H), 6.98–7.25(m, 5H), 7.73(s, 1H), 8.85(s, 1H), 8.86(s 1H); IR (KBr) 1573, 1560, 1521, 1414, 1299, 1277, 1260, 1238, 1130, 997 cm⁻¹.

Ib-403 mp 107–108° C.; ¹H NMR (CDCl₃) δ 1.74(s, 3H), 1.77(s, 3H), 1.81(s, 3H), 1.83(s, 3H), 2.32(s, 3H), 2.39(s, 3H), 3.67(br s, 1H), 3.74(d, J=6.8Hz, 2H), 5.10(d, J=7.1Hz, 2H), 5.37(br t, J=6.8Hz, 1H), 5.62(br t, J=7.1 Hz, 1H), 6.67(d, J=8.5Hz, 2H), 7.02(d, J=9.0Hz, 1H), 7.17(s, 1H), 7.20 (d, J=8.5Hz, 2H), 7.33(s, 1H), 7.52(d, J=9.0Hz, 1H)

Ib-404 mp 149–151° C.; ¹H NMR (CDCl₃) δ 1.78(s, 6H), 1.82(s, 3H), 2.31(s, 3H), 2.38(s, 3H), 4.57(d, J=6.6Hz, 2H), 5.54(t, J=6.6Hz, 1H), 6.99(d, J= 9.0Hz, 2H), 7.20(s, 1H), 7.27(d, J=9.0Hz, 2H), 7.34(s, 1H), 7.58(d, J= 9.0Hz, 1H), 7.60(d, J=9.0Hz, 1H); IR (KBr) 1610, 1572, 1517, 1496, 1421, 1411, 1249, 1179, 1142, 1012, 1004, 857, 841 cm⁻¹.

TABLE 131

Ib-405 mp 94–94.5° C.; ¹H NMR (CDCl₃) δ 1.77 (s, 3H), 1.82 (s, 3H), 2.30 (s, 3H), 2.39(s, 3H), 4.20(s, 3H), 4.57(d, J=6.6 Hz, 2H), 5.54(tm, J=6.6 Hz, 1H), 6.98(d, J=8.7 Hz, 2H), 7.04(d, J=9.0 Hz, 1H), 7.18(s, 1H), 7.28(d, J= 8.7 Hz, 2H), 7.34(s, 1H), 7.53(d, J=9.0 Hz, 1H) ; IR (KBr) 1610, 1592, 1518, 1464, 1415, 1295, 1235, 1175, 1107, 1016, 867, 830 cm⁻¹.

Ib-406 mp 165–167° C.; ¹H NMR (CDCl₃) δ 1.77(s, 3H), 1.82(s, 3H), 2.29(s, 3H), 2.41(s, 3H), 3.24(s. 6H), 4.56(d, J=6.6 Hz, 2H), 5.54(tm, J=6.6 Hz, 1H), 6.87(d, J=9.3 Hz. 1H), 6.97(d, J=9.0 Hz, 2H), 7.15(s, 1H), 7.28(d, J= 9.0 Hz, 2H), 7.36(s, 1H), 7.38(d, J=9.3 Hz, 1H) ; IR (KBr) 1606, 1593, 1493, 1427, 1387, 1237, 1178, 1003, 847, 826 cm⁻¹.

Ib-407 mp 138–140° C.; ¹H NMR (CDCl₃) δ 1.78(s, 3H), 1.82(s, 3H), 2.30(s, 3H), 2.38(s, 3H), 4.64(d, J=6.6 Hz, 2H), 5.55(t, J=6.6 Hz, 1H), 7.00–7.13(m, 3H), 7.19(s, 1H), 7.34(s, 1H), 7.56(m, 1H) 7.62(m, 1H) ; IR (KBr) 1518, 1496, 1414, 1385, 1299, 1266, 1233, 1127, 994, 851 cm⁻¹.

Ib-408 mp 91–92° C.; ¹H NMR (CDCl₃) δ 1.77(s, 3H), 1.82(s, 3H), 2.29(s, 3H), 2.39 (s, 3H), 4.20(s, 3H), 4.64(d, J=6.6 Hz, 2H), 5.55(t, J=6.6 Hz, 1H), 6.90–7.14(m, 4H), 7.16(s, 1H), 7.34(s, 1H), 7.53(d, J=9.0 Hz, 1H) ; IR (KBr) 1593, 1519, 1496, 1469, 1417, 1294, 1274, 1263, 1231, 1126, 1010, 995, 845 cm⁻¹.

Ib-409 mp 132–134° C.; ¹H NMR (CDCl₃) δ 1.77(s, 3H), 1.82(s, 3H), 2.29(s, 3H), 2.41(s, 3H), 3.24(s, 6H), 4.64(d, J=6.6 Hz, 2H), 5.55(t, J=6.6 Hz, 1H), 6.87(d, J=9.6 Hz, 1H), 6.97–7.15(m, 4H), 7.36(s, 1H), 7.37(d, J=9.6 Hz, 1H); IR (KBr) 1597, 1547, 1519, 1495, 1422, 1404, 1297, 1272, 1233, 1197, 1133, 993, 849 cm⁻¹.

Ib-410 mp 197–200° C.; ¹H NMR (CDCl₃) δ 1.77(s, 3H), 1.82(s, 3H), 2.29(s, 3H), 2.36(s, 3H), 4.56(d, J=6.9 Hz, 2H), 4.82(s, 2H), 5.54(tm, J=6.9 Hz, 1H), 6.83(d, J=9.0 Hz, 1H), 6.97(d, J=9.0 Hz, 2H), 7.16(s, 1H), 7.27(d, J= 9.0 Hz, 2H), 7.31(s, 1H), 7.39(d, J=9.0 Hz, 1H) ; IR (KBr) 3486, 3370, 3308, 3164, 1649, 1625, 1606, 1516, 1495, 1461, 1234, 1216, 1173, 1011, 999, 982, 846, 835 cm⁻¹.

Ib-411 mp 183–185° C.; ¹H NMR (CDCl₃) δ 1.77(s, 3H), 1.82(s, 3H), 2.28(s, 3H), 2.36(s, 3H), 4.64(d, J=6.6 Hz, 2H), 4.89(brs, 2H), 5.55(tm, J=6.6 Hz, 1H), 6.85(d, J=9.0 Hz, 1H), 6.98–7.12(m, 3H), 7.14(s, 1H), 7.32(s, 1H), 7.38(d, J=9.0 Hz, 1H) ; IR (KBr) 3486, 3368, 3308, 3161, 1649, 1624, 1519, 1497, 1461, 1261, 1123, 982, 844 cm⁻¹.

Ib-412 mp 138–140° C.; ¹H NMR (CDCl₃) δ 1.76(s, 6H), 1.77(s, 3H), 1.82(s, 3H), 2.29(s, 3H), 2.39(s, 3H), 4.03(t, J=6.3 Hz, 2H), 4.56(d, J=6.9 Hz, 2H), 4.77(m, 1H), 5.38(tm, J=6.9 Hz, 1H), 5.54(tm, J=6.9 Hz, 1H), 6.70(d, J= 9.0 Hz, 1H), 6.97(d, J=9.0 Hz, 2H), 7.15(s, 1H), 7.28(d, J=9.0 Hz, 2H), 7.33(s, 1H), 7.35(d, J=9.0 Hz, 1H) ; IR (KBr) 3213, 1605, 1530, 1492, 1234, 1180, 994, 841 cm⁻¹.

Ib-413 mp 113–115° C.; ¹H NMR (CDCl₃) δ 1.76(s, 3H), 1.77(s, 3H), 1.78(s, 3H), 1.81(s, 3H), 2.28(s, 3H), 2.39(s, 3H), 3.98–4.15(m, 2H), 4.64(d, J=6.9 Hz, 2H), 4.76(m, 1H), 5.38(m, 1H), 5.55(tm, J=6.9 Hz, 1H), 6.70(d J=9.3 Hz, 1H). 6.98–7.15(m, 4H), 7.33(s, 1H), 7.35(d, J=9.3 Hz, 1H) ; IR (KBr) 3424, 3214, 1601, 1534, 1492, 1416, 1296, 1261, 1232, 1126, 983, 829 cm⁻¹.

TABLE 132

Ib-414 mp 159–161° C.; ¹H NMR (CDCl₃) δ 1.76(s, 3H), 1.78(s, 3H), 2.29(s, 3H), 2.38(s, 3H), 4.03(dd, J=6.6, 5.7 Hz, 2H), 4.91(m, 1H), 5.38(tm, J=6.6 Hz, 1H), 6.71(d, J=9.0 Hz, 2H), 6.75(d, J=8.7 Hz, 2H), 7.15(s, 1H), 7.17(d, J=8.7 Hz, 2H), 7.32(s, 1H), 7.37(d, J=9.0 Hz, 1H) ; IR (KBr) 3440, 3363, 3220, 1621, 1599, 1531, 1491, 1458, 1410, 1279, 1181, 1140, 1045, 1026, 835 cm⁻¹

Ib-415 mp 131–133° C.; ¹H NMR (CDCl₃) δ 1.74(s, 3H), 1.76(s, 3H), 1.77(s, 6H), 2.31(s, 3H), 2.38(s, 3H), 3.74(d, J=6.9 Hz, 2H), 4.03(dd, J=6.0, 6.0 Hz,

TABLE 132-continued

| | |
|---|---|
| | 2H), 4.87(brs, 1H) 5.38(m, 2H), 6.67(d, J=8.4 Hz, 2H), 6.71(d, J=9.3 Hz, 1H), 7.15(s, 1H), 7.19(d, J=8.4 Hz, 2H), 7.32(s, 1H), 7.36(d, J=9.3 Hz, 1H) ; IR (KBr) 3385, 3207, 1609, 1529, 1493, 1457, 1186, 1045, 834 cm$^{-1}$ |
| Ib-416 | mp 174–175° C.; $^1$H NMR (CDCl$_3$) δ 1.72(s, 6H), 1.74(s, 3H), 1.75(s, 3H), 1.76(s, 3H), 1.78(s, 3H), 2.33(s, 3), 2.38(s, 3H), 3.91(d, J=6.0 Hz, 4H), 4.03(dd, J=6.0, 6.0 Hz, 2H), 4.88(m, 1H), 5.26(m, 2H), 5.38(m, 1H), 6.71 (d, J=9.0 Hz, 1H), 6.75(d, J=9.0 Hz, 2H), 7.17(s, 1H), 7.22(d, J=9.0 Hz, 2H), 7.32(s, 1H), 7.37(d, J=9.0 Hz, 1H); IR (KBr) 3432, 3252, 3133, 1615, 1578, 1524, 1473, 1449, 1350, 1316, 1305, 1234, 1195, 1162, 1057, 854, 819 cm$^{-1}$. |
| Ib-417 | mp 224–227° C.; $^1$H NMR (CDCl$_3$) δ 1.77(s, 6H); 1.82(s, 3H); 1.95(s, 6H); 1.96(s, 6H); 4.64(d, J=6.6 Hz, 2H); 4.91(br s, 2H); 5.57(m, 1H); 6.75–7.07 (m, 4H) 7.20(dd, J=1.8, 9.0 Hz, 1H); IR (KBr): 3341, 3163, 1637, 1513, 1460, 1297, 1263, 1243, 1114, 1001 cm$^{-1}$. |
| Ib-418 | mp 215–216° C.; $^1$H NMR (CDCl$_3$) δ 1.77(s, 6H); 1.79(s, 3H); 1.82(s, 3H); 1.95(s, 6H); 1.97(s, 6H); 4.02(t, J=6.3 Hz, 2H); 4.64(d, J=7.2 Hz, 2H); 4.84(br, 1H); 5.39(m, 1H); 5.57(m, 1H); 6.74(dd, J=1.2, 9.0 Hz, 1H); 6.76–6.93(m, 2H); 7.04(t, J=8.4 Hz, 1H); 7.15(dd, J=1.8, 9.0 Hz, 1H); IR (KBr): 3258, 2917, 1609, 1513, 1486, 1466, 1426, 1297, 1264, 1241, 1118 cm$^{-1}$. |
| Ib-419 | mp 178–180° C.; $^1$H NMR (CDCl$_3$) δ 1.74(s, 3H), 1.78(s, 3H), 1.82(s, 3H), 1.85(s, 3H), 1.95(s, 6H), 1.98(s, 6H), 3.4(br s, 1H), 3.75(d, J=6.9 Hz, 2H), 5.11(d, J=6.9 Hz, 2H), 5.40(t, J=6.9 Hz, 1H), 5.63(d, J=6.9 Hz, 1H), 6.70–6.74(m, 2H), 6.92–6.99(m, 2H), 7.04(d, J=9.2 Hz, 1H), 7.32(d, J= 9.2 Hz, 1H) ; IR (KBr): 3368, 2979, 2932, 2915, 1612, 1520, 1438, 1303, 1285, 966, 821, 529 cm$^{-1}$. |
| Ib-420 | $^1$H NMR (300 MHz, CDCl$_3$) δ 1.77(s, 6H), 1.79(d, J=1.2 Hz, 3H), 1.82(d, J=0.9 Hz, 3H), 2.04(s, 3H), 2.12(s, 3H), 3.35(s, 3H), 3.42(s, 3H), 4.02(t, J=6.2 Hz, 2H), 4.65(d, J=6.9 Hz, 2H), 4.81(t, J=5.0 Hz, 1H), 5.35–5.42(m, 1H), 5.53–5.60(m, 1H), 6.72(d, J=9.2 Hz, 1H), 6.95–7.08(m, 3H), 7.29(d, J=9.2 Hz, 1H). |
| Ib-421 | mp 88–89° C.: $^1$H NMR (CDCl$_3$) δ 1.78(s, 3H), 1.82(s, 3H), 2.31(s, 3H), 2.40 (s, 3H), 4.57(d, J=6.6 Hz, 2H), 5.54(t, J=6.6 Hz, 1H), 6.98(d, J=9.0 Hz, 2H), 7.19(s, 1H), 7.28(d, J=9.0 Hz, 2H), 7.35(s, 1H), 8.53(d, J=2.7 Hz, 1H), 8.68(dd, J=2.7, 1.2 Hz, 1H), 8.78(d, J=1.2 Hz, 1H) ; IR (KBr) 1606, 1574, 1516, 1496, 1469, 1386, 1241, 1178, 1145, 1011, 1002, 982, 840, 833 cm$^{-1}$. |
| Ib-422 | mp 87–88° C.; $^1$H NMR (CDCl$_3$) δ 1.77(s, 3H), 1.82(s, 3H), 2.31(s, 3H), 2.40 (s, 3H), 4.64(d, J=6.6 Hz, 2H), 5.55(t, J=6.6 Hz, 1H), 6.99–7.14(m 3H), 7.17(s, 1H), 7.35(s, 1H), 8.54(m, 1H), 8.68(m, 1H), 8.77(m, 1H) ; IR (KBr) 1517, 1501, 1476, 1447, 1397, 1387, 1315, 1297, 1265, 1234, 1198, 1127, 996, 849 cm$^{-1}$. |

TABLE 133

| | |
|---|---|
| Ib-423 | mp 74–77° C.; $^1$H NMR (CDCl$_3$) δ 1.77(s, 3H), 1.82(s, 3H), 2.29(s, 3H), 2.37 (s, 3H), 4.56(d, J=6.9 Hz, 2H), 4.60(s, 2H), 5.54(tm, J=6.9 Hz, 1H), 6.97 (d, J=8.7 Hz, 2H), 7.14(s, 1H), 7.27(d, J=8.7 Hz, 2H), 7.29(s, 1H), 8.10(s, 1H), 8.18(s 1H); IR (KBr) 3464, 3319, 3165, 1606, 1477, 1381, 1241, 1178, 1023, 1002, 839, 832 cm$^{-1}$. |
| Ib-424 | mp 127–128° C.; $^1$H NMR (CDCl$_3$) δ 1.77(s, 3H), 1.81(s, 3H), 2.28(s, 3H), 2.37(s, 3H), 4.62(s, 2H), 4.63(d, J=6.6 Hz, 2H), 5.55(t, J=6.6 Hz, 1H), 6.98–7.12(m, 3H), 7.13(s, 1H), 7.29(s 1H), 8.09(d, J=1.5 Hz, 1H), 8.17(d, J=1.5 Hz, 1H) ; IR (KBr) 3426, 3306, 3189, 1641, 1580, 1536, 1517, 1498, 1482, 1393, 1292, 1281, 1265, 1231, 1121, 982 cm$^{-1}$. |
| Ib-425 | mp 136–138° C.; $^1$H NMR (CDCl$_3$) δ 1.77(s, 3H), 1.82(s, 3H), 2.28(s, 3H), 2.38(s, 3H), 3.74(m, 1H), 4.56(d, J=6.9 Hz, 2H), 5.54(tm, J=6.9 Hz, 1H), 6.97(d, J=8.7 Hz, 2H), 7.13(s, 1H), 7.27(d, J=8.7 Hz, 2H), 7.29(s, 1H), 7.96(d, J=1.2 Hz, 2H), 8.16(d, J=1.2 Hz, 1H) ; IR (KBr) 3282, 1597, 1527, 1492, 1241, 1174, 1018, 885, 826 cm$^{-1}$. |
| Ib-426 | mp 119–121° C.; $^1$H NMR (CDCl$_3$) δ 1.77(s, 3H), 1.81(s, 3H), 2.28(s, 3H), 2.38(s, 3H), 3.74(m, 1H), 4.57(d, J=8.1 Hz, 1H), 4.63(d, J=6.6 Hz, 2H), 5.55(t, J=6.6 Hz, 1H), 6.98–7.12(m, 3H), 7.11(s, 1H), 7.29(s, 1H), 7.96(d, J=1.5 Hz, 1H), 8.15(d, J=1.5 Hz, 1H) ; IR (KBr) 3424, 3275, 1598, 1528, 1495, 1280, 1265, 1173, 1018, 1007 cm$^{-1}$. |
| Ib-427 | mp 134–136° C.; $^1$H NMR (CDCl$_3$) δ 1.77(s, 3H), 1.78(s, 6H), 1.82(s, 3H), 2.29(s, 3H), 2.38(s, 3H), 3.98(t, J=5.4 Hz, 2H), 4.56(d, J=6.9 Hz, 2H), 5.36(tm, J=6.9 Hz, 1H), 5.54(tm, J=6.9 Hz, 1H), 6.97(d, J=8.7 Hz, 2H), 7.14(s, 1H), 7.27(d, J=8.7 Hz, 2H), 7.29(s, 1H), 7.98(d, J=1.5 Hz, 1H), 8.19(d,J=1.5 Hz, 1H) ; IR (KBr) 3215, 1608, 1578, 1561, 1492, 1380, 1362, 1243, 1179, 1166, 1017, 1003, 830 cm$^{-1}$. |
| Ib-428 | mp 99–100° C.; $^1$H NMR (CDCl$_3$) δ 1.76(s, 6H), 1.78(s, 3H), 1.81(s, 3H), 2.28 (s, 3H), 2.38(s, 3H), 3.98(dd, J=6.6, 5.4 Hz, 2H), 4.59 (brs, 1H), 4.63(d, J= |

TABLE 133-continued

| | |
|---|---|
| | 6.6 Hz, 2H), 5.36(t, J=6.6 Hz, 1H), 5.55(t, J=6.6 Hz, 1H), 6.98–7.12(m, 3H), 7.12(s, 1H), 7.30(s, 1H), 7.98(d, J=1.5 Hz, 1H), 8.18(d, J=1.5 Hz, 1H) ; IR (KBr) 3239, 1578, 1565, 1492, 1390, 1362, 1303, 1277, 1261, 1122, 995, 873, 827 cm$^{-1}$ |
| Ib-429 | mp 133–134° C.; $^1$H NMR (CDCl$_3$) δ 1.74(s, 3H), 1.76(s, 3H), 1.77(s, 3H), 1.78(s, 3H), 2.31(s, 3H), 2.38(s, 3H), 3.73(d, J=6.6 Hz, 2H), 3.97(dd, J= 6.0, 6.0 Hz, 2H), 4.57(m, 1H), 5.37(m, 2H), 6.67(d, J=8.4 Hz, 2H), 7.14(s, 1H), 7.19(d, J=8.4 Hz, 2H), 7.28(s, 1H), 7.97(d, J=1.5 Hz, 1H), 8.19(d, J=1.5 Hz, 1H) ; IR (KBr) 3413, 3222, 1612, 1580, 1561, 1523, 1493, 1457, 1379, 1362, 1319, 1186, 1165, 1094, 1056, 1017, 822 cm$^{-1}$ |
| Ib-430 | Oil $^1$H NMR (CDCl$_3$) δ 1.72(s, 6H), 1.74(s, 6H), 1.76(s, 3H), 1.78(s, 3H), 2.33(s, 3H), 2.37(s, 3H), 3.90(d, J=6.3 Hz, 4H), 3.97(dd, J=6.0, 5.1 Hz, 2H), 4.54(m, 1H), 5.26(m, 2H), 5.36(m, 1H), 6.74(d, J=8.7 Hz, 2H), 7.15 (s, 1H), 7.21(d, J=8.7 Hz, 2H), 7.15(s, 1H), 7.21(d, J=8.7 Hz, 2H), 7.28(s, 1H), 7.98(d, J=1.5 Hz, 1H) 8.19(d, J=1.5 Hz, 1H) |

TABLE 134

| | |
|---|---|
| Ib-431 | mp 167–168° C.; $^1$H NMR (CDCl$_3$) δ 1.75(s, 3H), 1.78(s, 3H), 1.81(s, 3H), 1.84(s, 3H), 1.95(s, 6H), 1.98(s, 6H), 3.63 (br s, 1H), 3.74(d, J=6.6 Hz, 2H), 4.90(d, J=7.1 Hz, 2H), 5.39(t, J=6.6 Hz, 1H), 5.58(d, J=7.1 Hz, 1H), 6.67–6.71(m, 2H), 6.87–7.00(m, 2H), 8.07(d, J=1.5 Hz, 1H), 8.35(d, J= 1.5 Hz, 1H); IR (KBr): 3355, 2964, 2926, 2874, 1614, 1521, 1458, 1345, 1312, 1270, 1029, 977, 820 cm$^{-1}$. |
| Ib-432 | mp 161–162° C.; $^1$H NMR (CDCl$_3$) δ 1.77(s, 3H); 1.82(s, 3H); 1.94(s, 6H); 1.97(s, 6H); 4.64(d, J=6.3 Hz, 2H); 4.64(br s, 2H); 5.57(m, 1H); 6.74–7.07 (m, 3H); 7.98(s, 1H); 8.15(s, 1H); IR (KBr): 3450, 3340, 2921, 1624, 1527, 1514, 1461, 1374, 1295, 1261, 1245, 1192, 1116 cm$^{-1}$. |
| Ib-433 | mp 130–132° C.; $^1$H NMR (CDCl$_3$) δ 1.77(s, 6H); 1.80(s, 3H); 1.82(s, 3H); 1.94(s, 6H); 1.98(s, 6H); 3.98 (br t, J=5.4 Hz, 2H); 4.56(br, 1H); 4.64(d, J=6.6 Hz, 2H); 5.39(m, 1H); 5.57(m, 1H); 6.74–7.08(m, 3H); 7.99(s, 1H); 8.02(s, 1H); IR (KBr): 3244, 2918, 1584, 1560, 1514, 1468, 1380, 1295, 1264, 1241, 1114 cm$^{-1}$. |
| Ib-434 | amorphous; $^1$H NMR (CDCl$_3$) δ 1.77(s, 3H), 1.80(s, 3H), 1.96(s, 6H), 1.98(s, 6H), 3.5(br s, 2H), 3.98(m, 2H), 4.64(m, 1H), 5.39(m, 1H), 6.74– 6.79(m, 2H), 6.84–6.99(m, 2H), 7.99(d, J=1.4 Hz, 1H), 8.04(d, J=1.4 Hz, 1H); IR (KBr): 3334, 1620, 1588, 1519, 1462, 1276, 1161, 1024, 824, 525 cm$^{-1}$ |
| Ib-435 | mp 180–182° C.; $^1$H NMR (CDCl$_3$) δ 1.74(s, 3H), 1.74(s, 3H), 1.78(s, 3H), 1.79(s, 3H), 1.97(s, 6H), 1.98(s, 6H), 3.4(br s, 1H), 3.74(d, J=6.9 Hz, 2H), 3.98(t, J=6.0 Hz, 2H), 4.50(t, J=5.1 Hz, 1H), 5.36–5.41(m, 2H), 6.66–6.72(m, 2H), 6.86–7.02(m, 2H), 8.00(d, J=1.4 Hz, 1H), 8.02(d, J= 1.4 Hz, 1H); IR (CHCl$_3$): 3439, 1613, 1585, 1519, 1468 cm$^{-1}$ |
| Ib-436 | $^1$H NMR (300 M Hz, CDCl$_3$) δ 1.77(s, 6H), 1.79(d, J=0.9 Hz, 3H), 1.81(s, 3H), 2.04(s, 3H), 2.08(s, 3H), 3.34(s, 3H), 3.41(s, 3H), 3.99(t, J=5.3 Hz, 2H), 4.64(d, J=6.9 Hz, 2H), 4.58–4.67(m, 1H), 5.34–5.42(m, 1H), 5.53–5.60 (m, 1H), 6.93–7.07(m, 3H), 8.02(d, J=1.5 Hz, 1H), 8.11(d, J=1.5 Hz, 1H). |
| Ib-437 | foam; $^1$H NMR (CDCl$_3$) δ 2.21(s, 3H), 2.28(s, 3H), 6.34–6.49(m, 2H), 6.80 (d, J=2.1 Hz, 1H), 7.03–7.12(m, 3H), 7.40(d, J=2.4 Hz, 1H), 7.61(m, 1H) IR (KBr): 3414, 2862, 2589, 1652, 1601, 1541, 1492, 1430, 1330, 1186, 1222, 1186, 1147, 1123, 1040, 998 cm$^{-1}$ |
| Ib-438 | foam; $^1$H NMR (CDCl$_3$) δ 2.12(s, 3H), 2.78(s, 3H), 6.61–6.81(m, 3H), 6.99–7.06(m, 3H), 7.41(d, J=2.1 Hz, 1H), 7.58(dd, J=2.4, 8.7 Hz, 1H) IR (KBr): 3423, 2857, 2604, 1654, 1602, 1539, 1447, 1413, 1215, 1133, 1074 cm$^{-1}$ |
| Ib-439 | foam; $^1$H NMR (CDCl$_3$) δ 1.73(s, 3H), 1.79(s, 3H), 2.14(s, 3H), 2.28(s, 3H), 3.71(d, J=6.6 Hz, 2H), 5.33–5.39(m, 1H), 6.65–6.83(m, 3H), 6.99–7.09(m, 3H), 7.36(d, J=2.7 Hz, 1H), 7.55–7.60(m, 1H) IR (KBr): 3431, 2923, 2550, 1654, 1604, 1480, 1455, 1376, 1357, 1284, 971 cm$^{-1}$ |
| Ib-440 | mp 193–195° C.; $^1$H NMR (CDCl$_3$) δ 1.74(s, 3H), 1.78(s, 3H), 2.21(s, 3H), 2.28(s, 3H), 3.72(d, J=6.9 Hz, 2H), 5.35(t, J=6.9 Hz, 1H), 6.40(dd, J=12.3, 2.1 Hz, 1H), 6.46(dd, J=8.4, 2.4 Hz, 1H), 6.67(dd, J=9.3, 0.6 Hz, 1H), 7.04(t, J=8.4 Hz, 1H), 7.07(s, 1H), 7.11(s, 1H), 7.39(dd, J=2.4, 0.6 Hz, 1H), 7.56(dd, J=9.3, 2.4 Hz, 1H); IR (KBr): 3413, 3302, 1660, 1620, 1497, 1466, 1421, 1337, 1232, 1174, 835 cm$^{-1}$ |

TABLE 135

| | |
|---|---|
| Ib-441 | mp 247–249° C.; $^1$H NMR (CDCl$_3$) δ 1.78(s, 3H); 1.82(s, 3H); 1.96(s, 6H); 2.04 (s, 6H); 4.64(d, J=6.9 Hz, 2H); 5.58(m, 1H); 6.72(d, J=9.3 Hz, 1H); 6.80– 6.92(m, 2H); 7.05(dt, J=1.2, 8.4 Hz, 1H); 7.22(d, J=1.8 Hz, 1H); 7.35(ddd, J=1.8, 2.4, 9.3 Hz, 1H); IR (KBr): 3444, 2917, 1661, 1619, 1512, 1294, 1262 cm$^{-1}$. |

TABLE 135-continued

| | |
|---|---|
| Ib-442 | mp 172–176° C.; $^1$H NMR (CDCl$_3$) δ 1.78(s, 3H); 1.82(s, 3H); 1.95(s, 6H); 2.05 (s, 6H); 4.64(d, J=6.9 Hz, 2H); 5.57(m, 1H); 6.75–7.25(m, 5H); 10.81(br s, 1H); IR (KBr): 2925, 1689, 1677, 1592, 1514, 1295, 1264, 1243, 1113, 1008 cm$^{-1}$. |
| Ib-443 | mp 240–242° C.; $^1$H NMR (CDCl$_3$) δ 1.77(s, 3H); 1.82(s, 3H); 1.96(s, 6H); 2.06 (s, 6H); 4.64(d, J=6.3 Hz, 2H); 5.57(m, 1H); 6.74–7.09(m, 3H); 7.22(d, J= 1.2 Hz, 1H); 8.42(d, J=1.2 Hz, 1H); IR (KBr): 2916, 1655, 1616, 1512, 1261 cm$^{-1}$. |
| Ib-539 | $^1$HMR(CDCl$_3$): δ 1.59(3H, s), 1.74(3H, s), 1.79(3H, s), 1.83(3H, s), 2.20(3H, s), 2.28(3H, s), 4.32(2H, d, J 7.2 Hz), 4.89(2H, d, J 6.9 Hz), 5.32(1H, bt, J 7.2 Hz), 5.58(2H, bt, J 6.9 Hz), 5.81(2H, bs), 6.83(1H, d, J 8.4 Hz), 7.14(2H, bs 7.03–7.30(3H), 7.60(1H, dd, J 8.4 Hz, 2.4 Hz), 8.18(1H, d, J 2.4 Hz). |
| Ib-540 | $^1$HNMR (CDCl$_3$): δ 1.58(3H, s), 1.73(3H, s), 1.80(3H, s), 1.82(3H, s), 2.20 (3H, s), 2.28(3H, s), 2.33(1H, bs), 4.25(2H, bs), 4.30(2H, d, J 6.9 Hz), 4.88 (2H, d, J 6.9 Hz), 5.30(1H, bt, J 6.9 Hz), 5.58(2H, bt, J 6.9 Hz), 5.90(2H, bs), 6.83(1H, d, J 8.4 Hz), 6.95–7.30(3H), 7.13(2H, bs), 7.60(1H, dd, J 8.4 Hz, 2.4 Hz, 8.18 1H, d, J 2.4 Hz.) |
| Ib-541 | $^1$HMR(CDCl$_3$): δH 1.58(3H, s), 1.73(3H, s), 1.79(3H, s), 1.82(3H, s), 2.20(3H, s), 2.28(3H, s), 2.71(4H, s), 4.29(2H, d, J 7.2 Hz), 4.88(2H, d, J 6.9 Hz), 5.30(1H, bt, J 6.9 Hz), 5.57(2H, bt, J 7.2 Hz), 5.80(2H, bs,), 6.82(1H, d, J 8.1 Hz), 6.97–7.27(3H), 7.13(1H, d, J 2.4 Hz), 7.60(1H, dd, J 8.1 Hz, 2.4 Hz), 8.18(1H, bs). |
| Ic-1 | 119–120° C., $^1$H-NMR (CDCl$_3$) δ 1.76(3H, s), 1.82(3H, s), 2.17(3H, s), 2.24(3H, s), 4.61(2H, d, J=6.8), 4.63(1H, s), 5.52(1H, br t, J=6.8), 5.71(1H, s), 6.66 (1H, s), 6.76(JH, dd, J=2.2, 8.3), 6.80(2H, d, J=8.3), 6.86–6.91(4H, m), 7.07 (1H, s) |
| Ic-2 | oil, $^1$H-NMR (CDCl$_3$) δ 1.75(3H, s), 1.78(3H, s), 2.17(3H, s), 2.25(3H, s), 3.87 (3H, s), 4.62(2H, d, J=6.6), 4.67(1H, s), 5.56(1H, br t, J=6.6), 6.68(1H, s), 6.79–6.93(7H, m), 7.09(1H, s) |
| Ic-3 | oil, $^1$H-NMR (CDCl$_3$) δ 2.18(3H, s), 2.22(3H, s), 3.14(3H, s), 5.16(2H, s), 5.71 (1H, s), 6.77(1H, dd, J=2.0, 8.3), 6.81(1H, s), 6.93–6.99(4H, m), 7.10(1H, s), 7.22(2H, d, J=9.0), 7.39–7.47(5H, m) |
| Ic-4 | oil, $^1$H-NMR (CDCl$_3$) δ 2.19(3H, s), 2.21(3H, s), 3.11(3H, s), 3.15(3H, s), 5.15 (2H, s), 6.82(1H, s), 6.95(2H, d, J=9.3), 7.10(1H, s), 7.11(1H, d, J=8.3), 7.21(1H, dd, J=2.2, 8.3), 7.23(2H, d, J=9.3), 7.31(1H, d, J=2.2), 7.37–7.49(5H, m) |
| Ic-5 | oil, $^1$H-NMR (CDCl$_3$) δ 2.19(3H, s), 2.20(3H, s), 3.14(3H, s), 3.91(3H, s), 5.20 (2H, s), 6.79(1H, dd, J=2.0, 8.1), 6.81(1H, s), 6.86(1H, d, J=2.0), 6.93(1H, d, J=8.1), 6.95(2H, d, J=9.0), 7.11(1H, s), 7.22(2H, d, J=9.0), 7.32–7.49 (5H, m) |
| Ic-6 | oil, $^1$H-NMR (CDCl$_3$) δ 1.77(3H, s), 1.82(3H, s), 2.19(3H, s), 2.21(3H, s), 3.14 (3H, s), 3.22(3H, s), 4.63(2H, d, J=6.8), 5.51(1H, br t, J=6.8), 6.82(1H, s), 6.95(2H, d, J=9.0), 7.04(1H, d, J=8.3), 7.11(1H, s), 7.21(1H, dd, J=2.2, 8.3), 7.23(2H, d, J=9.0), 7.29 1H, d, J=2.2) |

TABLE 136

| | |
|---|---|
| Ic-7 | oil, $^1$H-NMR (CDCl$_3$) δ 1.76(3H, s), 1.80(3H, s), 2.20(3H, s), 2.22(3H, s), 3.15(3H, s), 3.89(3H, s), 4.63(2H, d, J=6.8), 5.57(1H, br t, J=6.8), 6.81–6.85(3H, m), 6.93(1H, d, J=8.8), 6.96(2H, d, J=8.8), 7.13(1H, s), 7.22(2H, d, J=8.8) |
| Ic-8 | 162–163° C., $^1$H-NMR (CDCl$_3$) δ 2.14(3H, s), 2.26(3H, s), 3.55(2H, br s), 3.89 (3H, s), 5.19(2H, s), 6.64(1H, s), 6.68(2H, d, J=8.8), 6.77(1H, dd, J=2.0, 8.7), 6.84(2H, d, J=8.8), 6.85(1H, d, J=2.0), 6.91(1H, d, J=8.7), 7.06(1H, s), 7.31–7.49(5H, m) |
| Ic-9 | 111–112° C., $^1$H-NMR (CDCl$_3$) δ 1.75(3H, s), 1.79(3H, s), 2.16(3H, s), 2.27 (3H, s), 3.56(2H, br s), 3.87(3H, s), 4.62(2H, d, J=6.8), 5.56(1H, br t, J=6.8), 6.65(1H, s), 6.68(2H, d, J=9.0), 6.79–6.92(5H, m), 7.08(1H, s) |
| Ic-12 | oil, $^1$H-NMR (CDCl$_3$) δ 2.14(3H, s), 2.28(3H, s), 2.93(6H, s), 3.89(3H, s), 5.19(2H, s), 6.64(1H, s), 6.74(2H, d, J=9.0), 6.78(1H, dd, J=2.0, 8.3), 6.85 (1H, d, J=2.0), 6.91(1H, d, J=8.3), 6.93(2H, d, J=9.0), 7.31–7.49(5H, m) |
| Ic-14 | oil, $^1$H-NMR (CDCJ3) δ 1.75(3H, s), 1.79(3H, s), 2.16(3H, s), 2.28(3H, s), 2.93(6H, s), 3.87(3H, s), 4.62(2H, d, J=6.8), 5.56(1H, br t, J=6.8), 6.65 (1H, s), 6.75(2H, d, J=9.0), 6.80–6.83(2H, m), 6.90(1H, d, J=8.6), 6.93(2H, d, J=9.0), 7.08(1H, s) |
| Ic-16 | 119–120° C., $^1$H-NMR (CDCl$_3$) δ 2.13(3H, s), 2.27(3H, s), 3.01(6H, s), 6.78 (1H, d, J=9.3), 6.80(2H, d, J=8.8), 6.89(1H, s), 7.16(1H, s), 7.22(2H, d, J= 8.8), 8.04(1H, dd, J=2.7, 9.3), 8.39(1H, d, J=2.7) |
| Ic-17 | 80–82° C., $^1$H-NMR (CDCl$_3$) δ 2.17(3H, s), 2.30(3H, s), 2.98(6H, s), 3.61(2H, br s), 6.50(1H, s), 6.55(1H, dd, J=2.7, 8.6), 6.77(2H, d, J=9.0), 6.81(1H, d, J=2.7), 6.82(1H, d, J=8.6), 7.07(1H, s), 7.20(2H, d, J=9.0), |
| Ic-18 | 141–142° C., $^1$H-NMR (CDCl$_3$) δ 2.21(3H, s), 2.22(3H, s), 3.00(6H, s), 3.03 (3H, s), 6.41(1H, br s), 6.71(1H, s), 6.78(2H, d, J=8.8), 6.82(1H, d, J=8.8), |

TABLE 136-continued 7.06(1H, dd, J=2.7, 8.8), 7.11(1H, s), 7.21(2H, d, J=8.8), 7.39(1H, d, J=2.7)

Ic-19 138–139° C., $^1$H-NMR (CDCl$_3$) δ 2.20(3H, s), 2.22(3H, s), 3.00(6H, s), 6.72 (1H, s), 6.78(2H, d, J=8.8), 6.85(1H, d, J=8.8), 7.12(1H, s), 7.21(2H, d, J=8.8), 7.35(1H, dd, J=2.7, 8.8), 7.77(1H, d, J=2.7), 7.82(1H, br s),

Ic-20 oil, $^1$H-NMR (CDCl$_3$) δ 1.73(3H, s), 1.77(3H, s), 2.16(3H, s), 2.31(3H, s), 2.98(6H, s), 3.67(2H, d, J=6.6), 5.33(1H, br t, J=6.6), 6.48(1H, dd, J=2.7, 8.8), 6.49(1H, s), 6.71(1H, d, J=2.7), 6.77(2H, d, J=8.8), 6.85(1H, d, J=8.8), 7.07(1H,s), 7.20(2H, d, J=8.8)

Ic-23 126–128° C., $^1$H-NMR (CDCl$_3$) δ 1.76(3H, s), 1.82(3H, s), 2.26(3H, s), 2.35 (3H, s), 4.58(1H, br s), 4.61(2H, d, J=6.8), 4.96(2H, s), 5.52(1H, br t, J=6.8), 5.72(1H, s), 6.75–6.81(3H, m), 6.89–6.92(4H, m), 7.08(1H, s), 7.27(1H, s)

Ic-24 oil, $^1$H-NMR (CDCl$_3$) δ 1.76(3H, s), 1.81(3H, s), 2.26(3H, s), 2.35(3H, s), 3.21(3H, s), 4.53(1H, s), 4.62(2H, d, J=6.8), 4.96(2H, s) 5.50(1H, br t, J=6.8), 6.78(2H, d, J=9.0), 6.90(2H, d, J=9.0), 7.03(1H, d, J=8.5), 7.07 (1H, s), 7.20(1H, dd, J=2.2, 8.5), 7.28(1H, s), 7.29(1H, d, J=2.2)

Ic-25 146–147° C., $^1$H-NMR (CDCl$_3$) δ 1.75(3H, s), 1.79(3H, s), 2.25(3H, s), 2.26 (3H, s), 3.86(3H, s), 4.62(2H, d, J=6.8), 4.78(1H, s), 5.02(2H, s), 5.56(1H, br t, J=6.8), 6.79–6.82(3H, m), 6.86(2H, d, J=8.5), 6.90(1H, d, J=8.8), 7.04(1H.s), 7.35(2H, d, J=8.5)

Ic-32 123–124° C., $^1$H-NMR (CDCl$_3$) δ 1.76(3H, s), 1.81(3H, s), 2.26(6H, s9, 3.17 (3H, s), 3.21(3H, s), 4.61(2H, d, J=6.8), 5.10(2H, s), 5.50(1H, br t, J=6.8), 6.76(1H, s), 7.02(1H, d, J=8.3), 7.04(1H, s), 7.18(1H, dd, J=2.2, 8.3), 7.27 (1h, d, J=2.2), 7.33(2H, d, J=8.8), 7.53(2H, d, J=8.8)

TABLE 137

Ic-33 125–127° C., $^1$H-NMR (CDCl$_3$) δ 1.75(3H, s.), 1.79(3H, s), 2.24(3H, s), 2.35 (3H, s), 3.87(3H, s), 4.21(2H, s9, 4.61(2H, d, J=6.6), 5.56(1H, br t, J=6.59(2H, d, J=8.8), 6.73(2H, d, J=8.8), 6.81–6.85(2H, m), 6.92(1H, d, J=8.8), 7.08(1H, s), (7.23 1H, s)

Ic-35 141–142° C., $^1$H-NMR (CDCl$_3$) δ 1.77(3H, s), 1.82(3H, s), 2.30(3H, s), 2.40 (3H, s), 4.61(2H, d, J=6.8), 4.79(1H, s), 5.53(1H, br t, J=6.8), 5.70(1H, s), 6.79(1H, dd, J=2.2, 8.3), 6.84(2H, d, J=8.8), 6.91(1H, d, J=8.3), 6.93 (1H, d, J=2.2), 6.97(1H, d, J=16.1) 7.04(1H, s), 7.18(1H, d, J=16.1), 7.43 (2H, d, J=8.8), 7.46 1H, s).

Ic-38 140–142° C., $^1$H-NMR (CDCl$_3$) δ 1.77(3H, s), 1.82(3H, s), 2.30(3H, s), 2.41 (3H, s), 3.16(3H, s), 3.22(3H, s), 4.63(2H, d, J=6.8), 5.51(1H, br t, J=6.8), 7.02(1H, d, J=15.4), 7.04(1H, d, J=8.3), 7.05(1H, s), 7.22(1H, dd, J=2.2, 8.3), 7.29(2H, d, J=8.8), 7.30(1H, d, J=2.2), 7.31(1H, d, J=15.4), 7.48(1H, s, 7.57(2H, d, J=8.8)

Ic-43 146–147° C., $^1$H-NMR (CDCl$_3$) δ 1.75(3H, s), 1.79(3H, s), 2.25(3H, s), 2.48 (3H, s), 3.88(3H, s), 4.62(2H, d, J=6.8), 5.04(1H, s), 5.56(1H, br t, J=6.8), 6.81–6.85(4H, m), 6.92(1H, d, J=8.8), 7.10(1H, s), 7.38(1H, s), 7.44(2H, d, J=8.6)

Ic-44 121–122° C., $^1$H-NMR (CDCl$_3$) δ 1.76(3H, s), 1.79(3H, s), 2.26(3H, s), 2.49 (3H, s), 3.17(3H, s), 3.88(3H, s), 4.63(2H, d, J=6.8), 5.56(1H, br t, J=6.8), 6.81–6.85(2H, m), 6.93(1H, d, J=8.8), 7.12(1H, s), 7.29(2H, d, J=8.8), 7.40 1H, s), 7.59(2H, d, J=8.8)

Ic-47 oil, $^1$H-NMR (CDCl$_3$) δ 1.76(3H, s), 1.79(3H, s9, 2.26(3H, s), 2.29(3H, s), 3.89(3H, s), 4.64(2H, d, J=6.6), 5.57(1H, br t, J=6.6), 5.82(1H, s), 6.85–6.88(2H, m), 6.90(2H, d, J=8.8), 6.95(1H, d, J=8.5), 7.14(1H, s), 7.18(1H, s), 7.81(2H, d, J=8.8)

Ic-49 oil, $^1$H-NMR (CDCl$_3$) δ 1.75(3H, s), 1.79(3H, s), 2.07(1H, d, 3.7), 2.21(3H, s), 2.28(3H, s), 3.87(3H, s), 4.62(2H, d, J=6.8), 4.81(1H, s), 5.56(1H, br t, J=6.8), 5.96(1H, d, J=3.7), 6.81(1H, d, J=8.8)6.82–6.85(2H, m), 6.92(1H, d, J=8.8), 7.02(1H, s), 7.25(2H, d, J=8.8), 7.42(1H, s)

Ie-4 170–170.5° C., $^1$H-NMR (CDCl$_3$) δ 5.15(2H, s), 5.75(1H, s), 6.94(1H, dd, J=0.7, 8.5), 6.98(2H, m), 7.06–7.16(5H, m), 7.37–7,44(5H, m), 7.83(1H, dd, J=2.4, 8.5), 8.34(1H, dd, J=0.7, 2.4)

Ie-5 122–122.5° C.

Ie-6 175–176° C., $^1$H-NMR (CDCl$_3$) δ 2.38(3H, s), 5.11(2H, s), 5.75(1H, s), 6.94 (1H, d, J=8.3), 6.98(2H, m), 7.05–7.17(5H, m), 7.22(2H, d, J=8.1), 7.32 2H, d, J=8.1), 7.83(1H, dd, J=2.4, 8.6), 8.34(1H, d, J=2.4)

Ie-7 144.5–145,5° C., $^1$H-NMR (CDCl$_3$) δ 2.37(3H, s), 3.11(3H, s), 5.12(2H, s), 6.96 (1H, d, J=8.6), 7.10–7.15(5H, m), 7.21(2H, d, J=8.1), 7.33(2H, d, J=8.1), 7.39(1H, dd, J=2.2, 8.6), 7.47(1H, d, J=2.2), 7.83(1H, dd, J=2.7, 8.6), 8.33 (1H, d, J=2.7)

Ie-8 125–127° C., $^1$H-NMR (CDCl$_3$) δ 1.76(3H, s), 1.81(3H, s), 4.61(2H, d, J=6.8), 5.51(1H, br t, J=6.8), 5.76(1H, s), 6.91–7.01(3H, m), 7.06–7.16(5H, m), 7.83 (1H, dd, J=2.4, 8.6), 8.34(1H, dd, J=0.7, 2.4)

Ie-9 127–128° C., $^1$H-NMR (CDCl$_3$) δ 1.76(3H, s), 1.81(3H, s), 3.22(3H, s), 4.62 (2H, d, J=6.8), 5.48(1H, br t, J=6.8), 6.96(1H, dd, J=0.7, 8.6), 7.06–7.15 (5H, m), 7.40(1H, dd, J=2.2, 8.6), 7.46(1H, d, J=2.2), 7.83(1H, dd, J=2.4, 8.6), 8.33(1H, dd, J=0.7, 2.4)

TABLE 137-continued

Ie-13 153–154° C., ¹H-NMR (CDCl₃) δ 2.25(3H, s), 3.10(3H, s), 3.78(3H, s), 5.16 (2H, s), 7.13(2H, s), 7.19–7.25(4H, m), 7.36–7.48(7H, m)

TABLE 138

Ie-14 oil, ¹H-NMR (CDCl₃) δ 2.23(3H, s), 2.39(3H, s), 3.77(3H, s), 5.09(2H, s), 5.74(1H, s), 6.69(1H, dd, J=1.8, 8.5), 6.82(1H, d, J=1.8), 6.98(1H, d, J=8.5), 7.18–7.43(9H, m)

Ie-15 166–167° C., ¹H-NMR (CDCl₃) δ 2.25(3H, s), 2.38(3H, s), 3.09(3H, s), 3.78 (3H, s), 5.11(2H, s), 7.12(2H, s), 7.15–7.44(10H, m)

Ie-17 132–133° C., ¹H-NMR (CDCl₃) δ 2.25(3H, s), 3.10(3H, s), 3.79(3H, s), 3.83 (3H, s), 5.16(2H, s), 6.91(2H, d, J=9.1), 6.94–7.23(5H, m), 7.36–7.48(5H, m)

Ie-18 oil, ¹H-NMR (CDCl₃) δ 2.24(3H, s), 2.39(3H, s), 3.78(3H, s), 3.83(3H, s), 5.09(2H, s), 5.71(1H, d, J=1.8), 6.68(1H, dd, J=1.8, 7.9), 6.82(1H, d, J=1.8), 6.90(2H, d, J=1.8), 6.98(1H, d, J=7.9), 7.16(2H, d, J=1.8), 7.23(2H, d, J=7.9), 7.33(2H, d, J=7.9)

Ie-19 113–114° C., ¹H-NMR (CDCl₃) δ 2.24(3H, s), 2.38(3H, s), 3.09(3H, s), 3.78 (3H, s), 3.83(3H, s), 5.11(2H, s), 6.91(2H, d, J=8.5), 7.34(2H, d, J=8.5)

Ie-23 157–158° C.

Ie-24 114–116° C., ¹H-NMR (CDCl₃) δ 1.76(3H,s), 1.82(3H, s), 2.23(3H, s), 3.78 (3H, s), 4.60(2H, d, J=6.8), 5.52(1H, br t, J=6.8), 5.74(1H, s), 6.67(1H, dd, J=2.0, 8.3), 6.79(1H, d, J=2.0), 6.91(1H, d, J=8.3), 7.07(1H, dd, J=8.3, 9.3), 7.21(1H, dd, J=4.6, 8.3)

Ie-25 107–108° C., ¹H-NMR (CDCl₃) δ 1.76(3H,s), 1.81(3H, s), 2.25(3H, s), 3.21 (3H, s), 3.79(3H, s), 4.62(2H, d, J=6.6), 5.50(1H, br t, J=6.6), 7.03–7.23 (7H, m)

Ie-27 177–178° C., ¹H-NMR (CDCl₃) δ 2.24(3H, s), 3.10(3H, s), 3.92(3H, s), 5.16 (2H, s), 6.99–7.49(11H, m), 7.66(2H, d, J=7.9)

Ie-28 170–172° C., ¹H-NMR (CDCl₃) δ 2.22(3H, s), 2.39(3H, s), 3.92(3H, s), 5.09 (2H, s), 5.71(1H, s), 6.71(1H, dd, J=1.8, 7.9), 6.84(1H, d, J=1.8), 6.98(1H, d, J=7.9), 7.03(2H, d, J=7.3), 7.23(2H, d, J=7.9), 7.29–7.36(3H, m), 7.67 (2H, dd, J=1.2, 8.5)

Ie-29 169–170° C., ¹H-NMR (CDCl₃) δ 2.24(3H, s), 2.38(3H, s), 3.10(3H, s), 3.92 (3H, s), 5.11(2H, s), 6.99–7.37(10H, m), 7.66(2H, d, J=7.9)

Ie-31 150–15I° C., ¹H-NMR (CDCl₃) δ 2.22(3H, s), 3.10(3H, s), 3.81(3H, s), 3.88 (3H, s), 5.15(2H, s), 6.87(1H, s), 6.89(2H, d, J=9.1), 7.09(1H, d, J=8.5), 7.14(1H, dd, J=1.8, 8.5), 7.24(1H, d, J=1.8), 7.36–7.53(5H, m), 7.55(2H, d, J=9.1)

Ie-32 175–176° C., ¹H-NMR (CDCl₃) δ 2.20(3H, s), 2.39(3H, s), 3.81(3H, s), 3.88 (3H, s), 5.09(2H, s), 5.68(1H, s), 6.70(1H, dd, J=1.8, 7.9), 6.83(1H, d, J=1.8), 6.85(1H, br s), 6.88(2H, d, J=9.2), 6.97(1H, d, J=7.9), 7.23(2H, d, J=7.9), 7.34(2H, d, J=7.9), 7.55(2H, d, J=9.2)

Ie-33 176–177° C., ¹H-NMR (CDCl₃) δ 2.22(3H, s), 2.37(3H, s), 3.09(3H, s), 3.81 (3H, s), 3.88(3H, s), 5.10(2H, s), 6.87(1H, s), 6.89(2H, d, J=8.5), 7.09(1H, d, J=8.5), 7.14(1H, dd, J=1.8, 8.5), 7.22(2H, d, J=8.5), 7.23(1H, s), 7.34 (2H, d, J=8.5), 7.55(2H, d, J=8.5)

Ie-38 188–189° C., ¹H-NMR (CDCl₃) δ 2.21(3H, s), 2.39(3H, s), 3.89(3H, s), 5.09 (2H, s), 5.68(1H, s), 6.70(1H, dd, J=1.8, 7.9), 6.83(1H, d, J=1.8), 6.91–7.06 (4H, m), 7.23(2H, d, J=8.5), 7.34(2H, d, J=8.5), 7.56–7.65(2H, m)

Ie-39 194–195° C., ¹H-NMR (CDCl₃) δ 2.23(3H, s), 2.38(3H, s), 3.09(3H, s), 3.89 (3H, s), 5.11(2H, s), 6.94–7.21(5H, m), 7.22(1H, d, J=1.8), 7.23(1H, s), 7.35 (2H, d, J=7.9), 7.57–7.63(2H, m)

Ie-40 159–160° C., ¹H-NMR (CDCl₃) δ 1.76(3H, s), 1.82(3H, s), 2.21(3H, s), 3.89 (3H, s), 4.60(2H, d, J=6.7), 5.52(1H, t, J=6.7), 5.71(1H, s), 6.68(1H, dd, J=1.8, 8.5), 6.81(1H, d, J=1.8), 6.90(1H, d, J=8.5), 7.02(2H, t, J=8.5), 7.57–7.65 2H, m)

TABLE 139

Ie-41 142–143° C., ¹H-NMR (CDCl₃) δ 1.76(3H, s), 1.81(3H, s), 2.24(3H, s), 3.21 (3H, s), 3.89(3H, s), 4.62(2H, d, J=7.3), 5.50(1H, t, J=7.3), 6.94(1H, s), 6.99–7.08(3H, m), 7.13(1H, dd, J=2.4, 8.5), 7.22(1H, d, J=2.4), 7.56–7.65 (2H, m)

If-10 151–152° C., ¹H-NMR (CDCl₃) δ 2.18(3H, s), 3.09(3H, s), 3.75–3.81(8H, m), 3.83(3H, s), 5.14(2H, s), 7.08(1H, d, J=8.5), 7.11(1H, dd, J=1.7, 8.5), 7.21 (1H, d, J=1.7), 7.35–7.47(5H, m)

If-14 140–141° C., ¹H-NMR (CDCl₃) δ 2.18(3H, s), 2.36(3H, s), 2.48(4H, t, J=5.5), 3.09(3H, s), 3.83(3H, s), 3.87(4H, t, J=5.5), 5.14(2H, s), 7.07(1H, d, J=8.5), 7.11(1H, dd, J=1.8, 8.5), 7.21(1H, d, J=1.8), 7.33–7.49(5H, m)

If-18 152–153° C., ¹H-NMR (CDCl₃) δ 2.20(3H, s), 3.09(3H, s), 3.26(4H, t, J=5.5), 3.86(3H, s), 4.01(4H, t, J=5.5), 5.14(2H, s), 6.90(1H, d, J=7.3), 7.00(2H, d, J=7.3), 7.08(1H, d, J=8.5), 7.12(1H, dd, J=1.8, 8.5), 7.21–7.49(8H, m)

TABLE 139-continued

If-26 195–197° C., $^1$H-NMR (CDCl$_3$) δ 2.44(3H, s), 3.12(3H, s), 4.05(3H, s), 5.18 (2H, s), 7.14–7.21(2H, m), 7.28(1H, m), 7.38–7.48(5H, m), 8.17(1H, s), 9.22 (1H, s)

If-29 mp 122.5–123.5° C., $^1$H NMR (CDCl$_3$) δ 1.74(s, 3H), 1.78(s, 6H), 1.81 (s, 3H), 2.36(s, 3H), 2.57 (br s, 3H), 3.74(d, J=6.9 Hz, 2H), 4.88(d, J=6.9 Hz, 2H), 5.37(br t, J=6.9 Hz, 1H), 5.56(br t, J=6.9 Hz, 1H), 6.68(d, J=8.7 Hz, 2H), 6.84(dd, J=0.6, 8.7, 1H), 7.19(d, J=8.7 Hz, 2H), 7.43(br s, 1H), 7.83(dd, J=2.4, 8.7 Hz, 1H), 8.38(dd, J=0.6, 2.4 Hz, 1H)

If-30 mp 122.5–123.5° C., $^1$H NMR (CDCl$_3$) δ 1.78(s, 3H), 1.81(s, 3H), 2.37(s, 3H), 2.58(br s, 3H), 4.88(d, J=7.2 Hz, 2H), 5.56(br t, J=7.2 Hz, 1H), 6.77(d, J=8.4 Hz, 2H), 6.85(dd, J=0.6, 8.4, 1H), 7.16(d, J=8.4 Hz, 2H), 7.45(br s, 1H), 7.84(dd, J=2.4, 8.4 Hz, 1H), 8.38(dd, J=0.6, 2.4 Hz, 1H)

Ig-1 mp 176–177° C.; $^1$H NMR (CDCl$_3$) δ 1.80(s, 3H); 1.83(s, 3H); 1.98(s, 6H); 2.00 (s, 6H); 4.51(br s, 2H); 4.88(d, J=6.9 Hz, 2H); 5.90(m, 1H); 6.63(m, 1H); 6.85(ddd, J=0.9, 1.5, 8.4 Hz, 1H); 7.29(ddd, J=2.1, 4.2, 8.4 Hz, 1H); 7.39 (ddd, J=1.2, 2.4, 8.4 Hz, 1H); 7.90(m, 1H); 7.97 (m, 1H); IR (KBr): 3464, 3302, 3164, 2916, 1638, 1603, 1512, 1491, 1459, 1385, 1360, 1300, 1279, 1242 cm − 1.

Ig-2 mp 162–164° C.; $^1$H NMR (CDCl$_3$) δ 1.75(s, 3H); 1.78(s, 3H); 1.80(s, 3H); 1.83 (s, 3H); 1.98(s, 6H); 2.02(s, 6H); 3.91(t, J=5.7 Hz, 2H); 4.51(br t, 1H); 4.88 (d, J=7.2 Hz, 2H); 5.38(m, 1H); 5.59(m, 1H); 6.50(m, 1H); 6.85(ddd, J= 0.9, 1.5, 8.7 Hz, 1H); 7.27(ddd, J=2.1, 4.2, 8.7 Hz, 1H); 7.40(ddd, J=2.4, 3.3, 8.4 Hz, 1H); 7.92(m, 1H); 7.98(dt, J=0.9, 2.4 Hz, 1H); IR (KBr): 3420, 3242, 2913, 1605, 1503, 1462, 1378, 1350, 1277, 1240 cm$^{-1}$.

Ig-3 $^1$H NMR (300 MHz, CDCl$_3$) δ 1.80(s, 3H), 1.83(s, 3H), 2.07(s, 3H), 2.09(s, 3H), 3.34(s, 3H), 3.36(s, 3H), 4.59(br s, 2H), 4.89(d, J=7.2 Hz, 2H), 5.54–5.62(m, 1H), 6.62(d, J=8.4 Hz, 1H), 6.84(dd, J=8.4, 0.7 Hz, 1H), 7.45(dd, J=8.4, 2.2 Hz, 1H), 7.54(dd, J=8.4 Hz, 1H), 8.04(d, J=2.2 Hz, 1H), 8.10 (dd, J=2.5, 0.7 Hz, 1H)

Ig-4 $^1$H NMR (300 MHz, CDCl$_3$) δ 1.76(s, 3H), 1.78(d, J=0.9 Hz, 3H), 1.80(d, J=0.9 Hz, 3H), 1.83(d, J=0.9 Hz, 3H), 2.07(s, 3H), 2.10(s, 3H), 3.34(s, 3H), 3.36(s, 3H), 3.91(t, J=6.0 Hz, 2H), 4.58(br s, 1H), 4.88(d, J=6.9 Hz, 2H), 5.34–5.41(m, 1H), 5.55–5.62(m, 1H), 6.49(dd, J=8.6, 0.7 Hz, 1H), 6.84(dd, J=8.3, 0.8 Hz, 1H), 7.43(dd, J=8.6, 2.3 Hz, 1H), 7.55(dd, J=8.3, 2.3 Hz, 1H), 8.05(dd, J=2.3, 0.7 Hz, 1H), 8.11(dd, J=2.3, 0.8 Hz, 1H)

TABLE 140

Ig-5 mp 126–128 2 C.; $^1$H NMR (CDCl$_3$) δ 1.75(s, 6H), 1.78(s, 6H), 2.07(s, 6H), 2.55(s, 6H), 3.90(t, J=6.0 Hz, 4H), 4.53(m, 2H), 5.37(t, J=6.6 Hz, 2H), 6.47(dd, J=8.4, 0.9 Hz, 2H), 7.17(dd, J=8.4, 2.4 Hz, 2H), 7.82(dd, J=2.4, 0.9 Hz, 2H); IR (KBr): 3222, 1607, 1532, 1389, 1313, 981, 811 cm$^{-1}$

Ig-6 $^1$H NMR (300 MHz, CDCl$_3$) δ 1.75(s, 6H), 1.78(d, J=0.9 Hz, 6H), 2.10(s, 6H), 3.36(s, 6H), 3.91(t, J=0.9 Hz, 4H), 4.53(t, J=5.0 Hz, 2H), 5.34–5.42 (m, 2H), 6.48(d, J=8.5 Hz, 2H), 7.42(dd, J=8.5, 2.3 Hz, 2H), 8.05(dd, J= 2.3, 0.8 Hz, 2H)

Ig-7 $^1$H NMR (300 MHz, CDCl$_3$) δ 1.80(s, 3H), 1.83(s, 3H), 2.08(s, 3H), 2.12(s, 3H), 3.34(s, 3H), 3.39(s, 3H), 4.89(d, J=6.9 Hz, 2H), 5.17(br s, 2H), 5.54–5.62(m, 1H), 6.84(dd, J=8.6, 0.8 Hz, 1H), 7.53(dd, J=8.6, 2.3 Hz, 1H), 8.09(dd, J=2.3, 0.8 Hz, 1H), 8.32(s, 2H)

Ig-8 $^1$H NMR (300 MHz, CDCl$_3$) δ 1.76(s, 3H), 1.78(s, 3H), 1.80(s, 3H), 1.83(s, 3H), 2.08(s, 3H), 2.13(s, 3H), 3.34(s, 3H), 3.40(s, 3H), 4.05(s, J=6.2 Hz, 2H), 4.88(d, J=6.9 Hz, 2H), 5.14–5.18(m, 1H), 5.35–5.42(m, 1H), 5.55–5.61 (m, 1H), 6.85(dd, J=8.5, 0.7 Hz, 1H), 7.54(dd, J=8.5, 2.7 Hz, 1H), 8.10 (dd, J=2.7, 0.7 Hz, 1H), 8.30(s, 2H)

Ig-9 $^1$H NMR (300 MHz, CDCl$_3$) δ 1.79(s, 3H), 1.83(d, J=0.9 Hz, 3H), 2.07(s, 3H), 2.08(s, 3H), 3.34(s, 3H), 3.40(s, 3H), 4.67(br s, 2H), 4.89(d, J=7.2 Hz, 2H), 5.54–5.62(m, 1H), 6.84(dd, J=8.6, 0.7 Hz, 1H), 7.53(dd, J=8.6, 2.5 Hz, 1H), 8.09(dd, J=2.5, 0.7 Hz, 1H), 8.12(d, J=1.5 Hz, 1H), 8.15(d, J= 1.5 Hz, 1H)

Ig-10 $^1$H NMR (300 MHz, CDCl$_3$) δ 1.77(s, 3H), 1.79(s, 6H), 1.83(s, 3H), 2.07(s, 3H), 2.09(s, 3H), 3.34(s, 3H), 3.41(s, 3H), 3.99(t, J=5.7 Hz, 2H), 4.62(br s, 1H), 4.88(d, J=6.9 Hz, 2H), 5.34–5.42(m, 1H), 5.55–5.62(m, 1H), 6.84(dd, J=8.4, 0.8 Hz, 1H), 7.53(dd, J=8.4, 2.5 Hz, 1H), 8.02(d, J=1.5 Hz, 1H), 8.09(dd, J=2.5, 0.8 Hz, 1H)

Experiment 1

Suppressive Effect on a Mitogenic Activity of Mouse Splenocytes in Vitro

In 96-well microtiter plate, 5×10$^5$ C3H/HeN mouse splenocytes suspended in 0.1 ml of 10% fetal bovine serum-fortified RPMI 1640 medium containing 2 mM of sodium bicarbonate, 50 units/ml of penicillin, 50 μg/ml of streptomycin and 5×10$^{-5}$ M of 2-mercaptoethanol were added. Then, 5 μg/ml of Concanavalin A (Con A) or 10 μg/ml of lipopolysaccharide (LPS) as a mitogen and the compound of a pre-determined concentration of the present invention were added to each well so that the final volume of each well reached 0.2 ml. Each compound of the present invention was dissolved in dimethylsulfoxide (DMSO) and diluted with the above RPMI 1640 medium to adjust the final concentration of 100 ng/ml or less. The splenocytes in the 96-well microtiter plate were cultivated at 37° C. for 3 days in an incubator keeping the humidity 100%, carbon dioxide 6% and air 95%. Then, 25 µl of 6 mg/ml MTT {3-(4,5-dimethylthiazol-2-yl)-2,5-diphenyltetrazolium bromide} (Sigma) was added to the each well and cultivated at 37° C. for 4 hours under the same conditions. After the cultivation, 50 µl of 20% sodium dodecyl sulfate (SDS) containing 0.02 N hydrochloric acid was added to the generated formazan and the mixture was allowed to stand at 37° C. for 24 hours for dissolving formazan. The absorption intensity (OD) of formazan generated in proportion to the number of living cells was measured with an immunoreader (InterMed) equipped with a 570 nm filter The Journal of Immunological Method, 65, 55–63, 1983). The 50% inhibitory concentration of a cell proliferation ($IC_{50}$) was calculated from a correlation between the concentration of the compound of the present invention and the absorption intensity.

Experiment 2

Anti-proliferative Activity on EL4 Cells

In 96-well microtiter plate $4 \times 10^4/0.1$ ml of mouse thymoma strain EL4 cells were added and 0.1 ml of the compound of the present invention was added thereto so that the concentration was in a range of 0–5,000 ng/ml. After the cultivation for 3 days, the $IC_{50}$ was calculated by the MTT method as described in Experiment 1.

The results of Experiments 1 and 2 are shown in Table 141.

TABLE 141

| Compound No. | ConA $IC_{50}$ (ng/ml) | LPS $IC_{50}$ (ng/ml) | EL-4 $IC_{50}$ (ng/ml) |
|---|---|---|---|
| Ia-2 | ≦10 | ≦10 | 33 |
| Ia-42 | 16 | 31 | 200 |
| Ia-43 | 74 | 154 | 500 |
| Ia-45 | 66 | 373 | 811 |
| Ia-66 | 52 | 39 | 80 |
| Ia-94 | 12 | 21 | 50 |
| Ib-3 | 41 | 145 | 307 |
| Ib-13 | 58 | 179 | 426 |
| Ib-16 | 3.1 | 6.7 | 400 |
| Ib-17 | 29 | 60 | 78 |
| Ib-20 | 51 | 196 | 576 |
| Ib-23 | 78 | 283 | 651 |
| Ib-37 | 92 | 361 | 114 |
| Ib-40 | 16 | 55 | 60 |
| Ib-44 | 60 | 317 | 426 |
| Ib-54 | <20 | 53 | 91 |
| Ib-65 | 92 | 134 | 553 |
| Ib-71 | 18 | 54 | 69 |
| Ib-82 | <20 | <20 | <20 |
| Ib-101 | 42 | 261 | 493 |
| Ic-1 | 48 | 158 | 473 |
| Ic-14 | 15 | 53 | 207 |

As shown in the above, the compound of the present invention has immunosuppressive and anti-allergic effects.

Experiment 3

Suppressive effect on the IgE Production Against ovalbumin (OVA)

1) Animals

BALB/c mice (female, 8–10 weeks old) and Wistar rats (female, 8–10 weeks old) which were bought from Japan SLC, Inc. (Shizuoka) were used.

2) Immunizing Method

BALB/c mice were immunized by an intraperitoneal administration of 0.2 ml suspension of 2 µg of ovalbumin (OVA) and 2 mg of aluminium hydroxide gel in physiological saline. After 10 days, blood was collected from hearts, then sera were separated and stocked at −40° C. till the measurement of IgE antibody titer.

3) Compounds

After the compound of the present invention was dissolved or suspended in N,N-dimethylacetoamide, the mixture was diluted 20 times with miglyol 812 neutral oil. The obtained solution was orally administered to mice at 0.1 ml per mouse (dose 40 mg/kg). The administration was continued for 10 days from the immunizing day to the day before the blood collection.

4) Measurement of Anti-OVA IgE Antibody Titer (PCA Titer)

The obtained mouse serum was 2-fold diluted with physiological saline, then each 50 µl of the solution was intradermally injected at dorsal skin of Wistar rats which previously hair cut. After 24 hours, a passive cutaneous anaphylaxis reaction (PCA) was induced by an intravenous injection of 0.5 ml of physiological saline containing 1 mg of OVA and 5 mg of Evans' blue dye. The rats were sacrified 30 minutes later and the highest dilution giving bluing with a diameter of 5 mm or more was recorded as the PCA titer. For example, when a serum is positive for the PCA reaction till $2^7$ times dilution, the anti-OVA IgE antibody titer of the mouse is defined as 7. The results are shown in Table 142.

TABLE 142

| Compound | PCA Titer |
|---|---|
| Ia-356 | 5.3 |
| Ib-37 | 0 |
| Ib-69 | 1.5 |
| Ib-90 | 1.7 |
| Ib-218 | 5.5 |
| Ib-219 | <0 |
| Ib-220 | <0 |
| Ib-221 | 0.3 |
| Ib-222 | <0 |
| Ib-223 | 3.8 |
| Ib-224 | 0 |
| Ib-225 | 0 |
| Ib-226 | 0 |
| Ib-227 | 4.5 |
| Ib-228 | 2.5 |
| Ib-229 | 3 |
| Ib-230 | 0 |
| Ib-231 | <0 |
| Ib-232 | 1 |
| Ib-233 | 2 |
| Ib-234 | <0 |
| Ib-235 | <0 |
| Ib-239 | 0 |
| Ib-240 | 0 |
| Ib-241 | 0 |
| Ib-242 | 1 |
| Ib-243 | 2.3 |
| Ib-244 | 0 |
| Ib-245 | 5.3 |
| Ib-246 | 0 |
| Ib-247 | 0 |
| Ib-248 | 0 |
| Ib-249 | 0 |
| Ib-250 | 0 |
| Ib-259 | 0 |
| Ib-272 | 5.3 |
| Ib-279 | 1 |
| Ib-280 | 0 |
| Ib-281 | 0 |
| Ib-283 | 3 |

TABLE 142-continued

| Compound | PCA Titer |
|---|---|
| Ib-284 | 6.8 |
| Ib-285 | 2 |
| Ib-293 | 5 |
| Ib-297 | 3 |
| Ib-298 | 2.3 |
| Ib-299 | 0 |
| Ib-301 | 3 |
| Ib-302 | 1.5 |
| Ib-305 | 3 |
| Ib-306 | 5.3 |
| Ib-307 | 5 |
| Ib-309 | 4.3 |
| Ib-310 | 5.8 |
| Ib-311 | 6.3 |
| Ib-312 | 0 |
| Ib-322 | 4 |
| Ib-329 | 3.8 |
| Ib-330 | 0.5 |
| Ib-331 | <0 |
| Ib-332 | 2.3 |
| Ib-333 | <0 |
| Ib-334 | <0 |
| Ib-342 | <0 |
| Ib-343 | 0 |
| Ib-344 | 0 |
| Ib-350 | 2.3 |
| Ib-351 | 2.8 |
| Ib-352 | <0 |
| Ib-353 | 2.5 |
| Ib-354 | <0 |
| Ib-358 | <0 |
| Ib-361 | <0 |
| Ib-396 | <0 |
| Ib-431 | 6.5 |
| Ib-433 | 5.5 |
| Ib-439 | 5.3 |
| Ig-2 | 6.8 |

As shown in the above, the compound of the present invention has a suppressive effect on the IgE production.

Formulation Example 1

| | |
|---|---|
| The compound of the present invention (Ia-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate were uniformly mixed, the mixture was crushed and granulated, and dried to obtain a suitable size of granules. After calcium stearate was added to the granules, tablets were formed by compression molding.

Industrial Applicability

As explained in the above experiments, the compound of the present invention has a potent immunosuppressive and/or anti-allergic activity. The compound of the present invention is very useful as an immunosuppressant, an anti-allergic agent and/or a suppressant of the IgE production.

What is claimed is:
1. A compound of the formula (I):

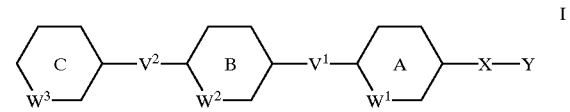

wherein A ring, B ring and C ring are each independently optionally substituted aromatic carbocycle or optionally substituted 5- or 6-membered heterocycle which may fuse with benzene ring, $W^1$, $W^2$ and/or $W^3$ represents a single bond when A ring, B ring and/or C ring is optionally substituted 5-membered heterocycle, X is —O—, —CH$_2$—, —NR$^1$— wherein R$^1$ is hydrogen, optionally substituted lower alkyl, lower alkenyl, lower alkylcarbonyl or optionally substituted lower alkoxycarbonyl or —S(O)p— wherein p is an integer of 0 to 2, Y is hydrogen, optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH$_2$—, Y may be optionally substituted lower alkoxycarbonyl, optionally substituted lower alkylsulfonyl or optionally substituted arylsulfonyl when X is —O— or —NR$^1$—, one of $V^1$ and $V^2$ is a single bond and the other is a single bond, an —O— bond, an —NH— bond, an —OCH$_2$— bond, a —CH$_2$O— bond, a —CH=CH— bond, a —C≡C— bond, a —CH(OR$^2$)— bond, wherein R$^2$ is hydrogen or lower alkyl, a —CO— bond, or an —NHCHR$^3$— bond, wherein R$^3$ is hydrogen or hydroxy, and at least one of A ring, B ring and C ring is optionally substituted aromatic carbocycle and at least another one is optionally substituted 5- or 6-membered heterocycle which may fuse with benzene ring when both of $V^1$ and $V^2$ are single bonds, excluding
(i) a compound wherein B ring is optionally substituted imidazole ring, optionally substituted furan ring, optionally substituted thiophene ring, optionally substituted pyrrole ring, optionally substituted oxazole ring, or optionally substituted thiazole ring,
(ii) a compound wherein both of A ring and C ring are optionally substituted pyrazole ring and —X—Y is methyl,
(iii) a compound wherein one of A ring and C ring is optionally substituted oxadiazole ring or optionally substituted tetrazole ring, and provided that
(iv) when at least one of A ring, B ring and c ring is optionally pyrimidine ring or when all of A ring, B ring and C ring are optionally substituted benzene ring, (iv-1) C ring is substituted with X'—Y' at para-position of V² wherein X' is the same as X and Y' is the same as Y' and (iv-2) at least one of —X—Y and —X'—Y' is other than unsubstituted lower alkyl, unsubstituted lower alkoxy, unsubstituted alkanoyloxy and unsubstituted lower alkylamino, salt or hydrate thereof.

2. The compound as claimed in claim 1 wherein A ring is optionally substituted benzene ring, salt or hydrate thereof.

3. The compound as claimed in claim 1 wherein B ring is optionally substituted benzene ring, optionally substituted pyridine ring, optionally substituted pyrimidine ring, optionally substituted pyridazine ring, optionally substituted pyrazine ring, or optionally substituted pyrazole ring salt or hydrate thereof.

4. The compound as claimed in claim 1 wherein C ring is optionally substituted benzene ring, optionally substituted pyridine ring, optionally substituted pyrimidine ring, optionally substituted pyridazine ring, optionally substituted pyrazine ring, optionally substituted isoxazole ring, optionally substituted pyrazole ring, optionally substituted benzothiazole ring, optionally substituted morpholine ring, optionally substituted piperazine ring, optionally substituted imidazole ring or optionally substituted triazole ring, salt or hydrate thereof.

5. The compound as claimed in claim 1 wherein X is —O— or —NR¹— wherein R¹ is hydrogen, methyl or prenyl, salt or hydrate thereof.

6. The compound as claimed in claim 1 wherein Y is hydrogen, optionally substituted lower alkyl, optionally substituted lower alkenyl, lower alkylsulfonyl or optionally substituted acyl, salt or hydrate thereof.

7. The compound as claimed in claim 1 wherein one of V¹ and V² is a single bond and the other is a single bond, —O— or —NH—, salt or hydrate thereof.

8. The compound as claimed in claim 1 wherein A ring is optionally substituted benzene ring, B ring is optionally substituted benzene ring, optionally substituted pyridine ring, optionally substituted pyrimidine ring, optionally substituted pyridazine ring, optionally substituted pyrazine ring, or optionally substituted pyrazole ring, C ring is optionally substituted benzene ring, optionally substituted pyridine ring, optionally substituted pyrimidine ring, optionally substituted pyridazine ring, optionally substituted pyrazine ring, optionally substituted isoxazole ring, optionally substituted pyrazole ring, optionally substituted benzothiazole ring, optionally substituted morpholine ring, optionally substituted piperazine ring, optionally substituted imidazole ring or optionally substituted triazole ring, X is —O— or —NR¹— wherein R¹ is hydrogen, methyl or prenyl, Y is optionally substituted lower alkyl or optionally substituted lower alkenyl, and one of V¹ and V² is a single bond and the other is a single bond, —O— or —NH—, salt or hydrate thereof.

9. The compound as claimed in claim 1 wherein two of A ring, B ring and C ring are optionally substituted benzene ring and the other is optionally substituted 5- or 6-membered heterocycle which may fuse with benzene ring, salt or hydrate thereof.

10. A pharmaceutical composition comprising the compound of the formula (I):

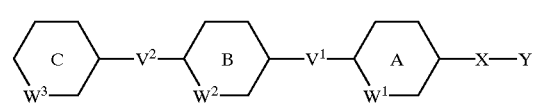

wherein A ring, B ring and C ring are each independently optionally substituted aromatic carbocycle or optionally substituted 5- or 6-membered heterocycle which may fuse with benzene ring, W¹, W² and/or W³ represents a single bond when A ring, B ring and/or C ring is optionally substituted 5-membered heterocycle, X is —O—, —CH₂—, —NR¹— wherein R¹ is hydrogen, optionally substituted lower alkyl, lower alkenyl, lower alkylcarbonyl or optionally substituted lower alkoxycarbonyl or —S(O)p— wherein p is an integer of 0 to 2, Y is hydrogen, optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH₂—, Y may be optionally substituted lower alkoxycarbonyl, optionally substituted lower alkylsulfonyl or optionally substituted arylsulfonyl when X is —O— or —NR¹—, one of V¹ and V² is a single bond and the other is a single bond, an —O— bond, an —NH— bond, an —OCH₂— bond, a —CH₂O— bond, a —CH=CH— bond, a —C≡C— bond, a —CH(OR²)— bond, wherein R² is hydrogen or lower alkyl, a —CO— bond, or an —NHCHR³— bond, wherein R³ is hydrogen or hydroxy, and at least one of A ring, B ring and C ring is optionally substituted aromatic carbocycle and at least another one is optionally substituted 5- or 6-membered heterocycle which may fuse with benzene ring when both of V¹ and V² are single bonds, excluding
(i) a compound wherein B ring is optionally substituted imidazole ring, optionally substituted furan ring, optionally substituted thiophene ring, optionally substituted pyrrole ring, optionally substituted oxazole ring, or optionally substituted thiazole ring and
(ii) a compound wherein one of A ring and C ring is optionally substituted oxadiazole ring or optionally substituted tetrazole ring, salt or hydrate thereof and a pharmaceutically acceptable carrier.

11. A method for suppressing an immune response or treating allergic diseases in a patient in need thereof, comprising:

administering the pharmaceutical composition according to claim 10 to said patient, wherein said pharmaceutical composition suppresses an immune response or treats allergic diseases in said patient.

12. A method for suppressing IgE production in a patient in need thereof, comprising:
   administering the pharmaceutical composition according to claim 10 to said patient, wherein said pharmaceutical composition suppresses IgE production in said patient.

13. A compound of the formula (Ib'):

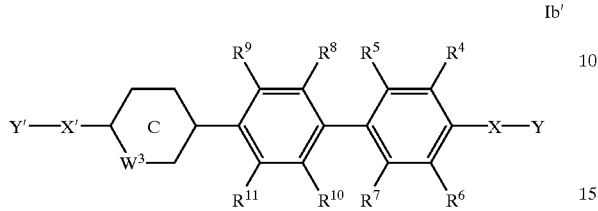

wherein C ring is optionally substituted 5- or 6-membered heterocycle which contains one or two hetero atoms, $W^3$ represents a bond when C ring is 5-membered heterocycle, X and X' are each independently —O—, —$CH_2$—, —$NR^1$— (wherein $R^1$ is hydrogen, optionally substituted lower alkyl, lower alkenyl, lower alkylcarbonyl or optionally substituted lower alkoxycarbonyl) or —S(O)p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, $R^1$, taken together with Y or Y', may form —$(CH_2)$m—, —$(CH_2)_2$—Q—$(CH_2)_2$— (wherein Q is $CH_2$, O, S or NR'), —CR'=CH—CH=CR'—, —CH=N—CH=CH—, —N=CH—N=CH—, —C(=O)—O($CH_2$)n—, —C(=O) —NR'—$(CH_2)$n— or —C(=O)—NR'—N=CH— wherein m is 4 or 5, n is 2 or 3, R' is hydrogen, lower alkyl or lower alkenyl, Y may be optionally substituted lower alkoxy when X is —$CH_2$—, Y' may be optionally substituted lower alkoxy when XI is —$CH_2$—, Y may be optionally substituted lower alkoxycarbonyl, optionally substituted lower alkylsulfonyl or optionally substituted arylsulfonyl when X is —O— or —$NR^1$—, Y' may be optionally substituted lower alkoxycarbonyl, optionally substituted lower alkylsulfonyl or optionally substituted arylsulfonyl when X' is —O— or —$NR^1$—, Y may be hydrogen or halogen when X is —$CH_2$— or —$NR^1$—, Y' may be hydrogen or halogen when X' is —$CH_2$— or —$NR^1$—, $R^4$, $R^5$, $R^6$, $R^7$, $R^8$, $R^9$, $R^{10}$ and $R^{11}$ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)—O wherein R is hydrogen, alkyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding
   (i) a compound wherein all of $R^8$, $R^9$, $R^{10}$ and $R^{11}$ are selected from hydrogen and halogen,
   (ii) a compound wherein C ring is optionally substituted pyrimidine ring, and at least one of —X—Y and —X'—Y' is unsubstituted lower alkyl, unsubstituted lower alkoxy, unsubstituted alkanoyloxy or unsubstituted lower alkylamino, and
   (iii) a compound wherein one of A ring and C ring is substituted with optionally substituted phenylaminocarbonyl or optionally substituted benzoylamino, salt or hydrate thereof.

14. The compound as claimed in claim 13 wherein $R^4$ and $R^5$ are each independently hydrogen, halogen or lower alkoxy, salt or hydrate thereof.

15. The compound as claimed in clam 13 wherein one of $R^4$ and R5 is hydrogen and the other is halogen, salt or hydrate thereof.

16. The compound as claimed in any one of claims 13 to 15 wherein both of R6 and R7 are hydrogen, salt or hydrate thereof.

17. The compound as claimed in claim 17 wherein $R^8$ and $R^{11}$ are each independently optionally substituted lower alkyl or optionally substituted lower alkoxy, salt or hydrate thereof.

18. The compound as claimed in claim 13 wherein $R^8$ and $R^{11}$ are each independently methyl or methoxy, salt or hydrate thereof.

19. The compound as claimed in any one of claims 13, 17 and 18 wherein $R^9$ and $R^{10}$ are each independently hydrogen or optionally substituted lower alkyl, salt or hydrate thereof.

20. The compound as claimed in claim 13 wherein both of $R^8$ and $R^{11}$ are optionally substituted lower alkyl or both of $R^8$ and $R^{11}$ are optionally substituted lower alkoxy, and both of $R^9$ and $R^{10}$ are simultaneously hydrogen or both of $R^9$ and $R^{10}$ are optionally substituted lower alkyl, salt or hydrate thereof.

21. The compound as claimed in any one of claims 13, 15 and 20 wherein C ring is 5- or 6-membered heterocycle which contains at least one N atoms, salt or hydrate thereof.

22. The compound as claimed in any one of claims 13, 15 and 20 wherein C ring is 6-membered heterocycle which contains at least one N atom, salt or hydrate thereof.

23. The compound as claimed in any one of claims 13, 15 and 20 wherein C ring is optionally substituted pyridine or optionally substituted pyrimidine, salt or hydrate thereof.

24. A compound of the formula (Ia'):

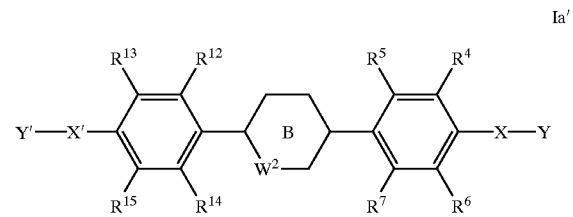

wherein B ring is optionally substituted 5- or 6-membered ring which contains one or two hetero atoms (wherein the substituent is halogen, hydroxy, optionally substituted lower alkyl, optionally substituted lower alkoxy, optionally substituted lower alkenyl, optionally substituted lower alkenyloxy, optionally substituted acyloxy, carboxy, optionally substituted lower alkoxycarbonyl, optionally substituted lower alkenyloxycarbonyl, optionally substituted alkylthio, optionally substituted lower alkenylthio, optionally substituted amino, guanidino, nitro, optionally substituted lower alkylsulfonyl, optionally substituted lower alkylsulfonyloxy, optionally substituted arylsulfonyl or optionally substituted arylsulfonyloxy, excluding a compound wherein B ring is substituted with only halogen(s)), and $W^2$ represents a bond when B ring is 5-membered heterocycle, X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O)p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R$^1$, taken together with Y or Y', may form —(CH$_2$)m, —(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O(CH$_2$)n—, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or —NR$^1$, Y' may be hydrogen or halogen when X' is —CH$_2$— or —NR$^1$—, R$^4$, R$^5$, R$^6$, R$^7$, R$^{12}$, R$^{13}$, R$^{14}$ and R$^{15}$ are each independently hydrogen, halogen, hydroxy, optionally substituted lower alkyl, optionally substituted lower alkoxy, optionally substituted lower alkenyl, optionally substituted lower alkenyloxy, optionally substituted acyloxy, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding (i) a compound wherein Y and Y' are simultaneously hydrogen, (ii) a compound wherein at least one of Y and Y' is optionally substituted acyl, (iii) a compound wherein at least one of —X—Y and —X'—Y' is unsubstituted lower alkoxy, and (iv) a compound wherein —X—Y and —X'—Y' are simultaneously optionally substituted lower alkoxy or amino substituted with phenyl, salt or hydrate thereof.

25. The compound as claimed in claim 24 wherein R$^4$ and R$^5$ are ach independently hydrogen, halogen or lower alkyl, salt or hydrate thereof.

26. The compound as claimed in claim 24 wherein one of R$^4$ and R$^5$ is hydrogen and the other is halogen, salt or hydrate thereof.

27. The compound as claimed in claim 24 or 26 wherein both of R$^6$ band R$^7$ are hydrogen, salt or hydrate thereof.

28. The compound as claimed in claim 24 or 26 wherein B ring is 5- or 6-membered heterocycle which contains at least one N atom, salt or hydrate thereof.

29. The compound as claimed in claim 24 or 26 wherein B ring is 6-membered heterocycle which contains at least one N atom, salt or hydrate thereof.

30. The compound as claimed in claim 24 or 26 wherein B ring is optionally substituted pyridine or optionally substituted pyrimidine, salt or hydrate thereof.

31. The compound as claimed in claim 24 or 26 wherein R$^{12}$, R$^{13}$, R$^{14}$ and R$^{15}$ are each independently hydrogen, halogen or lower alkyl, salt or hydrate threof.

32. The compound as claimed in claim 13 or 24 wherein one of X and X' is —O— and the other is —NR$^1$— wherein R$^1$ is hydrogen, optionally substituted lower alkyl, lower alkenyl, lower alkylcarbonyl or optionally substituted lower alkoxycarbonyl, salt or hydrate thereof.

33. The compound as claimed in claim 13 or 24 wherein one of X and X' is —O— and the other is —NR$^1$— wherein R$^1$ is hydrogen, lower alkyl or lower alkenyl and Y and Y' are each independently optionally substituted lower alkyl or optionally substituted lower alkenyl, salt or hydrate thereof.

34. The compound as claimed in claim 32 wherein R$^1$ is hydrogen, salt or hydrate thereof.

35. The compound as claimed in claim 13 or 24 wherein one of —X—Y and —X'—Y' is optionally substituted lower alkylamino or optionally substituted lower alkenylamino and the other is optionally substituted lower alkoxy or optionally substituted lower alkenyloxy, salt or hydrate thereof.

36. The compound as claimed in claim 13 or 24 wherein one of —X—Y and —X'—Y' is optionally substituted lower alkylamino or optionally substituted lower alkenylamino and the other is prenyloxy, salt or hydrate thereof.

37. The compound as claimed in claim 13 wherein R$^4$, R$^5$, R$^6$ and R$^7$ are each independently hydrogen, halogen or lower alkyl, R$^8$ and R$^{11}$ are each independently hydrogen, halogen, optionally substituted lower alkyl, optionally substituted lower alkoxy or lower alkoxycarbonyl, R$^9$ and R$^{10}$ are each independently hydrogen, optionally substituted lower alkyl or optionally substituted lower alkoxy, one of X and X' is —O— and the other is —NR$^1$— wherein R$^1$ is hydrogen, lower alkyl, lower alkenyl or lower alkylcarbonyl, Y and Y' are each independently optionally substituted lower alkyl, optionally substituted lower alkenyl or optionally substituted lower alkynyl, and C ring is optionally substituted pyridine or optionally substituted pyrimidine, salt or hydrate thereof.

38. The compound as claimed in claim 13 wherein X' is —O—, —NR$^1$— or —S(O)p— and C ring is optionally substituted 5-membered heteorcycle which contains one or two hetero atoms, salt or hydrate thereof.

39. The compound as claimed in claim 24 wherein R$^4$, R$^5$, R$^6$ and R$^7$ are each independently hydrogen, halogen or lower alkyl, R$^{12}$, R$^{13}$, R$^{14}$ and R$^{15}$ are each independently hydrogen, halogen or lower alkyl, B ring is optionally substituted pyridine or optionally substituted pyrimidine wherein the substituent is optionally substituted lower alkyl or optionally substituted lower alkoxy, one of X and X' is —O— and the other is —NR$^1$— wherein R$^1$ is hydrogen, lower alkyl, lower alkenyl or lower alkylcarbonyl and Y and Y' are each independently optionally substituted lower alkyl, optionally substituted lower alkenyl or optionally substituted lower alkynyl, salt or hydrate thereof.

40. A compound of the formula (If'):

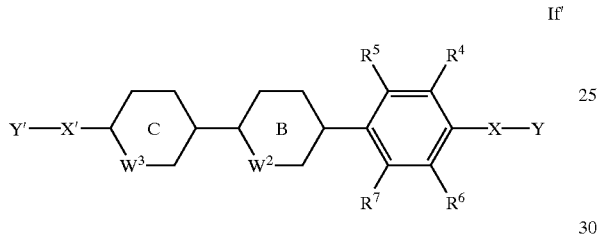

If' wherein one of B ring and C ring is optionally substituted 5- or 6-membered heterocycle which contains one or two hetero atoms and the other is 6-membered heterocycle which contains at least one N atom, excluding a compound wherein every substituent of B ring is selected from cyano and halogen, X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O) p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, W$^2$ represents a bond when B ring is 5-membered heterocycle, and W$^3$ represents a bond when C ring is 5-membered heterocycle, R$^1$, taken together with Y or Y', may form —(CH$_2$)m—, —C(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O (CH$_2$)n—, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$, Y may be hydrogen or halogen when X is —CH$_2$— or —NR$^1$, Y' may be hydrogen or halogen when X' is —CH$_2$— or —NR$^1$—, R$^4$, R$^5$, R$^6$ and R$^7$ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)—O wherein R is hydrogen, alkyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, salt or hydrate thereof.

41. A compound of the formula (Ig'):

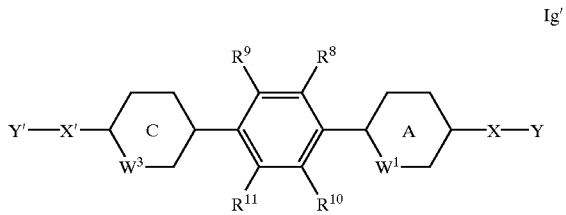

Ig' wherein A ring and C ring are each independently optionally substituted 5- or 6-membered which contains one or two hetero atoms, W$^1$ represents a bond when A ring is 5-membered heterocycle, W$^3$ represents a bond when C ring is 5-membered heterocycle, X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O) p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R$^1$, taken together with Y or Y', may form —(CH$_2$)m—, —C(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O (CH$_2$)n—, —C(=O)—NR'—(CH$_2$)n— or —C(=O)—NR'—N=CH— wherein m is 4 or 5, n is 2 or 3, and R' is hydrogen, lower alkyl or lower alkenyl, Y may be optionally substituted lower alkoxy when X is
—CH₂—, Y' may be optionally substituted lower alkoxy when X' is
—CH₂—, Y may be optionally substituted lower alkoxycarbonyl,
optionally substituted lower alkylsulfonyl or optionally
substituted arylsulfonyl when X is —O— or —NR¹—, Y' may be optionally substituted lower alkoxycarbonyl,
optionally substituted lower alkylsulfonyl or optionally
substituted arylsulfonyl when X' is —O— or —NR¹—, Y may be hydrogen or halogen when X is —NR¹—, Y' may be hydrogen or halogen when X' is —NR¹—, R⁸,
R⁹, R¹⁰ and R¹¹ are each independently hydrogen,
halogen, hydroxy, optionally substituted lower alkyl,
optionally substituted lower alkoxy, optionally substituted lower alkenyl, optionally substituted lower alkenyloxy, optionally substituted cycloalkyloxy, optionally substituted RC(O)—O wherein R is hydrogen, alkyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding a compound wherein all of R⁸, R⁹, R¹⁰ and R¹¹ are selected from hydrogen and halogen, salt or hydrate thereof.

42. A pharmaceutical composition for use as an immunosuppressant comprising a compound of the formula (Ib'):

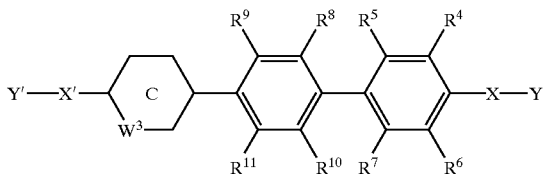

Ib' wherein C ring is optionally substituted 5- or 6-membered heterocycle which contains one or two hetero atoms, W³ represents a bond when C ring is 5-membered heterocycle, X and X' are each independently —O—, —CH₂—, —NR¹— (wherein R¹ is hydrogen, optionally substituted lower alkyl, lower alkenyl, lower alkylcarbonyl or optionally substituted lower alkoxycarbonyl), —S(O)$_p$— (wherein p is an integer of 0 to 2) or a single bond, Y and Y' are each independently optionally substituted lower alkyl, optionally substituted lower alkenyl, optionally substituted lower alkynyl, optionally substituted RC(O) wherein R is alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R¹, taken together with Y or Y', may form —(CH₂)m—, —C(CH₂)₂—Q—(CH₂)₂— (wherein Q is CH₂, O, S or NR'), —CR'═CH—CH═CR'—, —CH═N— CH═CH—, —N═CH—N═CH—, —C(═O)—O (CH₂)n—, —C(═O) —NR'—(CH₂)n— or
—C(═O)—NR'—N═CH— wherein m is 4 or 5, n is 2 or 3, and R¹ is hydrogen, lower alkyl or lower alkenyl, Y may be optionally substituted lower alkoxy when X is
—CH₂—, Y' may be optionally substituted lower alkoxy when X' is
—CH₂—, Y may be optionally substituted lower alkoxycarbonyl,
optionally substituted lower alkylsulfonyl or optionally
substituted arylsulfonyl when X is —O— or —NR¹—, Y' may be optionally substituted lower alkoxycarbonyl,
optionally substituted lower alkylsulfonyl or optionally
substituted arylsulfonyl when X' is —O— or —NR¹—, Y may be hydrogen or halogen when X is —CH₂— or
—NR¹—, Y' may be hydrogen or halogen when X' is —CH₂— or
NR¹—, Y' may be hydrogen, hydroxy, halogen, nitro or oxo when X' is a single bond, R⁴, R⁵, R⁶, R⁷, R⁸, R⁹, R¹⁰ and R¹¹ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)—O wherein R is hydrogen, alkyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding a compound wherein all of R⁸, R⁹, R¹⁰ and R¹¹ are selected from hydrogen and halogen, salt or hydrate thereof.

43. A pharmaceutical composition for use as an immunosuppressant comprising a compound of the formula (Ia'):

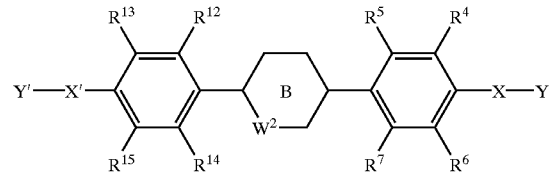

Ia' wherein B ring is optionally substituted 5- or 6- membered heterocycle which contains one or two hetero atoms excluding a compound wherein every substituent of B ring is selected from cyano and halogen, W² represents a bond when B ring is 5-membered heterocycle, X and X' are each independently —O—, —CH₂—, —NR¹— (wherein R¹ is hydrogen, optionally substituted lower alkyl, lower alkenyl, lower alkylcarbonyl or optionally substituted lower alkoxycarbonyl) or —S(O) p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R¹, taken together with Y or Y', may form —(CH₂)m—, —C(CH₂)₂—Q—(CH₂)₂— (wherein Q is CH₂, O, S or NR'), —CR'=CH—CH=CR'—, —CH=N—CH=CH—, —N=CH—N=CH—, —C(=O)—O(CH₂)n—, —C(=O)—NR'—(CH₂)n— or —C(=O)—NR'—N=CH— wherein m is 4 or 5, n is 2 or 3, R' is hydrogen, lower alkyl or lower alkenyl, Y may be optionally substituted lower alkoxy when X is —CH₂—, Y' may be optionally substituted lower alkoxy when X' is —CH₂—, Y may be optionally substituted lower alkoxycarbonyl, optionally substituted lower alkylsulfonyl or optionally substituted arylsulfonyl when X is —O— or —NR¹—, Y' may be optionally substituted lower alkoxycarbonyl, optionally substituted lower alkylsulfonyl or optionally substituted arylsulfonyl when X' is —O— or, —NR¹—, Y may be hydrogen or halogen when X is —CH₂— or —NR¹—, Y' may be hydrogen or halogen when X' is —CH₂— or —NR¹—, R⁴, R⁵, R⁶, R¹², R¹³, R¹⁴ and R¹⁵ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)—O wherein R is hydrogen, alkyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding
  (i) a compound wherein —X—Y and X'—Y' are simultaneously unsubstituted lower alkyl, optionally substituted lower alkoxy or unsubstituted acyloxy,
  (ii) a compound wherein one of —X—Y and —X'—Y' is methyl and the other is methoxy, and
  (iii) a compound wherein —X'—Y' is hydrogen or halogen and —X—Y is unsubstituted lower alkyl, unsubstituted lower alkoxy or di(lower) alkylamino, salt or hydrate thereof.

44. A pharmaceutical composition comprising the compound of the formula (If), salt or hydrate thereof according to claim 40 and a pharmaceutically acceptable carrier.

45. A pharmaceutical composition comprising the compound of the formula (Ig'), salt or hydrate thereof according to claim 41 and a pharmaceutically acceptable carrier.

46. A pharmaceutical composition comprising the compound of the formula (If') according to claim 40, the compound of the formula (Ig') according to claim 41, the compound of the formula (Ib') according to claim 42, the compound of the formula (Ia') according to claim 43, salt or hydrate thereof according to claim 41 and a pharmaceutically acceptable carrier.

47. A method for suppressing IgE production in a human in need thereof comprising administering the compound of the formula (If') according to claim 40, the compound of the formula (Ig') according to claim 41, the compound of the formula (Ib') according to claim 42, the compound of the formula (Ia') according to claim 43, salt or hydrate thereof according to claim 41 and a pharmaceutically acceptable carrier to said human, wherein a combination of said compounds suppresses IgE production in said human.

48. A method for suppressing an immune response, comprising administering the compound of the formula (If) according to claim 40, the compound of the formula (Ig') according to claim 41, the compound of the formula (Ib') according to claim 42, the compound of the formula (Ia') according to claim 43, salt or hydrate thereof.

49. A method for treating allergic diseases, comprising administering the compound of the formula (If') according to claim 40, the compound of the formula (Ig') according to claim 41, the compound of the formula (Ib') according to claim 42, the compound of the formula (Ia') according to claim 43, salt or hydrate thereof and a pharmaceutically acceptable carrier to said human, wherein a combination of said compounds suppresses immune response or treats allergic diseases in said human.

50. A compound of the formula:

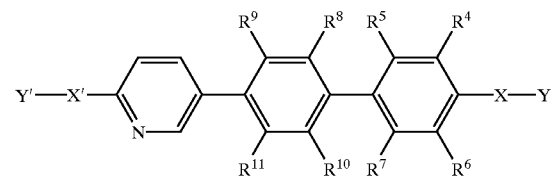

wherein R⁴ and R⁵ are each independently hydrogen, halogen or lower alkoxy, R⁶ and R⁷ are each independently hydrogen, halogen or lower alkyl, both of R⁸ and R¹¹ are lower alkyl or one of R⁸ and R¹¹ is lower alkyl and the other is lower alkoxy, both of R⁹ and R¹⁰ are hydrogen or both of R⁹ and R¹⁰ are lower alkyl, one of —X—Y and —X'—Y' is optionally substituted lower alkylamino or optionally substituted lower alkenylamino and the other is prenyloxy, salt or hydrate thereof.

51. A compound of the formula:

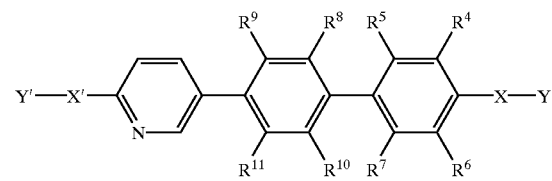

wherein

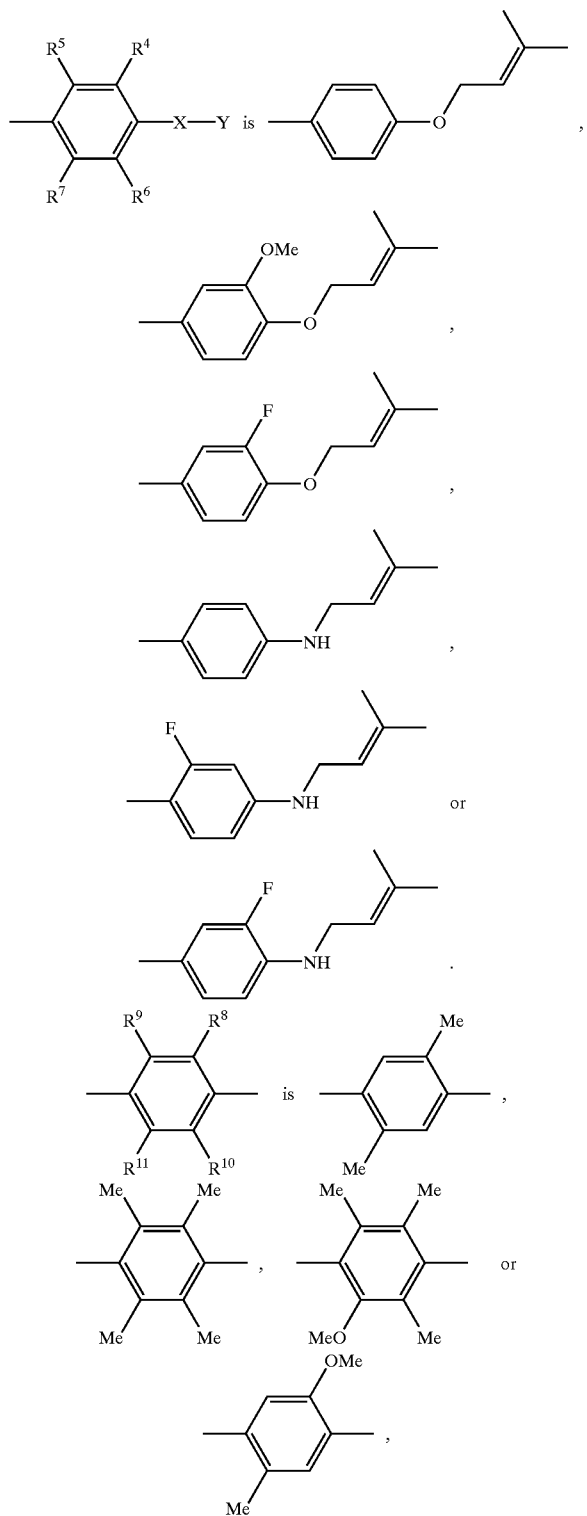

and —X'—Y' is the same as defined in claim 13, salt or hydrate thereof.

52. The compound as claimed in claim 33, wherein $R^1$ is hydrogen, salt or hydrate thereof.

53. The compound according to claim 1, 13, or 24, wherein a substituent of said optionally substituted lower alkyl is selected from the group consisting of: halogen; hydroxy; lower alkoxy optionally substituted with lower alkoxy; acyl; acyloxy; carboxy; lower alkoxycarbonyl; mercapt; lower alkylthio; amino optionally substituted with hydroxy, lower alkyl or optionally substituted acyl; imino optionally substituted with hydroxy, lower alkoxy, carboxy (lower)alkoxy, aryl(lower)alkoxy or 5- or 6-membered heterocycle; hydrazono optionally substituted with carbamoyl or lower alkoxycarbonyl; carbamoyl optionally substituted with lower alkyl or amino; thiocarbamoyl optionally substituted with lower alkyl; cycloalkyl optionally substituted with lower alkyl or lower alkoxy; cycloalkenyl optionally substituted with lower alkyl; cyano; phenyl optionally substituted with at least one substituent selected from the group of hydroxy, lower alkyl, carboxy, lower alkoxycarbonyl and lower alkoxy; and 5- or 6-membered heterocycle which may be substituted with lower alkyl and may fuse with benzene ring.

54. The compound according to claim 1, 13, or 24, wherein a substituent for said optionally substituted lower alkoxy is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; and heterocyclylcarbonyloxy.

55. The compound according to claim 1, 13, or 24, wherein a substituent of said optionally substituted lower alkoxycarbonyl, optionally substituted lower alkylsulfonyl, optionally substituted alkylsulfonyloxy, optionally substituted lower alkylthio, optionally substituted lower alkylamino, or optionally substituted lower alkylenedioxy is selected from the group consisting of: halogen; hydroxy; lower alkoxy optionally substituted with lower alkoxy; acyl; acyloxy; carboxy; lower alkoxycarbonyl; mercapt; lower alkylthio; amino optionally substituted with hydroxy, lower alkyl or optionally substituted acyl; imino optionally substituted with hydroxy, lower alkoxy, carboxy(lower)alkoxy, aryl(lower)alkoxy or 5- or 6-membered heterocycle; hydrazono optionally substituted with carbamoyl or lower alkoxycarbonyl; carbamoyl optionally substituted with lower alkyl or amino; thiocarbamoyl optionally substituted with lower alkyl; cycloalkyl optionally substituted with lower alkyl or lower alkoxy; cycloalkenyl optionally substituted with lower alkyl; cyano; phenyl optionally substituted with at least one substituent selected from the group of hydroxy, lower alkyl, carboxy, lower alkoxycarbonyl and lower alkoxy; and 5- or 6-membered heterocycle which may be substituted with lower alkyl and may fuse with benzene ring.

56. The compound according to claim 1, 13, or 24, wherein a substituent of said optionally substituted lower alkoxycarbonyl, said optionally substituted lower alkylsulfonyl, or said optionally substituted lower alkylthio is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl.

57. The compound according to claim 1, 13, or 24, wherein a substituent of said optionally substituted lower alkenyl is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; and heterocyclylcarbonyloxy.

58. The compound according to claim 1, 13, or 24, wherein a substituent for said optionally substituted lower alkenyloxy, said optionally substituted lower alkenyloxycarbonyl, or said optionally substituted lower alkenylthio is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; and heterocyclylcarbonyloxy.

59. The compound according to claim 1, 13, or 24, wherein a substituent for said optionally substituted lower alkynyl is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; and heterocyclylcarbonyloxy.

60. The compound according to claim 1, 13, or 24, wherein a substituent for said optionally substituted lower acyl or said optionally substituted acyloxy is selected from the group consisting of: halogen; hydroxy; lower alkoxy optionally substituted with acyloxy; acyl; acyloxy optionally substituted with hydroxy or carboxy; carboxy; lower alkoxycarbonyl; lower alkylthio; amino optionally substituted with lower alkyl; phenyl optionally substituted with lower alkyl or lower alkoxy; heterocycle; and heterocyclylcarbonyloxy.

61. The compound according to claim 1, 13, or 24, wherein a substituent of said optionally substituted lower cycloalkyl, or said optionally substituted cycloalkenyl is selected from the group consisting of: lower alkyl, halogen, hydroxy, carboxy, lower alkoxycarbonyl, lower alkoxy, lower alkylenedioxy, imino optionally substituted with lower alkoxy, aryl, and 5- or 6-membered heterocycle.

62. The compound according to claim 1, 13, or 24, wherein a substituent for said optionally substituted lower amino is selected from the group consisting of: optionally substituted lower alkyl, wherein the substituents are lower alkoxy, cycloalkyl, optionally substituted amino (wherein the substituents are aroyl optionally substituted with acyloxy (lower)alkoxy), optionally substituted aryl (wherein the substituents are lower alkyl, lower alkoxy, carboxy or lower alkoxycarbonyl) or heterocycle; lower alkenyl; lower alkynyl; cycloalkyl; aryl optionally substituted with lower alkyl, carboxy, acyl, lower alkoxycarbonyl; sulfamoyl optionally substituted with lower alkyl; optionally substituted lower alkoxycarbonyl, wherein the substituents are halogen, acyloxy, acyloxy substituted with hydroxy, acyloxy substituted with carboxy or heterocyclylcarbonyloxy; and lower alkylsulfonyl.

63. The compound according to claim 1, 13, or 24, wherein a substituent of said optionally substituted carbamoyl is selected from the group consisting of: lower alkyl, lower alkenyl, and lower alkynyl.

64. The compound according to claim 1, 13, or 24, wherein a substituent for said optionally substituted sulfamoyl is selected from the group consisting of: lower alkyl, lower alkenyl, and lower alkynyl.

65. The compound according to claim 1, 13, or 24, wherein a substituent for said optionally substituted aromatic carbocycle, said optionally substituted aryl, or said optionally substituted arylsulfonyl is selected from the group consisting of: halogen; hydroxy; lower alkyl optionally substituted with halogen or carboxy; lower alkoxy optionally substituted with halogen, aryl, heteroaryl or lower alkoxy; lower alkenyl; lower alkynyl; cycloalkyl; lower alkenyloxy; lower alkynyloxy; cycloalkoxy; acyl; acyloxy; carboxy; lower alkoxycarbonyl; lower alkenyloxycarbonyl; lower alkylthio; lower alkynylthio; amino optionally substituted with lower alkyl, cycloalkyl(lower)alkyl, heteroaryl (lower)alkyl, lower alkenyl, cycloalkyl, acyl optionally substituted with halogen, lower alkoxycarbonyl, or lower alkylsulfonyl; guanidino; nitro; lower alkylsulfonyl; dihydroxyborane; lower alkylsulfonyloxy optionally substituted with halogen; arylsulfonyl; arylsulfonyloxy; aryl; and 5- or 6-membered heterocycle.

66. The compound according to claim 1, 13, or 24, wherein said substituent of said optionally substituted 5- or 6-membered heterocycle, said optionally substituted 5- or 6-membered ring which may fuse with benzene ring, or said optionally substituted 5- or 6-membered heterocycle which contains one or two of hetero atoms is selected from the group consisting of: halogen; hydroxy; lower alkyl optionally substituted with hydroxy or acyloxy; lower alkoxy optionally substituted with halogen, aryl or 5- or 6-membered heterocycle; lower alkenyl; lower alkenyloxy; lower alkynyl; lower alkynyloxy; acyloxy; carboxy; lower alkoxycarbonyl; mercapt; lower alkylthio; lower alkenylthio; amino which may be mono- or di-substituted with halogen, optionally substituted lower alkyl wherein the substituents are cycloalkyl or 5- or 6-membered heterocycle, acyl optionally substituted with halogen, lower alkenyl, cycloalkyl, or lower alkylsulfonyl; imino optionally substituted with lower alkylsulfonyl; nitro; lower alkylsulfonyl; aryl; 5- or 6-membered heterocycle; oxo; and oxide.

67. A compound of the formula (I):

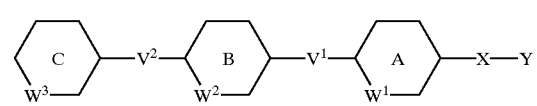

wherein A ring and C ring are each independently optionally substituted aromatic carbocycle or optionally substituted 5- or 6-membered heterocycle which may fuse with benzene ring, wherein 5- or 6-membered heterocycle is pyrrole ring, imidazole ring, pyridine ring, pyridazine ring, pyrazine ring, triazole ring, triazine ring, isoxazole ring, oxazolo ring, isothiazole ring, thiazole ring, thiadiazole ring, furan ring, thiophene ring, tetrahydropyrane ring, dihydropyridine ring, dihydropyridazine, dihydropyrazine ring, dioxane ring, oxathiorane ring, thiane ring, pyrrolidine ring, pyrroline ring, imidazolidine ring, imidazoline ring, pyrazolidine ring, pyrazoline ring, piperidine ring, piperazine ring or morpholine ring, B ring is optionally substituted aromatic carbocycle or optionally substituted 5- or 6-membered heterocycle which may fuse with benzene ring, wherein 5- or 6-membered heterocycle is pyrazole ring, pyridine ring, pyridazine ring, pyrazine ring, triazole ring, triazine ring, isoxazole ring, oxadiazole ring, isothiazole ring, thiadiazole ring, tetrahydropyrane ring, dihydropyridine ring, dihydropyridazine, dihydropyrazine ring, dioxane ring, oxathiorane ring, thiane ring, pyrrolidine ring, pyrroline ring, imidazolidine ring, imidazoline ring, pyrazolidine ring, pyrazoline ring, piperdine ring, piperzine ring, morpholine ring,

229

W¹, W² and/or W³ represents a single bond when A ring, B ring and/or C ring is optionally substituted 5-membered heterocycle, X is —O—, —CH₂—, —NR¹— wherein R¹ is hydrogen, optionally substituted lower alkyl, lower alkenyl, lower alkylcarbonyl or optionally substituted lower alkoxycarbonyl or —S(O)p— wherein p is an integer of 0 to 2, Y is hydrogen, optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH₂—, Y may be optionally substituted lower alkoxycarbonyl, optionally substituted lower alkylsulfonyl or optionally substituted arylsulfonyl when X is —O— or —NR¹—, one of V¹ and V² is a single bond and the other is a single bond, an —O— bond, an —NH— bond, an —OCH₂— bond, a —CH₂O— bond, a —CH=CH— bond, a —C≡C— bond, a —CH(OR²)— bond, wherein R² is hydrogen or lower alkyl, a —CO— bond, or an —NHCHR³— bond, wherein R³ is hydrogen or hydroxy, and at least one of A ring, B ring and C ring is optionally substituted aromatic carbocycle and at least another one is optionally substituted 5- or 6-membered heterocycle which may fuse with benzene ring when both of V¹ and V² are single bonds, salt or hydrate thereof.

68. A compound of the formula (I):

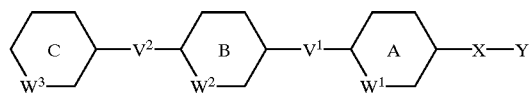

I wherein A ring is optionally substituted aromatic carbocycle or optionally substituted- 5- or 6-membered heterocycle which may fuse with benzene ring, wherein 5- or 6-membered heterocycle is pyrrole ring, imidazole ring, pyridine ring, pyridazine ring, pyrimidine ring, pyrazine ring, triazole ring, triazine ring, isoxazole ring, oxazole ring, oxadiazole ring, isothiazole ring, thiazole ring, thiadiazole ring, furan ring, thiophene ring, tetrahydropyrane ring, dihydropyridine ring, dihydropyridazine, dihydropyrazine ring, dioxane ring, oxathiorane ring, thiane ring, pyrrolidine ring, pyrroline ring, imidazolidine ring, imidazoline ring, pyrazolidine ring, pyrazoline ring, piperidine ring, piperazine ring or morpholine ring, B ring is optionally substituted aromatic carbocycle or optionally substituted 5- or 6-membered heterocycle which may fuse with benzene ring, C ring is optionally substituted pyrazole ring, W¹, W² and/or W³ represents a single bond when A ring, B ring and/or C ring is optionally substituted 5-membered heterocycle, X is —O—, —CH₂—, —NR¹— wherein R¹ is hydrogen, optionally substituted lower alkyl, lower alkenyl, lower

230 alkylcarbonyl or optionally substituted lower alkoxycarbonyl or —S(O)p— wherein p is an integer of 0 to 2, Y is hydrogen, optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH₂—, Y may be optionally substituted lower alkoxycarbonyl, optionally substituted lower alkylsulfonyl or optionally substituted arylsulfonyl when X is —O— or —NR¹—, one of V¹ and V² is a single bond and the other is a single bond, an —O— bond, an —NH— bond, an —OCH₂— bond, a —CH₂O— bond, a —CH=CH— bond, a —C≡C— bond, a —CH(OR²)— bond, wherein R² is hydrogen or lower alkyl, a —CO— bond, or an —NHCHR³— bond, wherein R³ is hydrogen or hydroxy, and at least one of A ring, B ring and C ring is optionally substituted aromatic carbocycle and at least another one is optionally substituted 5- or 6-membered heterocycle which may fuse with benzene ring when both of V¹ and V² are single bonds, salt or hydrate thereof.

69. A compound of the formula (I):

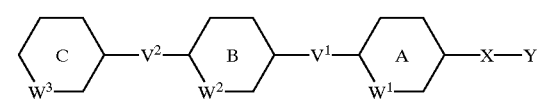

I wherein A ring and B ring are each independently optionally substituted aromatic carbocycle or optionally substituted 5- or 6-membered heterocycle which may fuse with benzene ring, C ring is optionally substituted pyrimidine ring, W¹ and/or W² represents a single bond when A ring and/or B ring is optionally substituted 5-membered heterocycle, X is —O—, —CH₂—, —NR¹— wherein R¹ is hydrogen, optionally substituted lower alkyl, lower alkenyl, lower alkylcarbonyl or optionally substituted lower alkoxycarbonyl or —S(O)p— wherein p is an integer of 0 to 2, Y is optionally substituted lower alkenyl, optionally substituted lower alkynyl, optionally substituted cycloalkyl optionally substituted cycloalkenyl, optionally substituted lower alkoxycarbonyl, optionally substituted sulfamoyl, optionally substituted amino, optionally substituted aryl or optionally substituted 5- or 6-membered heterocycle, Y may be optionally substituted lower alkoxy when X is —CH₂—, Y may be optionally substituted lower alkoxycarbonyl, optionally substituted lower alkylsulfonyl or optionally substituted arylsulfonyl when X is —O— or —NR¹—, Y may be optionally substituted RC(O) wherein R is hydrogen, alkyl, alkenyl, cycloalkyl or aryl when X is —NR¹—, Y may be hydrogen when X is —O— or —S(O)p—,
one of $V^1$ and $V^2$ is a single bond and the other is a single bond, an —O— bond, an —NH— bond, an —OCH$_2$— bond, a —CH$_2$O— bond, a —CH=CH— bond, a —C≡C— bond, a —CH(OR$^2$)— bond, wherein R$^2$ is hydrogen or lower alkyl, a —CO— bond, or an —NHCHR$^3$— bond, wherein R$^3$ is hydrogen or hydroxy, and
at least one of A ring, B ring and C ring is optionally substituted aromatic carbocycle and at least another one is optionally substituted 5- or 6-membered heterocycle which may fuse with benzene ring when both of $V^1$ and $V^2$ are single bonds, salt or hydrate thereof.

70. A compound of the formula (Ib'):

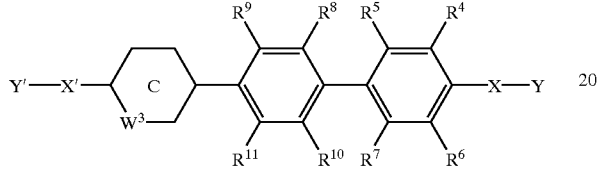

Ib' wherein C ring is optionally substituted 5- or 6-membered heterocycle, $W^3$ represents a bond when C ring is 5-membered heterocycle, wherein 5- or 6-heterocycle is pyrrole ring, imidazole ring, pyrazole ring, pyridine ring, pyridazine ring, pyrazine ring, isoxazole ring, oxazole ring, isothiazole ring, thiazole ring, furan ring, thiophene ring, tetrahydropyrane ring, dihydropyridine ring, dihydropyridazine, dihydropyrazine ring, dioxane ring, oxathiorane ring, thiane ring, pyrrolidine ring, pyrroline ring, imidazolidine ring, imidazoline ring, pyrazolidine ring, pyrazoline ring, piperidine ring, piperazine ring or morpholine ring, X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O)p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R$^1$, taken together with Y or Y', may form —(CH$_2$)m—, —C(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O(CH$_2$)n—, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or —NR$^1$—, Y' may be hydrogen or halogen when X' is —CH$_2$— or —NR$^1$—, R$^4$, R$^5$, R$^6$, R$^7$, R$^8$, R$^9$, R$^{10}$ and R$^{11}$ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)O wherein R is hydrogen, alkyl, alkenyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding a compound wherein all of R$^8$, R$^9$, R$^{10}$ and R$^{11}$ are selected from hydrogen and halogen, salt or hydrate thereof.

71. A compound of the formula (Ib'):

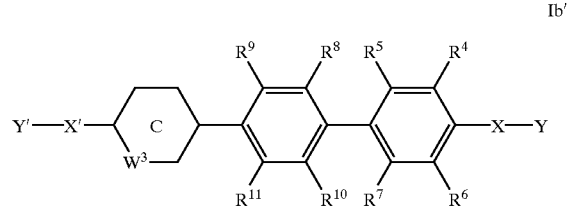

Ib' wherein C ring is optionally substituted pyrimidine,

X and X' are each independently —O—, —CH$_2$—, —NR$^1$— (wherein R$^1$ is hydrogen, optionally substituted lower alkyl, lower alkenyl, lower alkylcarbonyl or optionally substituted lower alkoxycarbonyl) or —S(O)p— wherein p is an integer of 0 to 2, Y and Y' are each independently optionally substituted lower alkenyl, optionally substituted lower alkynyl, optionally substituted cycloalkyl optionally substituted cycloalkenyl, optionally substituted lower alkoxycarbonyl, optionally substituted amino, optionally substituted sulfamoyl, optionally substituted aryl or optionally substituted 5- or 6-membered heterocycle, R$^1$, taken together with Y or Y', may form —(CH$_2$)m—, —C(CH$_2$)$_2$—Q—(CH$_2$)$_2$— (wherein Q is CH$_2$, O, S or NR'), —CR'=CH—CH=CR'—, —CH=N—CH=CH—, —N=CH—N=CH—, —C(=O)—O(CH$_2$)n—, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—,

233

Y may be halogen when X is —CH$_2$— or —NR$^1$—,

Y' may be halogen when X' is —CH$_2$— or —NR$^1$—,

Y may be optionally substituted RC(O) wherein R is hydrogen, alkyl, alkenyl, cycloalkyl or aryl when X is —NR$^1$—, Y' may be optionally substituted RC(O) wherein R is hydrogen, alkyl, alkenyl, cycloalkyl or aryl when X' is —NR$^1$—, Y may be hydrogen when X is —NR$^1$—, Y' may be hydrogen when X' is —NR$^1$—, R$^4$, R$^5$, R$^6$, R$^7$, R$^8$, R$^9$, R$^{10}$ and R$^{11}$ are each independently hydrogen, halogen, hydroxy, optionally substituted lower alkyl, optionally substituted lower alkoxy, optionally substituted lower alkenyl, optionally substituted lower alkenyloxy, optionally substituted cycloalkyloxy, optionally substituted RC(O)O wherein R is hydrogen, alkyl, alkenyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding a compound wherein all of R$^8$, R$^9$, R$^{10}$ and R$^{11}$ are selected from hydrogen and halogen, salt or hydrate thereof.

72. A compound of the formula (Ia'):

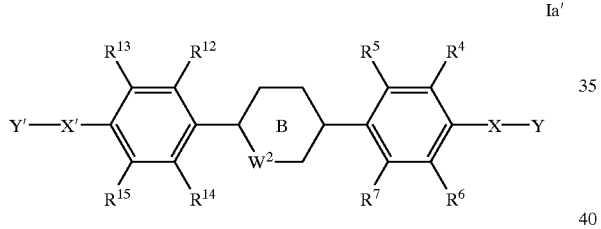

Ia' wherein B ring is optionally substituted 5- or 6-membered heterocycle (wherein 5- or 6-heterocycle is pyrazole ring, pyridine ring, pyridazine ring, pyrazine ring, isoxazole ring, isothiazole ring, tetrahydropyrane ring, thiane ring, pyrrolidine ring, pyrroline ring, imidazolidine ring, imidazoline ring, pyrazolidine ring, pyrazoline ring, piperidine ring, piperazine ring, morpholine ring, and the substituent is halogen, hydroxy, optionally substituted lower alkyl, optionally substituted acyloxy, optionally substituted lower alkenyl, optionally substituted lower alkenyloxy, optionally substituted RC(Q)Q wherein R is hydrogen, alkyl, alkenyl, cycloalkyl or aryl, carboxy, optionally substituted lower alkoxycarbonyl, optionally substituted lower alkenyloxycarbonyl, optionally substituted alkylthio, optionally substituted lower alkenylthio, optionally substituted amino, guanidine, nitro, optionally substituted lower alkylsulfonyl, optionally substituted lower alkylsulfonyloxy, optionally substituted arylsulfonyl or optionally substituted arylsulfonyloxy, excluding a compound wherein B ring is substituted with only halogen(s)), and W$^2$ represents a bond when B ring is 5-membered heterocycle, X and X' are each independently —O—, —CH$_2$—, —NR$^1$— (wherein R$^1$ is hydrogen, optionally substituted lower alkyl, lower alkenyl, lower alkylcarbonyl or

234 optionally substituted lower alkoxycarbonyl) or —S(O)p— wherein p is an integer of 0 to 2, Y and Y' are each independently optionally substituted lower alkyl, optionally substituted lower alkenyl, optionally substituted lower alkynyl, optionally substituted RC(O) wherein R is hydrogen, alkyl, alkenyl, cycloalkyl or aryl, optionally substituted cycloalkyl, optionally substituted cycloalkenyl, optionally substituted lower alkoxycarbonyl, optionally substituted amino, optionally substituted sulfamoyl, optionally substituted aryl or optionally substituted 5- or 6-membered heterocycle, R$^1$, taken together with Y or Y', may form —(CH$_2$)m, —C(CH$_2$)$_2$—Q—(CH$_2$)$_2$— (wherein Q is CH$_2$, O, S or NR'), —CR'=CH—CH=CR'—, —CH=N—CH=CH—, —N—CH—N=CH—, —C(=O)—O(CH$_2$)n—, —C(=O)—NR'—(CH$_2$)n— or —C(=O)—NR'—N=CH— wherein m is 4 or 5, n is 2 or 3, R' is hydrogen, lower alkyl or lower alkenyl, Y may be optionally substituted lower alkoxy when X is —CH$_2$—, Y' may be optionally substituted lower alkoxy when X' is —CH$_2$—, Y may be optionally substituted lower alkoxycarbonyl, optionally substituted lower alkylsulfonyl or optionally substituted arylsulfonyl when X is —O— or —NR$^1$—, Y' may be optionally substituted lower alkoxycarbonyl, optionally substituted lower alkylsulfonyl or optionally substituted arylsulfonyl when X' is —O— or —NR$^1$—, Y may be hydrogen or halogen when X is —CH$_2$— or —NR$^1$, Y' may be hydrogen or halogen when X' is —CH$_2$— or —NR$^1$—, R$^4$, R$^5$, R$^6$, R$^7$, R$^{12}$, R$^{13}$, R$^{14}$ and R$^{15}$ are each independently hydrogen, halogen, hydroxy, optionally substituted lower alkyl, optionally substituted lower alkoxy, optionally substituted lower alkenyl, optionally substituted lower alkenyloxy, optionally substituted RC(O)O wherein R is hydrogen, alkyl, alkenyl, cycloalkyl or aryl, carboxy, optionally substituted lower alkoxycarbonyl, optionally substituted lower alkenyloxycarbonyl, optionally substituted lower alkylthio, optionally substituted lower alkenylthio, optionally substituted amino, optionally substituted carbamoyl, guanidino, nitro, optionally substituted lower alkylsulfonyl, optionally substituted lower alkylsulfonyloxy, optionally substituted arylsulfonyl or optionally substituted arylsulfonyloxy, excluding
(i) a compound wherein Y and Y' are simultaneously hydrogen,
(ii) a compound wherein at least one of Y and Y' is optionally substituted RC(O),
(iii) a compound wherein at least one of —X—Y and —X'—Y' is unsubstituted lower alkoxy, and
(iv) a compound wherein —X—Y and —X'—Y' are simultaneously optionally substituted lower alkoxy or amino substituted with phenyl, salt or hydrate thereof.

73. A pharmaceutical composition comprising the compound, salt or hydrate thereof according to any one of claims 67 to 72 and a pharmaceutically acceptable carrier.

74. A method for suppressing an immune response or treating allergic diseases in a patient in need thereof, comprising administering the pharmaceutical composition according to any one of claims 67 to 72 to said patient, wherein said pharmaceutical composition suppresses an immune response or treats allergic diseases in said patient.

75. A method for suppressing IgE production in a patient in need thereof, comprising administering the pharmaceutical composition according to any one of claims 67 to 72 to said patient, wherein said pharmaceutical composition suppresses IgE production in said patient.

* * * * *